United States Patent
Xia et al.

(10) Patent No.: US 8,907,095 B2
(45) Date of Patent: Dec. 9, 2014

(54) BICYCLIC HETEROCYCLE DERIVATIVES AND THEIR USE AS MODULATORS OF THE ACTIVITY OF GPR119

(75) Inventors: Yan Xia, Edison, NJ (US); Craig D. Boyle, Branchburg, NJ (US); William J. Greenlee, Teaneck, NJ (US); Samuel Chackalamannil, Califon, NJ (US); Charles Lee Jayne, Staten Island, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1267 days.

(21) Appl. No.: 12/739,531

(22) PCT Filed: Oct. 20, 2008

(86) PCT No.: PCT/US2008/080462
§ 371 (c)(1),
(2), (4) Date: May 9, 2011

(87) PCT Pub. No.: WO2009/055331
PCT Pub. Date: Apr. 30, 2009

(65) Prior Publication Data
US 2011/0212938 A1    Sep. 1, 2011

Related U.S. Application Data

(60) Provisional application No. 60/981,677, filed on Oct. 22, 2007.

(51) Int. Cl.
*C07D 221/02* (2006.01)
*A61K 31/439* (2006.01)
*C07D 451/14* (2006.01)
*C07D 491/08* (2006.01)
*C07D 495/08* (2006.01)
*C07D 471/08* (2006.01)
*C07D 451/06* (2006.01)
*C07D 487/08* (2006.01)
*C07D 401/14* (2006.01)
*C07D 498/08* (2006.01)

(52) U.S. Cl.
CPC ............ *C07D 451/06* (2013.01); *C07D 451/14* (2013.01); *C07D 491/08* (2013.01); *C07D 495/08* (2013.01); *C07D 471/08* (2013.01); *A61K 31/439* (2013.01); *C07D 487/08* (2013.01); *C07D 401/14* (2013.01); *C07D 498/08* (2013.01)
USPC ............ 546/183; 514/269; 514/299; 544/319

(58) Field of Classification Search
CPC ............................ C07D 451/14; A61K 31/439
USPC .................... 546/183; 514/269, 299; 544/319
See application file for complete search history.

(56) References Cited

U.S. PATENT DOCUMENTS

2006/0155128 A1    7/2006  Jones et al.
2007/0155726 A1 *  7/2007  Arnaiz et al. ................. 514/218

FOREIGN PATENT DOCUMENTS

WO    2005/007647        1/2005
WO    2005/121121        12/2005
WO    2007/063071 A1     6/2007

OTHER PUBLICATIONS

Int'l Search Report in PCT/US2008/080462, dated Jun. 19, 2009.

* cited by examiner

*Primary Examiner* — Barbara P Badio
*Assistant Examiner* — Sara E Townsley
(74) *Attorney, Agent, or Firm* — Anna L. Cocuzzo; Catherine D. Fitch

(57) ABSTRACT

The present invention relates to Bicyclic Heterocycle Derivatives, compositions comprising a Bicyclic Heterocycle Derivative, and methods of using the Bicyclic Heterocycle Derivatives for treating or preventing obesity, diabetes, a metabolic disorder, a cardiovascular disease or a disorder related to the activity of GPR119 in a patient.

14 Claims, No Drawings

BICYCLIC HETEROCYCLE DERIVATIVES AND THEIR USE AS MODULATORS OF THE ACTIVITY OF GPR119

FIELD OF THE INVENTION

The present invention relates to Bicyclic Heterocycle Derivatives, compositions comprising a Bicyclic Heterocycle Derivative, and methods of using the Bicyclic Heterocycle Derivatives for treating or preventing obesity, diabetes, a diabetic complication, a metabolic disorder, a cardiovascular disease or a disorder related to the activity of GPR119 in a patient.

BACKGROUND OF THE INVENTION

Although a number of receptor classes exist in humans, by far the most abundant and therapeutically relevant is represented by the G protein-coupled receptor (GPCR or GPCRs) class. It is estimated that there are some 100,000 genes within the human genome, and of these, approximately 2% or 2,000 genes, are estimated to code for GPCRs. Receptors, including GPCRs, for which the endogenous ligand has been identified are referred to as "known" receptors, while receptors for which the endogenous ligand has not been identified are referred to as "orphan" receptors. GPCRs represent an important area for the development of pharmaceutical products, as evidenced by the fact that pharmaceutical products have been developed from approximately 20 of the 100 known GPCRs. This distinction is not merely semantic, particularly in the case of GPCRs.

GPCRs share a common structural motif. All these receptors have seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane- and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when an endogenous ligand binds with the receptor (often referred to as "activation" of the receptor), there is a change in the conformation of the intracellular region that allows for coupling between the intracellular region and an intracellular "G-protein." it has been reported that GPCRs are "promiscuous" with respect to G proteins, i.e., that a GPCR can interact with more than one G protein. See, Kenakin, T., *Life Sciences* 43, 1095 (1988). Although other G proteins exist, currently, Gq, Gs, Gi, and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein.

Under physiological conditions, GPCRs exist in the cell membrane in equilibrium between two different conformations: an "inactive" state and an "active" state. A receptor in an inactive state is unable to link to the intracellular signaling transduction pathway to produce a biological response. Changing the receptor conformation to the active state allows linkage to the transduction pathway (via the G-protein) and produces a biological response. A receptor can be stabilized in an active state by an endogenous ligand or a compound such as a drug.

Modulation of G-protein coupled receptors has been well-studied for controlling various metabolic disorders. Small molecule modulators of the receptor GPR119, a G-protein coupled-receptor described in, for example, GenBank (see, e.g., accession numbers XM.sub.—066873 and AY288416), have been shown to be useful for treating or preventing certain metabolic disorders. GPR119 is a G protein-coupled receptor that is selectively expressed on pancreatic beta cells. GPR119 activation leads to elevation of a level of intracellular cAMP, consistent with GPR119 being coupled to Gs. Agonists to GPR119 stimulate glucose-dependent insulin secretion in vitro and lower an elevated blood glucose level in See, e.g., International Applications WO 04/065380, WO 04/076413, and EP 1338651, the disclosure of each of which is herein incorporated by reference in its entirety.

U.S. Ser. No. 10/890,549 discloses pyrazolo[3,4-d]pyrimidine ethers and related compounds as modulators of the GPR119 receptor that are useful for the treatment of various metabolic-related disorders such as type I diabetes, type II diabetes, inadequate glucose tolerance, insulin resistance, hyperglycemia, hyperlipidemia, hypertriglyceridemia, hypercholesterolemia, dyslipidemia or syndrome X. The compounds are also reported as being useful for controlling weight gain, controlling food intake, and inducing satiety in mammals. The promising nature of these GPR119 modulators indicates a need in the art for additional small molecule GRP119 modulators with improved efficacy and safety profiles. This invention addresses that need.

SUMMARY OF THE INVENTION

In one aspect, the present invention provides compounds of Formula (I):

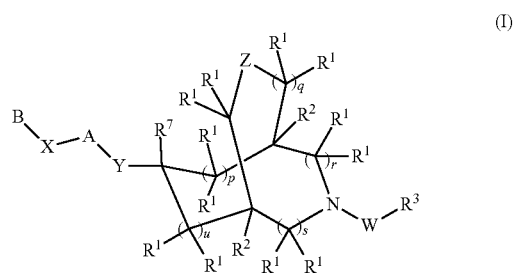

and pharmaceutically acceptable salts, solvates, esters, prodrugs and stereoisomers thereof, wherein:

A is aryl or -5- or 6-membered heteroaryl, any of which can be optionally substituted with up to 4 groups, which can be the same or different, and are selected from: alkyl, aryl, alkenyl, cycloalkyl, cycloalkenyl, haloalkyl, hydroxyalkyl, halo, —OH, —O-haloalkyl, —O-alkyl, —O-alkyl-OH, —O-alkyl-O-alkyl, -alkylene-O-alkyl, —CN, —N(R$^4$)$_2$, —C(O)H, —C(O)R$^4$, —C(O)OR$^4$, —C(O)N(R$^4$)$_2$, —NHC(O)R$^4$, —NHS(O)$_m$R$^4$, —S(O)$_n$R$^4$ and —S(O)$_m$N(R$^4$)$_2$;

B is aryl or heteroaryl, any of which can be optionally substituted with up to 4 groups, which can be the same or different, and are selected from: alkyl, aryl, alkenyl, cycloalkyl, cycloalkenyl, haloalkyl, hydroxyalkyl, heteroaryl, halo, —OH, —O-haloalkyl, —O-alkyl, —O-aryl, -alkylene-O-alkyl, -alkylene-S(O)$_2$-alkyl, —CN, —N(R$^4$)$_2$, —C(O)H, —C(O)R$^4$, —C(O)OR$^4$C(O)N(R$^4$)$_2$, —NHC(O)R$^4$, —NHS(O)$_m$R$^4$, —S(O)$_n$R$^4$ and —S(O)$_m$N(R$^4$)$_2$, wherein a cycloalkyl or heteroaryl substituent group can be unsubstituted or optionally substituted with R$^9$, and wherein when B is aryl, the aryl group can be optionally fused to a 4 to 7-membered cycloalkyl group or cycloalkanoyl group;

W is a bond, alkylene, —C(O)—, —C(O)—O—, —C(O)—S—, —S(O)—, —S(O)$_2$—, —S(O)$_2$—N(R$^{10}$)— or —C(O)—N(R$^{10}$)—;

X is —C(R$^1$)$_2$—, —O—, —N(R$^{10}$)— or —S—;

Y is —O—(alkylene)$_t$-, —N(R$^{10}$)-(alkylene)$_t$-, or —S—;

Z is a single bond, a double bond, —C(O)—, —C=NOR$^{12}$, —C=C(R$^{14}$)$_2$, —C(R$^1$)$_2$—, —O—, —N(R$^{10}$)— or —S(O)$_n$—, such that when q is 0, Z is other than a double bond;

each occurrence of R$^1$ is independently H, alkyl, cycloalkyl, halo or —OR$^7$; wherein an alkyl group can be unsubstituted or optionally substituted with one or more of the following groups: —O-alkyl, —OH or —N(R$^4$)$_2$; and wherein any two geminal R$^1$ groups, together with the common carbon atom to which they are attached, can join to form a spirocyclic 3- to 6-membered cycloalkyl group, a spirocyclic 3- to 6-membered heterocycloalkyl group or a spirocyclic 3- to 6-membered heterocycloalkenyl group; and wherein any two R$^1$ groups present on separate ring carbon atoms can join to form a cycloalkyl or heterocycloalkyl bridge; and wherein when any R$^1$ group is —OH, then the carbon atom to which the R$^1$ group is attached is not also attached to another oxygen atom or to a nitrogen or halogen atom;

each occurrence of R$^2$ is independently H or alkyl;

R$^3$ is alkyl, -(alkylene)$_t$-alkenyl, -(alkylene)$_t$-alkynyl, -(alkylene)$_t$-C(O)R$^4$, -(alkylene)$_t$-haloalkyl, -alkylene-O-alkyl, -alkylene-O-(alkylene)$_t$-aryl, -alkylene-S-aryl, -alkylene-N(R$^4$)C(O)O-alkyl, —CH(cycloalkyl)$_2$, —CH(heterocycloalkyl)$_2$, -(alkylene)$_t$-aryl, -(alkylene)$_t$-cycloalkyl, -(alkylene)$_t$-cycloalkenyl, -(alkylene)$_t$heterocycloalkyl, -(alkylene)$_t$-heterocycloalkenyl or -(alkylene)$_t$-heteroaryl, wherein an aryl, cycloalkyl, cycloalkenyl, heterocycloalkyl, heterocycloalkenyl or heteroaryl group can be unsubstituted or optionally substituted with R$^9$;

each occurrence of R$^4$ is H, alkyl, cycloalkyl or -(alkylene)$_t$-alkenyl, wherein an alkyl group is unsubstituted or optionally substituted with halo, —OH or —O-alkyl;

R$^7$ is H or alkyl;

R$^9$ represents from 1 to 4 optional substituents, which can be the same or different, and which are selected from alkyl, alkenyl, alkynyl, halo, haloalkyl, —CN, —NO$_2$, —O-(alkylene)$_t$-R$^{13}$, —N(R$^{13}$)-(alkylene)$_t$-R$^{13}$, -(alkylene)$_t$-R$^{13}$, —C(O)-(alkylene)$_t$-R$^{13}$, —C(O)O-(alkylene)$_t$-R$^{13}$, —N(R$^7$)C(O)-(alkylene)$_t$R$^{13}$, —C(O)N(R$^7$)-(alkylene)$_t$-R$^{13}$, —OC(O)-(alkylene)$_t$—R$^{13}$, —N(R$^7$)C(O)N(R$^7$)-(alkylene)$_t$-R$^{13}$, —N(R$^7$)C(O)O-(alkylene)$_t$-R$^{13}$, —S(O)-(alkylene)$_t$-R$^{13}$ or —S(O)$_2$(alkylene)$_t$-R$^{13}$;

R$^{10}$ is H, alkyl, aryl, or —C(O)OR$^4$, wherein an alkyl group is unsubstituted car optionally substituted with —OH or —O-alkyl;

R$^{12}$ is H, alkyl or aryl;

each occurrence of R$^{13}$ is independently H, haloalkyl, aryl, cycloalkyl, cycloalkenyl, heterocycloalkyl, heterocycloalkenyl or heteroaryl;

each occurrence of R$^{14}$ is independently H, alkyl or aryl, or both R$^{14}$ groups, and the carbon atom to which they are attached, combine to form a cycloalkyl or heterocycloalkyl group;

each occurrence of m is independently 1 or 2;
each occurrence of n is independently 0, 1 or 2;
p is 0, 1 or 2;
q is 0, 1 or 2;
r is 0, 1 or 2;
s is 0, 1 or 2;
each occurrence oft is independently 0 or 1; and
u is 0, 1 or 2.

In another aspect, the present invention provides compounds of Formula (II):

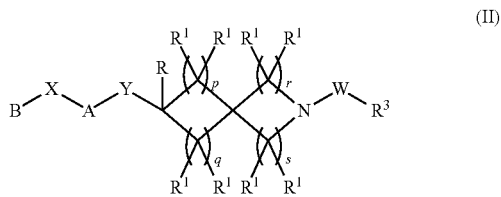

(II)

and pharmaceutically acceptable salts, solvates, esters, prodrugs and stereoisomers thereof, wherein:

A is aryl or -5- or 6-membered heteroaryl, any of which can be optionally substituted with up to 4 groups, which can be the same or different, and are selected from: alkyl, aryl, alkenyl, cycloalkyl, cycloalkenyl, haloalkyl, hydroxyalkyl, halo, —OH, —O-haloalkyl, —O-alkyl, —O-alkyl-OH, —O-alkyl-O-alkyl, —O-aryl, alkylene-O-alkyl, —CN, —N(R$^4$)$_2$, —C(O)R$^4$, —C(O)OR$^4$, —C(O)N(R$^4$)$_2$, —NHC(O)R$^4$, —NHS(O)$_m$R$^4$, —S(O)$_n$R$^4$ and —S(O)$_m$N(R$^4$)$_2$ such that when Y is —O—, A is other than phenyl or pyridyl;

B is aryl or heteroaryl, any of which can be optionally substituted with up to 4 groups, which can be the same or different, and are selected from: alkyl, aryl, alkenyl, cycloalkyl, cycloalkenyl, haloalkyl, hydroxyalkyl, heteroaryl, halo, —OH, —O-haloalkyl, —O-alkyl, —O-aryl, -alkylene-O-alkyl, —CN, —N(R$^4$)$_2$, —C(O)H, —C(O)R$^4$, —C(O)OR$^4$, —C(O)N(R$^4$)$_2$, —NHC(O)R$^4$, —NHS(O)$_m$R$^4$, —S(O)$_n$R$^4$ and —S(O)$_m$N(R$^4$)$_2$, wherein a cycloalkyl or heteroaryl substituent group can be unsubstituted or optionally substituted with R$^9$, and wherein when B is aryl, the aryl group can be optionally fused to a 4 to 7-membered cycloalkyl group or cycloalkanoyl group, wherein the 4 to 7-membered cycloalkyl group or cycloalkanoyl group can be unsubstituted or optionally substituted with R$^9$;

W is a bond, alkylene, —C(O)—, —S(O)—, —S(O)$_2$—, —S(O)$_2$—N(R$^{10}$)— or —C(O)—N(R$^{10}$)—;

X is —C(R$^1$)$_2$—, —O—, —N(R$^{10}$)— or —S—;

Y is —O-(alkylene)$_t$-, —N(R$^{10}$)-(alkylene)$_t$-, or —S—; such that the group —Y-A-X—B can be in an exo- or endo-configuration with respect to the bicyclic ring to which variable Y is attached;

R is R$^1$ when Y is —C(R$^1$)$_2$—, and R is R$^4$ when Y is other than —C(R$^1$)$_2$—;

each occurrence of R$^1$ is independently H, alkyl, cycloalkyl, halo or —OR$^7$; or any two geminal R$^1$ groups, together with the common carbon atom to which they are attached, join to form a spirocyclic 3- to 6-membered cycloalkyl group or a spirocyclic 3- to 6-membered heteroaryl group; or any two $R^1$ groups present on adjacent carbon atoms, together with the adjacent carbon atoms to which they are attached, join to form a fused 3- to 6-membered cycloalkyl group, a fused 3- to 6-membered heteroaryl group or a fused aryl group; and wherein an alkyl group can be unsubstituted or optionally substituted with one or more of the following groups: —O-alkyl, —OH or —N$(R^4)_2$; and wherein an optional endocyclic double bond can be present between any two adjacent ring carbon atoms;

$R^3$ is alkyl, -(alkylene)$_r$-alkenyl, -(alkylene)$_r$-alkynyl, -(alkylene —C(O)$R^4$, -(alkylene)$_r$-haloalkyl, -alkylene-O-alkyl, -alkylene-O-(alkylene)$_r$-aryl, -alkylene-S-aryl, -alkylene-N($R^4$)C(O)O-alkyl, —CH(cycloalkyl)$_2$, —CH(heterocycloalkyl)$_2$, -(alkylene)$_r$-aryl, -(alkylene)$_r$-cycloalkyl, -(alkylene)$_r$-cycloalkenyl, -(alkylene)$_r$-heterocycloalkyl, -(alkylene)$_r$-heterocycloalkenyl or -(alkylene)$_r$-heteroaryl, wherein an aryl, cycloalkyl, cycloalkenyl, heterocycloalkyl, heterocycloalkenyl or heteroaryl group can be unsubstituted or option substituted with $R^9$;

each occurrence of $R^4$ is H, alkyl, cycloalkyl or -(alkylene)$_r$-alkenyl, wherein an alkyl group is unsubstituted or optionally substituted with halo, —OH or —O-alkyl;

each occurrence of $R^5$ is independently H, alkyl, -(alkylene)$_r$-aryl, heterocycloalkyl, heteroaryl or cycloalkyl;

each occurrence of $R^7$ is independently H or alkyl;

$R^9$ represents from 1 to 4 optional substituents, which can be the same or different, and which are selected from alkyl, alkenyl, alkynyl, halo, haloalkyl, —CN, —NO$_2$, —O-(alkylene)$_r$-$R^{13}$, —S-(alkylene)$_r$-$R^{13}$ —N($R^{13}$)-(alkylene)$_r$-$R^{13}$, -(alkylene)$_r$-$R^{13}$, —C(O)-(alkylene)$_r$-$R^{13}$, —C(O)-(alkylene)$_r$-$R^{13}$, —N($R^7$)C(O)-(alkylene)$_r$$R^{13}$, —C(O)N($R^7$)-(alkylene)$_r$-$R^{13}$, —OC(O)-(alkylene)$_r$-$R^{13}$, —N($R^7$)C(O)N ($R^7$)-(alkylene)$_r$-$R^{13}$, —N($R^7$)C(O)O-(alkylene)$_r$-$R^{13}$, —S(O)-(alkylene)$_r$-$R^{13}$ or —S(O)$_2$(alkylene)$_r$-$R^{13}$;

$R^{10}$-is H, alkyl, aryl, or —C(O)O$R^4$, wherein an alkyl group is unsubstituted or optionally substituted with —OH or —O-alkyl;

each occurrence of $R^{13}$ is independently H, haloalkyl, aryl, cycloalkyl, cycloalkenyl, heterocycloalkyl, heterocycloalkenyl or heteroaryl;

each occurrence of m is independently 1 or 2;

each occurrence of n is independently 0, 1 or 2;

p is an integer ranging from 0 to 3, such that the sum of p and q is at least 1;

q is an integer ranging from 0 to 3;

r is an integer ranging from 0 to 3, such that the sum of r and s is at least 1;

s is an integer ranging from 0 to 3; and each occurrence of t is independently 0 or 1.

In another aspect, the present invention provides compounds of Formula (III):

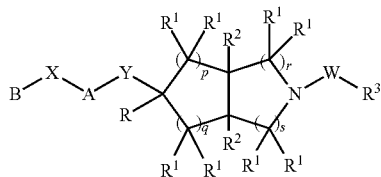

(III)

and pharmaceutically acceptable salts, solvates, esters, prodrugs and stereoisomers thereof, wherein:

A is aryl or -5- or 6-membered heteroaryl, any of which can be optionally substituted with up to 4 groups, which can be the same or different, and are selected from: alkyl, aryl, alkenyl, cycloalkyl, cycloalkenyl, haloalkyl, hydroxyalkyl, halo, —OH, —O-haloalkyl, —O-alkyl, —O-alkyl-OH, —O-alkyl-O-alkyl, —O-aryl, -alkylene-O-alkyl, —CN, —N$(R^4)_2$, —C(O)H, —C(O)$R^4$, C(O)O$R^4$, —C(O)N$(R^4)_2$, —NHC(O)$R^4$, —NHS(O)$_m$$R^4$, —S(O)$_n$$R^4$ and —S(O)$_m$N $(R^4)_2$, such that when Y is —O—, A is other than phenyl or pyridyl;

B is aryl or heteroaryl, any of which can be optionally substituted with up to 4 groups, which can be the same or different, and are selected from: alkyl, aryl, alkenyl, cycloalkenyl, haloalkyl, hydroxyalkyl, halo, —OH, —O-haloalkyl, —O-alkyl, —O-aryl, -alkylene-O-alkyl, —CN, —N$(R^4)_2$, —C(O)H, —C(O)$R^4$, —C(O)O$R^4$, —C(O)N$(R^4)_2$, —NHC (O)$R^4$, —NHS(O)$_m$$R^4$, —S(O)$_n$$R^4$ and —S(O)$_m$N$(R^4)_2$, wherein a cycloalkyl substituent group can be unsubstituted or optionally substituted with $R^9$, and wherein when B is aryl, the aryl group can be optionally fused to a 4 to 7-membered cycloalkyl group or cycloalkanoyl group;

W is a bond, alkylene, —S(O)—, —S(O)$_2$—, —S(O)$_2$—N($R^{10}$)— or —C(O)—N($R^{10}$)—;

X is —C($R^1$)$_2$—, —O—, —N($R^{10}$)— or —S—;

Y is —O-(alkylene)$_r$-, —N($R^{10}$)-(alkylene)$_r$-, or —S—; such that the group —Y-A-X—B can be in an exo- or endo-configuration with respect to the bicyclic ring to which variable Y is attached;

R is $R^1$ when Y is —C(R)$_2$—, and R is $R^4$ when Y is other than —C($R^1$)$_2$—;

each occurrence of $R^1$ is independently H, alkyl, cycloalkyl, halo or —O$R^7$; or any two geminal $R^1$ groups, together with the common carbon atom to which they are attached, join to form a spirocyclic 3- to 6-membered cycloalkyl group or a spirocyclic 3- to 6-membered heteroaryl group; or any two $R^1$ groups present on adjacent carbon atoms, together with the adjacent carbon atoms to which they are attached, join to form a fused 3- to 6-membered cycloalkyl group, a fused 3- to 6-membered heteroaryl group or a fused aryl group; and wherein an alkyl group can be unsubstituted or optionally substituted with one or more of the following groups: —O-alkyl, —OH or —N$(R^4)_2$; and wherein an optional endocyclic double bond can be present between any two adjacent ring carbon atoms;

each occurrence of $R^2$ is independently H, alkyl, halo or —OH;

$R^3$ is alkyl, -(alkylene)$_r$alkenyl, -(alkylene)$_r$-alkynyl, -(alkylene)$_1$-C(O)$R^4$, -(alkylene)$_r$-haloalkyl, -alkylene-O-alkyl, -alkylene-O-(alkylene)$_r$-aryl, -alkylene-S-aryl, -alkylene-N($R^4$)C(O)O-alkyl, —CH(cycloalkyl)$_2$, —CH(heterocycloalkyl)$_2$, -(alkylene)$_r$-aryl, -(alkylene)$_r$-cycloalkyl, -(alkylene)$_r$-cycloalkenyl, -(alkylene)$_r$-heterocycloalkyl, -(alkylene)$_r$-heterocycloalkenyl or -(alkylene)$_r$-heteroaryl, wherein an aryl, cycloalkyl, cycloalkenyl, heterocycloalkyl, heterocycloalkenyl or heteroaryl group can be unsubstituted or optionally substituted with $R^9$;

each occurrence of $R^4$ is H, alkyl, cycloalkyl or -(alkylene)$_r$-alkenyl, wherein an alkyl group is unsubstituted or optionally substituted with halo, —OH or —O-alkyl;

each occurrence of $R^5$ is independently H, alkyl, -(alkylene)$_r$-aryl, heterocycloalkyl, heteroaryl or cycloalkyl;

each occurrence of $R^7$ is independently H or alkyl;

$R^9$ represents from 1 to 4 optional substituents, which can be the same or different, and which are selected from alkyl, alkenyl, alkynyl, halo, haloalkyl, —CN, —NO$_2$, —O-(alkylene)$_r$-$R^{13}$, —S-(alkylene)$_r$-$R^{13}$, —N($R^{13}$)-(alkylene)$_r$-$R^{13}$, -(alkylene)$_r$-$R^{13}$, —C(O)-(alkylene)$_r$-$R^{13}$, —C(O)O-(alkylene)$_r$-$R^{13}$, —N($R^7$)C(O)-(alkylene)$_r$$R^{13}$, —C(O)N($R^7$)-(alkylene)$_r$-$R^{13}$, —OC(O)-(alkylene)$_r$-$R^{13}$, —N($R^7$)C(O)N $(R^7)$-(alkylene)$_t$-R$^{13}$, —N(R$^7$)C(O)O-(alkylene)$_t$-R$^{13}$, —S(O)-(alkylene)$_t$-R$^{13}$ or —S(O)$_2$(alkylene)$_t$-R$^{13}$;

$R^{10}$ is H, alkyl, aryl, or —C(O)OR$^4$, wherein an alkyl soup is unsubstituted or optionally substituted with —OH or —O-alkyl;

each occurrence of R$^{13}$ is independently H, haloalkyl, aryl, cycloalkyl, cycloalkenyl, heterocycloalkyl, heterocycloalkenyl or heteroaryl;

each occurrence of m is independently 1 or 2;
each occurrence of n is independently 0, 1 or 2;
p is 0, 1 or 2;
q is 0, 1 or 2;
r is 0, 1 or 2;
s is 0, 1 or 2; and
each occurrence of t is independently 0 or 1.

In a further aspect, the present invention provides compounds of Formula (IV):

$$\text{(IV)}$$

and pharmaceutically acceptable salts, solvates, esters, prodrugs and stereoisomers thereof, wherein:

W is a bond, —C(O)—, —S(O)$_2$—, —S(O)$_2$—N(R$^{10}$)— or —C(O)—N(R$^{10}$)—;

X is —C(R$^1$)$_2$—, —O—, —N(R$^{10}$)— or —S—;

Y is —C(R$^1$)$_2$—, —O—, —N(R$^{10}$)— or —S—; such that the group —Y-A-X—B can be in an exo- or endo-configuration with respect to the bicyclic ring to which variable Y is attached;

Z is a bond, —C(R$^1$)$_2$—, —O—, —N(R$^{10}$)— or —S—;

R is R$^1$ when Y is —C(R$^1$)$_2$—, and R is R$^4$ when Y is other than —C(R$^1$)$_2$—;

each occurrence of R$^1$ is independently H, alkyl, halo or —OH; or any two geminal R$^1$ groups, together with the common carbon atom to which they are attached, join to form a spirocyclic 3- to 6-membered cycloalkyl group or a spirocyclic 3- to 6-membered heteroaryl group; or any two R$^1$ groups present on adjacent carbon atoms, together with the adjacent carbon atoms to which they are attached, join to form a fused 3- to 6-membered cycloalkyl group, a fused 3- to 6-membered heteroaryl group or a fused aryl group; and wherein an alkyl group can be unsubstituted or optionally substituted with one or more of the following groups: —O-alkyl, —OH or —N(R$^4$)$_2$; and wherein an optional endocyclic double bond can be present between any two adjacent ring carbon atoms;

A is independently aryl or a -5- or 6-membered heteroaryl group which can be optionally substituted with up to 4 groups, which can be the same or different, and are selected from: alkyl, aryl, alkenyl, cycloalkyl., cycloalkenyl, haloalkyl, hydroxyalkyl, halo, —OH, —O-haloalkyl, —O-alkyl, —O-aryl, -alkylene-O-alkyl, —CN, —N(R$^4$)$_2$, —C(O)H, —C(O)R$^4$, —C(O)OR$^4$, —C(O)N(R$^4$)$_2$, —NHC(O)R$^4$, —NHS(O)$_m$R$^4$, —S(O)$_n$R$^4$ and —S(O)$_m$N(R$^4$)$_2$;

B is independently aryl or a -5- or 6-membered heteroaryl group which can be optionally substituted with up to 4 groups, which can be the same or different, and are selected from: alkyl, aryl, alkenyl, cycloalkyl, cycloalkenyl, haloalkyl, hydroxyalkyl, halo, —OH, —O-haloalkyl, —O-alkyl, —O-aryl, -alkylene-O-alkyl, —CN, —N(R$^4$)$_2$, —C(O)H, —C(O)R$^4$, —C(O)OR$^4$, —C(O)N(R$^4$)$_2$, —NHC(O)R$^4$, —NHS(O)R$^4$, —S(O)$_m$R$^4$ and —S(O)$_m$N(R$^4$)$_2$;

each occurrence of R$^2$ is independently H, alkyl, halo or —OH;

R$^3$ is alkyl, alkenyl, alkynyl, haloalkyl, -alkylene-O-(alkylene)$_t$-aryl, -alkylene-S-aryl, -alkylene-N(R$^4$)C(O)O-alkyl, —CH(cycloalkyl)$_2$, —CH(heterocycloalkyl)$_2$, -(alkylene)$_t$-aryl, -(alkylene)$_t$-cycloalkyl, -(alkylene)$_t$-cycloalkenyl, -(alkylene)$_t$-heterocycloalkyl, -(alkylene)$_t$-heterocycloalkenyl or -(alkylene)$_t$-heteroaryl, wherein an aryl, cycloalkyl, cycloalkenyl, heterocycloalkyl, heterocycloalkenyl or heteroaryl group can be unsubstituted or substituted with up to 4 substituents, which can be the same or different, and are selected from alkyl, haloalkyl, hydroxyalkyl, halo, —OH, —O-haloalkyl, —O-alkyl, —O-aryl, —S-haloalkyl, -alkylene-O-alkyl, —CN, —N(R$^5$)$_2$, —C(O)H, —C(O)R$^5$, —C(O)OR$^5$, —C(O)N(R$^5$)$_2$, —NHC(O)R$^5$, —NHS(O)$_m$R$^5$, —S(O)$_n$R$^5$ and —S(O)$_m$N(R$^5$)$_2$;

R$^4$ is H or alkyl;

each occurrence of R$^5$ is independently H, alkyl, -(alkylene)$_t$-aryl, heterocycloalkyl, heteroaryl or cycloalkyl;

R$^{10}$ is H, alkyl, aryl, or —C(O)OR$^3$;

each occurrence of m is independently 1 or 2;
each occurrence of n is independently 0, 1 or 2;
p is 0, 1 or 2;
q is 0, 1 or 2;
r is 0, 1 or 2;
s is 0, 1 or 2;
each occurrence of t is independently 0 or
u is 0, 1 or 2.

The compounds of formulas (I), (II), (III) and (IV) and pharmaceutically acceptable salts, solvates, esters or prodrugs thereof (referred to collectively herein as the "Bicyclic Heterocycle Derivatives") can be useful for treating or preventing obesity, diabetes, a diabetic complication, metabolic syndrome, a cardiovascular disease or a disorder related to the activity of GPR119 (each being a "Condition") in a patient.

Also provided by the invention are methods for treating or preventing a Condition in a patient, comprising administering to the patient an effective amount of one or more Bicyclic Heterocycle Derivatives.

The present invention further provides compositions comprising an effective amount of one or more Bicyclic Heterocycle Derivatives or a pharmaceutically acceptable salt, solvate, ester, prodrug or stereoisomer thereof, and a pharmaceutically acceptable carrier. The compositions can be useful for treating or preventing a Condition in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides Bicyclic Heterocycle Derivatives of Formulas (I), (II), (III) and (IV), compositions comprising one or more Bicyclic Heterocycle Derivatives, and methods of using the Bicyclic Heterocycle Derivatives for treating or preventing a Condition in a patient.

DEFINITIONS AND ABBREVIATIONS

As used above, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "obesity" as used herein, refers to a patient being overweight and having a body mass index (BMI) of 25 or greater. In one embodiment, an obese patient has a BMI of 25 or greater. In another embodiment, an obese patient has a BMI from 25 to 30. In another embodiment, an obese patient has a BMI greater than 30. In still another embodiment, an obese patient has a BMI greater than 40.

The term "obesity-related disorder" as used herein refers to: (1) disorders which result from a patient having a BMI of 25 or greater; and (ii) eating disorders and other disorders associated with excessive food intake. Non-limiting examples of an obesity-related disorder include edema, shortness of breath, sleep apnea, skin disorders and high blood pressure.

The term "metabolic syndrome" as used herein, refers to a set of risk factors that make a patient more susceptible to cardiovascular disease and/or type 2 diabetes. A patient is said to have metabolic syndrome if the patient simultaneously has three or more of the following five risk factors:

1) central/abdominal obesity as measured by a waist circumference of greater than 40 inches in a male and greater than 35 inches in a female;
2) a fasting triglyceride level of greater than or equal to 150 mg/dL;
3) an HDL cholesterol level in a male of less than 40 mg/dL or in a female of less than 50 mg/dL;
4) blood pressure greater than or equal to 130/85 mm Hg; and
5) a fasting glucose level of greater than or equal to 110 mg/dL.

The term "effective amount" as used herein, refers to an amount of Bicyclic Heterocycle Derivative and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

The term "alkyl," as used herein, refers to an aliphatic hydrocarbon group which may be straight or branched and which contains from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is unsubstituted. In another embodiment, an alkyl group is linear. In another embodiment, an alkyl group is branched.

The term "alkenyl," as used herein, refers to an aliphatic hydrocarbon group containing at least one carbon-carbon double bond and which may be straight or branched and contains from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkenyl group is unsubstituted.

The term "alkynyl," as used herein, refers to an aliphatic hydrocarbon group containing at least one carbon-carbon triple bond and which may be straight or branched and contains from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$CH$_2$—, —CH$_2$CH$_2$CH$_2$CH$_2$— CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is unsubstituted. In another embodiment, an aryl group is phenyl.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 5 to about 7 ring atoms. The term "cycloalkyl" also encompasses a cycloalkyl group, as defined above, that is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. A ring carbon atom of a cycloalkyl group may be functionalized as a carbonyl group. An illustrative example of such a cycloalkyl group is cyclopentanyl:

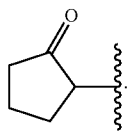

The term "cycloalkenyl," as used herein, refers to a non-aromatic mono- or multicyclic ring system comprising from about 3- to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted. In another embodiment, a cycloalkenyl group is a 5-membered cycloalkenyl.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In one embodiment, a heteroaryl group is monocyclic and has 5 or 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, that is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl., benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is unsubstituted. In another embodiment, a heteroaryl group is a 5-membered heteroaryl. In another embodiment, a heteroaryl group is a 6-membered heteroaryl.

The term "heterocycloalkyl," as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, that is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide, examples of monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

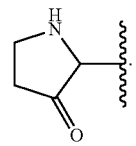

In one embodiment, a heterocycloalkyl group is unsubstituted. In another embodiment, a heterocycloalkyl group is a 5-membered heterocycloalkyl. In another embodiment, a heterocycloalkyl group is a 6-membered heterocycloalkyl.

The term "heterocycloalkenyl," as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide, examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocycloalkenyl group may be functionalized as a carbonyl group. Illustrative examples of such heterocycloalkenyl groups include, but are not limited to:

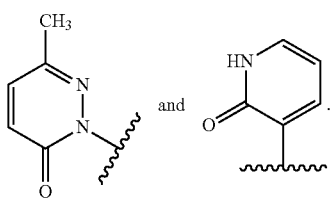

In one embodiment, a heterocycloalkenyl group is unsubstituted. In another embodiment, a heterocycloalkenyl group is a 5-membered heterocycloalkenyl.

The term "5-membered heterocycloalkenyl," as used herein, refers to a heterocycloalkenyl group, as defined above, which has 5 ring atoms.

It should also be noted that tautomeric forms such as, for example, the moieties:

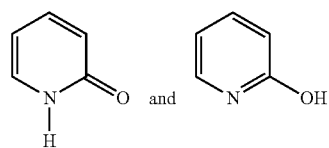 [SMILES: O=c1cccc[nH]1 ; "and" ; Oc1ccccn1]

are considered equivalent in certain embodiments of this invention.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkyl-aryl, -aryl-alkyl, -alkylene-heteroaryl, -alkenylene-heteroaryl, -alkynylene-heteroaryl, hydroxy, hydroxyalkyl, haloalkyl, —O-alkyl, —O-haloalkyl, -alkylene-O-alkyl, —O-aryl, aralkoxy, acyl, aroyl, halo, nitro, cyano, carboxy, —C(O)O-alkyl, —C(O)O-aryl, —C(O)O-alkelene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NS(O)$_2$— and —S(O)$_2$NY$_1$Y$_2$, wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two, available hydrogens on two adjacent carbon atoms (one H on each carbon) on a ring system. Examples of such moiety are methylenedioxy, ethylenedioxy, —C(CH$_3$)$_2$— and the like which form moieties such as, for example:

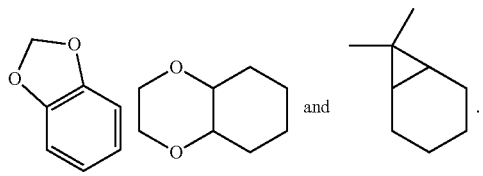

"Halo" means —F, —Cl, —Br or —I. In one embodiment, halo refers to —F, —Cl or —Br.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "purified", "in purified form" or "in isolated and purified form" for a compound refers to the physical state of the compound after being isolated from a synthetic process (e.g. from a reaction mixture), or natural source or combination thereof. Thus, the term "purified", "in purified form" or "in isolated and purified form" for a compound refers to the physical state of the compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, R$^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a Bicyclic Heterocycle Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a Bicyclic Heterocycle Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a Bicyclic Heterocycle Derivative contains an alcohol functional group, a prodrug can be formed by the replacement of the hydrogen atom of the alcohol group with a group such as, for example, $(C_1-C_6)$alkanoyloxymethyl, 1((C; —$C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a Bicyclic Heterocycle Derivative incorporates an amine functional group, a prodrug can be formed by the replacement of a hydrogen atom in the amine group with a group such as, for example, R-carbonyl, RO-carbonyl, NRR'-carbonyl where R and $R^{40}$ are each independently $(C_1-C_{10})$alkyl, $(C_3-C_7)$ cycloalkyl, benzyl, or R-carbonyl is a natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. "Hydrate" is a solvate wherein the solvent molecule is H$_2$O.

One or more compounds of the invention may optionally be converted to a solvate. Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The Bicyclic Heterocycle Derivatives can form salts which are also within the scope of this invention. Reference to a Bicyclic Heterocycle Derivative herein is understood to include reference to salts thereof, unless otherwise indicated. The term "salt(s)", as employed herein, denotes acidic salts fanned with inorganic and/or organic acids, as well as basic salts formed with inorganic and/or organic bases. In addition, when a Bicyclic Heterocycle Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the compounds of the Formula (I) may be formed, for example, by reacting a Bicyclic Heterocycle Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food &

Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (for example, methyl, ethyl, n-propyl, isopropyl, t-butyl, sec-butyl or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$-alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Bicyclic Heterocycle Derivatives may be atropisomers (e.g., substituted biaryls) and are considered as part of this invention. Enantiomers can also be separated by use of chiral HPLC column.

It is also possible that the Bicyclic Heterocycle Derivatives may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a Bicyclic Heterocycle Derivative incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{17}O$, $^{31}P$, $^{32}P$, $^{35}S$, $^{18}F$, and $^{36}Cl$, respectively.

Certain isotopically-labelled Bicyclic Heterocycle Derivatives (e.g., those labeled with $^3H$ and $^{14}C$) are useful in compound and/or substrate tissue distribution assays. In one embodiment, ritiated (i.e., $^3H$) and carbon-14 (i.e., $^{14}C$) isotopes are employed for their ease of preparation and detectability. In another embodiment, substitution with heavier isotopes such as deuterium (i.e., $^2H$) may afford certain therapeutic advantages resulting from greater metabolic stability (e.g., increased in vivo half-life or reduced dosage requirements).

Isotopically Labelled Bicyclic Heterocycle Derivatives

Synthetic chemical procedures analogous to those disclosed herein for making the Bicyclic Heterocycle Derivatives, by substituting an appropriate isotopically labelled starting material or reagent for a non-isotopically labelled starting material or reagent.

Polymorphic forms of the Bicyclic Heterocycle Derivatives, and of the salts, solvates, hydrates, esters and prodrugs of the Bicyclic Heterocycle Derivatives, are intended to be included in the present invention.

The following abbreviations are used below and have the following meanings: AcOH is acetic acid, Boc or BOC is —C(O)O-(t-butyl), n-BuLi is n-butyllithium, t-butyl is tertiary butyl, DAST is diethylaminosulfur trichloride, dba is dibenzylidene acetone, DCE is dichloroethane, DCM is dichloromethane, DIAD is diisopropylazodicarboxylate, DIEA is diisopropylethylamine, DMEM is Dulbecco's modified eagle medium, DMF is N,N-dimethylformamide, DMSO is dimethylsulfoxide, dppf is 1,1'-bis(diphenylphosphino)ferrocene, EDC is 1-(dimethylaminopropyl)-3-ethylcarbodiimide, EtOAc is ethyl acetate, EtOH is ethanol, $Et_3N$ is triethylamine, $EtNH_2$ is ethylamine, HOBt is 1-hydroxybenzotriazole, LCMS is liquid chromatography mass spectrometry, LDA is lithium diisopropylamide, mCPBA is meta-chloroperoxybenzoic acid, MeOH is methanol, NaOEt is sodium ethoxide, NaOtBu is sodium t-butoxide, NMM is n-methylmorpholine, NMR is nuclear magnetic resonance, Ph is phenyl, PhMe is toluene, PLC is preparative thin-layer chromatography, PS-EDC is polystyrene functionalized with EDC—available from Polymer Laboratories, PS-DIEA is polystyrene functionalized with disopropylethylamine, TBAF is tetra-n-butyl-ammonium fluoride, THF is tetrahydrofuran, and TLC is thin-layer chromatography.

The Bicyclic Heterocycle Derivatives of Formula (I)

The present invention provides Bicyclic Heterocycle Derivatives of Formula (I):

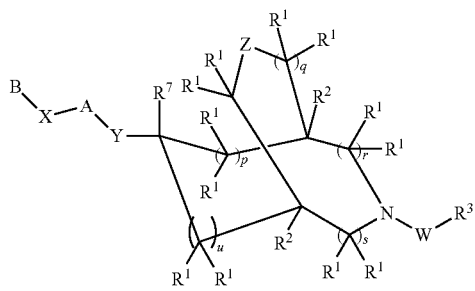

and pharmaceutically acceptable salts, solvates, esters, prodrugs and stereoisomers thereof, wherein A, B, X, Y, Z, $R^1$, $R^2$, $R^3$, $R^7$, p, q, r, s and u are defined above for the compounds of formula (I).

In one embodiment, W is —C(O)O— or —S(O)$_2$—.
In another embodiment, W is a bond.
In another embodiment, W is —C(O)O—.
In another embodiment, W is —C(O)—.
In still another embodiment, W is —S(O)$_2$—.
In yet another embodiment, W is —S(O)$_2$N($R^{10}$)—.
In a further embodiment, W is —C(O)N($R^{10}$)—,
In another embodiment, when W is —C(O)O—, then $R^3$ is other than alkyl.
In still another embodiment, when W is —S(O)$_2$—, then $R^3$ is other than alkyl.
In one embodiment, X is —C($R^1$)$_2$—.
In another embodiment, X is —O—.
In another embodiment, X is —S—.
In yet another embodiment, X is —N($R^{10}$)—.
In another embodiment, X is —NH—.
In one embodiment, Y is —O—.
In another embodiment, Y is —S—.
In another embodiment, Y is —NH—.
In still another embodiment, when Y is —O—, A is other than phenyl or pyridyl.
In one embodiment, Z is —C($R^1$)$_2$—.
In another embodiment, Z is a bond.
In another embodiment, Z is —O—.
In another embodiment, Z is —S—.
In yet another embodiment, Z is —N($R^{10}$)—.
In another embodiment, Z is —CH$R^1$—.
In another embodiment, Z is —CH$_3$—.
In still another embodiment, Z is —NH—.
In one embodiment, W is —C(O)O— and Z is a bond.
In another embodiment, W is —S(O)$_2$— and Z is a bond.
In one embodiment, X and Y are each —O—.
In another embodiment, X and Y are each —NH—.
In another embodiment, X is —NH— and Y is —O—.
In still another embodiment, X is —O— and Y is —NH—.
In one embodiment, W is —C(O)O—, Z is a bond, X is —O— and Y is —O—.

In another embodiment, $R^7$ is H, W is —C(O)O—, Z is a bond, X is —O— and Y is —O—.
In another embodiment, W is —S(O)$_2$—. Z is a bond, X is —O— and Y is —O—.
In still another embodiment, $R^7$ is H, W is —S(O)$_2$—, Z is a bond, X is —O— and Y is —O—.
In another embodiment, W is —C(O)O—, Z is a bond, X is —O— and Y is —NH—.
In another embodiment, $R^7$ is H, W is —C(O)O—, Z is a bond, X is —O— and Y is —NH—.
In yet another embodiment, W is —S(O)$_2$—, Z is a bond, X is —O— and Y is —NH—.
In a further embodiment, $R^1$ is W is —S(O)$_2$—, Z is a bond, X is —O— and Y is —NH—.
In another embodiment, W is —C(O)O—, Z is a bond, X is —NH— and Y is —O—.
In one embodiment, $R^7$ is H, W is —C(O)O—, Z is a bond, X is —NH— and Y is —O—.
In another embodiment, W is —S(O)$_2$—, Z is a bond, X is —NH— and Y is —O—.
In another embodiment, $R^7$ is H, W is —S(O)$_2$—, Z is a bond, X is —NH— and Y is —O—.
In still another embodiment, W is —(O)O—, Z is a bond, X is —NH— and Y is —NH—.
In another embodiment, $R^7$ is H, W is —C(O)O—, Z is a bond, X is —NH— and Y is —NH—.
In another embodiment, W is —S(O)$_2$—, Z is a bond, X is —NH— and Y is —NH—.
In a further embodiment, $R^7$ is H, W is —S(O)$_2$—, Z is a bond, X is —NH— and Y is —NH—.
In one embodiment, A is aryl.
In another embodiment, A is 5 or 6-membered heteroaryl.
In another embodiment, A is phenyl.
In still another embodiment, A is pyri idinyl.
In one embodiment, -A- is:

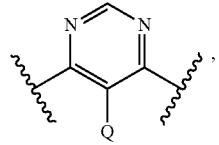

wherein Q is H, alkyl, halo or —O-alkyl.
In another embodiment, -A- is:

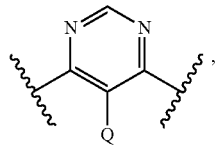

wherein Q is H, methyl, F or —OCH$_3$.
In another embodiment, A is:

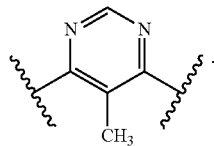 [SMILES: *c1ncnc(*)c1C]

In another embodiment, A is pyridyl.

In yet another embodiment, Y is —O— and A is pyrimidinyl

In a further embodiment, X and Y are each —O— and A is pyrimidinyl.

In another embodiment, X is —NH—, Y is —O— and A is pyrimidinyl.

In one embodiment, Y is —O— and A is:

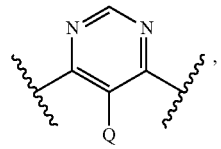

wherein H, methyl, F or —OCH$_3$.

In a further embodiment, X and Y are each —O— and A is:

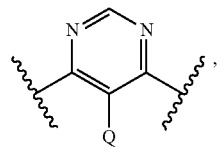

wherein Q is H, methyl, F or —OCH$_3$.

In another embodiment, X is —NH—, Y is —O— and A is:

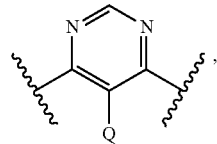

wherein Q is H, methyl, F or —OCH$_3$.

In one embodiment, Y is —O— and A is:

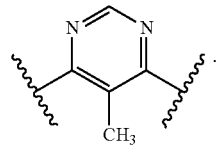

In a further embodiment, X and Y are each and A is:

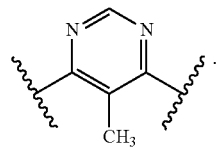 [SMILES: *c1ncnc(*)c1C]

In another embodiment, X is —NH—, Y is —O— and A is:

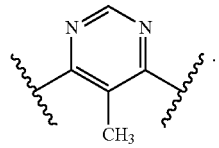

In one embodiment, B is aryl.
In another embodiment. B is heteroaryl.
In another embodiment. B is 5 or 6-membered heteroaryl.
In another embodiment, B is phenyl.
In still another embodiment, B is pyrimidinyl.
In another embodiment, B is pyridyl.
In yet another embodiment, B is phenyl, which is unsubstituted or optionally substituted with up to 3 groups, each independently selected from alkyl, —CN, —S(O)$_2$alkyl, —S(O)$_2$-cycloalkyl, heteroaryl and halo.

In one embodiment, B is:

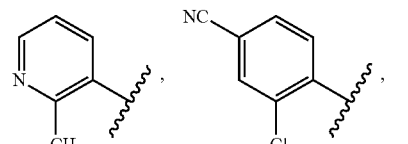

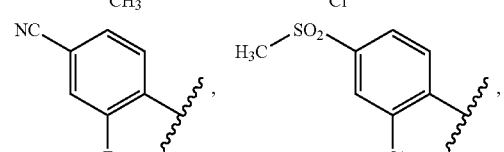

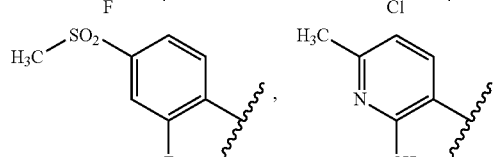

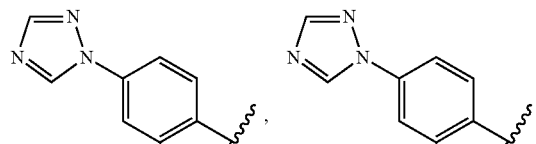

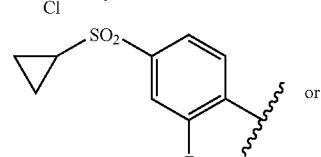 or

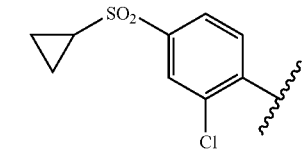

In another embodiment, X is —NH— or —O—, and B is:

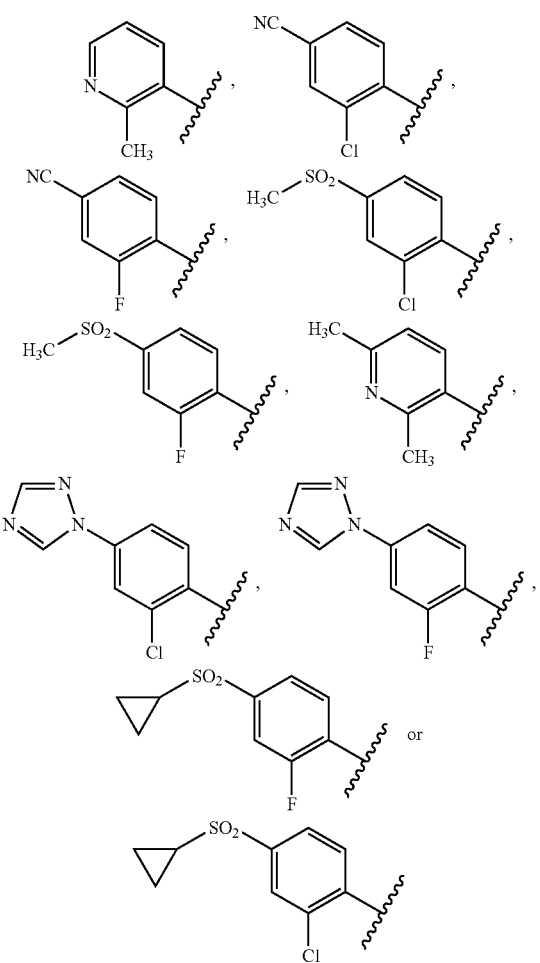
In another embodiment, X is —O— and B is;
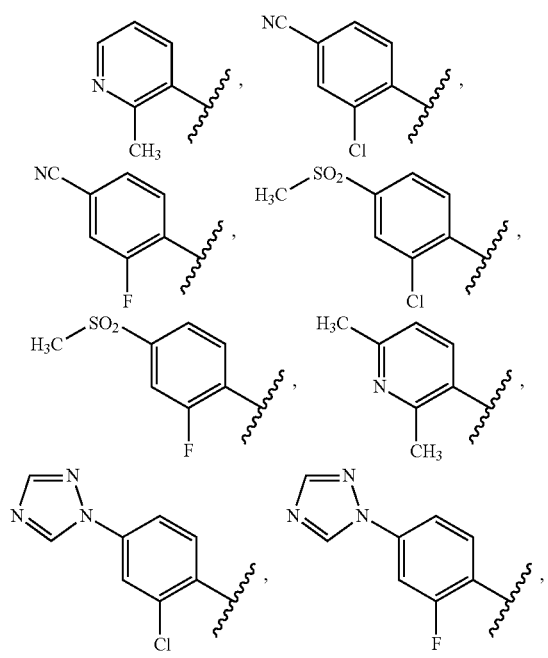
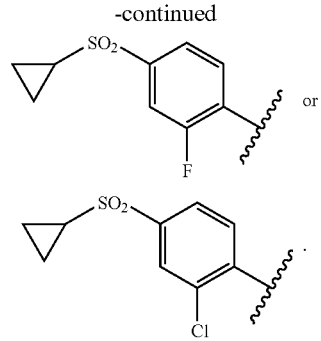
In still another embodiment, X is —NH— and B is:
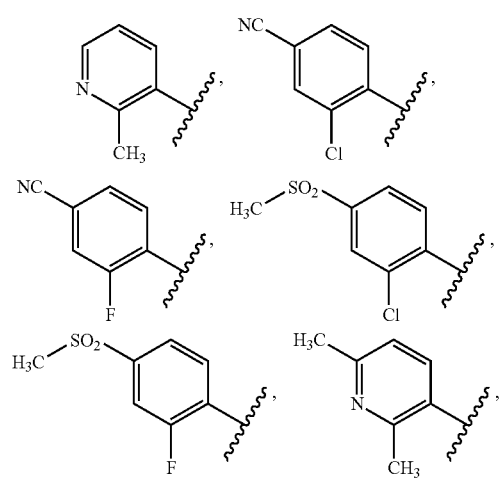
In yet another embodiment, is —O— and B is pyridyl.
In one embodiment, A and B are each independently heteroaryl.
In another embodiment, A and B are each independently a 5 or 6-membered heteroaryl.
In another embodiment, A is a 5 or 6-membered heteroaryl and B is pyridyl.

In one embodiment, -A- is:
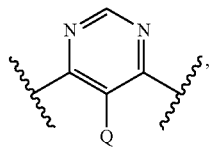
wherein Q is H, alkyl, halo or —O-alkyl; and B is:
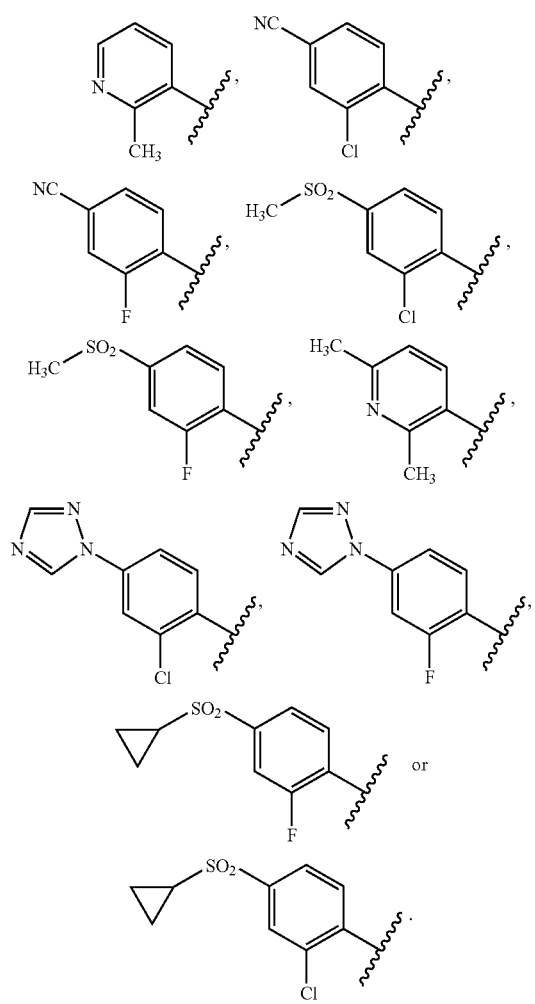
In another embodiment, X is —NH— or —O—; Y is —O—; -A- is:
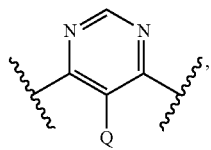
wherein Q is H, alkyl, halo or —O-alkyl; and B is:
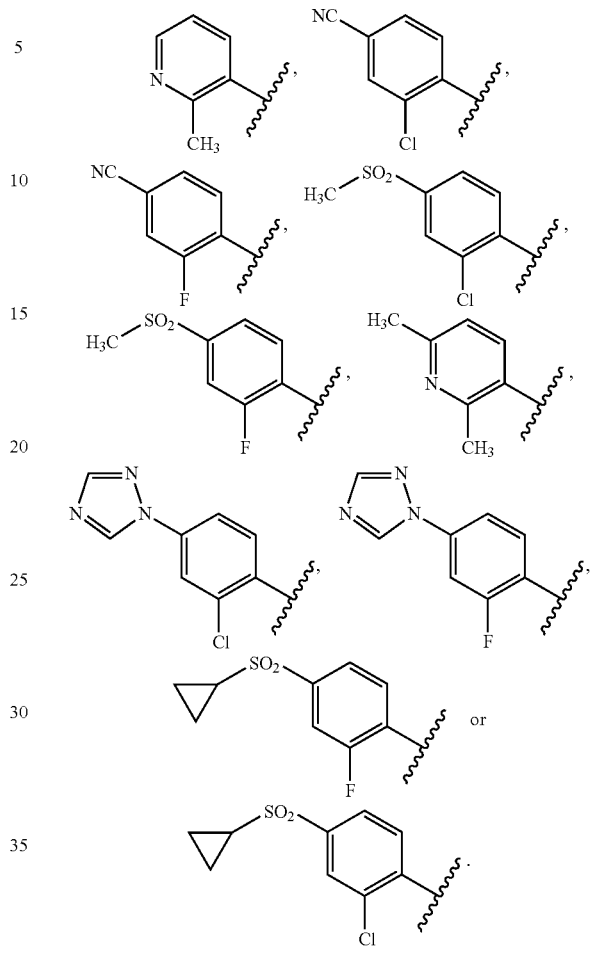
In another embodiment, X is —NH— or —O—; Y is —O—; -A- is:
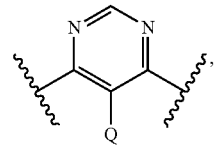
wherein Q is H, methyl, F or —OCH; and B is:
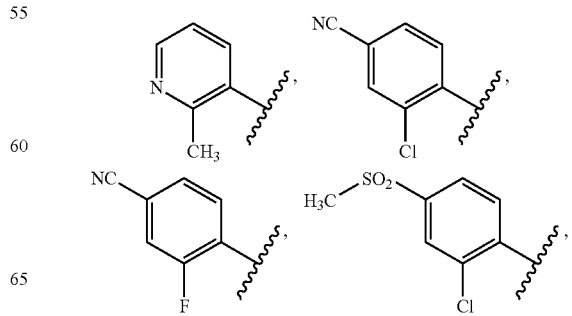

-continued

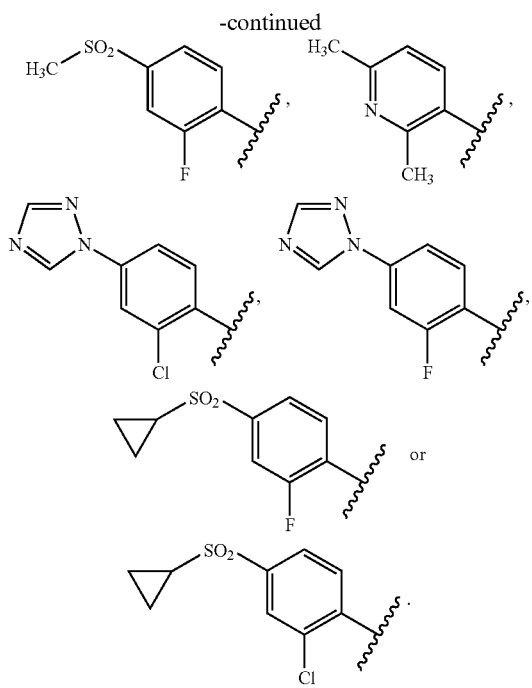

In one embodiment, A is:

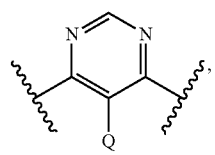

wherein Q is H, alkyl, halo or —O-alkyl; and B is heteroaryl.

In another embodiment, A is:

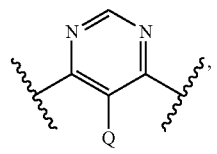

wherein Q is H, alkyl, halo or —O-alkyl; and B is pyridyl.

In another embodiment, A is:

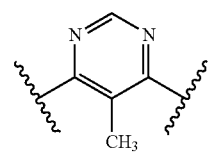

and B is heteroaryl.

In another embodiment, A is:

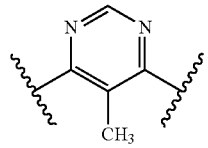 [SMILES: *c1ncnc(*)c1C]

and B is pyridyl.

in one embodiment. A is 5 or 6-membered heteroaryl and B is phenyl.

In another embodiment, A is pyrimidinyl and B is phenyl.

In another embodiment, A is pyrimidinyl and B is pyridyl.

In a further embodiment, B is phenyl and A is:

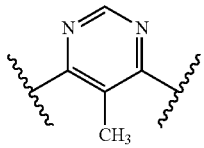

In one embodiment, B is phenyl which is optionally substituted with up to 3 groups, each independently selected from alkyl, —CN, —S(O)$_2$-alkyl, —S(O)$_2$-cycloalkyl, heteroaryl and halo; and A is:

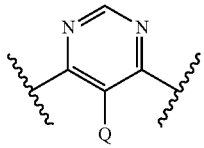

wherein Q is H, alkyl, halo or —O-alkyl.

In another embodiment, B is phenyl which is optionally substituted with up to 3 groups, each independently selected from methyl, triazolyl, —CN, —Cl, —F, —S(O)$_2$CH$_3$ and —S(O)$_2$-cyclopropyl; and A is:

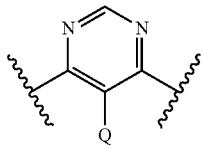

wherein Q is H, methyl, F or methoxy.

In another embodiment, B is pyridyl and A is:

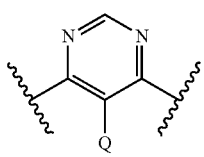

wherein Q is H, alkyl, halo or —O-alkyl.

In one embodiment, B is phenyl and A is:

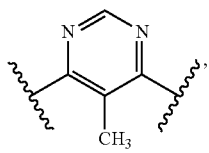

wherein B is optionally substituted with up to 3 groups, each independently selected from alkyl, —CN, —S(O)₂-alkyl, —S(O)₂-cycloalkyl, heteroaryl and halo.

In another embodiment, B is phenyl and A is:

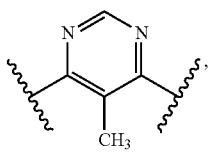

wherein B is optionally substituted with up to 3 groups, each independently selected from methyl, triazolyl, —CN, —Cl, —F, —S(O)₂CH₃ and —S(O)₂-cyclopropyl.

In one embodiment, Y is —O—, A is pyrimidinyl and B is pyridyl.

In another embodiment, X and Y are each —O—, A is pyrimidinyl and B is pyridyl.

In another embodiment, Y is —NH—, A is pyrimidinyl and B is pyridyl.

In still another embodiment, X and Y are each —NH—, A is pyrimidinyl and B is pyridyl.

In another embodiment, X is —O—, Y is —NH—, A is pyrimidinyl and B is pyridyl.

In another embodiment, X is —NH—, Y is —O—, A is pyrimidinyl and B is pyridyl.

In one embodiment, Y is —O—, A is pyrimidinyl and B is phenyl, which is unsubstituted or optionally substituted with up to 3 groups, each independently selected from alkyl, —CN, —S(O)₂-alkyl, —S(O)₂-cycloalkyl, heteroaryl and halo.

In another embodiment, X and Y are each —O—, A is pyrimidinyl and B is phenyl, which unsubstituted or optionally substituted with up to 3 groups, each independently selected from alkyl, —CN, —S(O)₂-alkyl, —S(O)₂-cycloalkyl, heteroaryl and halo.

In another embodiment, Y is —NH—, A is pyrimidinyl and B is phenyl, which is unsubstituted or optionally substituted with up to 3 groups, each independently selected from alkyl, —CN, —S(O)₂-alkyl, —S(O)₂-cycloalkyl, heteroaryl and halo.

In still another embodiment, X and Y are each —NH—, A is pyrimidinyl and B is phenyl, which is unsubstituted or optionally substituted with up to 3 groups, each independently selected from alkyl, —CN, —S(O)₂-alkyl, —S(O)₂-cycloalkyl, heteroaryl and halo.

In another embodiment., X is —O—, Y is —NH—, A is pyrimidinyl and B is phenyl, which is unsubstituted or optionally substituted with up to 3 groups, each independently selected from alkyl, —CN, —S(O)₂-alkyl, —S(O)₂-cycloalkyl, heteroaryl and halo.

In another embodiment, X is —NH—, Y is —O—, A is pyrimidinyl and B is phenyl, which is unsubstituted or optionally substituted with up to 3 groups, each independently selected from alkyl, —CN, —S(O)₂-alkyl, —S(O)₂-cycloalkyl, heteroaryl and halo.

In one embodiment, A and B are each independently a 5 or 6-membered heteroaryl, each of which is unsubstituted or optionally substituted with one substituent, independently selected from alkyl, —CN, —S(O)₂-alkyl, —S(O)₂-cycloalkyl, heteroaryl and halo.

In another embodiment, A and B are each independently selected from phenyl, pyridyl and pyrimidinyl, each of which is unsubstituted or optionally substituted with one substituent, independently selected from alkyl, —CN, —S(O)₂-alkyl, —S(O)₂-cycloalkyl, heteroaryl and halo.

In another embodiment. A and B are each independently selected from phenyl, pyridyl and pyrimidinyl, each of which is unsubstituted or optionally substituted with one or more substituents, each independently selected from methyl, triazolyl, —CN, —Cl, —F, —S(O)₂CH₃ or —S(O)₂-cyclopropyl.

In still another embodiment, X and Y are each —O—, A is pyrimidinyl and B is pyridyl, wherein each of A and B can be optionally substituted with one substituent, independently selected from alkyl, —CN, —S(O)₂-alkyl, —S(O)₂-cycloalkyl, heteroaryl and halo.

In a further embodiment, X and Y are each —O—, A is pyrimidinyl and B is pyridyl, wherein each of A and B can be optionally substituted with one or more substituents, each independently selected from methyl, triazolyl, —CN, —Cl, —F, —S(O)₂CH₃ or —S(O)₂-cyclopropyl.

In one embodiment, X and Y are each —O—, A is pyrimidinyl and B is pyridyl, wherein A and B are each substituted with at least one alkyl group.

In another embodiment, X and Y are each —O—, A is pyrimidinyl and B is pyridyl, wherein A and B are each substituted with a methyl group.

In one embodiment, X and Y are each —O—, A is pyrimidinyl and B is pyridyl.

In another embodiment, X and Y are each —O—, A is pyrimidinyl and B is phenyl,

In another embodiment, X is —NH—, Y is —O—, A is pyrimidinyl and B is pyridyl.

In another embodiment, X is —NH—, Y is —O—, A is pyrimidinyl and B is phenyl.

In one embodiment, the group B—X-A-Y— is:

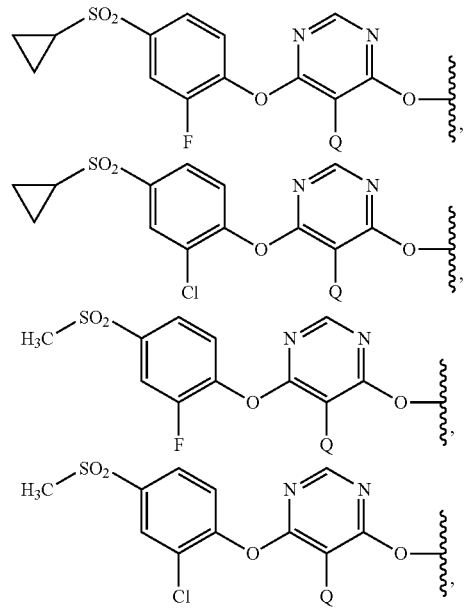

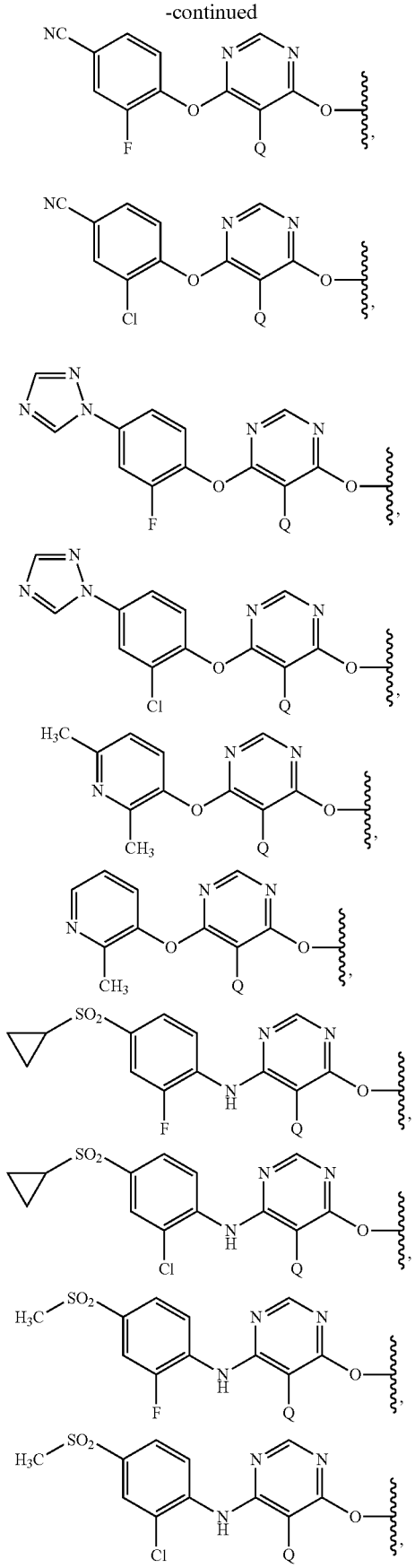
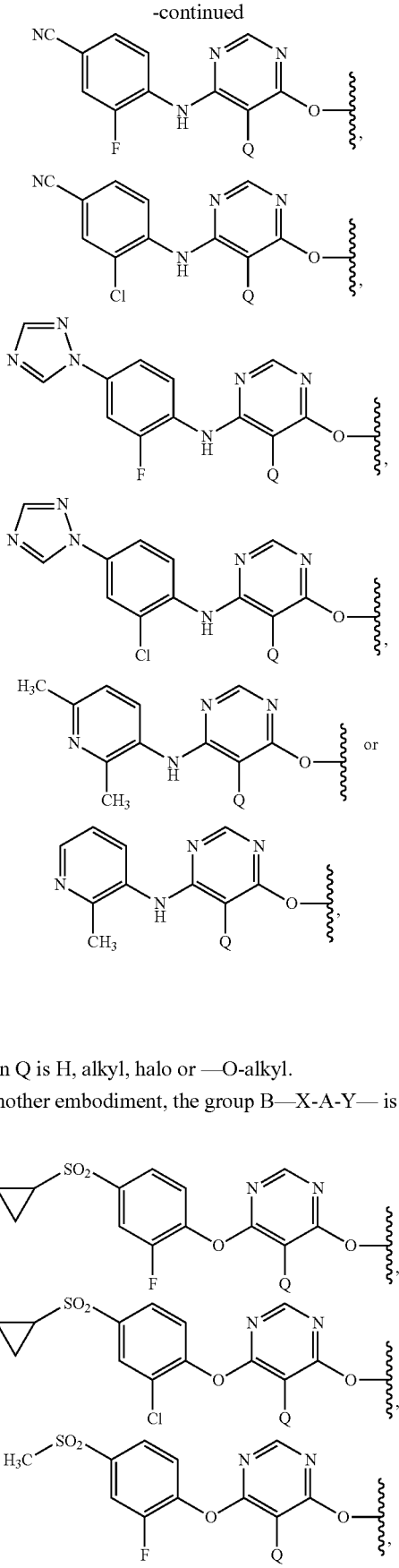
wherein Q is H, alkyl, halo or —O-alkyl.
In another embodiment, the group B—X-A-Y— is:

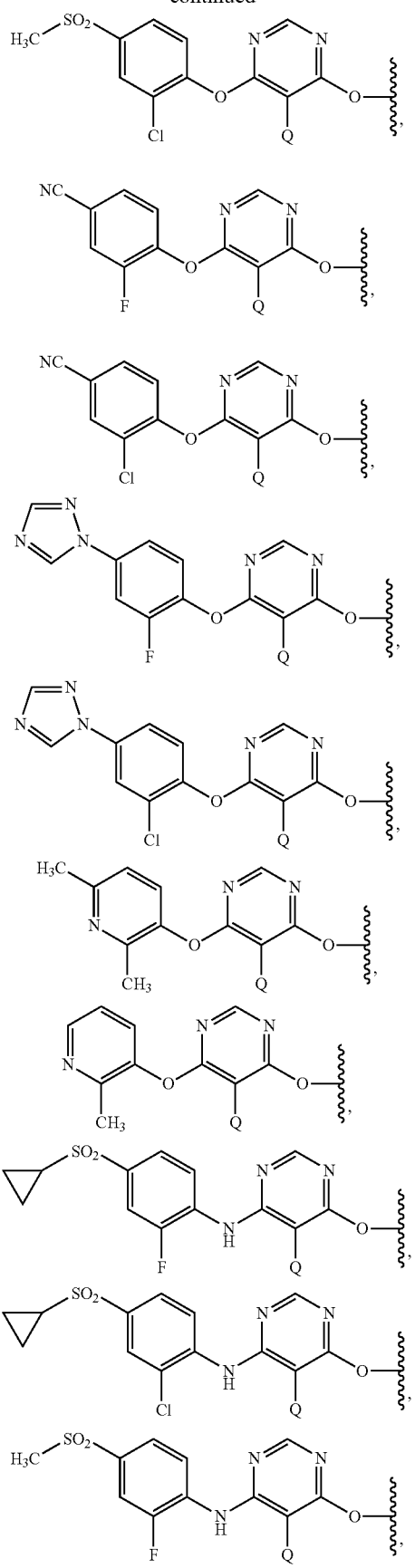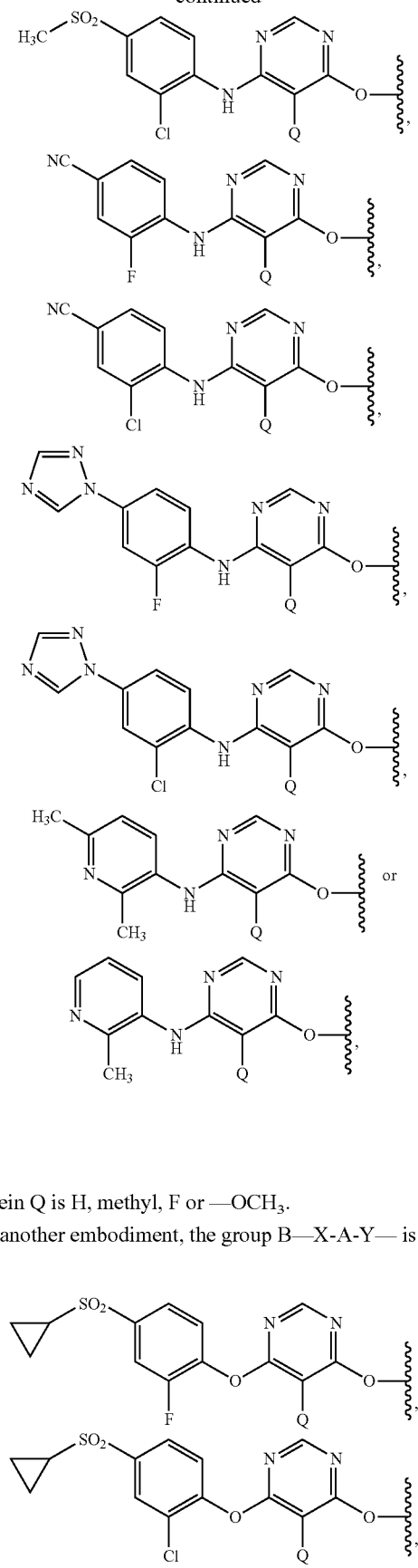
wherein Q is H, methyl, F or —OCH$_3$.
In another embodiment, the group B—X-A-Y— is:
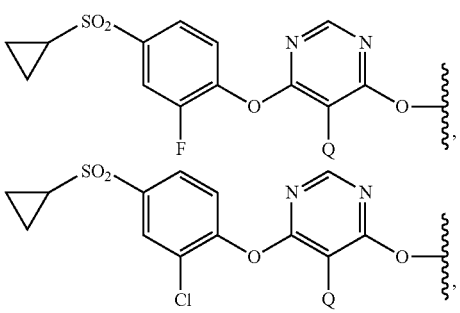

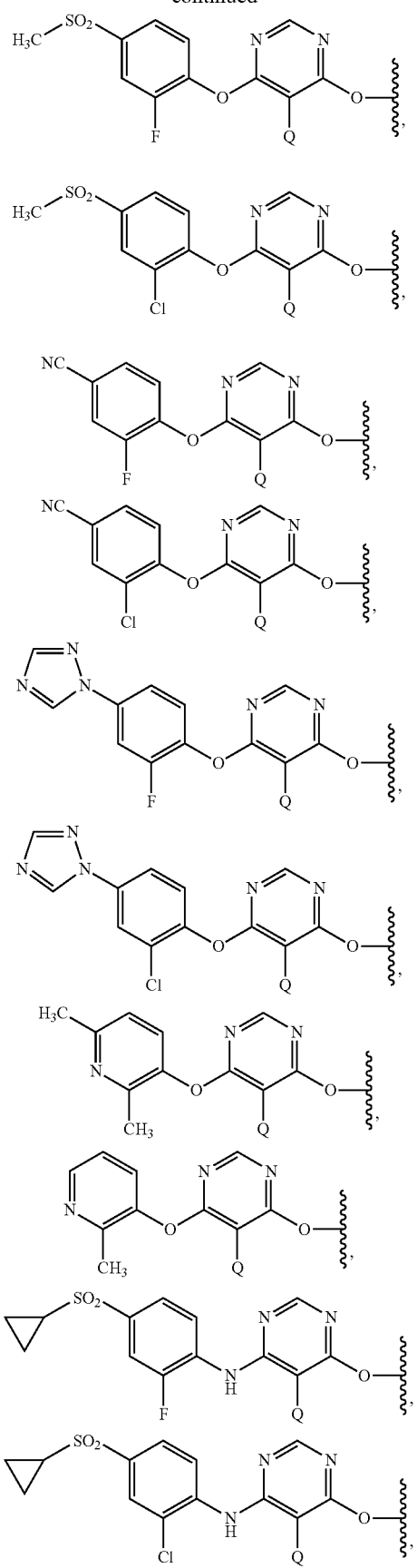
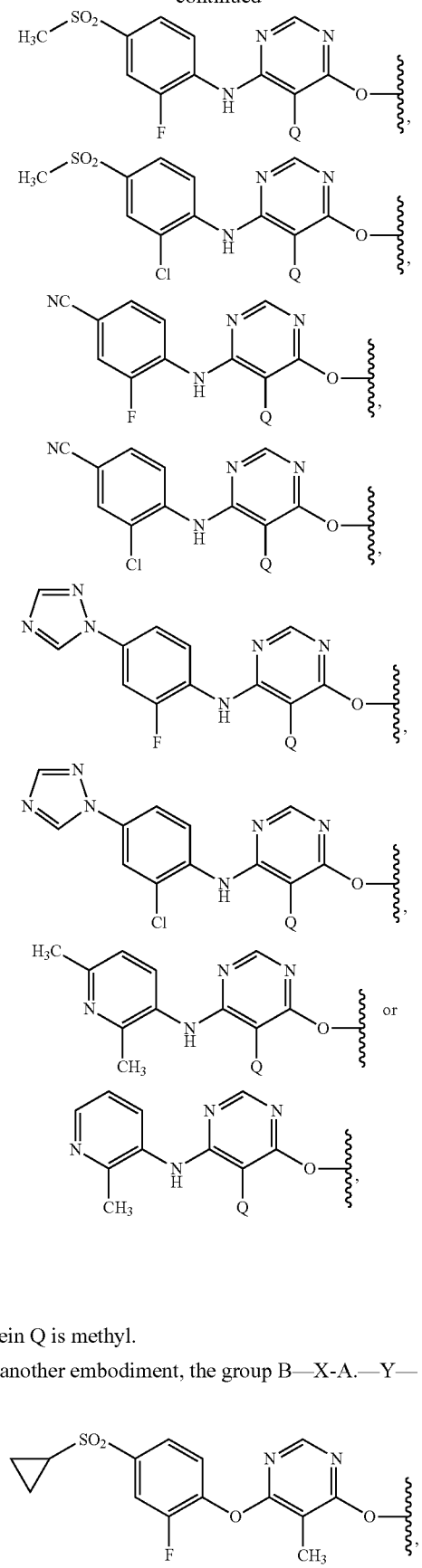
wherein Q is methyl.
In another embodiment, the group B—X-A.—Y— is
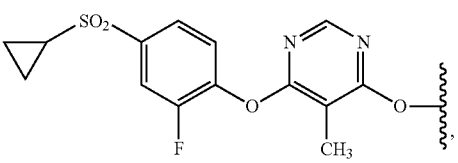

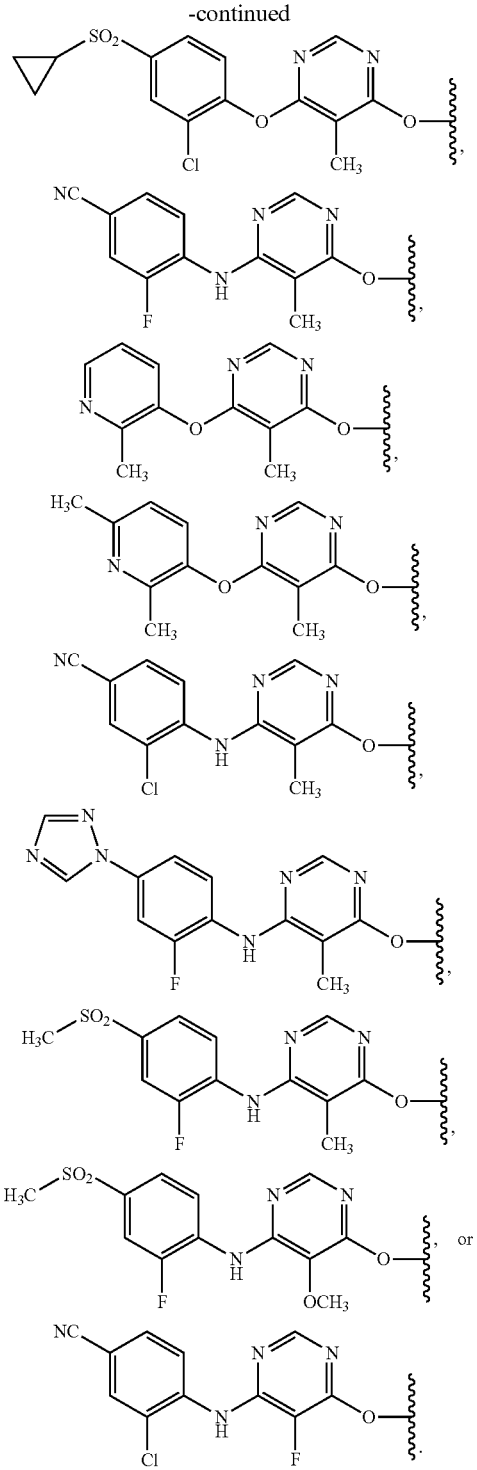

In another embodiment, the group B—X-A-Y— is:

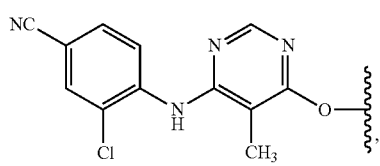

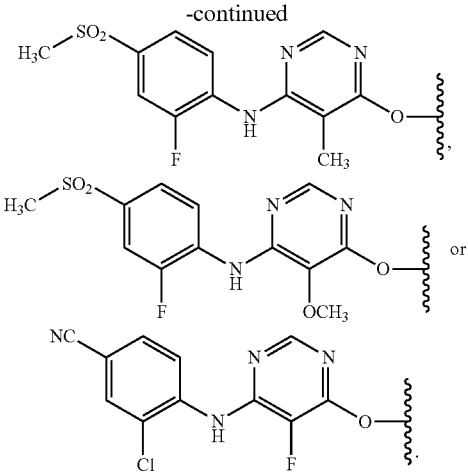

In another embodiment, the group B—X-A-Y— is:

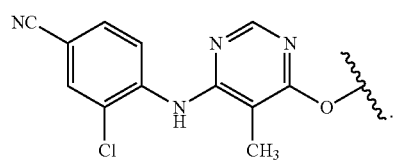 [SMILES: *Oc1ncnc(Nc2ccc(C#N)cc2Cl)c1C]

In another embodiment, the group B—X-A-Y— is:

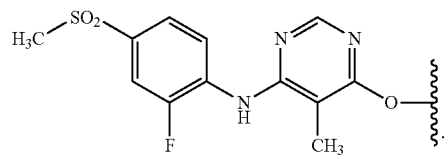 [SMILES: *Oc1ncnc(Nc2ccc(S(C)(=O)=O)cc2F)c1C]

In another embodiment, the group B—X-A-Y— is:

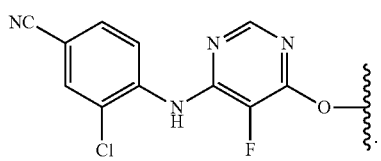 [SMILES: *Oc1ncnc(Nc2ccc(C#N)cc2Cl)c1F]

In another embodiment, the group B—X-A-Y— is:

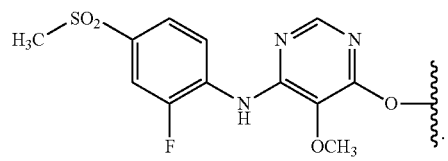 [SMILES: *Oc1ncnc(Nc2ccc(S(C)(=O)=O)cc2F)c1OC]

In one embodiment, each occurrence of R¹ is selected from H, halo or —OH.
In another embodiment, each occurrence of R¹ is H.
In still another embodiment, at least one occurrence of R¹ is OH.
In another embodiment, at least one occurrence of R¹ is halo.

In another embodiment, at least one occurrence of $R^1$ is F.

In another embodiment, at least one occurrence of $R^2$ is H, alkyl or —OH.

In another embodiment, at least one occurrence of $R^2$ is —OH.

In still another embodiment, at least one occurrence of $R^2$ is alkyl.

In another embodiment, at least one occurrence of $R^2$ is H.

In another embodiment, each occurrence of $R^2$ is H.

In one embodiment, $R^3$ is alkyl.

In another embodiment, $R^3$ is a linear alkyl group.

In another embodiment, $R^3$ is a branched alkyl group.

In still another embodiment, $R^3$ is methyl.

In another embodiment, $R^3$ is ethyl.

In another embodiment, $R^3$ is isopropyl.

In a further embodiment, $R^3$ is t-butyl.

In another embodiment, $R^3$ is alkenyl.

In another embodiment, $R^3$ is alkynyl.

In yet another embodiment, $R^3$ is haloalkyl.

In one embodiment, $R^3$ is cycloalkyl.

In another embodiment, $R^3$ is cyclopropyl.

In another embodiment, $R^3$ is substituted with a with a methyl group.

In another embodiment, $R^3$ is cyclobutyl.

In still another embodiment, is cyclopentyl.

In another embodiment, $R^3$ is cyclohexyl.

In yet another embodiment, $R^3$ is aryl.

In another embodiment, $R^3$ is phenyl.

In still another embodiment, $R^3$ is naphthyl.

In another embodiment, $R^3$ is -alkylene-aryl.

In another embodiment, $R^3$ is benzyl.

In one embodiment, $R^3$ is -alkylene-O-alkylene-aryl.

In another embodiment, $R^3$ is aryl, alkyl, -alkylene-aryl, alkenyl, alkynyl, cycloalkyl, heteroaryl, -alkylene-O-alkylene-aryl or -alkylene-cycloalkyl, wherein a cycloalkyl group can be optionally substituted with an alkyl group.

In another embodiment, $R^3$ is alkyl or cycloalkyl, wherein a cycloalkyl group can be optionally substituted with an alkyl group.

In another embodiment, $R^3$ is methyl, isopropyl, cyclopropyl or cyclobutyl, wherein a cyclopropyl or cyclobutyl group can be optionally substituted with an alkyl group.

In one embodiment, the group —W—$R^3$ is —S(O)$_2$-cyclopropyl, —S(O)$_2$-cyclobutyl, —S(O)$_2$CF$_3$, —S(O)$_2$CH$_2$CH$_2$OCH$_3$, —C(O)O-cyclopropyl, —C(O)O-cyclobutyl, —C(O)O-(1-methylcyclopropyl), —C(O)O-(1-methylcyclobutyl), —C(O)O-(1-methylcyclopropyl), —C(O)O-isopropyl or benzyl.

In one embodiment, $R^7$ is H.

In another embodiment, $R^7$ is alkyl.

In one embodiment, the group:

is:

In another embodiment, the group:

is:
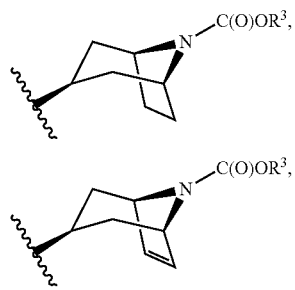
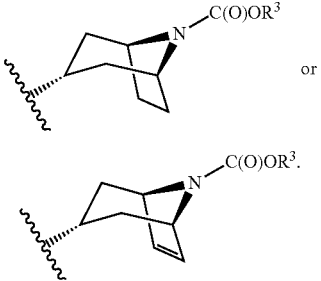
In another embodiment, the group:
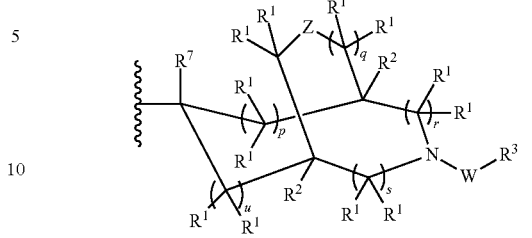
is:
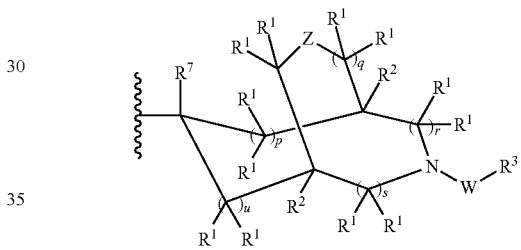
In another embodiment, the group:
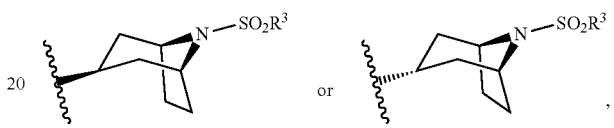
is:
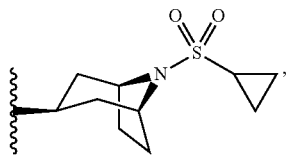
or a mixture thereof.
In still another embodiment, the group:
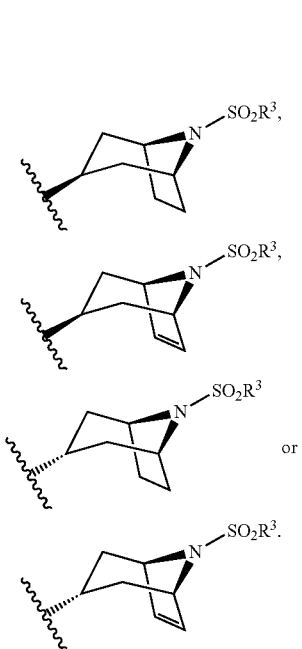
is:
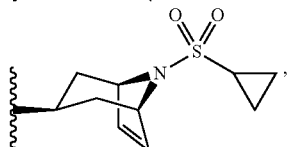
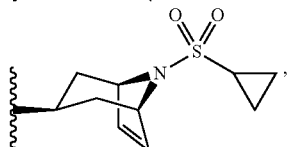
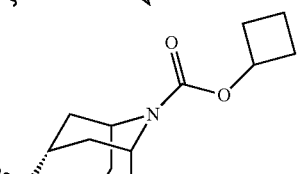
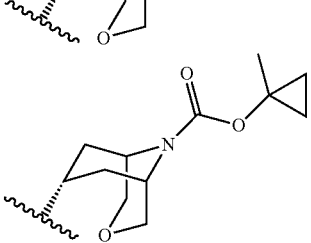

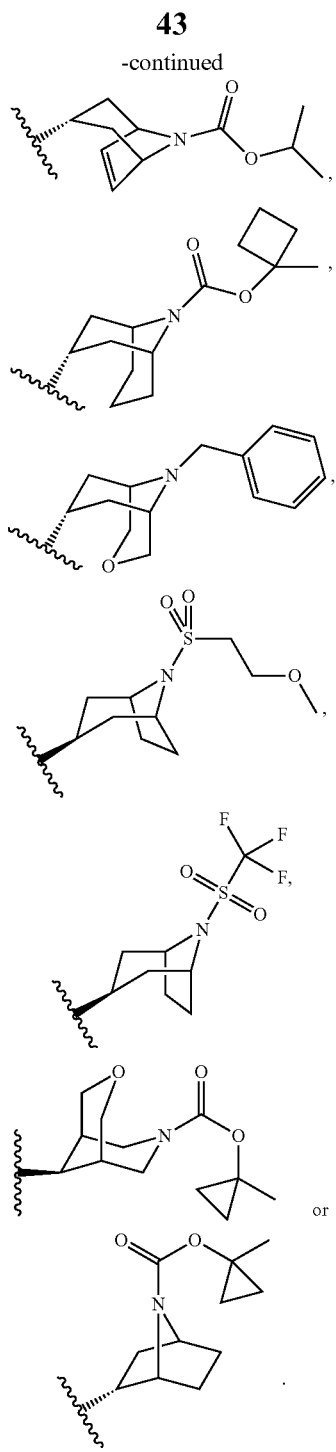
In one embodiment, the group —B—X-A-Y— is:
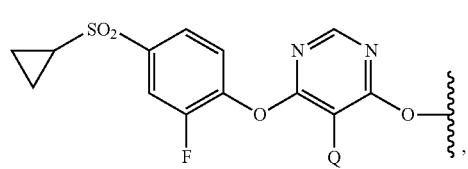
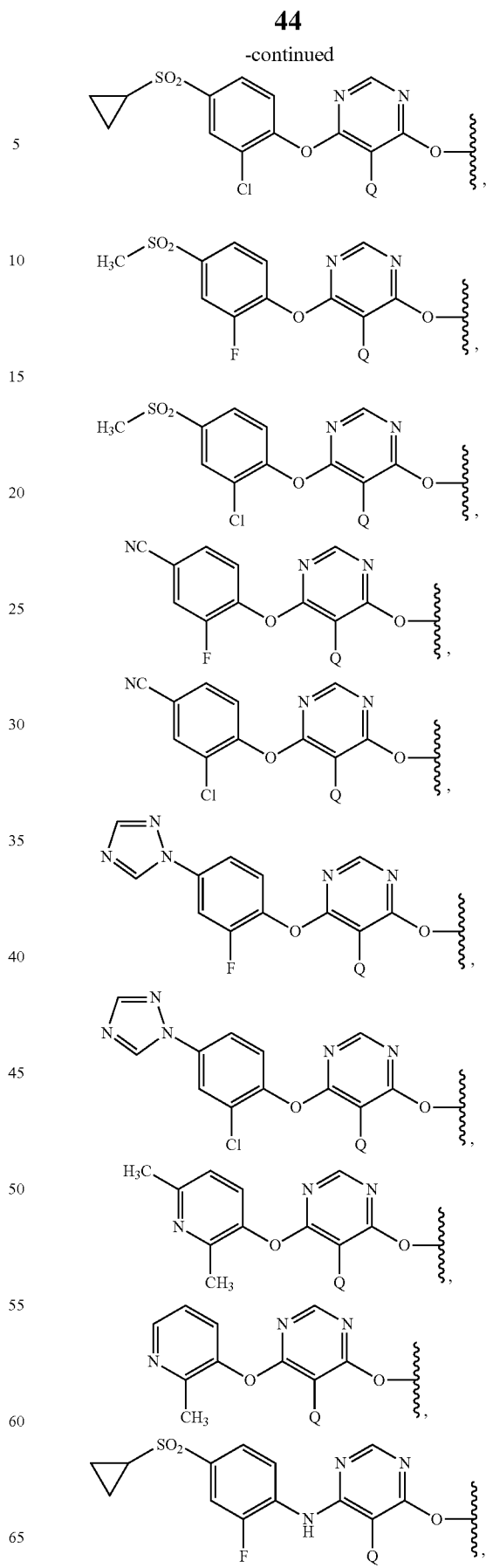

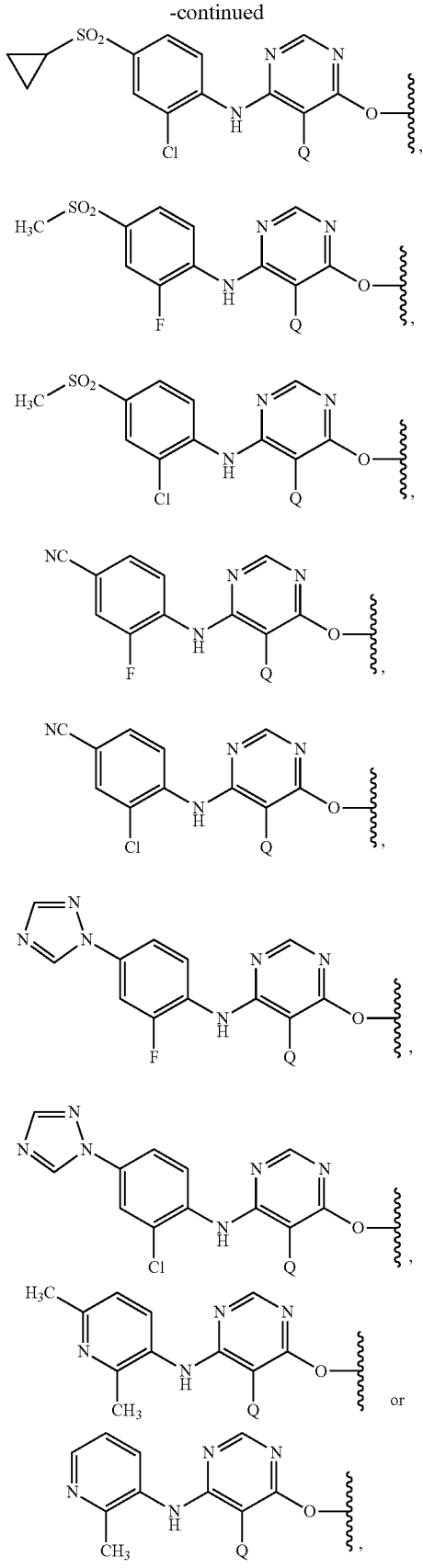
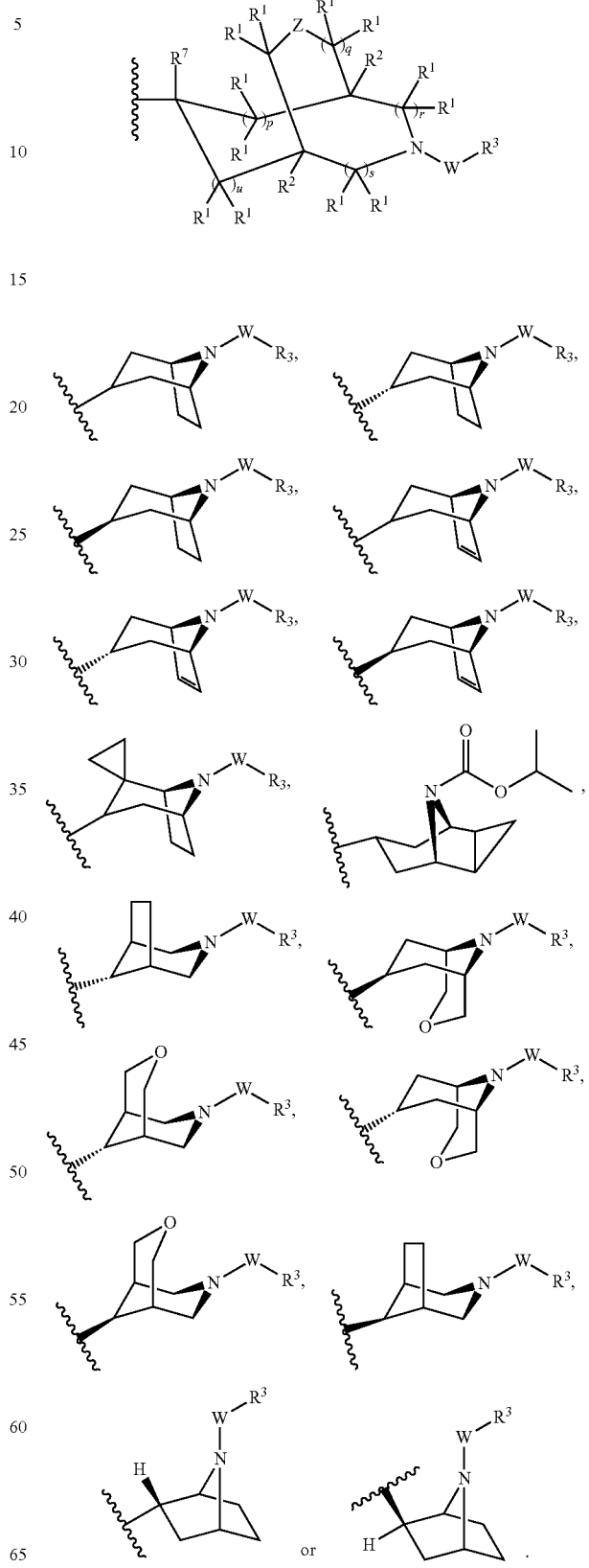
wherein Q is H, alkyl, halo or —O-alkyl,

In another embodiment, the group —B—X-A-Y— is:
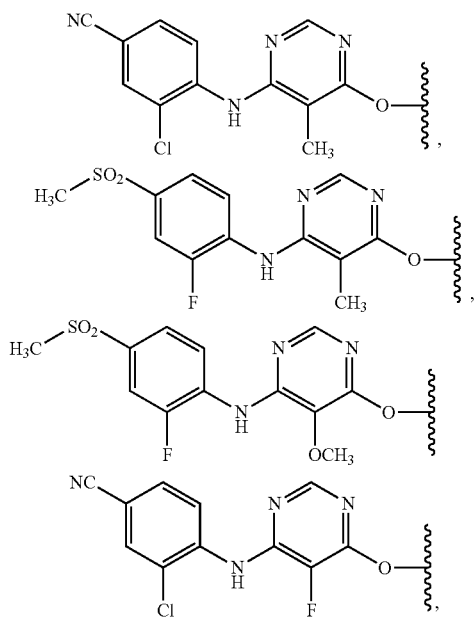
and the group:
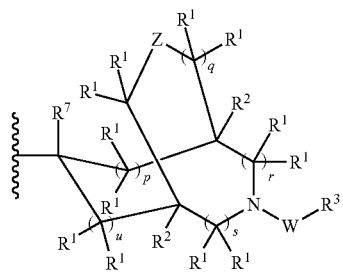
is:
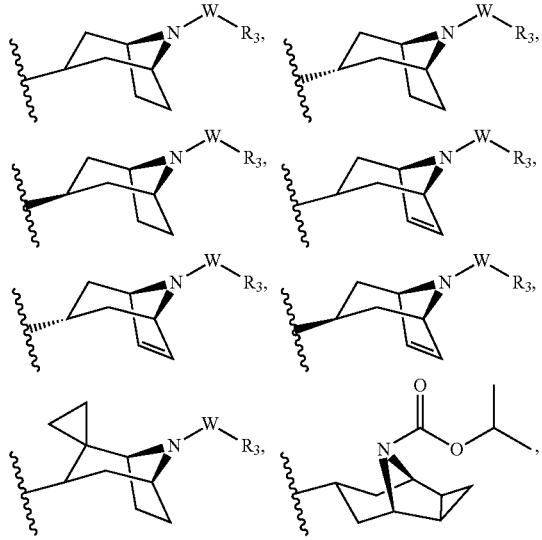
-continued
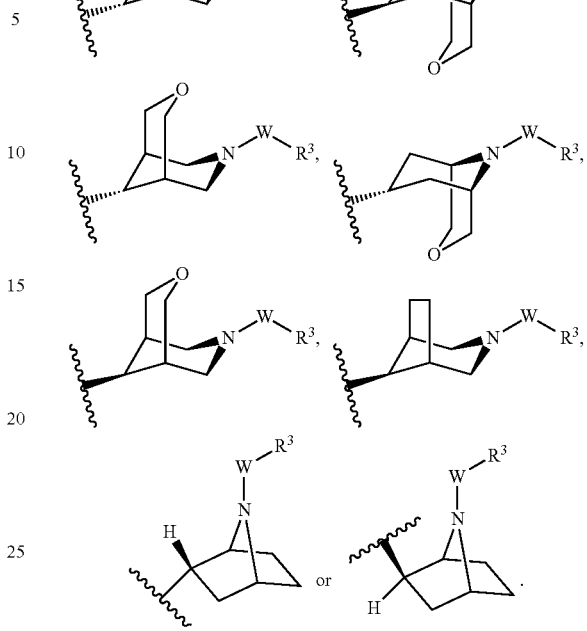
In another embodiment, the group —B—X-A-Y— is:
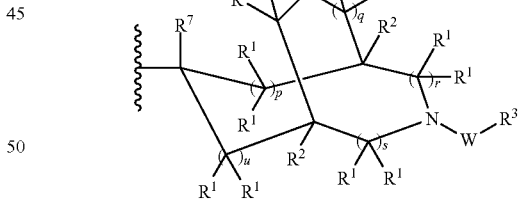
and the group:
is:
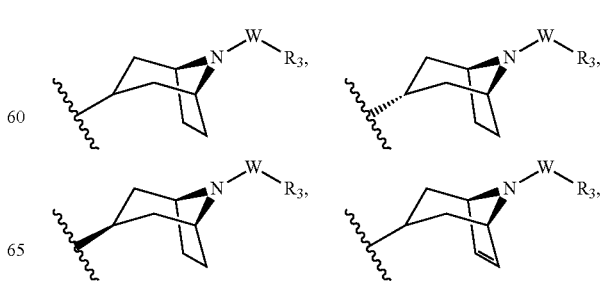

-continued
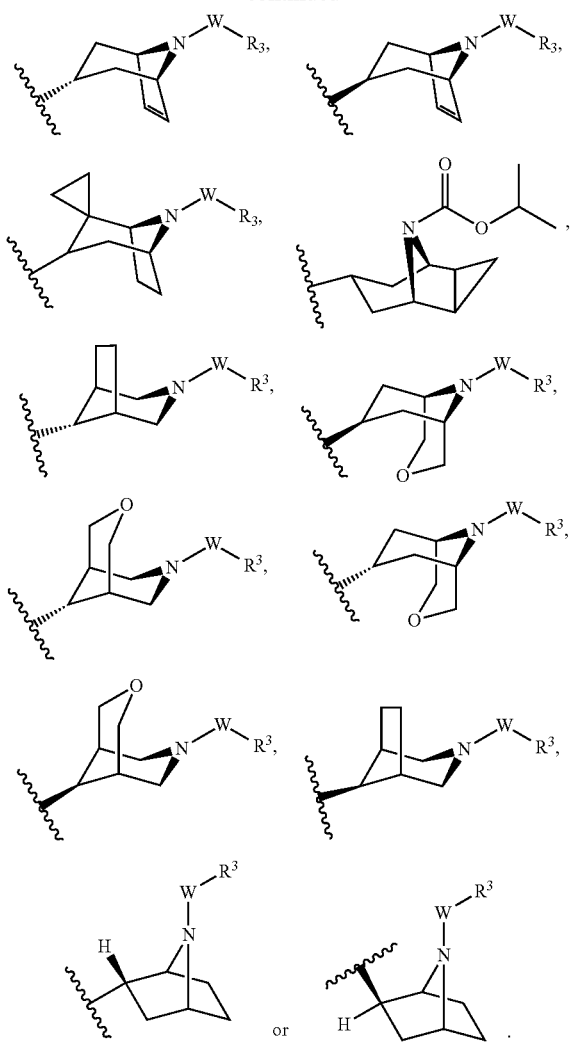
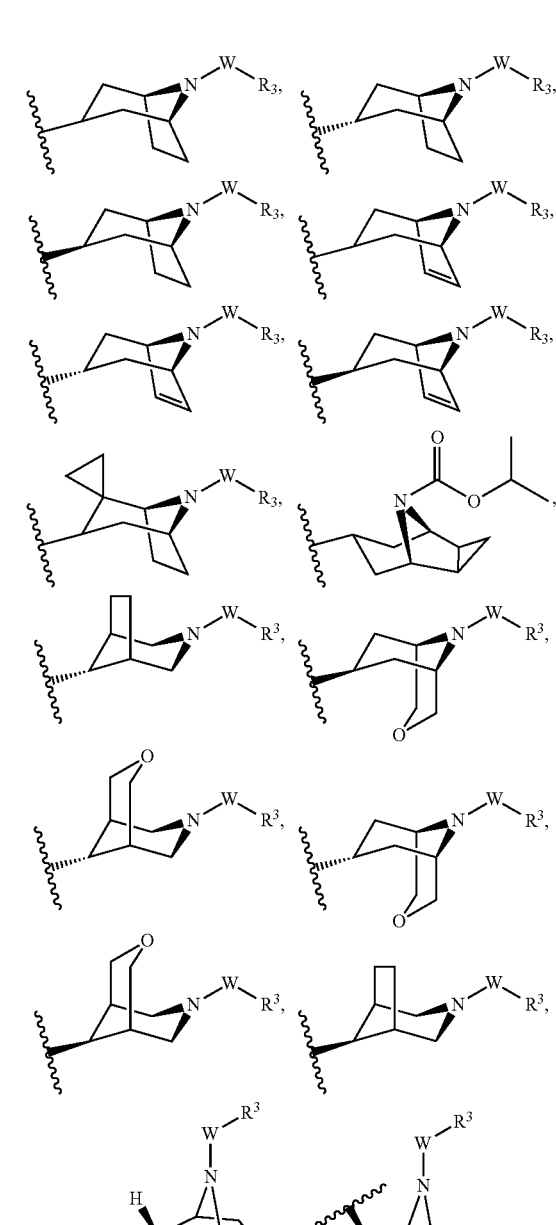
In another embodiment, the group —B—X-A-Y— is:
and the group:
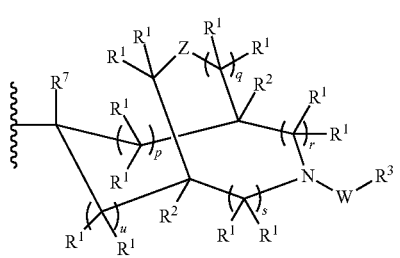
is:
In one embodiment, the group —B—X-A-Y— is:
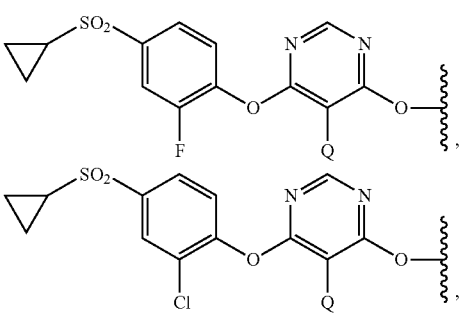

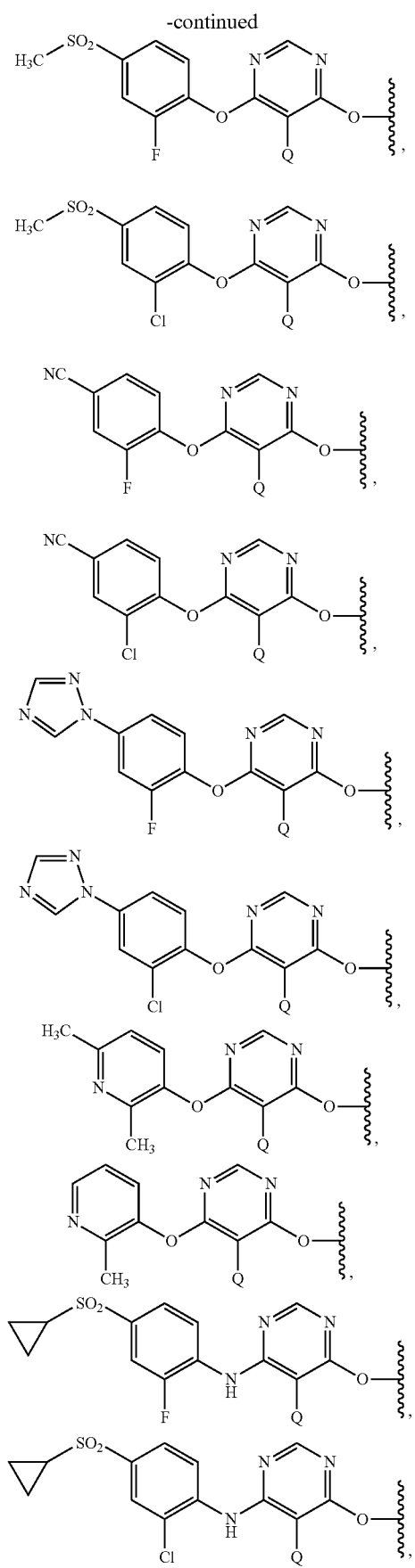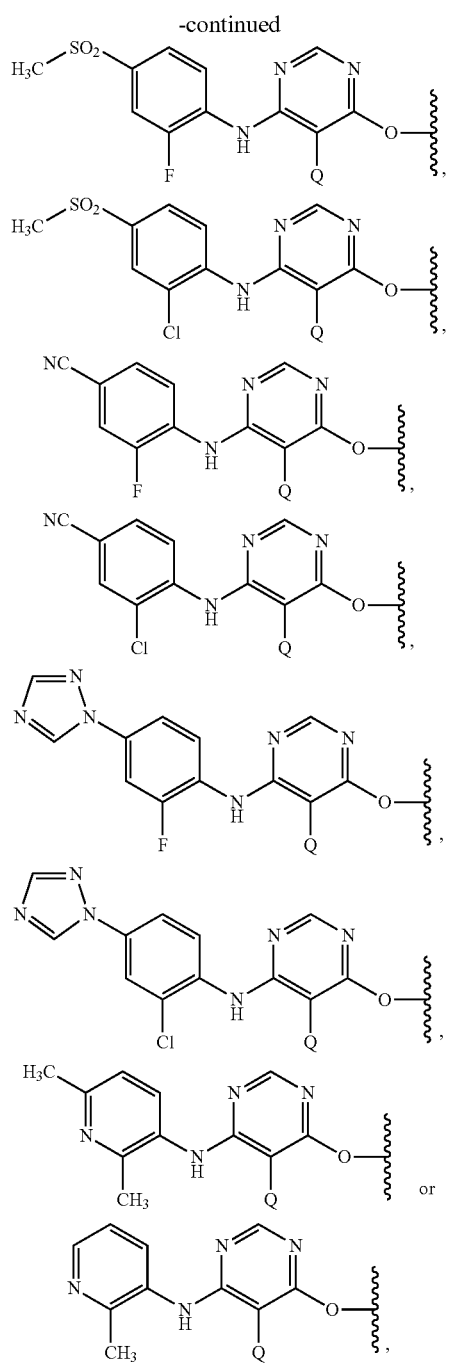
wherein Q is H, alkyl, halo or —O-alkyl, and the group:
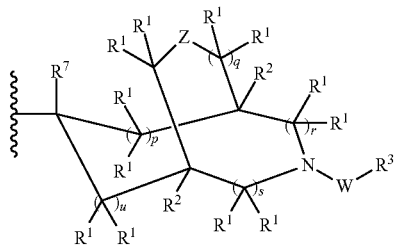

is:
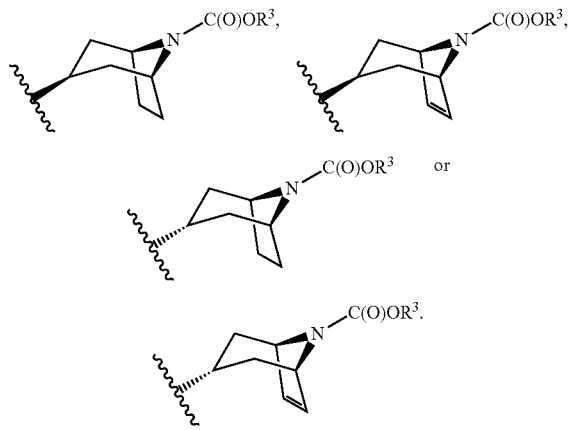
In another embodiment, the group —B—X-A-Y— is:
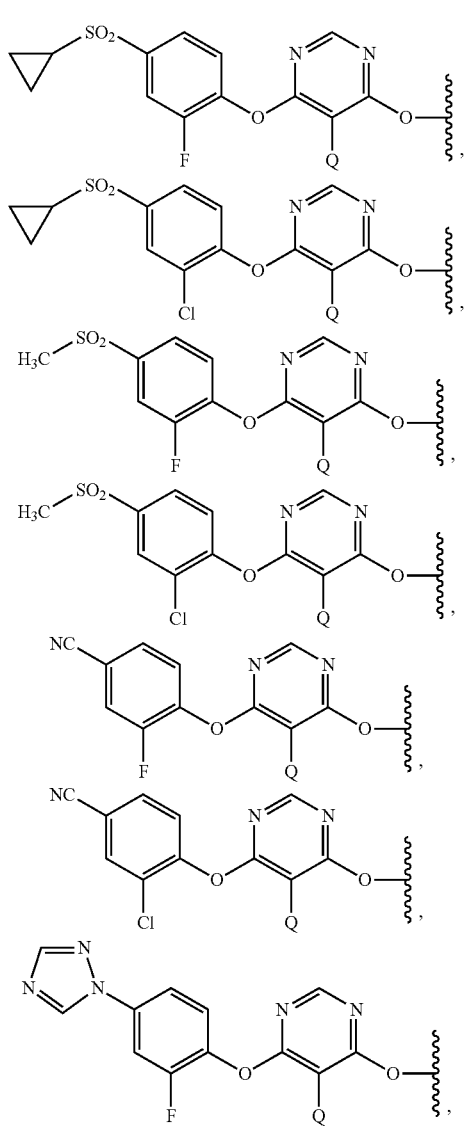
-continued
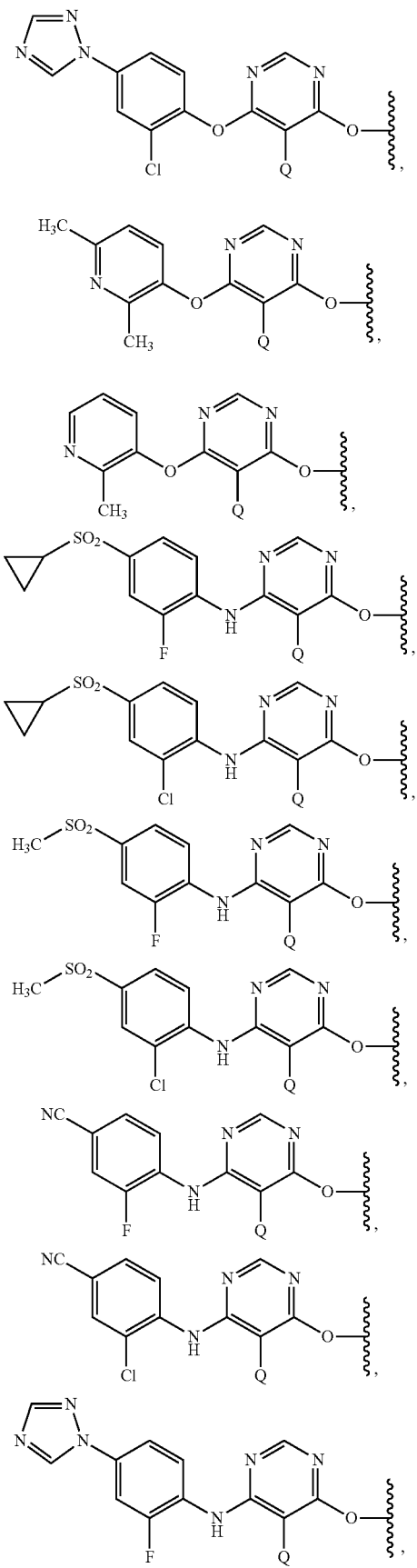

-continued
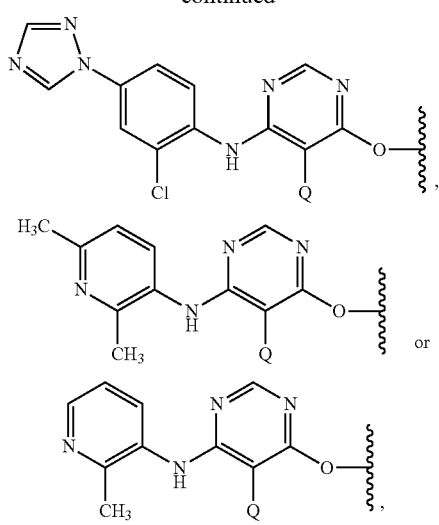
wherein Q is H, alkyl, halo or the group:
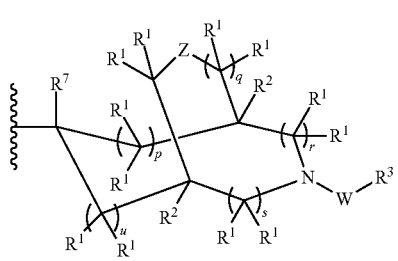
is:
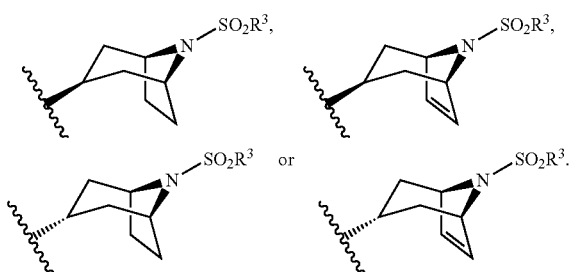
In another embodiment, the group —B—X-A-Y— is:
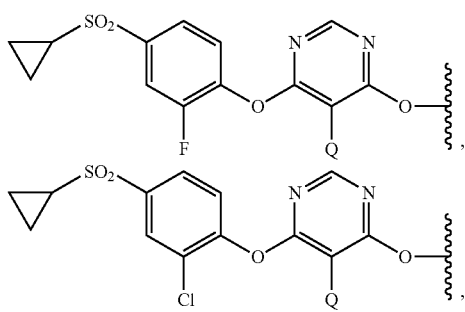
-continued
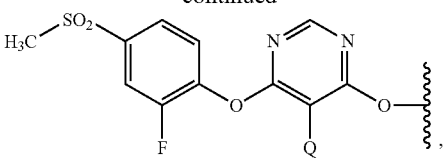
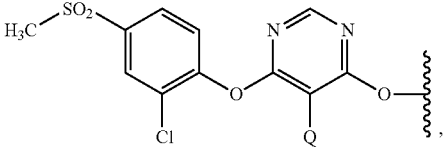
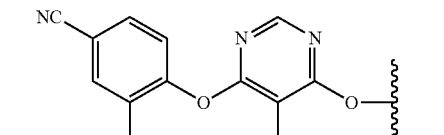
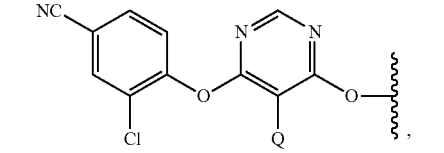
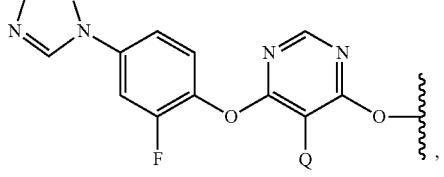
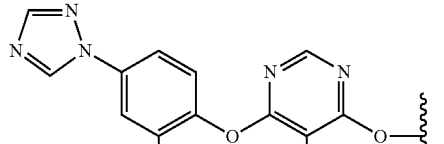
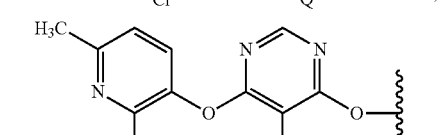
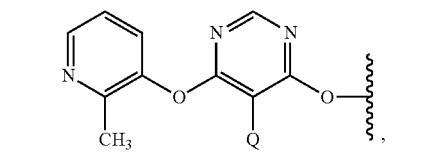
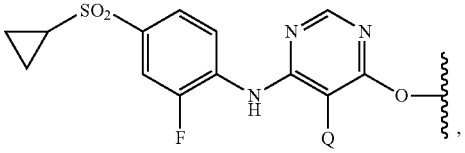
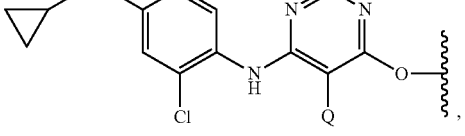

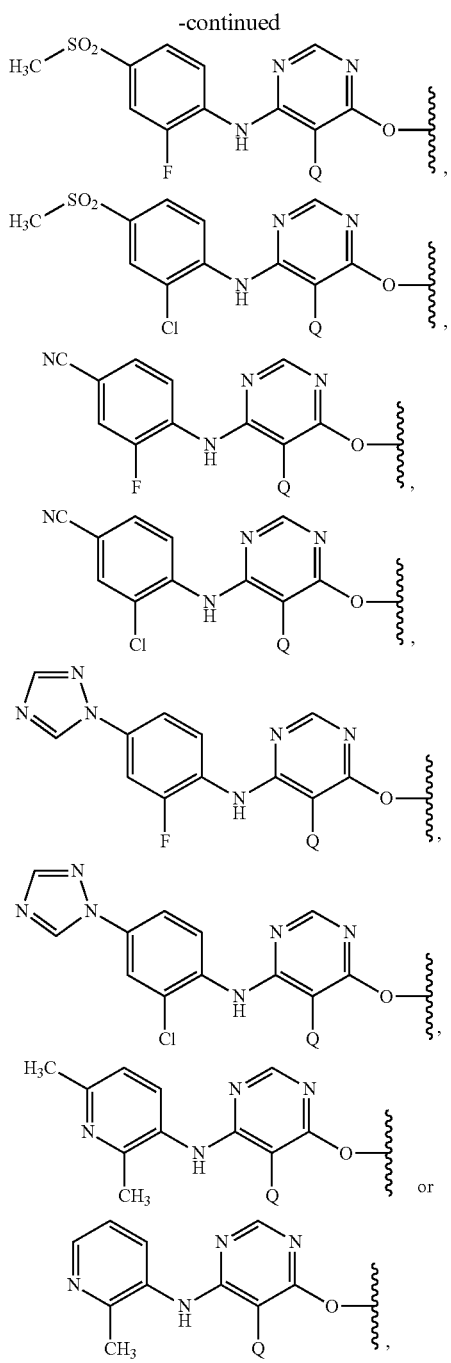
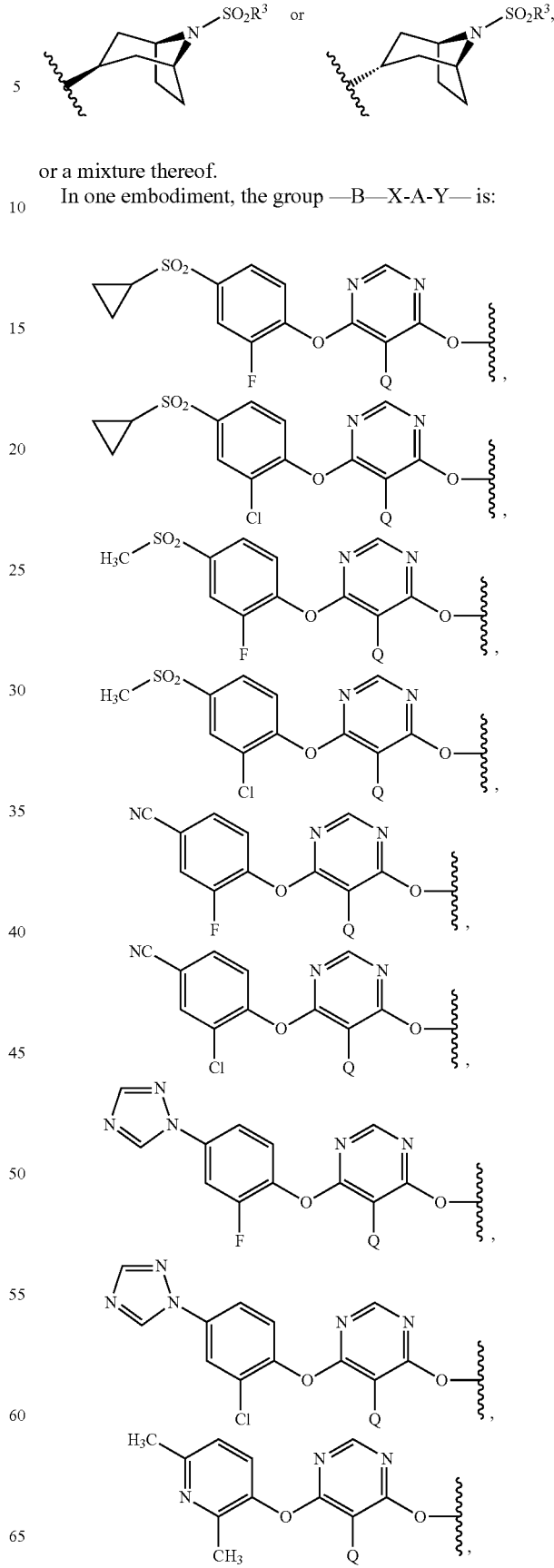
or a mixture thereof.
In one embodiment, the group —B—X-A-Y— is:
wherein Q is H, alkyl, halo or —O-alkyl, and the group:
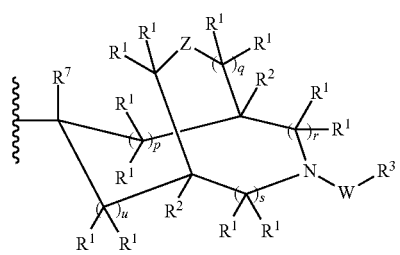

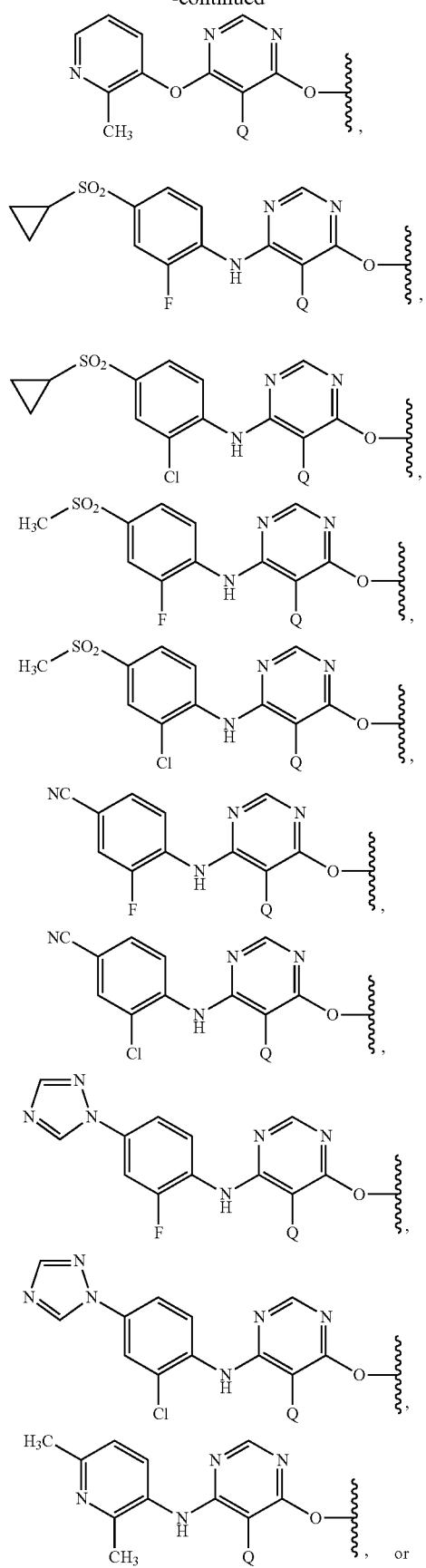
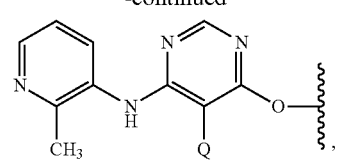
wherein Q is H, alkyl, halo or —O-alkyl, and the group:
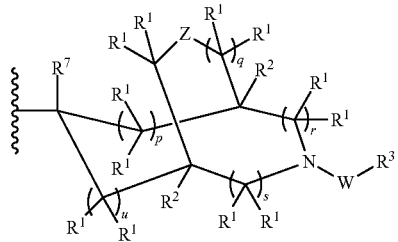
is:
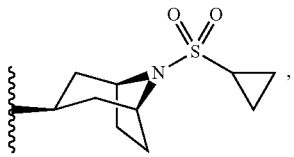
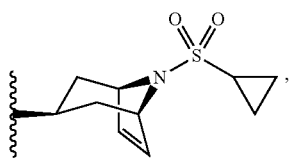
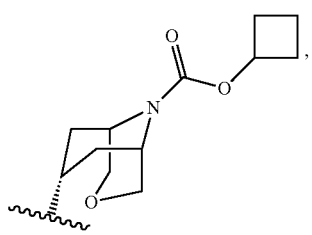
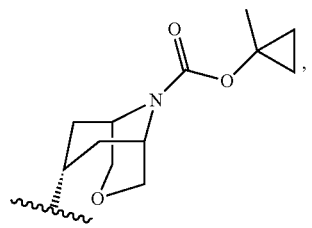
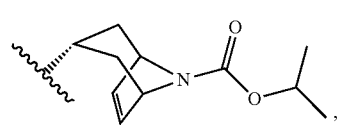

-continued
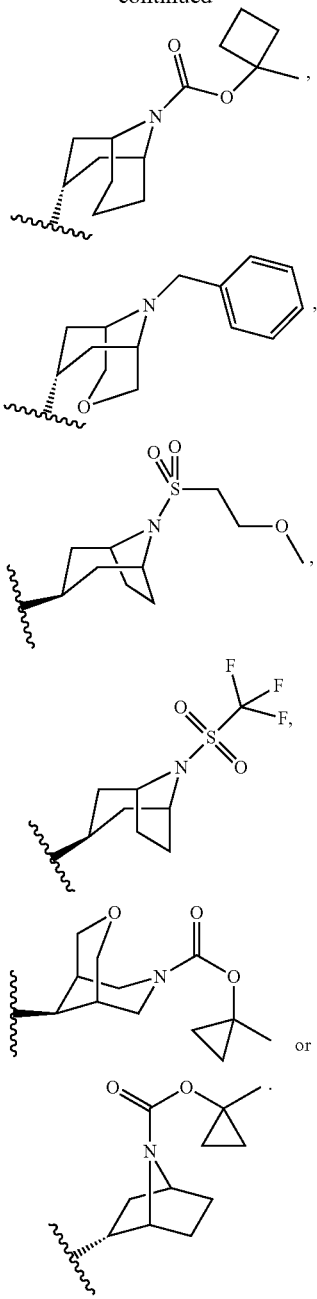
In one embodiment, the group —B—X-A-Y— is:
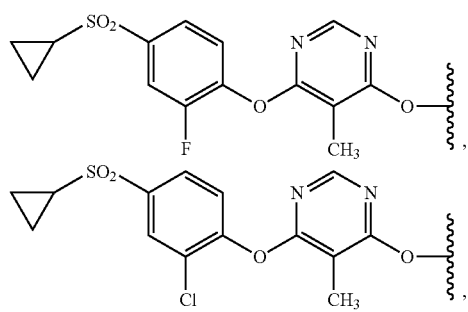
-continued
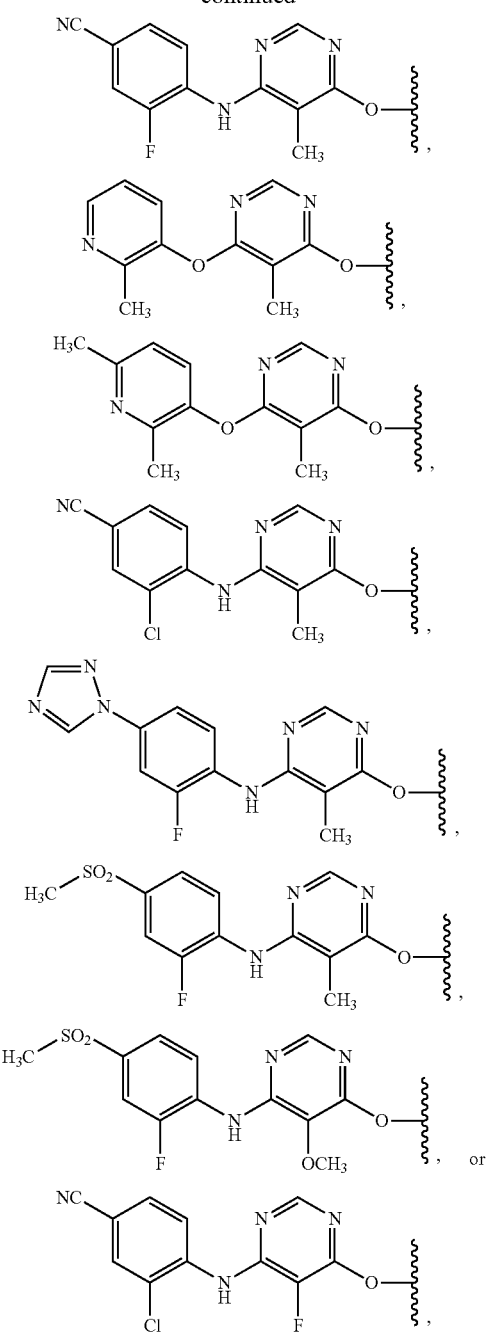
and the group:
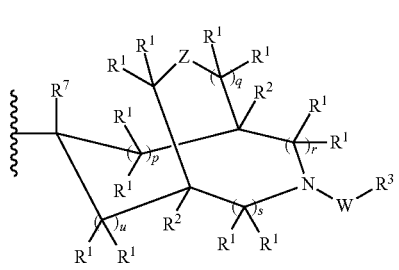

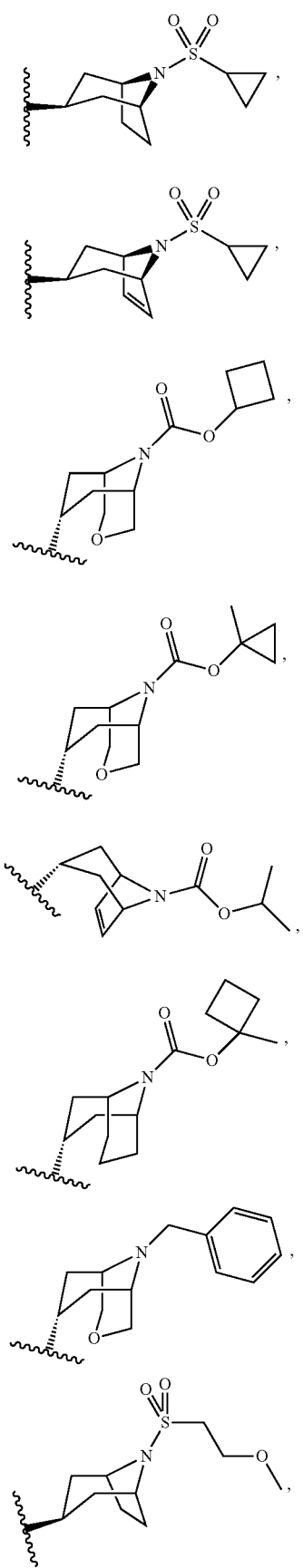
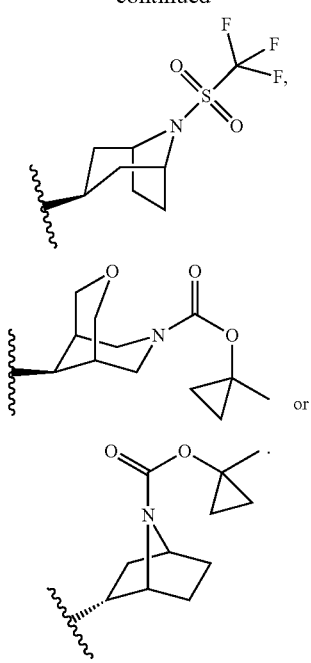
In another embodiment, the group —B—X-A-Y— is:
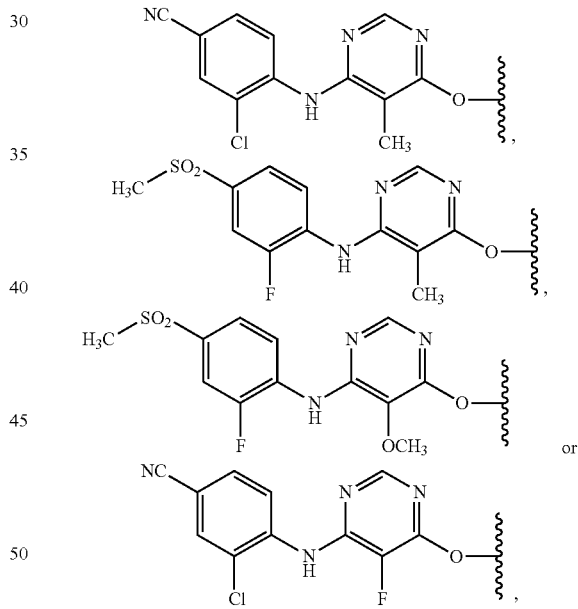
and
the group:
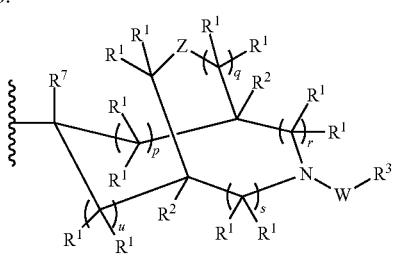

is:
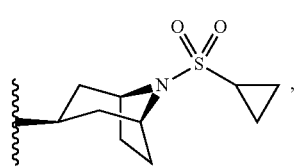
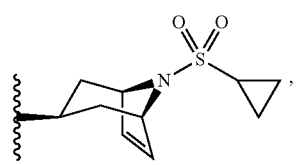
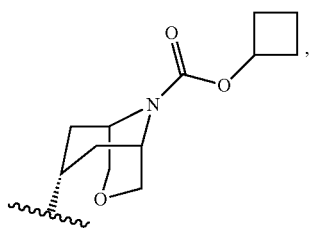
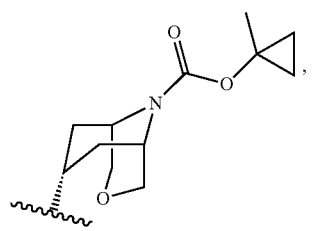
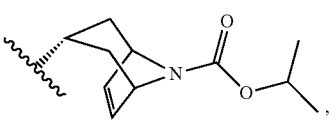
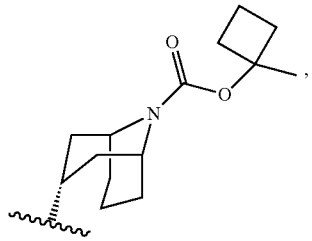
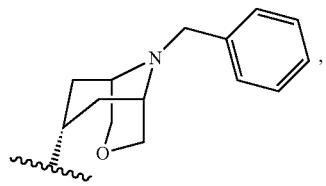
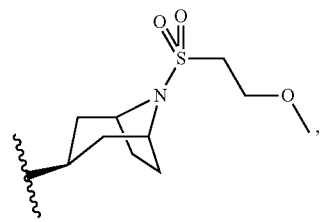
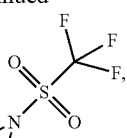
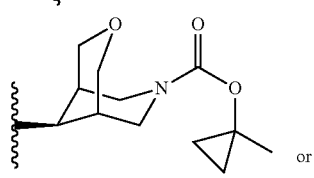
or
In another embodiment, the group —B—X-A-Y—
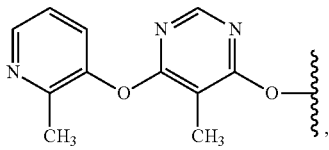 [SMILES: *Oc1ncnc(Oc2cccnc2C)c1C]
and the group:
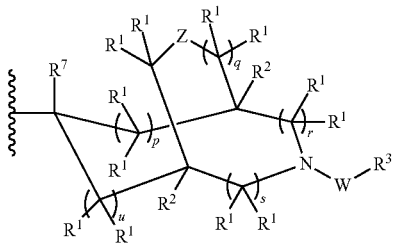
is:
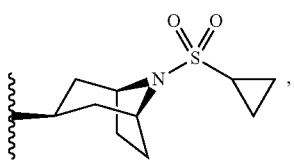
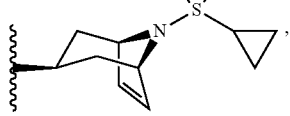

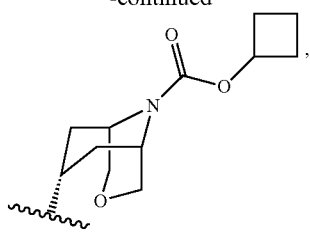,
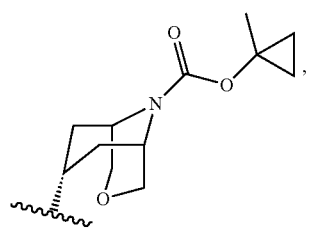,
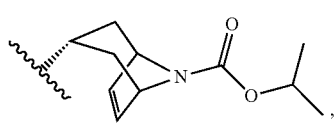,
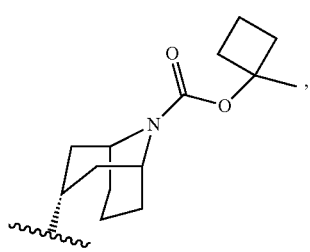,
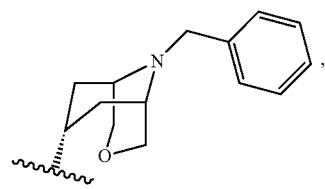,
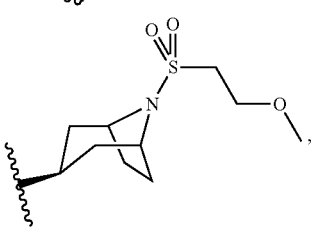,
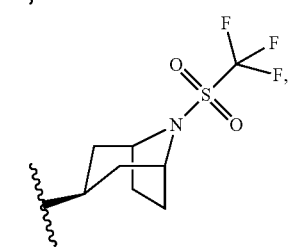,
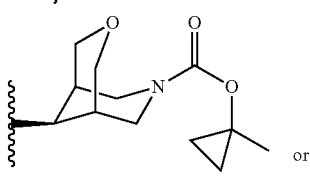 or
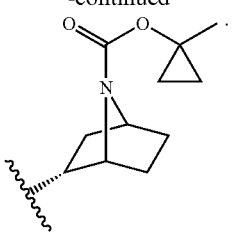.
In another embodiment, the group is:
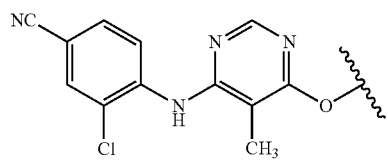
and the group:
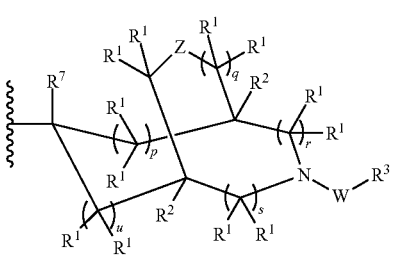
is:
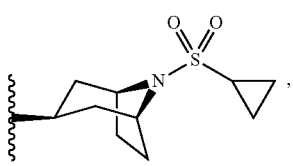,
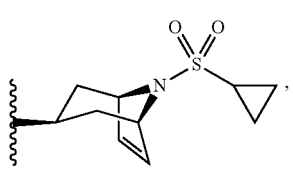,
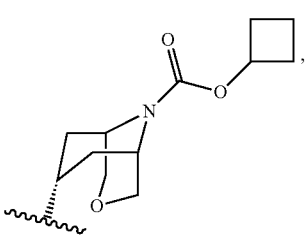, -continued
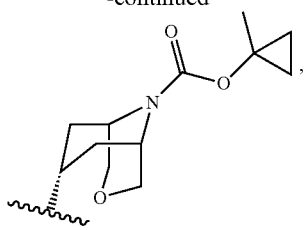,
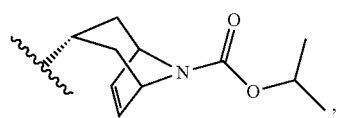,
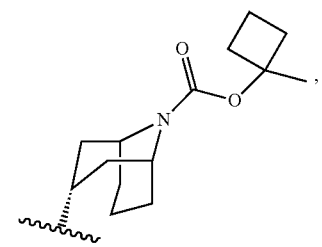,
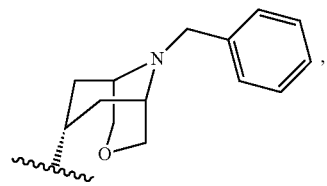,
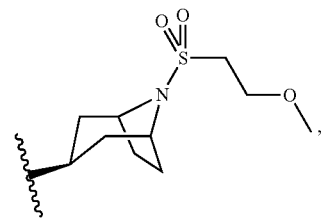,
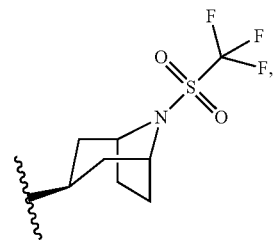,
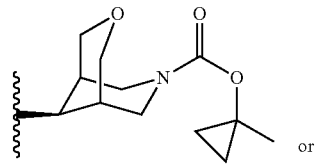 or
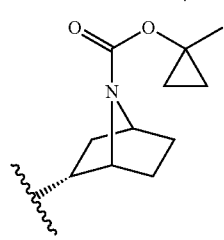.
In another embodiment, the group —B—X-A-Y— is:
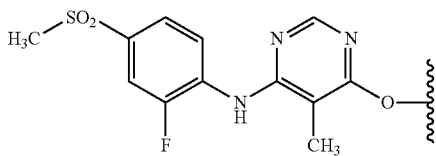 [SMILES: *Oc1ncnc(Nc2ccc(S(C)(=O)=O)cc2F)c1C]
and the group:
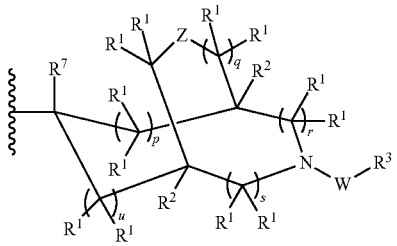
is:
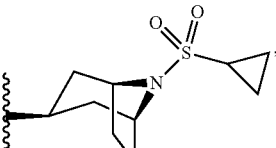,
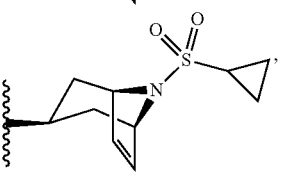,
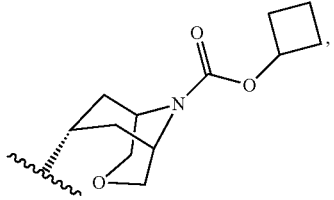,
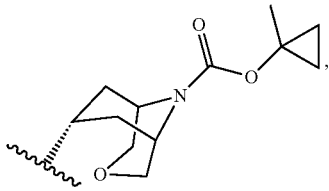,
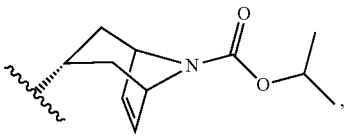,
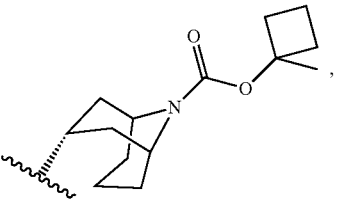,

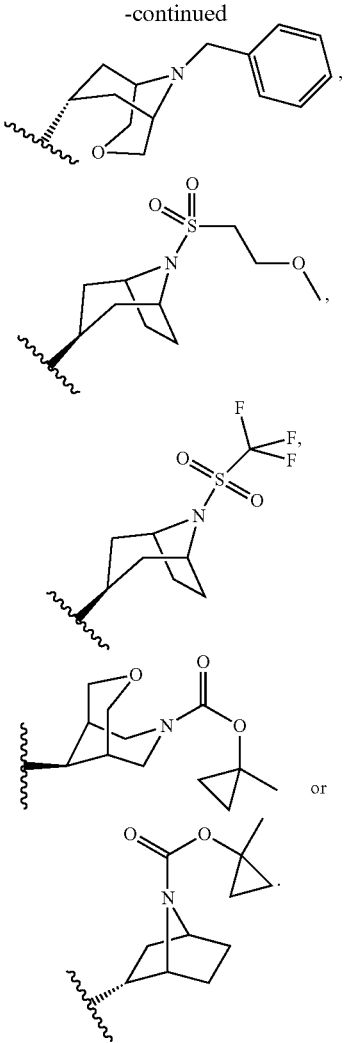

In one embodiment, W is —C(O)O— and R³ is aryl, -alkylene-aryl, alkyl, alkenyl, alkynyl, cycloalkyl, heteroaryl, -alkylene-O-alkylene-aryl or -alkylene-cycloalkyl.

In another embodiment, W is —C(O)O— and R³ is phenyl, t-butyl, 4-bromophenyl, 3-trifluoromethylphenyl, 4-nitrobenzyl, 4-(C(O)OCH₃)phenyl, naphthyl, 2-chlorobenzyl, methyl, ethyl, propyl, butyl, pentyl, hexyl, heptyl, octyl, nonyl, 4-chlorophenyl, 4-methoxyphenyl, 2-methoxyphenyl, 4-fluorophenyl, benzyl, 4-methylphenyl, neopentyl, cyclopentyl, sec-butyl, butenyl, butynyl, propenyl, propynyl, isopropenyl, cyclobutyl, isopropyl, —CH₂-cyclopropyl, —CH(cyclopropyl)(CH₃), —CH(cyclopropanyl)₂ or —CH(CH₃)phenyl.

In another embodiment, W is —S(O)₂— and R³ is aryl, alkyl, heteroaryl, -alkylene-aryl or cycloalkyl.

In still another embodiment, W is S(O)₂— and R³ is 4-fluorophenyl, methyl, ethyl, propyl, butyl, 5-chloro-thiophenyl, cyclopropyl, 4-(NHC(O)CH₃)phenyl, benzyl, 3-chlorobenzyl, 4-chlorobenzyl, sec-butyl, 4-methylbenzyl or 2-chlorobenzyl.

In another embodiment, W is —S(O)₂— and R³ is cycloalkyl, haloalkyl or -alkylene-O-alkyl, wherein a cycloalkyl group can be optionally substituted with an alkyl group.

In another embodiment, W is —S(O)₂— and R³ is cycloalkyl, which is unsubstituted or optionally substituted with an alkyl group.

In yet another embodiment, W is —S(O)₂— and R³ is cyclopropyl or cyclobutyl, each of which is unsubstituted or optionally substituted with an alkyl group.

In a further embodiment, W is —S(O)₂— and R³ is cyclopropyl.

In one embodiment, W is —C(O)O— and R³ is alkyl, cycloalkyl or alkyl-substituted cycloalkyl.

In another embodiment, W is —C(O)O— and R³ is methyl, isopropyl, isobutyl, cyclopropyl, cyclobutyl, methyl-substituted cyclopropyl or methyl-substituted cyclobutyl.

In another embodiment, W is —S(O)₂— and R³ is haloalkyl, -alkylene-O-alkyl, cycloalkyl or alkyl-substituted cycloalkyl.

In still another embodiment, W is —S(O)₂— and R³ is cyclopropyl, cyclobutyl, trifluoromethyl, —CH₂CH—, OCH₃, methyl-substituted cyclopropyl, methyl-substituted cyclobutyl.

In one embodiment, W is —NH— and R³ is aryl or alkyl.

In another embodiment, W is a bond and R¹ is aryl, -alkylene-aryl or alkyl.

In another embodiment, W is a bond and R³ is phenyl.

In another embodiment, W is a bond and R³ is benzyl.

In one embodiment, p and u are each 1,

In another embodiment, u, p, q, r, and s are each independently 0 or

In another embodiment, p and u are each 1, and r and s are each 0.

In another embodiment, q, p and u are each 1, r and s are each 0 and Z is a bond.

In still another embodiment, q, p and u are each 1, r and s are each 0, Z is a bond, and W is —C(O)O—.

In a further embodiment, q, p and u are each 1, r and s are each 0, Z is a bond, W is —C(O)O—, and each of X and Y are —O—.

In another embodiment, q, p and u are each 1, r and s are each 0, Z is a bond, W is —C(O)O—, each of X and Y are —O—, A is a 5 or 6-membered heteroaryl, and B is phenyl or a 5 or 6-membered heteroaryl.

In another embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, and R³ is alkyl.

In one embodiment, q, p and a are each 1, r and s are each 0, Z is a bond, W is —C(O)O—, each of X and Y are —O—, A is a 5 or 6-membered heteroaryl, B is phenyl or a 5 or 6-membered heteroaryl, and R³ is alkyl.

In another embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, each occurrence of R¹ is H, and R³ is alkyl.

In another embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, each occurrence of R¹ and R² is H, and R³ is alkyl.

In still another embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, each occurrence of R¹ and R² is H, and R³ is isopropyl or t-butyl.

In yet another embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, each occurrence of R¹ and R² is H, R³ is isopropyl or t-butyl, and the compound of formula CO contains at least one endocyclic double bond.

In a further embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, each occurrence of $R^1$ and $R^2$ is H, $R^1$ is isopropyl or t-butyl, and the bicyclic moiety of the compound of formula (I) contains one endocyclic double bond.

In one embodiment, q, p and u are each 1, r and s are each 0, Z is a bond, W is —S(O)$_2$—,
each of X and Y are —O—, A is a 5 or 6-membered heteroaryl, B is phenyl or a 5 or 6-membered heteroaryl, and $R^3$ is alkyl.

In a further embodiment, q, p and u are each 1, r and s are each 0, Z is a bond, W is —C(O)O—, and each of X and Y are —O—.

In another embodiment, q, p and u are each 1, r and s are each 0, Z is a bond, W is —C(O)O—, each of X and Y are —O—, A is a 5 or 6-membered heteroaryl, and B is phenyl or a 5 or 6-membered heteroaryl.

In another embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, and $R^3$ is alkyl.

In one embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, and $R^3$ is alkyl.

In another embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, each occurrence of $R^1$ is H, and $R^3$ is alkyl.

In another embodiment, q, p and u are each 1, r and s are each 0. Z is a bond, W is —C(O)O—, each of X and Y are —O—, A is a 5 or 6-membered heteroaryl, B is phenyl or a 5 or 6-membered heteroaryl, each occurrence of $R^1$ and $R^2$ is H, and $R^3$ is alkyl.

In still another embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, each occurrence of $R^1$ and $R^2$ is H, and $R^3$ is isopropyl or t-butyl.

In yet another embodiment, q, p and u are each 1, r and s are each 0, Z is a bond, W is —C(O)O—, each of X and Y are —O—, A is a 5 or 6-membered heteroaryl, B is phenyl or a 5 or 6-membered heteroaryl, each occurrence of R and $R^2$ is H, $R^3$ is isopropyl or t-butyl, and the compound of formula (I) contains at least one endocyclic double bond.

In a further embodiment, q, p and u are each 1, r and s are each 0, Z is a bond, W is C(O)O—, each of X and Y are —O—, A is a 5 or 6-membered heteroaryl, B is phenyl or a 5 or 6-membered heteroaryl, each occurrence of $R^1$ and $R^2$ is H, $R^3$ is isopropyl or t-butyl, and the bicyclic moiety of the compound of formula (I) contains one endocyclic double bond.

In one embodiment, q, p and u are each 1, r and s are each 0, Z is a bond, W is —S(O)$_2$—, each of X and Y are —O—, A is a 5 or 6-membered heteroaryl, B is phenyl or a 5 or 6-membered heteroaryl, and $R^3$ is alkyl, In another embodiment, q, p and u are each 1, r and s are each 0, Z is a bond, W is —S(O)$_2$—, each of X and Y are —O—, A is a 5 or 6-membered heteroaryl, B is phenyl or a 5 or 6-membered heteroaryl, each occurrence of $R^1$ is H, and $R^3$ is alkyl.

In another embodiment, q, p and u are each 1, r and s are each 0, Z is a bond, W is —S(O)$_2$—, each of X and Y are —O—, A is a 5 or 6-membered heteroaryl. B is phenyl or a 5 or 6-membered heteroaryl, each occurrence of $R^1$ and $R^2$ is H, and $R^3$ is alkyl.

In still another embodiment, q, p and u are each 1, r and s are each 0, Z is a bond, W is —S(O)$_2$—, each of X and Y are —O—, A is a 5 or 6-membered heteroaryl, B is phenyl or a 5 or 6-membered heteroaryl, each occurrence of $R^1$ and $R^2$ is H, and $R^3$ is isopropyl or t-butyl.

In one embodiment, q, p and u are each 1, r and s are each 0, Z is a bond, W is —C(O)O—, and Y is —NH— and X is —O—.

In another embodiment, q, p and u are each 1, r and s are each 0, Z is a bond, W is —C(O)O—, Y is —NH— and X is —O—, A is a 5 or 6-membered heteroaryl, and B is phenyl or a 5 or 6-membered heteroaryl.

In another embodiment, q, p and u are each 1, r and s are each 0, Z is a bond, W is —C(O)O—, Y is —NH— and X is —O—, A is a 5 or 6-membered heteroaryl, B is phenyl or 6-membered heteroaryl, and $R^3$ is alkyl.

In one embodiment, q, p and u are each 1, r and s are each 0, Z is a bond, W is —C(O)O—, Y is —NH— and X is —O—, A is a 5 or 6-membered heteroaryl, B is phenyl or a 5 or 6-membered heteroaryl, and $R^3$ is alkyl.

In another embodiment, q, p and u are each 1, r and s are each 0, Z is a bond, W is —C(O)O—, Y is —NH— and X is —O—, A is a 5 or 6-membered heteroaryl, B is phenyl or a 5 or 6-membered heteroaryl, each occurrence of $R^1$ is H, and $R^3$ is alkyl.

In another embodiment, q, p and u are each 1 r and s are each 0, Z is a bond. W is —C(O)O—, Y is —NH— and X is —O—. A is a 5 or 6-membered heteroaryl, B is phenyl or a 5 or 6-membered heteroaryl, each occurrence of $R^1$ and $R^2$ is H, and $R^3$ is alkyl.

In still another embodiment, q, p and u are each 1, r and s are each 0, Z is a bond, —C(O)O—, Y is —NH— and X is —O—, A is a 5 or 6-membered heteroaryl, B is phenyl or a 5 or 6-membered heteroaryl, each occurrence of $R^1$ and $R^2$ is H, and $R^3$ is isopropyl or t-butyl.

In yet another embodiment, q, p and u are each 1, r and s are each 0, Z is a bond, C(O) Y is —NH— and X is —O—, A is a 5 or 6-membered heteroaryl, B is phenyl or a 5 or 6-membered heteroaryl, each occurrence of $R^1$ and $R^2$ is H, $R^3$ is isopropyl or t-butyl, and the compound of formula (I) contains at least one endocyclic double bond.

In a further embodiment, q, p and u are each 1, r and s are each 0, Z is a bond, W is —C(O)O—. Y is —NH— and X is —O—, A is a 5 or 6-membered heteroaryl, B is phenyl or a 5 or 6-membered heteroaryl, each occurrence of $R^1$ and $R^2$ is H, $R^3$ is isopropyl or t-butyl, and the bicyclic moiety of the compound of formula (I) contains one endocyclic double bond.

In one embodiment, q, p and u are each 1, r and s are each 0, Z is a bond, W is —S(O)$_2$—, Y is —NH— and X is —O—, A is a 5 or 6-membered heteroaryl, B is phenyl or a 5 or 6-membered heteroaryl, and $R^3$ is alkyl.

In another embodiment, q, p and u are each 1, r and s are each 0, Z is a bond, W is —S(O)$_2$—, Y is —NH— and X is —O—, A is a 5 or 6-membered heteroaryl, B is phenyl or a 5 or 6-membered heteroaryl, each occurrence of $R^1$ is H, and $R^3$ is alkyl.

In another embodiment, q, p and u are each 1, r and s are each 0, Z is a bond, W is S(O)$_2$—, Y is —NH— and X is —O—, A is a 5 or 6-membered heteroaryl, B is phenyl or a 5 or 6-membered heteroaryl, each occurrence of $R^1$ and $R^2$ is H, and $R^3$ is alkyl.

In still another embodiment, q, p and u are each 1, r and s are each 0, Z is a bond, W is —S(O)$_2$—, Y is —NH— and X is —O—, A is a 5 or 6-membered heteroaryl, B is phenyl or a 5 or 6-membered heteroaryl, each occurrence of $R^1$ and $R^2$ is H, and $R^3$ is isopropyl or t-butyl.

In yet another embodiment, q, p and u are each 1, r and s are each 0, Z is a bond, W is —C(O)O—, Y is —NH— and X is —O—, A is a 5 or 6-membered heteroaryl, B is phenyl or a 5 or 6-membered heteroaryl, each occurrence of $R^1$ and $R^2$ is H, is isopropyl or t-butyl, and the compound of formula (I) contains at least one endocyclic double bond.

In a further embodiment, q, p and u are each 1, r and s are each 0, Z is a bond, W is —C(O)O—, Y is —NH— and X is —O—, A is a 3 or 6-membered heteroaryl, B is phenyl or a 5 or 6-membered heteroaryl, each occurrence of Rt and $R^2$ is H, $R^2$ is isopropyl or t-butyl, and the bicyclic moiety of the compound of formula (I) contains one endocyclic double bond.

In one embodiment, the present invention provides compounds of Formula (I), wherein A, B, W, X, Y, Z, $R^3$, p, q, r, s and u, and each occurrence of $R^1$ and $R^2$ are selected independently of each other.

In another embodiment, a compound of formula in purified form.

In one another embodiment, a compound of for (I) has the formula:

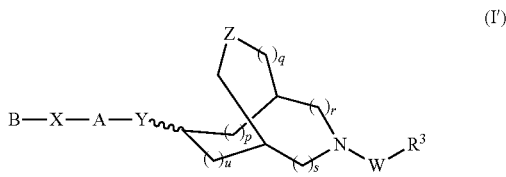

(I')

and pharmaceutically acceptable salts, solvates, esters, prodrugs and stereoisomers thereof, wherein:
W is a bond, —C(O)—O— or —S(O)$_2$—;
X is —O— or —NH—;
Y is —O—;
Z is a bond, —CH$_2$— or —O—;
A is a heteroaryl, which is unsubstituted or optionally substituted with up to 2 groups, which can be the same or different, and are selected from alkyl, halo and —O-alkyl, such that when Y is —O—, A is other than pyridyl;
B is aryl or a -5- or 6-membered heteroaryl group, each of which can be unsubstituted or optionally substituted with up to 3 groups, which can be the same or different, and are selected from: alkyl, heteroaryl, halo, —CN, —S(O)$_2$-alkyl and —S(O)$_2$-cycloalkyl;
$R^3$ is alkyl, -alkylene-aryl, -cycloalkyl, -alkylene-O-alkyl or haloalkyl, wherein a cycloalkyl group can be unsubstituted or substituted with an alkyl group;
$R^7$ is H;
p is 0, 1 or 2;
q is 0, 1 or 2;
r is 0, 1 or 2;
s is 0, 1 or 2; and
u is 0, 1 or 2.

one embodiment, for the compounds of formula (I'), W is a bond.

In another embodiment, for the compounds of formula (I'), W is —C(O)O—.

In another embodiment, for the compounds of formula (I'), W is —S—(O)$_2$—.

In another embodiment, W is a bond and $R^3$ is aryl, -alkylene-aryl or alkyl.

In another embodiment, W is a bond and $R^3$ is phenyl.
In another embodiment, W is a bond and $R^3$ is benzyl.
In one embodiment, for the compounds of formula (I'), $R^3$ is cycloalkyl or alkyl, wherein a cycloalkyl group is unsubstituted or optionally substituted with an alkyl group.

In another embodiment, for the compounds of formula (I'), $R^3$ is cyclopropyl, 1-methylcyclopropyl, isopropyl, 1-methylcyclobutyl, benzyl, —CH$_2$CH$_2$—O—CH$_3$ or —CF$_3$.

In one embodiment, for the compounds of formula (I'), the group —W—$R^3$ is —S(O)$_2$-cyclopropyl, —S(O)$_2$-cyclobutyl, —S(O)$_2$CF$_3$, —S(O)$_2$CH$_2$CH$_2$OCH$_3$, —C(O)O-cyclopropyl, —C(O)O-cyclobutyl, —C(O)O-(1-methylcyclopropyl), —C(O)O(1-methylcyclobutyl), —C(O)O-(1-methylcyclopropyl), —C(O)O-isopropyl or benzyl.

In one embodiment, for the compounds of formula (I'), X is —NH— or —O— and Y is —O—.

In another embodiment, for the compounds of formula (I'), X is —NH— and Y is —O—.

In another embodiment, for the compounds of formula (I'), X and Y are each —O—.

In another embodiment, for the compounds of formula (I'), A is -5 or -6-membered heteroaryl.

In another embodiment, for the compounds of formula (I'), A is:

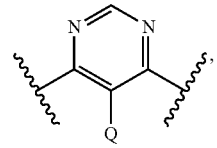

wherein Q is H, alkyl, halo or —O-alkyl.

In still another embodiment, for the compounds of formula (I'), A is:

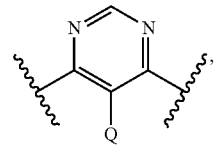

wherein Q is H, methyl, For methoxy.

In still another embodiment, for the compounds of formula (I'), A is:

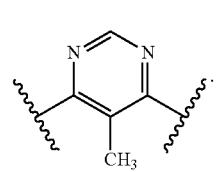

In one embodiment, for the compounds of formula (I'), B is phenyl or -5 or -6-membered heteroaryl.

In another embodiment, for lie compounds of formula (I'), B is pyridyl, which is unsubstituted or optionally substituted with up to alkyl groups.

In another embodiment, for the compounds of formula (I'), B is phenyl, which is unsubstituted or optionally substituted with up to 3 groups, each independently selected from alkyl, —CN, —S(O)$_2$-alkyl, —S(O)$_2$-cycloalkyl, heteroaryl and halo.

In still another embodiment, for the compounds of formula (I'), B is phenyl, which is unsubstituted or optionally substituted with up to 3 groups, each independently selected from methyl, thiazolyl, —CN, —Cl, —F, —S(O)₂CH₃ and —S(O)₂-cyclopropyl.

In one embodiment, for the compounds of formula (I'), X is —NH— or —O—; Y is —O—; A is:

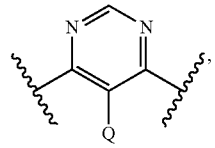

wherein Q is H, alkyl, halo or —O-alkyl: and B is phenyl or -5 or -6-membered heteroaryl.

In another embodiment, for the compounds of formula (I'), X is —NH— or —O—; Y is —O—; A is:

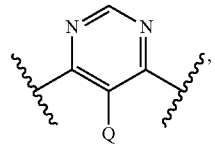

wherein Q is H, alkyl, halo or —O-alkyl; and B is phenyl, which is unsubstituted or optionally substituted with up to 3 groups, each independently selected from alkyl, —CN, —S(O)₂-alkyl, —S(O)₂-cycloalkyl, heteroaryl and halo.

In another embodiment, for the compounds of formula (I'), X is —NH— or Y is —O—; A is:

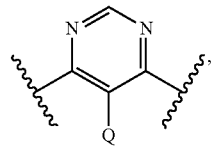

wherein Q is H, alkyl, halo or —O-alkyl; and B is pyridyl, which is unsubstituted or optionally substituted with up to 3 alkyl groups, In one embodiment, for the compounds of formula (I'), X and Y are each —O—; Y is —O—; A is:

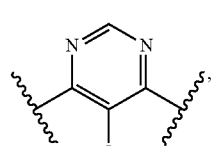

wherein Q is H, alkyl, halo or —O-alkyl; and B is phenyl or 6-membered heteroaryl, In another embodiment, for the compounds of formula (I'), X and Y are each —O—; Y is —O—; A is:

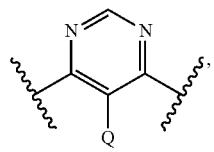

wherein Q is H, alkyl, halo or —O-alkyl; and B is phenyl, which is unsubstituted or optionally substituted with up to 3 groups, each independently selected from alkyl, —CN, —S(O)₂-alkyl, —S(O)₂-cycloalkyl, heteroaryl and halo.

In another embodiment, for the compounds of formula (I'), X and Y are each Y is —O—; A is:

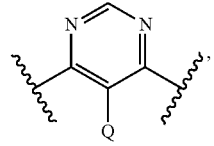

wherein Q is H, alkyl, halo or —O-alkyl; and B is pyridyl, which is unsubstituted or optionally substituted with up to 3 alkyl groups.

In one embodiment, the group B—X-A-Y— is:

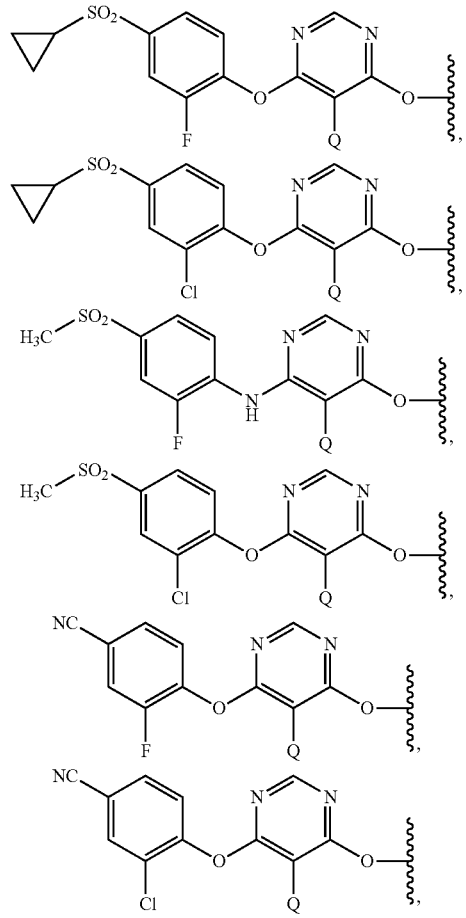

-continued
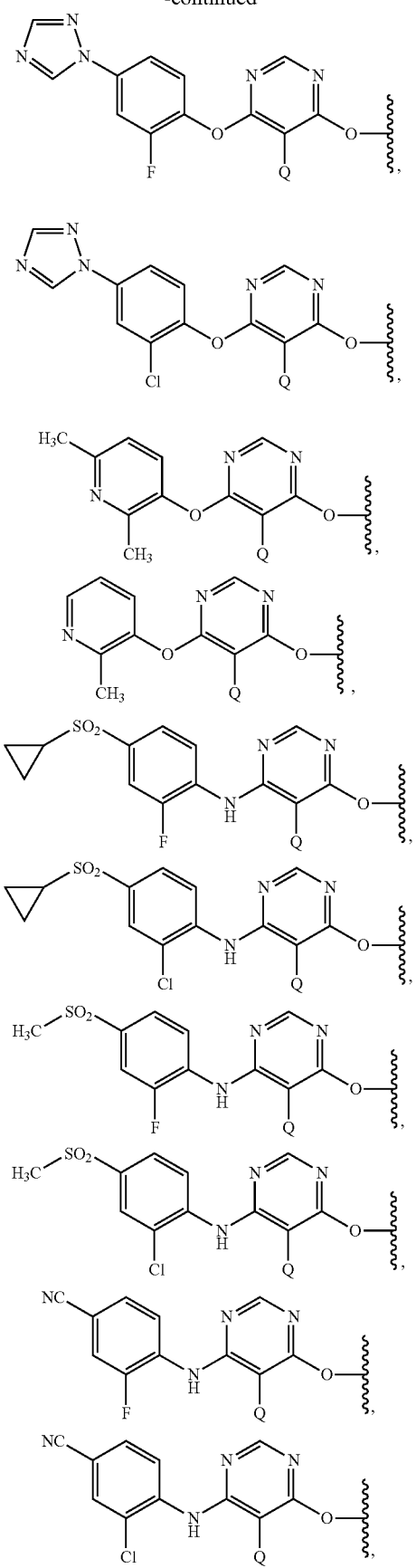
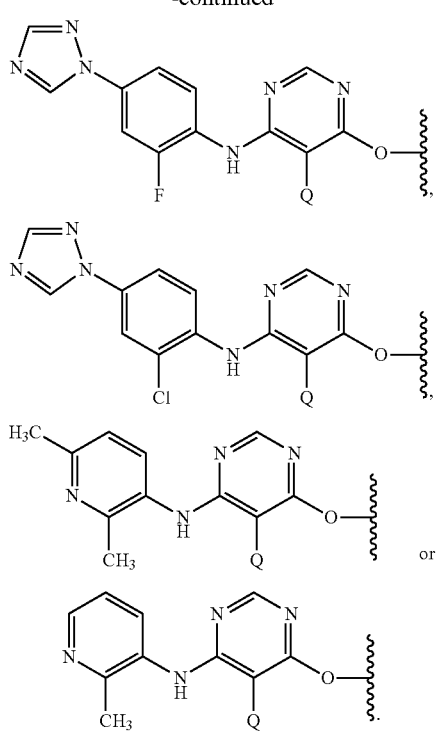
wherein Q is H, alkyl, halo or —O-alkyl.
In another embodiment, the group B—X-A-Y— is:
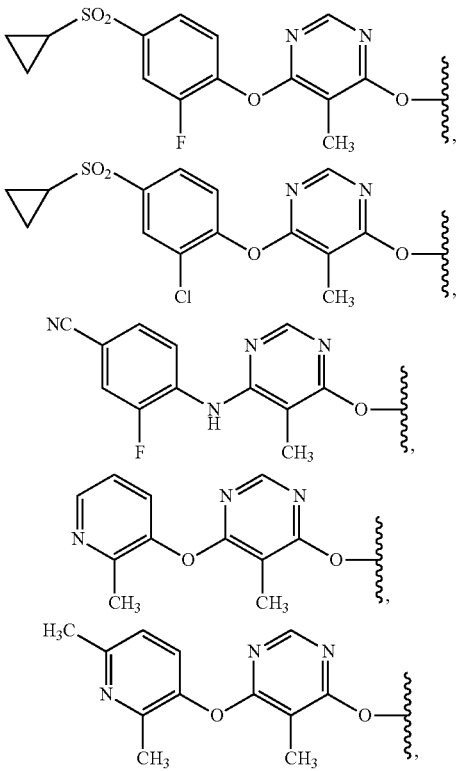

-continued
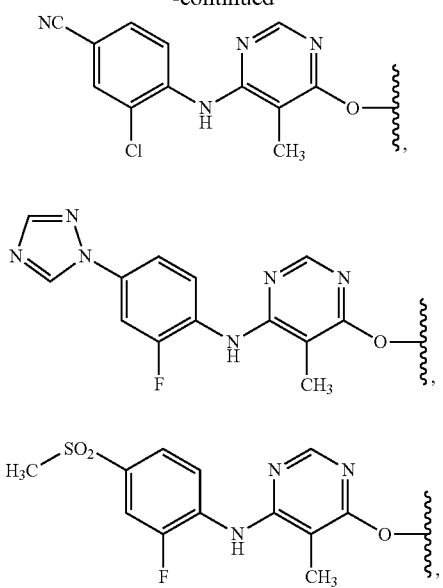
In another embodiment, the group B—X-A-Y— is:
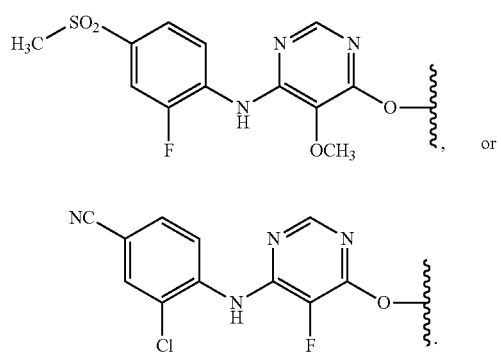
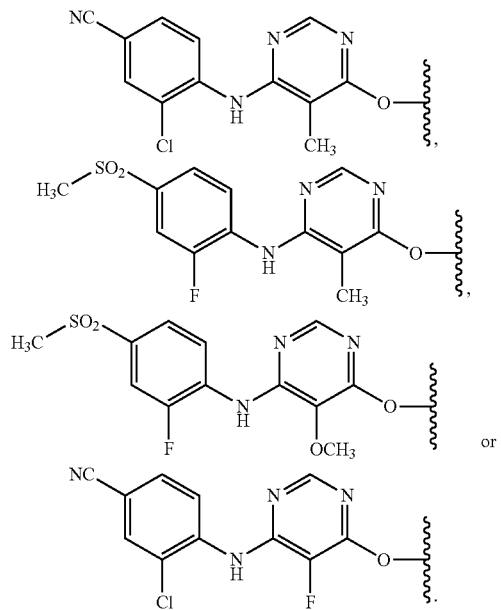
In another embodiment, the group B—X-A-Y— is:
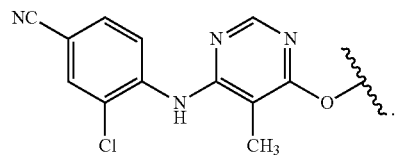 [SMILES: *Oc1ncnc(Nc2ccc(C#N)cc2Cl)c1C]
In another embodiment, the group B—X-A-Y— is:
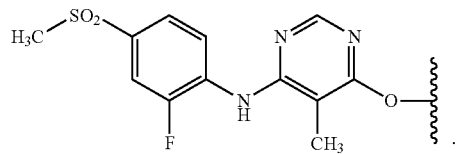 [SMILES: *Oc1ncnc(Nc2ccc(S(C)(=O)=O)cc2F)c1C]
In another embodiment, the group B—X-A-Y— is:
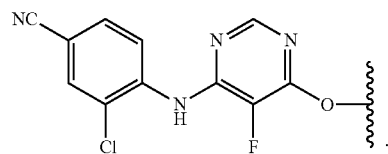 [SMILES: *Oc1ncnc(Nc2ccc(C#N)cc2Cl)c1F]
In another embodiment, the group B—X-A-Y— is
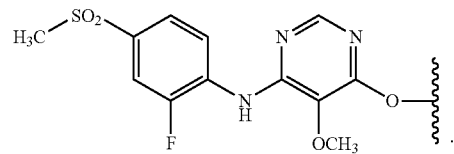 [SMILES: *Oc1ncnc(Nc2ccc(S(C)(=O)=O)cc2F)c1OC]
In another embodiment, the group:
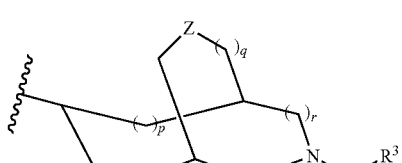
is:
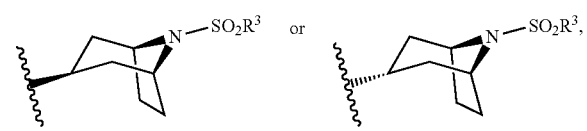
or a mixture thereof.

In still another embodiment, the group:
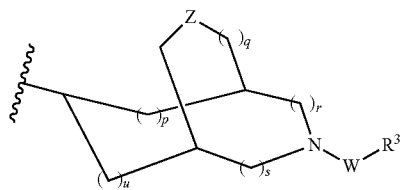
is:
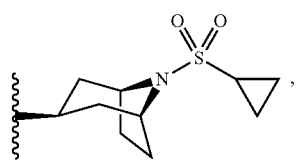
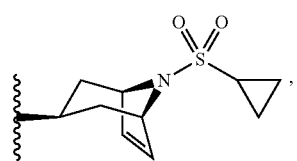
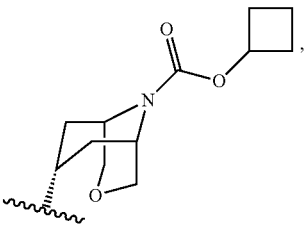
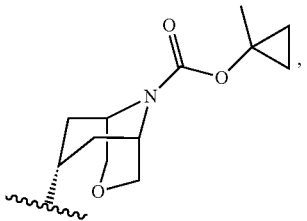
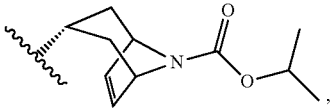
-continued
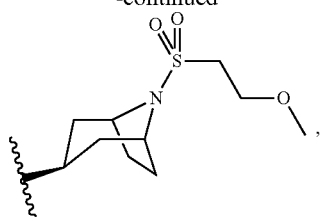
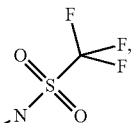
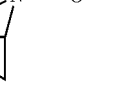
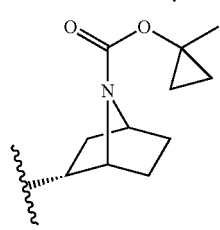
or
In one embodiment, the group —B—X-A-Y— is:
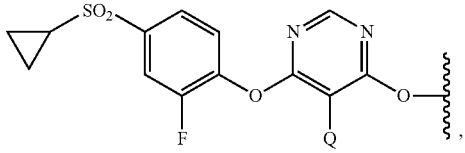
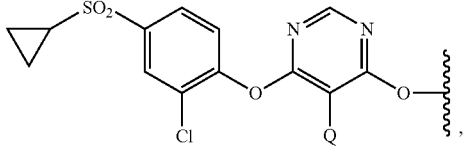
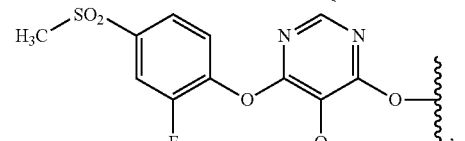
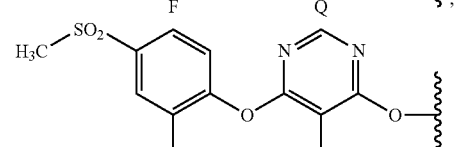
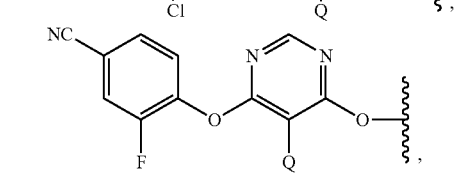

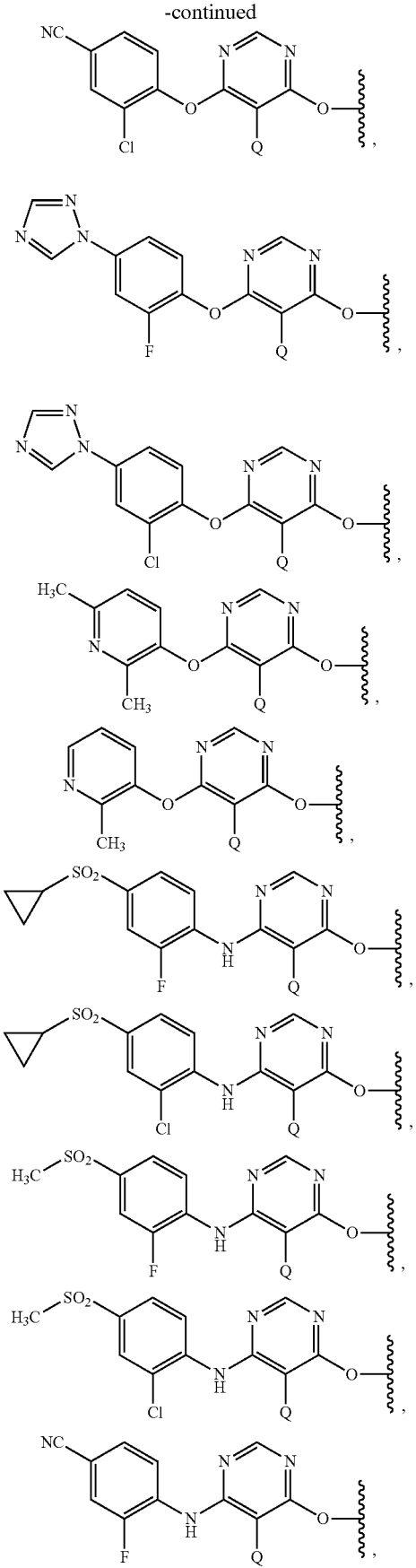
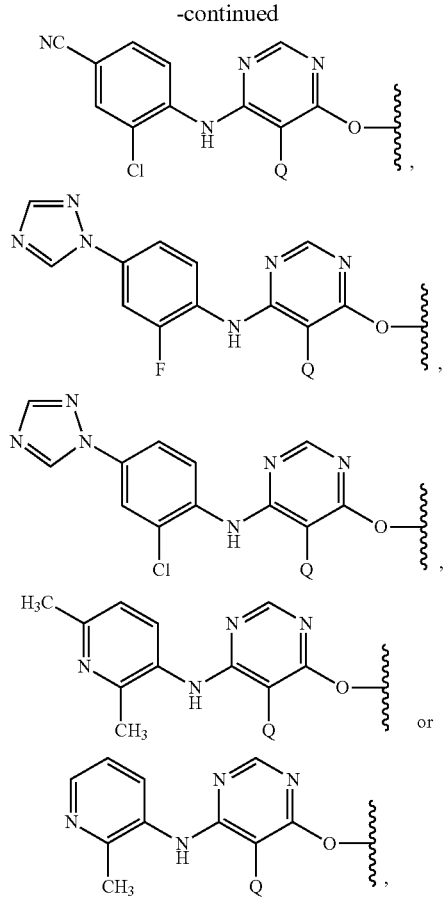
wherein Q is H, alkyl, halo or —O-alkyl, and the group:
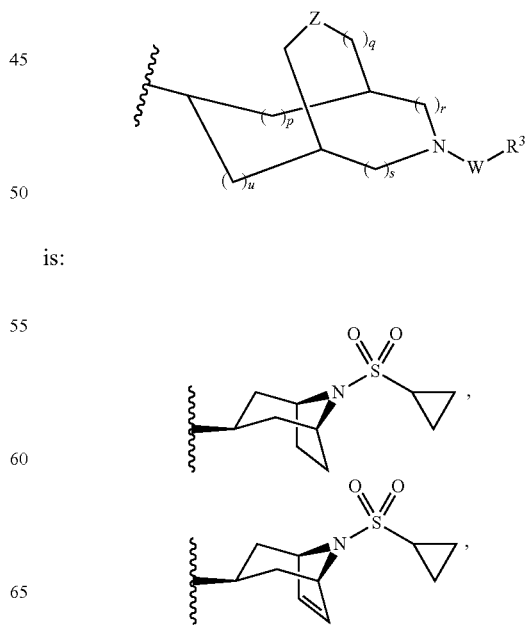
is:

-continued
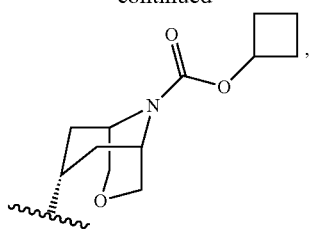
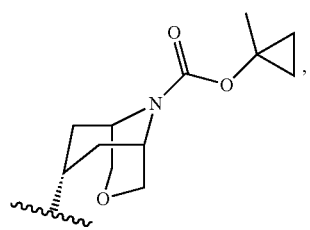
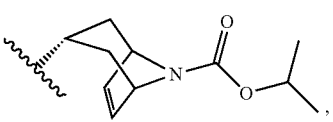
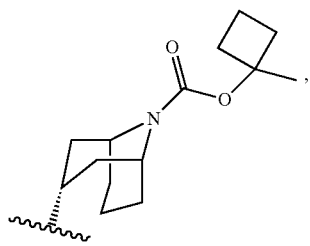
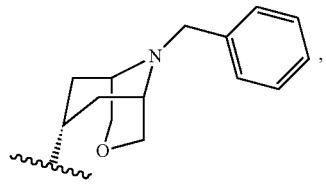
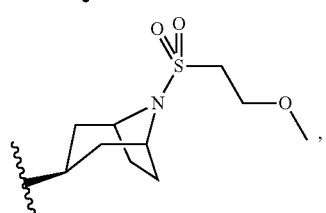
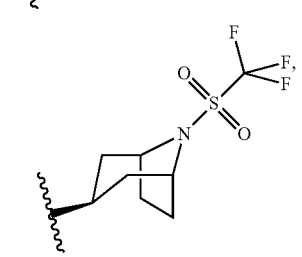
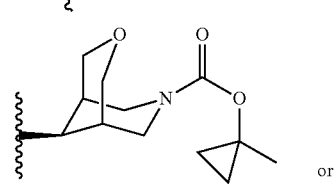 or
-continued
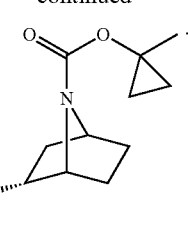
In one embodiment, the group —B—X-A-Y— is:
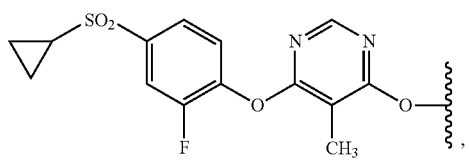
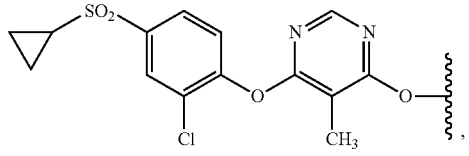
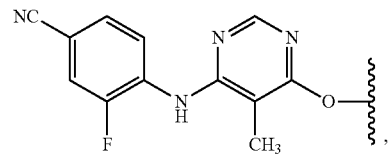
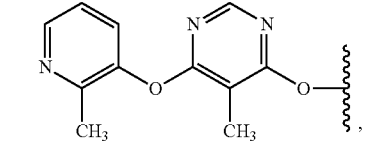
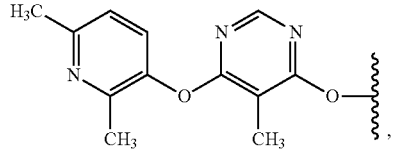
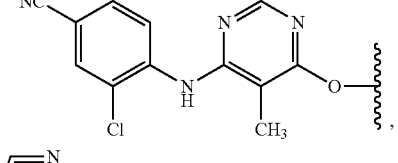
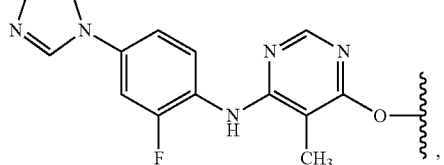
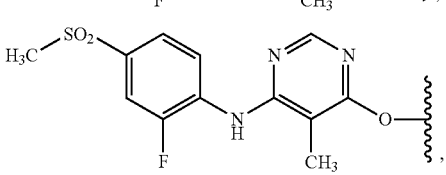

-continued
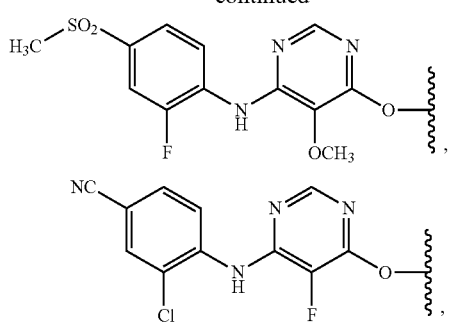, or
and the group:
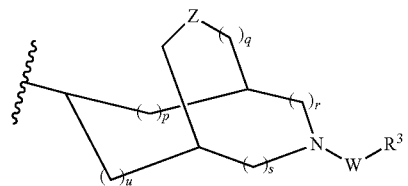
is:
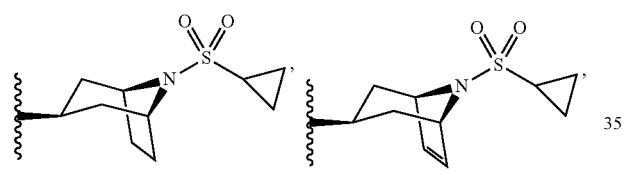
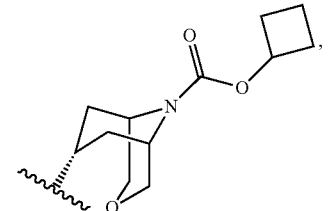
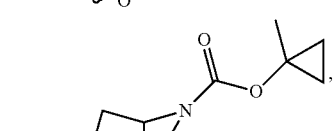
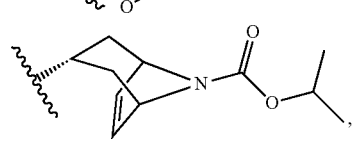
-continued
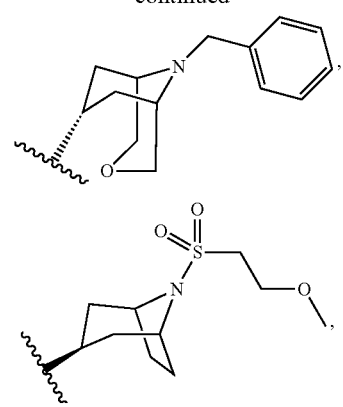
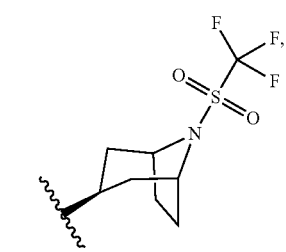
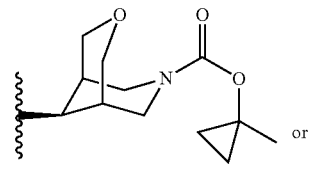
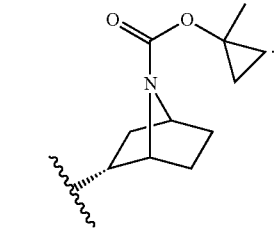
In another embodiment, the group —B—X-A-Y— is:
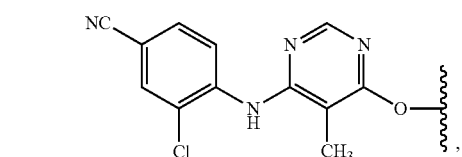
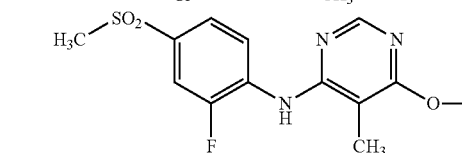
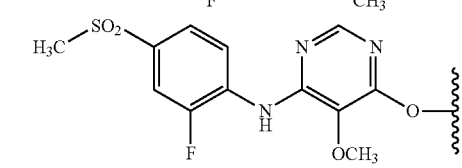 or -continued
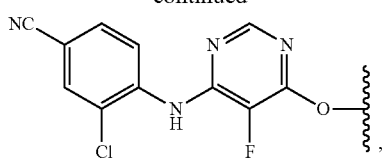
and the group:
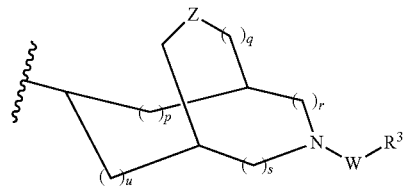
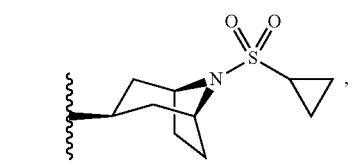
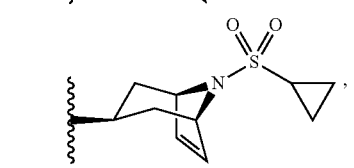
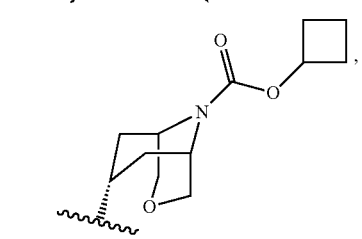
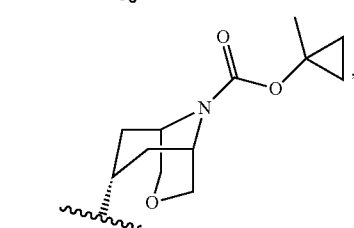
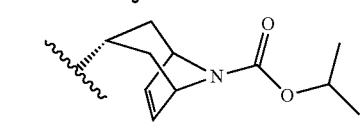
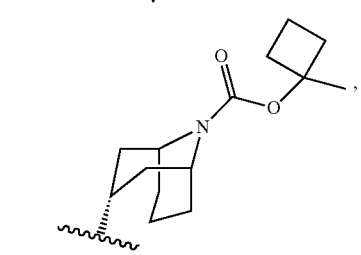
-continued
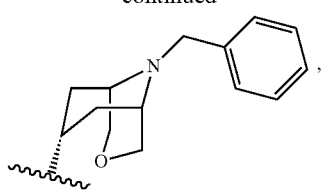
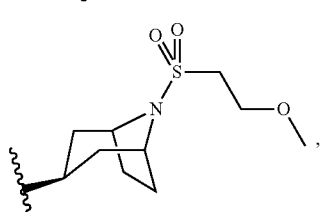
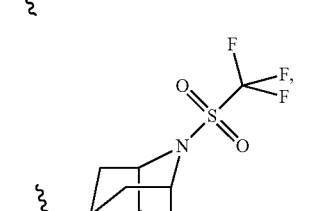
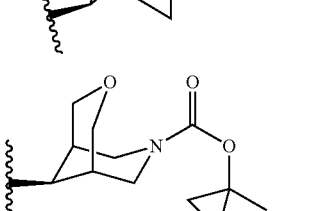
or
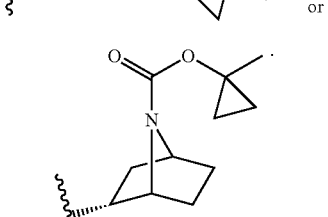
In another embodiment, the group —B—X-A-Y— is:
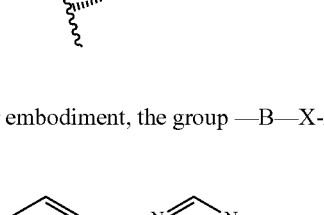
and the group:
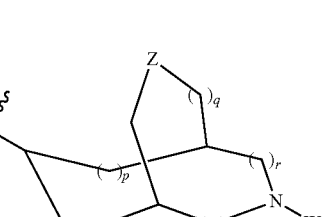

is:
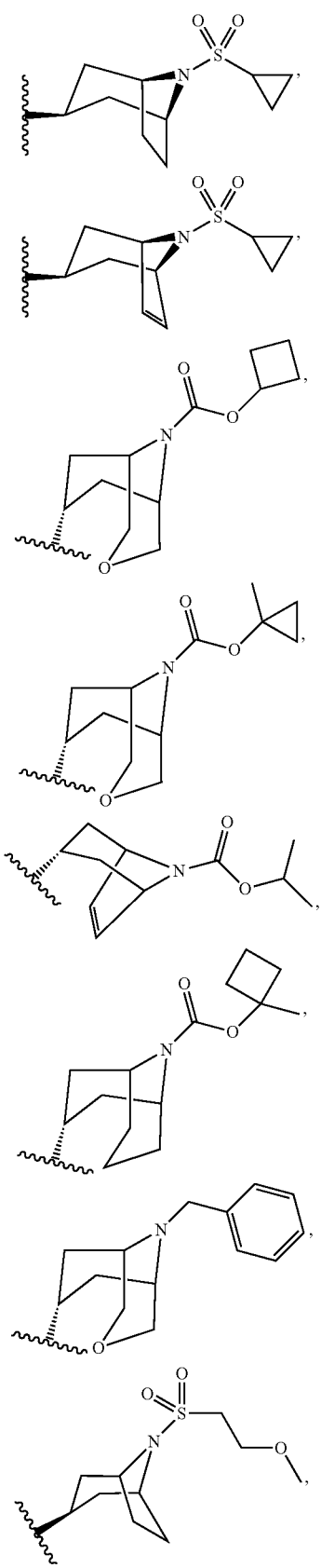
-continued
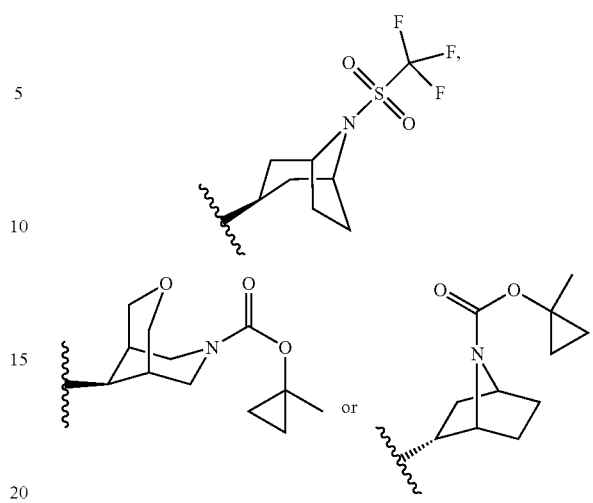
In another embodiment, the group —B—X-A-Y— is:
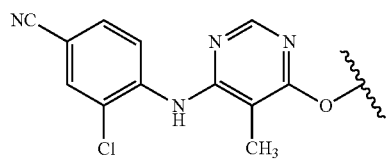
and the group:
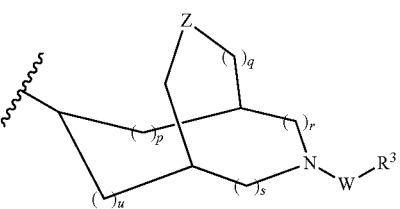
is:
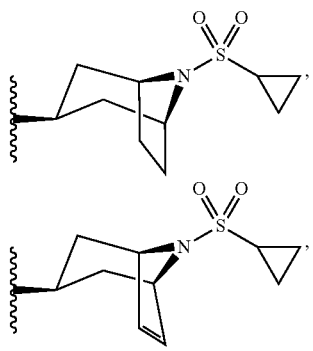

95
-continued
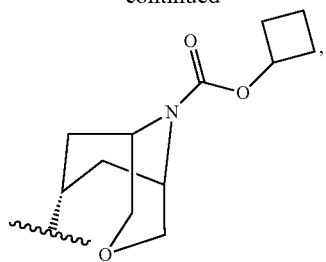
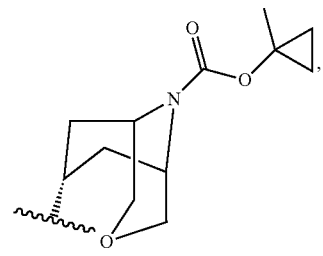
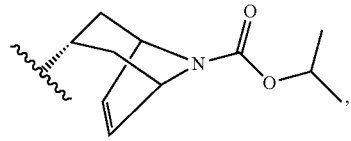
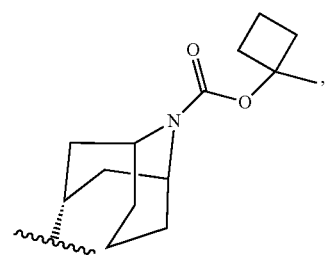
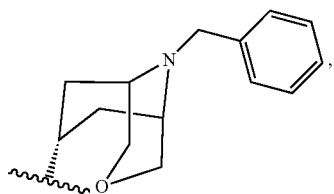
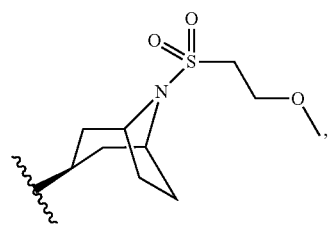
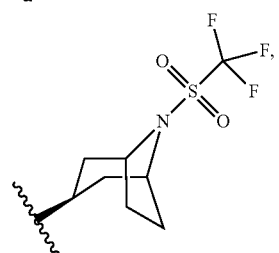
96
-continued
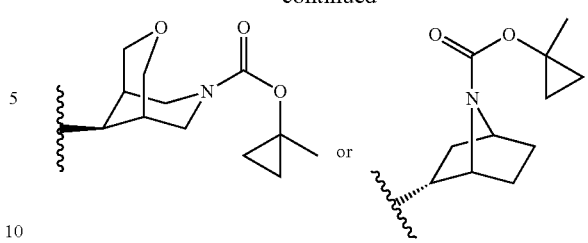
In another embodiment, the group 43-X-A-Y— is:
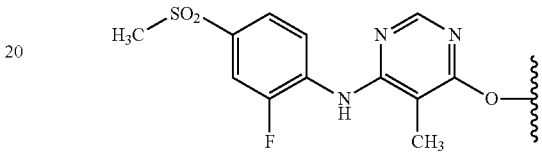
and the group:
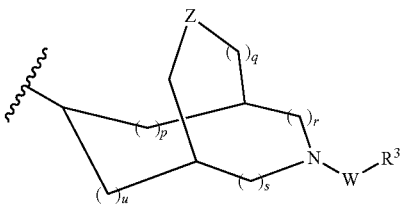
is:
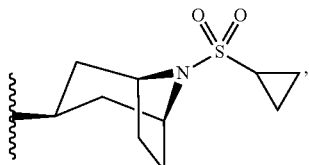
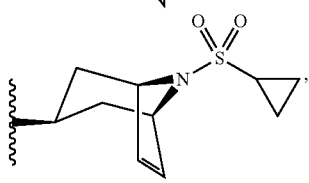
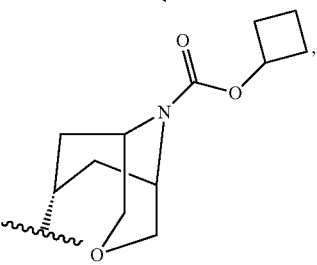

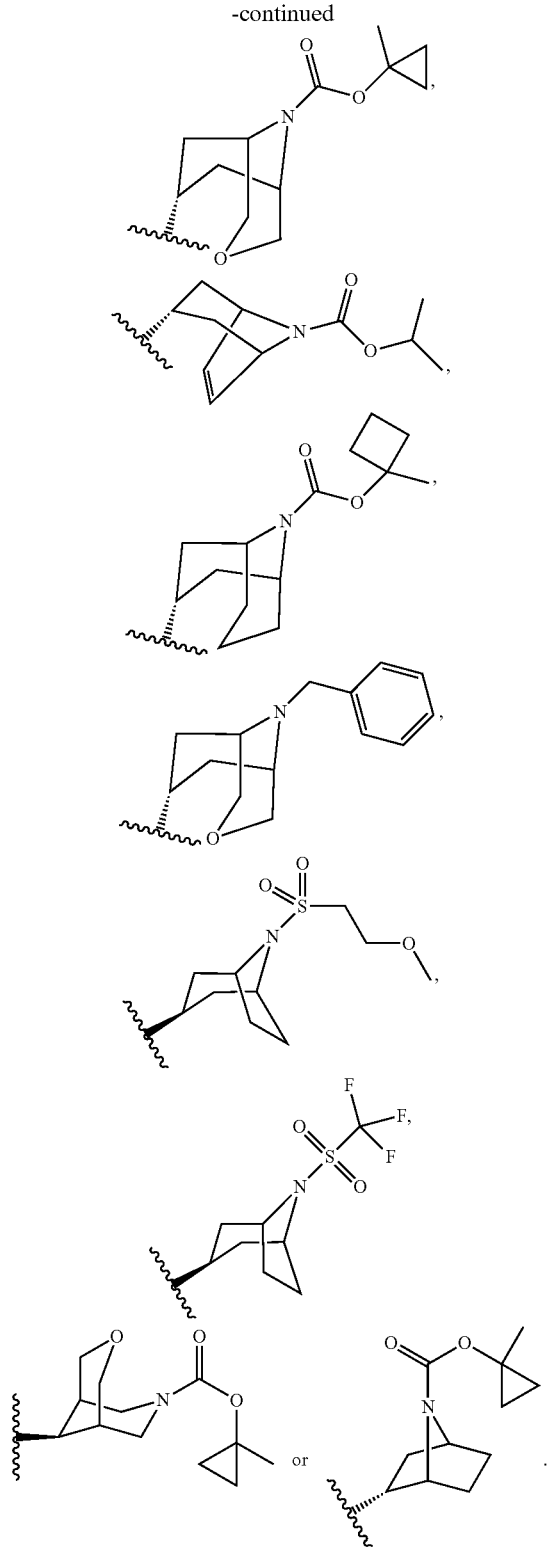

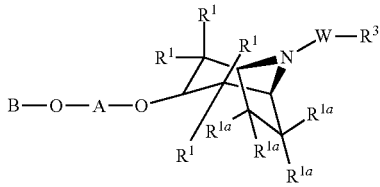

wherein $R^1$, A, B and $R^3$ are defined above for the compounds of formula (I), W is —C(O)O— or —S(O)$_2$—, and each occurrence of $R^1$ is independently selected from H, halo or alkyl.

In one embodiment, W is —C(O)—.

In another embodiment, W is —S(O)$_2$—.

In still another embodiment, each occurrence of $R^1$ is H.

In another embodiment, each occurrence of $R^2$ is H.

In another embodiment, at least one occurrence of $R^2$ is halo.

In a further embodiment, at least one occurrence of $R^2$ is F.

In one embodiment, $R^3$ is alkyl.

In another embodiment, $R^3$ is cycloalkyl.

In one embodiment, $R^1$ is isopropyl or t-butyl.

In another, $R^3$ is cyclopropyl.

In another embodiment, W is —C(O)— and $R^3$ is alkyl.

In yet another embodiment, W is —S(O)$_2$— and $R^3$ is cycloalkyl.

In another embodiment, A and B are each independently a 5 or 6-membered heteroaryl.

In still another embodiment, A is pyrimidinyl and B is pyridyl.

In yet another embodiment, the group —O-A-O—B is:

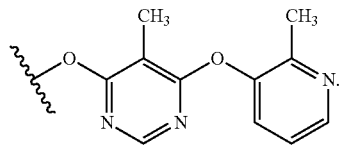 [SMILES: *Oc1ncnc(Oc2cccnc2C)c1C]

In a further embodiment, the group —O-A-O—B is:

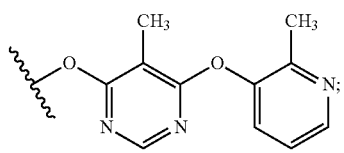 [SMILES: *Oc1ncnc(Oc2cccnc2C)c1C]

W is —C(O)O—; and $R^3$ is alkyl,

In another embodiment, the group —O-A-O—B is:

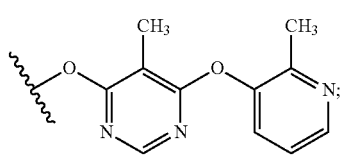 [SMILES: *Oc1ncnc(Oc2cccnc2C)c1C]

W is —S(O)$_2$— and $R^3$ is cycloalkyl.

In one embodiment, a compound of formula (I) has the formula:

In one embodiment, the present invention provides compounds of Formula (I'), wherein A, B, W, X, Y, Z, $R^3$, p, q, r, s and u are selected independently of each other.

In another embodiment, a compound of formula (I') is in purified form.

In one embodiment, a compound of formula (I) has the formula:

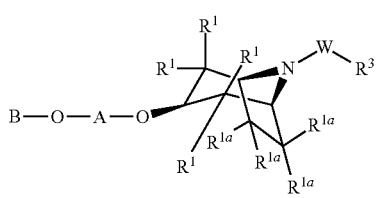 (Ib)

wherein $R^1$, A, B and $R^3$ are defined above for the compounds of formula (I), W is —C(O)O— or —S(O)$_2$—, and each occurrence of $R^{1a}$ is independently selected from H, halo or alkyl.

In one embodiment, W is —C(O)—.
In another embodiment, W is —S(O)$_2$—.
In still another embodiment, each occurrence of $R^1$ is H.
In another embodiment, each occurrence of $R^2$ is H.
In another embodiment, at least one occurrence of $R^2$ is halo.
In a further embodiment, at least one occurrence of $R^2$ is F.
In one embodiment, $R^3$ is alkyl.
In another embodiment, $R^3$ is cycloalkyl.
In one embodiment, $R^3$ is isopropyl or t-butyl.
In another, $R^3$ is cyclopropyl.
In another embodiment, W is —C(O)— and $R^3$ is alkyl.
In yet another embodiment, W is —S(O)$_2$— and $R^3$ is cycloalkyl.
In another embodiment, A and B are each independently a 5 or 6-membered heteroaryl.
In still another embodiment, A is pyrimidinyl and B is pyridyl.
In yet another embodiment, the soup —O-A-O—B is:

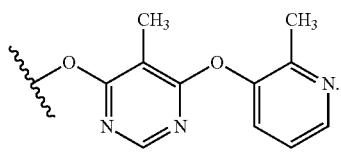 [SMILES: *Oc1ncnc(Oc2cccnc2C)c1C]

In a further embodiment, the group —O-A-O—B is:

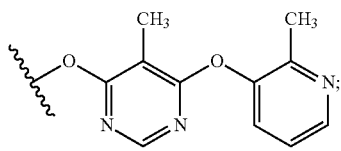 [SMILES: *Oc1ncnc(Oc2cccnc2C)c1C]

W is —C(O)O—; and $R^3$ is alkyl.
In another embodiment, the group —O-A-O—B is:

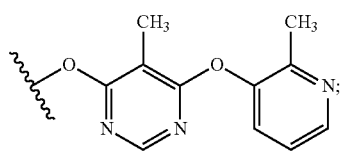 [SMILES: *Oc1ncnc(Oc2cccnc2C)c1C]

W is —S(O)$_2$—; and $R^3$ is cycloalkyl.
In one embodiment, a compound of formula (I) has the formula:

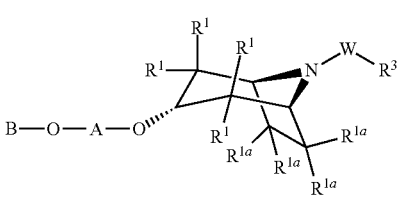 (Ic)

wherein $R^1$, A, B and $R^3$ are defined above for the compounds of formula (f), W is —C(O)O— or —S(O)$_2$—, and each occurrence of $R^{1a}$ is independently selected from H, halo or alkyl, In one embodiment, W is —C(O)—.
In another embodiment, W is —S(O)$_2$—.
In still another embodiment, each occurrence of $R^1$ is H.
In another embodiment, each occurrence of $R^2$ is H.
In another embodiment, at least one occurrence of $R^2$ is halo.
In a further embodiment, at least one occurrence of $R^2$ is F.
In one embodiment, $R^3$ is alkyl.
In another embodiment, $R^3$ is cycloalkyl.
In one embodiment, $R^3$ is isopropyl or t-butyl.
In another, $R^3$ is cyclopropyl.
In another embodiment, W is —C(O)— and $R^3$ is alkyl.
In yet another embodiment, W is —S(O)$_2$— and $R^3$ is cycloalkyl.
In another embodiment, A and B are each independently a 5 or 6-membered heteroaryl.
In still another embodiment, A is pyrimidinyl and B is pyridyl.
In yet another embodiment, the group —O-A-O—B is:

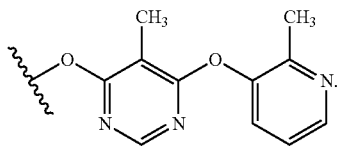 [SMILES: *Oc1ncnc(Oc2cccnc2C)c1C]

In a further embodiment, the group —O-A-O—B is:

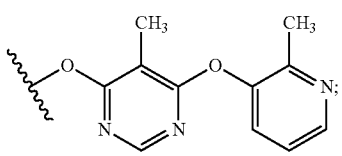 [SMILES: *Oc1ncnc(Oc2cccnc2C)c1C]

W is —C(O)O—; and $R^3$ is alkyl.
In another embodiment, the group —O-A-O—B is:

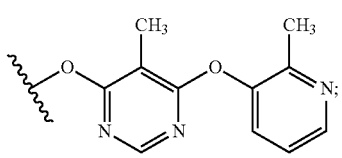 [SMILES: *Oc1ncnc(Oc2cccnc2C)c1C]

W is —S(O)$_2$—; and $R^3$ is cycloalkyl.
In one embodiment, a compound of formula (I) has the formula:

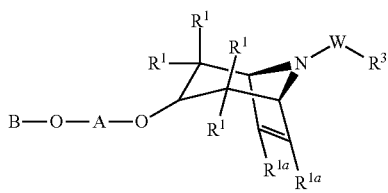

(Id)

wherein A, B and $R^3$ are defined above for the compounds of formula (V is —C, O)O— or —S(O)$_2$—; and each occurrence of $R^{1a}$ is independently selected from H, halo or alkyl.

In one embodiment, W is —C(O)—.
In another embodiment, W is —S(O)$_2$—.
In still another embodiment, each occurrence of $R^1$ is H.
In another embodiment, each occurrence of $R^2$ is H.
In another embodiment, at least one occurrence of R is halo.
In a further embodiment, at least one occurrence of $R^2$ is F.
In one embodiment, $R^3$ is alkyl.
In another embodiment, $R^3$ is cycloalkyl.
In one embodiment, $R^3$ is isopropyl or t-butyl.
In another, $R^3$ is cyclopropyl.
In another embodiment, W is —C(O)— and $R^3$ is alkyl.
In yet another embodiment, W is —S(O)$_2$— and $R^3$ is cycloalkyl.
In another embodiment, A and B are each independently a 5 or 6-membered heteroaryl.
In still another embodiment, A is pyrimidinyl and B is pyridyl.
In yet another embodiment, the group —O-A-O—B is:

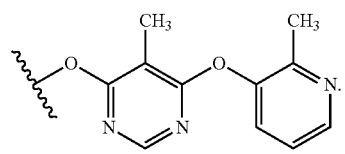 [SMILES: *Oc1ncnc(Oc2cccnc2C)c1C]

In a further embodiment, the group —O-A-O—B is:

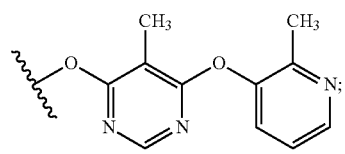 [SMILES: *Oc1ncnc(Oc2cccnc2C)c1C]

W is —C(O)O—; and $R^3$ is alkyl.
In another embodiment, the group —O-A-O—B is:

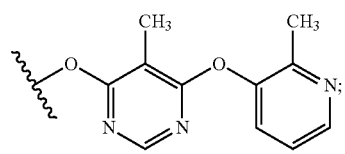 [SMILES: *Oc1ncnc(Oc2cccnc2C)c1C]

W is —S(O)$_2$—; and $R^3$ is cycloalkyl.
In one embodiment, a compound of formula (I) has the formula:

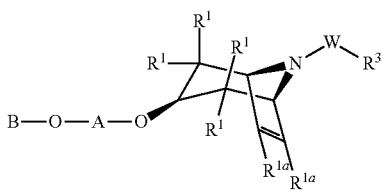

(Ie)

wherein $R^1$, A, B and $R^3$ are defined above for the compounds of formula (I), W is —C(O)O— or —S(O)$_2$—, and each occurrence of $R^{1a}$ is independently selected from H, halo or alkyl.

In one embodiment, W is —C(O)—.
In another embodiment, W is —S(O)$_2$—.
In still another embodiment, each occurrence of $R^1$ is H.
In another embodiment, each occurrence of $R^2$ is H.
In another embodiment, at least one occurrence of $R^2$ is halo.
In a further embodiment, at least one occurrence of $R^2$ is F.
In one embodiment, $R^3$ is alkyl.
In another embodiment, $R^3$ is cycloalkyl.
In one embodiment, $R^3$ is isopropyl or t-butyl.
In another, $R^3$ is cyclopropyl.
In another embodiment, W is —C(O)— and $R^1$ is alkyl.
In yet another embodiment, W is —S(O)$_2$— and $R^3$ is cycloalkyl.
In another embodiment, A and B are each independently a 5 or 6-membered heteroaryl.
In still another embodiment, A is pyrimidinyl and B is pyridyl.
In yet another embodiment, the group —O-A-O—B is:

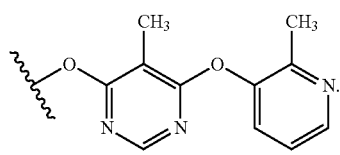 [SMILES: *Oc1ncnc(Oc2cccnc2C)c1C]

In a further embodiment, the group —O-A-O—B is:

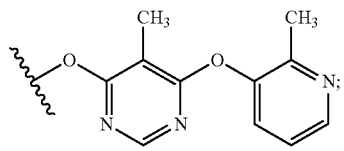 [SMILES: *Oc1ncnc(Oc2cccnc2C)c1C]

W is —C(O)O—; and $R^3$ is alkyl.
In another embodiment, the group —O-A-O—B is:

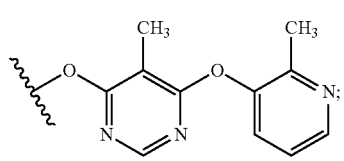 [SMILES: *Oc1ncnc(Oc2cccnc2C)c1C]

W is —S(O)$_2$—; and $R^3$ is cycloalkyl.
In one embodiment, a compound of formula (I) has the formula:

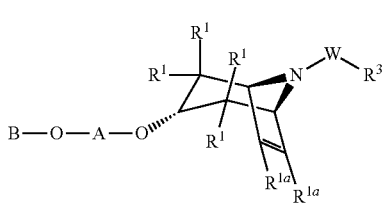
(If)

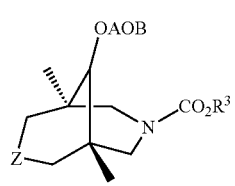
(Ig)

wherein $R^1$, A, B and $R^3$ are defined above for the compounds of formula (I), W is —C(O)O— or —S(O)$_2$—, and each occurrence of $R^{1a}$ is independently selected from H, halo or alkyl.

In one embodiment, W is —C(O)—.
In another embodiment, W is —S(O)$_2$—.
In still another embodiment, each occurrence of $R^1$ is H.
In another embodiment, each occurrence of $R^2$ is H.
In another embodiment, at least one occurrence of $R^2$ is halo.
In a further embodiment, at least one occurrence of $R^2$ is F.
In one embodiment, $R^3$ is alkyl.
In another embodiment, $R^3$ is cycloalkyl.
In one embodiment, $R^3$ is isopropyl or t-butyl.
In another, $R^3$ is cyclopropyl.
In another embodiment, W is —C(O)— and $R^3$ is alkyl.
In yet another embodiment, W is —S(O)$_2$— and $R^3$ is cycloalkyl.
In another embodiment, A and B are each independently a 5 or 6-membered heteroaryl.
In still another embodiment, A is pyrimidinyl and B is pyridyl.
In yet another embodiment, the group —O-A-O—B is:

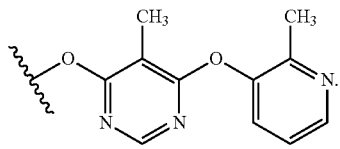 [SMILES: *Oc1ncnc(Oc2cccnc2C)c1C]

In a further embodiment, the group —O-A-O—B is:

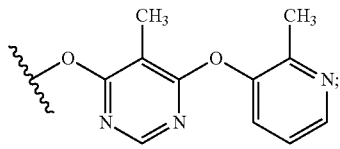 [SMILES: *Oc1ncnc(Oc2cccnc2C)c1C]

W is —C(O)O—; and $R^3$ is alkyl.
In another embodiment, the group —O-A-O—B is:

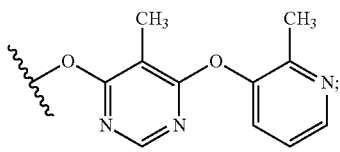 [SMILES: *Oc1ncnc(Oc2cccnc2C)c1C]

W is —S(O)$_2$—; and $R^3$ is cycloalkyl.
In one embodiment, the compounds of formula (I) have the formula (Ig):

wherein A, B, Z and $R^3$ are defined above for the compounds of formula (I).

In one embodiment; $R^3$ is alkyl.
In another embodiment, Z is —N($R^{10}$)—.
In another embodiment, Z is —S—.
In still another embodiment, Z is —S—.
In another embodiment, Z is —C($R^1$)$_2$—.
In yet another embodiment, Z is —CH$_2$—.
In another embodiment, A and B are each independently a 5 or 6-membered heteroaryl.
In another embodiment, A is pyrimidinyl and B is pyridyl.
In a further another embodiment, the group —O-A-O—B

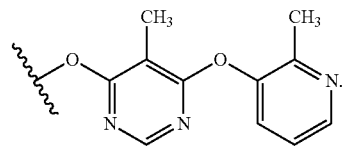 [SMILES: *Oc1ncnc(Oc2cccnc2C)c1C]

In one embodiment, the group —O-A-O—B is:

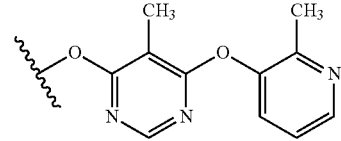 [SMILES: *Oc1ncnc(Oc2cccnc2C)c1C]

and $R^3$ is alkyl.
In one embodiment, the present invention provides compounds of Formula (I), wherein A, B, W, X, Y, Z, R, p, q, r, s, u, each occurrence of $R^1$, each occurrence of $R^2$, and $R^3$ are selected independently of each other.
In one embodiment, the compounds of formula (I) have the formula (Ih):

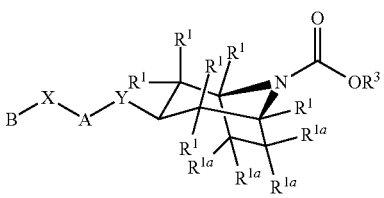
(Ih)

or a pharmaceutically acceptable salt, solvate, ester, prodrug or stereoisomer thereof, wherein A, B, X, Y, $R^3$ and each occurrence of $R^1$ are defined above for the compounds of for (I), and $R^{1a}$ is H, halo or alkyl.

In another embodiment, the compounds of formula (I) have the formula (Ij):

(Ij)

or a pharmaceutically acceptable salt, solvate, ester, prodrug or stereoisomer thereof, wherein A, B, X, Y, $R^3$ and each occurrence of $R^1$ are defined above for the compounds of formula (I), and $R^{1a}$ is H, halo or alkyl.

In another embodiment, the compounds of formula (I) have the formula (Ik):

(Ik)

or a pharmaceutically acceptable salt, solvate, ester, prodrug or stereoisomer thereof, wherein A, B, X, Y, $R^3$ and each occurrence of $R^1$ are defined above for the compounds of formula (I), and $R^{1a}$ is H, halo or alkyl.

In another embodiment, the compounds of formula (I) have the formula (Im):

(Im)

or a pharmaceutically acceptable salt, solvate, ester, prodrug or stereoisomer thereof, wherein A, B, X, Y, $R^3$ and each occurrence of $R^1$ are defined above for the compounds of formula (I), and $R^{1a}$ is H, halo or alkyl.

In one embodiment, a compound of formula (I) is in purified form.

In another embodiment, the compounds of formula (I) have the formula (In):

(In)

or a pharmaceutically acceptable salt, solvate, ester, prodrug or stereoisomer thereof, wherein A is 6-membered heteroaryl;
B is phenyl or 6-membered heteroaryl;
W is a bond, —C(O)O— or —S(O)$_2$—;
X is —O— or —NH—;
Y is —O—;
Z is a bond or —O—;
$R^3$ is alkyl, -(alkylene)$_t$-cycloalkyl, haloalkyl or aryl, wherein a cycloalkyl group can be unsubstituted or optionally substituted with an alkyl group, such that when W is —S(O)$_2$—, then $R^3$ is other than alkyl; and
q is 0, 1 or 2.

In one embodiment, a compound of formula (In) is in purified form.

In one embodiment, the compounds of formula (I) have the formula:

(Io)

wherein G is —N— or —CH—;
W is —C(O)O— or —S(O)$_2$—;
X is —O— or —NH—;
Z is a bond or —O—;
$R^3$ is alkyl or cycloalkyl;
$R^{20}$ represents up to 3 optional ring substituents, which are each independently selected from methyl, —F, —CN, —S(O)$_2$-alkyl and —S(O)$_2$-cycloalkyl, such that when G is —N—, an $R^{20}$ group cannot be attached to G, and when G is —CH—, than an $R^{20}$ group can be attached to G; and
q is 0 or 1.

In one embodiment, W is —S(O)$_2$— and $R^3$ is cycloalkyl.

In another embodiment, W is —C(O)O— and $R^3$ is alkyl or cycloalkyl,

In another embodiment, G is X is —CH—; X is —NH—; q is 1; Z is a bond; W is —S(O)$^2$—; and $R^3$ is cycloalkyl.

In another embodiment, G is —CH—; X is —NH—, q is 1; Z is a bond; W is —S(O)$^2$—; $R^3$ is cycloalkyl; and two $R^{20}$ groups are present.

In still another embodiment, G is —CH—; X is —NH—, q is 1; Z is a bond; W is —S(O)$^2$—; $R^3$ is cycloalkyl; and two $R^{20}$ groups are present, wherein one of the $R^{20}$ groups is —F or —Cl and the other is —CN.

In yet another embodiment, G is —CH—; X is —NH—, q is 1; Z is a bond; W is —S(O)$^2$—; $R^3$ is cyclopropyl or cyclobutyl; and two $R^{20}$ groups are present, wherein one of the $R^{20}$ groups is —F or —Cl and the other is —CN.

In one embodiment, the present invention provides compounds of Formula (Io), wherein G, W, X, Z, $R^3$, $R^{20}$ and q are selected independently of each other.

In another embodiment, a compound of formula (Io) is in purified form.

The Bicyclic Heterocycle Derivatives of Formula (II)

The present invention further provides Bicyclic Heterocycle Derivatives of Formula (II):

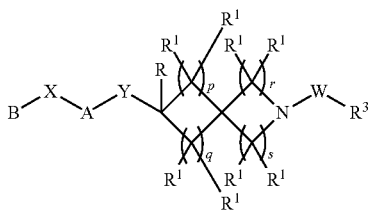

(II)

and pharmaceutically acceptable salts, solvates, esters, prodrugs and stereoisomers thereof, wherein A, B, X, Y Z, R, $R^1$, $R^2$, $R^3$, p, q, r and s are defined above for the compounds of formula (II).

In one embodiment, W is —C(O)O—.
In another embodiment, W is a bond.
In another embodiment, W is —C(O)—.
In still another embodiment, W is —S(O)$_2$—.
In yet another embodiment, W is —S(O)$_2$N($R^{10}$)—.
In a further embodiment, W is —C(O)N($R^{10}$)—.
In one embodiment, X is —C($R^1$)$_2$—.
In another embodiment, X is —O—.
In another embodiment, X is —S—.
In yet another embodiment, X is —N($R^{10}$).
In one embodiment, Y is —C($R^1$)$_2$—.
In another embodiment, Y is —O—.
In another embodiment, Y is —S—.
In yet another embodiment, Y is —N($R^{10}$)—.
In another embodiment, X and Y are each —O—.
In another embodiment, W is —C(O)O—, X is —O— and Y is —O—.
In a further embodiment, R is H, W is —C(O)O—, X is —O— and Y is —O—.
In another embodiment, W is —S(O)$_2$—, X is —O— and Y is —O—.
In a further embodiment, R is H, W is —S(O)$_2$—, X is —O— and Y is
In one embodiment, A is aryl.
In another embodiment, A is 5 or 6-membered heteroaryl.
In another embodiment, A is phenyl.
In still another embodiment, A is pyrimidinyl.
In another embodiment, A is pyridyl.
In yet another embodiment, Y is —O— and A is pyrimidinyl.
In a further embodiment, X and Y are each —O— and A is pyrimidinyl.
In one embodiment, B is aryl.
In another embodiment, B is 5 or 6-membered heteroaryl.
In another embodiment, B is phenyl.
In still another embodiment, B is pyrimidinyl.
In another embodiment, B is pyridyl.
In yet another embodiment, Y is —O— and B is pyridyl.
In one embodiment, A and B are each independently a 5 or 6-membered heteroaryl.
In a further embodiment, Y is —O—, A is pyrimidinyl and B is pyridyl.
In another embodiment, X and Y are each —O—, A is pyrimidinyl and B is pyridyl.
In one embodiment, A and B are each independently a 5 or 6-membered heteroaryl, each of which can be optionally substituted with one substituent, independently selected from alkyl, aryl and halo.
In another embodiment, A and B are each independently selected from phenyl, pyridyl and pyrimidinyl, each of which can be optionally substituted with one substituent, independently selected from alkyl, aryl and halo.

In another embodiment, A and B are each independently selected from phenyl, pyridyl and pyrimidinyl, each of which can be optionally substituted with one or more substituents, each independently selected from methyl, phenyl and chloro.

In still another embodiment, X and Y are each —O—, A is pyrimidinyl and B is pyridyl, wherein each of A and B can be optionally substituted with one substituent, independently selected from alkyl, aryl and halo.

In a further embodiment, X and Y are each —O—, A is pyrimidinyl and B is pyridyl, wherein each of A and B can be optionally substituted with one or more substituents, each independently selected from methyl, phenyl and chloro.

In one embodiment, X and Y are each —O—, A is pyrimidinyl and B is pyridyl, wherein A and B are each substituted with at least one alkyl group.

In another embodiment, X and Y are each —O—, A is pyrimidinyl and B is pyridyl, wherein A and B are each substituted with a methyl group.

In one embodiment, the group B—X-A-Y— is:

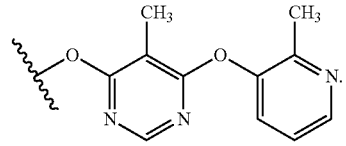 [SMILES: *Oc1ncnc(Oc2cccnc2C)c1C]

In one embodiment, each occurrence of $R^1$ is selected from H, halo or —OH.
In another embodiment, each occurrence of $R^1$ is H.
In still another embodiment, at least one occurrence of $R^1$ is OH.
In another embodiment, at least one occurrence of $R^1$ is halo.
In another embodiment, at least one occurrence of $R^1$ is F.
In one embodiment, $R^1$ is alkyl.
In another embodiment, $R^3$ is a linear alkyl group.
In another embodiment, $R^3$ is a branched alkyl group.
In still another embodiment, $R^3$ is methyl.
In another embodiment, $R^3$ is ethyl.
In another embodiment, $R^3$ is isopropyl.
In a further embodiment, $R^3$ is t-butyl.
In another embodiment, $R^3$ is alkenyl.
In another embodiment, $R^3$ is alkenyl.
In yet another embodiment, $R^3$ is haloalkyl
In one embodiment, $R^3$ is cycloalkyl.
In another embodiment, $R^3$ is cyclopropyl.
In another embodiment, $R^3$ is cyclobutyl.
In still another embodiment, $R^3$ is cyclopentyl.
In another embodiment, $R^3$ is cyclohexyl.
In yet another embodiment, $R^3$ is aryl.
In another embodiment, $R^3$ is phenyl.
In still another embodiment, $R^3$ is naphthyl.
In another embodiment, $R^3$ is -alkylene-aryl.
In another embodiment, $R^3$ is benzyl.
In yet another embodiment, $R^3$ is -alkylene-O-alkylene-aryl.
In one embodiment, R is H.
In another embodiment, R is alkyl.
In one embodiment, W is —C(O)O— and $R^3$ is aryl, -alkylene-aryl, alkyl, alkenyl, alkynyl, cycloalkyl, heteroaryl, -alkylene-O-alkylene-aryl or -alkylene-cycloalkyl.
In another embodiment, W is —C(O)O— and $R^3$ is phenyl, t-butyl, 4-bromophenyl, 3-trifluoromethylphenyl, 4-nitrobenzyl, 4-(C(O)OCH₃)phenyl, naphthyl, 2-chlorobenzyl, methyl, ethyl, propyl, butyl, pentyl, hexyl, heptyl, octyl, nonyl, 4-chlorophenyl, 4-methoxyphenyl, 2-methoxyphenyl, 4-fluorophenyl, benzyl, 4-methylphenyl, neopentyl, cyclopentyl, sec-butyl, butenyl, butynyl, propenyl, propynyl, isopropenyl, cyclobutyl, isopropyl, —C -cyclopropyl, —CH(cyclopropyl)(CH₃), —CH(cyclopropanyl)₂ or —C—H(CH₃)phenyl.

In another embodiment, W is —S(O)₂— and $R^3$ is aryl, alkyl, heteroaryl, alkylene-aryl or cycloalkyl.

In still another embodiment, W is —S(O)₂— and $R^3$ is 4-fluorophenyl, methyl, ethyl, propyl, butyl, 5-chlorothiophenyl, cyclopropyl, 4-(NHC(O)CH₁)phenyl, benzyl, 3-chlorobenzyl, 4-chlorobenzyl, sec-butyl, 4-methylbenzyl 2-chlorobenzyl.

In another embodiment, W is —NH— and $R^3$ is aryl or alkyl.

In one embodiment, p and q are each 1.
In another embodiment, r and s are each 0.
In another embodiment, p, q, r and s are each 1.
In one embodiment, the sum of p and q is 1.
In another embodiment, the sum of p and q is 2.
In another embodiment, the sum of p and q is 3.
In still another embodiment, the sum of p and q is 4.
In another embodiment, the sum of p and q is 5.
In yet another embodiment, the sum of p and q is 6.
In one embodiment, the sum of r and s is 1.
In another embodiment, the sum of r and s is 2.
In another embodiment, the sum of r and s is 3.
In still another embodiment, the sum of r and s is 4.
In another embodiment, the sum of r and s is 5.
In yet another embodiment, the sum of r and s is 6.
In another embodiment, p and r are each 1, q is 0 and s is 2.
In another embodiment, W is —C(O)O—, each of X and Y are —O—, and A and B are each independently a 5 or 6-membered heteroaryl.

In one embodiment, W is —C(O)O—, each of X and Y are —O—, A and B are each independently a 5 or 6-membered heteroaryl, and $R^3$ is alkyl.

In another embodiment, W is —C(O)O—, each of X and Y are —O—, A and B are each independently a 5 or 6-membered heteroaryl, each occurrence of $R^1$ is H, and $R^3$ is alkyl.

In another embodiment, W is —C(O)O—, each occurrence of $R^1$ is H, $R^3$ is alkyl, and B—X-A-Y— is:

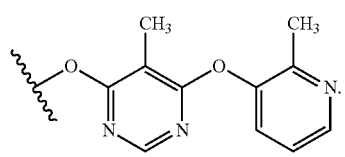 [SMILES: *Oc1ncnc(Oc2cccnc2C)c1C]

In still another embodiment, W is —C(O)O—, each of X and Y are —O—, A and B are each independently a 0.5 or 6-membered heteroaryl, each occurrence of $R^1$ is H, and $R^3$ is isopropyl or t-butyl.

In yet another embodiment, W is —C(O)O—, each of X and Y are —O—, A and B are each independently a 5 or 6-membered heteroaryl, each occurrence of $R^1$ is H, $R^3$ is isopropyl or t-butyl, and the compound of formula (II) contains at least one endocyclic double bond.

In one embodiment, W is —S(O)₂—, each of X and Y are —O—, A and B are each independently a 5 or 6-membered heteroaryl, and $R^3$ is alkyl or cycloalkyl.

In another embodiment, W is —S(O)₂—, each of X and Y are —O—, A and B are each independently a 5 or 6-membered heteroaryl, each occurrence of $R^1$ is H, and $R^3$ is alkyl or cycloalkyl.

In another embodiment, W is —S(O)₂—, each occurrence of $R^1$ is H, $R^3$ is alkyl or cycloalkyl, and the group B—X-A-Y— is:

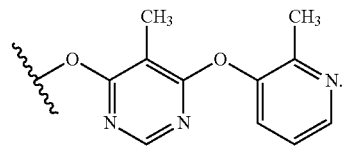 [SMILES: *Oc1ncnc(Oc2cccnc2C)c1C]

In still another embodiment, W is —S(O)₂—, each of X and Y are —O—, A and B are each independently a 5 or 6-membered heteroaryl, each occurrence of $R^1$ is H, and $R^3$ is cycloalkyl.

In yet another embodiment, W is —S(O)₂—, each of X and Y are —O—, A and B are each independently a 5 or 6-membered heteroaryl, each occurrence of $R^1$ is H, $R^3$ is cycloalkyl, and the compound of formula (II) contains at least one endocyclic double bond.

In one embodiment, the compounds of formula (II) have the formula (IIa):

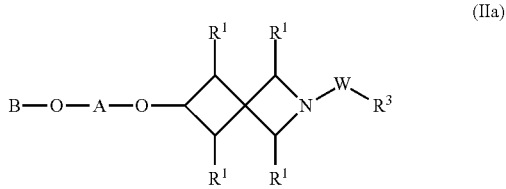

wherein A, B, W, $R^1$ and $R^3$ are defined above for the compounds of formula

In one embodiment, each occurrence of $R^1$ is H.
In another embodiment, at least one occurrence of $R^1$ is other than H.
In one embodiment, W is —C(O)O—.
In another embodiment, W is —S(O)—.
In another embodiment, A and B are each independently a 5 or 6-membered heteroaryl.
In still another embodiment, —O-A-O—B is:

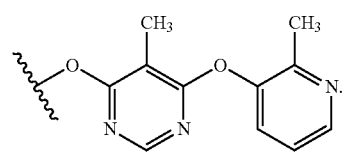

In another embodiment, is —C(O)O— and A and B are each independently a 5 or 6-membered heteroaryl.

In yet another embodiment, W is —C(O)O—, A and B are each independently a 5 or 6-membered heteroaryl, and $R^3$ is alkyl.

In a further embodiment, W is —C(O)O—, $R^3$ is alkyl, and —O-A-O—B is:

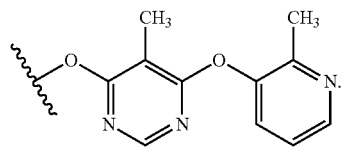

In one embodiment, W is —C(O)O—, A and B are each independently a 5 or 6-membered heteroaryl, and R³ is isopropyl or t-butyl.

In one embodiment, W is —S(O)₂—, A and B are each independently a 5 or 6-membered heteroaryl, and R³ is alkyl or cycloalkyl.

In another embodiment, W is —S(O)₂—, R³ is alkyl or cycloalkyl, and the group —O-A-O—B is:

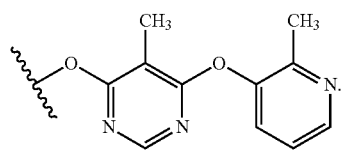

In still another embodiment, W is —S(O)₂—, A and B are each independently a 5 or 6-membered heteroaryl, and R³ is cycloalkyl.

In one embodiment, the compounds of formula (II) have the formula (IIb):

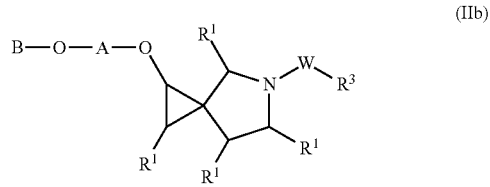

(IIb)

wherein A, B, W, R¹ and R³ are defined above for the compounds of formula (II).

In one embodiment, each occurrence of R¹ is H.

In another embodiment, at least one occurrence of R¹ is other than H.

In one embodiment, W is —C(O)O—.

In another embodiment, W is —S(O)₂—.

In another embodiment, A and B are each independently a 5 or 6-membered heteroaryl.

In still another embodiment, —O-A-O—B is:

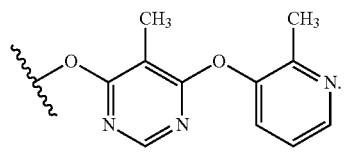 [SMILES: *Oc1ncnc(Oc2cccnc2C)c1C]

In another embodiment, W is —C(O)O— and A and B are each independently a 5 or 6-membered heteroaryl.

In yet another embodiment, W is —C(O)O—, A and B are each independently a 5 or 6-membered heteroaryl, and R³ is alkyl.

In a further embodiment, W is —C(O)O—, R³ is alkyl, and —O-A-O—B is:

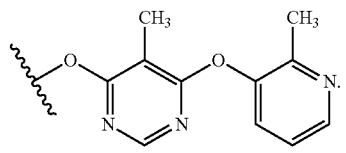 [SMILES: *Oc1ncnc(Oc2cccnc2C)c1C]

In one embodiment, W is —C(O)O—, A and B are each independently a 5 or 6-membered heteroaryl, and R³ is isopropyl or t-butyl.

In one embodiment, W is —S(O)₂—, A and B are each independently a 5 or 6-membered heteroaryl, and R³ is alkyl or cycloalkyl.

In another embodiment, W is —S(O)₂—R³ is alkyl or cycloalkyl, and the group —O—O—B is:

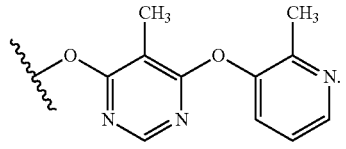 [SMILES: *Oc1ncnc(Oc2cccnc2C)c1C]

In still another embodiment, W is —S(O)₂—, A and B are each independently a 5 or 6-membered heteroaryl, and R³ is cycloalkyl.

In one embodiment, the present invention provides compounds of Formula (II), wherein A, B, W, X, Y, Z, R, p, q, r and s, each occurrence of R¹, and R³ are selected independently of each other.

In another embodiment, a compound of formula (II) is in purified form.

The Bicyclic Heterocycle Derivatives of Formula (III)

The present invention further provides Bicyclic Heterocycle Derivatives of Formula (III):

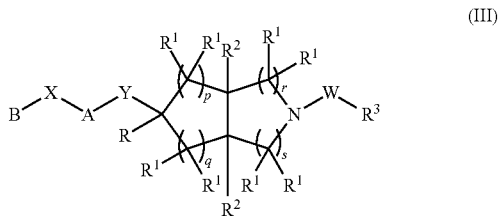

(III)

and pharmaceutically acceptable salts, solvates, esters, prodrugs and stereoisomers thereof, wherein A, B, X, Y, Z, R, R¹, R², R³, p, q, r and s are defined above for the compounds of formula (III).

In one embodiment, W is —C(O)O—.
In another embodiment, W is a bond.
In another embodiment, W is —C(O)—,
In still another embodiment, W is —S(O)₂—.
In yet another embodiment, W is —S(O), (R¹⁰)—.
In a further embodiment, W is —C(O)N(R¹⁰)—.
In one embodiment, X is —C(R¹)₂—.
In another embodiment, X is —O—.
In another embodiment, X is
In yet another embodiment, X is —N(R¹⁰)—.
In one embodiment, Y is —C(R¹)₂—.
In another embodiment, Y is —O—.

In another embodiment, Y is —S—.

In yet another embodiment, Y is —N(R$^{10}$)—.

In another embodiment, X and Y are each —O—.

In another embodiment, W is —C(O)O—, X is —O— and Y is —O—.

In a further embodiment, R is H, W is —C(O)OX is —O— and Y is —O—.

In another embodiment, W is —S(O)$_2$—, X is —O— and Y is —O—.

In a further embodiment, R is H, W is —S(O)$_2$—, X is —O— and Y is —O—.

In one embodiment, A is aryl.

In another embodiment, A is 5 or 6-membered heteroaryl.

In another embodiment, A is phenyl.

In still another embodiment, A is pyrimidinyl.

In another embodiment, A is pyridyl.

In yet another embodiment, Y is —O— and A is pyrimidinyl.

In a further embodiment, X and Y are each —O— and A is pyrimidinyl.

In one embodiment, B is aryl.

In another embodiment, B is 5 or 6-membered heteroaryl.

In another embodiment, B is phenyl.

In still another embodiment, B is pyrimidinyl.

In another embodiment, B is pyridyl.

In yet another embodiment, Y is —O— and B is pyridyl.

In one embodiment, A and B are each independently a 5 or 6-membered heteroaryl.

In a further embodiment, Y is —O—, A is pyrimidinyl and B is pyridyl.

In another embodiment, X and Y are each —O—, A is pyrimidinyl and B is pyridyl.

In one embodiment, A and B are each independently a 5 or 6-membered heteroaryl, each of which can be optionally substituted with one substituent, independently selected from alkyl, aryl and halo.

In another embodiment, A and B are each independently selected from phenyl, pyridyl and pyrimidinyl, each of which can be optionally substituted with one substituent, independently selected from alkyl, aryl and halo.

In another embodiment, A and B are each independently selected from phenyl, pyridyl and pyrimidinyl, each of which can be optionally substituted with one or more substituents, each independently selected from methyl, phenyl and chloro.

In still another embodiment, X and Y are each —O—, A is pyrimidinyl and B is pyridyl, wherein each of A and B can be optionally substituted with one substituent, independently selected from alkyl, aryl and halo.

In a further embodiment, X and Y are each —O—, A is pyrimidinyl and B is pyridyl, wherein each of A and B can be optionally substituted with one or more substituents, each independently selected from methyl, phenyl and chloro.

In one embodiment, X and Y are each —O—, A is pyrimidinyl and B is pyridyl, wherein A and B are each substituted with at least one alkyl group.

In another embodiment, X and Y are each —O—, A is pyrimidinyl and B is pyridyl, wherein A and B are each substituted with a methyl group.

In one embodiment, the group B—X-A-Y— is:

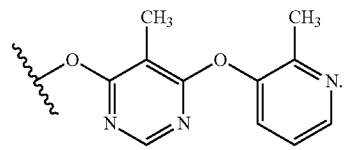 [SMILES: *Oc1ncnc(Oc2cccnc2C)c1C]

In one embodiment, each occurrence of R$^1$ is selected from H, halo or —OH.

In another embodiment, each occurrence of R$^1$ is H.

In still another embodiment, at least one occurrence of R$^1$ is OH.

In another embodiment, at least one occurrence of R$^1$ is halo.

In another embodiment, at least one occurrence of R$^1$ is F.

In another embodiment, at least one occurrence of R$^2$ is H, alkyl or —OH.

In another embodiment, at least one occurrence of R$^2$ is —OH.

In still another embodiment, at least one occurrence of R$^2$ is alkyl.

In another embodiment, at least one occurrence of R$^2$ is H.

In another embodiment, each occurrence of R$^2$ is H.

In one embodiment. R$^3$ is alkyl.

In another embodiment, R$^3$ is a linear alkyl group.

In another embodiment, R$^3$ is a branched alkyl group.

In still another embodiment, R$^3$ is methyl.

In another embodiment, R$^3$ is ethyl.

In another embodiment, R$^3$ is isopropyl.

In a further embodiment, R$^3$ is t-butyl.

In another embodiment, R$^3$ is alkenyl.

In another embodiment, R$^3$ is alkenyl.

In yet another embodiment, R$^3$ is haloalkyl.

In one embodiment, R$^3$ is cycloalkyl.

In another embodiment, R$^3$ is cyclopropyl.

In another embodiment, R$^3$ is cyclobutyl.

In still another embodiment, R$^3$ is cyclopentyl.

In another embodiment, R$^3$ is cyclohexyl.

In yet another embodiment, R$^3$ is aryl.

In another embodiment, R$^3$ is phenyl.

In still another embodiment, R$^3$ is naphthyl.

In another embodiment, R$^3$ is -alkylene-aryl.

In another embodiment, R$^3$ is benzyl.

In yet another embodiment, R$^3$ is -alkylene-O-alkylene-aryl.

In one embodiment, R is H.

In another embodiment, R is alkyl.

In one embodiment, W is —C(O)O— and R$^1$ is aryl., -alkylene-aryl, alkyl, alkenyl, alkynyl, cycloalkyl, heteroaryl, -alkylene-O-alkylene-aryl or -alkylene-cycloalkyl.

In another embodiment, W is —C(O)O— and R$^3$ is phenyl, t-butyl, 4-bromophenyl, 3-trifluoromethylphenyl, 4-nitrobenzyl, 4-(C(O)OCH$_3$)phenyl, naphthyl, 2-chlorobenzyl, methyl, ethyl, propyl, butyl, pentyl, hexyl, heptyl, octyl, amyl, 4-chlorophenyl, 4-methoxyphenyl, 2-methoxyphenyl, 4-fluorophenyl, benzyl, 4-methylphenyl, neopentyl, cyclopentyl, sec-butyl, butenyl, butyryl, propenyl, propynyl, isopropenyl, cyclobutyl, isopropyl, —CH$_2$-cyclopropyl, —CH(cyclopropyl)(CH$_3$), —CH(cyclopropanyl)$_2$ or —CH(CH$_3$)phenyl.

In another embodiment, W is —S(O)$_2$— and R$^3$ is aryl, alkyl, heteroaryl, -alkylene-aryl or cycloalkyl.

In still another embodiment, W is —S(O)— and R$^3$ is 4-fluorophenyl, methyl, ethyl, propyl, butyl, 5-chlorothiophenyl, cyclopropyl, 4-(NHC(O)CH₃)phenyl, benzyl, 3-chlorobenzyl, 4-chlorobenzyl, sec-butyl, 4-methylbenzyl or 2-chlorobenzyl.

In another embodiment, W is —NH— and $R^3$ is aryl or alkyl.

In one embodiment, p and u are each 1.

In another embodiment, p and u are each 1, and r and s are each 0.

In one embodiment, p and q are each 1.

In another embodiment, r and s are each 0.

In another embodiment, p, q, r and s are each 1.

In one embodiment, the sum of p and q is 1.

In another embodiment, the sum of p and q is 2.

In another embodiment, the sum of p and q is 3.

In still another embodiment, the sum of p and q is 4.

In another embodiment, the sum of p and q is 5.

In yet another embodiment, the sum of p and q is 6.

In one embodiment, the sum of r and s is 1.

In another embodiment, the sum of r and s is 2.

In another embodiment, the sum of r and s is 3.

In still another embodiment, the sum of r and s is 4.

In another embodiment, the sum of r and s is 5.

In yet another embodiment, the sum of r and s is 6.

In another embodiment, W is —C(O)O—, each of X and Y are —O—, and A and B are each independently a 5 or 6-membered heteroaryl.

In one embodiment, W is —C(O)O—, each of X and Y are —O—, A and B are each independently a 5 or 6-membered heteroaryl, and $R^3$ is alkyl.

In another embodiment, W is —C(O)O—, each of X and Y are —O—, A and B are each independently a 5 or 6-membered heteroaryl, each occurrence of $R^1$ is H, and $R^3$ is alkyl.

In another embodiment, W is —C(O)O—, each occurrence of $R^1$ is H, $R^3$ is alkyl, and B—X-A-Y— is:

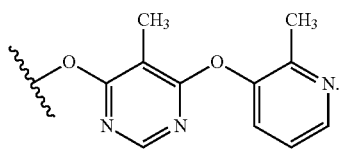

In still another embodiment, W is —C(O)O—, each of X and Y are —O—, A and B are each independently a 5 or 6-membered heteroaryl, each occurrence of $R^1$ is H, and $R^3$ is isopropyl or t-butyl.

In yet another embodiment, W is —C(O)O—, each of X and Y are —O—, A and B are each independently a 5 or 6-membered heteroaryl, each occurrence of $R^1$ is H, $R^3$ is isopropyl or t-butyl, and the compound of formula (III) contains at least one endocyclic double bond.

In one embodiment, W is —S(O)₂—, each of X and Y are —O—, A and B are each independently a 5 or 6-membered heteroaryl, and $R^3$ is alkyl or cycloalkyl.

In another embodiment, W is —S(O)₂—, each of X and Y are —O—, A and B are each independently a 5 or 6-membered heteroaryl, each occurrence of $R^1$ is H, and $R^3$ is alkyl or cycloalkyl.

In another embodiment, W is —S(O)—, each occurrence of $R^1$ is H, $R^3$ is alkyl cycloalkyl, and the group B—X-A-Y— is:

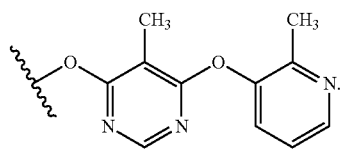 [SMILES: *Oc1ncnc(Oc2cccnc2C)c1C]

In still another embodiment, W is —S(O)₂—, each of X and Y are —O—, A and B are each independently a 5 or 6-membered heteroaryl, each occurrence of $R^1$ is H, and $R^3$ is cycloalkyl.

In yet another embodiment, W is —S(O)₂—, each of X and Y are —O—, A and B are each independently a 5 or 6-membered heteroaryl, each occurrence of $R^1$ is H, $R^3$ is cycloalkyl, and the compound of formula (III) contains at least one endocyclic double bond.

In one embodiment, the compounds of formula (III) have the formula (IIIa)

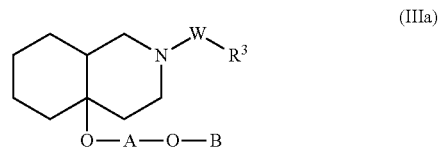

wherein A, B, W and $R^3$ are defined above for the e compounds of formula I).

In one embodiment, W is —C(O)O—.

In another embodiment, W is —S(O)₂—,

In another embodiment, A and B are each independently a 5 or 6-membered heteroaryl.

In still another embodiment, —O-A-O—B is:

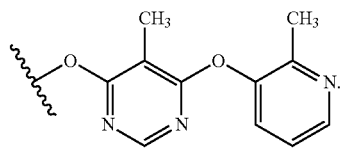 [SMILES: *Oc1ncnc(Oc2cccnc2C)c1C]

In another embodiment, W is —C(O)O— and A and B are each independently a 5 or 6-membered heteroaryl.

In yet another embodiment, W is —C(O)O—, A and B are each independently a 5 or 6-membered heteroaryl, and $R^3$ is alkyl.

In a further embodiment, W is —C(O)O—, $R^3$ is alkyl, and —O-A-O—B is:

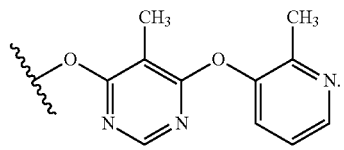 [SMILES: *Oc1ncnc(Oc2cccnc2C)c1C]

In one embodiment, W is —C(O)O—, A and B are each independently a 5 or 6-membered heteroaryl, and $R^3$ is isopropyl or t-butyl.

In one embodiment, W is —S(O)₂—, A and B are each independently a 5 or 6-membered heteroaryl, and $R^3$ is alkyl or cycloalkyl.

In another embodiment. W is —S(O)₂—, $R^3$ is alkyl or cycloalkyl, and the group —O-A-O—B is:

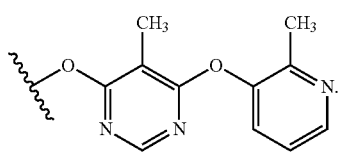 [SMILES: *Oc1ncnc(Oc2cccnc2C)c1C]

In still another embodiment, W is —S(O)₂—, A and B are each independently a 5 or 6-membered heteroaryl, and R³ is cycloalkyl.

In one embodiment, the compounds of formula (III) have the formula (IIIb):

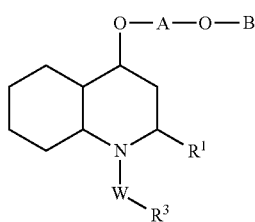

(IIIb)

wherein A, B, W, R¹ and R³ are defined above for the compounds of formula (III).

In one embodiment, R¹ is H.
In another embodiment, R¹ is alkyl.
In another embodiment, R¹ is methyl.
In one embodiment, W is —C(O)O—.
In another embodiment. W is —S(O)₂—.
In another embodiment, A and B are each independently a 5 or 6-membered heteroaryl.
In still another embodiment, —O-A-O—B is:

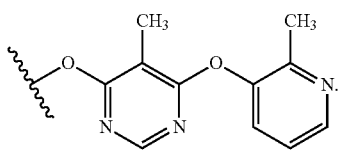

In another embodiment, W is —C(O)O— and A and B are each independently a 5 or 6-membered heteroaryl.

In yet another embodiment, W is —C(O)O—, A and B are each independently a 5 or 6-membered heteroaryl, and R³ is alkyl.

In a further embodiment, W is —C(O)O—, R³ is alkyl, and —O-A-O—B is:

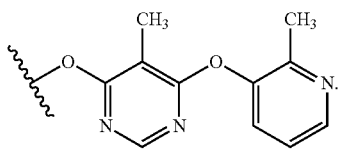 [SMILES: *Oc1ncnc(Oc2cccnc2C)c1C]

In one embodiment, W is —C(O)O—, A and B are each independently a 5 or 6-membered heteroaryl, and R³ is isopropyl or t-butyl, In one embodiment, W is —S(O)₂—, A and B are each independently a 5 or 6-membered heteroaryl, and R³ is alkyl or cycloalkyl, In another embodiment, W is —S(O)₂—, R³ is alkyl or cycloalkyl, and the group —O-A-O—B is:

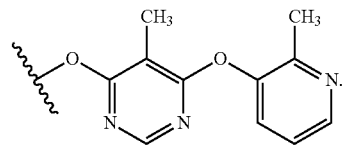 [SMILES: *Oc1ncnc(Oc2cccnc2C)c1C]

In still another embodiment, W is —S(O)₂—, A and B are each independently a 5 or 6-membered heteroaryl, and R³ is cycloalkyl.

In one embodiment, the compounds of formula (III) have the formula (IIIc):

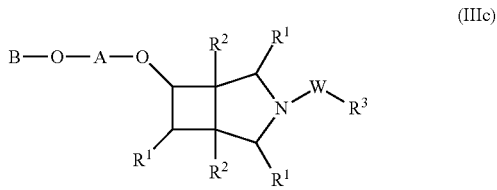

(IIIc)

wherein A, B, W, R¹, R² and R³ are defined above for the compounds of formula (III).

In one embodiment, each occurrence of R¹ is H.
In another embodiment, at least one occurrence of R¹ is other than H.
In another embodiment, each occurrence of R² is H.
In another embodiment, at least one occurrence of R² is other than H.
In another embodiment, at least one occurrence of R² is alkyl.
In one embodiment, W is —C(O)O—.
In another embodiment, W is —S(O)₂—,
In another embodiment, A and B are each independently a 5 or 6-membered heteroaryl.
In still another embodiment, —O-A-O—B is:

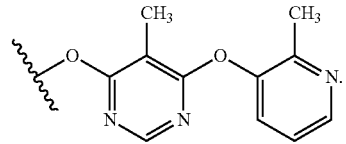 [SMILES: *Oc1ncnc(Oc2cccnc2C)c1C]

In another embodiment, W is —C(O)O— and A and B are each independently a 5 or 6-membered heteroaryl.

In yet another embodiment, W is —C(O)O—, A and B are each independently a 5 or 6-membered heteroaryl, and R³ is alkyl.

In a further embodiment, W is —C(O)O—, R³ is alkyl, and —O-A-O—B is:

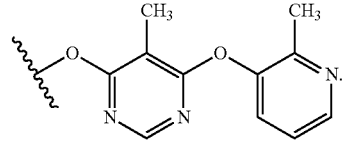 [SMILES: *Oc1ncnc(Oc2cccnc2C)c1C]

In one embodiment, W is —C(O)O—, A and B are each independently 5 or 6-membered heteroaryl, and $R^3$ is isopropyl or t-butyl.

In one embodiment, W is —S(O)$_2$—, A and B are each independently a 5 or 6-membered heteroaryl, and $R^3$ is alkyl or cycloalkyl.

In another embodiment, W is —S(O)$_2$—, $R^3$ is alkyl or cycloalkyl, and the group —O-A-O—B is:

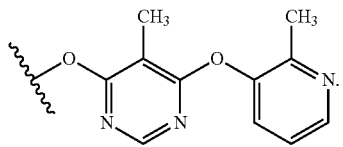 [SMILES: *Oc1ncnc(Oc2cccnc2C)c1C]

In still another embodiment, W is —S(O)$_2$—, A and B are each independently a 5 or 6-membered heteroaryl, and $R^3$ is cycloalkyl.

In one embodiment, the compounds of formula (III) have the formula (IIId):

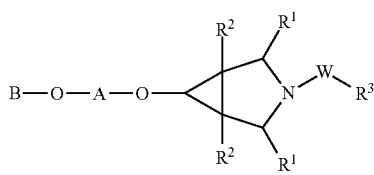

(IIId)

wherein A, B, W, $R^1$, $R^2$ and $R^3$ are defined above for the compounds of formula (III).

In one embodiment, each occurrence of $R^1$ is H.

In another embodiment, at least one occurrence of $R^1$ is other than H.

In one embodiment, each occurrence of $R^2$ is H.

In another embodiment, at least one occurrence of $R^2$ is other than H.

In another embodiment, at least one occurrence of $R^2$ is alkyl.

In one embodiment, W is —C(O)O—.

In another embodiment, W is —S(O)$_2$—.

In another embodiment, A and B are each independently a 5 or 6-membered heteroaryl.

In still another embodiment, —O-A-O—B is:

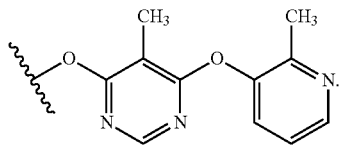 [SMILES: *Oc1ncnc(Oc2cccnc2C)c1C]

In another embodiment, W is —CO—(O) and A and B are each independently a 5 or 6-membered heteroaryl.

In yet another embodiment, W is —C(O)O—, A and B are each independently a 5 or 6-membered heteroaryl, and $R^3$ is alkyl.

In a further embodiment, W is —C(O)O—, $R^3$ is alkyl, and —O-A-O—B is:

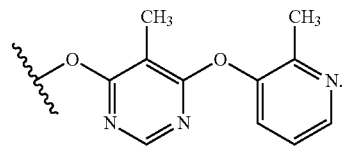 [SMILES: *Oc1ncnc(Oc2cccnc2C)c1C]

In one embodiment, W is —C(O)O—, A and B are each independently a 5 or 6-membered heteroaryl, and $R^3$ is isopropyl or t-butyl.

In one embodiment, W is —S(O)$_2$—, A and B are each independently a 5 or 6-membered heteroaryl, and $R^3$ is alkyl or cycloalkyl.

In another embodiment, W is —S(O)$_2$—, $R^3$ is alkyl or cycloalkyl; and the group —O-A-O—B is:

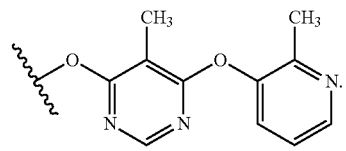 [SMILES: *Oc1ncnc(Oc2cccnc2C)c1C]

In still another embodiment, W is —S(O)$_2$—, A and B are each independently a 5 or 6-membered heteroaryl, and $R^3$ is cycloalkyl.

In one embodiment, the present invention provides compounds of Formula (III), wherein A, B, W, X, Y, Z, R, p, q, r, s, each occurrence of $R^1$, each occurrence of $R^2$, and $R^3$ are selected independently of each other.

In one embodiment, a compound of formula (Is in purified form.

The Bicyclic Heterocycle Derivatives of Formula (IV)

The present invention further provides Bicyclic Heterocycle Derivatives of Formula (IV):

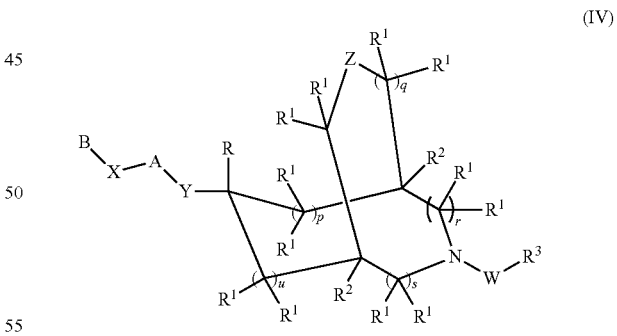

(IV)

and pharmaceutically acceptable salts, solvates, esters, prodrugs and stereoisomers thereof, wherein A, B, W, X, Y, Z, R, $R^1$, $R^2$, $R^3$, p, q, r, s and u are defined above for the compounds of formula (IV).

In one embodiment, W is —C(O)O—.

In another embodiment, W is a bond.

In another embodiment, W is —C(O)—.

In still another embodiment, W is —S(O)$_2$—.

In yet another embodiment, W is —S(O)$_2$N($R^{10}$)—.

In a further embodiment, W is —C(O)N($R^{10}$)—.

In one embodiment, X is —C($R^1$)$_2$—.

In another embodiment, X is —O—.
In another embodiment, X is —S—,
In yet another embodiment, X is —N($R^{10}$)—.
In one embodiment, Y is —C($R^1$)$_2$—.
In another embodiment, Y is —O—.
In another embodiment, Y is —S—.
In yet another embodiment, Y is —N($R^{10}$)—.
In one embodiment, Z is —C($R^1$)$_2$—.
In another embodiment, Z is —O—.
In another embodiment, Z is —S—.
In yet another embodiment, Z is —N($R^{10}$)—.
In another embodiment, Z is —CH$R^1$—.
In another embodiment, Z is —CH$_2$—.
In still another embodiment, Z is —NH—.
In one embodiment, W is —C(O)O— and Z is a bond.
In one embodiment, W is —S(O)$_2$— and Z is a bond.
In another embodiment, X and Y are each —O—.
In another embodiment, W is —C(O)O—, Z is a bond, X is —O— and Y is —O—.
In a further embodiment. R is H, W is —C(O)O—, Z is a bond, X is —O— and Y is —O—.
In another embodiment, W is —S(O)$_2$—, Z is a bond, X is —O— and Y is —O—.
In a further embodiment, R is H, W is —S(O)$_2$—, Z is a bond, X is —O— and Y is —O—.
In one embodiment, A is aryl.
In another embodiment, A is 5 or 6-membered heteroaryl.
In another embodiment, A is phenyl.
In still another embodiment, A is pyridinyl,
In another embodiment, A is pyridyl.
In yet another embodiment, Y is —O— and A is pyrimidinyl.
In a further embodiment, X and Y are each —O— and A is pyrimidinyl.
In one embodiment, B is aryl.
In another embodiment, B is 5 or 6-membered heteroaryl,
In another embodiment, B is phenyl.
In still another embodiment, B is pyrimidinyl.
In another embodiment, B is pyridyl.
In yet another embodiment, Y is —O— and B is pyridyl,
In one embodiment, A and B are each independently a 5 or 6-membered heteroaryl.
In a further embodiment, Y is —O—, A is pyrimidinyl and B is pyridyl.
In another embodiment, X and Y are each A is pyrimidinyl and B is pyridyl.
In one embodiment, A and B are each independently a 5 or 6-membered heteroaryl, each of which can be optionally substituted with one substituent, independently selected from alkyl, aryl and halo.
In another embodiment. A and B are each independently selected from phenyl, pyridyl and pyrimidinyl, each of which can be optionally substituted with one substituent, independently selected from alkyl, aryl and halo.
In another embodiment, A and B are each independently selected from phenyl, pyridyl and pyrimidinyl, each of which can be optionally substituted with one or more substituents, each independently selected from methyl, phenyl and chloro.
In still another embodiment, X and Y are each —O—. A is pyrimidinyl and B is pyridyl, wherein each of A and B can be optionally substituted with one substituent, independently selected from alkyl, aryl and halo.
In a further embodiment, X and Y are each —O—, A is pyrimidinyl and B is pyridyl, wherein each of A and B can be optionally substituted with one or more substituents, each independently selected from methyl, phenyl and chloro.

In one embodiment, X and Y are each is —O—, A is pyrimidinyl and B is pyridyl, wherein A and B are each substituted with at least one alkyl group.
In another embodiment, X and Y are each —O—, A is pyrimidinyl and B is pyridyl, wherein A and B are each substituted with a methyl group.
In one embodiment, the group B—X-A-Y— is:

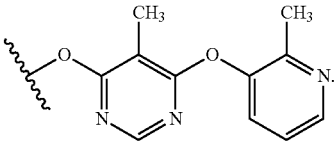 [SMILES: *Oc1ncnc(Oc2cccnc2C)c1C]

In one embodiment, each occurrence of $R^1$ is selected from , halo or —OH.
In another embodiment, each occurrence of $R^1$ is H.
In still another embodiment, at least one occurrence of $R^1$ is OH.
In another embodiment, at least one occurrence of $R^1$ is halo.
In another embodiment, at least one occurrence of $R^1$ is F.
In another embodiment, at least one occurrence of $R^2$ is H, alkyl or —OH.
In another embodiment, at least one occurrence of $R^2$ is —OH.
In still another embodiment, at least one occurrence of $R^2$ is alkyl.
In another embodiment, at least one occurrence of $R^2$ is H.
In another embodiment, each occurrence of $R^2$ is H.
In one embodiment, $R^3$ is alkyl.
In another embodiment, $R^3$ is a linear alkyl group.
In another embodiment, $R^3$ is a branched alkyl group.
In still another embodiment, $R^3$ is methyl.
In another embodiment, $R^3$ is ethyl.
In another embodiment, $R^3$ is isopropyl.
In a further embodiment, $R^3$ is t-butyl.
In another embodiment, $R^3$ is alkenyl.
In another embodiment, $R^3$ is alkynyl.
In yet another embodiment, $R^3$ is haloalkyl
In one embodiment, $R^3$ is cycloalkyl.
In another embodiment, $R^3$ is cyclopropyl.
In another embodiment, $R^3$ is cyclobutyl.
In still another embodiment, $R^3$ is cyclopentyl.
In another embodiment, $R^3$ is cyclohexyl.
In yet another embodiment, $R^3$ is aryl.
In another embodiment, $R^3$ is phenyl.
In still another embodiment, $R^3$ is naphth
In another embodiment, $R^3$ is -alkylene-aryl.
In another embodiment, $R^3$ is benzyl.
In yet another embodiment, $R^3$ is -alkylene-O-alkylene-aryl.
In one embodiment, W is —C(O)O— and $R^3$ is aryl, -alkylene-aryl, alkyl, alkenyl, alkynyl, cycloalkyl, heteroaryl, -alkylene-O-alkylene-aryl or -alkylene-cycloalkyl.
In another embodiment, W is —C(O)O— and $R^3$ is phenyl, t-butyl, 4-bromophenyl, 3-trifluoromethylphenyl, 4-nitrobenzyl, 4-(C(O)OCH$_3$)phenyl, naphthyl, 2-chlorobenzyl, methyl, ethyl, propyl, butyl, pentyl, hexyl, heptyl, octyl, nonyl, 4-chlorophenyl, 4-methoxyphenyl, 2-methoxyphenyl, 4-fluorophenyl, benzyl, 4-methylphenyl, neopentyl, cyclopentyl, sec-butyl, butenyl, butyryl, propenyl, propynyl, isopropenyl, cyclobutyl, isopropyl, —C$_{1-12}$-cyclopropyl, —CH(cyclopropyl)(CH$_3$), —CH(cyclopropanyl)$_2$ or —CH(CH$_3$)phenyl.

In another embodiment, W is —S(O)$_2$— and R$^3$ is aryl, alkyl, heteroaryl, -alkylene-aryl or cycloalkyl.

In still another embodiment, W is —S(O)$_2$— and R$^3$ is 4-fluorophenyl, methyl, ethyl, propyl, butyl, 5-chloro-thiophenyl, cyclopropyl, 4-(NHC(O)CH$_3$)phenyl, benzyl, 3-chlorobenzyl, 4-chlorobenzyl, sec-butyl, 4-methylbenzyl or 2-chlorobenzyl.

In another embodiment, W is —NH— and R$^3$ is aryl or alkyl.

In one embodiment, p and u are each 1.

In another embodiment, p and u are each 1, and r and s are each 0.

In another embodiment, q, p and a are each 1, r and s are each 0 and Z is a bond.

In still another embodiment, q, p and u are each 1, r and s are each 0, Z is a bond, and W is —C(O)O—.

In a further embodiment, q, p and u are each 1, r and s are each 0, Z is a bond, W is —C(O)O—, and each of X, and Y are In another embodiment, q, p and a are each 1, r and s are each 0, Z is a bond, W is —C(O)O—, each of X and Y are —O—, and A and B are each independently a 5 or 6-membered heteroaryl.

In another embodiment, q, p and u are each 1, r and s are each 0, Z is a bond, W is —C(O)O—, each of X and Y are —O—, A and B are each independently a 5 or 6-membered heteroaryl, and R$^3$ is alkyl.

In one embodiment, q, p and u are each 1, r and s are each 0, Z is a bond, W is —C(O)O—, each of X and Y are —O—, A and B are each independently a 5 or 6-membered heteroaryl, and R$^3$ is alkyl.

In another embodiment, q, p and u are each 1, r and s are each 0, Z is a bond, W is C(O)O—, each of X and Y are —O—, A and B are each independently a 5 or 6-membered heteroaryl, each occurrence of R$^1$ is H, and R$^3$ is alkyl, In another embodiment, q, p and u are each 1, r and s are each 0, Z is a bond, W is —C(O)O—, each of X and Y are —O—, A and B are each independently a 5 or 6-membered heteroaryl, each occurrence of R$^1$ and R$^2$ is H, and R$^3$ is alkyl.

In still another embodiment, q, p and u are each 1, r and s are each 0, Z is a bond, W is —C(O)O—, each of X and Y are —O—, A and B are each independently a 5 or 6-membered heteroaryl, each occurrence of R$^1$ and R$^2$ is H, and R$^3$ is isopropyl or t-butyl.

In yet another embodiment, q, p and u are each 1, r and s are each 0, Z is a bond, W is —C(O)O—, each of X and Y are —O—, A and B are each independently a 5 or 6-membered heteroaryl, each occurrence of R$^1$ and R is H, R$^3$ is isopropyl or t-butyl, and the compound of formula (IV) contains at least one endocyclic double bond.

In a further embodiment, q, p and u are each 1, r and s are each 0, Z is a bond, W is —C(O)O—, each of X and Y are —O—, A and B are each independently a 5 or 6-membered heteroaryl, each occurrence of R$^1$ and R$^2$ is H, R$^3$ is isopropyl or t-butyl, and the compound of formula (IV) contains one endocyclic double bond.

In one embodiment, q, p and u are each 1, r and s are each 0, Z is a bond, W is —S(O)$_2$—, each of X and Y are —O—, A and B are each independently a 5 or 6-membered heteroaryl, and R$^3$ is alkyl.

In another embodiment, q, p and u are each 1, r and s are each 0, Z is a bond, W is —S(O)$_3$—, each of X and Y are —O—, A and B are each independently a 5 or 6-membered heteroaryl, each occurrence of R$^1$ is H, and R$^3$ is alkyl, In another embodiment, q, p and u are each 1, r and s are each 0, Z, is a bond, W is S(O)$_2$—, each of X and Y are —O—, A and B are each independently a 5 or 6-membered heteroaryl, each occurrence of R$^1$ and R$^2$ is H, and R$^3$ is alkyl.

In still another embodiment, q, p and u are each 1, r and s are each 0, Z is a bond, W is —S(O)$_2$—, each of X and Y are —O—, A, and B are each independently a 5 or 6-membered heteroaryl, each occurrence of R$^1$ and R$^2$ is H, and R$^3$ is isopropyl or t-butyl.

In yet another embodiment, q, p and u are each 1, r and s are each 0, Z is a bond, W is —S(O)$_2$—, each of X and Y are —O—, A and B are each independently a 5 or 6-membered heteroaryl, each occurrence of R$^1$ and R$^2$ is H, R$^3$ is isopropyl or t-butyl, and the compound of formula (IV) contains at least one endocyclic double bond.

In a further embodiment, q, p and u are each 1, r and s are each 0, Z is a bond, W is —S(O)$_2$—, each of X and Y are —O—, A and B are each independently a 5 or 6-membered heteroaryl, each occurrence of R$^1$ and R$^2$ is H, R$^3$ is isopropyl or t-butyl, and the compound of formula (IV) contains one endocyclic double bond.

In one embodiment, a compound of formula (IV) has the formula:

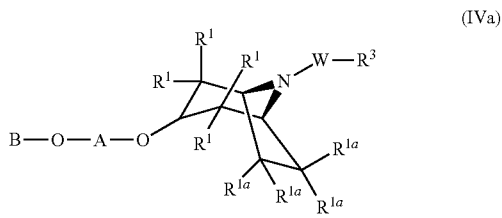

(IVa)

wherein , A, B and R$^3$ are defined above for the compounds of formula (IV), W is —C(O)O— or —S(O)$_2$—, and each occurrence of R$^{1a}$ is independently selected from H, halo or alkyl.

In one embodiment, W is —C(O)—.

In another embodiment, W is —S(O)$_2$—.

In still another embodiment, each occurrence of R$^1$ is H.

In another embodiment, each occurrence of R$^2$ is H.

In another embodiment, at least one occurrence of R$^2$ is halo.

In a further embodiment, at least one occurrence of R$^2$ is F.

In one embodiment, R$^3$ is alkyl.

In another embodiment, R$^3$ is cycloalkyl.

In one embodiment, R$^3$ is isopropyl or t-butyl.

In another, R$^3$ is cyclopropyl.

In another embodiment, W is —C(O)— and R$^3$ is alkyl.

In yet another embodiment, W is —S(O)$_2$— and R$^3$ is cycloalkyl.

In another embodiment, A and B are each independently a 5 or 6-membered heteroaryl.

In still another embodiment, A is pyrimidinyl and B is pyridyl.

In yet another embodiment, the group —O-A-O—B is:

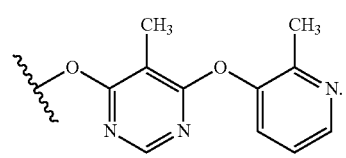 [SMILES: *Oc1ncnc(Oc2cccnc2C)c1C]

In a further embodiment, the group —O-A-O—B is:

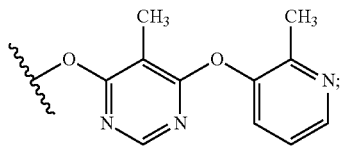 [SMILES: *Oc1ncnc(Oc2cccnc2C)c1C]

W is —C(O)O—; and $R^3$ is alkyl.

In another embodiment, the group —O-A-O—B is:

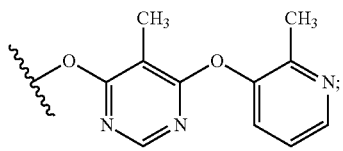 [SMILES: *Oc1ncnc(Oc2cccnc2C)c1C]

W is —S(O)$_2$—; and $R^3$ is cycloalkyl.

In one embodiment, a compound of formula (IV) has the formula:

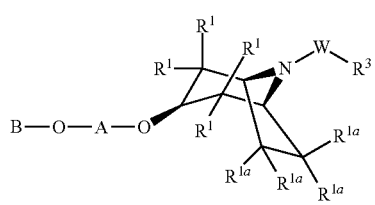

(IVb)

wherein $R^1$, A, B and $R^3$ are defined above for the compounds of formula (IV), W is —C(O)O— or —S(O)$_2$—, and each occurrence of $R^{1a}$ is independently selected from H, halo or alkyl.

In one embodiment, W is —C(O)—.
In another embodiment, W is —S(O)$_2$—.
In still another embodiment, each occurrence of $R^1$ is H.
In another embodiment, each occurrence of $R^2$ is H.
In another embodiment, at least one occurrence of $R^2$ is halo.
In a further embodiment, at least one occurrence of $R^2$ is F.
In one embodiment, $R^3$ is alkyl.
In another embodiment, $R^3$ is cycloalkyl.
In one embodiment, $R^3$ is isopropyl or t-butyl.
In another, $R^3$ is cyclopropyl,
In another embodiment, W is —C(O)— and $R^3$ is alkyl.
In yet another embodiment, W is —S(O)$_2$— and $R^3$ is cycloalkyl.
In another embodiment, A and B are each independently a 5 or 6-membered heteroaryl.
In still another embodiment, A is pyrimidinyl and B is pyridyl.
In yet another embodiment, the group —O-A-O—B is:

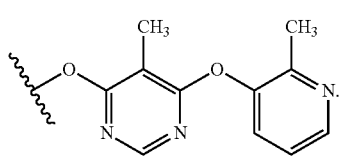 [SMILES: *Oc1ncnc(Oc2cccnc2C)c1C]

In a further embodiment, the group —O-A-O—B is:

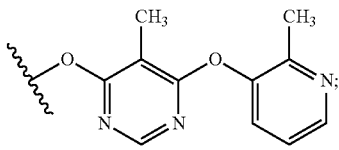 [SMILES: *Oc1ncnc(Oc2cccnc2C)c1C]

W is —C(O)O—; and $R^3$ is alkyl.

In another embodiment, the group —O-A-O—B is:

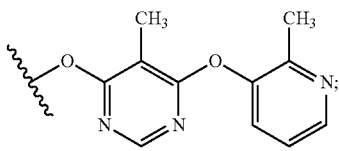 [SMILES: *Oc1ncnc(Oc2cccnc2C)c1C]

W is —S(O)$_2$—; and $R^3$ is cycloalkyl.

In one embodiment, a compound of formula (IV) has the formula:

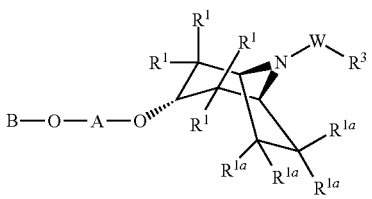

(IVc)

wherein $R^1$, A, B and $R^3$ are defined above for the compounds of formula (IV), W is —C(O)O— or —S(O)$_2$—, and each occurrence of $R^{1a}$ is independently selected from H, halo or alkyl.

In one embodiment, W is —C(O)—.
In another embodiment, W is —S(O)$_2$—.
In still another embodiment, each occurrence of $R^1$ is H.
In another embodiment, each occurrence of $R^2$ is H.
In another embodiment, at least one occurrence of $R^2$ is halo.
In a further embodiment, at least one occurrence of $R^2$ is F.
In one embodiment, $R^3$ is alkyl.
In another embodiment, $R^3$ is cycloalkyl.
In one embodiment, $R^3$ is isopropyl or t-butyl.
In another, $R^3$ is cyclopropyl.
In another embodiment, W is —C(O)— and $R^3$ is alkyl.
In yet another embodiment, W is —S(O)$_2$— and $R^3$ is cycloalkyl.
In another embodiment, A and B are each independently a 5 or 6-membered heteroaryl.
In still another embodiment, A is pyrimidinyl and B is pyridyl.
In yet another embodiment, the group —O-A-O—B is:

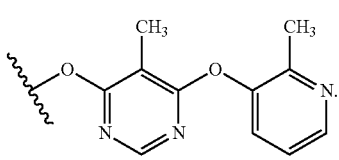 [SMILES: *Oc1ncnc(Oc2cccnc2C)c1C]

In a further embodiment, the group —O-A-O—B is:

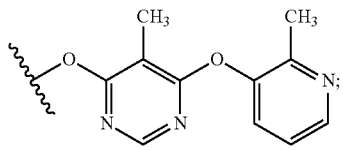 [SMILES: *Oc1ncnc(Oc2cccnc2C)c1C]

W is —C(O)O—; and R³ is alkyl.

In another embodiment, the group —O-A-O—B is:

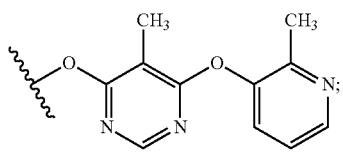 [SMILES: *Oc1ncnc(Oc2cccnc2C)c1C]

W is —S(O)₂—; and R³ is cycloalkyl,

In one embodiment, a compound of formula (IV) has the formula:

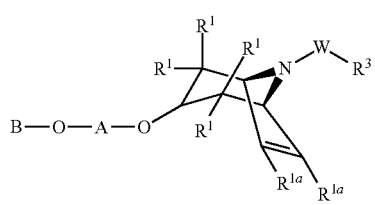

(IVd)

wherein R¹, A, B and R³ are defined above for the compounds of formula (IV), W is —C(O)O— or —S(O)₂—, and each occurrence of $R^{1a}$ is independently selected from H, halo or alkyl.

In one embodiment, W is —C(O)—.
In another embodiment, W is —S(O)₂—.
In still another embodiment, each occurrence of R¹ is H.
In another embodiment, each occurrence of R² is H.
In another embodiment, at least one occurrence of R² is halo.
In a further embodiment, at least one occurrence of R² is F.
In one embodiment, R³ is alkyl.
In another embodiment. R³ is cycloalkyl.
In one embodiment. R³ is isopropyl or t-butyl.
In another, R³ is cyclopropyl.
In another embodiment, W is —C(O)— and R³ is alkyl.
In yet another embodiment, W is —S(O)₂— and R³ is cycloalkyl.
In another embodiment, A and B are each independently a 5 or 6-membered heteroaryl.
In still another embodiment, A is pyrimidinyl and B is pyridyl.
In yet another embodiment, the group —O-A-O—B is:

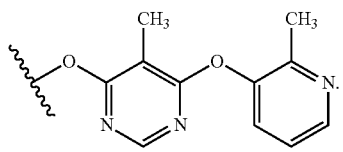 [SMILES: *Oc1ncnc(Oc2cccnc2C)c1C]

In a further embodiment, the group —O-A-O—B is:

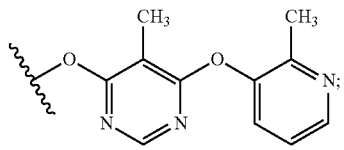 [SMILES: *Oc1ncnc(Oc2cccnc2C)c1C]

W is —C(O)O—; and R³ is alkyl.

In another embodiment, the group —O-A-O—B is:

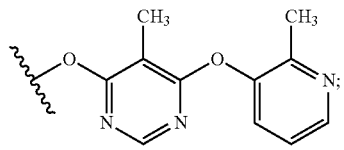 [SMILES: *Oc1ncnc(Oc2cccnc2C)c1C]

W is —S(O)₂—; and R³ is cycloalkyl.

In one embodiment, a compound of formula (IV) has the formula:

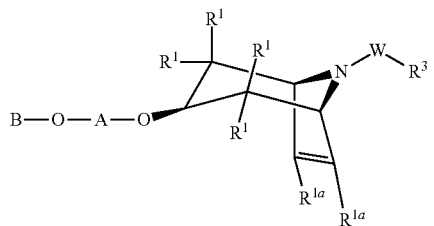

(IVe)

wherein R¹, A, B and R³ are defined above for the compounds of formula (IV), W is —C(O)O— or —S(O)₂—, and each occurrence of $R^{1a}$ is independently selected from H, halo or alkyl.

In one embodiment, W is —C(O)—.
In another embodiment, W is —S(O)₂—.
In still another embodiment, each occurrence of R¹ is H.
In another embodiment, each occurrence of R² is H.
In another embodiment, at least one occurrence of R² is halo.
In a further embodiment, at least one occurrence of R² is F.
In one embodiment, R³ is alkyl.
In another embodiment, R³ is cycloalkyl.
In one embodiment, R³ is isopropyl or t-butyl.
In another, R³ is cyclopropyl.
In another embodiment, W is —C(O)— and R³ is alkyl.
In yet another embodiment. W is —S(O)₂— and R³ is cycloalkyl.
In another embodiment, A and B are each independently a 5 or 6-membered heteroaryl.
In still another embodiment, A is pyrimidinyl and B is pyridyl.
In yet another embodiment, the group —O-A-O—B is:

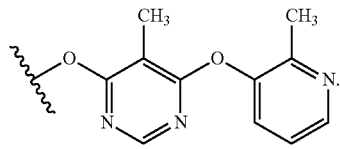 [SMILES: *Oc1ncnc(Oc2cccnc2C)c1C]

In a further embodiment, the group —O—B is:

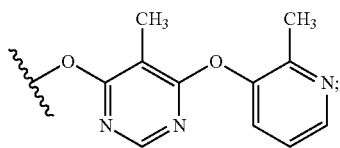 [SMILES: *Oc1ncnc(Oc2cccnc2C)c1C]

W is —C(O)O—; and $R^3$ is alkyl.

In another embodiment, the group —O-A-O—B is:

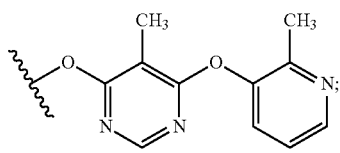 [SMILES: *Oc1ncnc(Oc2cccnc2C)c1C]

W is —S(O)$_2$—; and $R^3$ is cycloalkyl.

In one embodiment, a compound of formula (IV) has the formula:

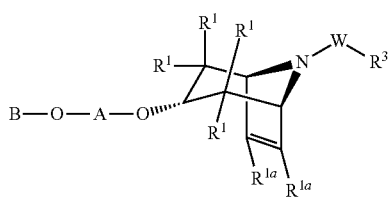

(IVf)

wherein $R^1$, A, B and $R^3$ are defined above for the compounds of formula (IV), W is —C(O)O— or —S(O)$_2$—, and each occurrence of $R^{1a}$ is independently selected from H, halo or alkyl.

In one embodiment, W is —C(O)—.
In another embodiment, W is —S(O)$_2$—.
In still another embodiment, each occurrence of $R^1$ is H.
In another embodiment, each occurrence of $R^2$ is H.
In another embodiment, at least one occurrence of $R^2$ is halo.
In a further embodiment, at least one occurrence of $R^2$ is F.
In one embodiment, $R^3$ is alkyl.
In another embodiment, $R^3$ is cycloalkyl.
In one embodiment $R^3$ is isopropyl or t-butyl.
In another, $R^3$ is cyclopropyl.
In another embodiment, W is —C(O)— and $R^3$ is alkyl.
In yet another embodiment, W is —S(O)$_2$— and $R^3$ is cycloalkyl.
In another embodiment, A and B are each independently a 5 or 6-membered heteroaryl.
In still another embodiment, A is pyrimidinyl and B is pyridyl.

In yet another embodiment, the group —O-A-O—B is:

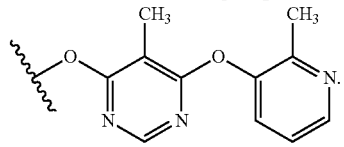 [SMILES: *Oc1ncnc(Oc2cccnc2C)c1C]

In a further embodiment, the group —O-A-O—B is:

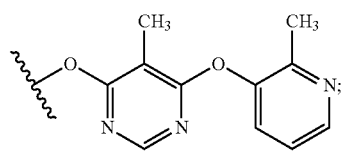 [SMILES: *Oc1ncnc(Oc2cccnc2C)c1C]

W is —C(O)O—; and $R^3$ is alkyl.
In another embodiment, the group —O-A-O—B is:

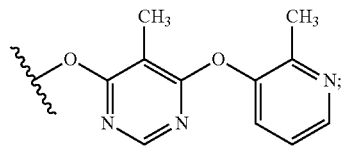 [SMILES: *Oc1ncnc(Oc2cccnc2C)c1C]

W is —S(O)$_2$—; and $R^3$ is cycloalkyl.
In one embodiment, the compounds of formula (IV) have the formula (IVg):

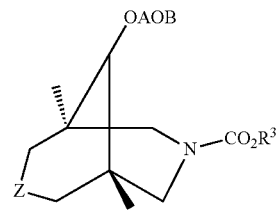

(IVg)

wherein A, B, Z and $R^3$ are defined above for the compounds of formula (IV).

In one embodiment, $R^3$ is alkyl.
In another embodiment, Z is —N($R^{10}$)—.
In another embodiment, Z is —O—.
In still another embodiment, Z is —S—.
In another embodiment, Z is —C($R^1$)$_2$—.
In yet another embodiment, Z is —CH$_2$—.
In another embodiment, A and B are each independently a 5 or 6-membered heteroaryl.
In another embodiment, A is pyrimidinyl and B is pyridyl.
In a further another embodiment, the group —O-A-O—B is:

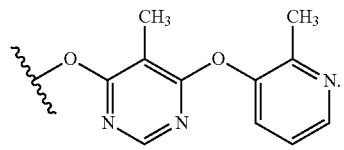 [SMILES: *Oc1ncnc(Oc2cccnc2C)c1C]

In one embodiment, the group —O-A-O—B is:

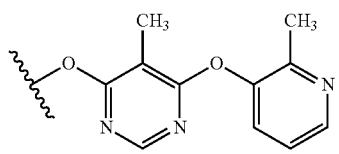 [SMILES: *Oc1ncnc(Oc2cccnc2C)c1C]

and R³ is alkyl.

In one embodiment, the present invention provides compounds of Formula (IV), wherein A, B, W, X, Y, Z, R, p, q, r, s, u, each occurrence of R¹, each occurrence of R², and R³ are selected independently of each other.

In one embodiment, a compound of formula (IV) is in purified form.

Non-limiting examples of the Bicyclic Heterocycle Derivatives include, but are not limited to compounds 1-86, depicted below:

| Compound No. | STRUCTURE |
|---|---|
| 1 | 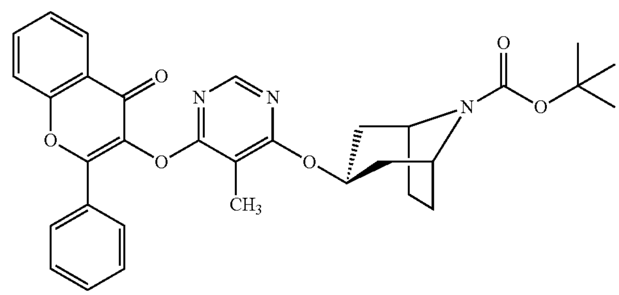 |
| 2 | 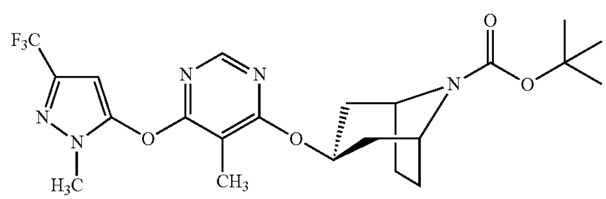 |
| 3 | 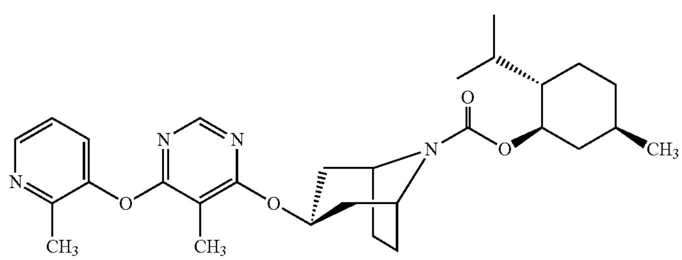 |
| 4 | 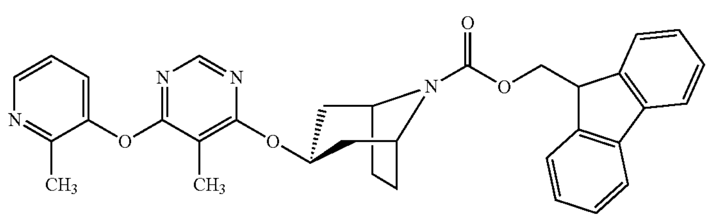 |
| 5 | 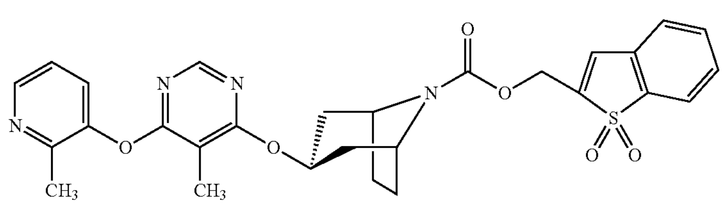 |

-continued
| Compound No. | STRUCTURE |
|---|---|
| 6 | 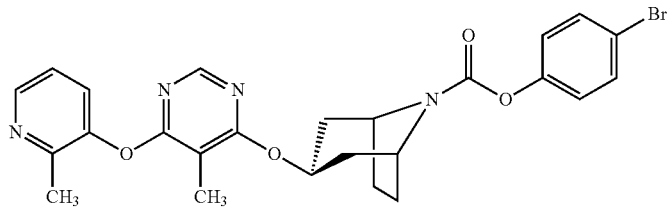 |
| 7 | 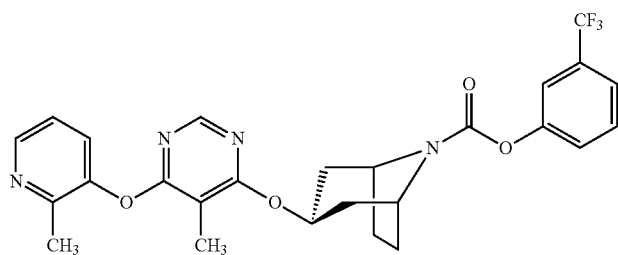 |
| 8 | 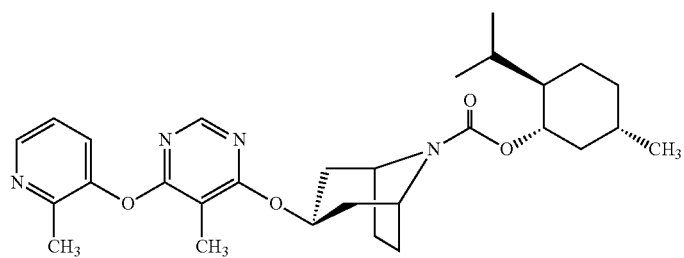 |
| 9 | 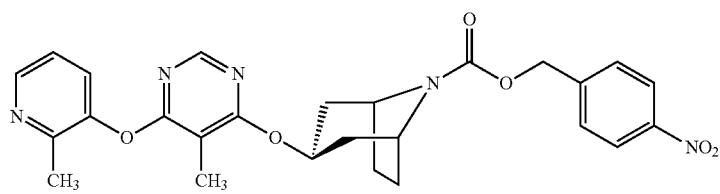 |
| 10 | 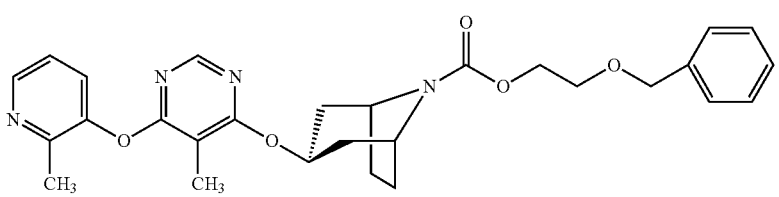 |
| 11 | 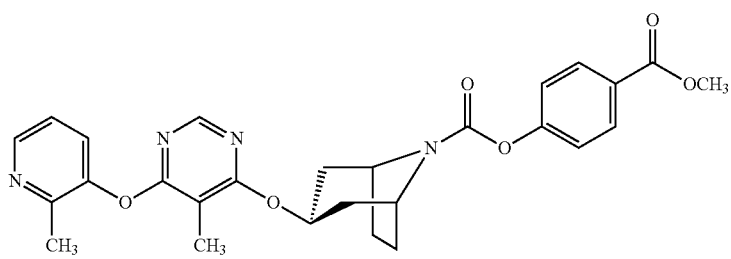 |

-continued
| Compound No. | STRUCTURE |
|---|---|
| 12 | 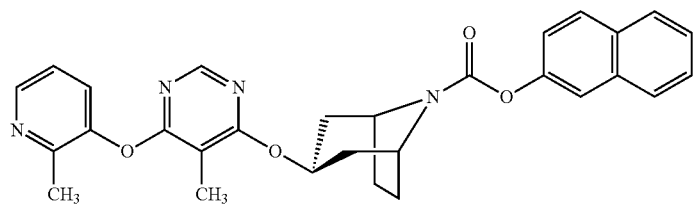 |
| 13 | 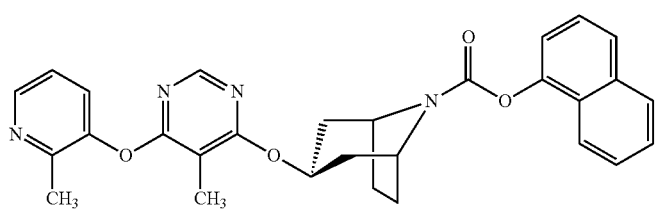 |
| 14 | 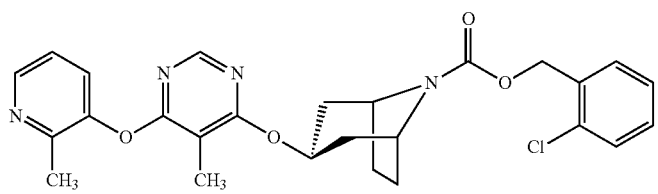 |
| 15 | 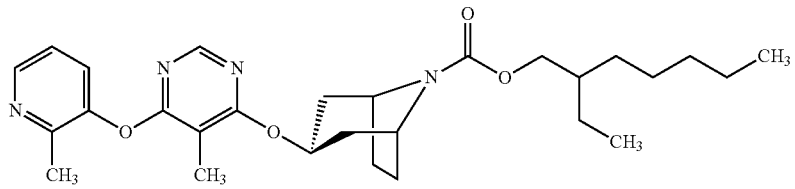 |
| 16 | 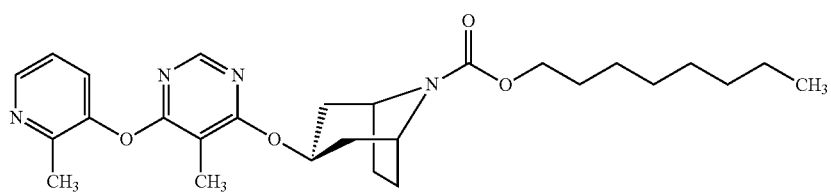 |
| 17 | 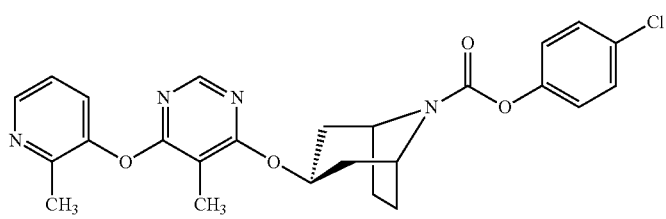 |
| 18 | 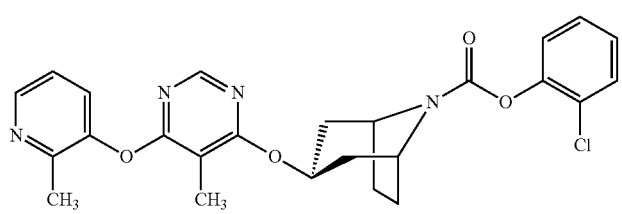 |

-continued
| Compound No. | STRUCTURE |
|---|---|
| 19 | 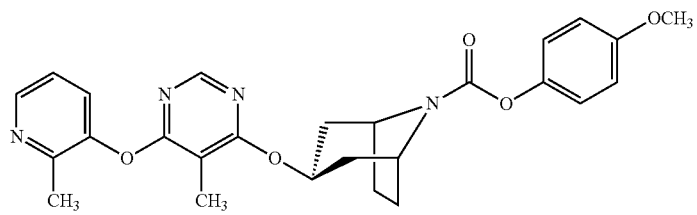 |
| 20 | 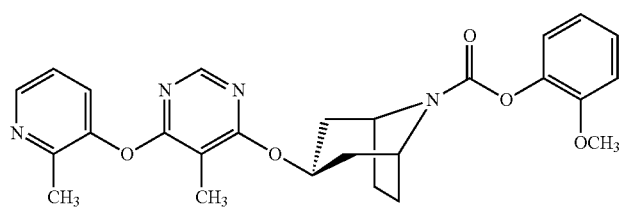 |
| 21 | 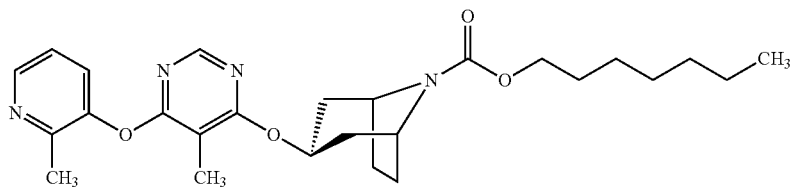 |
| 22 | 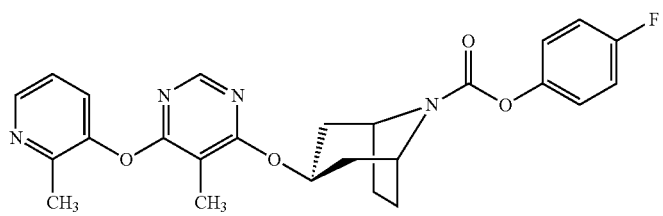 |
| 23 | 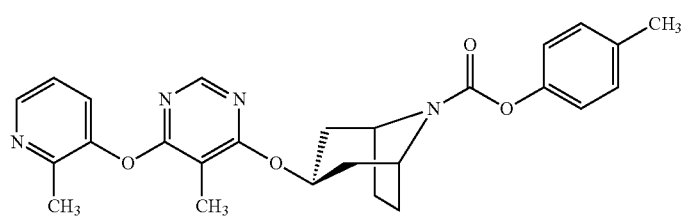 |
| 24 | 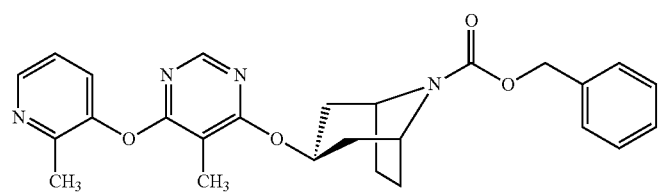 |
| 25 | 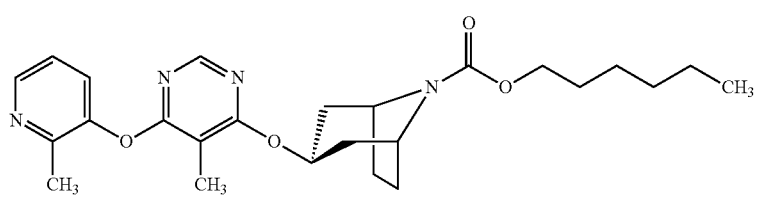 |

-continued
| Compound No. | STRUCTURE |
|---|---|
| 26 | 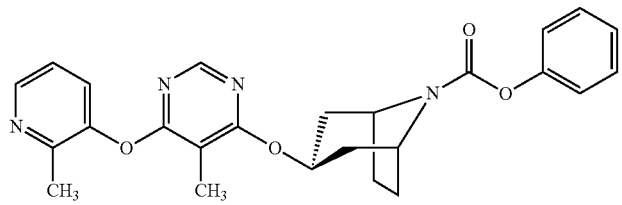 |
| 27 | 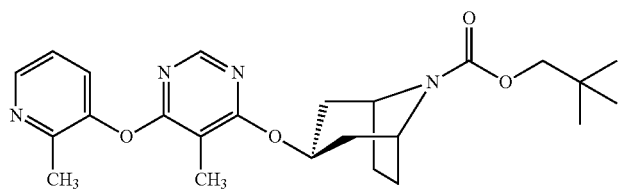 |
| 28 | 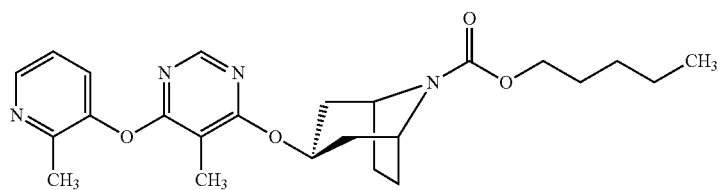 |
| 29 | 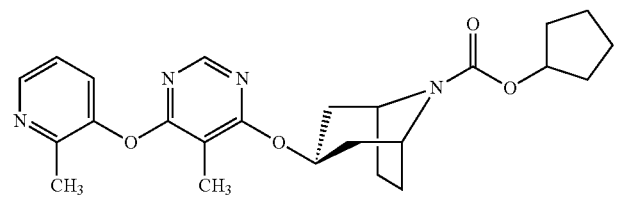 |
| 30 | 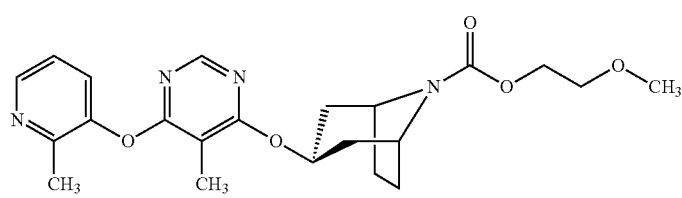 |
| 31 | 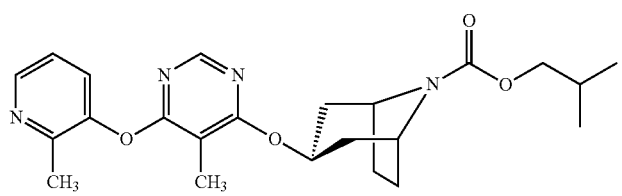 |
| 32 | 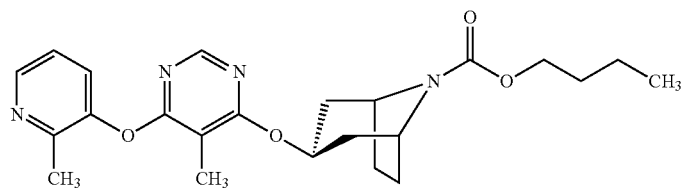 |

-continued
| Compound No. | STRUCTURE |
|---|---|
| 33 | 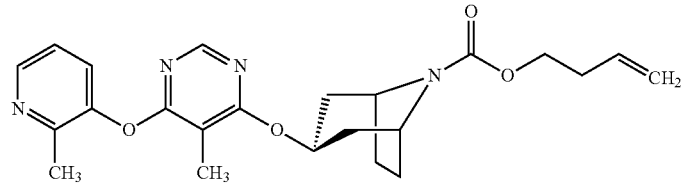 |
| 34 | 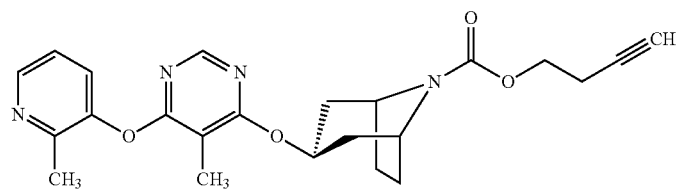 |
| 35 | 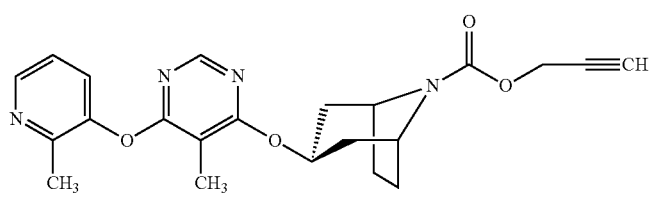 |
| 36 | 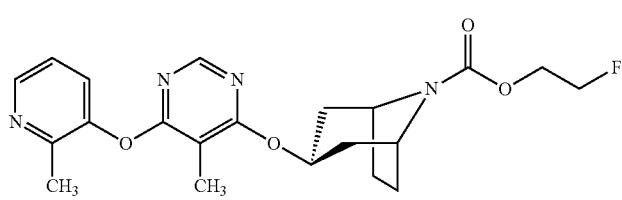 |
| 37 | 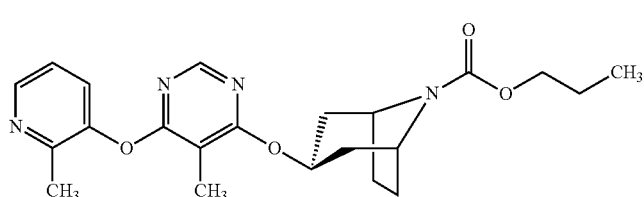 |
| 38 | 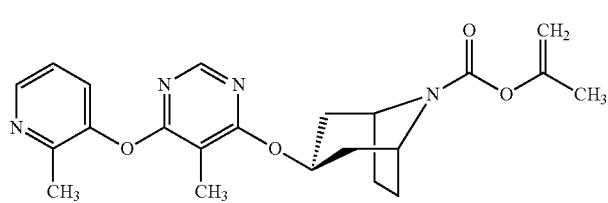 |
| 39 | 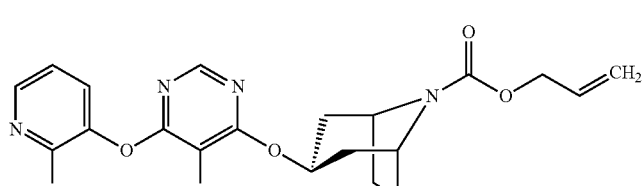 |
| 40 | 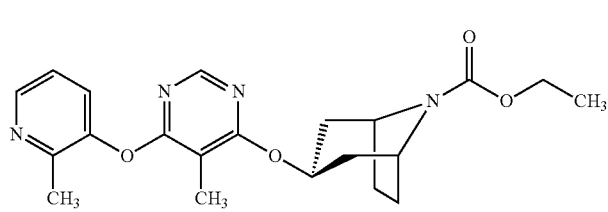 |

| Compound No. | STRUCTURE |
|---|---|
| 41 | 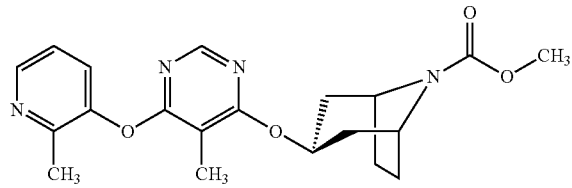 |
| 42 | 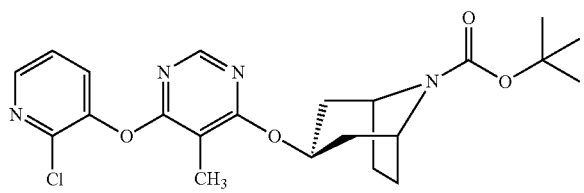 |
| 43 | 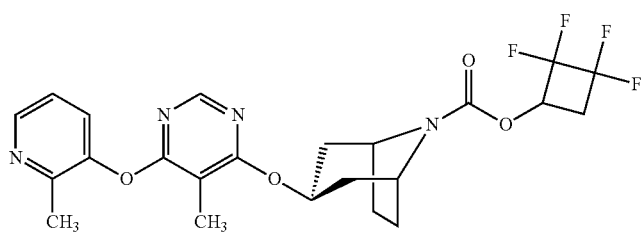 |
| 44 | 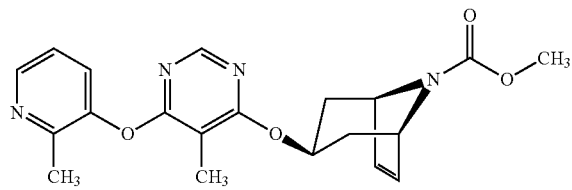 |
| 45 | 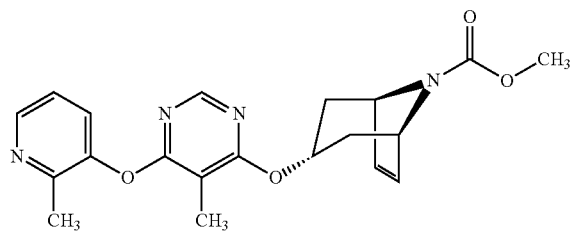 |
| 46 | 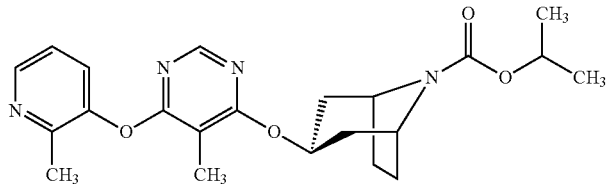 |
| 47 | 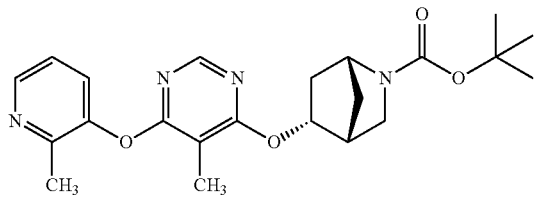 [SMILES: Cc1ncccc1Oc1ncnc(O[C@@H]2C[C@H]3C[C@@H]2CN3C(=O)OC(C)(C)C)c1C] |

| Compound No. | STRUCTURE |
|---|---|
| 48 | 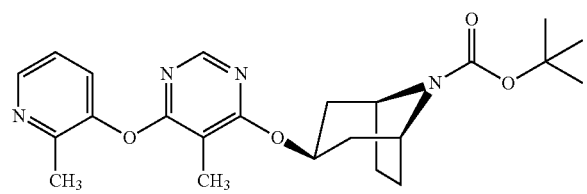 |
| 49 | 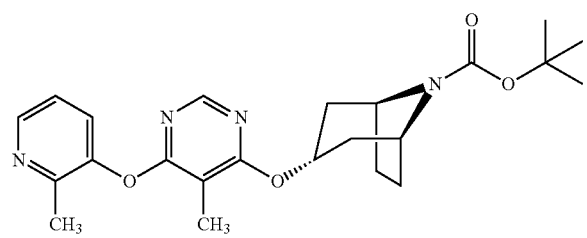 |
| 50 | 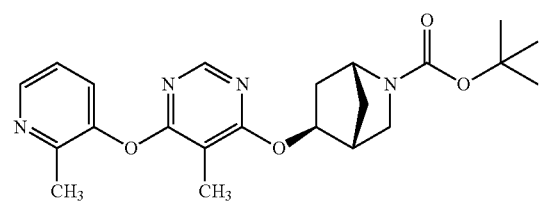 [SMILES: Cc1ncccc1Oc1ncnc(O[C@H]2C[C@H]3C[C@@H]2CN3C(=O)OC(C)(C)C)c1C] |
| 51 | 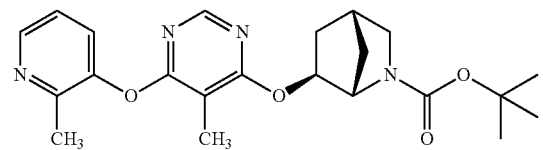 [SMILES: Cc1ncccc1Oc1ncnc(O[C@H]2C[C@H]3C[C@@H]2N(C(=O)OC(C)(C)C)C3)c1C] |
| 52 | 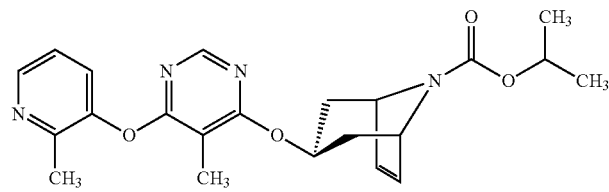 |
| 53 | 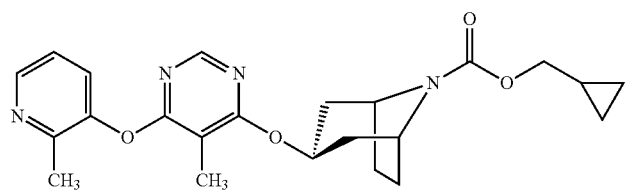 |
| 54 | 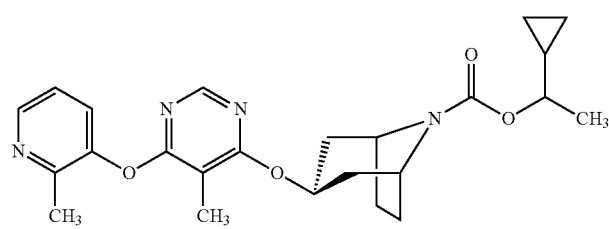 |

-continued
| Compound No. | STRUCTURE |
|---|---|
| 55 | 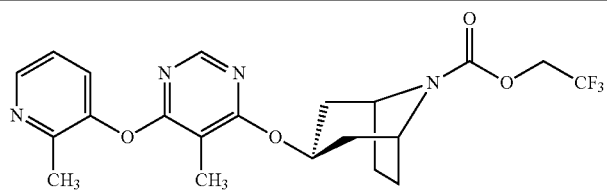 |
| 56 | 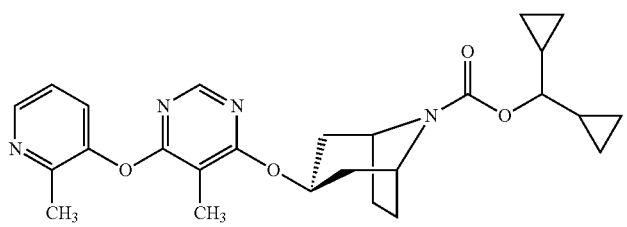 |
| 57 | 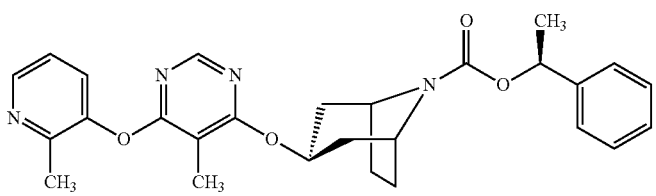 |
| 58 | 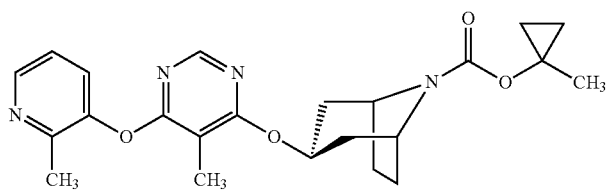 |
| 59 | 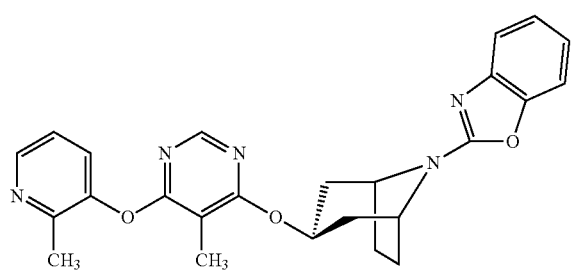 |
| 60 | 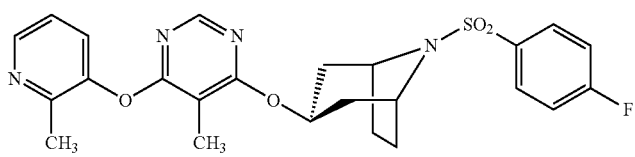 |
| 61 | 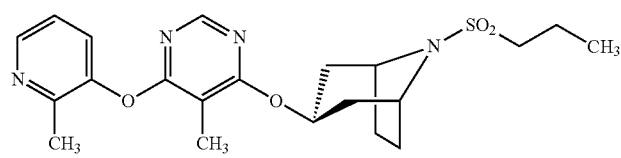 |
| 62 | 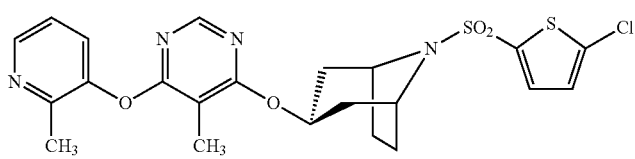 |

| Compound No. | STRUCTURE |
|---|---|
| 63 | 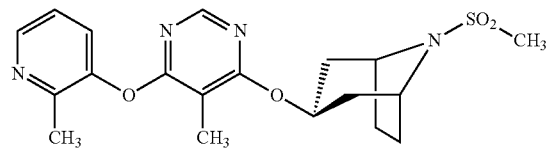 |
| 64 | 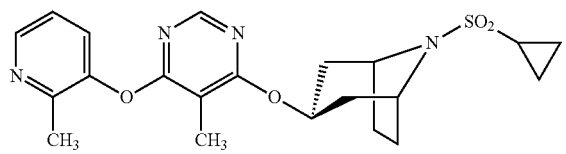 |
| 65 | 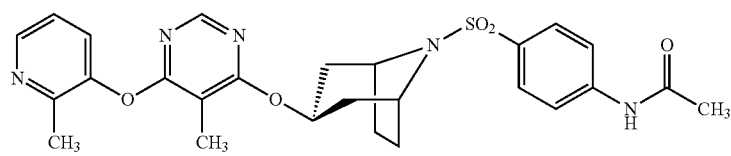 |
| 66 | 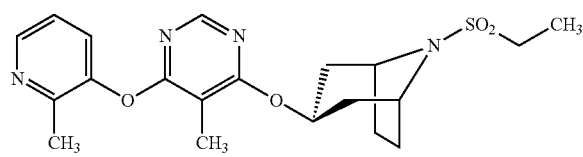 |
| 67 | 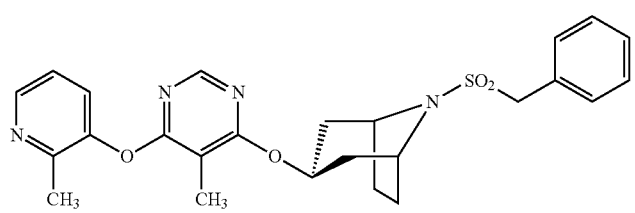 |
| 68 | 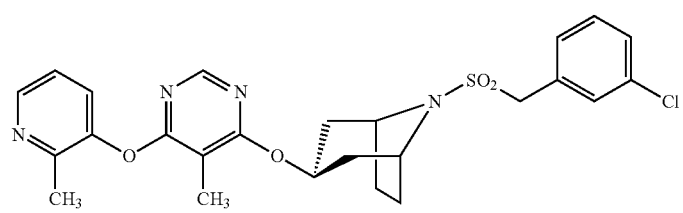 |
| 69 | 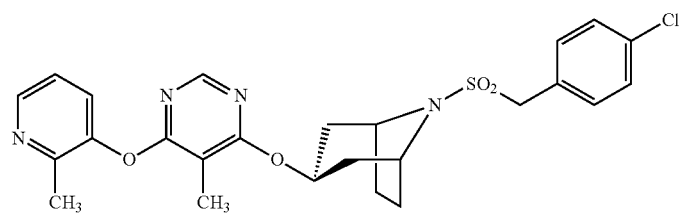 |
| 70 | 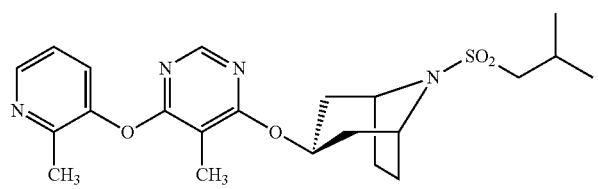 |

| Compound No. | STRUCTURE |
|---|---|
| 71 | 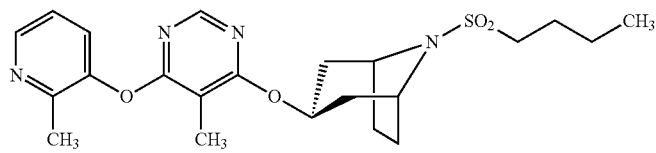 |
| 72 | 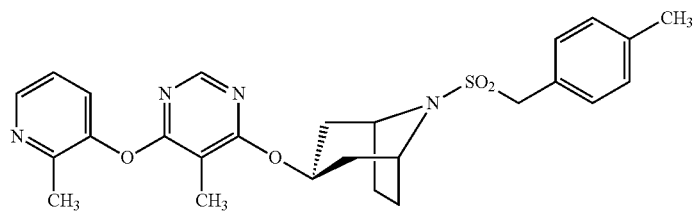 |
| 73 | 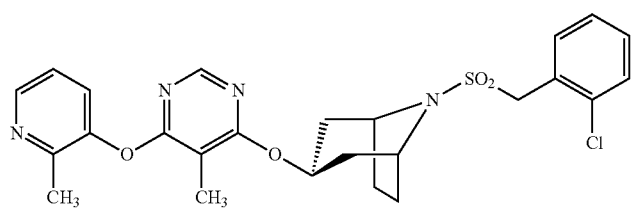 |
| 74 | 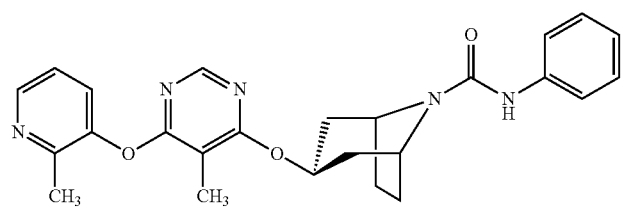 |
| 75 | 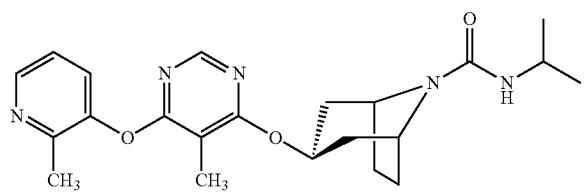 |
| 76 | 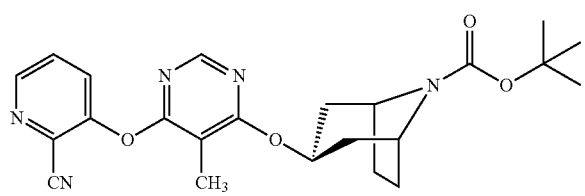 |
| 77 | 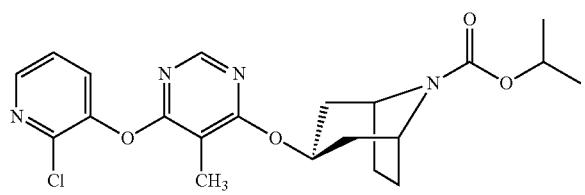 |

-continued
| Compound No. | STRUCTURE |
|---|---|
| 78 | 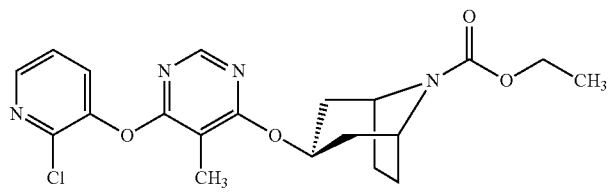 |
| 79 | 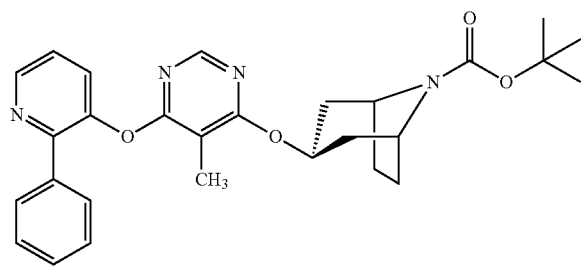 |
| 80 | 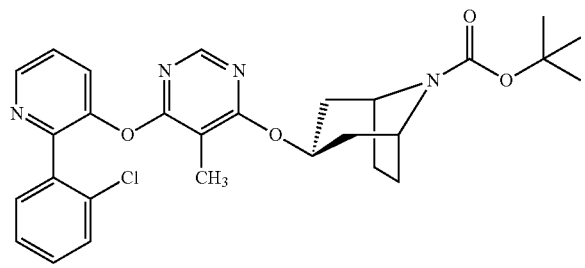 |
| 81 | 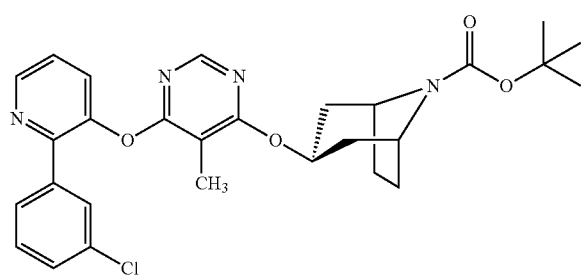 |
| 82 | 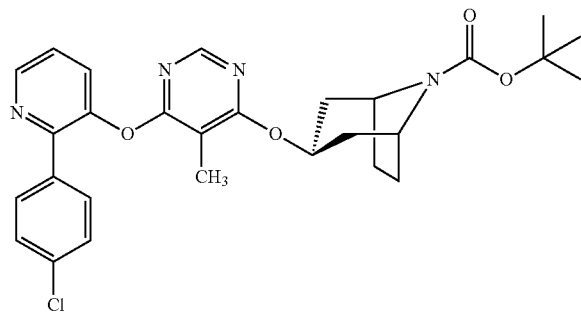 |
| 83 | 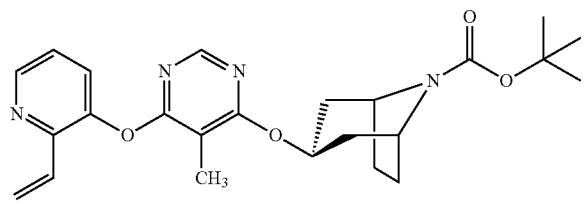 |

| Compound No. | STRUCTURE |
|---|---|
| 84 | 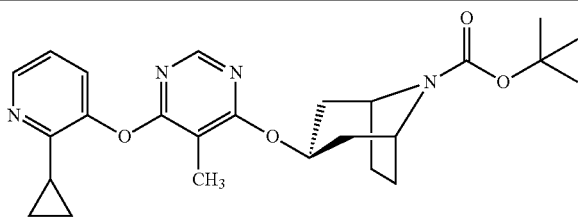 |
| 85 | 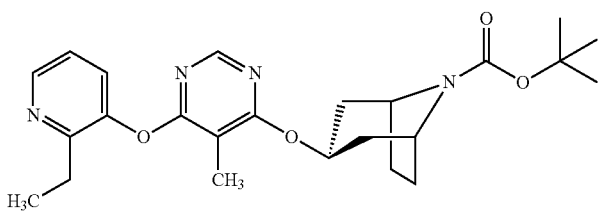 |
| 86 | 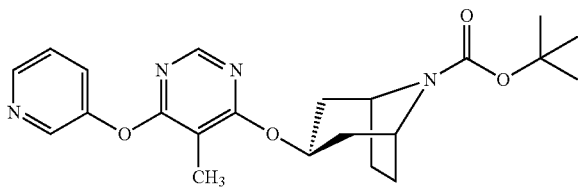 | and pharmaceutically acceptable salts, solvates, esters, prodrugs and stereoisomers thereof.

Additional illustrative compounds of the present invention include compounds 499-501, 511-523, and 564-610 as depicted in the tables immediately below, and pharmaceutically acceptable salts, solvates, esters, prodrugs and stereoisomers thereof.

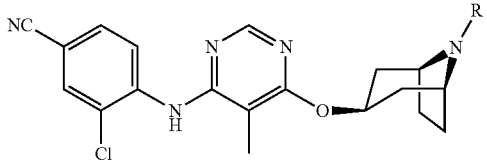

| Cpd. No. | R | LCMS (MH+) |
|---|---|---|
| 499 | 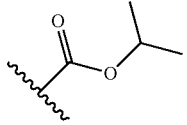 [SMILES: *C(=O)OC(C)C] | 456.3 |
| 500 | 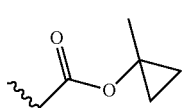 | 468.3 |
| 501 | 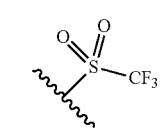 | 499.3 |

-continued

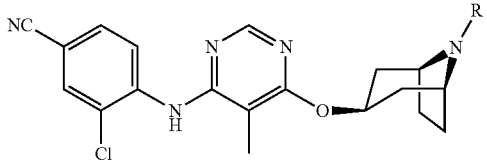

| Cpd. No. | R | LCMS (MH+) |
|---|---|---|
| 511 | 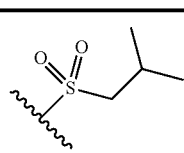 | 490.3 |
| 512 | 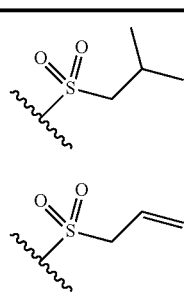 | 474.3 |
| 513 | 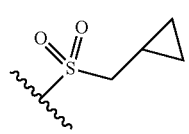 [SMILES: *S(=O)(=O)CC1CC1] | 488.3 |
| 514 | 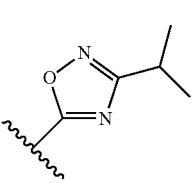 [SMILES: *c1nc(C(C)C)no1] | 480.3 |

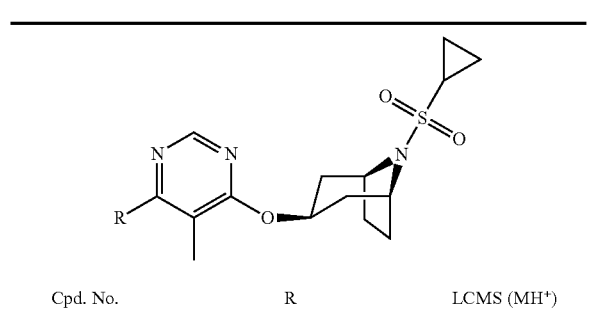
| Cpd. No. | R | LCMS (MH+) |
|---|---|---|
| 515 | 2,4,6-trifluorophenyl-NH- | 469.3 |
| 516 | 3-chloropyridin-4-yl-NH- | 450.2 |
| 517 | 2-chloropyridin-3-yl-NH- | 450.2 |
| 518 | 2,6-dichloropyridin-3-yl-NH- | 484.3 |
| 519 | 4-(MeO2C)-2-chlorophenyl-NH- | 507.2 |
| 520 | 4-acetyl-2-chlorophenyl-NH- | 491.3 |
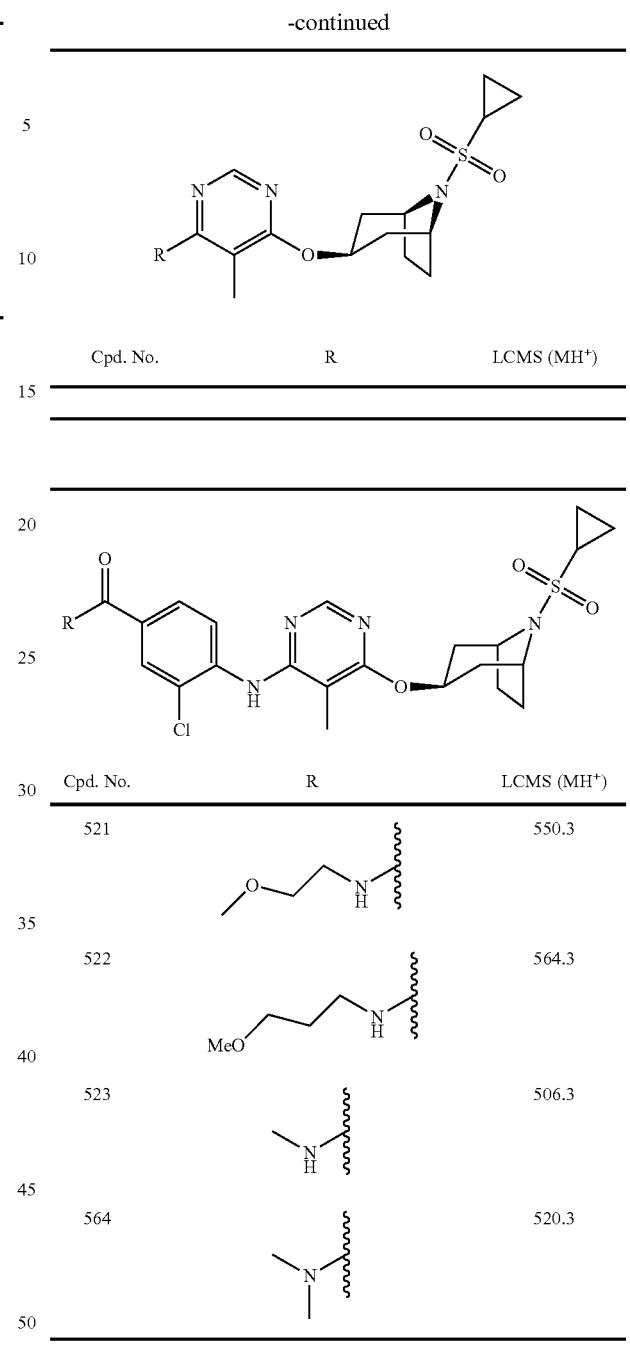
| Cpd. No. | R | LCMS (MH+) |
|---|---|---|
| 521 | MeOCH2CH2-NH- | 550.3 |
| 522 | MeO(CH2)3-NH- | 564.3 |
| 523 | MeNH- | 506.3 |
| 564 | Me2N- | 520.3 |
| Cpd. No. | Structure | LCMS (MH+) |
|---|---|---|
| 565 | 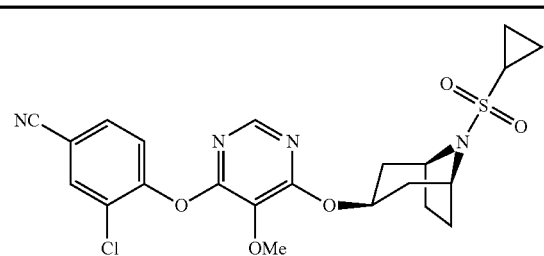 | 491.3 |

-continued

| Cpd. No. | Structure | LCMS (MH+) |
|---|---|---|
| 566 | 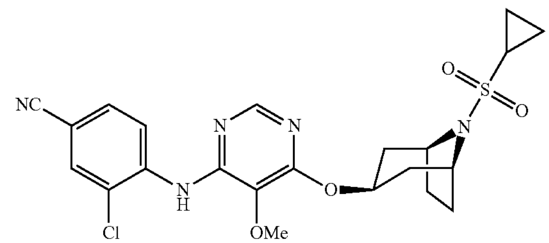 | 490.3 |
| 567 | 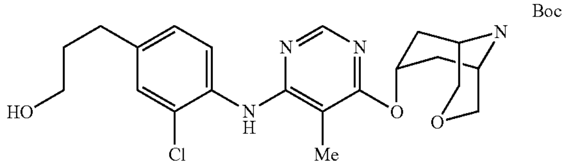 [SMILES: Cc1c(Nc2ccc(CCCO)cc2Cl)ncnc1OC1CC2COCC(C1)N2 ; "Boc"] | 505, 507 |
| 568 | 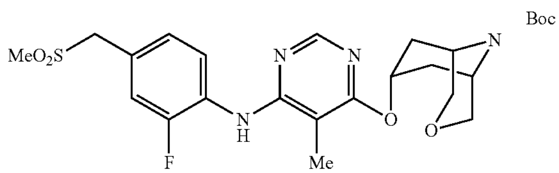 [SMILES: Cc1c(Nc2ccc(CS(C)(=O)=O)cc2F)ncnc1OC1CC2COCC(C1)N2 ; "Boc"] | 537 |
| 569 | 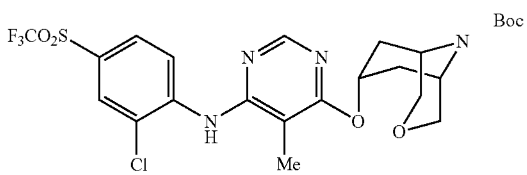 | 594 |
| 570 | 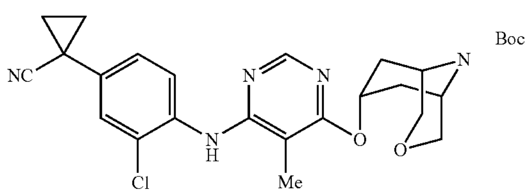 [SMILES: Cc1c(Nc2ccc(C3(C#N)CC3)cc2Cl)ncnc1OC1CC2COCC(C1)N2 ; "Boc"] | 526, 528 |
| 571 | 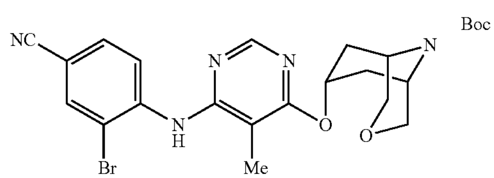 [SMILES: Cc1c(Nc2ccc(C#N)cc2Br)ncnc1OC1CC2COCC(C1)N2 ; "Boc"] | 530, 532 |
| 572 | 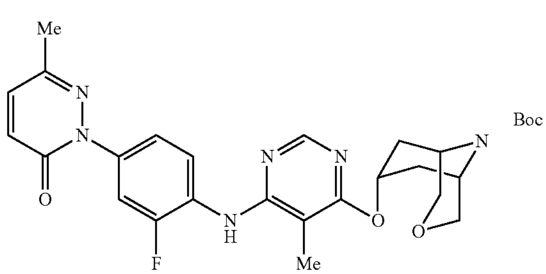 [SMILES: Cc1ccc(=O)n(-c2ccc(Nc3ncnc(OC4CC5COCC(C4)N5)c3C)c(F)c2)n1 ; "Boc"] | 553 |

-continued

| Cpd. No. | Structure | LCMS (MH+) |
|---|---|---|
| 573 | 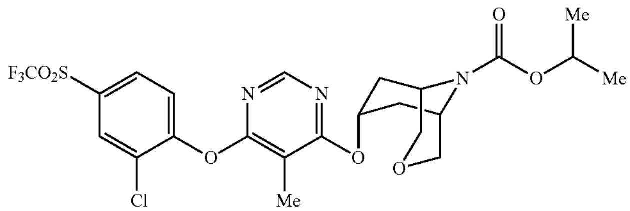 | 579, 581 |
| 574 | 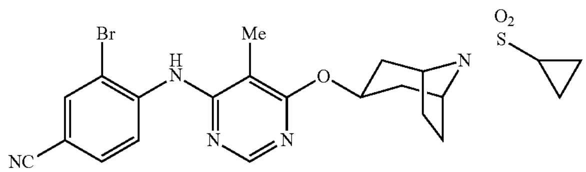 | 518, 520 |
| 575 | 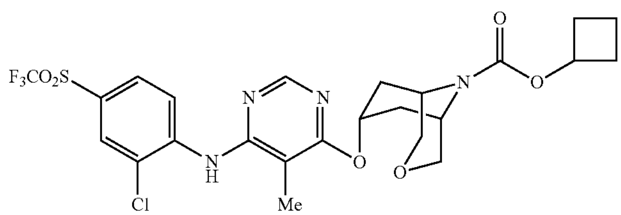 | 591, 593 |
| 576 | 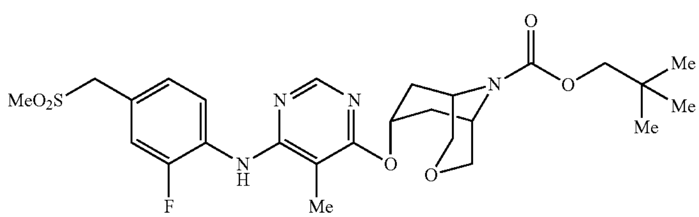 [SMILES: Cc1c(Nc2ccc(CS(C)(=O)=O)cc2F)ncnc1OC1CC2COCC(C1)N2C(=O)OCC(C)(C)C] | 505, 507 |
| 577 | 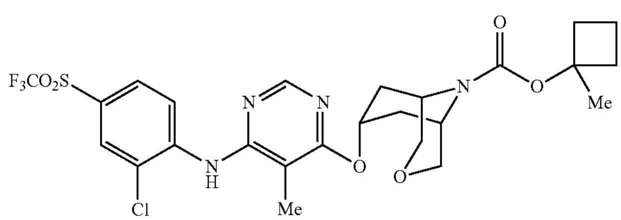 | 605, 607 |
| 578 | 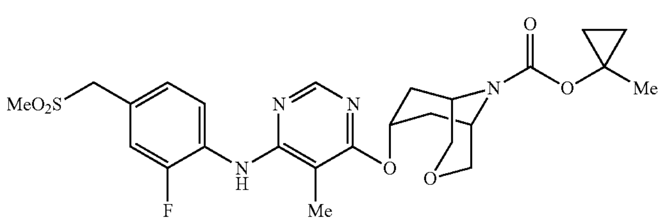 [SMILES: Cc1c(Nc2ccc(CS(C)(=O)=O)cc2F)ncnc1OC1CC2COCC(C1)N2C(=O)OC1(C)CC1] | 493 |
| 579 | 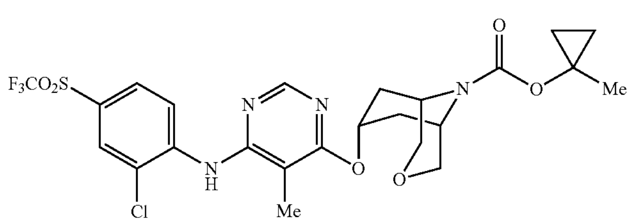 | 591, 593 |

| Cpd. No. | Structure | LCMS (MH+) |
|---|---|---|
| 580 | 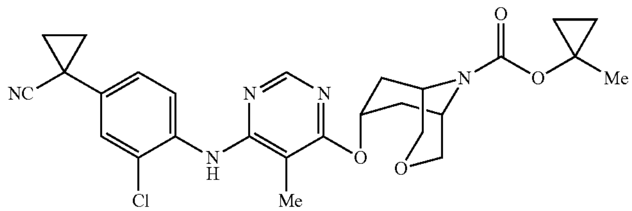 [SMILES: Cc1c(Nc2ccc(C3(C#N)CC3)cc2Cl)ncnc1OC1CC2COCC(C1)N2C(=O)OC1(C)CC1] | 524, 526 |
| 581 | 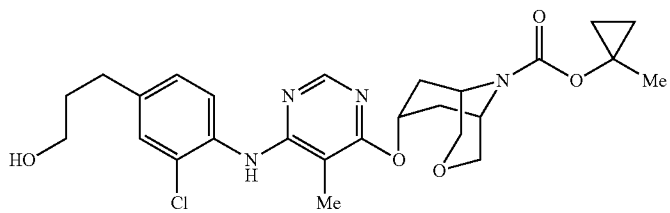 [SMILES: Cc1c(Nc2ccc(CCCO)cc2Cl)ncnc1OC1CC2COCC(C1)N2C(=O)OC1(C)CC1] | 503, 505 |
| 582 | 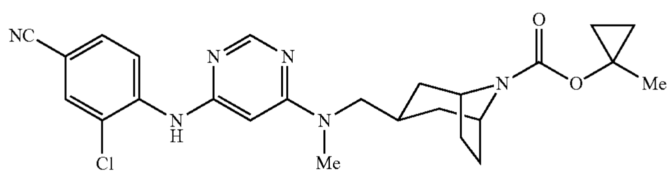 [SMILES: CN(CC1CC2CCC(C1)N2C(=O)OC1(C)CC1)c1cc(Nc2ccc(C#N)cc2Cl)ncn1] | 481, 483 |
| 583 | 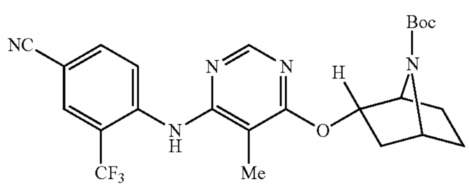 [SMILES: Cc1c(Nc2ccc(C#N)cc2C(F)(F)F)ncnc1OC1CC2CCC1N2C(=O)OC(C)(C)C] | 490 |
| 584 | 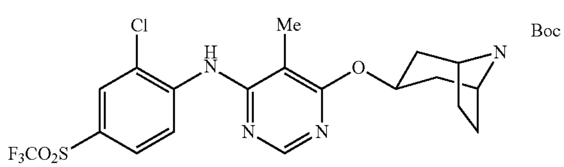 | 577, 579 |
| 585 | 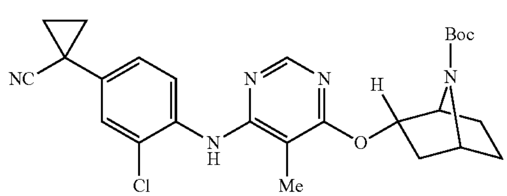 [SMILES: Cc1c(Nc2ccc(C3(C#N)CC3)cc2Cl)ncnc1OC1CC2CCC1N2C(=O)OC(C)(C)C] | 496, 498 |
| 586 | enantiomer B | 493 |

-continued
| Cpd. No. | Structure | LCMS (MH+) |
|---|---|---|
| 587 | 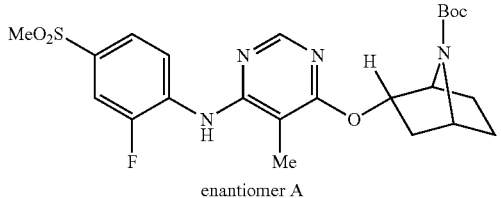 [SMILES: Cc1c(Nc2ccc(S(C)(=O)=O)cc2F)ncnc1OC1CC2CCC1N2C(=O)OC(C)(C)C] enantiomer A | 493 |
| 588 | 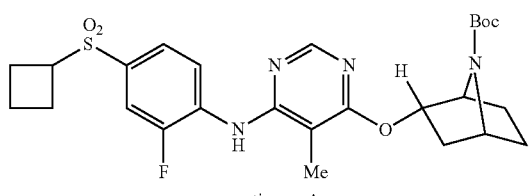 enantiomer A | 533 |
| 589 | 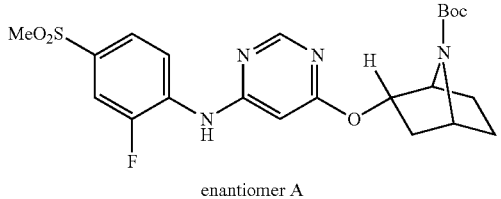 [SMILES: CC(C)(C)OC(=O)N1C2CCC1C(Oc1cc(Nc3ccc(S(C)(=O)=O)cc3F)ncn1)C2] enantiomer A | 479 |
| 590 | 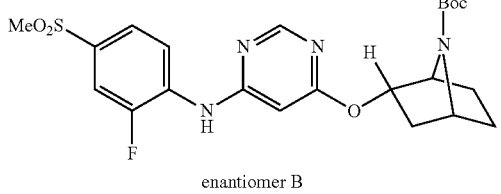 enantiomer B | 479 |
| 591 | 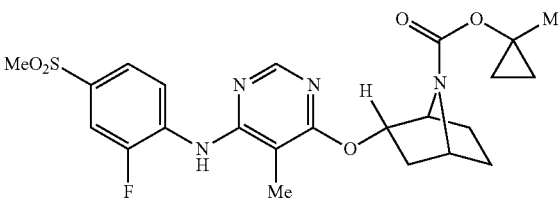 | 491 |
| 592 | 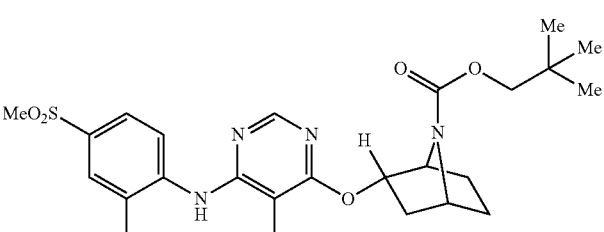 | 507 |
| 593 | 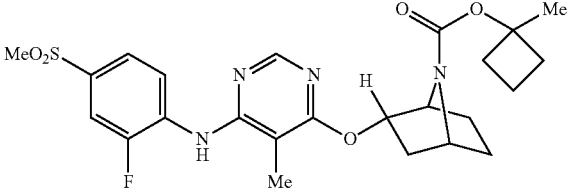 [SMILES: Cc1c(Nc2ccc(S(C)(=O)=O)cc2F)ncnc1OC1CC2CCC1N2C(=O)OC1(C)CCC1] | 505 |

| Cpd. No. | Structure | LCMS (MH+) |
|---|---|---|
| 594 | MeO₂S-C₆H₃(F)-NH-[pyrimidine-Me]-O-[bicyclic N-C(O)O-cyclobutyl] | 491 |
| 595 | MeO₂S-C₆H₃(F)-NH-[pyrimidine-Me]-O-[bicyclic N-C(O)O-C(Me)(cyclopropyl)], enantiomer A | 491 |
| 596 | MeO₂S-C₆H₃(F)-NH-[pyrimidine-Me]-O-[bicyclic N-C(O)O-C(Me)(cyclopropyl)], enantiomer B | 491 |
| 597 | MeO₂S-C₆H₃(F)-NH-[pyrimidine-Me]-O-[bicyclic N-C(O)O-cyclobutyl], enantiomer A | 491 |
| 598 | MeO₂S-C₆H₃(F)-NH-[pyrimidine-Me]-O-[bicyclic N-C(O)O-cyclobutyl], enantiomer B | 491 |
| 599 | MeO₂S-C₆H₃(F)-NH-[pyrimidine-Me]-O-[bicyclic N-C(O)O-CH(Me)₂], enantiomer A | 479 |

-continued

| Cpd. No. | Structure | LCMS (MH+) |
|---|---|---|
| 600 | enantiomer B | 479 |
| 601 | enantiomer A | 505 |
| 602 | enantiomer B | 505 |
| 603 | enantiomer A | 477 |
| 604 | enantiomer A | 480 |
| 605 | enantiomer A | 492 |

-continued

| Cpd. No. | Structure | LCMS (MH+) |
|---|---|---|
| 606 | 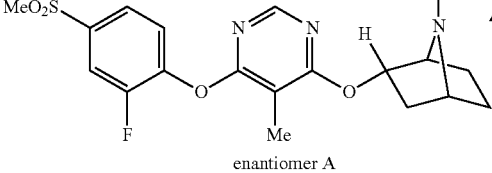<br>enantiomer A | 492 |
| 607 | 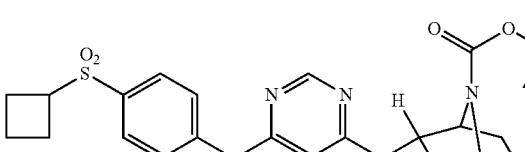<br>enantiomer A | 531 |
| 608 | 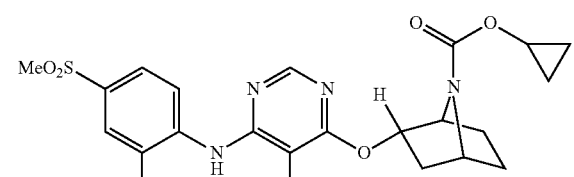<br>enantiomer A | 477 |
| 609 | 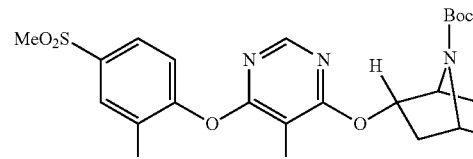<br>enantiomer A | 494 |
| 610 | 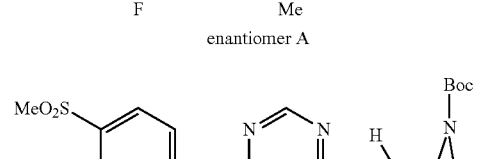<br>enantiomer B | 494 |

NA = not available

Further illustrative compounds of the present invention include compounds 87-498, 502-510, 524-563 and 611 as depicted in the Examples section below herein, and pharmaceutically acceptable salts, solvates, esters, prodrugs and stereoisomers thereof.

Methods for Making the Bicyclic Heterocycle Derivatives

Methods useful for making the Bicyclic Heterocycle Derivatives are set forth in the Examples below and generalized in Schemes 1-7. Alternative synthetic pathways and analogous structures will be apparent to those skilled in the art of organic synthesis.

Scheme 1 illustrates a method useful for making the compounds of formula iii, which are useful intermediates for making the Bicyclic Heterocycle Derivatives.

Scheme 1

-continued

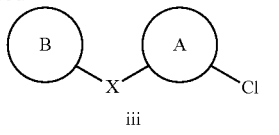
iii wherein A and B are defined above for the compounds of formulas (I), (II), (III) and (IV); G is —OH, —SH, —NHR$^{10}$ or a carbon nucleophile; and X is —S—, —O—, —C(R$^1$)$_2$— or —NR$^{10}$.

A dichloro aryl or heteroaryl compound of formula i can reacted with a compound of formula ii in the presence of a non-nucleophilic base, such as potassium carbonate to provide the intermediate compounds of formula Scheme 2 illustrates a general method useful for making the compounds of formula (I).

Scheme 2

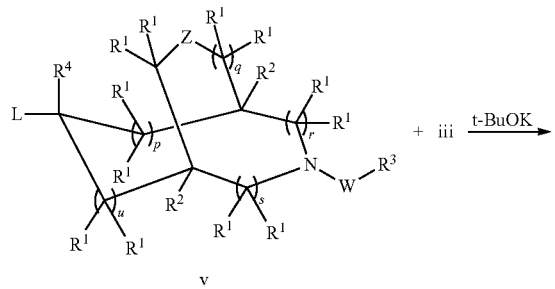
(I)

wherein L is -(alkylene)$_t$-OH, -(alkylene)$_t$-N(R$^{10}$)H or —SH; t is 0 or 1; and R, R$^1$, R$^2$, R$^3$, R$^{10}$, W, X, Y, Z, A, B, p, q, r, s and u are defined above for the compounds of formula (I).

A compound of formula v can be coupled with a compound of formula iii in the presence of potassium tert-butoxide using the method described in International Publication No. WO 07/035355 to Jones et al., to provide the compounds of formula (I).

The compounds of formula v can be commercially available or can be prepared using methods well-known to one skilled in the art of organic chemistry.

Scheme 3 illustrates a general method useful for making the compounds of formula Scheme 3

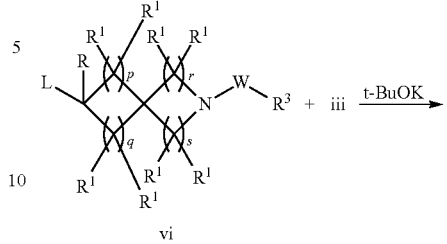
vi

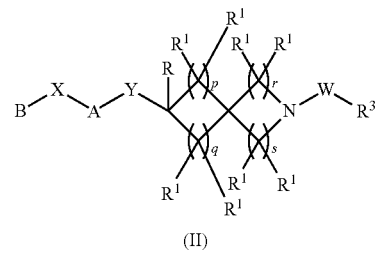
(II)

wherein L is —OH or —SH and R, R$^1$, R$^3$, W, X, Y, Z, A, B, p, q, r and s are defined above for the compounds of formula (II).

A compound of formula vi can be coupled with a compound of formula iii in the presence of potassium tert-butoxide using the method described in International Publication No. WO 07/035355 to Jones et al., to provide the compounds of formula (II).

The compounds of formula vi can be commercially available or can be prepared using methods well-known to one skilled in the art of organic chemistry. Alternatively, the compounds of formula vi can be prepared using the methods described below in Scheme 7 and in the Examples section below.

Scheme 4 illustrates a general method useful for making the compounds of formula (III).

Scheme 4

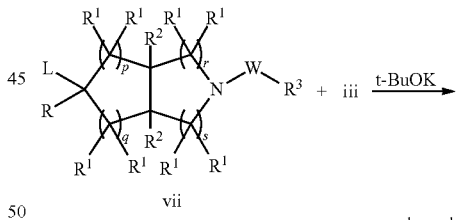
vii

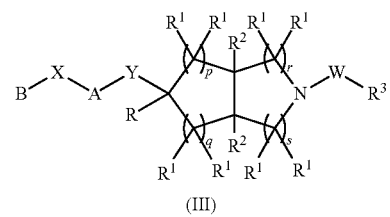
(III)

wherein L is —OH or —SH and R, R$^1$, R$^2$, R$^3$, R$^{10}$, X, Z, A, B, p, q, r, s and u are defined above for the compounds of formula (III).

A compound of formula vii can be coupled with a compound of formula iii in the presence of potassium tert-butoxide using the method described in International Publication No. WO 07/035355 to Jones et al., to provide the compounds of formula (III).

The compounds of formula vii can be commercially available or can be prepared using methods well-known to one skilled in the art of organic chemistry. Alternatively, the compounds of formula vi can be prepared using the methods described below in Schemes 5 and 6 and in the Examples section below.

Scheme 5 shows a method useful for making the compound of formula x, which is a compound of formula vii that is useful for making the compounds of formula (III) wherein Y is —O—; W is —C(O)—; each occurrence of $R^1$ and $R^2$ is H; p and q are each 0; and r and s are each 1.

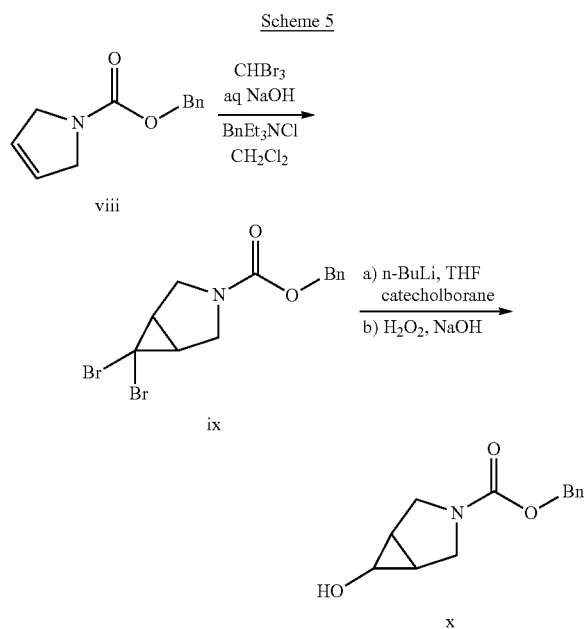

wherein Bn is benzyl.

The compound of formula viii is converted to compound x using the two-step process shown above, which is described in *J. Med. Chem.* 48:5009 (2005).

Scheme 6 shows a method useful for making the compound of formula x, which is a compound of formula vii that is useful for making the compounds of formula (III) wherein Y is —O—; W is —C(O)—; each occurrence of $R^1$ is H; $R^2$ is H car alkyl; p is 0; q is 2; and r and s are each 1.

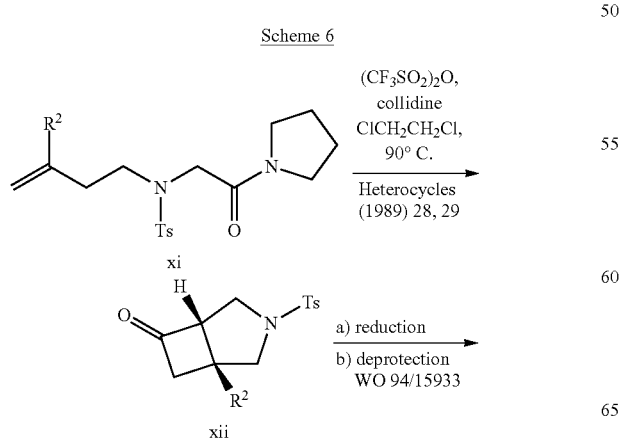

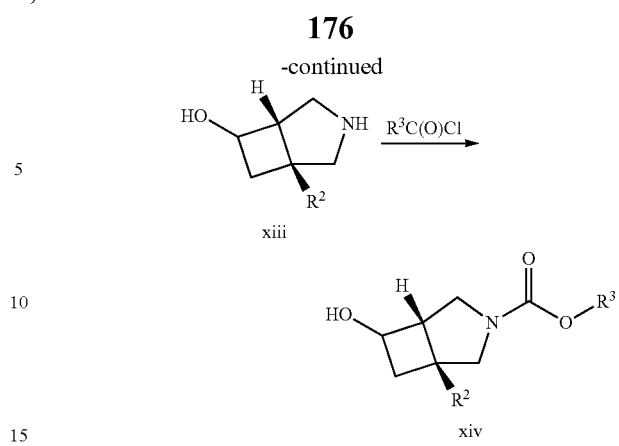

wherein $R^2$ is H or alkyl and $R^3$ is defined above for the Bicyclic Heterocycle Derivatives of formula (II).

A compound of formula xi is converted to a compound of formula xii using the method described in *Heterocycles* 28:29 (1989). The ketone group of the compound of formula xii is subsequently reduced using $NaBH_4$, for example, and then the tosyl group is removed to provide the compound of formula xiii, following the method described in International Publication No. WO 94/15933. Finally, a compound of formula can be reacted with a carbonyl chloride of formula $R^3C(O)Cl$ to provide the compounds of formula xiv.

Scheme 7 shows a method useful for making the compound of formula xvii, which is a compound of formula vi that is useful for making the compounds of formula (II) wherein Y is —O—; W is —C(O)—; each occurrence of $R^1$ is H; and p, q, r and s are each 1.

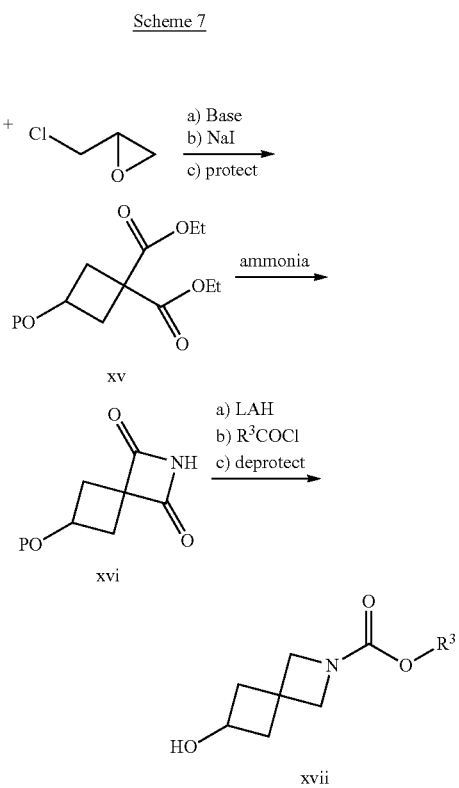

wherein $R^3$ is defined above for the Bicyclic Heterocycle Derivatives of formula (II).

Diethyl malonate is reacted with chloromethyl ethylene oxide in the presence of a non-nucleophilic base. The product of this reaction is treated with NaI to close the cyclobutyl ring and the hydroxy group on the cyclobutyl ring is subsequently protected with an appropriate protecting group to provide the compound of formula xv. The compound of formula xv is then reacted with ammonia to provide spirocyclic compound xvi. The compound of formula xvi is reduced using lithium aluminum hydride (LAH), then reacted with a carbonyl chloride of formula R³C(O)Cl. The resulting carbamate compound is then deprotected to provide the hydroxy intermediates of formula xvii.

The starting materials and reagents depicted in Schemes 1-7 are either available from commercial suppliers such as Sigma-Aldrieh (St. Louis, Mo.) and Acros Organics Co. (Fair Lawn, N.J.), or can be prepared using methods well-known to those of skill in the art of organic synthesis.

One skilled in the art will recognize that the synthesis of Bicyclic Heterocycle Derivatives may require the need for the protection of certain functional groups (i.e. derivatization for the purpose of chemical compatibility with a particular reaction condition). Suitable protecting groups for the various functional groups of the Bicyclic Heterocycle Derivatives and methods for their installation and removal may be found in Greene et al., *Protective Groups in Organic Synthesis*, Wiley-Interscience, New York, (1999).

EXAMPLES

The following examples exemplify illustrative examples of compounds of the present invention and are not to be construed as limiting the scope of the disclosure. Alternative mechanistic pathways and analogous structures within the scope of the invention may be apparent to those skilled in the art.

General Methods

Solvents, reagents, and intermediates that are commercially available were used as received. Reagents and intermediates that are not commercially available were prepared in the manner described below. ¹H NMR spectra were obtained on a Gemini AS-400 (400 MHz) and are reported as ppm down field from Me₄Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum Cl8, 3 micron, 33 mm×7 mm ID; gradient flow: 0 min-10% CH₃CN, 5 min-95% CH₃CN, 7 min-95% CH₃CN, 7.5 min-10% CH₃CN, 9 min-stop. The observed parent ions are given.

Example 1

Preparation of Compound 48

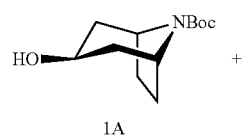

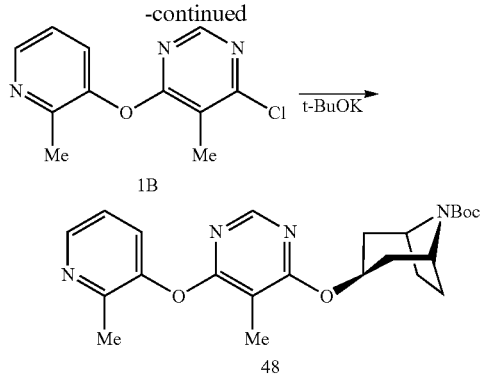

A solution KOBuᵗ (5.8 mL, 1.0 M in THF, 5.8 mmol) was added to a solution of compound 1A (1.1 g, 4.8 mmol, made according to the method described in International Publication No. WO 98/18788 to Blythin, et al.) and compound 1B (1.4 g, 5.8 mmol, made according to the method described in International Publication No. WO 07/035355 to Jones, et al.) in anhydrous THF (100 mL) under nitrogen at 0° C. The reaction was allowed to warm to room temperature on its own and was stirred for a total of 3.5 hours after the addition took place. The reaction was then quenched with water and extracted with 5% MeOH in dichloromethane. The organic layer was dried (MgSO₄) and concentrated in vacuo to provide a crude residue which was chromatographed on a silica gel cartridge (40-100% EtOAc in Hexanes) to provide compound 48 (1.0 g, 40%). LCMS: 427.2 (MH⁺).

Example 2

Preparation of Compound 49

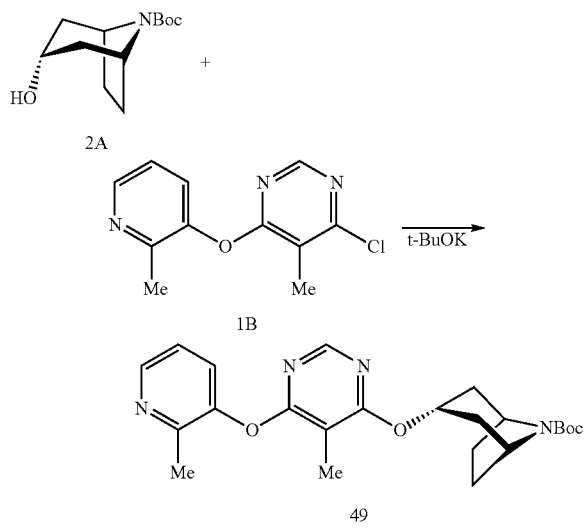

Using the method described in Example 1 and substituting compound 2A (prepared as described in WO98/18788, to Blythin et al.) for compound 1A, compound 49 was prepared. LCMS: 427.2 (MH+).

Example 3

Preparation of Compound 50

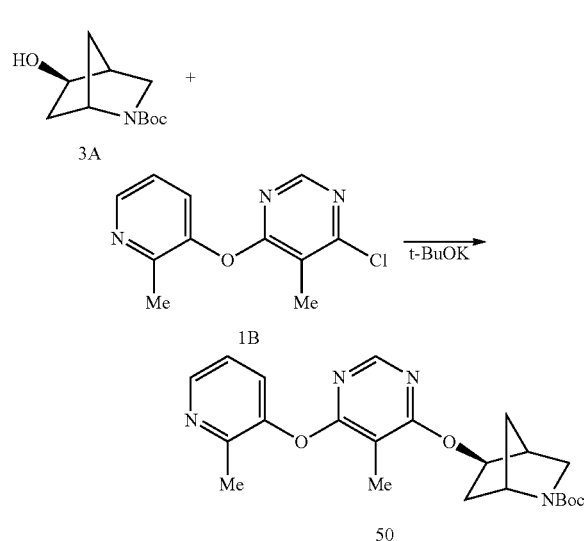

Using the method described in Example 1 and substituting compound 3A (prepared as described in U.S. Pat. No. 5,968,929 to Blythin et al.) for compound 1A, compound 50 was prepared. LCMS: 413.2 (MH+).

Example 4

Preparation of Compound 51

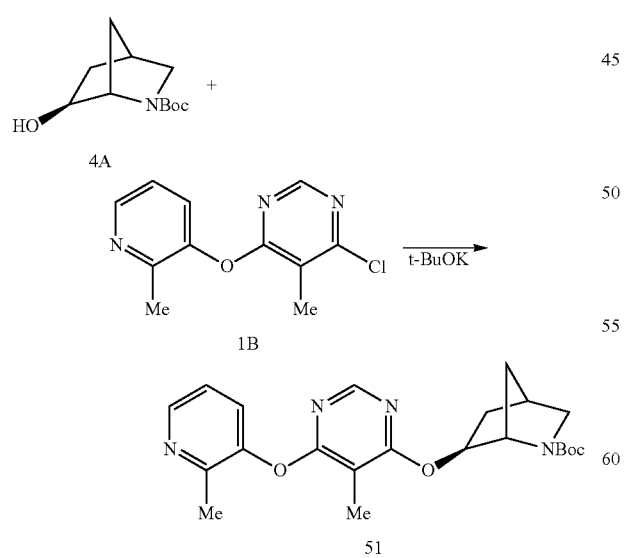

Using the method described in Example 1 and substituting compound 4A (prepared as described in U.S. Pat. No. 5,968,929 to Blythin et al.) for compound 1A, compound 51 was prepared. LCMS: 413.2 (MH+).

Example 5

Preparation of Compound 47

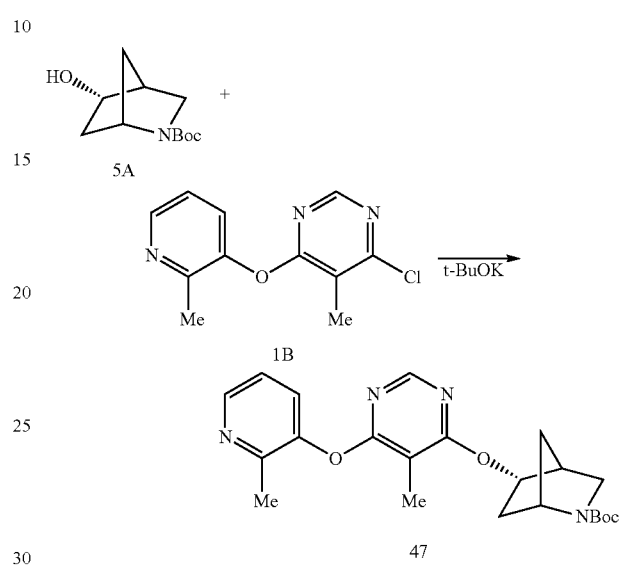

Using the method described in Example 1 and substituting compound 5A (prepared as described in WO 97/40016 to Mitch et al.) for compound 1A, compound 47 was prepared. LCMS: 413.2 (MH+).

Example 6

Preparation of Compound 45

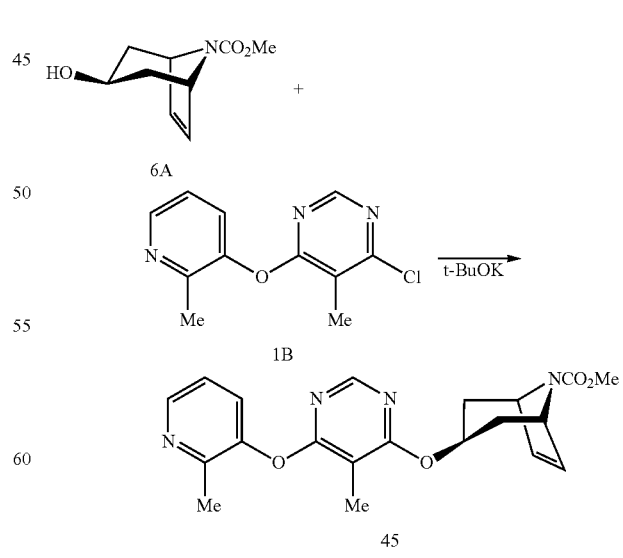

Using the method described in Example 1 and substituting compound 6A (prepared as described in Hodgson et al., *Tet-* rahedron 60:5185 (2004)) for compound 1A, compound 45 was prepared. LCMS: 383.2 (MH+).

Example 7

Preparation of Compound 44

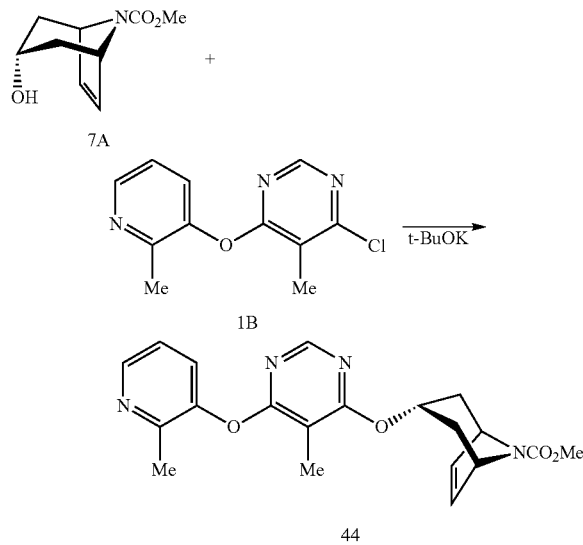

Using the method described in Example 1 and substituting compound 7A (prepared as described in Hodgson et al., *Tetrahedron* 60:5185 (2004)) for compound 1A, compound 44 was prepared. LCMS: 383.2 (MH+).

Example 8

Preparation of Compound 46

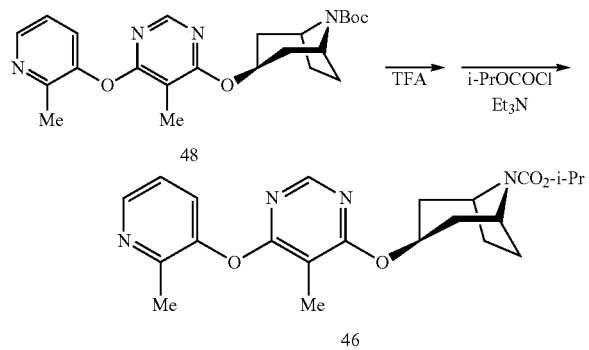

Trifluoroacetic acid (1 mL) was added to a solution of compound 48 (75 mg, 0.18 mmol, prepared as described in Example 1) in dichloromethane (2 mL) at room temperature and stirred for 3.5 hours. The solution was concentrated in vacuo. The residue was chromatographed on a silica gel cartridge with (2 N ammonia in MeOH) in dichloromethane (3→10%) to provide the intermediate amine (57 inv., 100%).

A solution of isopropyl chloroformate (0.20 mL, 1.0 M in toluene, 0.20 mmol) was added to a solution of the intermediate amine from above (33 mg, 0.10 mmol) and Et$_3$N (42 µL, 0.30 mmol) in dichloromethane (2 mL) at room temperature and stirred at room temperature for 2 hours. The reaction was quenched with saturated ammonium chloride solution and extracted with dichloromethane. The organic layer was dried (MgSO$_4$) and concentrated in vacuo. The residue was chromatographed on a silica gel cartridge with (2 N ammonia in MeOH) in dichloromethane (1→5%) to provide compound 46 (35 mg, 84%). LCMS: 413.2 (MH+).

Example 9

Preparation of Compound 42

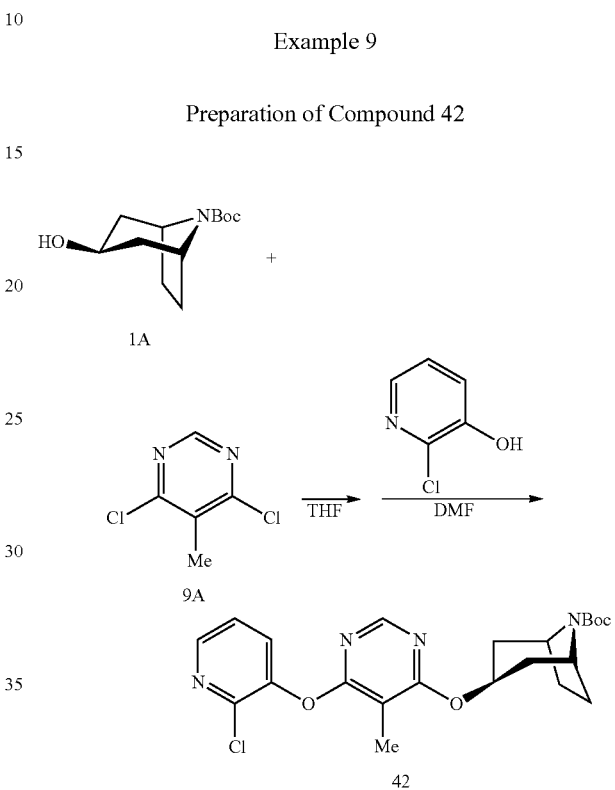

A solution of alcohol 1A (2.0 g, 8.8 mmol, made according to the method described in International Publication No. WO 98/18788 to Blythin, et al.) in 20 ml THF was added to a suspension of sodium hydride (0.44 g, 11 mmol) in THF (10 mL) at room temperature. The reaction was stirred for 30 minutes. A solution of the commercially available dichloride 9A (1.2 g, 7.3 mmol) and 10 ml of THF was added dropwise to the reaction. The reaction was allowed to stir for three hours. The reaction was quenched with water and extracted with dichloromethane. The organic layer was dried (NaSO$_4$) and concentrated in vacuo. A portion of the crude intermediate was carried on to the next step.

The crude intermediate (70 mg, 0.20 mmol) was added to a mixture of potassium carbonate (55 mg, 0.40 mmol) and 2-chloro-3-hydroxypyridine (40 mg, 0.30 mmol) in DMF (2 mL) in a microwave vial. The vial was sealed and heated on high absorbance in a microwave reactor for eight minutes at a temperature of 190° C. The reaction was concentrated in vacuo. The residue was dissolved in ethyl acetate and washed with water. The organic layer was dried (NaSO$_4$) and concentrated in vacuo. The residue was chromatographed on preparative TLC plates with dichloromethane/MeOH (97/3) to provide compound 42 (40 mg, 45%). LCMS: 447.2. (MH+).

The following compound was similarly prepared substituting 2-cyanophenol for 2-chloro-3-hydroxypyrine:

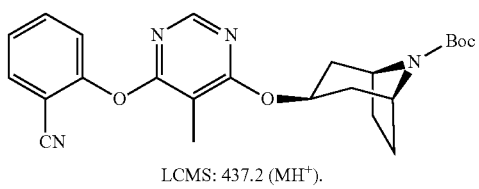

LCMS: 437.2 (MH⁺).

Example 10

Preparation of Compound 43

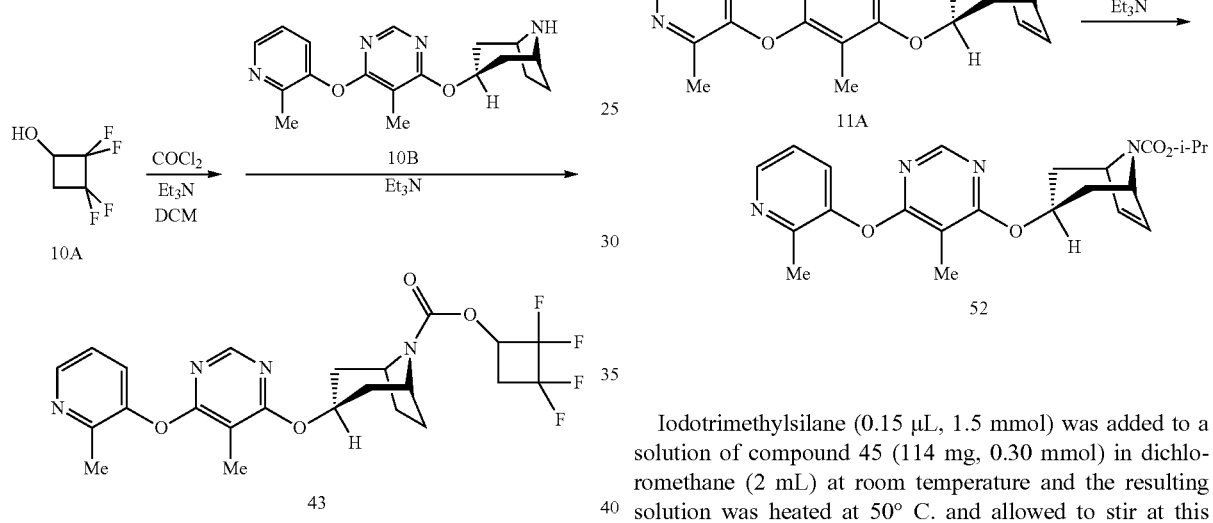

To a solution of tetrafluorocyclobutyl alcohol 10A (26 mg, 0.18 mmol) and triethyl amine (50 µL) in dichloromethane (1.5 mL) was added phosgene (0.15 mL, 1M solution in toluene, 0.15 mmol) and the reaction was allowed to stir at room temperature for 3 hours. Compound 10B (50 mg, 0.15 mmol, prepared by TFA deprotection of compound 48) was added to the reaction, followed by triethylamine (50 µL) and the resulting reaction was allowed to stir for 15 hours. The reaction mixture was concentrated in vacuo and the residue obtained was purified using preparative TLC (eluted with hexane/ethyl acetate (50/50)) to provide compound 43 (5 mg, 6%). LCMS: 497.3 (MH⁺).

Example 11

Preparation of Compound 52

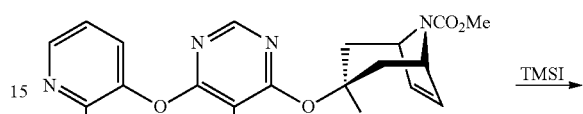

Iodotrimethylsilane (0.15 µL, 1.5 mmol) was added to a solution of compound 45 (114 mg, 0.30 mmol) in dichloromethane (2 mL) at room temperature and the resulting solution was heated at 50° C. and allowed to stir at this temperature for 2 hours. The reaction mixture was cooled to room temperature, saturated NaHCO₃ solution was added, and the resulting solution was allowed to stir for 10 minutes. The mixture was extracted with 5% MeOH in dichloromethane. The organic layer was dried (MgSO₄) and concentrated in vacuo to provide compound 11A, which was subsequently converted to compound 52 using the method described in Example 8. LCMS: 411.2 (MH⁺).

Example 12

Preparation of Compound 53

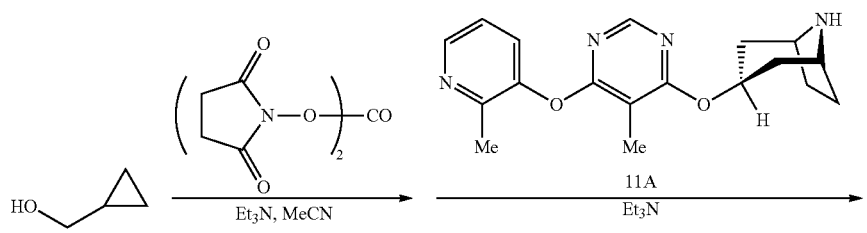

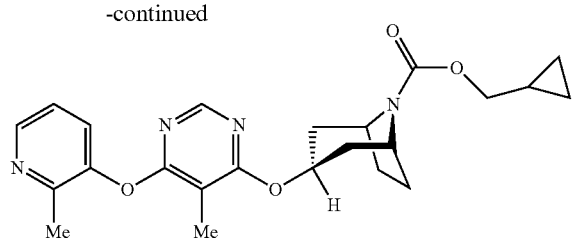

53

To a solution of cyclopropylmethanol (40 μL, 0.50 mmol) and triethylamine (70 μL, 0.50 mmol) in acetonitrile (1 mL) was added N,N'-disuccinimidyl carbonate (0.102 g, 0.40 mmol) and the resulting reaction was allowed to stir at room temperature for 16 hours. Compound 10B (33 mg, 0.10 mmol) was then added to the reaction followed by triethyl amine (35 μL, 0.25 mmol) and the reaction was allowed to stir at room temperature for 4 hours. The crude reaction mixture was diluted with EtOAc, washed with saturated aqueous $NH_4Cl$ solution, then the organic phase was dried ($MgSO_4$), and concentrated in vacuo. The residue obtained was purified using a silica gel cartridge (eluting with EtOAc in hexanes (40→100%)) to provide compound 53 as a clear oil (36 mg, 85%). LCMS: 425.2 ($MH^+$).

The following compounds of the invention were similarly prepared by substituting the appropriate alcohols for cyclopropylmethanol:

| Cpd. No. | Structure | LCMS ($MH^+$) |
| --- | --- | --- |
| 54 | 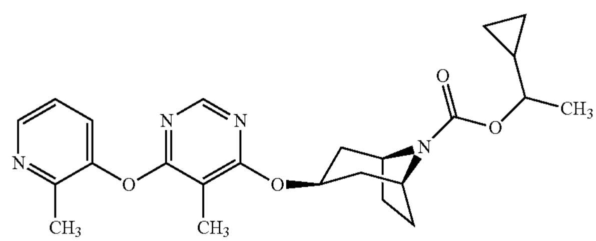 | 439.2 |
| 55 | 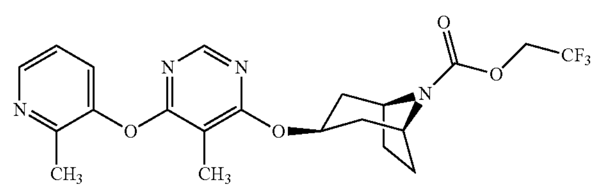 | 453.2 |
| 56 | 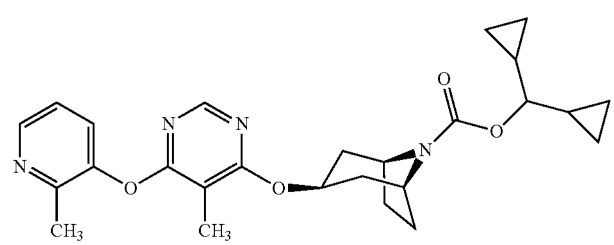 | 465.3 |
| 57 | 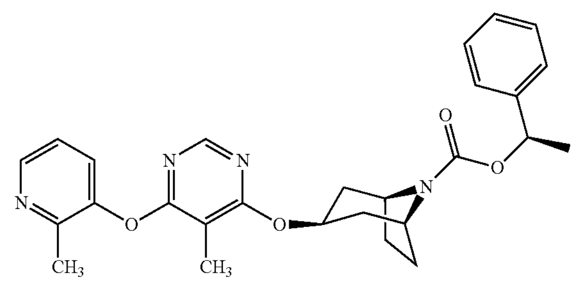 | 475.3 |

Example 16

Preparation of Compound 58

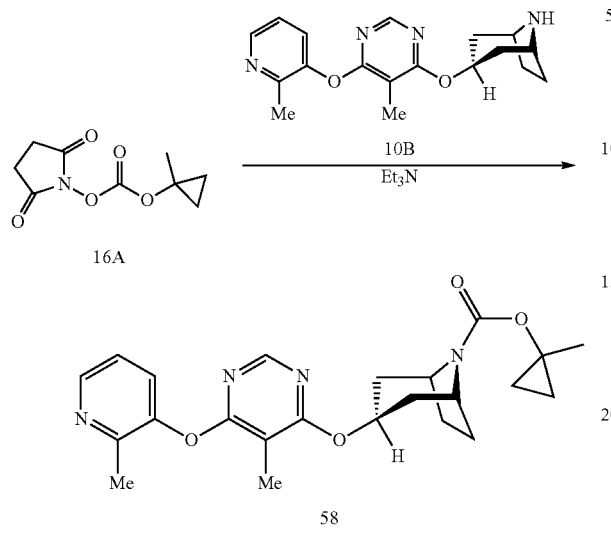

To a solution of compound 16A (83 mg, 0.39 mmol, prepared as described in WO 05/14577 to Zhu et al.) and triethylamine (105 µL, 0.75 mmol) in dichloromethane (1.5 mL) was added compound 10B (50 mg, 0.15 mmol) and the resulting reaction was allowed to stir for 15 hours at room temperature. The crude reaction mixture was then diluted with dichloromethane, washed with saturated aqueous NH$_4$Cl solution, and the organic phase was dried (MgSO$_4$), and concentrated in vacuo. The residue obtained was purified using a silica gel cartridge (eluting with EtOAc in hexanes (40→100%)) to provide compound 58 as a clear resin (44 mg, 69%). LCMS: 425.2 (MH$^+$).

Example 17

Preparation of Compound 59

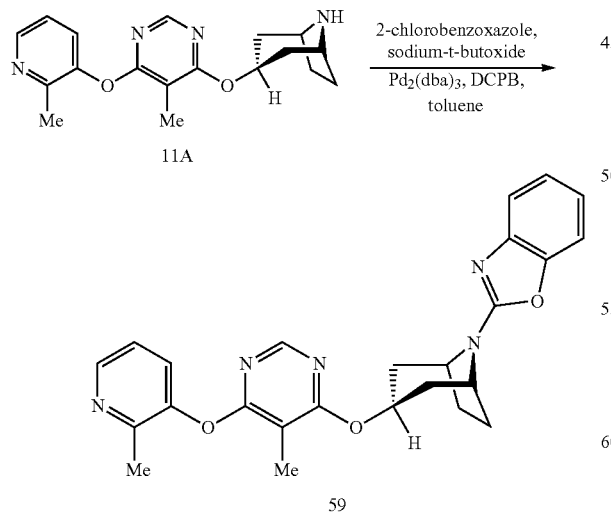

To a mixture of the compound 10B (0.06 g, 0.18 mmol), 2-chlorobenzoxazole 0.085 g, 0.55 mmol), and sodium-tert-butoxide (0.025 g, 0.26 mmol) in toluene (2 mL) was added tris(dibenzylideneacetone)dipalladium (1.6 mg, 0.0055 mmol) and 2-dicyclohexylphosphinobiphenyl (0.003 g, 0.01 mmol). The reaction was put under an argon atmosphere and allowed to stir at room temperature for 16 hours. The crude reaction mixture was concentrated in vacuo and the residue obtained was purified using preparative TLC plate (dichloromethane/MeOH (95/5)) to provide compound 59 as clear oil (31 mg, 39%). LCMS: 444.2 (MH$^+$).

Example 18

Preparation of Compound 18A

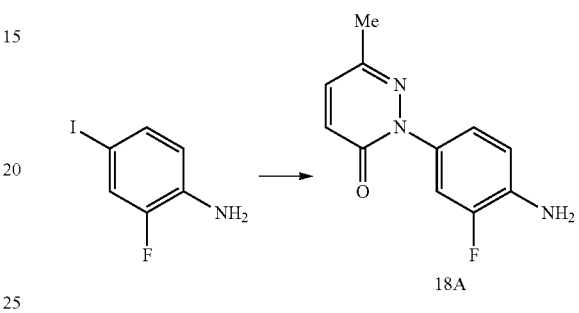

2-Fluoro-4-iodoaniline (3.00 g, 12.7 mmol), 6-methylpyridazine-2-one (1.74 g, 15.8 mmol), 8-hydroxyquinoline (0.276 g, 1.9 mmol), CuI (0.362 g, 1.9 mmol) and K$_2$CO$_3$ (1.92 g, 13.9 mmol) were combined in DMSO (12 mL) and the resulting reaction was heated to 130° C. and allowed to stir at this temperature for 20 hours. The reaction mixture was cooled to room temperature, then diluted with EtOAc and water. Charcoal was added to the resulting solution and the mixture was filtered. The filtrate was transferred to a separatory funnel and the organic phase was collected and washed with brine, dried (MgSO$_4$), filtered and concentrated in vacuo. The resulting residue was purified using flash column chromatography on silica to provide compound 18A as a yellow solid.

Example 19

Preparation of Compound 60

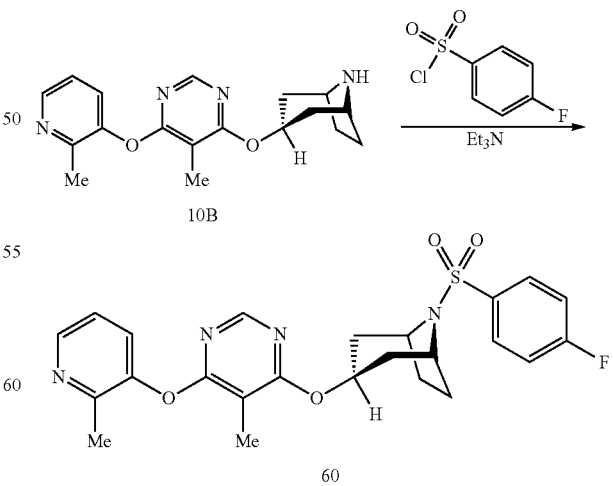

4-fluorobenzenesulfonyl chloride (48 mg, 0.25 mmol) was added to a solution of compound 10B (40 mg, 0.12 mmol) and triethylamine (51 μL, 0.37 mmol) in dichloromethane (1.2 mL) and the reaction was allowed to stir at room temperature for 1 hour. The reaction was then quenched with saturated aqueous NaHCO₃ solution and extracted with dichloromethane. The organic extract was dried (MgSO₄) and concentrated in vacuo to provide a crude residue which was chromatographed on a silica gel cartridge (5% MeOH/dichloromethane) in dichloromethane (0→50%) to provide compound 60 as a white solid (38 mg, 64%). LCMS: 485.3 (MH⁺).

The following compounds of the invention were similarly prepared by substituting the appropriate sulfonyl chlorides for 4-fluorobenzenesulfonyl chloride:

| Cpd. No. | Structure | LCMS (MH⁺) |
|---|---|---|
| 61 | 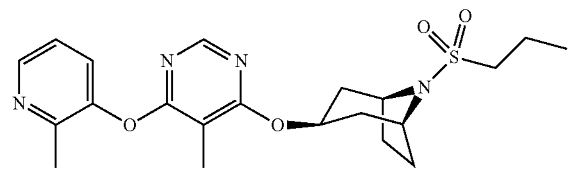 | 433.2 |
| 62 | 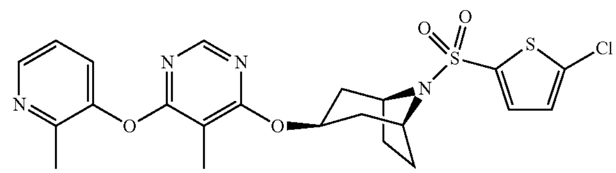 | 507.3 |
| 63 | 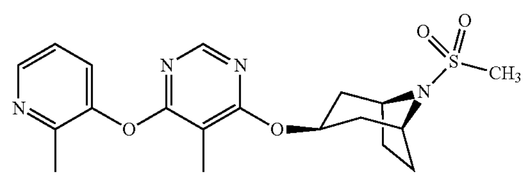 | 405.2 |
| 64 | 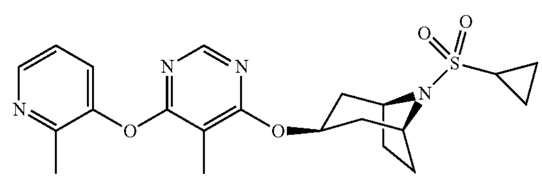 | 431.2 |
| 65 | 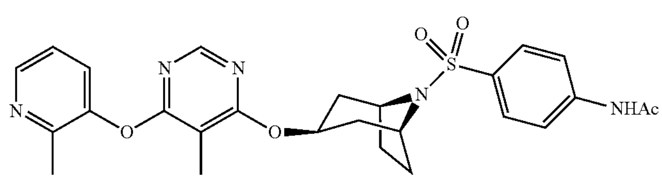 | 524.3 |
| 66 | 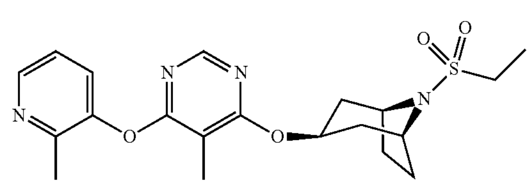 | 419.2 |
| 67 | 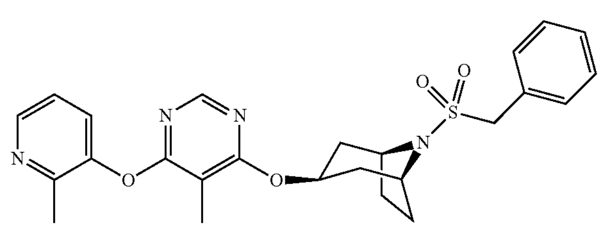 | 481.3 |

-continued

| Cpd. No. | Structure | LCMS (MH+) |
|---|---|---|
| 68 | 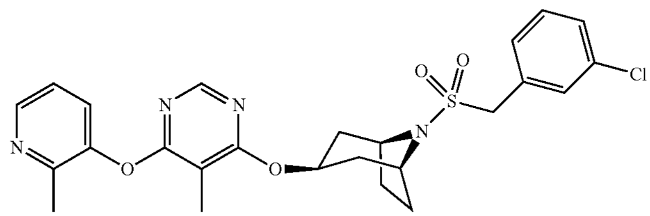 | 515.3 |
| 59 | 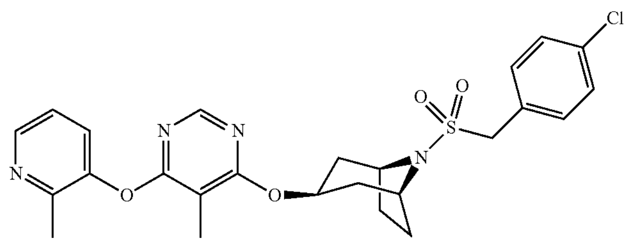 | 515.3 |
| 70 | 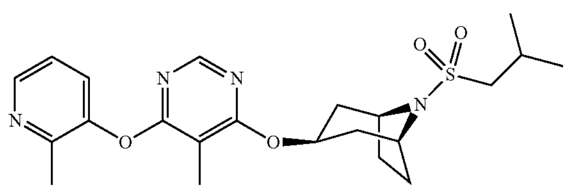 | 447.2 |
| 71 | 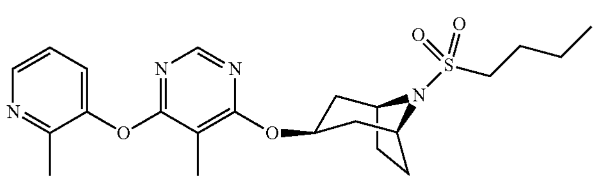 | 447.2 |
| 72 | 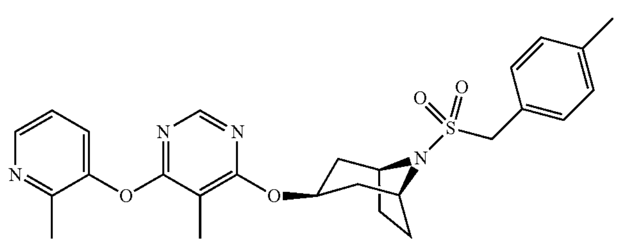 | 495.3 |
| 73 | 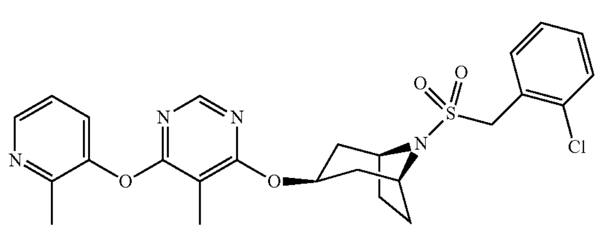 | 515.3 |

Example 20

Preparation of Compound 74

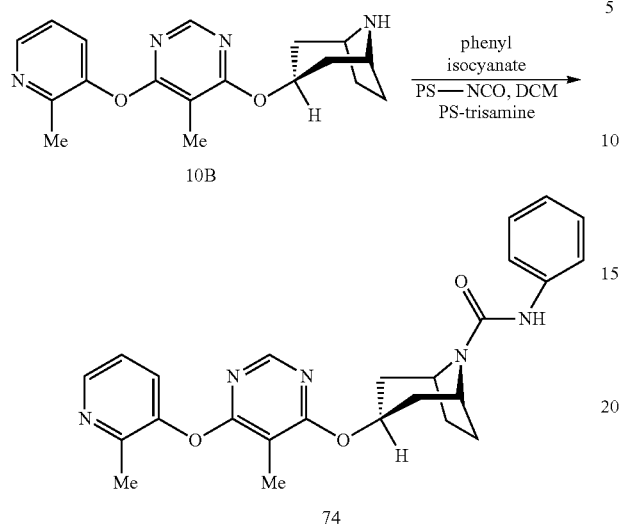

To a solution of compound 40B (8 mg, 0.025 mmol) and dichloroethane (1 mL) was added phenyl isocyanate (6 mg, 0.05 mmol) and the resulting reaction was shaken for 16 hours. PS-trisamine (33 mg, 0.05 mmol, from Biotage), PS-NCO (50 mg, 0.075 mmol, from Biotage), and dichloroethane (0.5 mL) was then added to the reaction mixture and the resulting reaction was shaken for an additional 16 hours. The crude reaction mixture was filtered, rinsed with dichloroethane and concentrated in vacuo to provide compound 74, which was used without further purification. LCMS: 446.2 (MH$^+$).

The following compound was similarly prepared using isopropyl isocyanate in place of phenyl isocyanate:

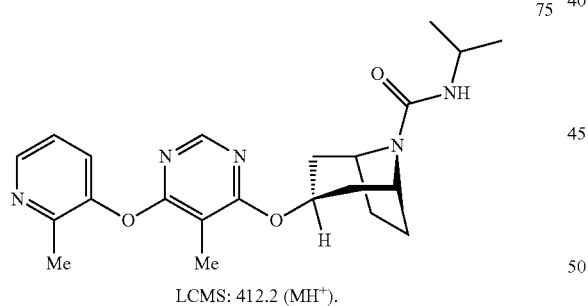

LCMS: 412.2 (MH$^+$).

Example 22

Preparation of Compound 77

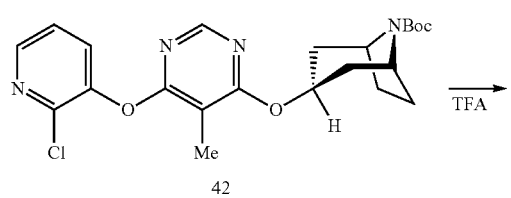

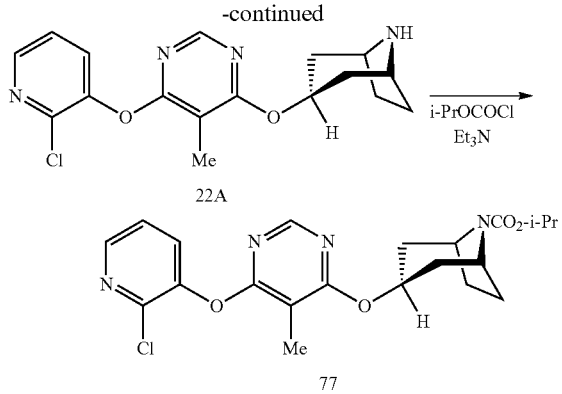

Compound 42 was converted to compound 77 via the intermediate compound 22A using the methods described in Example 8. LCMS: 433.2 (MH$^+$).

Compound 78 was also made using this method:

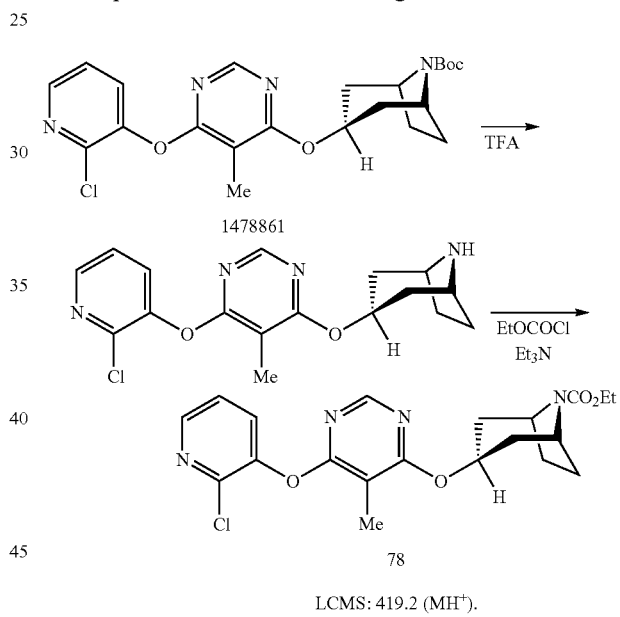

LCMS: 419.2 (MH$^+$).

Example 23

Preparation of Compound 79

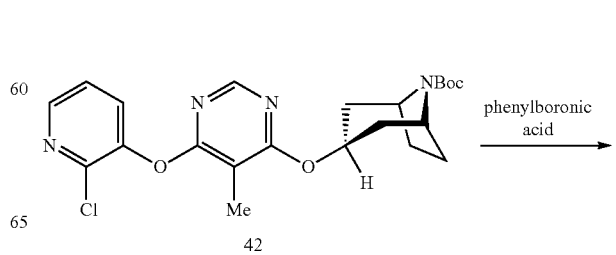

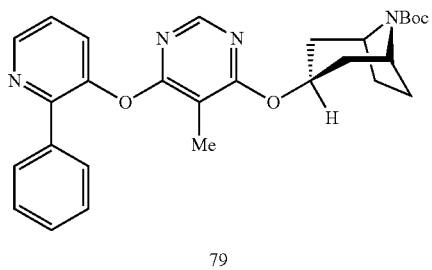

79

To a solution of compound 42 (0.09 g, 0.2 mmol), sodium carbonate (0.064 g, 0.6 mmol), phenyl boronic acid (0.073 g, 0.6 mmol), acetonitrile (3 mL), and water (0.6 mL) in a microwave vial was added trans-dichlorobis(triphenylphosphine)palladium (0.014 g, 0.02 mmol). The vial was sealed and heated on high absorbance in a microwave reactor for 14 minutes at a temperature of 140° C. The reaction was concentrated in vacuo and the resulting residue was dissolved in ethyl acetate and washed with water. The organic layer was dried (NaSO$_4$) and concentrated in vacuo and the resulting residue was purified using preparative TLC (Hexanes/Ethyl acetate (60/40)) to provide compound 79 (50 mg, 51%). LCMS: 489.3 (MH$^+$).

The following compounds of the invention were similarly prepared by substituting the appropriate substituted chlorophenylboronic acids for phenylboronic acid:

| Cpd. No. | Structure | LCMS (MH$^+$) |
|---|---|---|
| 80 | 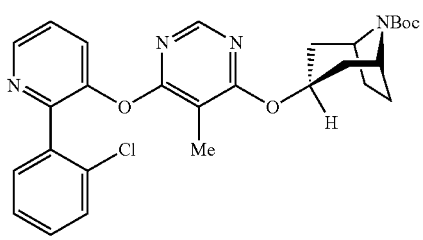 | 523.3 |
| 81 | 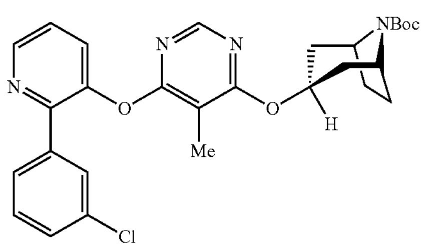 | 523.3 |
| 82 | 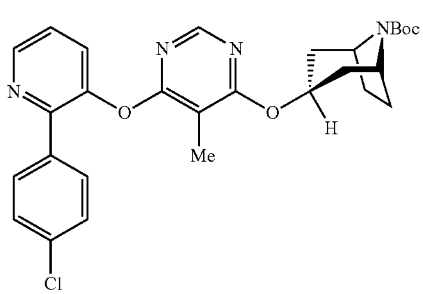 | 523.3 |

Example 24

Preparation of Compound 83

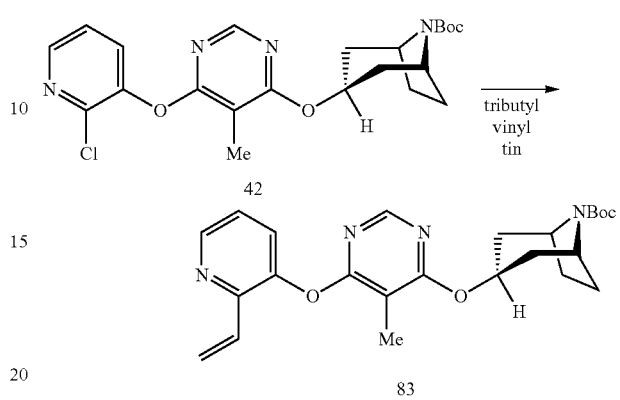

To a solution of the compound 42 (0.2 g, 0.45 mmol) in THF (2 mL) was added tri-n-butyl(vinyl)tin (089 g, 2.8 mmol) and tetrakis(triphenylphosphine)palladium (0.194 g, 0.17 mmol) in a nitrogen flushed pressure tube. The reaction was heated to 85° C. and allowed to at this temperature for 72 hours. The reaction was then cooled to room temperature and quenched with a saturated aqueous ammonium chloride solution. The mixture was extracted with dichloromethane and the organic extract was filtered to remove precipitates, then dried (NaSO$_4$) and concentrated in vacuo. The residue obtained was purified using, a silica gel cartridge (eluting with EtOAc in hexanes (0→40%)) to provide compound 83 as a clear oil (80 mg, 45%). LCMS: 439.2 (MH$^+$).

Example 25

Preparation of Compound 84

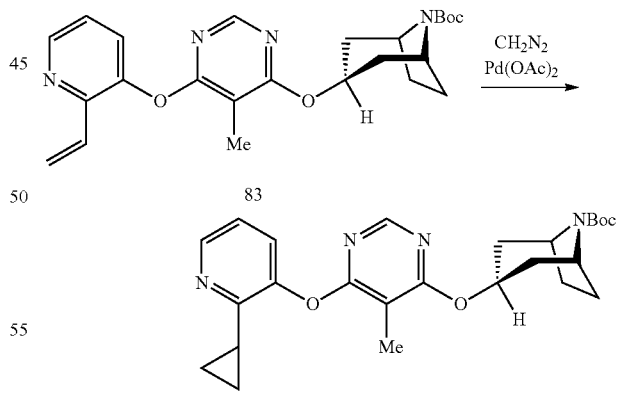

A solution of N-methyl-N-nitrosourea (0.175 g, 0.17 mmol) in ether (5 mL) was cooled to 0 and a 3 M aqueous solution of potassium hydroxide was added dropwise (5 mL). The resulting reaction was allowed to stir for 30 minutes at 0° C., then the organic layer was separated and added to a solution of compound 83 (0.075 g, 0.17 mmol) in dichloromethane (5 mL) at 0° C. Palladium acetate (0.015 g, 0.034 mmol) was added portionwise and the resulting mixture was allowed to stir for three hours at room temperature. It was then concentrated in vacuo. The residue obtained was purified using preparative TLC (eluting with Hexanes/Ethyl acetate (60/40)) to provide compound 84 as a resin (26 mg, 34%). LCMS: 453.2 (MH$^+$).

Example 26

Preparation of Compound 85 and 86

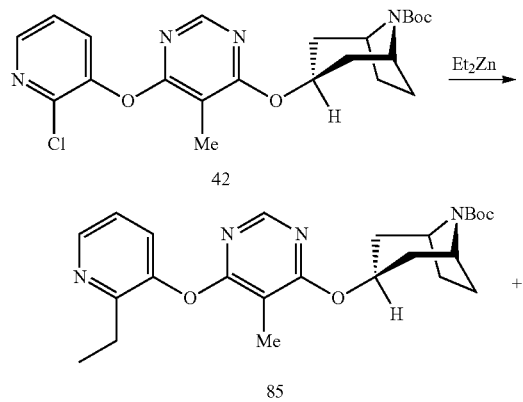

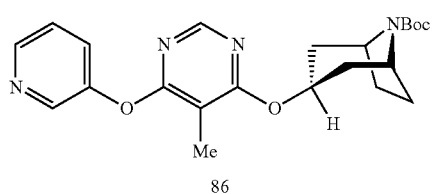

To a solution of compound 42 (0.03 g, 0.067 mmol) in THF (2 mL) in a sealed tube, was added a solution comprising tetrakis(triphenylphosphine)palladium (0.016 g, 0.013 mmol) and diethyl zinc in hexanes (0.67 mL, 1 M solution in THF, 0.67 mmol). The reaction was heated to 80° C. and allowed to stir at this temperature for about 72 hours. The reaction mixture was cooled to room temperature and quenched with a saturated aqueous ammonia chloride solution. The resulting solution was then extracted with dichloromethane and the organic extract was dried (NaSO$_4$) and concentrated in vacuo The residue obtained was purified using preparative TLC (eluting with hexanes/ethyl acetate (60/40)) to provide compounds 85 (1.5 mg, 5%, LCMS: 441.2) and 86 (6 mg, 22%) LCMS: 413.2 (MH$^+$).

The following compounds of the invention were similarly prepared as shown in Example 19 using appropriate sulfonyl chlorides:

| Cpd. No. | Structure | LCMS (MH$^+$) |
|---|---|---|
| 87 | 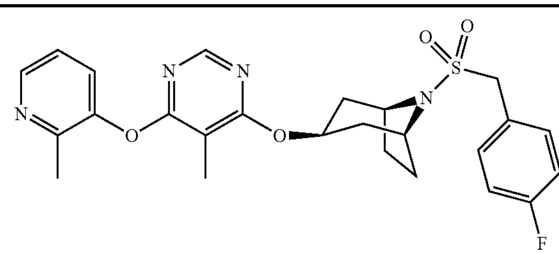 | 499.3 |
| 88 | 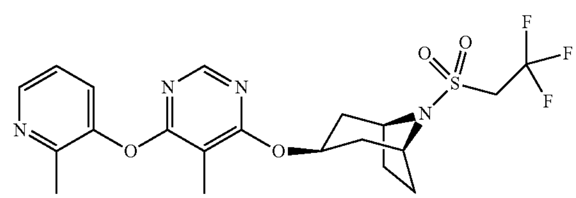 | 473.3 |
| 89 | 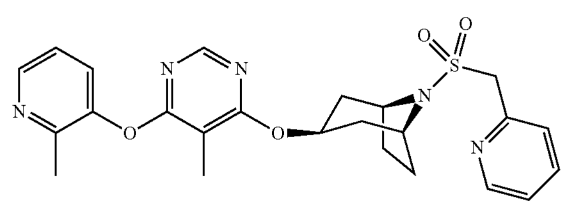 | 482.3 |
| 90 | 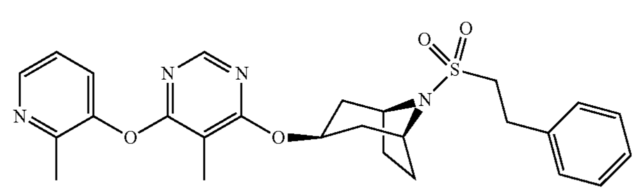 | 495.3 |

| Cpd. No. | Structure | LCMS (MH+) |
|---|---|---|
| 91 | 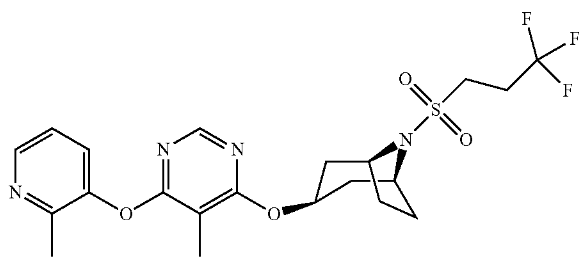 | 500.3 |

Example 27

Preparation of Compound 92

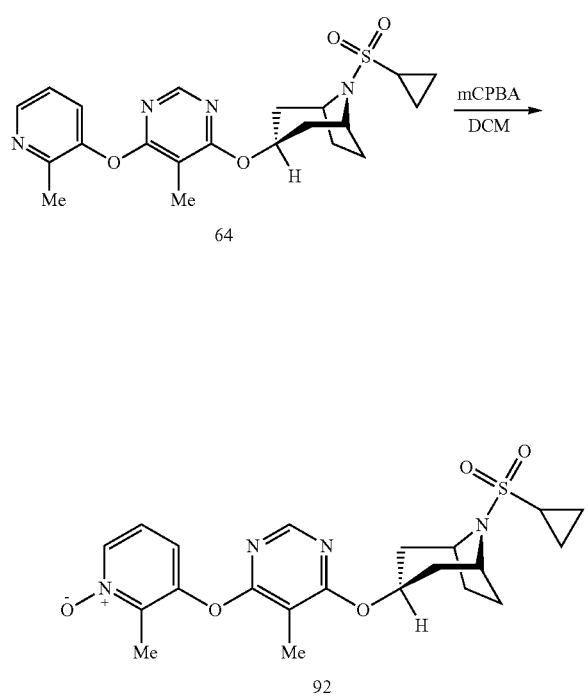

To a solution of compound 64 (76 mg, 0.18 mmol) in dichloromethane (1.5 mL) was added m-chloroperbenzoic acid (79 mg, 0.35 mmol) and the resulting solution was stirred for 20 h at room temperature. The reaction was then quenched with saturated aqueous NaHCO₃ solution and extracted with dichloromethane. The organic extract was dried (MgSO₄) and concentrated in vacuo to provide a crude residue which was chromatographed on a silica gel cartridge (10% [2N NH₃ in MeOH]/dichloromethane) in dichloromethane (10→60%) to provide compound 92 as a white solid (80 mg, ca 100%). LCMS: 447.2 (MH+).

Example 28

Preparation of Compound 93

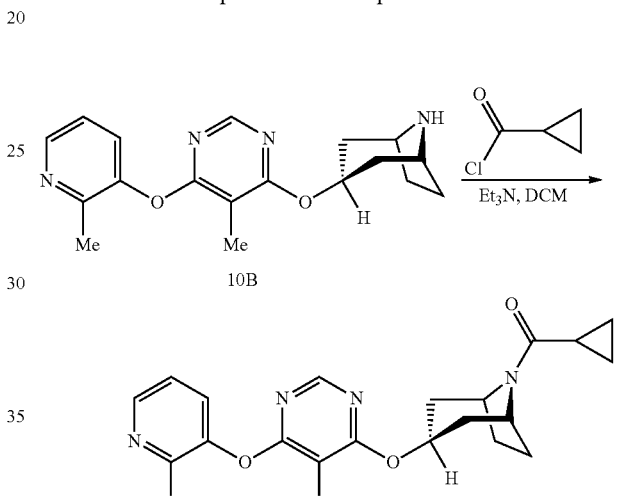

To a solution of compound 10B (51 mg, 0.16 mmol) and dichloromethane (1.5 mL) was added triethylamine (65 µL, 0.47 mmol) and cyclopropanecarbonyl chloride (28 µL, 0.31 mmol) and the resulting reaction was stirred for 0.5 h at room temperature. The reaction was then quenched with saturated aqueous NaHCO₃ solution and extracted with dichloromethane. The organic extract was dried (MgSO₄) and concentrated in vacuo to provide a crude residue which was chromatographed on a silica gel cartridge (EtOAc in dichloromethane, 5→20%) to provide compound 93 as a white semi-solid (50 mg, 81%). LCMS: 395.2 (MH+).

The following compounds of the invention were prepared using the method described above and substituting the appropriate acyl chloride or sulfonyl chloride for cyclopropanecarbonyl chloride:

| Cpd. No. | Structure | LCMS (MH+) |
|---|---|---|
| 94 | 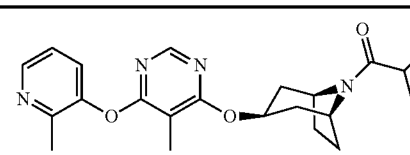 | 397.2 |

-continued

| Cpd. No. | Structure | LCMS (MH⁺) |
|---|---|---|
| 95 | 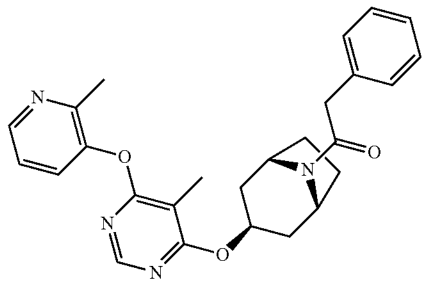 [SMILES: Cc1ncccc1Oc1ncnc(O[C@@H]2C[C@H]3CC[C@@H](C2)N3C(=O)Cc2ccccc2)c1C] | 445.2 |
| 96 | 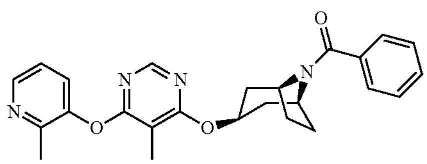 | 431.2 |
| 97 | 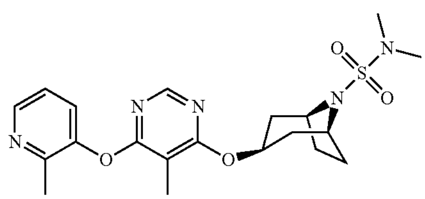 | 434.2 |

Example 29

Preparation of Compound 98

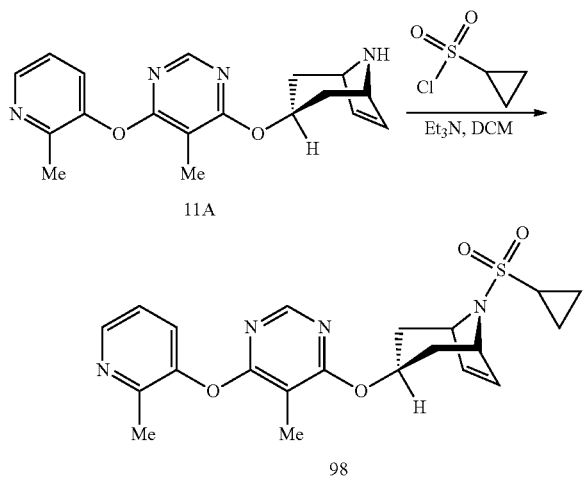

Compound 98 was prepared using the method described in Example 19 and reacting compound 11A with cyclopropanesulfonyl chloride. LCMS: 429.2 (MH⁺).

Example 30

Preparation of Compound 99

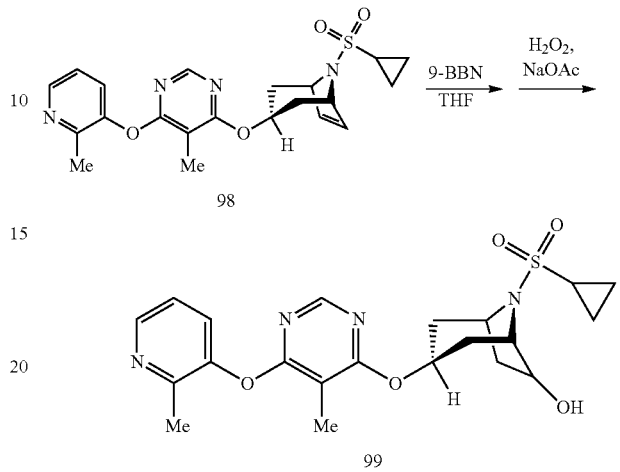

To a mixture of compound 98 (50 mg, 0.12 mmol) and THF (0.3 mL) was added a solution of 9-BBN (0.70 mL, 0.5 M in THF, 0.35 mmol) and the resulting solution was stirred for 7 h at room temperature. Water (0.2 mL) was added and stirred for 5 minutes. Then an aqueous NaOAc solution (0.20 mL, 3 M, 0.58 mmol) and an aqueous hydrogen peroxide solution (66 µL, 0.58 mmol) were added and the resulting mixture was stirred for 16 h at room temperature. The reaction was then diluted with brine and extracted with EtOAc. The organic extract was dried (MgSO₄) and concentrated in vacuo to provide a crude residue which was purified on a silica gel cartridge [(10% MeOH/DCM) in DCM 10→50%] to provide compound 99 as a white resin (17 mg, 33%). LCMS: 447.2 (MH⁺).

Example 31

Preparation of Compound 100

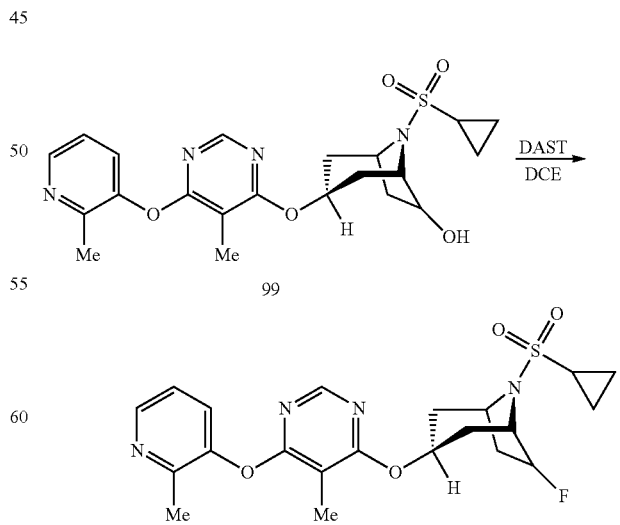

To a mixture of compound 99 (38 mg, 0.085 mmol) and dichloroethane (1 mL) was added DAST (40 μL, 0.43 mmol) and the resulting mixture was stirred for 1 h at room temperature and 1.5 h at 90° C. The reaction was quenched with saturated aqueous NaHCO₃ solution, stirred for 1 h at room temperature, and extracted with DCM. The organic extract was dried (MgSO₄) and concentrated in vacuo to provide a crude residue which was chromatographed on a preparative TLC plate (5% MeOH/DCM) to provide compound 100 as an off-white solid (3 mg, 8%). LCMS: 449.2 (MH⁺).

Example 32

Preparation of Compound 101

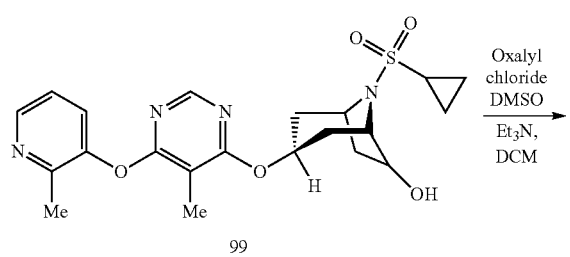

99

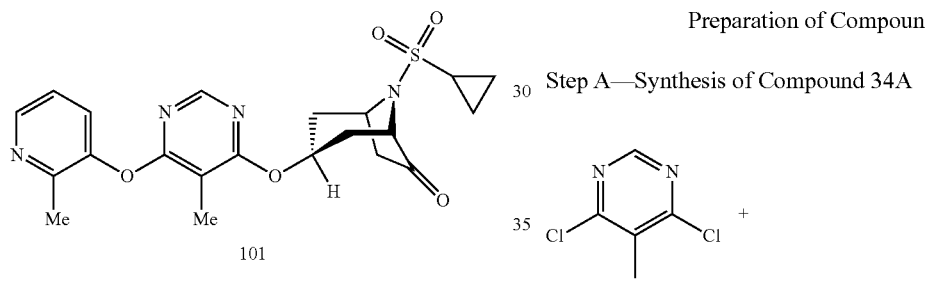

101

To a solution of oxalyl chloride (50 μL, 0.58 mmol) in DCM (1.5 mL) was added DMSO (90 μL, 1.16 mmol) at −78 CC and stirred for 5 minutes. A solution of compound 99 (130 mg, 0.29 mmol) in DCM (2 mL) was added at −78° C. and stirred for 15 minutes. Et₃N (0.2 mL, 1.45 mmol) was added at −78° C. and stirred for 2 h at −78° C. to RT. The mixture was diluted with brine and extracted with DCM. The organic extract was dried (MgSO₄) and concentrated in vacuo to provide a crude residue which was chromatographed on a silica gel cartridge [(10% MeOH/DCM) in DCM 0→50%] to provide compound 101 as a white solid (113 mg, 87%). LCMS: 445.2 (MH⁺).

Example 33

Preparation of Compound 102

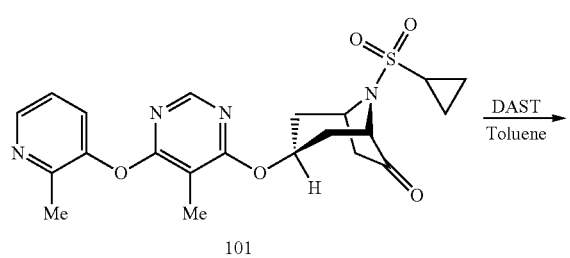

101

-continued

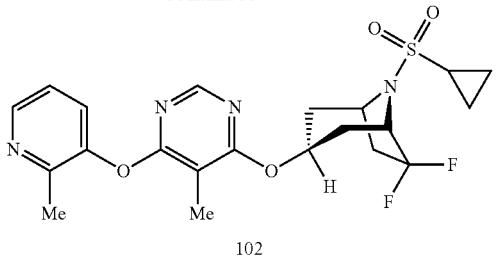

102

To a mixture of compound 101 (45 mg, 0.10 mmol) in toluene (1 mL) was added DAST (66 μL, 0.50 mmol) at RT and the resulting mixture was stirred for 1 h at 90° C. The reaction was quenched with saturated aqueous NaHCO₃ solution, stirred for 1 h at room temperature, and extracted with EtOAc. The organic extract was dried (MgSO₄) and concentrated in vacuo to provide a crude residue which was chromatographed on a preparative TLC plate (80% EtOAc/hexanes) to provide compound 102 as an off-white solid (5.6 mg, 12%). LCMS: 467.3 (MH⁺).

Example 34

Preparation of Compound 103

Step A—Synthesis of Compound 34A

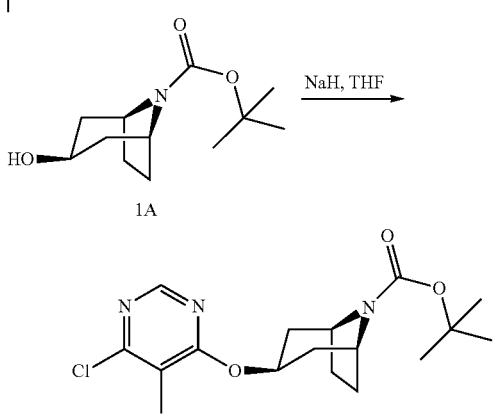

34A

To a solution of 1A (8.5 grams, 37.4 mmol) in THF (200 mL) chilled to 0° C. was added sodium hydride in 60% oil (6 grains, 150 mmol) and allowed to stir for 30 minutes. The reaction mixture was warmed to room temperature and 4,6-dichloro-5-methylpyrimidine (6.8 grams, 41.1 mmol) was added. This was permitted to stir for seven hours. The crude reaction mixture was quenched with water and extracted with DCM. The organic phase was dried (Na₂SO₄) and concentrated in vacuo. The crude product was purified using a silica gel cartridge with hexanes/ethyl acetate (50/50) to provide compound 34A as a light brown solid (12.3 grams, 93%). LCMS: 354.2 (MH⁺).

Step B—Synthesis of Compound 34B

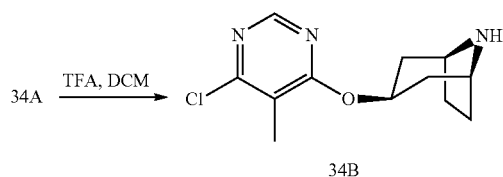

Compound 34A (12.3 grams, 34.8 mmol) was dissolved in THF (200 mL) and chilled to 0° C. Trifluoroacetic acid (100 mL) was added to the reaction. It was allowed to warm to room temperature and stirred for six hours. The solution was concentrated in vacuo, redissolved in DCM, and neutralized with a saturated sodium bicarbonate solution. The organic phase was dried ($Na_2SO_4$) and concentrated in vacuo to provide compound 34B (10 g), which was used without further purification. LCMS: 254.1 ($MH^+$).

Step C—Synthesis of Compound 34C

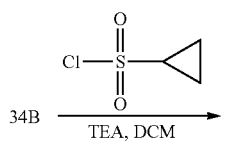

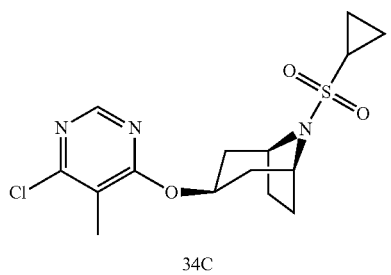

Compound 34B (10 grams, 3905 mmol) was dissolved in DCM (200 mL) and chilled to 0° C. Triethylamine (16 grams, 158 mmol) was added to the solution and stirred for 20 minutes. Cyclopropanesulfonyl chloride (16.6 grams, 118.5 mmol) was added to the reaction and allowed to stir at room temperature for six hours. The reaction mixture was washed with a saturated sodium bicarbonate solution and extracted with DCM. The organic phase was dried ($Na_2SO_4$) and concentrated in vacuo. The crude reaction mixture was purified using a silica gel cartridge with hexanes/ethyl acetate (60/40) to provide compound 34C as an off-white solid (8 grams, 57%). LCMS: 358.2 ($MH^+$).

Step D—Synthesis of Compound 103

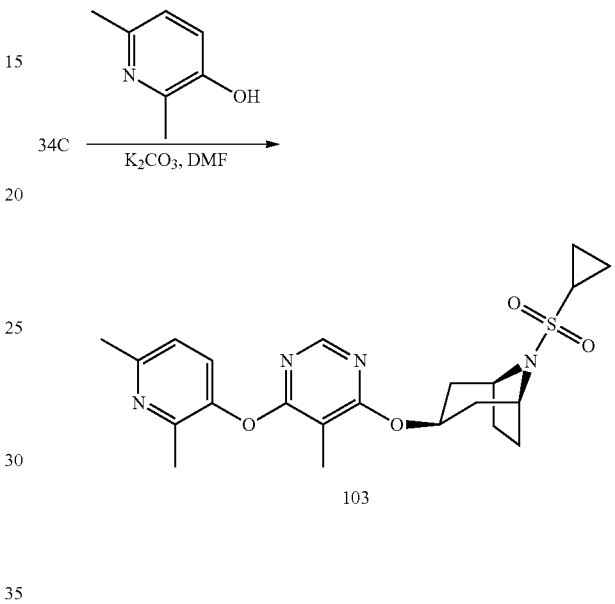

Compound 34C (50 mg, 0.14 mmol), potassium carbonate (39 mg, 0.28 mmol), and 2,6-dimethylpyridin-3-ol (51 mg, 0.42 mmol) were stirred in DMF (2.5 mL). The reaction was purged with nitrogen, sealed in a vial, and then heated in a microwave reactor at 190° C. for eight minutes on high absorbance. The crude reaction mixture was concentrated in vacuo, redissolved in DCM, and washed with water. The organic phase was dried ($Na_2SO_4$) and concentrated in vacuo. The crude reaction mixture was purified using a silica gel cartridge with DCM/methanol (95/5) to provide compound 103 as an off white solid (60 mg, 96%). LCMS: 445.2 ($MH^+$).

The following compounds of the invention were prepared using the method described above and substituting the appropriate substituted phenols or pyridinols for 2,6-dimethylpyridin-3-ol:

| Cpd. No. | Structure | LCMS ($MH^+$) |
| --- | --- | --- |
| 104 | 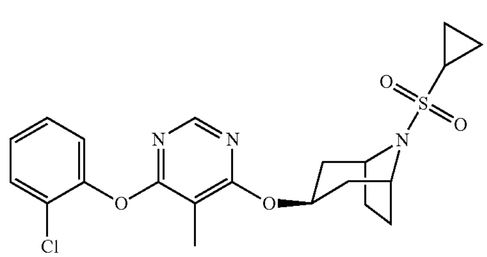 | 450.2 |

-continued

| Cpd. No. | Structure | LCMS (MH+) |
|---|---|---|
| 105 | 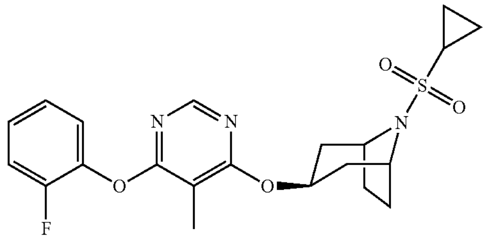 | 434.2 |
| 106 | 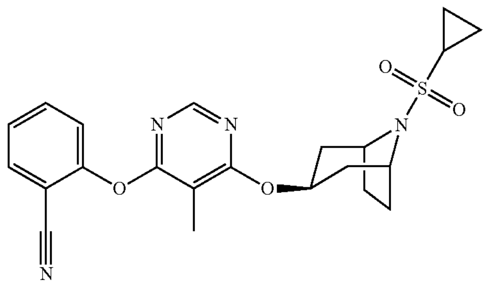 | 441.2 |
| 107 | 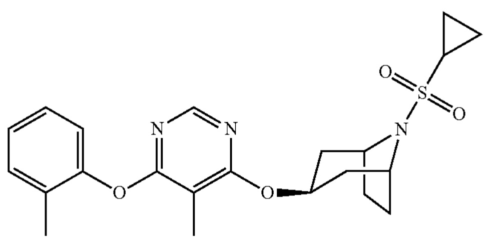 | 430.2 |
| 108 | 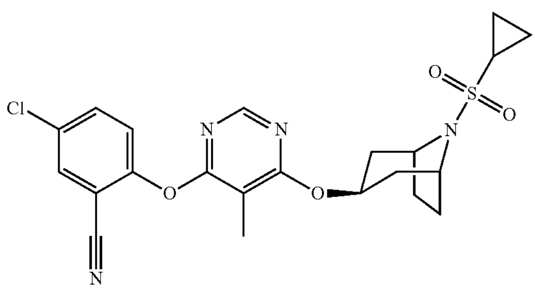 | 475.3 |
| 109 | 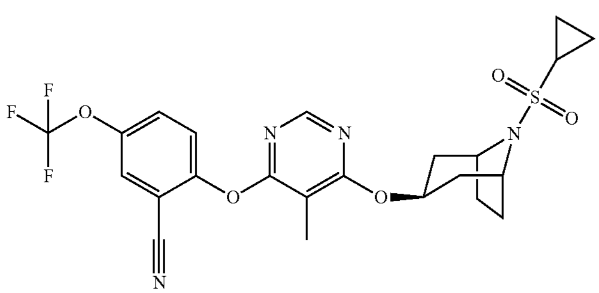 | 525.3 |
| 110 | 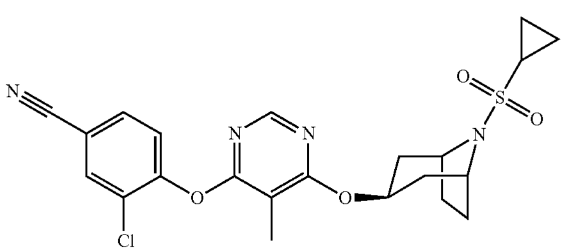 | 475.3 |

-continued
| Cpd. No. | Structure | LCMS (MH+) |
|---|---|---|
| 111 | 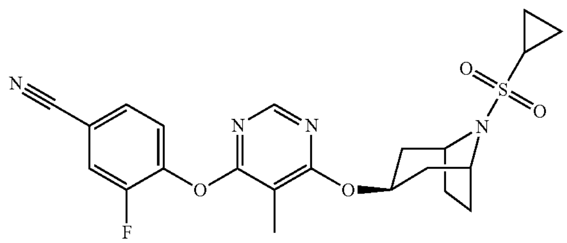 | 459.3 |
| 112 | 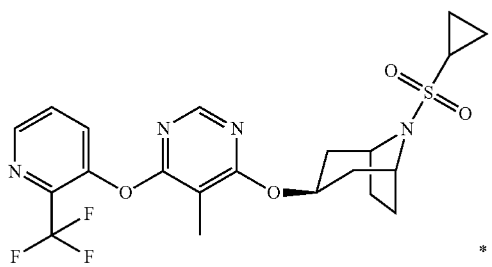 | 485.3 * |
| 113 | 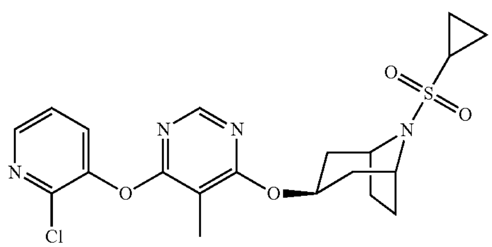 | 451.2 |
| 114 | 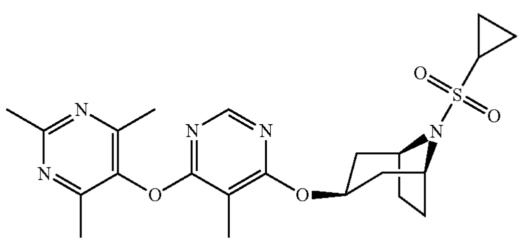 | 460.3 |
*The pyridinol was prepared from the corresponding pyridinylboronic acid by the conventional hydrogen peroxide oxidation protocol.
Example 35
Preparation of Compound 115
Step A—Synthesis of Compound 35A
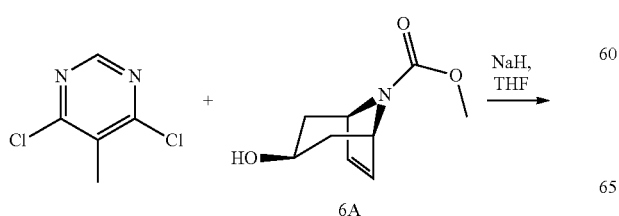
-continued
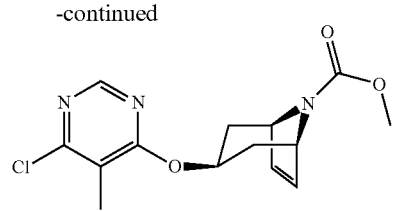
35A
The alcohol 6A was converted to compound 35A using the method described in Step A of Example 34.

Step B—Synthesis of Compound 35B

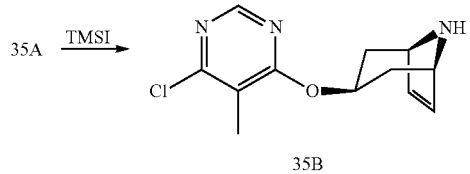

Compound 35A was converted to compound 35B using the method described in Example 11 for the preparation of compound 11A.

Step C—Synthesis of compound 115

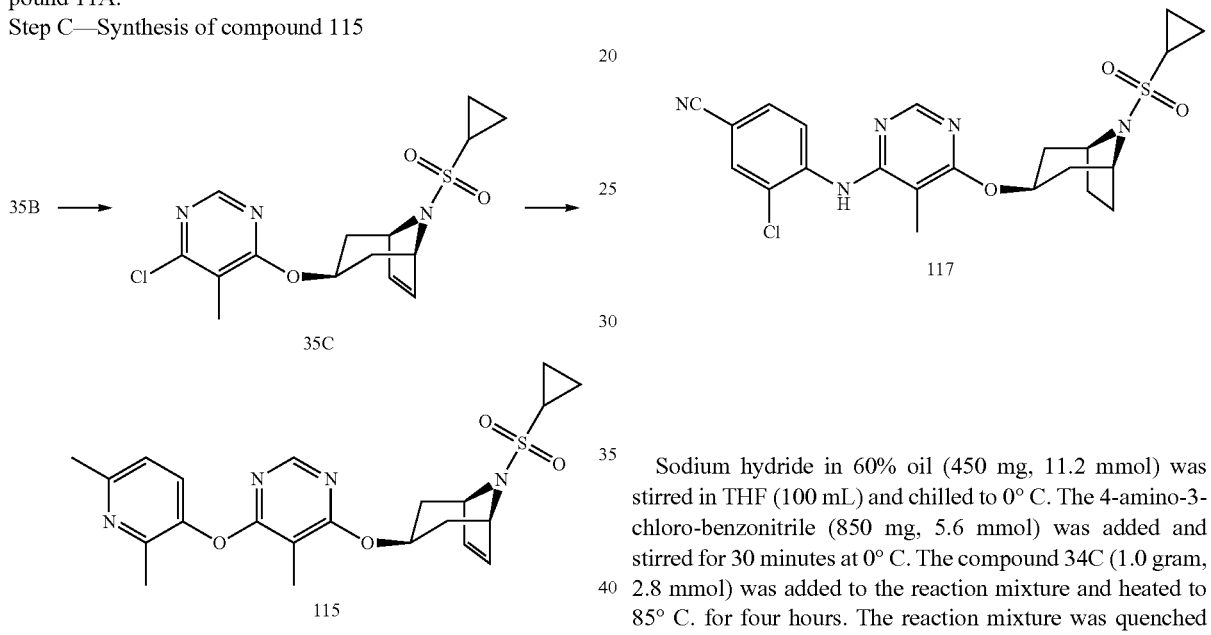

Compound 35B was converted to Compounds 35C and 115 using the methods describe in Steps C and D of Example 34. Compound 115, LCMS: 443.2 (MH+).

The following compound of the invention was prepared using the methods described above and substituting the appropriate substituted phenol reactant:

| Cpd. No. | Structure | LCMS (MH+) |
|---|---|---|
| 116 | 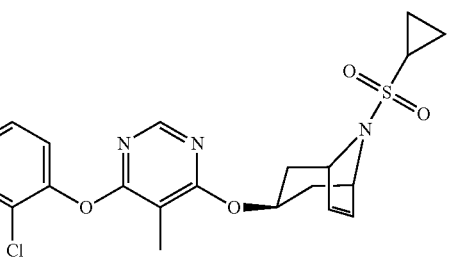 | 473.3 |

Example 36

Preparation of Compound 117

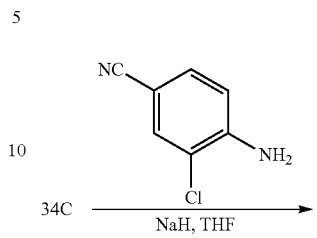

Sodium hydride in 60% oil (450 mg, 11.2 mmol) was stirred in THF (100 mL) and chilled to 0° C. The 4-amino-3-chloro-benzonitrile (850 mg, 5.6 mmol) was added and stirred for 30 minutes at 0° C. The compound 34C (1.0 gram, 2.8 mmol) was added to the reaction mixture and heated to 85° C. for four hours. The reaction mixture was quenched with water and extracted with DCM. The organic phase was dried ($Na_2SO_4$) and concentrated in vacuo. The crude reaction mixture was purified using a silica gel cartridge with DCM/ethyl acetate (90/10) to provide the product as an off-white solid. The solid was dissolved in 10 ml of DCM and poured into 1000 ml of hexanes. The solid precipitates were filtered; washed with hexanes, and dried to provide compound 117 as an off-white solid (800 mg, 60%). LCMS: 474.3 (MH+).

Example 37

Preparation of Compound 118

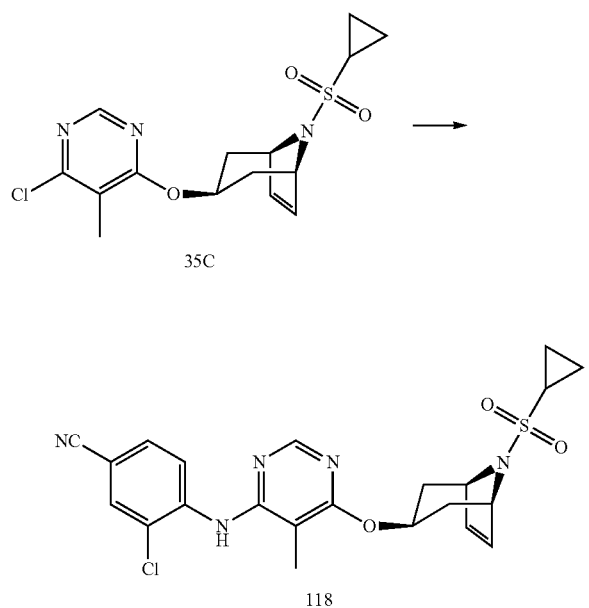

Compound 118 was prepared from compound 35C using the method described in Example 36. LCMS: 472.3 (MH+).

Example 38

Preparation of Compound 119

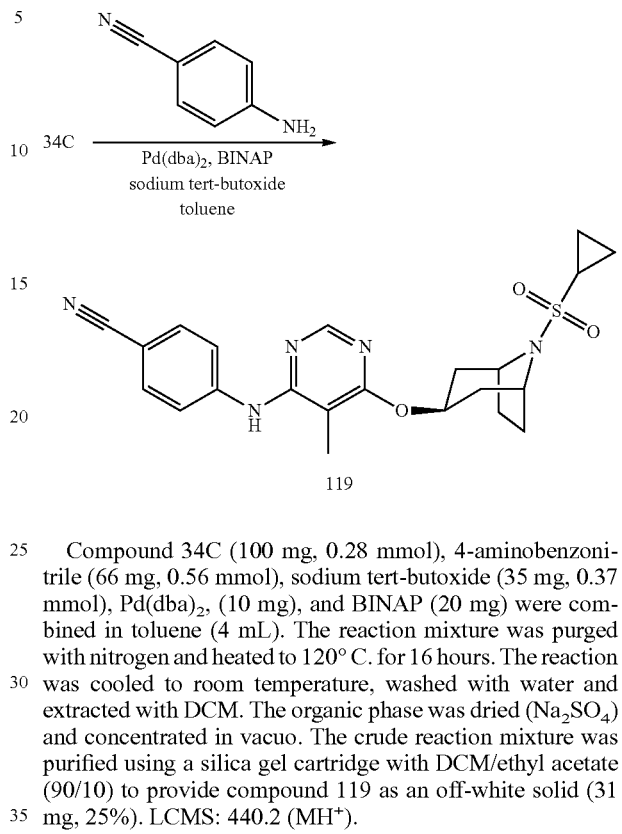

Compound 34C (100 mg, 0.28 mmol), 4-aminobenzonitrile (66 mg, 0.56 mmol), sodium tert-butoxide (35 mg, 0.37 mmol), Pd(dba)$_2$, (10 mg), and BINAP (20 mg) were combined in toluene (4 mL). The reaction mixture was purged with nitrogen and heated to 120° C. for 16 hours. The reaction was cooled to room temperature, washed with water and extracted with DCM. The organic phase was dried (Na$_2$SO$_4$) and concentrated in vacuo. The crude reaction mixture was purified using a silica gel cartridge with DCM/ethyl acetate (90/10) to provide compound 119 as an off-white solid (31 mg, 25%). LCMS: 440.2 (MH+).

The following compounds of the invention were similarly prepared using the appropriately substituted aniline or pyridinylamine reactants:

| Cpd. No. | Structure | LCMS (MH+) |
|---|---|---|
| 120 | 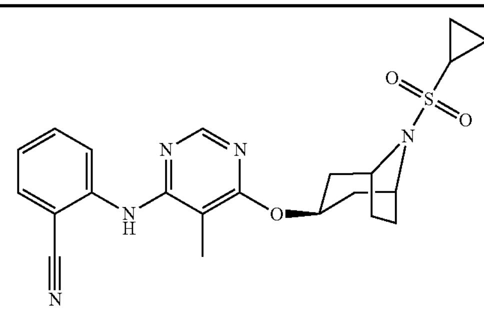 | 440.2 |
| 121 | 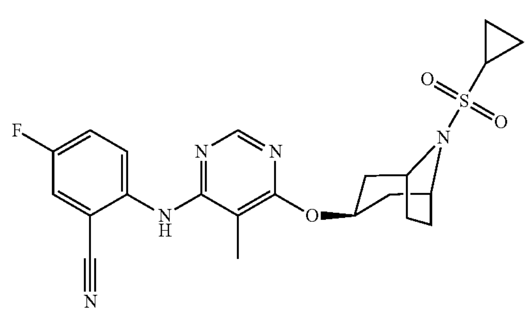 | 458.3 |

| Cpd. No. | Structure | LCMS (MH+) |
|---|---|---|
| 122 | 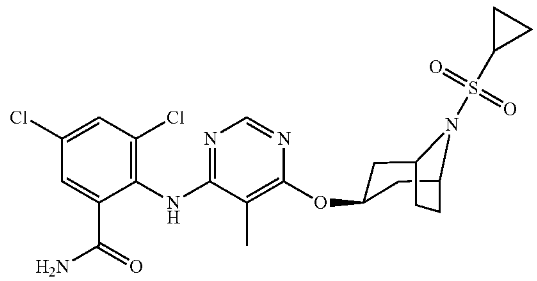 | 526.3 |
| 123 | 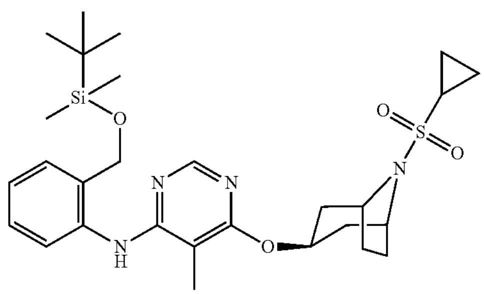 | 559.3 |

*The substituted aniline was prepared from (2-aminophenyl)methanol by the conventional method using triethylamine and TBDMSCl as reagents and DCM as solvent.

Example 39

Preparation of Compound 124

Step A—Synthesis of Compound 39A

Compound 2A was converted to compound 39A using the method described in Example 34, Step A.

Step B—Synthesis of Compound 124

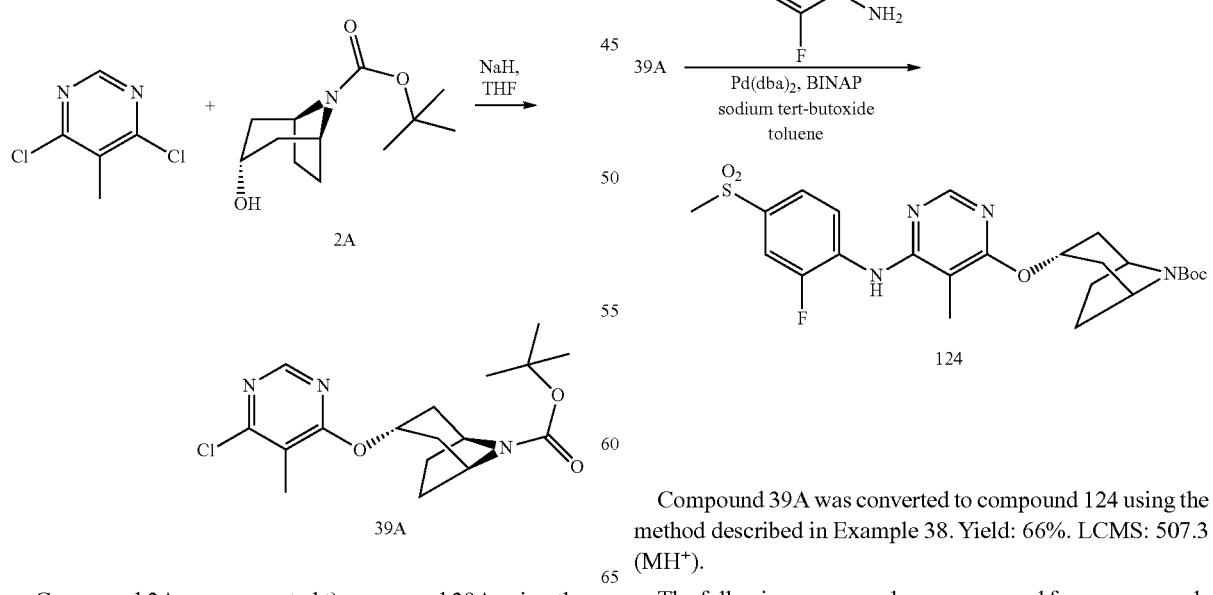

Compound 39A was converted to compound 124 using the method described in Example 38. Yield: 66%. LCMS: 507.3 (MH+).

The following compounds were prepared from compounds 6A or 7A using methods described above herein:

| Cpd. No. | Structure | LCMS (MH+) |
|---|---|---|
| 125 | 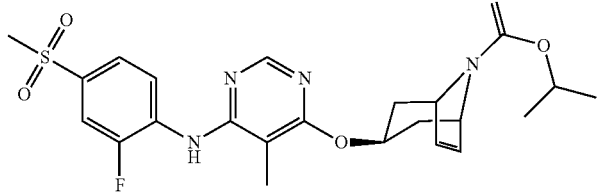 | 491.3 |
| 126 | 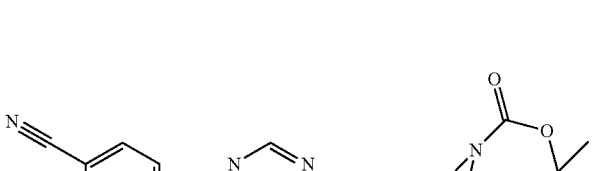 | 468.3 |
| 127 | 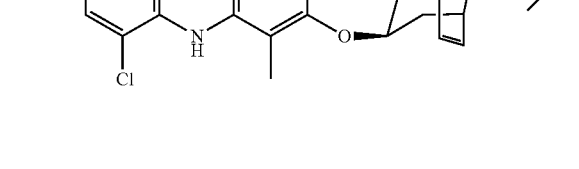 | 491.3 |
| 128 | 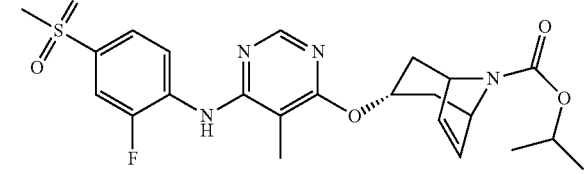 | 454.2 |
Example 40
Preparation of Compound 129
Step A—Synthesis of Compound 40A
Step B—Synthesis of Compound 129
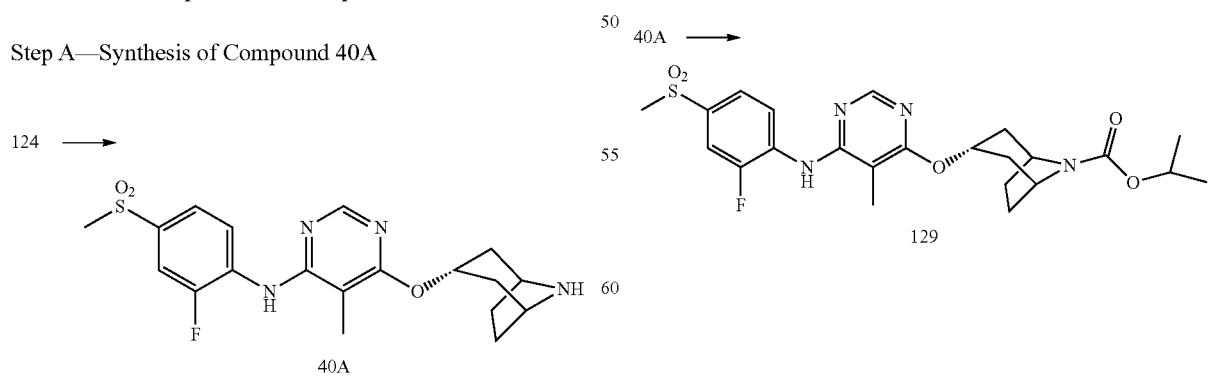
Compound 124 was converted to compound 40A using the method described in Example 34, Step B.
Compound 40A was converted to corn rid 129 using the method described in Example 11.

Example 41

Preparation of Compound 130

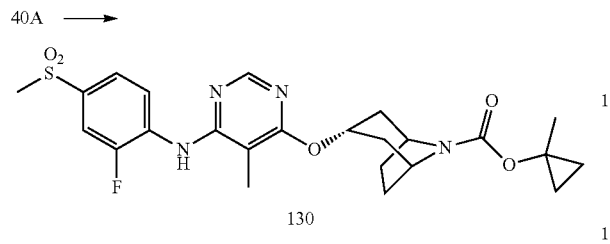

Compound 40A was converted to compound 130 similarly as in Example 16, Preparation of Compound 58.

Example 42

Preparation of Compound 131

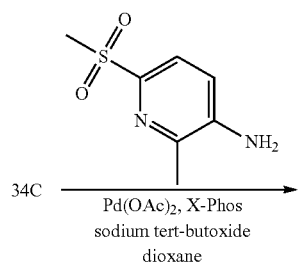

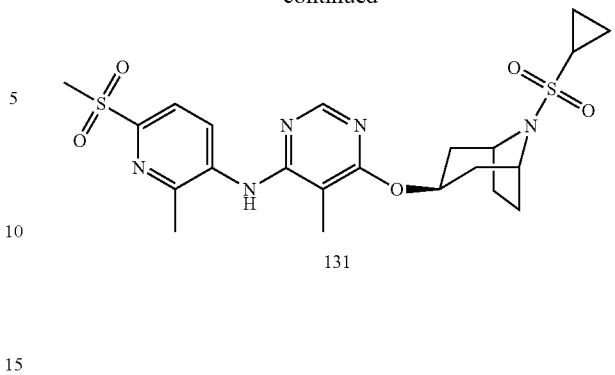

Compound 34C (65 mg, 0.18 mmol), 2-methyl-6-(methylsulfonyl)pyridine-3-amine (51 mg, 027 mmol), sodium-tert-butoxide (23 mg, 0.24 mmol), Pd(OAc)₂ (6.5 mg), and X-Phos (13 mg) were combined in dioxane (2 mL). The reaction mixture was purged with nitrogen and heated to 100° C. for 16 hours. The reaction was cooled to room temperature, washed with water and extracted with DCM. The organic phase was dried (Na₂SO₄) and concentrated in vacuo. The crude reaction mixture was purified using a silica gel cartridge with DCM/methanol (95/5) to provide compound 131 as an off-white solid (22 mg, 24%) LCMS: 508.3 (MH⁻).

The following compounds of the invention were prepared using the method described above and substituting the appropriate substituted anilines or pyridinylamines for 2-methyl-6-(methylsulfonyl)pyridine-3-amine:

| Cpd. No. | Structure | LCMS (MH⁺) |
|---|---|---|
| 132 | 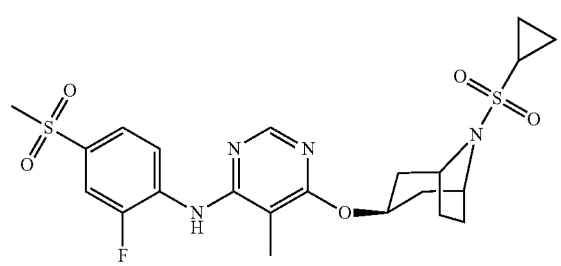 | 511.3 |
| 133 | 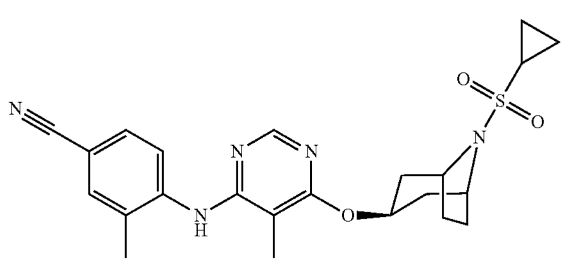 | 454.2 |

-continued
| Cpd. No. | Structure | LCMS (MH+) |
|---|---|---|
| 134 | 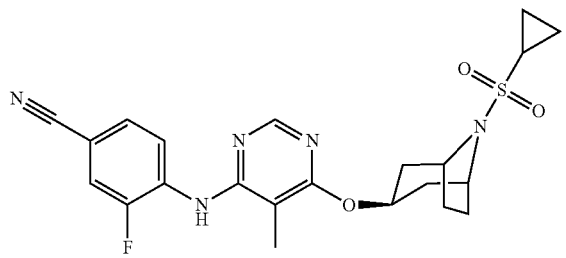 | 458.3 |
| 135 | 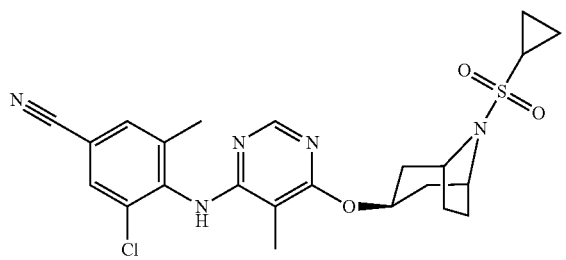 | 488.3 |
| 136 | 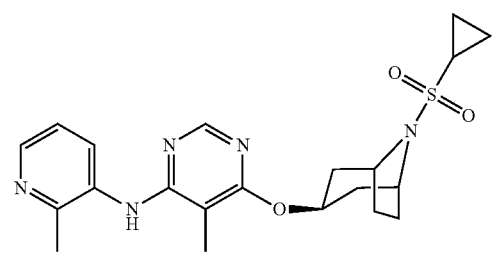 | 430.2 |
| 137 | 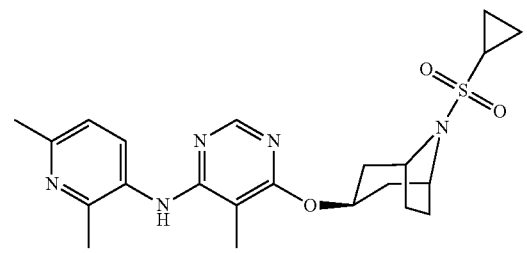 | 444.2 |
| 138 | 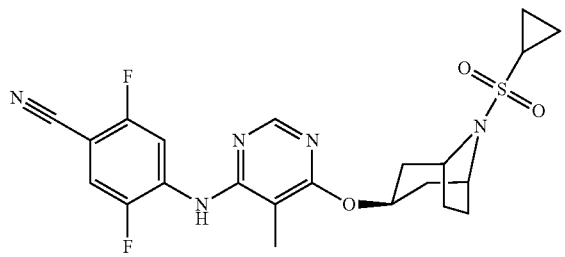 | 476.3 |
| 139 | 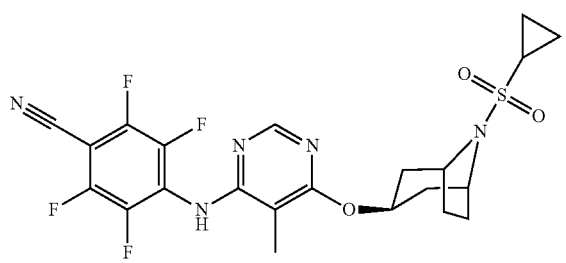 | 512.3 |

Example 43

Preparation of Compound 140

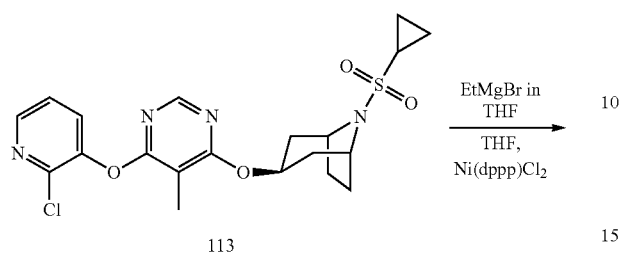

Compound 113 (50 mg, 0.11 mmol), Ni(dppp)Cl$_2$ (5.7 mg, 0.011 mmol), and THF (5 mL) were combined and stirred at 0° C. for 20 minutes. The EtMgBr in THF solution (0.44 mL, 1.0 M, 0.44 mmol) was added to the reaction mixture and stirred at 0° C. for one hour. The reaction mixture was then stirred at room temperature for two hours. The reaction solution was washed with a saturated ammonia chloride solution and extracted with DCM. The organic phase was dried (NaSO$_4$) and concentrated in vacuo. The crude reaction mixture was purified by preparatory thin-layer chromatography plates with DCM/methanol (95/5) to provide compound 140 as an off-white solid (25 ing, 51%). LCMS: 445.2 (MH$^+$).

Example 44

Preparation of Compound 141

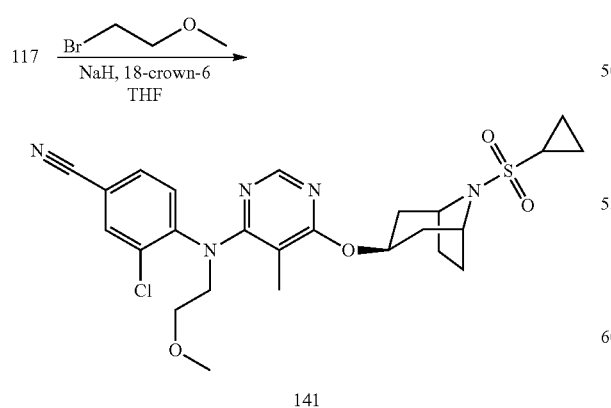

Compound 117 (50 mg, 0.10 mmol), NaH in 60% oil (12 mg, 0.30), 18-crown-6 (40 mg, 0.15 mmol), 1-bromo-2-methoxyethane (139 mg, 1.0 mmol), and THF (5 mL) were combined in a pressure tube and heated to 75° C. for 16 hours. The reaction was washed with water and extracted with DCM. The organic phase was dried (Na$_2$SO$_4$) and concentrated in vacuo. The crude reaction mixture was purified by using preparatory thin-layer chromatography Mates with DCM/ethyl acetate (70/30) to provide compound 141 as off-white solid (18 mg, 34%)). LCMS: 532.3 (MH$^+$).

Example 45

Preparation of Compound 142

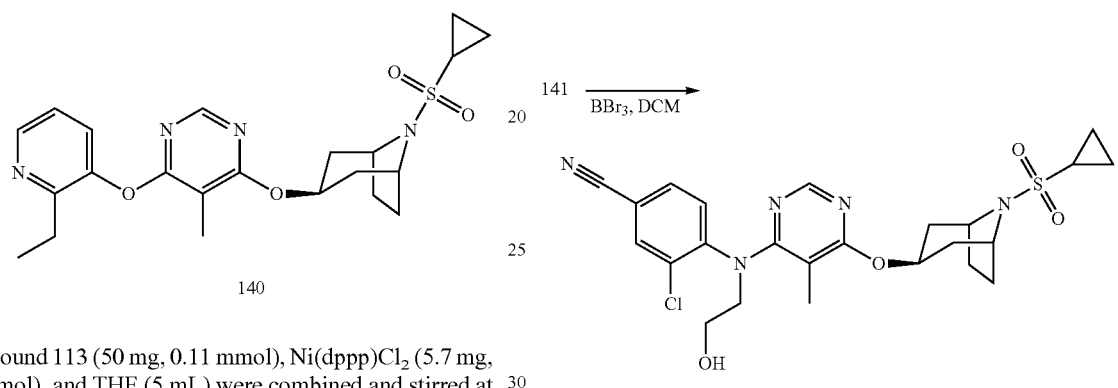

To a solution of compound 141 (11 mg) in DCM (1 mL) at 0° C. was added BBr$_3$ (10 µl ). The mixture was stirred at 0° C. to room temperature for 1 hour. The reaction was quenched with NaHCO$_3$ (saturated) and stirred for 1 h at room temperature. The mixture was extracted with DCM. The organic phase was dried (Na$_2$SO$_4$) and concentrated in vacuo. The crude reaction mixture was purified by using preparatory thin-layer chromatography plates with DCM/ethyl acetate (70/30) to provide compound 142 as off-white film (1.4 mg, 13%). LCMS: 518.3 (MH$^+$).

Example 46

Preparation of Compound 143

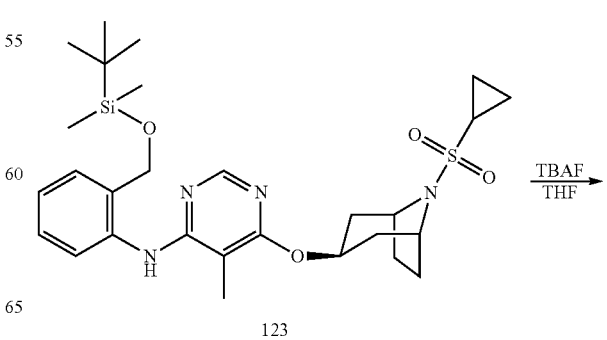

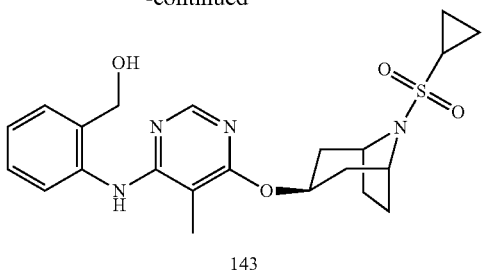

143

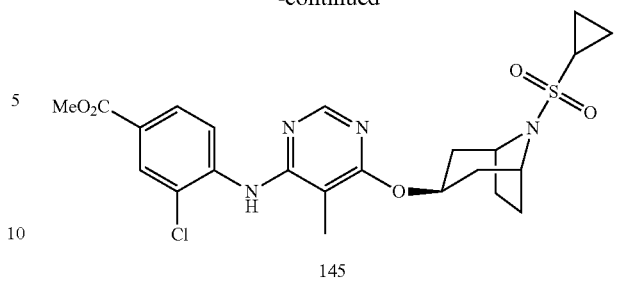

145

A solution of compound 123 (150 mg, 0.27 mmol) and TBAF (1.3 mL, 1 M, 1.34 mmol) in THF (8.5 mL) was allowed to stir at room temperature for four hours. The reaction was diluted with water and extracted with DCM. The organic phase was dried (Na$_2$SO$_4$) and concentrated in vacuo. The crude reaction mixture was purified using a silica gel cartridge with DCM/ethyl acetate (70/30) to provide compound 143 as a brown solid (95 mg, 80%). LCMS: 445.2.

Example 47

Preparation of Compound 144

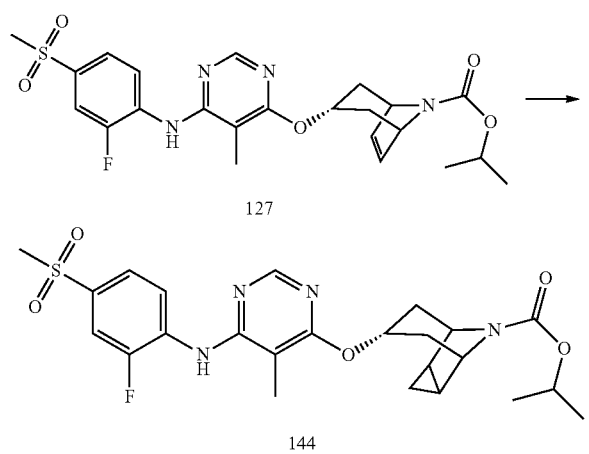

Compound 144 was prepared from compound 127 using the method described in Example 25. LCMS: 505.3.

Example 48

Preparation of Compounds 145-147

Step A:

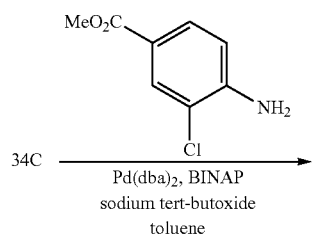

Compound 34C was converted to compound 145 using the method described in Example 38.

Step B:

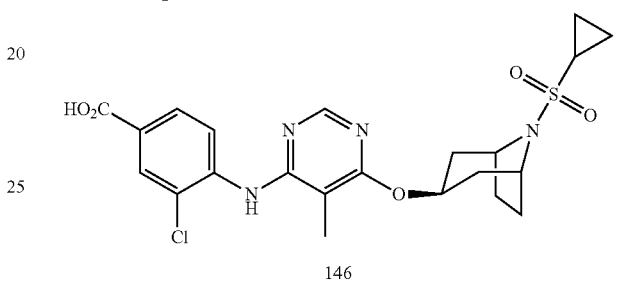

146

Compound 145 (39 mg, 0.077 mmol), NaOH (1.5 mL, 10% h by weight in water), MeOH (1.5 L) and THF (1.5 mL) were combined and stirred at room temperature for 1 hour. The reaction was diluted with water and extracted with DCM. The aqueous layer was acidified with HCl (10% by weight in water) and extracted with DCM. The organic phase was dried (Na$_2$SO$_4$) and concentrated in vacuo to provide compound 146 as a resin (17 mg, 45%).

Step C:

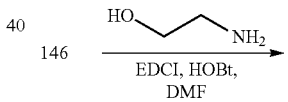

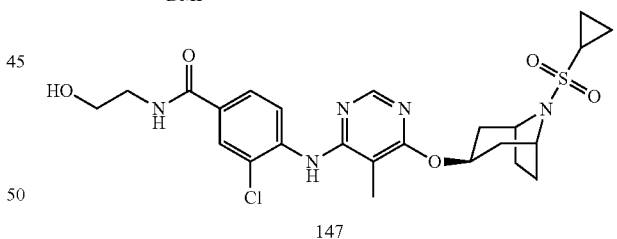

147

To a solution of compound 146 (17 mg, 0.034 mmol) in DMF (0.5 mL) was added EDCI (20 mg, 0.10 mmol), HOBt (14 mg, 0.10 mmol), and ethanolamine (6 μl, 0.10 mmol). The mixture was stirred at room temperature for 16 hours. The DMF solvent was evaporated off on a rotavap. The residue was dissolved in DCM and washed with NaHCO$_3$ (saturated solution). The organic phase was dried (Na$_2$SO$_4$) and concentrated in vacuo. The crude reaction mixture was purified by preparatory thin-layer chromatography plates using DCM/(2 N NH$_3$ in MeOH) (95/5) to provide compound 147 as white solid (15 mg, 81%). LCMS: 536.3 (MH$^+$).

The following compounds of the invention were prepared using the method described above and substituting the appropriate amines for ethanolamine:

| Cpd. No. | Structure | LCMS (MH+) |
|---|---|---|
| 148 | 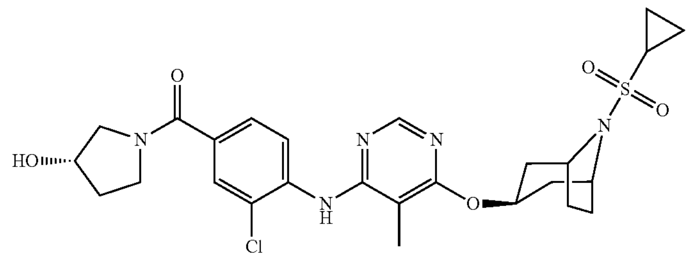 | 562.3 |
| 149 | 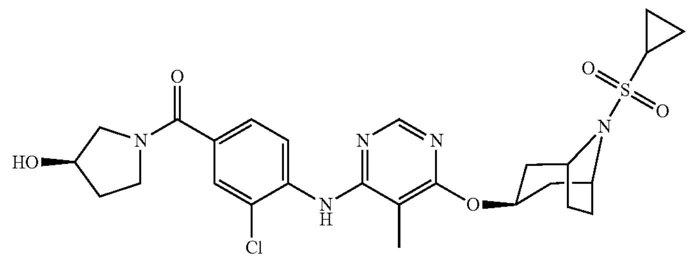 | 562.3 |

Example 49

Preparation of Compounds 150 and 151

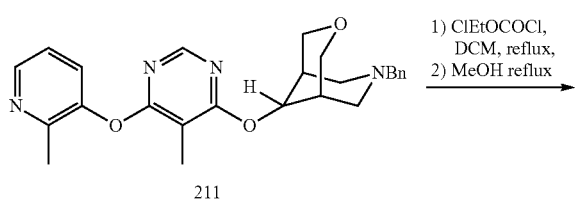

211

1) ClEtOCOCl, DCM, reflux,
2) MeOH reflux

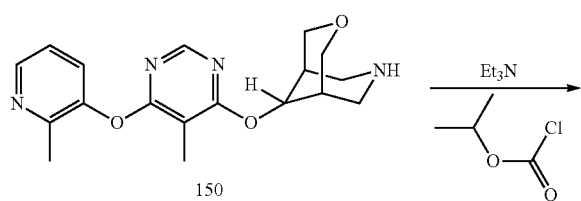

150

Et₃N

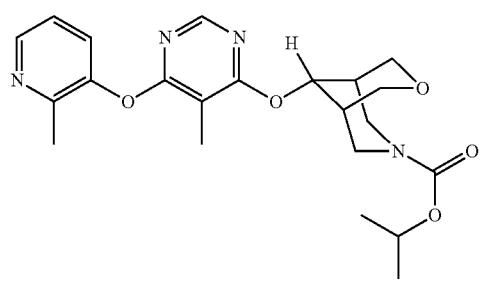

151

Under $N_2$ atmosphere, to a solution of compound 211 (1.05 g, 2.32 mmol) in anhydrous dichloromethane (50 mL) was added slowly 1-chloroethyl chloroformate (0.40 mL, 3.66 mmol) at 0° C. (the colorless solution changed to orange), then warmed up to room temperature gradually and stirred under reflux for 2 hours. The reaction mixture was cooled to room temperature and solvent was removed by rotary evaporator at room temperature. The residue was dissolved in methanol (50 mL) at room temperature under $N_2$ atmosphere and stirred under reflux for 1 hour. The reaction mixture was cooled to room temperature and concentrated in vacuo. The residue was dissolved in dichloromethane (100 mL) and water (100 mL), neutralized with saturated $NaHCO_3$ and then the organic layer was separated. Organic compounds were extracted with dichloromethane (2×100 mL). The combined organic layer was dried over $Na_2SO_4$ and concentrated in vacuo. The residue was purified on a silica gel column (ISCO) with MeOH ($NH_3$) in dichloromethane (0→10%) to provide compound 150 (0.34 g, 43% yield). LCMS: 342.4

To a solution of compound 150 (50 mg), isopropyl chloroformate (0.3 mL, 1.0 M in toluene) in dichloromethane (3 mL) at 0° C., was added $Et_3N$ (0.1 mL). The ice water bath was removed and the reaction was stirred at room temperature for 6 hours. The reaction was quenched with $NaHCO_3$, extracted with dichloromethane (3×10 mL). The combined organic layer was dried over $Na_2SO_4$ and concentrated in vacuo. The residue was purified on a silica gel column (ISCO) with MeOH($NH_3$) in dichloromethane (0→5%) to provide compound 151 (60 mg, 95% yield). LCMS: 428.5

The compounds of the present invention in the following table were prepared using the methods described above and substituting the appropriate reactants:

| Cpd. No. | Structure | LCMS |
|---|---|---|
| 152 | 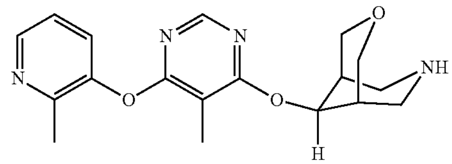 [SMILES: Cc1ncccc1Oc1ncnc(OC2C3CNCC2COC3)c1C] | 342.4 |
| 153 | 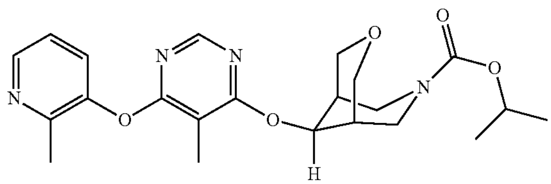 [SMILES: Cc1ncccc1Oc1ncnc(OC2C3COCC2CN(C(=O)OC(C)C)C3)c1C] | 428.5 |
| 154 | 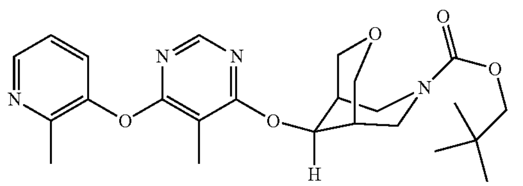 [SMILES: Cc1ncccc1Oc1ncnc(OC2C3COCC2CN(C(=O)OCC(C)(C)C)C3)c1C] | 456.5 |
| 155 | 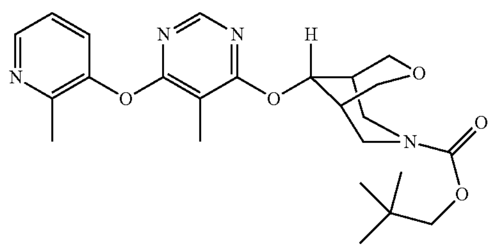 [SMILES: Cc1ncccc1Oc1ncnc(OC2C3COCC2CN(C(=O)OCC(C)(C)C)C3)c1C] | 456.5 |
| 156 | 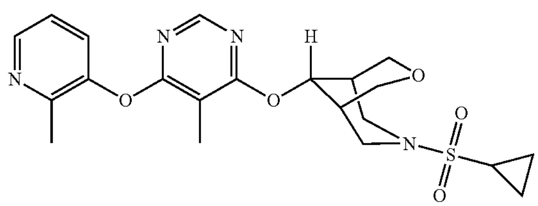 [SMILES: Cc1ncccc1Oc1ncnc(OC2C3COCC2CN(S(=O)(=O)C2CC2)C3)c1C] | 446.5 |
| 157 | 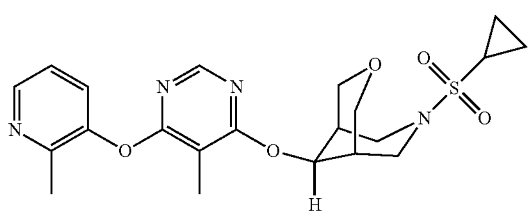 [SMILES: Cc1ncccc1Oc1ncnc(OC2C3COCC2CN(S(=O)(=O)C2CC2)C3)c1C] | 446.5 |
Example 50
Preparation of Compound 158
-continued
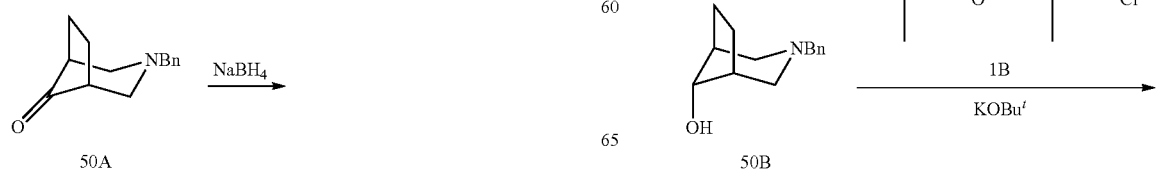

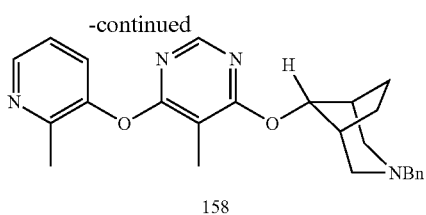

158

Step A—Synthesis of Compound 50B

To a solution of ketone 50A (0.50 g, 2.32 mmol, commercially available) in methanol (8 mL) at 0 was added NaBH$_4$ (0.12 g, 3.18 mmol) and stirred at 0° C. for 2 hours. The reaction was carefully quenched with water and extracted with dichloromethane (30 mL×3)

The combined organic layer was dried over Na$_2$SO$_4$ and concentrated in vacuo. The residue was purified on a silica gel column (ISCO) with MeOH(NH$_3$) in dichloromethane (0→5%) to provide alcohol 50B (0.42 g, 85% yield).

Step B—Synthesis of Compound 158

A solution of KOBu$^t$ (2.4 mL, 1.0 M in THF, 2.34 mmol) was added to a solution of alcohol 50B (0.42 g, 1.95 mmol) and the chloride 1B (0.56 g, 2.39 mmol) in anhydrous THF mL) under nitrogen at 0 and stirred at 0° C. to room temperature for 16 hours. The reaction was quenched with saturated NH$_4$Cl solution (15 mL) and extracted with. EtOAc (30 mL×3). The combined organic layer was dried over Na$_2$SO$_4$ and concentrated in vacuo. The residue was purified on a silica gel column (ISCO) with MeOH(NH$_3$) in dichloromethane (0→5%) to provide compound 158 (0.81 g, 99% yield). LCMS: 416.5

Example 51

Preparation of Compounds 159 and 160

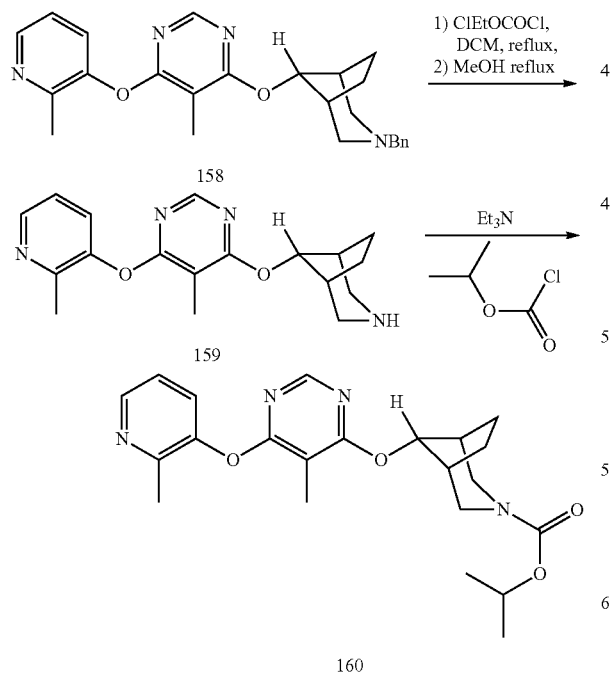

Compounds 159 and 160 were prepared from compound 158 using the method described in Example 49. Compound 159, LCMS: 326.4. Compound 160, LCMS: 412.5

The compounds of the present invention in the following table were prepared using the methods described above and substituting the appropriate reactants:

| Cpd No. | Structure | LCMS |
|---|---|---|
| 161 | 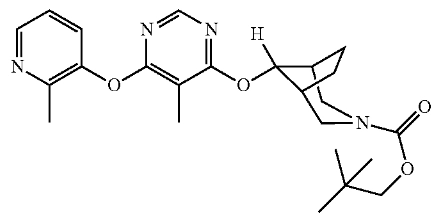 [SMILES: Cc1ncccc1Oc1ncnc(OC2C3CCC2CN(C(=O)OCC(C)(C)C)C3)c1C] | 440.5 |
| 162 | 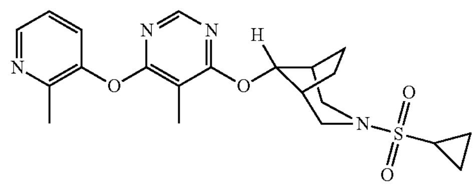 [SMILES: Cc1ncccc1Oc1ncnc(OC2C3CCC2CN(S(=O)(=O)C2CC2)C3)c1C] | 430.5 |
| 163 | 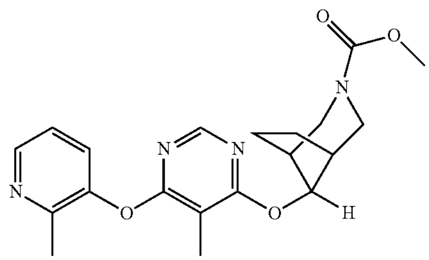 [SMILES: COC(=O)N1CC2CCC(C1)C2Oc1ncnc(Oc2cccnc2C)c1C] | 384.4 |

Example 52

Preparation of Compound 164

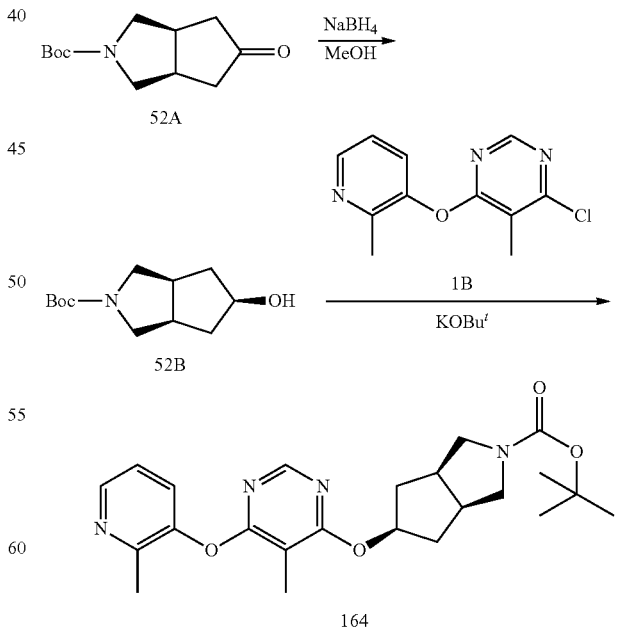

Compound 164 was prepared from ketone 52A (prepared as described in Lee, H.-Y.; An, M.; Sohn, J.-H. *Bull. Korean Chem. Soc.* 2003, 24, 539-540) using the method described in Example 50. LCMS: 426.5

Example 53

Preparation of Compound 165

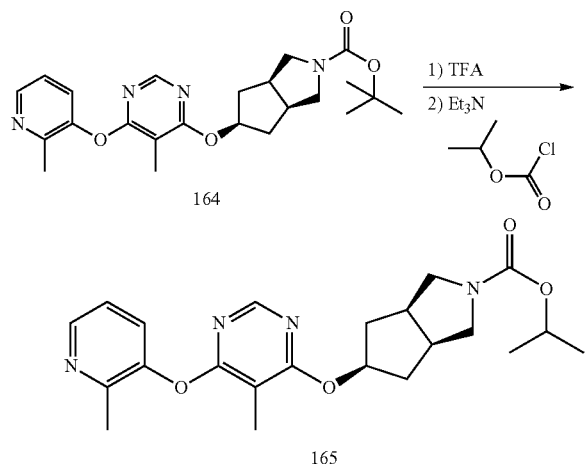

Trifluoroacetic acid (10 mL, 20% in DCVO was added to a solution of compound 164 (1.0 g) in DCM (5 mL) at room temperature and stirred for 2.0 hours. The solution was concentrated in vacuo. To a solution of the resulting residue (50 mg) and isopropyl chloroformate (0.3 mL, 1.0 M in toluene) in dichloromethane (3 mL) at 0° C., was added Et₃N (0.2 mL). The ice water bath was removed and the reaction was stirred at room temperature for 16 hours. The reaction was quenched with NaHCO₃ and extracted with dichloromethane (3×10 mL). The combined organic layer was dried over Na₂SO₄ and concentrated in vacuo, The residue was purified on a silica gel column. (ISCO) with MeOH (NH₃) in dichloromethane (0→%) to provide compound 165 (25 mg). LCMS: 412.5

The following compound of the present invention % as prepared using the method described above and substituting the appropriate reactants:

| Cpd. No. | Structure | LCMS |
|---|---|---|
| 166 | 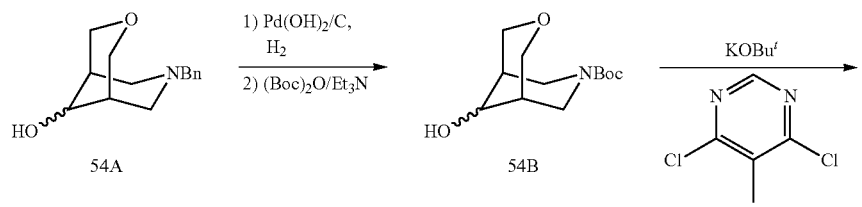 | 430.5 |

Example 54

Preparation of Compounds 167 and 168

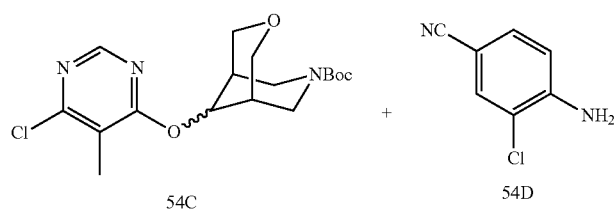

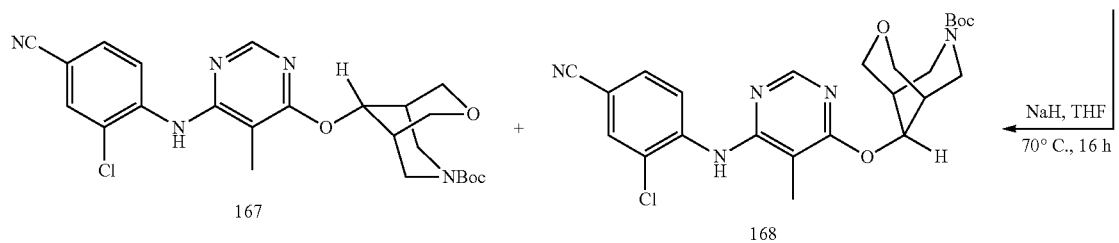

A solution of compound 54A (0.97 g, 4.16 mmol, prepared from the corresponding ketone [Huttenloch, O.; Laxman, E.; Waldmann, H. *Chem. Eur.* 2002, 8, 4767-4780.] by a NaBH$_4$ reduction), 20% Pd(OH)$_2$/C (873 mg, 1.25 mmol) in methanol (30 nit) was reacted under 1 atm H$_2$ for 24 hours. Then filtered through Celite and concentrated. The residue was dissolved in 20 mL DCM and cooled to 0° C. Followed by adding Boc$_2$O (0.95 mL, 4.11 mmol) and Et$_3$N (0.82 mL, 5.86 mmol). The reaction was warmed to room temperature overnight. The reaction was quenched with NaHCO$_3$, extracted with dichloromethane (3×30 The combined organic layer was dried over Na$_2$SO$_4$ and concentrated in vacuo. The residue was purified on a silica gel column (ISCO) with MeOH (NH$_3$) in dichloromethane (0→45%) to provide compound 548 (715 mg).

A solution of KOBu$^t$ (3.7 mL, 1.0 M in THF, 3.70 mmol) was added to a solution of the alcohol 54B (715 mg, 3.06 mmol) and the dichloropyrimidine (619 mg, 3.74 mmol) in anhydrous THF (20 mL) under nitrogen at 0° C. and stirred at 0° C. to room temperature for 16 hours. The reaction was quenched with saturated NH$_4$Cl solution (15 mL) and extracted with EtOAc (30 mL×3). The combined organic layer was dried over Na$_2$SO$_4$ and concentrated in vacuo. The residue was purified on a silica gel column (ISCO) with EtOAc in hexanes (0→30%) to provide 54C (986 mg).

To a sealable tube, a solution of 54C (460 mg, 1.25 mmol), aniline 54D (200 mg, 1.31 mmol) and NaH (250 mg, 60% on oil) in THF (20 mL) were added and sealed. The reaction was heated at 70° C. overnight. Then the reaction was cooled to room temperature and carefully quenched with saturated NH$_4$Cl solution. The mixture was extracted with EtOAc (3×50 mL). The combined organic layer was dried over Na$_2$SO$_4$ and concentrated in vacuo. The residue was purified on a silica gel column (ISCO) with MeOH (NH$_3$) in dichloromethane (0→5%) to provide compounds 167 (134 mg, 22% yield, LCMS: 486) and 168 (163 mg, 27% yield, LCMS: 486.0).

Example 55

Preparation of Compound 169

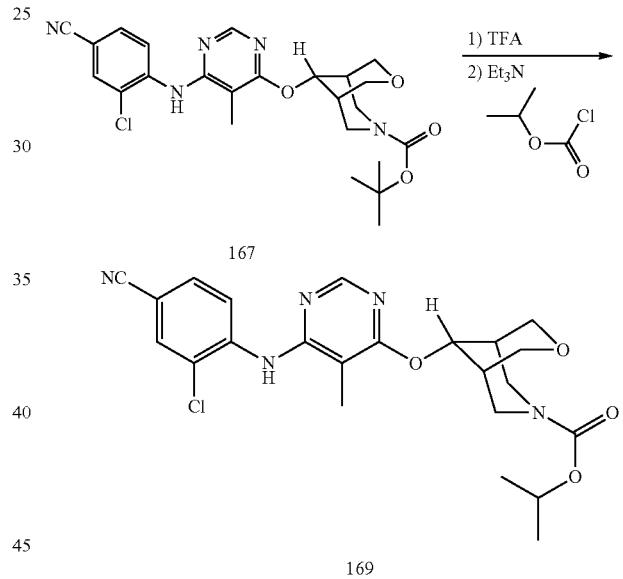

Compound 169 was prepared from Compound 167 using the method described in Example 53. LCMS: 471.9

The following compounds of the present invention were prepared using the method described above and substituting the appropriate reactants:

| Cpd. No. | Structure | LCMS |
|---|---|---|
| 170 | ![structure] | 490.0 |

| Cpd. No. | Structure | LCMS |
|---|---|---|
| 171 | 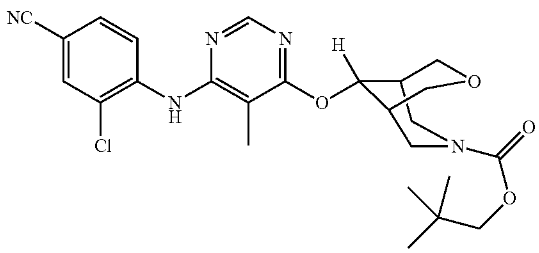 [SMILES: Cc1c(Nc2ccc(C#N)cc2Cl)ncnc1OC1C2COCC1CN(C(=O)OCC(C)(C)C)C2] | 500.0 |
| 172 | 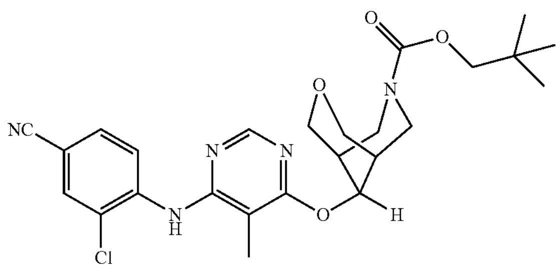 [SMILES: Cc1c(Nc2ccc(C#N)cc2Cl)ncnc1OC1C2COCC1CN(C(=O)OCC(C)(C)C)C2] | 500.0 |
| 173 | 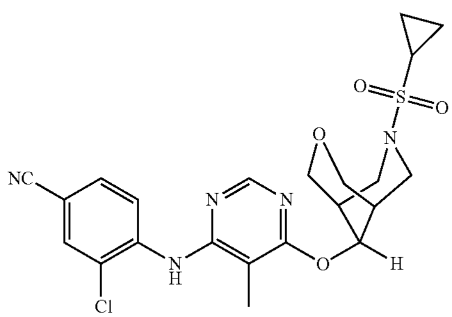 [SMILES: Cc1c(Nc2ccc(C#N)cc2Cl)ncnc1OC1C2COCC1CN(S(=O)(=O)C1CC1)C2] | 490.0 |
| 174 | 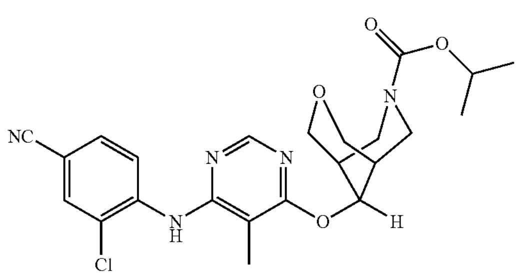 [SMILES: Cc1c(Nc2ccc(C#N)cc2Cl)ncnc1OC1C2COCC1CN(C(=O)OC(C)C)C2] | 471.9 |
| 175 | 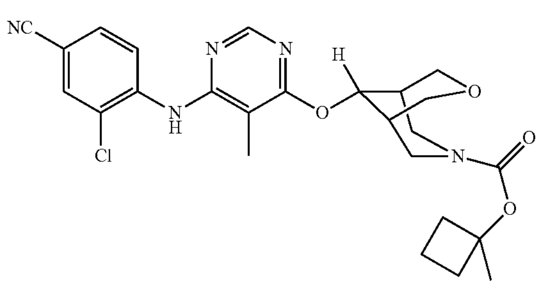 [SMILES: Cc1c(Nc2ccc(C#N)cc2Cl)ncnc1OC1C2COCC1CN(C(=O)OC1(C)CCC1)C2] | 498.0 |

| Cpd. No. | Structure | LCMS |
|---|---|---|
| 176 | 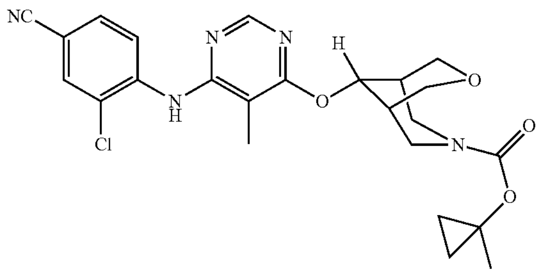 [SMILES: Cc1c(Nc2ccc(C#N)cc2Cl)ncnc1OC1C2COCC1CN(C(=O)OC1(C)CC1)C2] | 483.9 |
| 177 | 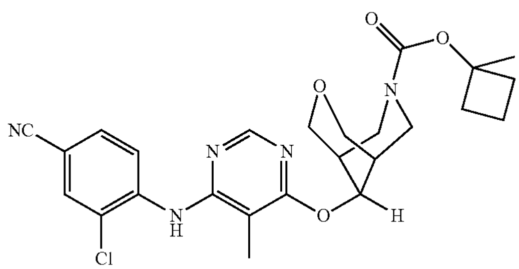 [SMILES: Cc1c(Nc2ccc(C#N)cc2Cl)ncnc1OC1C2COCC1CN(C(=O)OC1(C)CCC1)C2] | 498.0 |
| 178 | 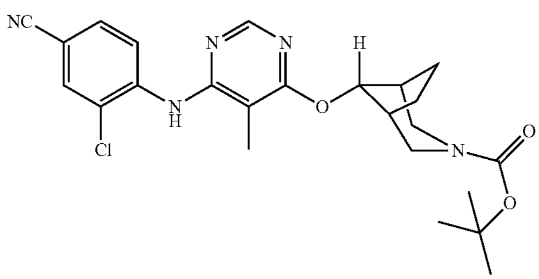 [SMILES: Cc1c(Nc2ccc(C#N)cc2Cl)ncnc1OC1C2CCC1CN(C(=O)OC(C)(C)C)C2] | 470.0 |
| 179 | 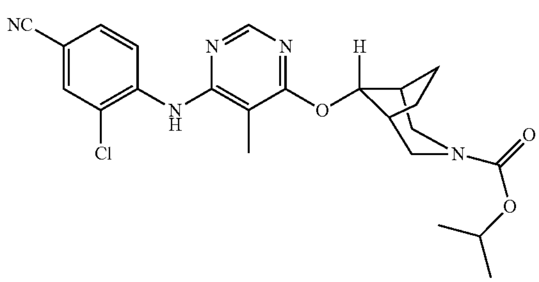 [SMILES: Cc1c(Nc2ccc(C#N)cc2Cl)ncnc1OC1C2CCC1CN(C(=O)OC(C)C)C2] | 455.9 |
| 180 | 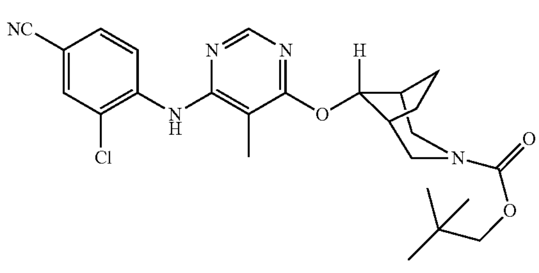 [SMILES: Cc1c(Nc2ccc(C#N)cc2Cl)ncnc1OC1C2CCC1CN(C(=O)OCC(C)(C)C)C2] | 484.0 |

241

-continued

| Cpd. No. | Structure | LCMS |
|---|---|---|
| 181 | 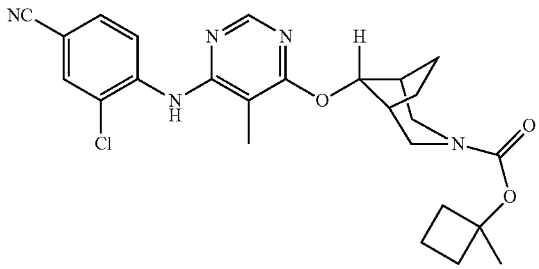 [SMILES: Cc1c(Nc2ccc(C#N)cc2Cl)ncnc1OC1C2CCC1CN(C(=O)OC1(C)CCC1)C2] | 482.0 |
| 182 | 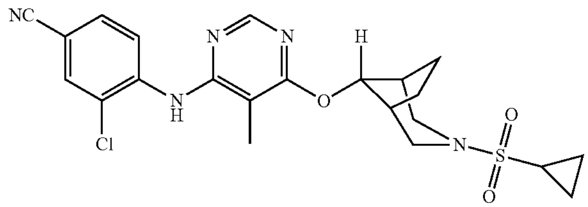 [SMILES: Cc1c(Nc2ccc(C#N)cc2Cl)ncnc1OC1C2CCC1CN(S(=O)(=O)C1CC1)C2] | 474.0 |

Example 56

Preparation of Compounds 183 and 184

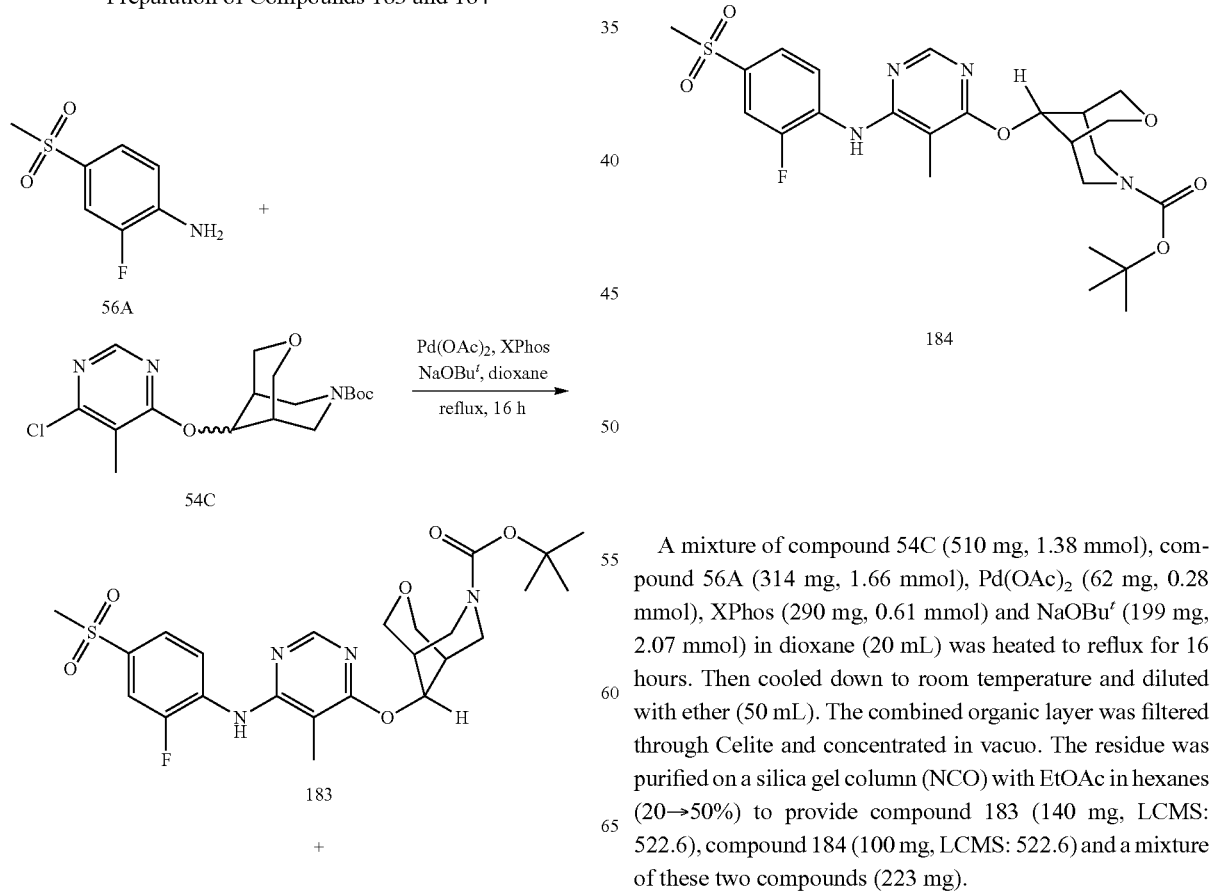

-continued

A mixture of compound 54C (510 mg, 1.38 mmol), compound 56A (314 mg, 1.66 mmol), Pd(OAc)$_2$ (62 mg, 0.28 mmol), XPhos (290 mg, 0.61 mmol) and NaOBu$^t$ (199 mg, 2.07 mmol) in dioxane (20 mL) was heated to reflux for 16 hours. Then cooled down to room temperature and diluted with ether (50 mL). The combined organic layer was filtered through Celite and concentrated in vacuo. The residue was purified on a silica gel column (NCO) with EtOAc in hexanes (20→50%) to provide compound 183 (140 mg, LCMS: 522.6), compound 184 (100 mg, LCMS: 522.6) and a mixture of these two compounds (223 mg).

Example 57
Preparation of Compound 185
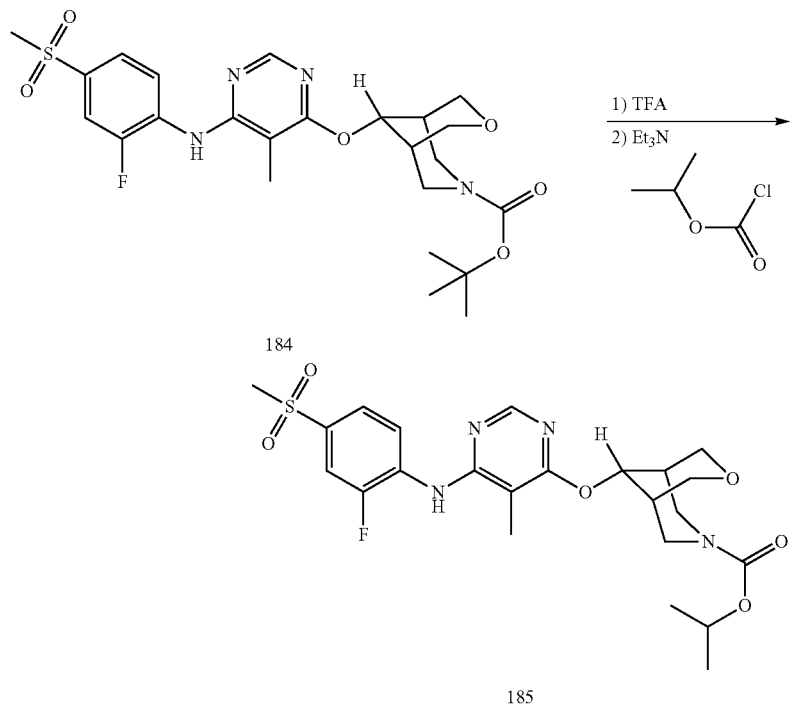
Compound 185 was prepared from Compound 184 using the method described in Example 53. LCMS: 508.6
The following compounds of the present invention were prepared using the method described above and substituting the appropriate reactants:
| Cpd. No. | Structure | LCMS |
|---|---|---|
| 186 | 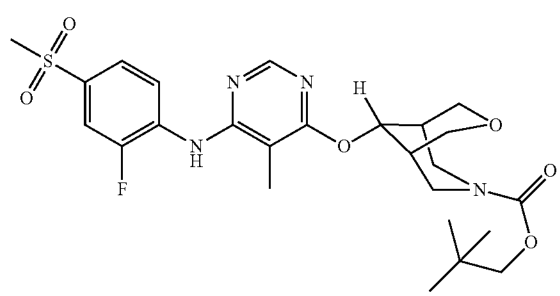 [SMILES: Cc1c(Nc2ccc(S(C)(=O)=O)cc2F)ncnc1OC1C2COCC1CN(C(=O)OCC(C)(C)C)C2] | 536.6 |
| 187 | 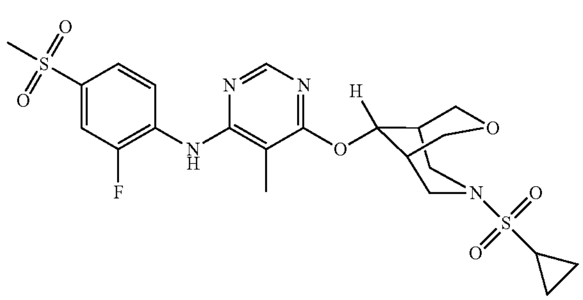 [SMILES: Cc1c(Nc2ccc(S(C)(=O)=O)cc2F)ncnc1OC1C2COCC1CN(S(=O)(=O)C1CC1)C2] | 526.6 |

-continued
| Cpd. No. | Structure | LCMS |
|---|---|---|
| 188 | 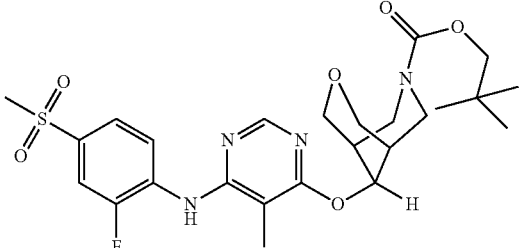 | 536.6 |
| 189 | 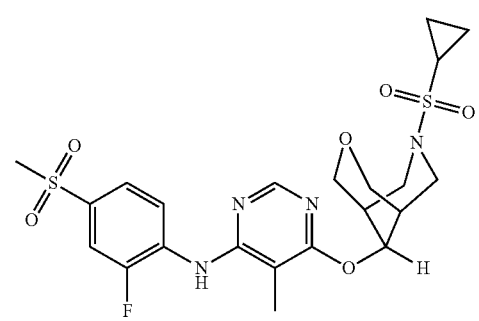 [SMILES: Cc1c(Nc2ccc(S(C)(=O)=O)cc2F)ncnc1OC1C2COCC1CN(S(=O)(=O)C1CC1)C2] | 526.6 |
| 190 | 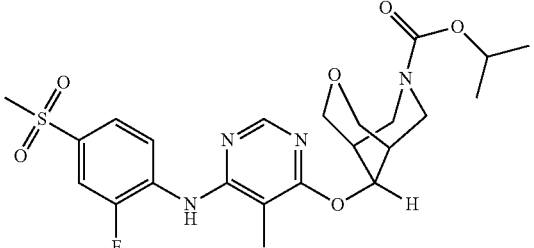 | 508.6 |
| 191 | 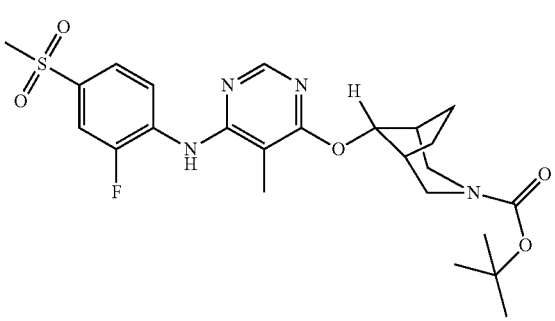 [SMILES: Cc1c(Nc2ccc(S(C)(=O)=O)cc2F)ncnc1OC1C2CCC1CN(C(=O)OC(C)(C)C)C2] | 506.6 |
| 192 | 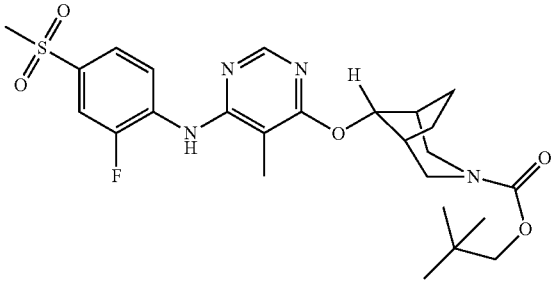 [SMILES: Cc1c(Nc2ccc(S(C)(=O)=O)cc2F)ncnc1OC1C2CCC1CN(C(=O)OCC(C)(C)C)C2] | 520.6 |

| Cpd. No. | Structure | LCMS |
|---|---|---|
| 193 | 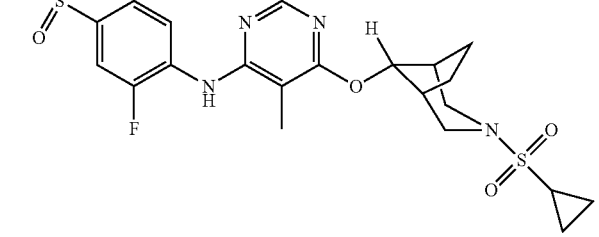 | 510.6 |
| 194 | 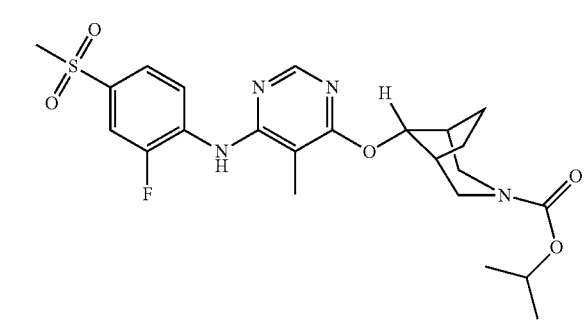 [SMILES: Cc1c(Nc2ccc(S(C)(=O)=O)cc2F)ncnc1OC1C2CCC1CN(C(=O)OC(C)C)C2] | 492.6 |
| 195 | 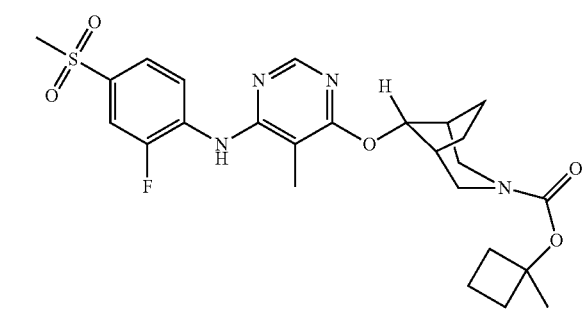 [SMILES: Cc1c(Nc2ccc(S(C)(=O)=O)cc2F)ncnc1OC1C2CCC1CN(C(=O)OC1(C)CCC1)C2] | 518.6 |

Example 58

Preparation of Compound 58D

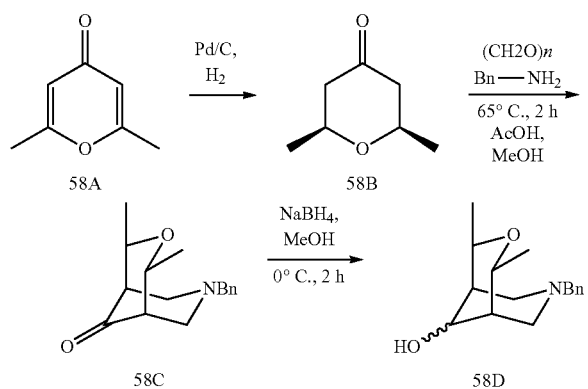

Step A—Synthesis of Compound 58B

A mixture of ketone 58A (13.0 g), Pd/C (10%) (1.5 g) in EtOH (80 mL) was reacted in a hydrogenation vessel under 45 psi for 8 hours. Then the mixture was filtered through Celite and concentrated in vacuo. The residue was purified on a silica gel column (ISCO) with EtOAc in hexanes (0→25%) to provide 58B (8.0 g, 61% yield).

Step B—Synthesis of Compound 58C

A solution of 58B (2.56 g, 20.0 mmol), benzylamine (4.6 mL, 42.0 mmol) and acetic acid (2.28 mL, 40.0 mmol) in dry methanol (80 mL) was added over a period of 1 h to a suspension of coarse-grained paraformaldehyde (2.66 g, 88.4 mmol) in dry methanol (80 mL) at 65° C., Another portion of paraformaldehyde (2.66 g, 88.4 mmol) was added and the mixture was stirred for 1 h at 65° C. After cooling water (200 mL) and 1 N MOH solution (40 mL) were added, and the aqueous phase was extracted with diethyl ether (3×400 mL). The combined organic layers were dried over MgSO$_4$ and the solvent was evaporated in vacuo. The residue was purified on a silica gel column (ISCO) with EtOAc in hexanes (0→20%) to provide 58C (4.45 g, 86% yield).

Step C—Synthesis of Compound 58D

To a solution of ketone 58C (4.45 g, 17.2 mmol) in methanol (50 mL) at 0° C. was added NaBH$_4$ (0.98 g, 25.8 mmol) and stirred at 0° C. for 2 hours. The reaction was carefully quenched with water and extracted with dichloromethane (100 mL×3). The combined organic layer was dried over Na$_2$SO$_4$ and concentrated in vacuo. The residue was purified on a silica gel column (ISCO) with MeOH(NH$_3$) in dichloromethane (0→5%) to provide alcohol 58D (3.81=85% yield).

Using compound 58D as a reactant, the following compounds of the present invention were prepared using methods described above herein:

| Cpd. No. | Structure | LCMS |
|---|---|---|
| 196 | 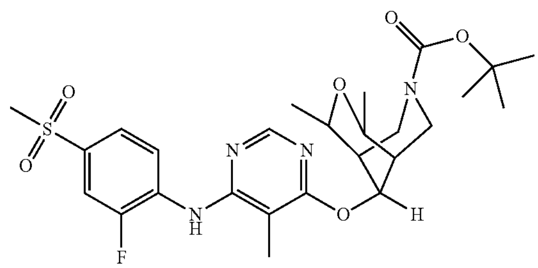 [SMILES: Cc1c(Nc2ccc(S(C)(=O)=O)cc2F)ncnc1OC1C2CN(C(=O)OC(C)(C)C)CC1C(C)OC2C] | 550.6 |
| 197 | 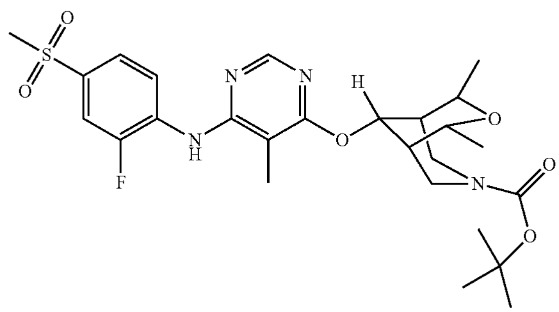 [SMILES: Cc1c(Nc2ccc(S(C)(=O)=O)cc2F)ncnc1OC1C2CN(C(=O)OC(C)(C)C)CC1C(C)OC2C] | 550.6 |
| 198 | 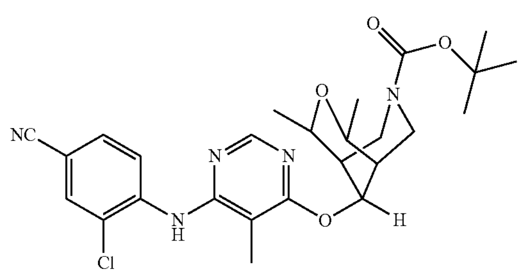 [SMILES: Cc1c(Nc2ccc(C#N)cc2Cl)ncnc1OC1C2CN(C(=O)OC(C)(C)C)CC1C(C)OC2C] | 514.0 |
| 199 | 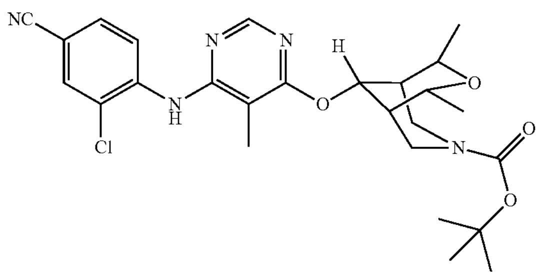 [SMILES: Cc1c(Nc2ccc(C#N)cc2Cl)ncnc1OC1C2CN(C(=O)OC(C)(C)C)CC1C(C)OC2C] | 514.0 |
| 200 | 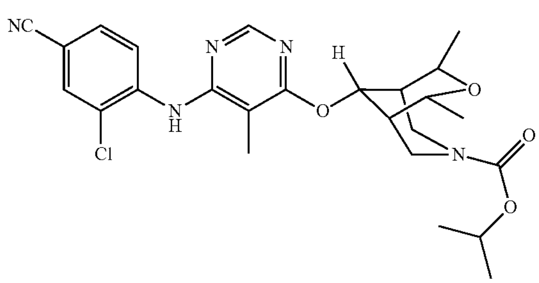 [SMILES: Cc1c(Nc2ccc(C#N)cc2Cl)ncnc1OC1C2CN(C(=O)OC(C)C)CC1C(C)OC2C] | 500.0 |

-continued

| Cpd. No. | Structure | LCMS |
|---|---|---|
| 201 | 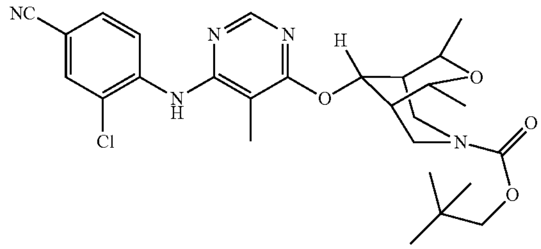 [SMILES: Cc1c(Nc2ccc(C#N)cc2Cl)ncnc1OC1C2CN(C(=O)OCC(C)(C)C)CC1C(C)OC2C] | 528.0 |
| 202 | 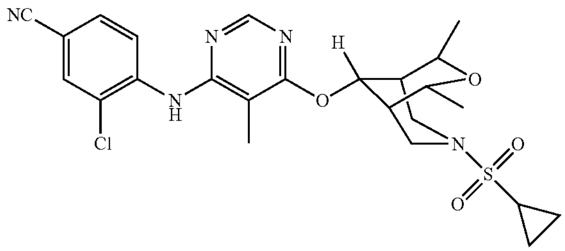 [SMILES: Cc1c(Nc2ccc(C#N)cc2Cl)ncnc1OC1C2CN(S(=O)(=O)C3CC3)CC1C(C)OC2C] | 518.0 |
| 203 | 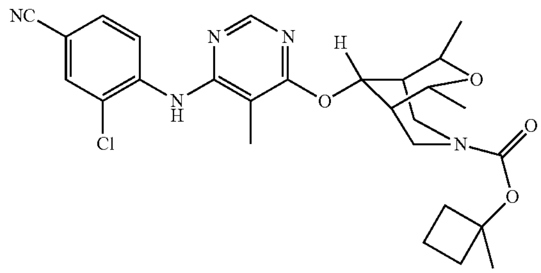 [SMILES: Cc1c(Nc2ccc(C#N)cc2Cl)ncnc1OC1C2CN(C(=O)OC3(C)CCC3)CC1C(C)OC2C] | 526.0 |
| 204 | 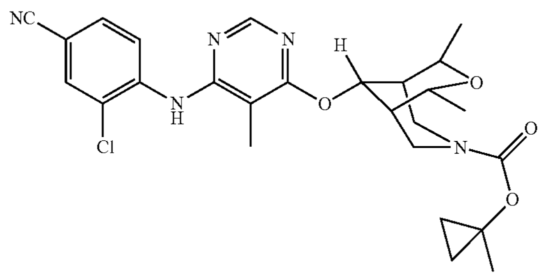 [SMILES: Cc1c(Nc2ccc(C#N)cc2Cl)ncnc1OC1C2CN(C(=O)OC3(C)CC3)CC1C(C)OC2C] | 512.0 |
| 205 | 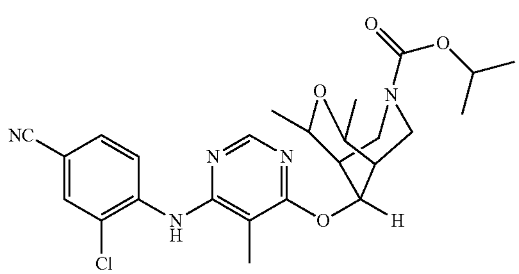 [SMILES: Cc1c(Nc2ccc(C#N)cc2Cl)ncnc1OC1C2CN(C(=O)OC(C)C)CC1C(C)OC2C] | 500.0 |
| 206 | 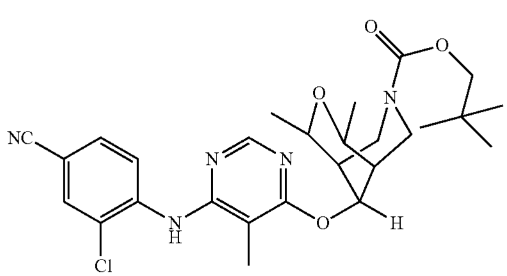 [SMILES: Cc1c(Nc2ccc(C#N)cc2Cl)ncnc1OC1C2CN(C(=O)OCC(C)(C)C)CC1C(C)OC2C] | 528.0 |

-continued
| Cpd. No. | Structure | LCMS |
|---|---|---|
| 207 | 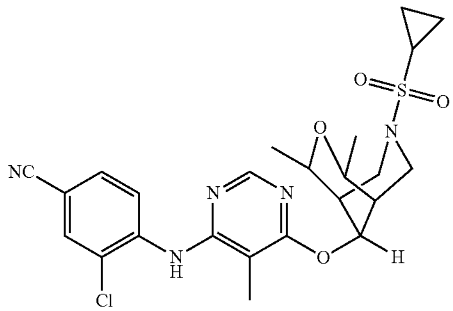 [SMILES: Cc1c(Nc2ccc(C#N)cc2Cl)ncnc1OC1C2CN(S(=O)(=O)C3CC3)CC1C(C)OC2C] | 518.0 |
| 208 | 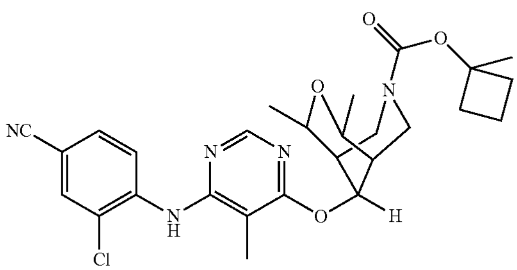 [SMILES: Cc1c(Nc2ccc(C#N)cc2Cl)ncnc1OC1C2CN(C(=O)OC3(C)CCC3)CC1C(C)OC2C] | 526.0 |
| 209 | 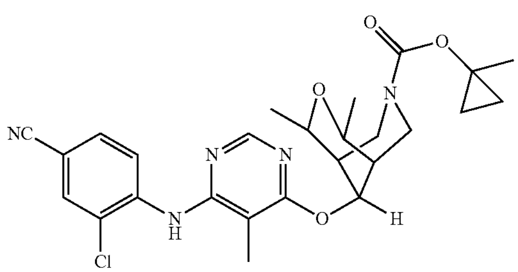 [SMILES: Cc1c(Nc2ccc(C#N)cc2Cl)ncnc1OC1C2CN(C(=O)OC3(C)CC3)CC1C(C)OC2C] | 512.0 |
Example 59
Preparation of Compounds 210 and 211
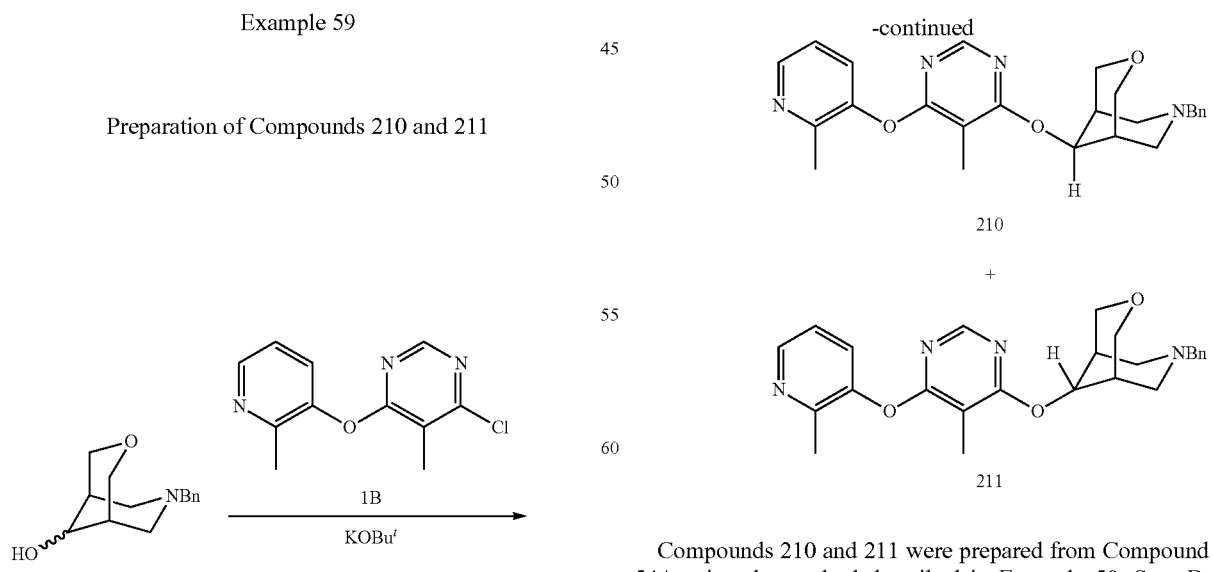
Compounds 210 and 211 were prepared from Compound 54A using the method described in Example 50, Step B. Compound 210, LCMS: 432.5. Compound 211, LCMS: 432.5

Example 60

Preparation of Compound 60F

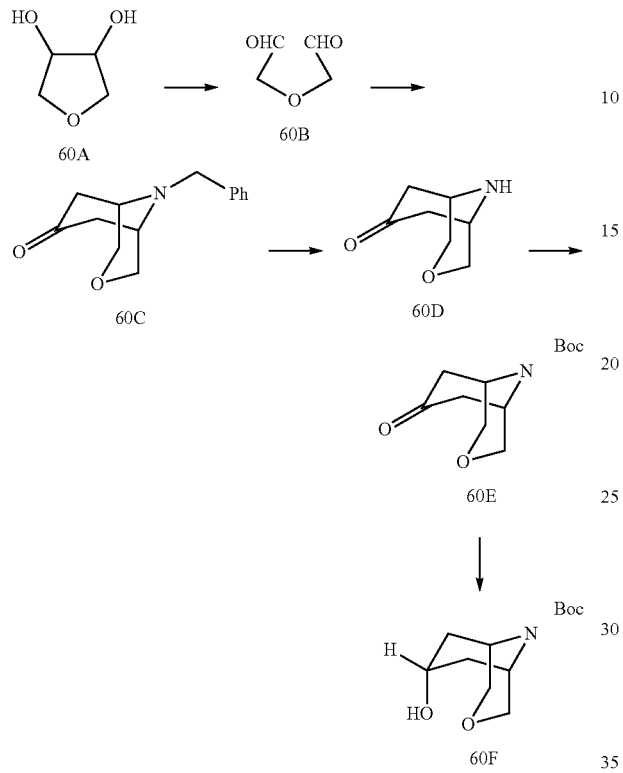

Step A—Synthesis of Compound 60B

To 1,4-anhydroerythritol (60A, 5.00 g, 48 mmol) in water (70 mL) was added NaIO$_4$ (5.10 g, 24 mmol). The solution was stirred 18 hours and MeCN (70 mL) added. After 30 minutes of additional stirring, the mixture was filtered and concentrated in vacuo to provide compound 60B.

Step B—Synthesis of Compound 60C

To compound 60B (from Step A) was added acetone-1,3-dicarboxylic acid (7.0 g, 48 mmole) and conc. HCl (2.5 mL), followed by dropwise addition of benzylamine (6.14 mL, 66 mol). The mixture was stirred 1.5 hours, heated to 50° C. and stirred at this temperature for 5 hours, then cooled to 0° C. The cooled mixture was basified to pH 10 using NaOH, and the basic solution was extracted with ether. The organic phase was dried (K$_2$CO$_3$) and concentrated in vacuo, and the resulting residue was chromatographed on silica to pro de compound 60C as an oil.

Step C—Synthesis of Compound 60D

Compound 60C (8.75 g, 38 mmol) was taken up in 1N HCl (40 mL) and EtOH (40 mL), then 10% Pd/C (1.00 g) was added. The reaction was hydrogenated at 50 psi for 18 hours, then filtered, and concentrated in vacuo to provide compound 60D as a brown solid.

Step D—Synthesis of Compound 60E

Compound 60E (3.90 g, 22 mmol) in EtOH (40 mL) was treated with Boc$_2$O (5.30 g, 24 mmol) and Et$_3$N (4.60 mL, 33 mmol) and the reaction was stirred for 3 hours. Water (100 mL) was added and the product extracted with EtOAc. The organic phase was dried over MgSO$_4$, filtered and concentrated in vacuo to provide compound 60E as a yellow solid.

Step E—Synthesis of Compound 60F

A solution of compound 60E in THF (50 mL) was treated with NaBH$_4$ (1.50 g, 39 mmol) and the reaction was stirred for 2 hours. MeOH (10 mL) was then added and after 1 hour of additional stirring, water (100 mL) was added. The resulting solution was extracted with ether, and the organic phase was dried over MgSO$_4$, filtered and concentrated in vacuo to provide compound 60F as a yellow solid.

Example 61

Preparation of Compound 61B

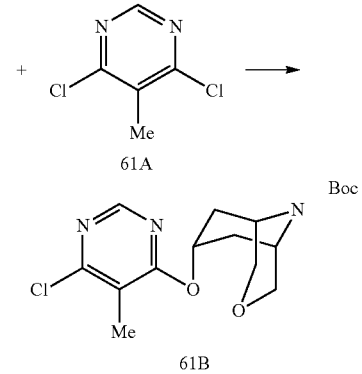

Compound 60F (0.148 g, 0.61 mmol) was dissolved in THF (2.0 mL) and to the resulting solution was added the dichloropyrimidine 61A (0.100 g, 0.61 mmol) and NaH (60% in oil, 0.030 g, 0.75 mmol). The mixture was stirred 18 hours, then heated for 5 hours at 50° C. Concentration and purification by PLC yielded compound 618 as a yellow solid.

Example 62

Preparation of Compound 62D

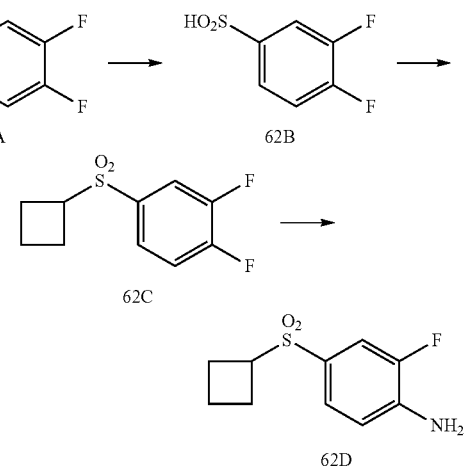

Step A—Synthesis of Compound 62B 3,4-Difluorobenzenesulfonyl chloride (62A, 2.50 g, 11.8 mmol) was added dropwise to Na$_2$SO$_3$ (11.2 g, 85 mmol) in water (50 mL). A solution of NaOH (1.20 g, 30 mmol) in water (10 mL) was added dropwise. After 1 h, MeOH (15 mL) was added. After another 1 h, the mixture was cooled to 0° C. and acidified to pH2 with conc. HCl. Extraction with ether, drying (MgSO$_4$) and concentration gave compound 62B as a white solid.

Step B—Synthesis of Compound 62C

Compound 62B (1.30 g, 7.3 mmol) was combined with cyclobutyl bromide (1.60 g, 12 mmol) and DIPEA (1.94 mL, 11 mmol) in DMF (4.0 mL). The mixture was heated in a sealed tube at 100° C. 72 h, then concentrated and purified using PLC to provide compound 62C as a yellow oil.

Step C—Synthesis of Compound 62D

Compound 62C (0.100 g, 0.53 mmol) was combined with 2.0M NH$_3$/isopropanol (10 mL) and heated in a sealed tube at 110° C. for 48 h. Concentration and purification by PLC provided compound 62D as a yellow solid.

Example 63

Preparation of Compound 63B

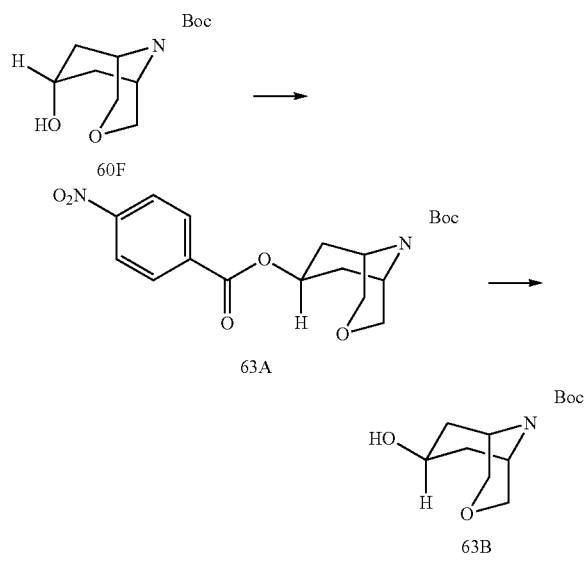

Step A—Synthesis of Compound 63A

Compound 60F (0.100 g, 0.41 mmol) was combined with Ph$_3$P (0.129 g, 0.49 mmol) and 4-nitrobenzoic acid (0.076 g, 0.46 mmol) in THF (2 mL). Diethyl azodicarboxylate (0.078 mL, 0.49 mmol) was then added and the reaction was allowed to stir for 24 hours, then concentrated in vacuo. The residue obtained was purified using PLC to provide compound 63A as a yellow oil.

Step B—Synthesis of Compound 63B

Compound 63A (0.098 g, 0.19 mmol) in THF (2 L) was treated with a solution of KOH (0.200 g) in water (1 mL) and the resultant reaction was stirred 48 hours, then partitioned with ether and water. The ether phase was dried over MgSO$_4$, filtered and concentrated in vacuo to provide compound 63B as a yellow oil.

Example 64

Preparation of Compound 64A

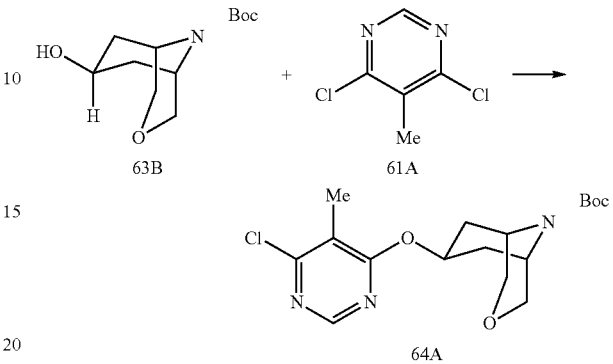

Similarly to Example 61, compound 63B was converted to the title compound, a yellow oil.

Example 65

Preparation of Compounds 65B and 65C

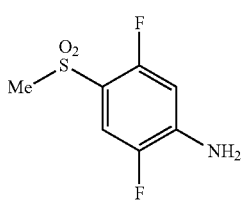

4-Bromo-2,6-difluoroaniline (65A, 0.500 g, 2.4 mmol) was combined with sodium methanesulfinate (0.98 g, 9.6 mmol), cuprous triflate benzene complex (0.121 g, 0.24 mmol), and N,N'-dimethylethylenediamine (0.027 mL, 0.23 mmol) ire DMF (5 mL). The mixture was heated to 150° C. and allowed to stir at this temperature for 24 hours, then was concentrated in vacuo and purified using PLC to provide compound 65B as a yellow solid.

Using this method, 4-bromo-2,5-difluoroaniline was converted to compound 65C:

Example 66

Preparation of Compound 66B

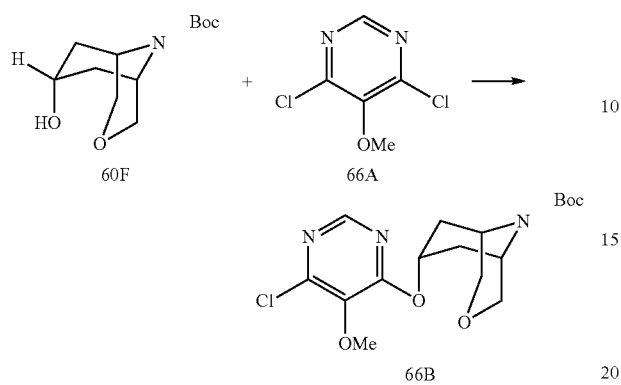

Similarly to Example 61, 4,6-dichloro-5-methoxypyrimidine was converted to the title compound, a yellow solid.

Example 67

Preparation of Compound 67B

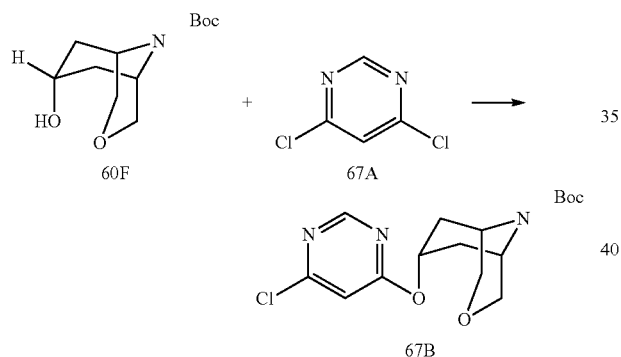

Using the method described in Example 61, 4,6-dichloropyrimidine was converted to compound 67B, a yellow oil.

Example 68

Preparation of Compound 68B-68E

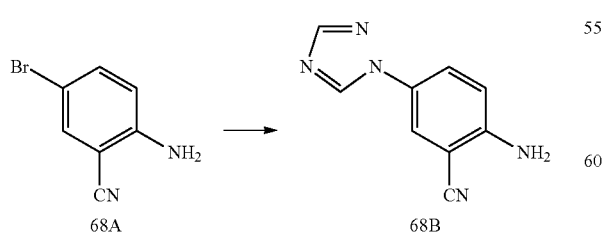

2-Amino-5-bromobenzonitrile (0.500 g, 2.5 mmol), 1,2,4-triazole (0.350 g, 5.1 mmol), N,N'-dimethylethylenediamine (0.055 mL, 0.5 mmol), CuI (0.028 g, 0.16 mmol), and Cs$_2$CO$_3$ (1.48 g, 4.6 mmol) were taken up in DMF (3 mL). The mixture was heated at 140° C. and allowed to stir at this temperature for 96 hours, then cooled to room temperature and concentrated in vacuo. The residue obtained was purified using PLC to provide compound 68B as a yellow solid.

Using the above method, 2-Chloro-4-iodoaniline was converted to compound 68C, and 2-fluo 4-iodoaniline was converted to compounds 68D and 68E.

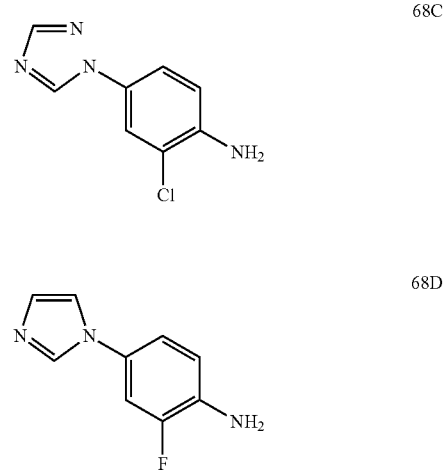

Example 69

Preparation of Compound 69B

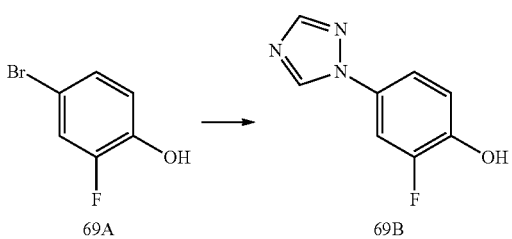 [SMILES: Oc1ccc(Br)cc1F ; Oc1ccc(-n2cncn2)cc1F]

Using the method described in Example 68 and employing K$_3$PO$_4$ as the base, 4-bromo-2-fluorophenol was converted to compound 69B, a yellow solid.

Example 70

Preparation of Compound 70G

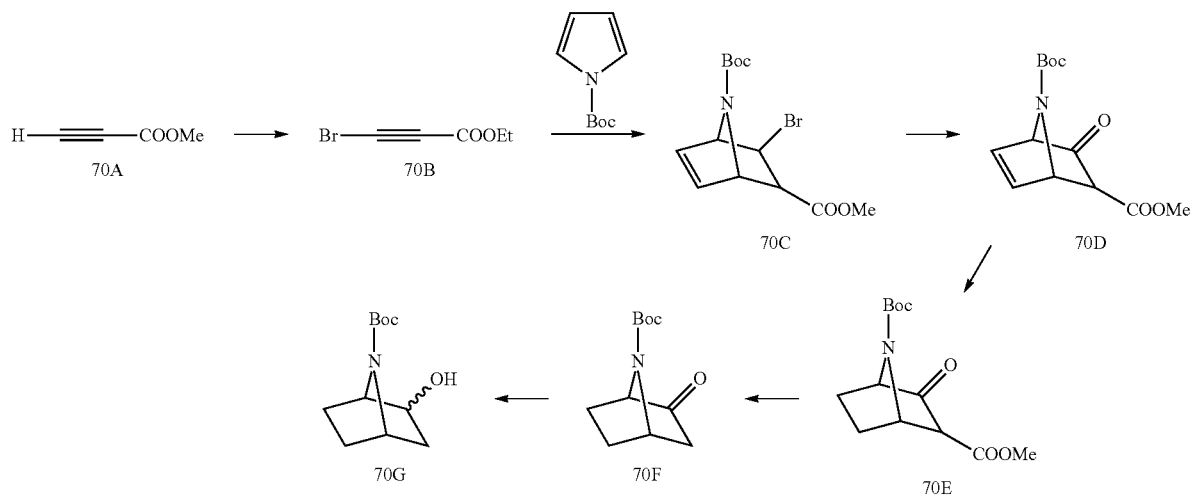

Step A—Preparation of Compound 70B

Methyl propiolate (10.0 g, 118 mmol), N-bromosuccinimide (21.2 g, 119 mmol) and AgNO$_3$ (0.20 g, 1.2 mmol) were combined in acetone (60 mL). The mixture was stirred 22 hours, filtered, concentrated, taken up in hexane, and filtered. The filtrate was concentrated in vacuo and the residue obtained was purified using Kugelrohr distillation to provide compound 70B as a yellow oil.

Step B—Preparation of Compound 70C

The product of Step A (11.3 g, 69 mmol) and t-butyl pyrrole-1-carboxylate (30 mL, 180 mmol) was combined and heated at 95° and allowed to stir at this temperature for 24 hours. The product was purified using chromatography on silica to provide compound 70C as a yellow oil.

Step C—Preparation of Compound 70D

The product of Step B (4.00 g, 12.1 mmol) and Et$_3$N (8.44 mL, 61 mmol) were combined in MeCN (25 mL). Et$_2$NH (1.38 mL, 13.4 mmol) in MeCN (15 mL) was added dropwise. After 1.5 hours, 10% HCl (20 mL) was added dropwise. After 4 hours, the mixture was partitioned with CH$_2$Cl$_2$ and water. The CH$_2$Cl$_2$ layer was washed with brine, dried over MgSO$_4$ and concentrated in vacuo. The resulting residue was purified using flash chromatography on silica to provide compound 70D as a yellow oil.

Step D—Preparation of Compound 70E

The product of Step C (2.18 g, 8.16 mmol) was combined with 10% Pd/C (0.302 MeOH (30 mL) and hydrogenated at atmospheric pressure for 20 hours. The reaction mixture was filtered and concentrated in vacuo to provide compound 70E as a yellow oil, which was used without further purification.

Step E—Preparation of Compound 70F

The product of Step D (2.08 g, 7.73 mmol) was combined with 10% HCl (70 mL) and the resulting solution was heated at 110° C. and allowed to stir at this temperature for 3.5 hours, then concentrated to provide a yellow solid residue. The residue was taken up in CH$_2$Cl$_2$ (15 mL) and Et$_3$N (4.84 mL, 35 mmol) was added, followed by Boc$_2$O (3.4 g, 15 mmol). After stirring for 18 hours, the mixture was washed with saturated NaHCO$_3$, then brine. The organic layer was dried over MgSO$_4$, filtered and concentrated in vacuo. The residue obtained was purified using flash chromatography on silica to provide compound 70F as a yellow oil.

Step F—Preparation of Compound 70G

To the product of Step E (1.34 g, 6.35 mmol) in THF (10 mL) was added NaBH$_4$ (0.480 g, 12.6 mmol). The reaction mixture was heated to 60° C. and allowed to stir at this temperature for 20 hours, then concentrated in vacuo. The residue obtained was partitioned with CH$_2$Cl$_2$ and water. The CH$_2$Cl$_2$ layer was washed with brine, dried over MgSO$_4$ and concentrated in vacuo to provide compound 70G as a mixture of exo- and endo-isomers, as a colorless oil.

Example 71

Preparation of Compounds 71A-71C

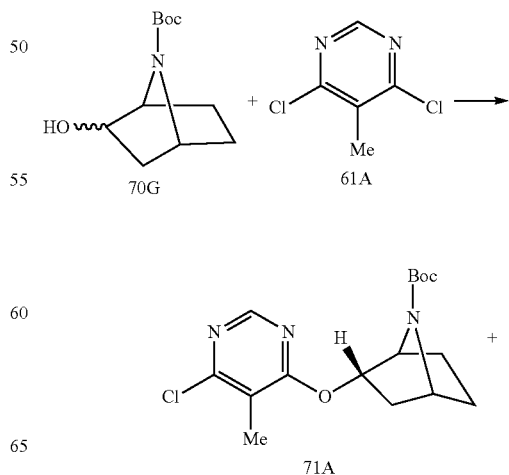

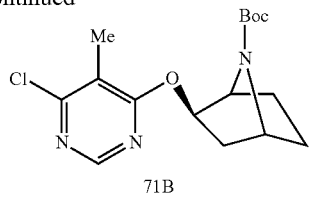

71B

Using the method described in Example 61, Compounds 70G and 61A were reacted to provide a mixture of compounds 71A and 71B. The mixture was purified using PLC to provide each the purified exo-isomer and the purified endo-isomer.

Using the above method, 4,6-dichloro-5-methoxypyrimidine was converted to compound 71C.

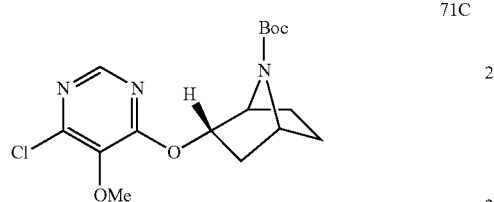

71C

Example 72

Preparation of Compound 72B

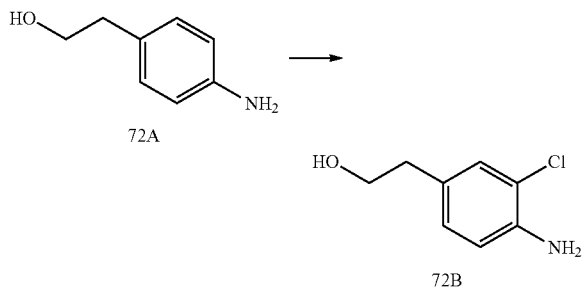

To 2-(4-aminophenyl)ethanol (72A, 1.00 g, 7.2 mmol) in DMF (10 mL) was slowly added N-chlorosuccinimide (0.973 g, 7.3 mmol) in DMF (3 mL). The reaction was allowed to stir for 24 hours, then was concentrated in vacuo and purified using flash chromatography on silica, followed by PLC to provide compound 72B as a brown oil.

Example 73

Preparation of Compound 73B

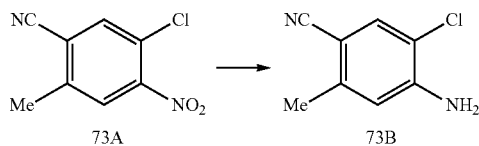 [SMILES: Cc1cc([N+](=O)[O-])c(Cl)cc1C#N ; Cc1cc(N)c(Cl)cc1C#N]

3-Chloro-6-methyl-4-nitrobenzonitrile (73A, 0.45 g, 2.3 mmol) and 10% Pd/C (0.10 g) were combined in MeOH (4 mL) and AcOH (3 mL). The mixture was hydrogenated at atmospheric pressure for 4 hours, filtered, concentrated, and purified using PLC to provide compound 73B as a yellow solid.

Example 74

Preparation of Compound 212

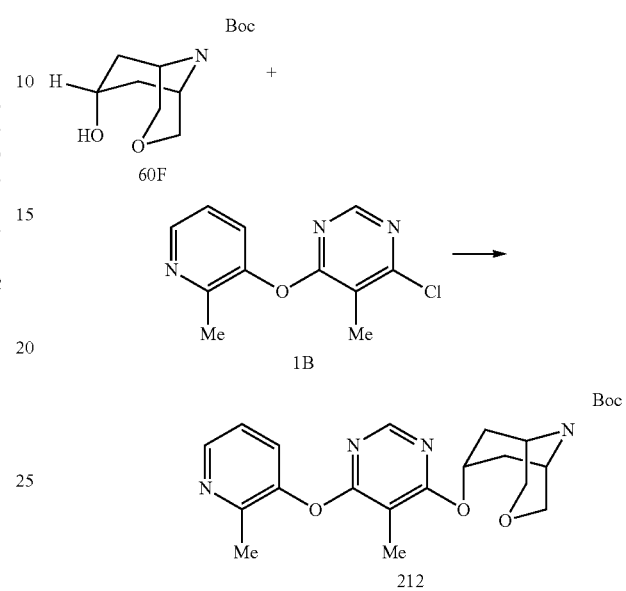

Compound 60F (0.113 g, 0.47 mmol) was dissolved in DMF (2.0 mL). 4-Chloro-5-methyl-6-(2-methyl-3-pyridinyloxy)pyrimidine (1B, 0.100 g, 0.43 mmol) and NaI-1 (60% in oil, 0.020 g, 0.50 mmol) were added and the resulting reaction was heated to 50° C. and allowed to stir at this temperature for 5 hours. The reaction mixture was cooled to room temperature, concentrated in vacuo and the residue obtained was purified using PLC to provide compound 212 as a yellow solid.

Example 75

Preparation of Compounds 213 and 214

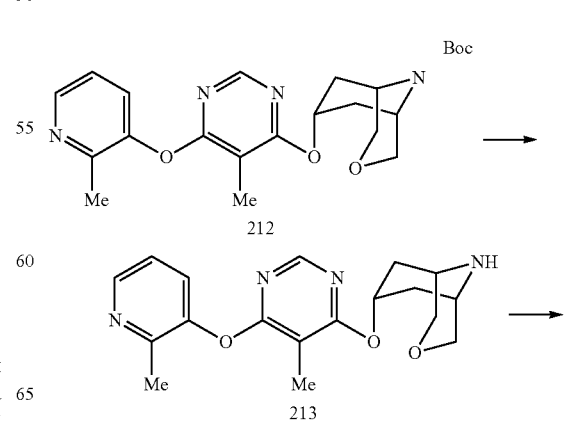

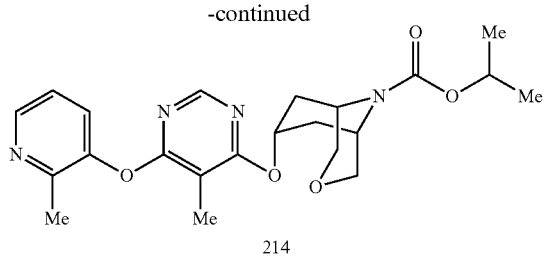

214

Step A—Synthesis of Compound 213

Compound 212 (0.0.024 g, 0.046 mmol) was treated with 4.0M HCl/dioxane (2.0 mL), stirred for 2 hours and concentrated in vacuo to provide compound 213.

Step B—Synthesis of Compound 214

To a solution of compound 213 (obtained from Step A) in CH$_2$Cl$_2$ (2.0 nit) was added Et$_3$N (0.019 mL, 0.14 mmol) and isopropyl chloroformate (1.0M in toluene, 0.069 ml, 0.069 mmol). After stirring 2 hours, the reaction mixture was concentrated in vacuo and the residue obtained was purified using PLC to provide compound 214 as a yellow solid.

Example 76

Preparation of Compound 215

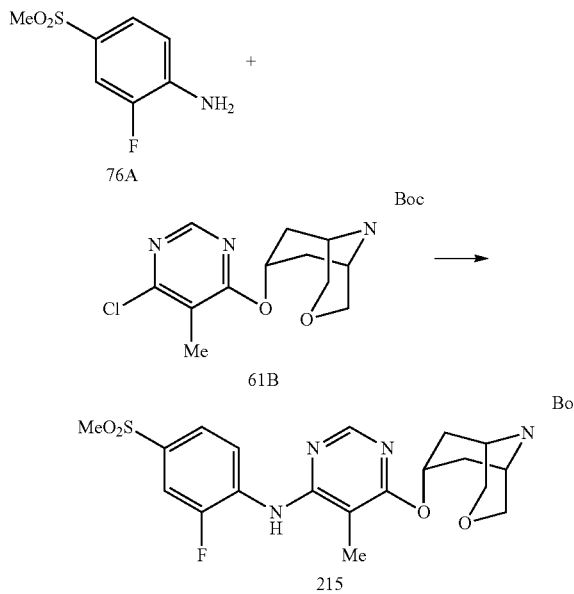

Compound 61B (0.40 g, 0.11 mmol), 2-fluoro-4-(mothylsulfonyl)aniline (76A, 0.27 g, 0.14 mmol), Pd(OAc)$_2$, (0.003 g, 0.01 mmol), NaO-tBu (0.15 g, 0.15 mmol), and X-phos (0.005 g, 0.01 mmol) were taken up in dioxane (1.5 mL). The mixture was heated in a sealed tube in a microwave reactor at 130° C. for 1 hour, then cooled to room temperature and concentrated in racuo. The resulting residue was purified using PLC to provide compound 215 as a yellow solid.

Using this method and substituting the appropriate anilines for compound 76A, the following compounds of the present invention were made:

| Cpd. No. | Structure |
|---|---|
| 216 | 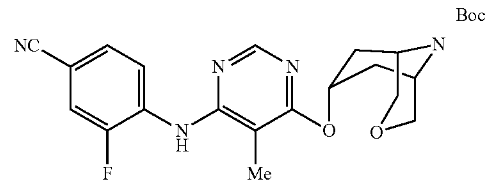 [SMILES: Cc1c(Nc2ccc(C#N)cc2F)ncnc1OC1CC2COCC(C1)N2] |
| 217 | 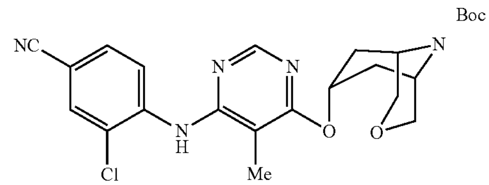 [SMILES: Cc1c(Nc2ccc(C#N)cc2Cl)ncnc1OC1CC2COCC(C1)N2] |
| 218 | 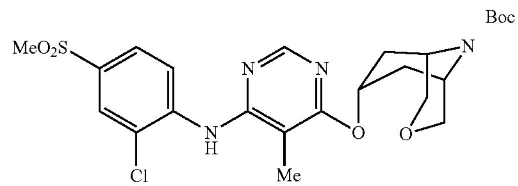 [SMILES: Cc1c(Nc2ccc(S(C)(=O)=O)cc2Cl)ncnc1OC1CC2COCC(C1)N2] |
| 219 | 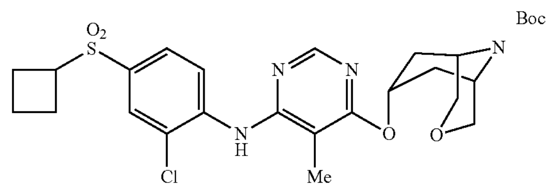 [SMILES: Cc1c(Nc2ccc(S(=O)(=O)C3CCC3)cc2Cl)ncnc1OC1CC2COCC(C1)N2] |
| 220 | 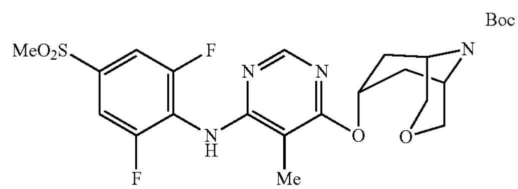 [SMILES: Cc1c(Nc2c(F)cc(S(C)(=O)=O)cc2F)ncnc1OC1CC2COCC(C1)N2] |
| 221 | 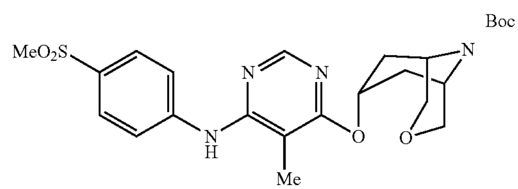 [SMILES: Cc1c(Nc2ccc(S(C)(=O)=O)cc2)ncnc1OC1CC2COCC(C1)N2] |
| 222 | 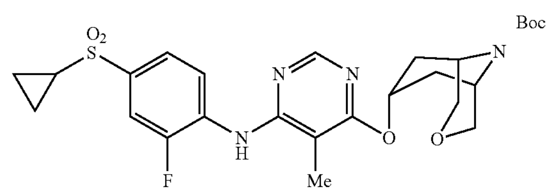 [SMILES: Cc1c(Nc2ccc(S(=O)(=O)C3CC3)cc2F)ncnc1OC1CC2COCC(C1)N2] |
| 223 | 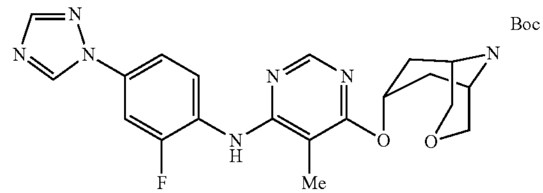 [SMILES: Cc1c(Nc2ccc(-n3cncn3)cc2F)ncnc1OC1CC2COCC(C1)N2] |

267
-continued
| Cpd. No. | Structure |
|---|---|
| 224 | 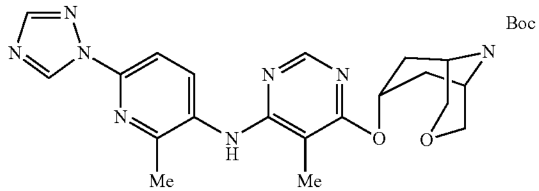 [SMILES: Cc1nc(-n2cncn2)ccc1Nc1ncnc(OC2CC3COCC(C2)N3)c1C] |
| 225 | 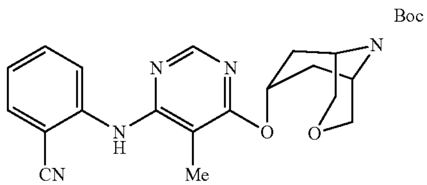 [SMILES: Cc1c(Nc2ccccc2C#N)ncnc1OC1CC2COCC(C1)N2] |
| 226 | 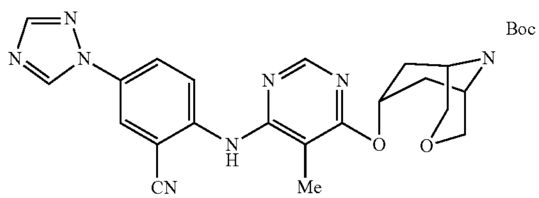 [SMILES: Cc1c(Nc2ccc(-n3cncn3)cc2C#N)ncnc1OC1CC2COCC(C1)N2] |
| 227 | 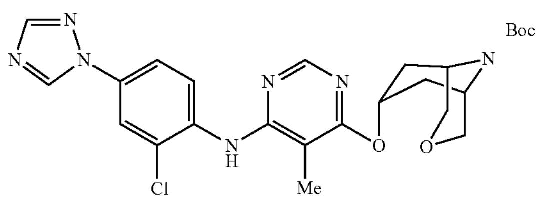 [SMILES: Cc1c(Nc2ccc(-n3cncn3)cc2Cl)ncnc1OC1CC2COCC(C1)N2] |
| 228 | 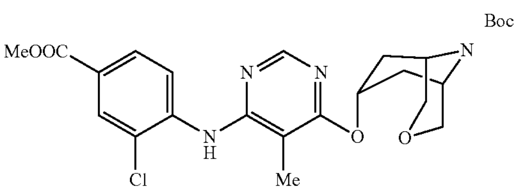 [SMILES: COC(=O)c1ccc(Nc2ncnc(OC3CC4COCC(C3)N4)c2C)c(Cl)c1] |
268
-continued
| Cpd. No. | Structure |
|---|---|
| 229 | 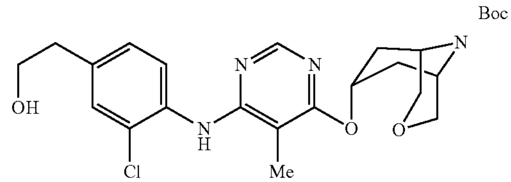 [SMILES: Cc1c(Nc2ccc(CCO)cc2Cl)ncnc1OC1CC2COCC(C1)N2] |
Example 77
Preparation of Compound 230
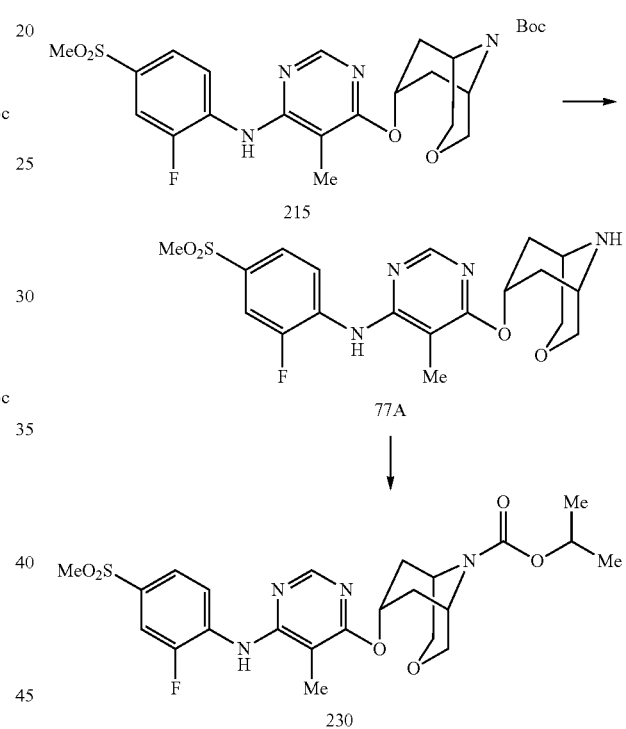
Treatment of compound 215 using the method described in Example 75 provided compound 230 as a yellow solid.
Using this method and substituting the appropriate Boc derivatives for compound 215, the following compounds of the present invention were made:
| Cpd. No. | Structure |
|---|---|
| 231 | 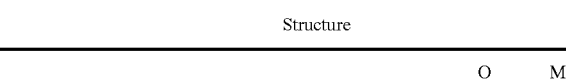 |

-continued
| Cpd. No. | Structure |
|---|---|
| 232 | 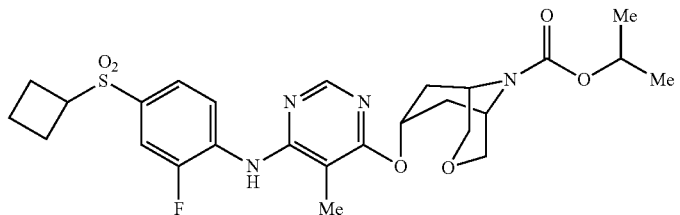 [SMILES: Cc1c(Nc2ccc(S(=O)(=O)C3CCC3)cc2F)ncnc1OC1CC2COCC(C1)N2C(=O)OC(C)C] |
| 233 | 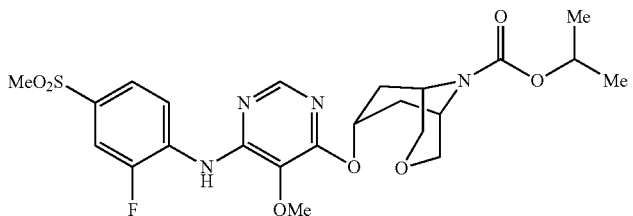 [SMILES: COc1c(Nc2ccc(S(C)(=O)=O)cc2F)ncnc1OC1CC2COCC(C1)N2C(=O)OC(C)C] |
| 234 | 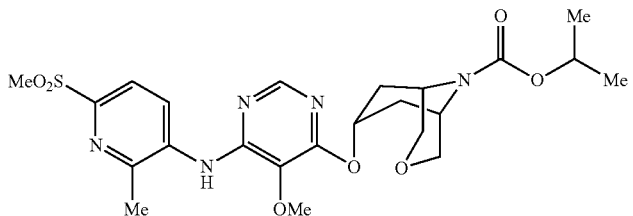 [SMILES: COc1c(Nc2ccc(S(C)(=O)=O)nc2C)ncnc1OC1CC2COCC(C1)N2C(=O)OC(C)C] |
| 235 | 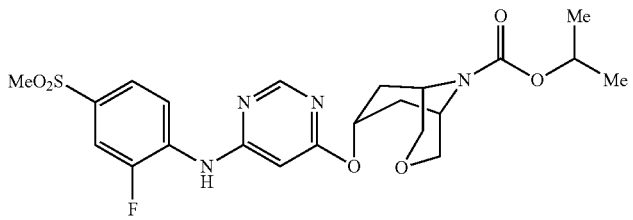 [SMILES: CC(C)OC(=O)N1C2COCC1CC(Oc1cc(Nc3ccc(S(C)(=O)=O)cc3F)ncn1)C2] |
| 236 | 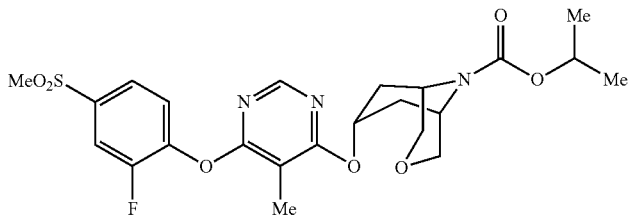 [SMILES: Cc1c(Oc2ccc(S(C)(=O)=O)cc2F)ncnc1OC1CC2COCC(C1)N2C(=O)OC(C)C] |
| 237 | 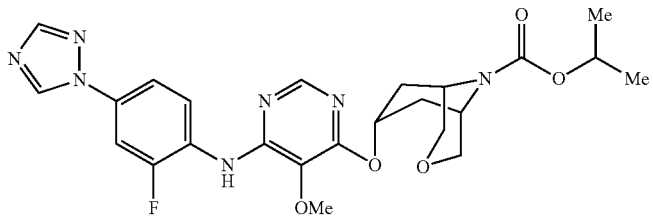 [SMILES: COc1c(Nc2ccc(-n3cncn3)cc2F)ncnc1OC1CC2COCC(C1)N2C(=O)OC(C)C] |

-continued
| Cpd. No. | Structure |
|---|---|
| 238 | 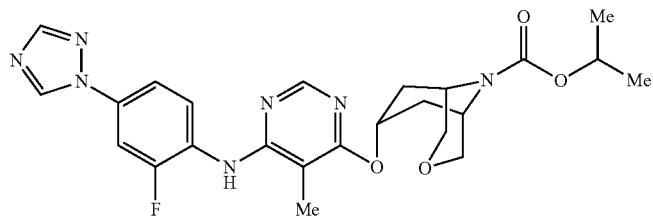 |
| 239 | 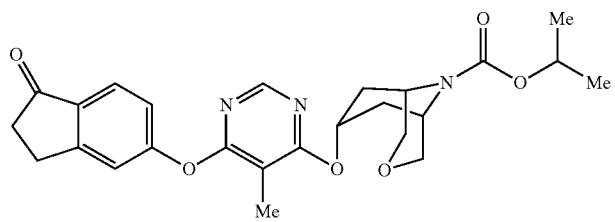 [SMILES: Cc1c(Oc2ccc3c(c2)CCC3=O)ncnc1OC1CC2COCC(C1)N2C(=O)OC(C)C] |
| 240 | 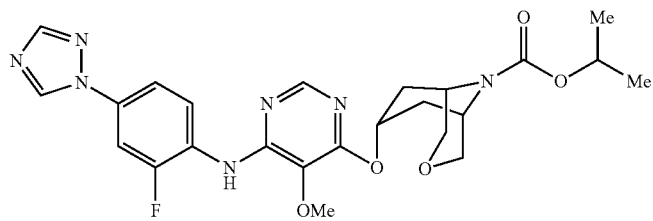 [SMILES: COc1c(Nc2ccc(-n3cncn3)cc2F)ncnc1OC1CC2COCC(C1)N2C(=O)OC(C)C] |
| 241 | 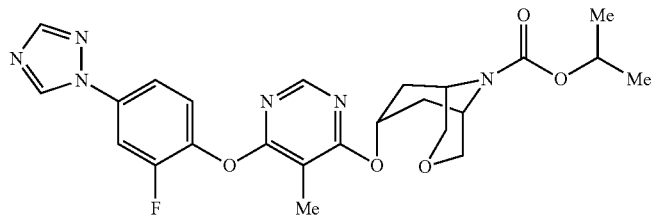 [SMILES: Cc1c(Oc2ccc(-n3cncn3)cc2F)ncnc1OC1CC2COCC(C1)N2C(=O)OC(C)C] |
| 242 | 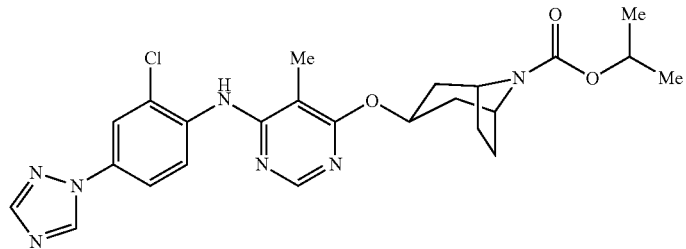 [SMILES: Cc1c(Nc2ccc(-n3cncn3)cc2Cl)ncnc1OC1CC2CCC(C1)N2C(=O)OC(C)C] |
| 243 | 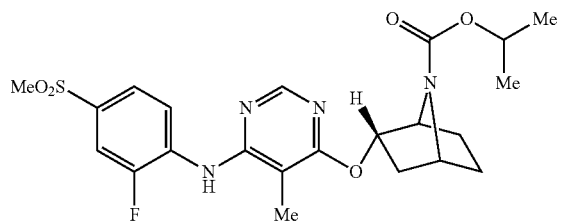 [SMILES: Cc1c(Nc2ccc(S(C)(=O)=O)cc2F)ncnc1O[C@H]1CC2CCC1N2C(=O)OC(C)C] |

-continued
| Cpd. No. | Structure |
|---|---|
| 244 | 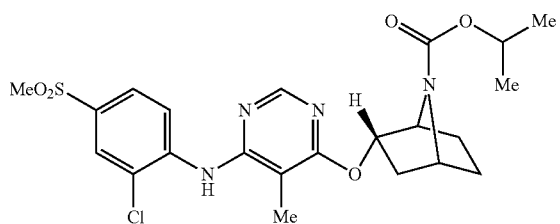 [SMILES: Cc1c(Nc2ccc(S(C)(=O)=O)cc2Cl)ncnc1O[C@H]1CC2CCC1N2C(=O)OC(C)C] |
| 245 | 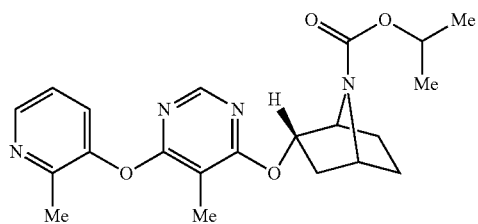 [SMILES: Cc1ncccc1Oc1ncnc(O[C@H]2CC3CCC2N3C(=O)OC(C)C)c1C] |
| 246 | 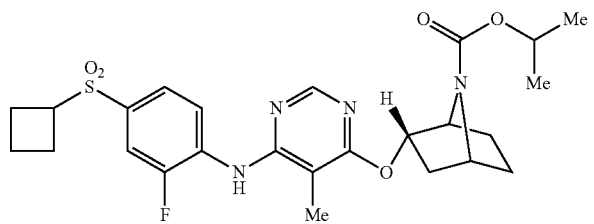 [SMILES: Cc1c(Nc2ccc(S(=O)(=O)C3CCC3)cc2F)ncnc1O[C@H]1CC2CCC1N2C(=O)OC(C)C] |
| 247 | 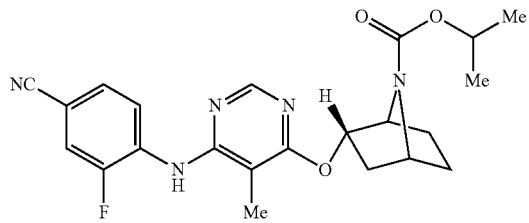 [SMILES: Cc1c(Nc2ccc(C#N)cc2F)ncnc1O[C@H]1CC2CCC1N2C(=O)OC(C)C] |
| 248 | 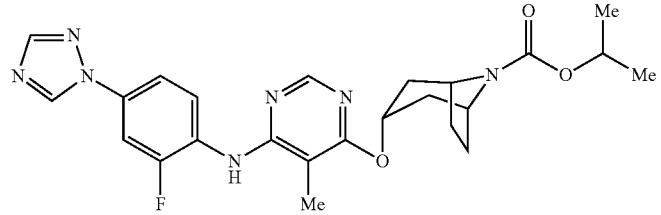 [SMILES: Cc1c(Nc2ccc(-n3cncn3)cc2F)ncnc1OC1CC2CCC(C1)N2C(=O)OC(C)C] |
| 249 | 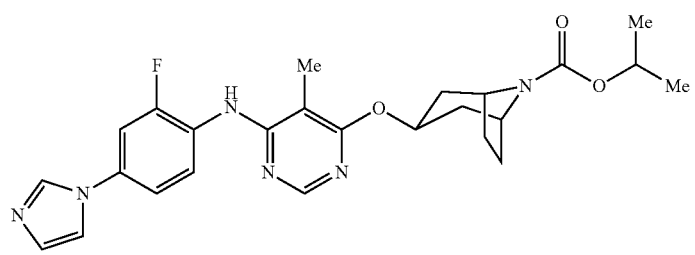 [SMILES: Cc1c(Nc2ccc(-n3ccnc3)cc2F)ncnc1OC1CC2CCC(C1)N2C(=O)OC(C)C] |

| Cpd. No. | Structure |
|---|---|
| 250 | *[structure: pyrazolyl-fluorophenyl-amino-methylpyrimidinyl-oxy-bicyclic-N-Boc-like with isopropyl carbamate]* |

Example 78

Preparation of Compound 251

*[Scheme: 2-fluoro-4-(methylsulfonyl)phenol (78A) + compound 61B → compound 251]*

78A: MeO₂S-phenyl-OH with F

61B: Cl-pyrimidine-Me with O-bicyclic-N-Boc

251: MeO₂S-fluorophenyl-O-pyrimidine(Me)-O-bicyclic-N-Boc

Compound 61B (0.40 g, 0.11 mmol), 2-fluoro-4-(methylsulfonyl)phenol (78A, 0.25 g, 0.13 mmol) and K₂CO₃, (0.022 g, 0.16 mmol) were taken up in DMF (1.0 mL). The reaction was heated in a sealed tube in a microwave reactor at 180° C. for 1 hour, then cooled to room temperature and concentrated in vacuo. The resulting residue was purified using PLC to provide compound 251 as a yellow solid.

Using this method, and substituting the appropriate phenols or compound 78A, the following compounds of the present invention were made:

| Cpd. No. | Structure |
|---|---|
| 252 | *[indanone-O-pyrimidine(Me)-O-bicyclic-N-Boc]* |
| 253 | *[triazolyl-fluorophenyl-O-pyrimidine(Me)-O-bicyclic-N-Boc]* |

Example 79

Preparation of Compounds 254 and 255

76A: MeO₂S-fluorophenyl-NH₂

64A: Cl-pyrimidine(Me)-O-bicyclic-N-Boc

254: MeO₂S-fluorophenyl-NH-pyrimidine(Me)-O-bicyclic-N-Boc

Using the method described in Example 76, compounds 76A and 64A were coupled to provide compound 254.

Using this method and substituting the appropriate aniline derivative for compound 76A, the following compound of the present invention was made:

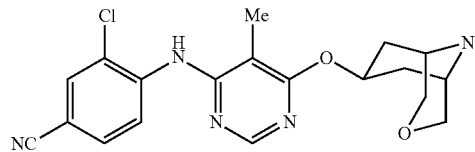

Example 80

Preparation of Compound 256

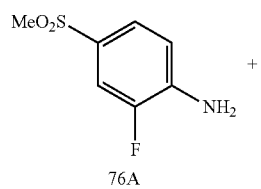

76A

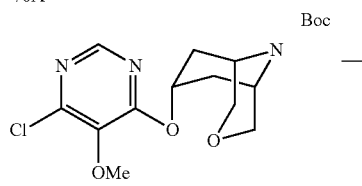

66B

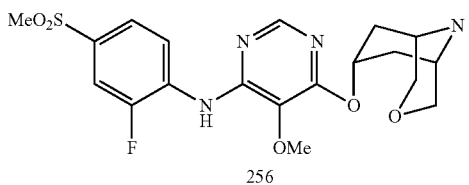

256

Using the method described in Example 76 compounds 76A and 66B were coupled to provide compound 256.

Using this method and substituting the appropriate aniline derivative for compound 76A, the following compounds of the present invention were made:

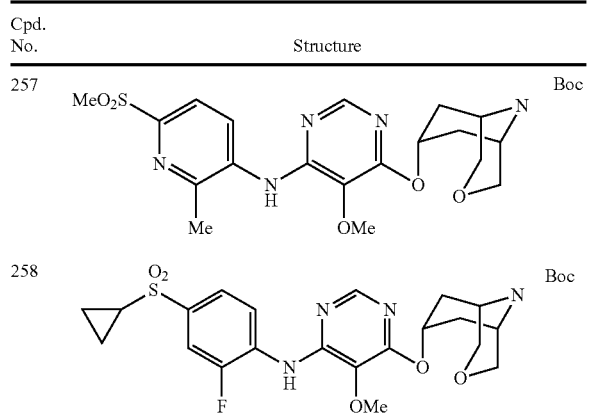

| Cpd. No. | Structure |
|---|---|
| 257 | 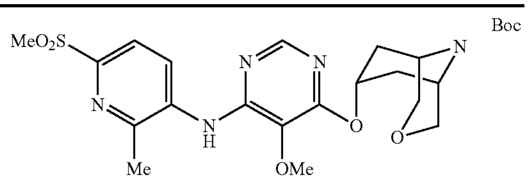 |
| 258 | 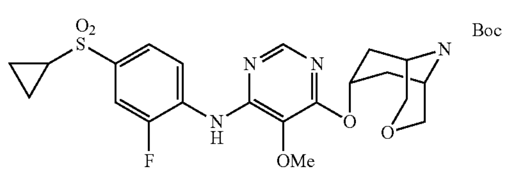 [SMILES: COc1c(Nc2ccc(S(=O)(=O)C3CC3)cc2F)ncnc1OC1CC2COCC(C1)N2 ; "Boc"] |
| 259 | 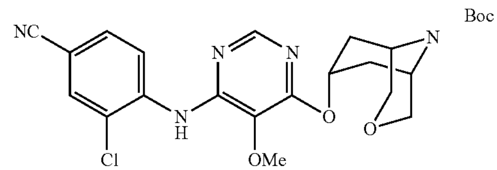 [SMILES: COc1c(Nc2ccc(C#N)cc2Cl)ncnc1OC1CC2COCC(C1)N2 ; "Boc"] |
| 260 | 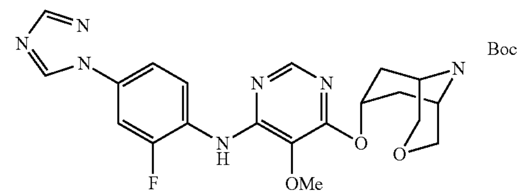 [SMILES: COc1c(Nc2ccc(N/C=N\C=N)cc2F)ncnc1OC1CC2COCC(C1)N2 ; "Boc"] |

Example 81

Preparation of Compounds 261 and 262

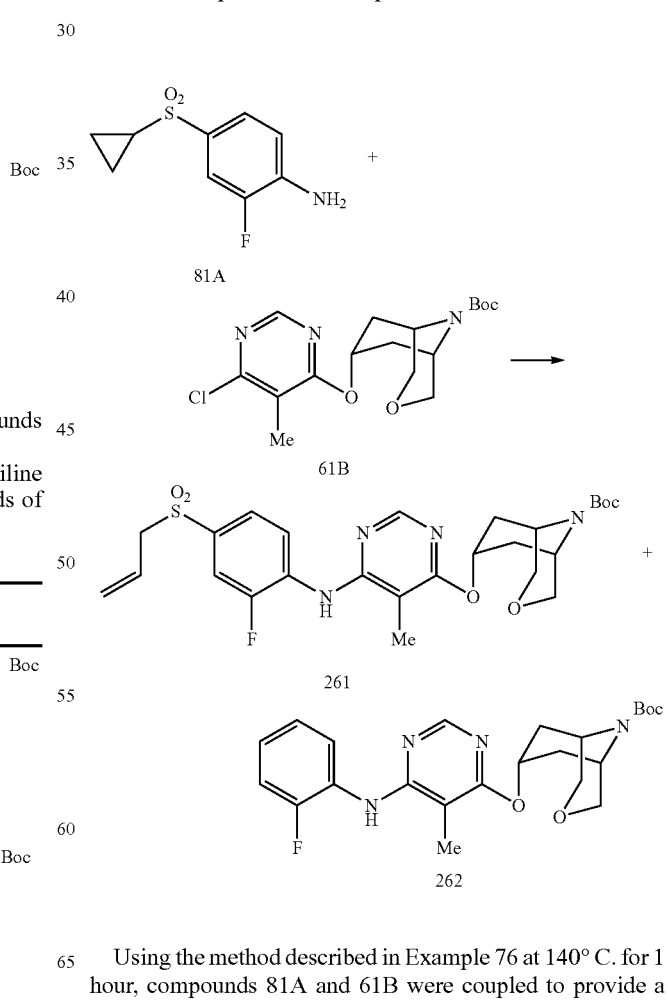

81A

61B

261

262

Using the method described in Example 76 at 140° C. for 1 hour, compounds 81A and 61B were coupled to provide a mixture of compounds 261 and 262.

Example 82

Preparation of Compound 263

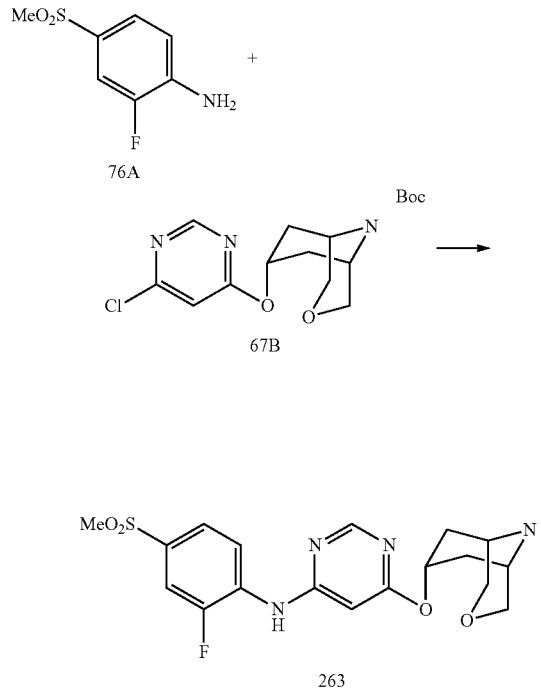

Using the method described in Example 76, compounds 76A and 67B were coupled to provide compound 263 as a yellow solid.

Example 83

Preparation of Compound 264

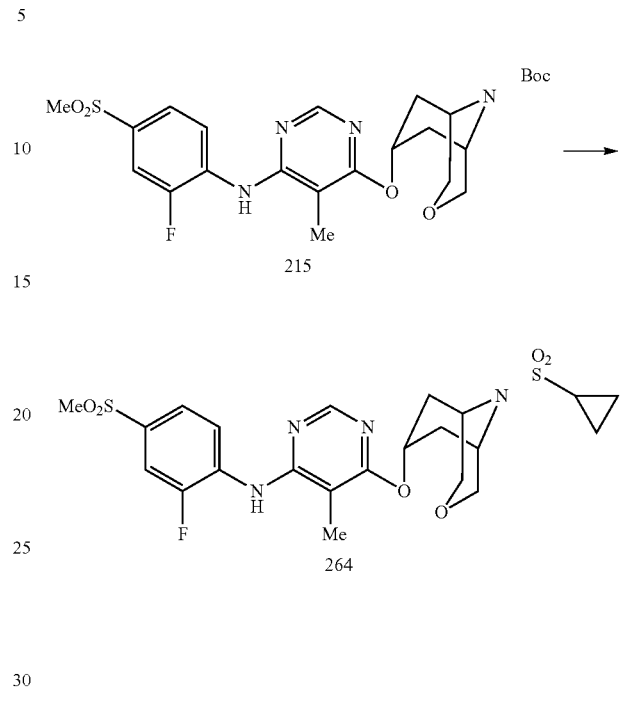

Compound 215 was reacted using the method described in Example 75, substituting cyclopropanesulfonyl chloride for isopropyl chloroformate, to provide compound 264 as a yellow solid.

Using this method and substituting the appropriate Boc derivative for compound 215, the following compounds of the present invention were made:

| Cpd. No. | Structure |
|---|---|
| 265 | 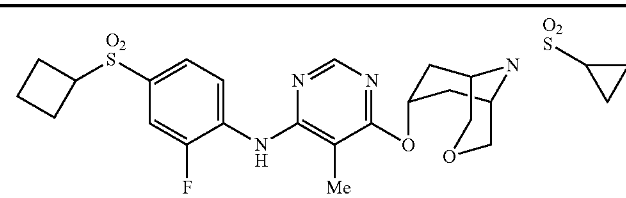 |
| 266 | 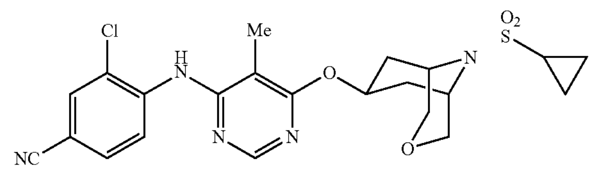 |
| 267 | 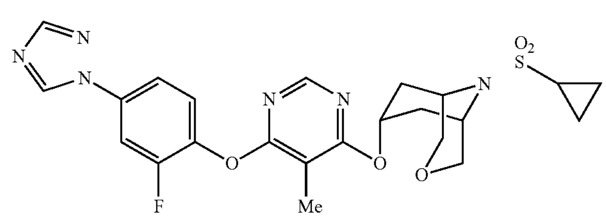 |

-continued

| Cpd. No. | Structure |
| --- | --- |
| 268 | 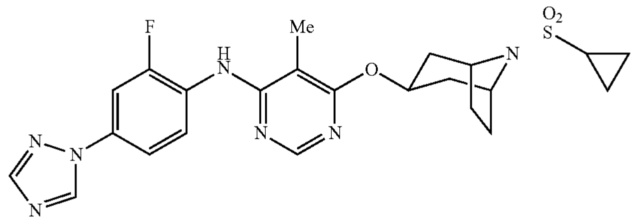 |
| 269 | 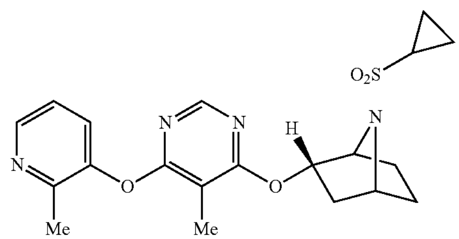 |
| 270 | 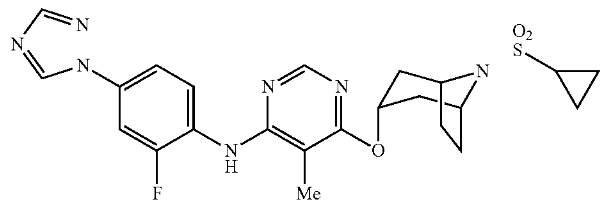 |
| 271 | 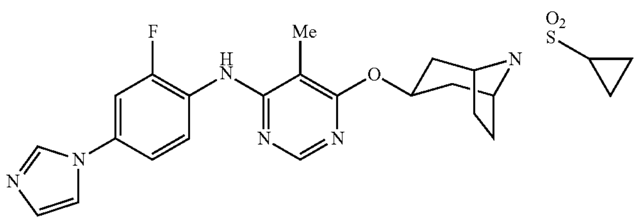 |
| 272 | 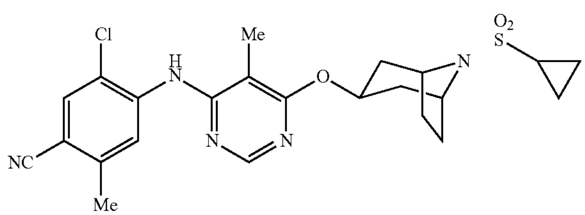 |
| 273 | 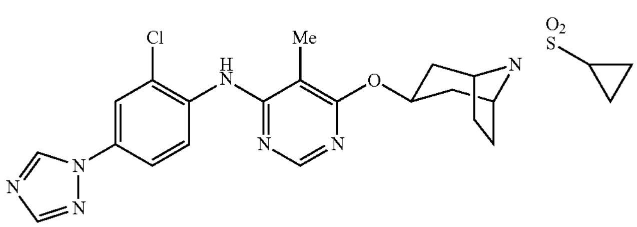 |
| 274 | 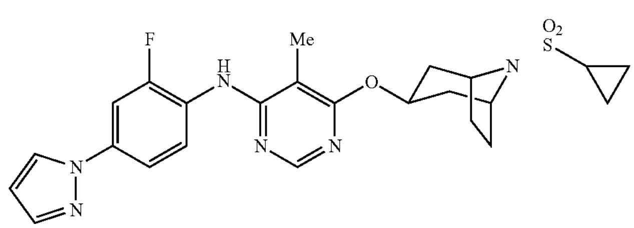 |

Example 84
Preparation of Compound 275

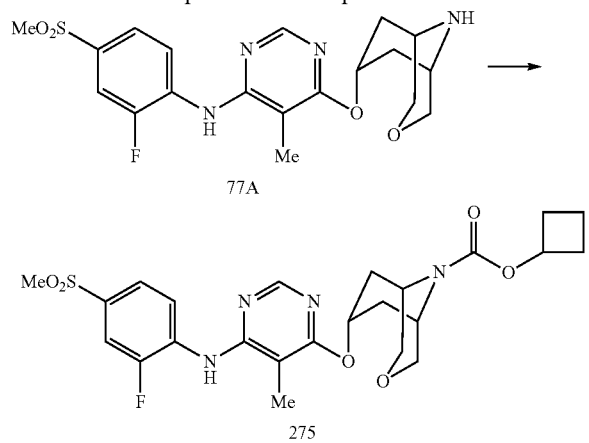

To cyclobutanol (0.013 g, 0.15 mmol) in CH$_2$Cl$_2$ (1.5 mL) was added Et$_3$N (0.024 mL, 0.17 mmol), followed by phosgene toluene solution (20%, 0.075 mL, 0.14 mmol). After 1 hour, compound 77A (0.030 g, 0.71 mmol) was added, followed by Et$_3$N (0.020 mL, 0.14 mmol). After being allowed to stir for an additional 2 hours, the reaction was concentrated in vacuo and the resulting residue was purified using PLC to provide compound 275 as a white solid.

Using this method and substituting the appropriate amine derivative for compound 77A, the following compounds of the present invention were made:

| Cpd. No. | Structure |
|---|---|
| 276 | 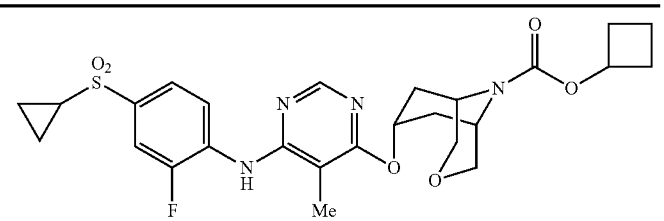 |
| 277 | 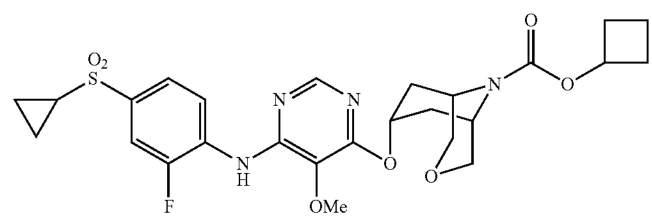 [SMILES: COc1c(Nc2ccc(S(=O)(=O)C3CC3)cc2F)ncnc1OC1CC2COCC(C1)N2C(=O)OC1CCC1] |
| 278 | 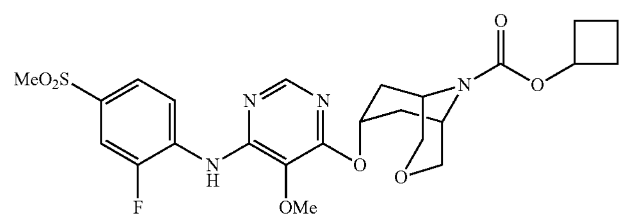 [SMILES: COc1c(Nc2ccc(S(C)(=O)=O)cc2F)ncnc1OC1CC2COCC(C1)N2C(=O)OC1CCC1] |
| 279 | 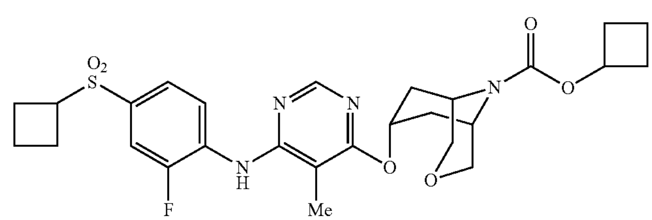 [SMILES: Cc1c(Nc2ccc(S(=O)(=O)C3CCC3)cc2F)ncnc1OC1CC2COCC(C1)N2C(=O)OC1CCC1] |
| 280 | 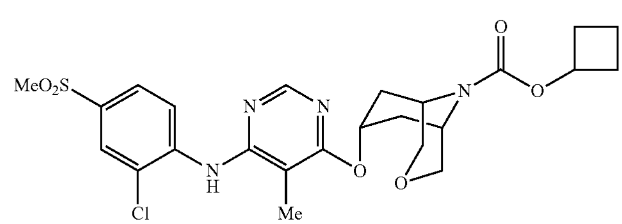 [SMILES: Cc1c(Nc2ccc(S(C)(=O)=O)cc2Cl)ncnc1OC1CC2COCC(C1)N2C(=O)OC1CCC1] |

-continued

| Cpd. No. | Structure |
|---|---|
| 281 | 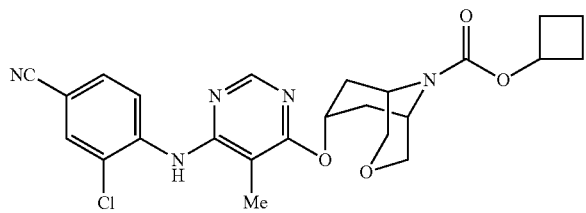 [SMILES: Cc1c(Nc2ccc(C#N)cc2Cl)ncnc1OC1CC2COCC(C1)N2C(=O)OC1CCC1] |
| 282 | 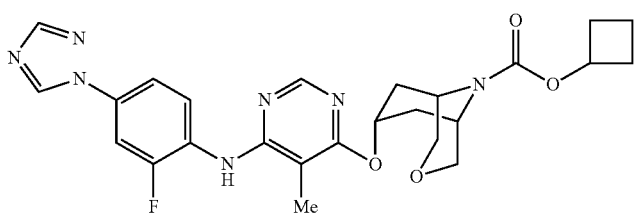 [SMILES: Cc1c(Nc2ccc(N/C=N\C=N)cc2F)ncnc1OC1CC2COCC(C1)N2C(=O)OC1CCC1] |
| 283 | 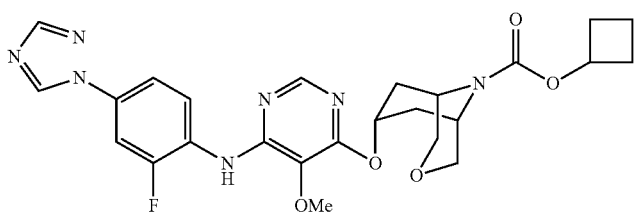 [SMILES: COc1c(Nc2ccc(N/C=N\C=N)cc2F)ncnc1OC1CC2COCC(C1)N2C(=O)OC1CCC1] |

Example 85

Preparation of Compound 284

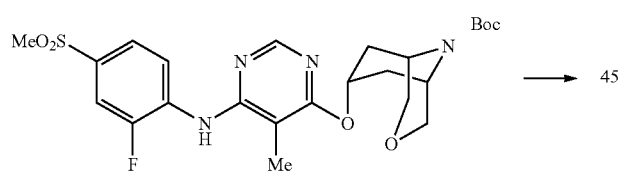

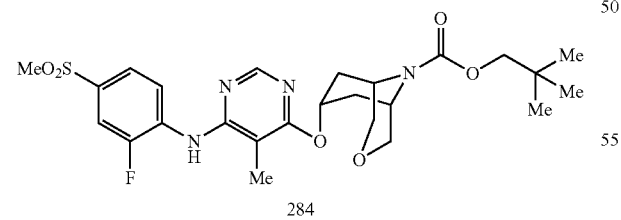

Compound 215 was treated using the method described in Example 75 and substituting neopentyl chloroformate for isopropyl chloroformate, to provide compound 284 as a yellow solid.

Using this method and substituting the appropriate Boc derivative fir compound 215, the following compounds of the present invention were made:

| Cpd. No. | Structure |
|---|---|
| 285 | 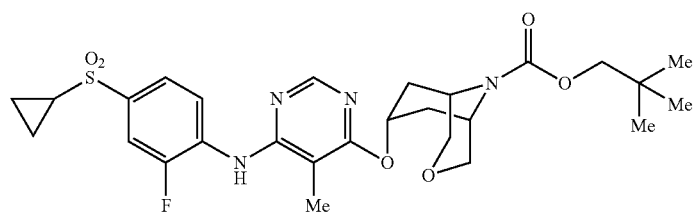 [SMILES: Cc1c(Nc2ccc(S(=O)(=O)C3CC3)cc2F)ncnc1OC1CC2COCC(C1)N2C(=O)OCC(C)(C)C] |
| 286 | 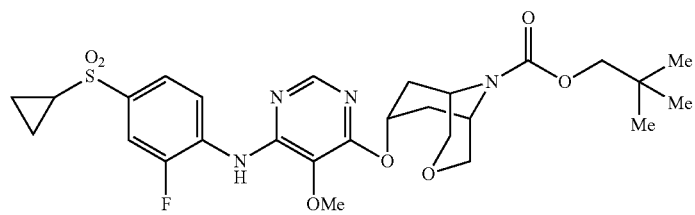 [SMILES: COc1c(Nc2ccc(S(=O)(=O)C3CC3)cc2F)ncnc1OC1CC2COCC(C1)N2C(=O)OCC(C)(C)C] |
| 287 | 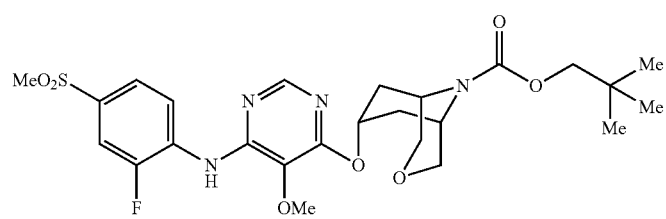 [SMILES: COc1c(Nc2ccc(S(C)(=O)=O)cc2F)ncnc1OC1CC2COCC(C1)N2C(=O)OCC(C)(C)C] |
| 288 | 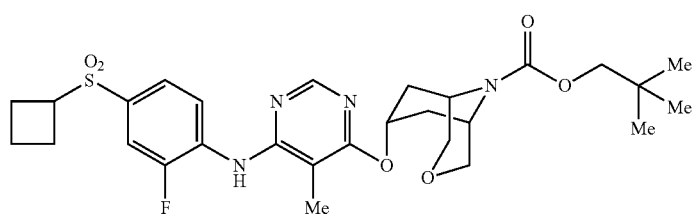 [SMILES: Cc1c(Nc2ccc(S(=O)(=O)C3CCC3)cc2F)ncnc1OC1CC2COCC(C1)N2C(=O)OCC(C)(C)C] |
| 289 | 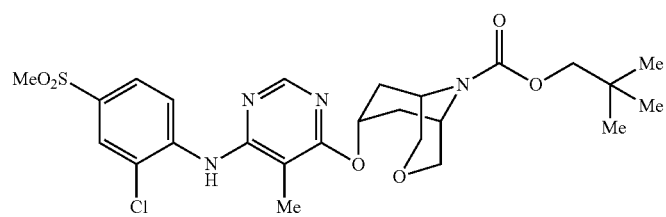 [SMILES: Cc1c(Nc2ccc(S(C)(=O)=O)cc2Cl)ncnc1OC1CC2COCC(C1)N2C(=O)OCC(C)(C)C] |
| 290 | 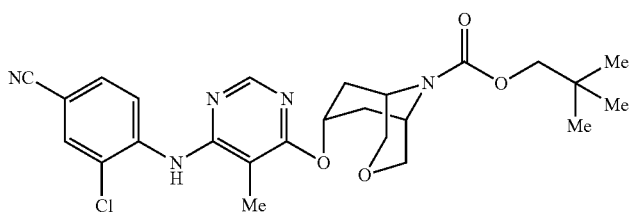 [SMILES: Cc1c(Nc2ccc(C#N)cc2Cl)ncnc1OC1CC2COCC(C1)N2C(=O)OCC(C)(C)C] |
| 291 | 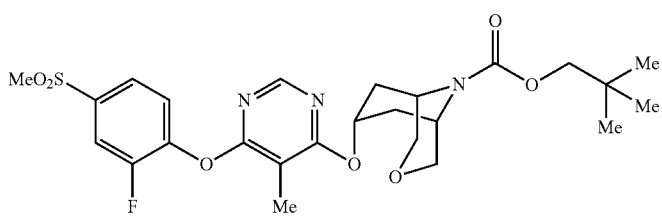 [SMILES: Cc1c(Oc2ccc(S(C)(=O)=O)cc2F)ncnc1OC1CC2COCC(C1)N2C(=O)OCC(C)(C)C] |

| Cpd. No. | Structure |
|---|---|
| 292 | 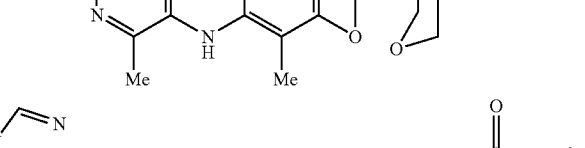 |
| 293 | 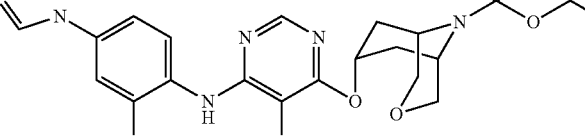 |
| 294 | 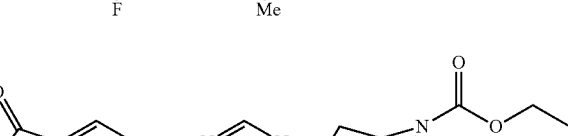 |
| 295 | 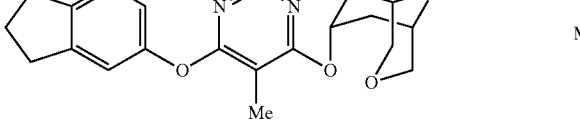 |
| 296 | 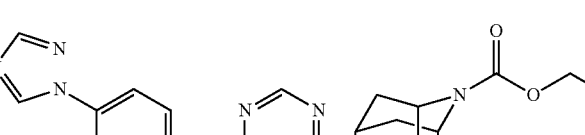 |
| 297 | 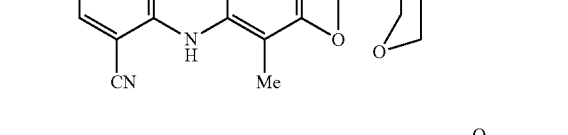 |
| 298 | 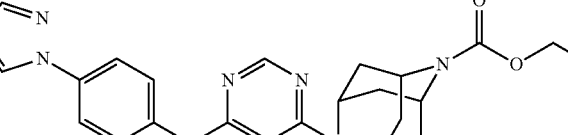 |

| Cpd. No. | Structure |
|---|---|
| 299 | 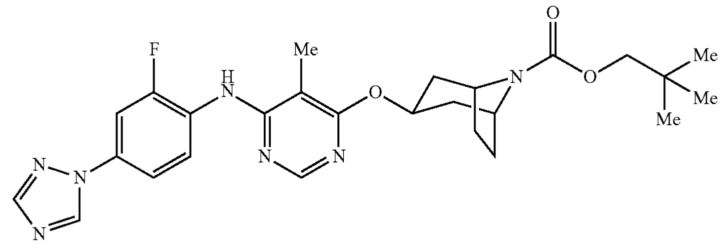 [SMILES: Cc1c(Nc2ccc(-n3cncn3)cc2F)ncnc1OC1CC2CCC(C1)N2C(=O)OCC(C)(C)C] |
| 300 | 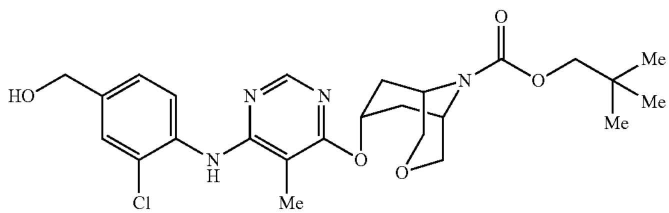 [SMILES: Cc1c(Nc2ccc(CO)cc2Cl)ncnc1OC1CC2COCC(C1)N2C(=O)OCC(C)(C)C] |
| 301 | 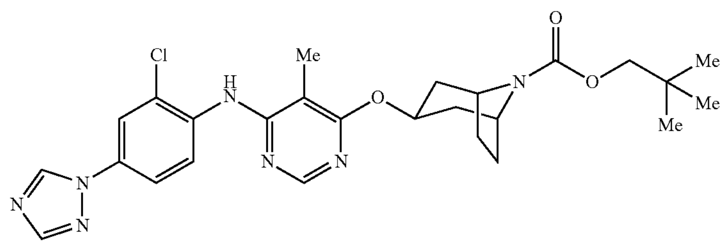 [SMILES: Cc1c(Nc2ccc(-n3cncn3)cc2Cl)ncnc1OC1CC2CCC(C1)N2C(=O)OCC(C)(C)C] |
| 302 | 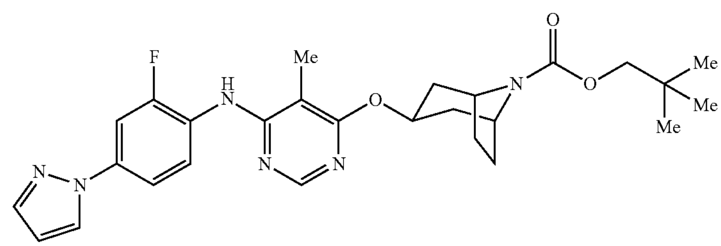 [SMILES: Cc1c(Nc2ccc(-n3cccn3)cc2F)ncnc1OC1CC2CCC(C1)N2C(=O)OCC(C)(C)C] |

Example 86

Preparation of Compound 303

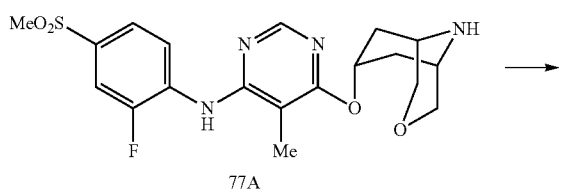

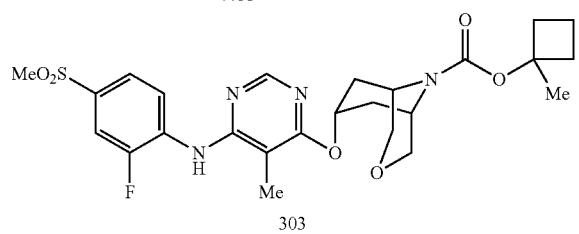

To cyclobutanone (0.800 g, 11.4 mmol) in ether (5 mL) was added dropwise MeMgBr (3.0M in ether, 5.7 mL, 17.1 mmol). After 0.5 hours, the reaction was quenched with saturated NH$_4$Cl, extracted with ether, dried over MgSO$_4$, filtered and concentrated in vacuo. The resulting residue was dissolved in CH$_2$Cl$_2$ (30 mL) and treated with disuccinimidyl carbonate (5.85 g, 22.9 mmol) and Et$_3$N (4.77 mL, 34 mmol). After stirring for 24 hours, the mixture was partitioned with EtOAc and saturated NaHCO$_3$, dried over MgSO$_4$, and concentrated in racuo to provide 1-methylcyclobutyl hydroxysuccinimidyl carbonate (0.048 g, 0.21 mmol) as a white solid intermediate, which was combined with compound 77A (0.050 g, 0.12 mmol) and Et$_3$N (0.059 mL, 0.43 mmol) in THF (1.0 mL). After stirring for 1 hour, the reaction was concentrated in vacuo and purified using PLC to provide compound 303 as a white solid.

Using this method and substituting the appropriate amine derivative for compound 77A, the following compounds of the present invention were made:

| Cpd. No. | Structure |
|---|---|
| 304 | 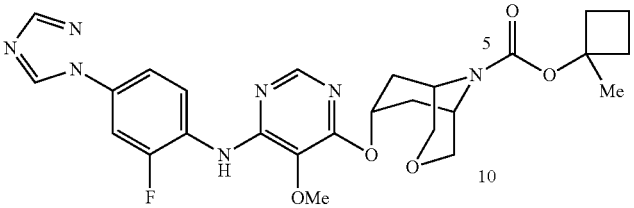 |
| 305 | 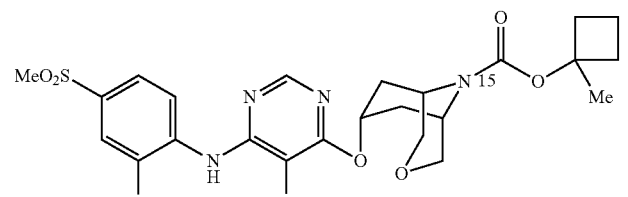 |
| 306 | 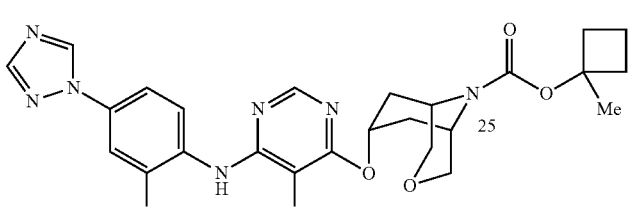 |
| 307 | 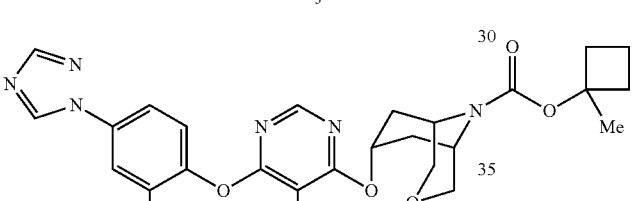 |
| 308 | 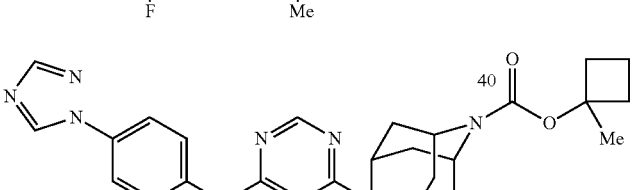 |
| 309 | 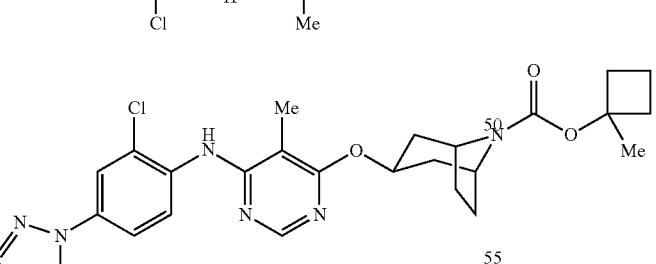 |
| 310 | 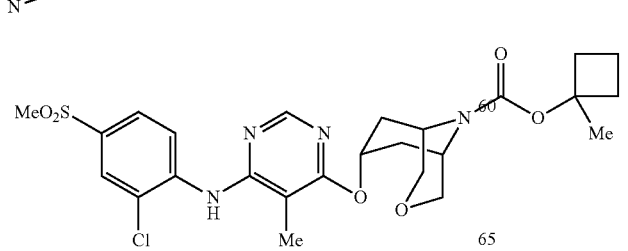 |

Example 87

Preparation of Compound 311

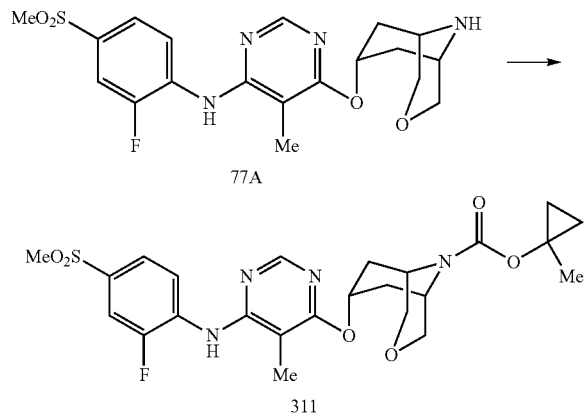

To methyl acetate (0.600 g, 8.1 mmol) and Ti(O-iPr)$_4$ (0.15 g, 0.43 mmol) in ether (30 mL) was added dropwise EtMgBr (3.0M in ether, 6.0 mL, 18 mmol) over a hour period. After stirring for 20 minutes, the mixture was poured onto 10% H$_2$SO$_4$ (80 mL) and extracted with ether. The ether was dried over MgSO$_4$ and concentrated in vacuo (0° C.) to one-quarter volume. The resulting solution was diluted with MeCN (20 mL) and treated with disuccinimidyl carbonate (4.15 g, 16.2 mmol). After stirring for an additional 20 minutes. Et$_3$N (3.4 mL, 25 mmol) was added. After stilling for an additional 24 hours, the mixture was partitioned with EtOAc and saturated NaHCO$_3$, dried over MgSO$_4$, filtered and concentrated in vacuo to provide 1-methylcyclopropyl hydroxysuccinimidyl carbonate as a yellow solid (0.191 g, 0.90 mmol) which was combined with compound 77A (0.190 g, 0.45 mmol) and Et$_3$N (0.25 mL, 1.8 mmol) in CH$_2$Cl, (5 mL). After stirring for 1 h, the reaction was concentrated and purified using PLC to provide compound 311 as a yellow solid.

Using this method and substituting the appropriate amine derivative for compound 77A, the following compounds of the present invention were made:

| Cpd. No. | Structure |
|---|---|
| 312 | 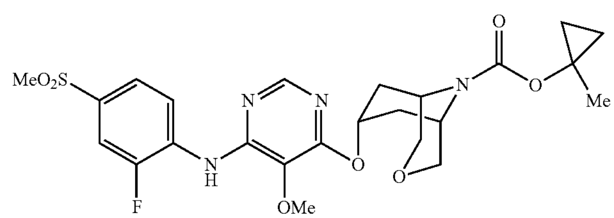 [SMILES: COc1c(Nc2ccc(S(C)(=O)=O)cc2F)ncnc1OC1CC2COCC(C1)N2C(=O)OC1(C)CC1] |
| 313 | 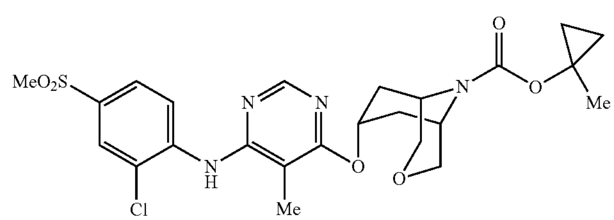 [SMILES: Cc1c(Nc2ccc(S(C)(=O)=O)cc2Cl)ncnc1OC1CC2COCC(C1)N2C(=O)OC1(C)CC1] |
| 314 | 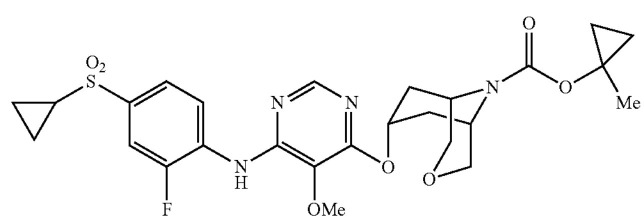 [SMILES: COc1c(Nc2ccc(S(=O)(=O)C3CC3)cc2F)ncnc1OC1CC2COCC(C1)N2C(=O)OC1(C)CC1] |
| 315 | 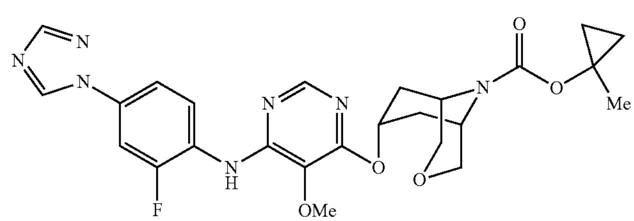 [SMILES: COc1c(Nc2ccc(N/C=N\C=N)cc2F)ncnc1OC1CC2COCC(C1)N2C(=O)OC1(C)CC1] |

-continued
| Cpd. No. | Structure |
|---|---|
| 316 | 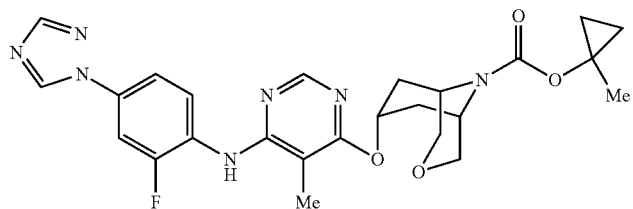 |
| 317 | 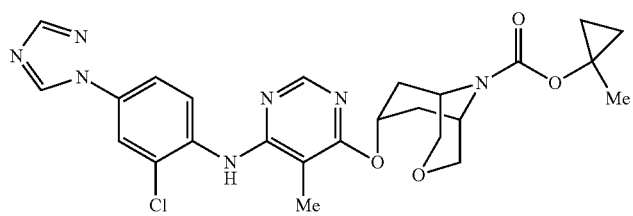 [SMILES: Cc1c(Nc2ccc(N/C=N\C=N)cc2F)ncnc1OC1CC2COCC(C1)N2C(=O)OC1(C)CC1] |
| 318 | 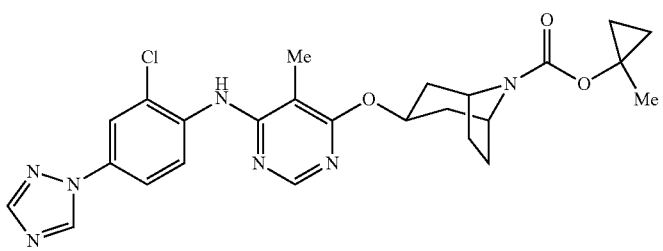 [SMILES: Cc1c(Nc2ccc(-n3cncn3)cc2Cl)ncnc1OC1CC2CCC(C1)N2C(=O)OC1(C)CC1] |
| 319 | 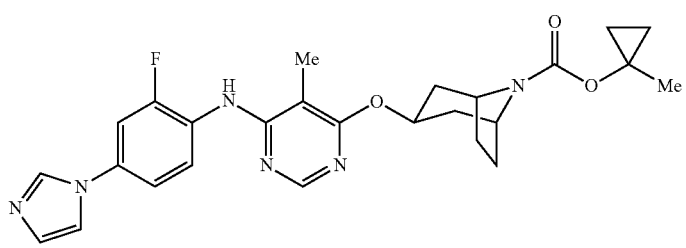 [SMILES: Cc1c(Nc2ccc(-n3ccnc3)cc2F)ncnc1OC1CC2CCC(C1)N2C(=O)OC1(C)CC1] |
| 320 | 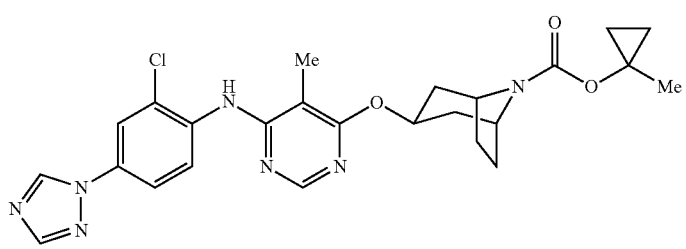 [SMILES: Cc1c(Nc2ccc(-n3cncn3)cc2Cl)ncnc1OC1CC2CCC(C1)N2C(=O)OC1(C)CC1] |
| 321 | 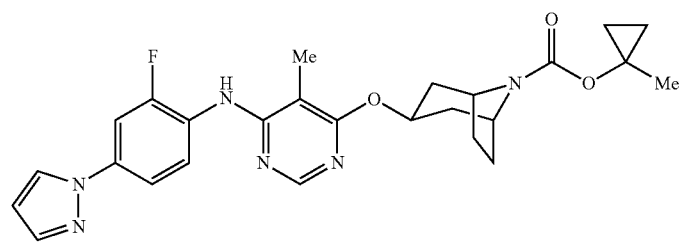 [SMILES: Cc1c(Nc2ccc(-n3cccn3)cc2F)ncnc1OC1CC2CCC(C1)N2C(=O)OC1(C)CC1] |

Example 88

Preparation of Compound 322

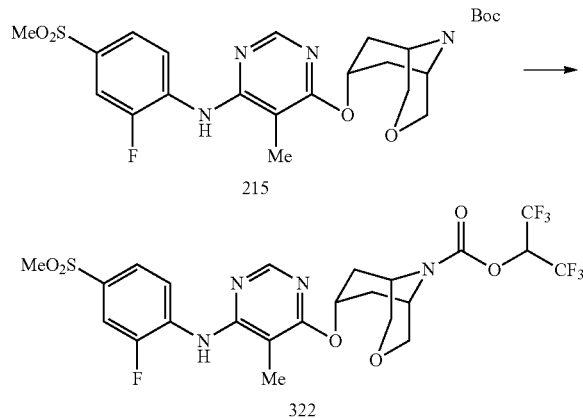

Compound 215 (0.0.030 g, 0.057 mmol) was diluted with 4.0M HCl/dioxane (1.0 mL), and the resulting reaction was allowed to stir for 18 hours, then concentrated in vacuo. The resulting residue was taken up in MeOH (2 mL), and treated with 7N NH$_3$/MeOH (1.0 mL). Ether (10 mL) was then added and the mixture was filtered and concentrated in vacuo to provide a yellow solid, which was taken up in CH$_2$Cl$_2$ (0.5 mL) and the resulting solution was added to a solution of COCl$_2$ (20% in toluene, 0.06 mL, 0.11 mmmol) in Cl$_2$Cl$_2$ (1.0 mL) at 0° C. To the resulting reaction was added Et$_3$N (0.019 mL, 0.14 mmol) and the reaction was allowed to stir for 20 minutes, then concentrated in vacuo. The resulting residue was taken up in THF (1.0 mL) and treated with (CF$_3$)$_2$CHOH (0.029 mL, 0.28 mmol), followed by a solution of NaO-tBu (0.026 g, 0.27 mmol) in THF (1.0 mL). After stirring for 20 minutes., the reaction was concentrated in vacuo and the residue obtained was purified using PLC to provide compound 322 as a white solid.

Using this method and substituting the appropriate Boc derivative for compound 215, the following compounds of the present invention were made:

Example 89

Preparation of Compound 325

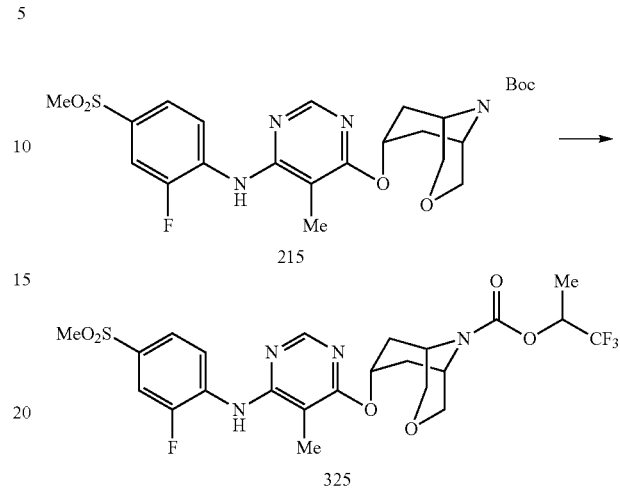

Using the method described in Example 88, and substituting CF$_3$(Me)CHOH for (CF$_3$)$_2$CHOH, compound 215 was converted to compound 325, a white solid.

Example 90

Preparation of Compound 326

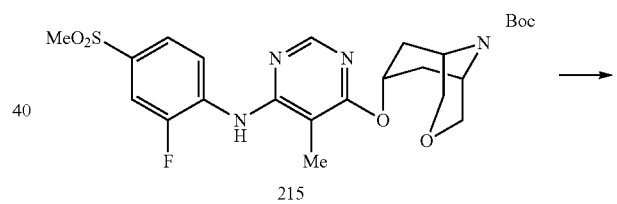

| Cpd. No. | Structure |
|---|---|
| 323 | 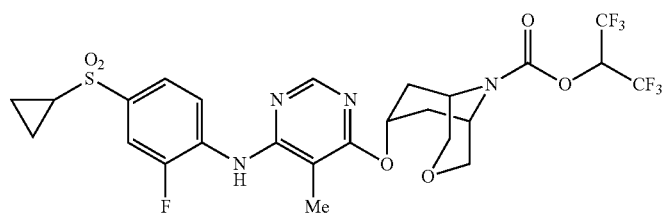 [SMILES: Cc1c(Nc2ccc(S(=O)(=O)C3CC3)cc2F)ncnc1OC1CC2COCC(C1)N2C(=O)OC(C(F)(F)F)C(F)(F)F] |
| 324 | 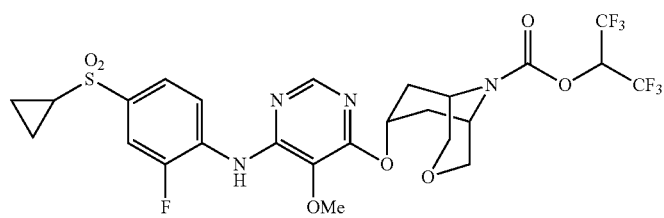 [SMILES: COc1c(Nc2ccc(S(=O)(=O)C3CC3)cc2F)ncnc1OC1CC2COCC(C1)N2C(=O)OC(C(F)(F)F)C(F)(F)F] |

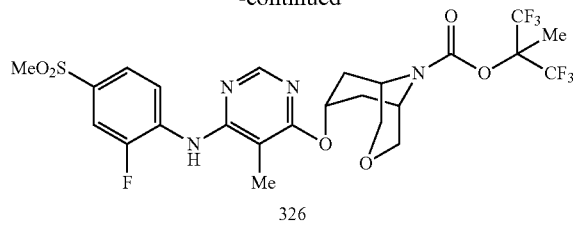

Using the method described in Example 88, and substituting Me(CF$_3$)$_2$COH for CF$_3$)$_2$CHOH, compound 215 was converted to compound 325, a white solid.

Using this method and substituting the appropriate Boc derivative fir compound 215, the following compound of the present invention was made:

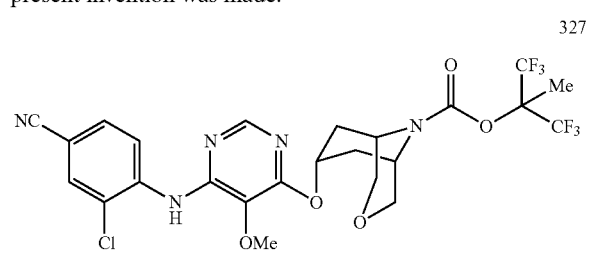

Example 91

Preparation of Compound 328

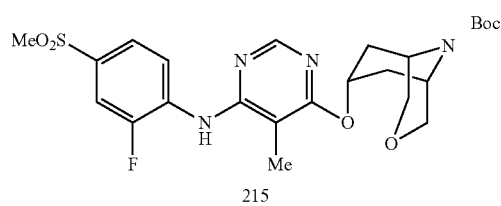

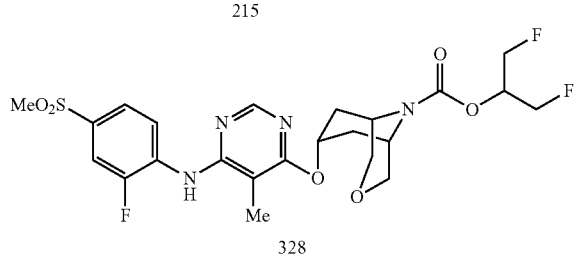

(CH$_2$F)$_2$CHOH was prepared by reducing 1,3-difluoroacetone with NaBH$_4$ in THF Then, using the method described in Example 88, and substituting (CH$_2$F)$_2$CHOH for (CF$_3$)$_2$CHOH, compound 215 was converted to compound 328, a white solid.

Using this method and substituting the appropriate Boc derivative for compound 215, the following compound of the present invention was made:

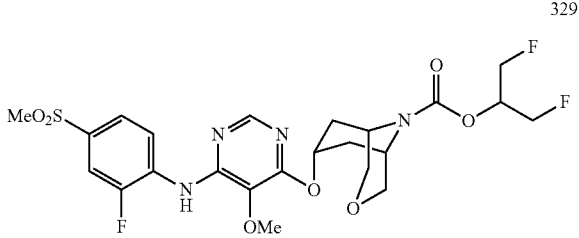 [SMILES: COc1c(Nc2ccc(S(C)(=O)=O)cc2F)ncnc1OC1CC2COCC(C1)N2C(=O)OC(CF)CF]

Example 92

Preparation of Compound 330

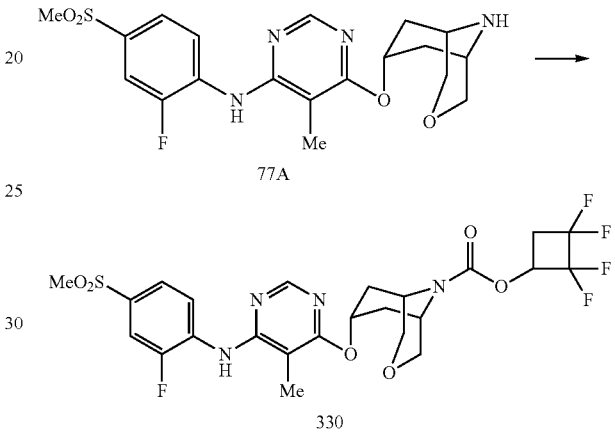

Using the method described in Example 84, and substituting 2,2,3,3-tetrafluorocyclobutanol for cyclobutanol, compound 77A was converted to compound 330, a white solid.

Using this method and substituting the appropriate amine derivative for compound 77A, the following compound of the present invention was made:

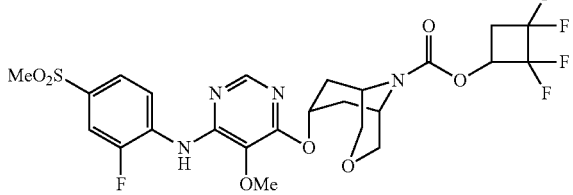

Example 93

Preparation of Compound 332

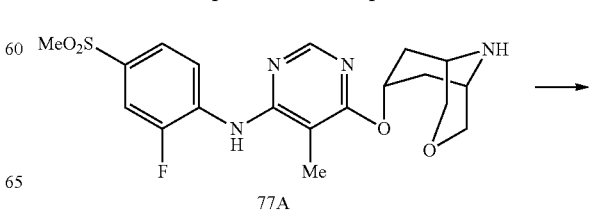

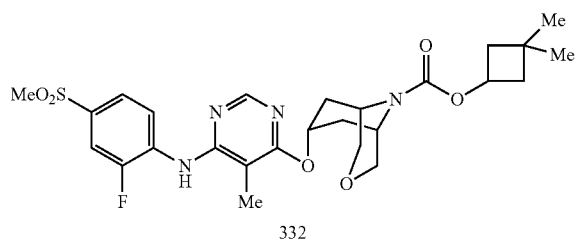

332

2-Methylpropene (10 g, 0.29 mol) was condensed into a −78° C. precooled volume of hexane (30 mL). To the resulting solution dichloroacetyl chloride (4.51 g, 31 mmol) was added dropwise, followed by Et₃N (3.0 g, 30 mmol). The cold solution was placed in a sealed vessel and heated at 55° C. for 18 hours. The solution was partitioned with ether and water, washed with saturated NaHCO₃, dried over MgSO₄, and concentrated in vacuo to provide a dichloroketone intermediate as a yellow oil (0.95, 5.7 mmol).

The dichloroketone intermediate was combined with zinc powder (1.84 g, 28 mmol) and acetic acid (10 mL) and the resulting reaction was heated to 70° C. and allowed to stir at this temperature for 2 hours, then it was cooled, treated with ether (20 mL), and filtered. The filtrate was washed with water, then saturated NaHCO₃, dried over MgSO₄ and filtered. The filtered solution was diluted with MeOH (1.0 mL) and treated with NaBH₄ (1.00 g, 26 mmol). The reaction mixture was heated to reflux and allowed to stir at this temperature for 1 hour, then was cooled to room temperature, washed with water, dried over MgSO₄, and concentrated in vacuo to provide 3,3-dimethyleyelobutanol as a yellow oil.

The 3,3-dimethylcyclobutanol was then subjected to the method described in Example 84, being used in place of cyclobutanol, to provide compound 332 as a white solid.

Example 94

Preparation of Compound 333

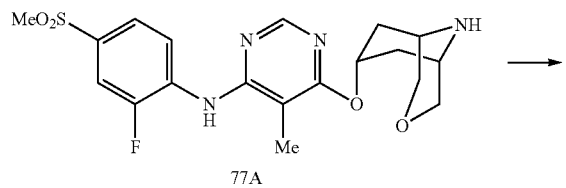

77A

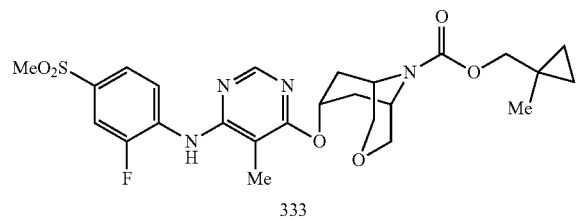

333

Using the method described in Example 84, and substituting 1-methyleyelopropanemethanol for cyclobutanol, compound 77A was converted to compound 333, a white solid.

Example 95

Preparation of Compound 334

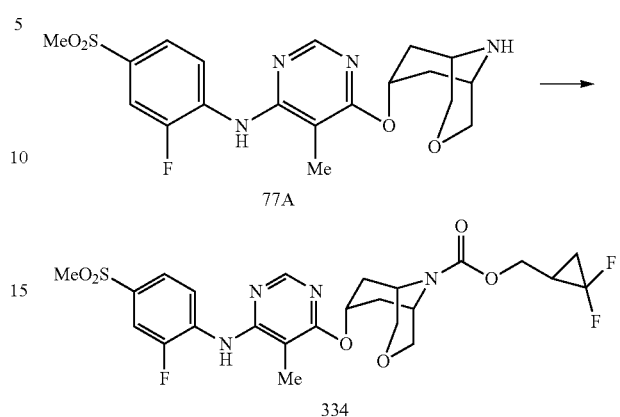

Using the method described in Example 84, and substituting 2,2-difluorocyclopropanemethanol for cyclobutanol, compound 77A was converted to compound 334, a white solid.

Example 96

Preparation of Compound 335

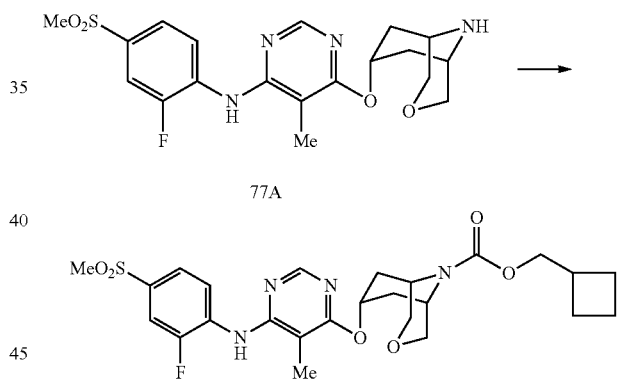

Using the method described in Example 84, and substituting cyclobutanemethanol for cyclobutanol, compound 77A was converted to compound 335, a white solid.

Example 97

Preparation of Compound 336

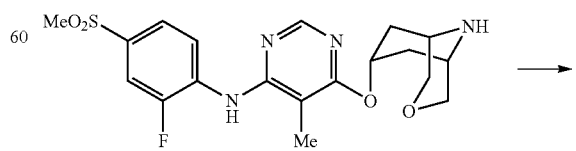

77A

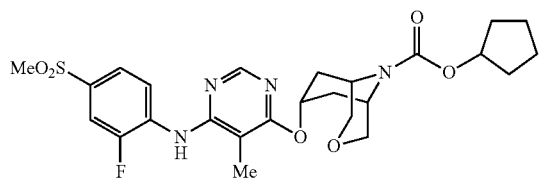

336

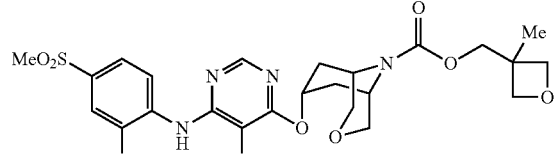

338

Using the method described in Example 84, and substituting cyclopentanol for cyclobutanol, compound 77A was converted to compound 336, a white solid.

Using the method described in Example 84, and substituting 3-methyl-3-oxetanemethanol for cyclobutanol, compound 77A was converted to compound 338, a white solid.

Example 98

Preparation of Compound 337

Example 100

Preparation of Compound 339

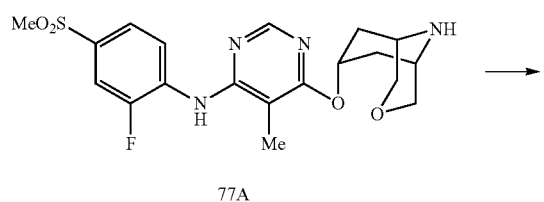

77A

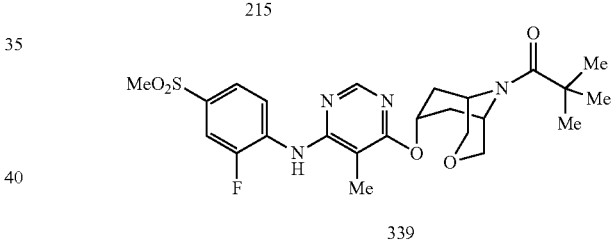

337

Using the method described in Example 84, and substituting cis-3-hydroxybicyclo[3.1.0]hexane for cyclobutanol, compound 77A was converted to compound 337, a white solid.

Using the method described in Example 75, and substituting pivaloyl chloride for isopropyl chloroformate, compound 215 was converted to compound 339, a white solid.

Using this method and substituting 3,3-dimethylbutyryl chloride for pivaloyl chloride, the following compound of the present invention was made:

Example 99

Preparation of Compound 338

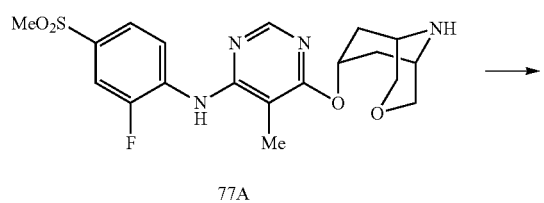

77A

340

Example 101

Preparation of Compound 341 and 342

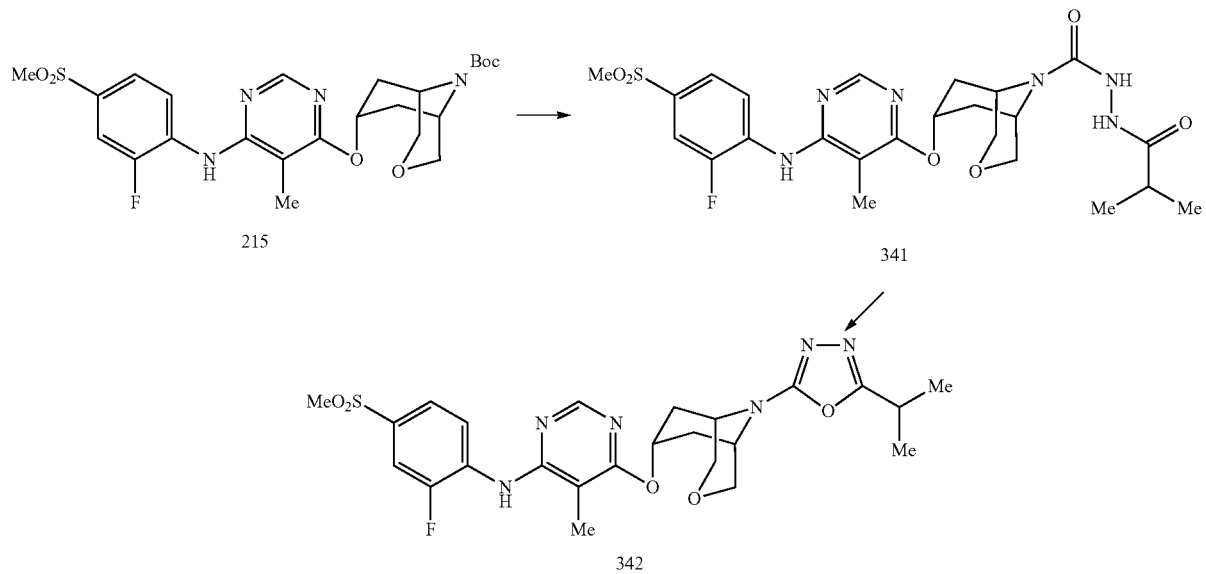

Step A—Synthesis of Compound 341

Compound 215 (0.049 g, 0.094 mmol) was deprotected and the resulting HCl salt was reacted with isobutyryl hydrazide using the method described in Example 84 (heating at 60° C. for 18 h) to provide compound 341.

Step B—Synthesis of Compound 342

To the solution of compound 341 (prepared in Step A) was added $POCl_3$ (0.100 mL, 1.1 mmol) and the mixture was heated to 80° C. and allowed to Stir at this temperature for 30 minutes. The temperature was then elevated to 110° C. and the reaction was allowed to stir at this temperature for 20 minutes, then cooled to 0° C. The cooled reaction mixture was treated with 7M $NH_3$/MeOH (5 mL), concentrated in vacuo, and the residue obtained was purified using PLC to provide compound 342 as a white solid.

Example 102

Preparation of Compound 343

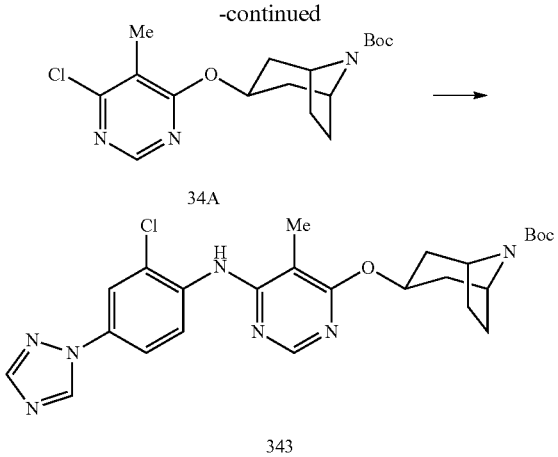

Using the method described in Example 76, compound 68C was reacted with compound 34A to provide compound 343 as a yellow solid.

Using this method and substituting the appropriate aniline and chloropyrimidine reactants, the following compounds of the present invention were made:

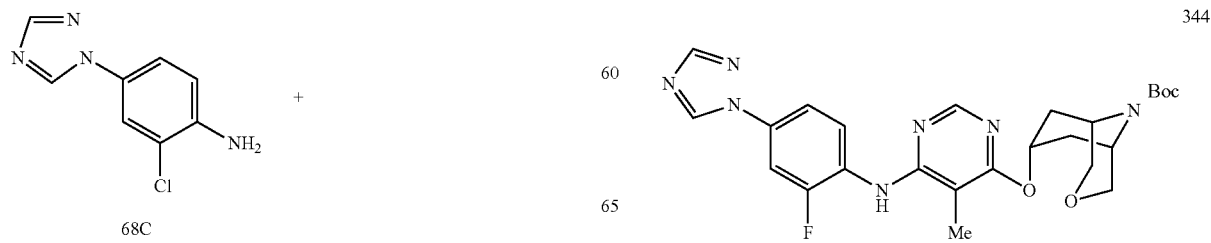

345

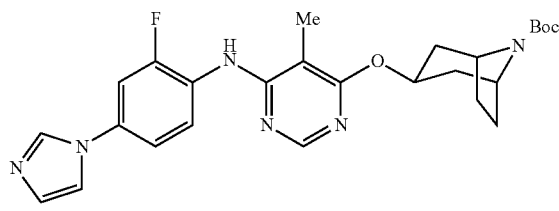

346

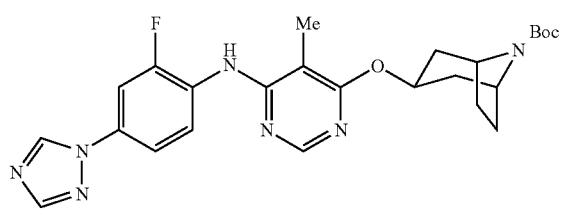

Example 103

Preparation of Compounds 347 and 348

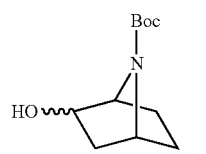

70G

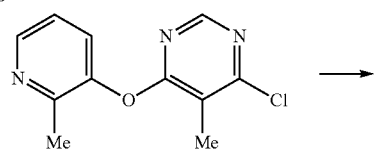

1B

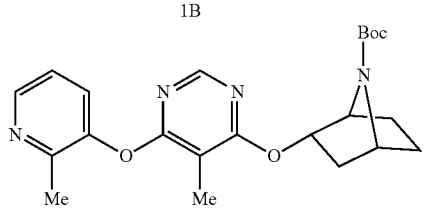

347

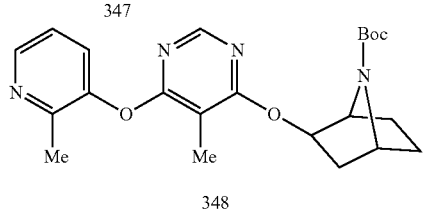

348

Compound 70G (0.114 g, 0.53 mmol), compound 1B (0.100 g, 0.43 mmol) and NaH (60% in oil, 0.025 g, 0.63 mmol) were combined in DMF (2 mL) and the resulting reaction was heated to 80° C. for 5 hours, then stirred 18 h at room temperature, and concentrated in vacuo. The resulting residue was purified using PLC (15% acetone/hexane) to provide compound 347 (the less polar endo-isomer) and compound 348 (the more polar exo-isomer) as yellow oils.

Example 104

Preparation of Compound 349

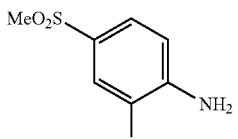

76A

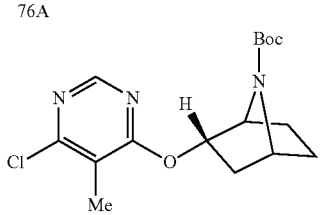

71A

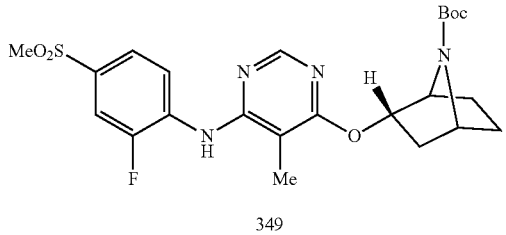

349

Using the method described in Example 76, compounds 76A and 71A were coupled to provide compound 349 as a yellow solid.

Using this method and substituting the appropriate anilines for compound 76A, compounds 71A or 71B were converted to the following compounds of the present invention:

350

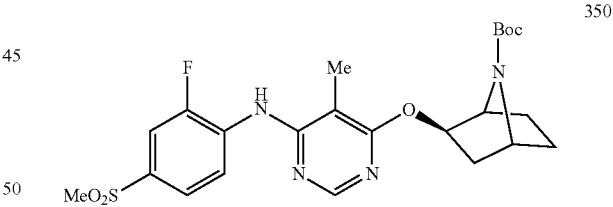

351

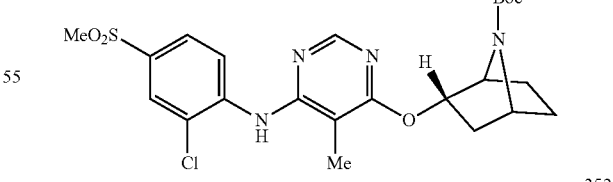

352

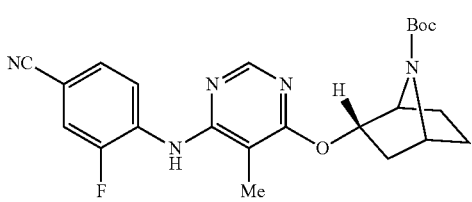

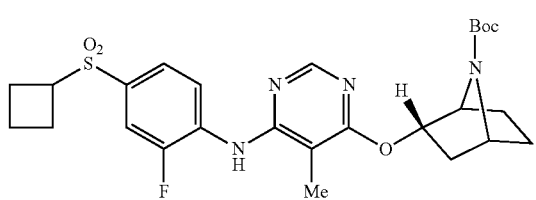

353

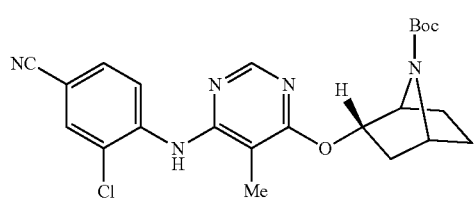

354

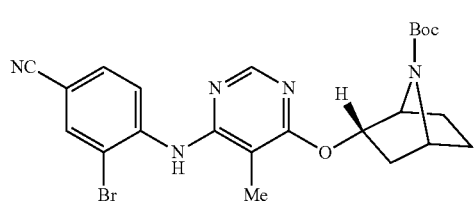

355

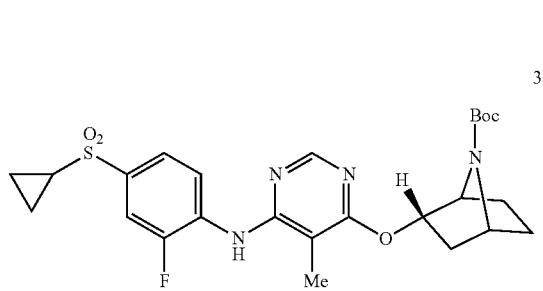

356

Example 105

Preparation of Compound 357

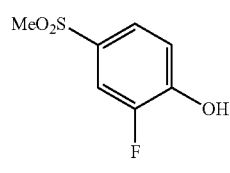

78A

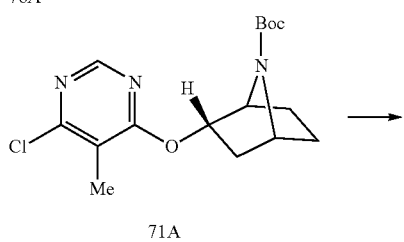

71A

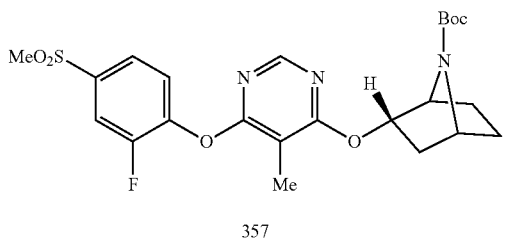

357

Using the method described in Example 78, compounds 78A and 71A were coupled to provide compound 357 as a yellow solid.

Using this method and substituting the appropriate phenol for compound 78A, the following compound of the present invention was made:

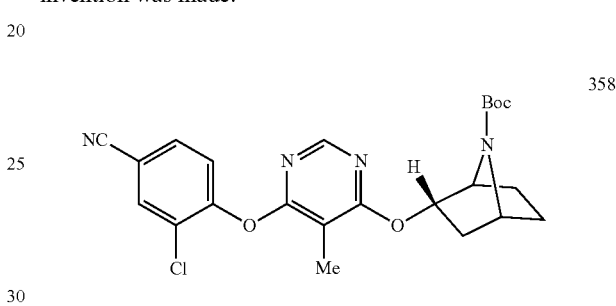

358

Example 106

Preparation of Compound 359

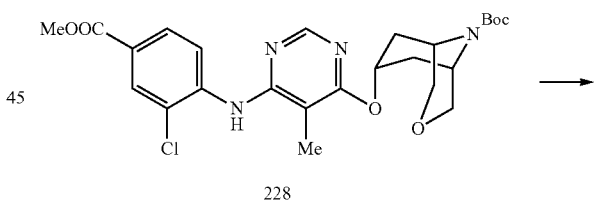

228

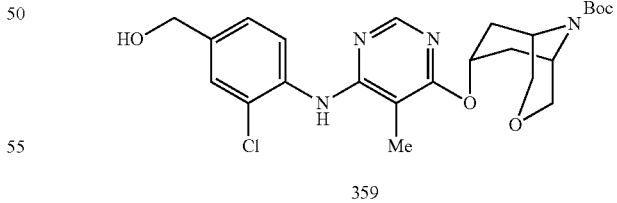

359

To a solution of compound 228 (0.024 g, 0.046 mmol) in THF (2 mL) was added LiAlH$_4$(1.0M in THF, 0.139 mL, 0.139 mmol). The mixture was heated to 60° C. and allowed to stir at this temperature for 1 hour, then it was quenched with water, then 10% NaOH, then water three times. The mixture was filtered, dried Over MgSO$_4$ and concentrated in vacuo, and the residue obtained was purified using PLC to provide compound 359 as a white film.

Example 107

Preparation of Compound 360

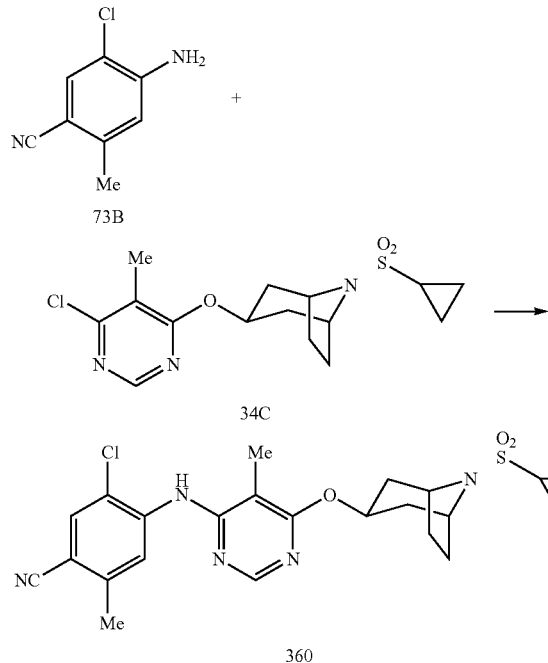

Compound 73B (0.035 g, 0.18 mmol) was combined with NaH (60% in oil, 0.0085 g, 0.21 mmol) in THF (4 mL). The resulting solution was allowed to stir for 30 minutes, then compound 34C (0.063 g, 0.22 mmol) was added and the reaction mixture was heated to 75° C. and allowed to stir at this temperature for 20 hours. An equal amount of NaH was added and heating continued 24 hours. The reaction mixture was cooled to room temperature, concentrated in vacuo and purified using PLC to provide compound 360 as a yellow solid.

Example 108

Preparation of Compound 361

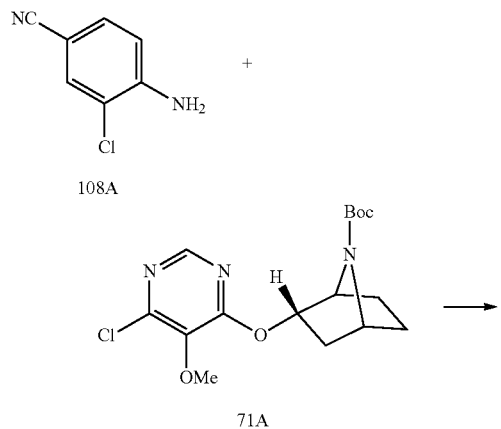

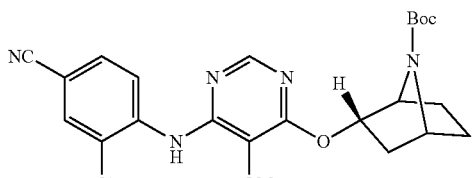

Using the method described in Example 76, compound 108A was coupled with compound 71A to provide compound 361 as a yellow oil.

Example 109

Preparation of Compound 362

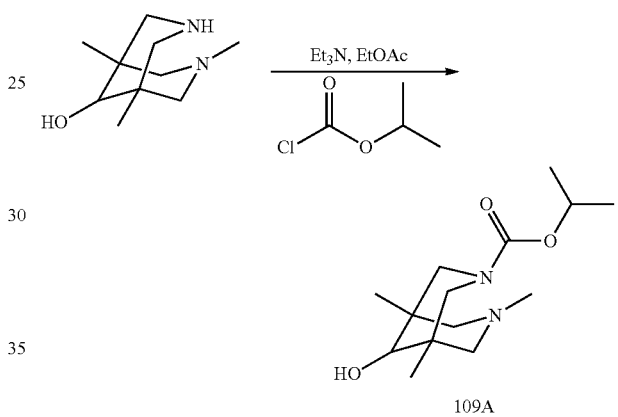

To a cooled solution of 1,3,5-trimethyl-diaza-bicyclo [3.3.1]-nonan-9-ol (100 mg, 0.54 mmol) in EtOAc (4.5 mL) was added triethylamine (0.1 mL, 0.7 mmol) followed by isopropyl chloroformate (1.0 M in toluene, 0.65 mL). The reaction was warmed to room temperature and stirred for 18 hours. The reaction was quenched with water and extracted with EtOAc, The organic layer was dried over MgSO$_4$, filtered and concentrated in vacuo to provide the crude carbamate 109A (135 rug, 93%) which was used without purification ire the next reaction.

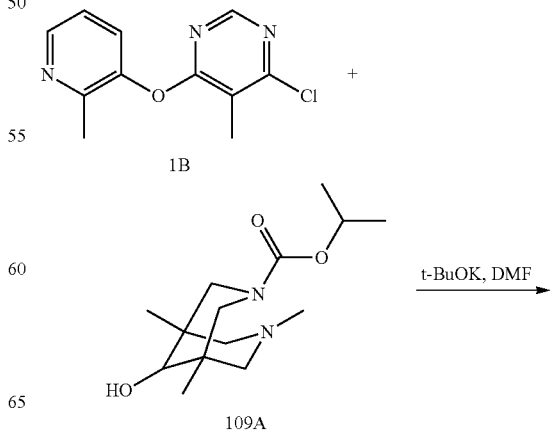

-continued

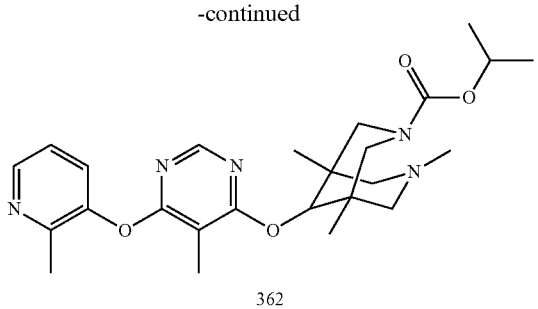

362

To a stirred solution of alcohol 109A (135 mg, 0.50 mmol) and 4-chloro-5-methyl-6(2-methyl-pyridine-3-yloxy)pyrimidine 1B (78 mg, 0.33 mmol) in DMF (4 mL) at 0° C. was added potassium t-butoxide (0.5 mL, 1M in THF). The reaction was warmed to room temperature and stirred for 72 hours. The reaction was quenched with water and extracted with EtOAc. The organic layer was washed with water, dried over Mc2SO$_4$, filtered and concentrated in vacuo. The residue was purified by preparative thin layer chromatography (25% acetone hexanes) to provide compound 362, which was treated with HCl (1.0 M in ether, 1 eq.) to provide the HCl salt of compound 362 (18.5 mg, 11%). M+H=470

Example 110

Preparation of Compound 359

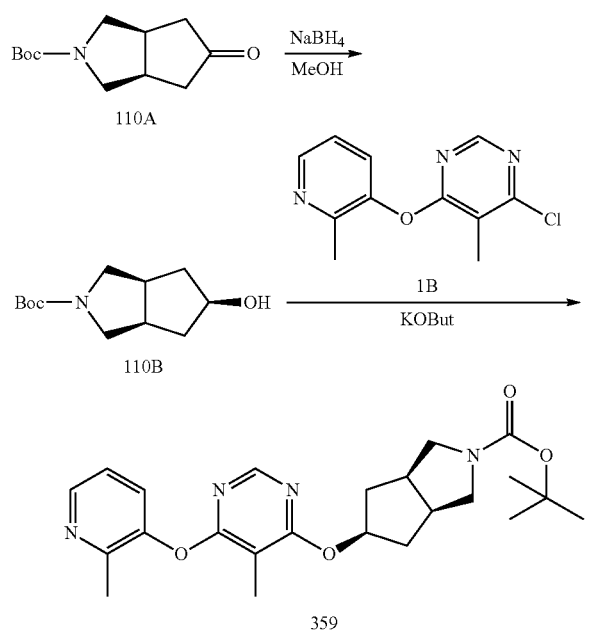

Step A—Synthesis of Compound 110B

To a solution of ketone 110A (1.83 g, 8.12 mmol, prepared as described in Lee et al., *Bull. Korean Chem. Soc.*, 24:539-540 (2003)) in methanol (30 mL) at 0° C., was added NaBH$_4$ (0.47 g, 12.46 mmol) and stirred at 0° C. for 2 hours. The reaction was carefully quenched with water and extracted with dichloromethane (100 mL×3). The combined organic layer was dried over Na$_2$SO$_4$ and concentrated in vacuo. The residue was purified on a silica gel column (ISCO) with EtOAc in hexanes (20→40%) to afford alcohol 110B (1.50 g, 82% yield Step B—Synthesis of 359

A solution of KOBu$^t$ (2.7 mL, 1.0 M in THF, 2.70 mmol) was added to a solution of the alcohol 110B (0.48 g, 2.11 mmol) and the chloride 1B (0.65 g, 2.74 mmol) in anhydrous THF (10 mL) under nitrogen at 0° C. and stirred at 0° C. to room temperature for 16 hours. The reaction was quenched with saturated NH$_4$Cl solution (15 mL) and extracted EtOAc (30 mL×3). The combined organic layer was dried over Na$_2$SO$_4$ and concentrated in vacuo. The residue was purified on a silica gel column (ISCO) with MeOH (NH$_3$) in dichloromethane (0→5%) to provide compound 359 (1.0 g, 86% yield). LCMS: 426.5

Example 111

Preparation of Compound 360

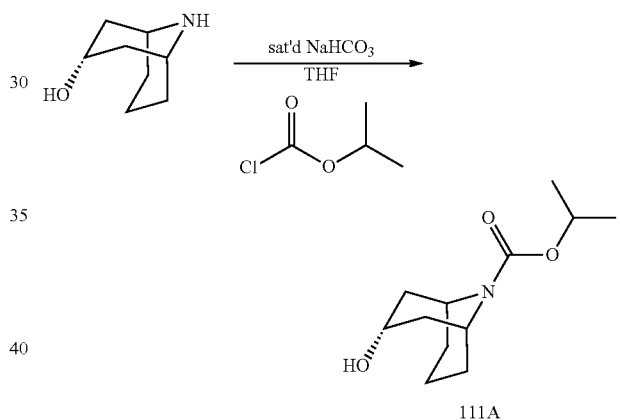

111A

To a mixture of 9-Azabicyclo[3.3.1]nonyl-endo-ol (50 mg, 0.35 mmol) in THF (3 mL) was added saturated aqueous NaHCO$_3$ (3 mL). The reaction was cooled to 0° C. and isopropyl chloroformate (1.0 M in toluene, 0.42 mmol) was added dropwise. The reaction was warmed to room temperature and stirred. After 16 hours, the reaction was quenched with water and extracted with EtOAc. The combined organics were dried over MgSO$_4$, filtered and concentrated in vacuo to provide the crude product 111A (58 mg, 73%) which was used in the next reaction without further purification.

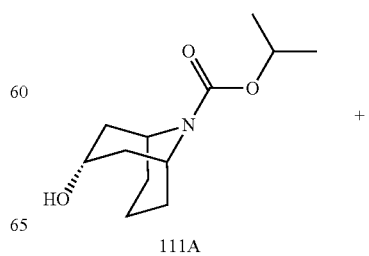

111A

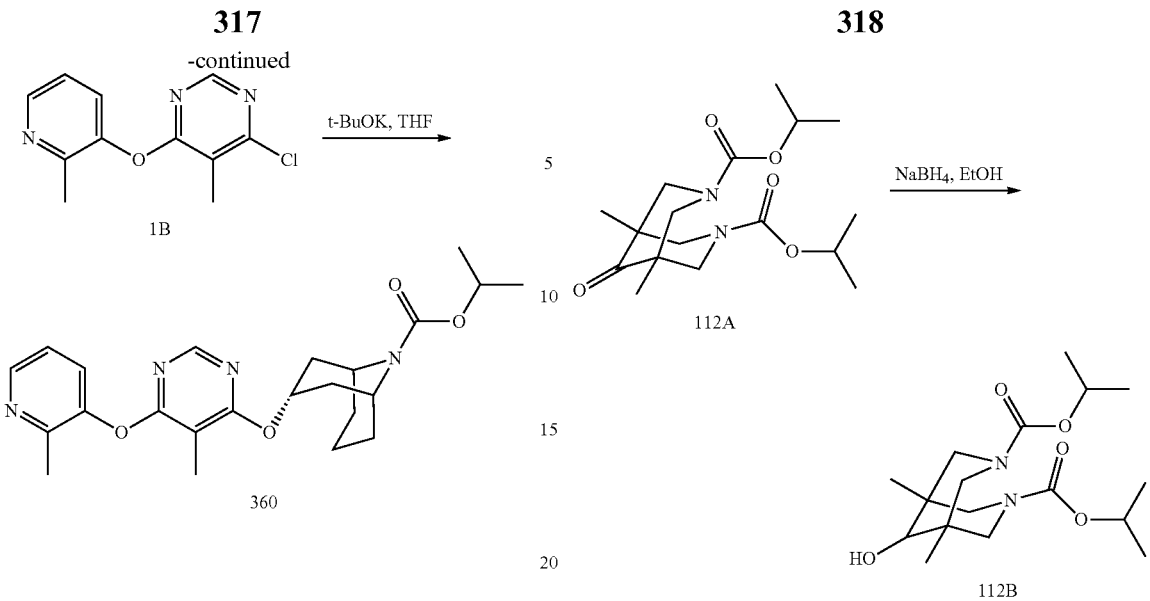

Potassium t-butoxide (1.0 M in THF, 0.3 mL) was added to a solution of alcohol 111A (57 mg, 0.24 mmol) and compound 1B (58 mg, 0.25 mmol) in anhydrous THF (2 mL) under nitrogen at 0° C. The reaction was gradually warmed to room temperature and stirred for 16 hours. The reaction was quenched with water and extracted with dichloromethane. The organic layer was dried over MgSO$_4$, filtered and concentrated in vacuo. The residue was purified by preparative thin layer chromatography (50° A EtOAc/hexanes) to provide compound 360 (18 mg, 18%). M+H=427.

To a solution of compound 112A (97 mg, 0.29 mmol) in EtOH (5 mL) was added sodium borohydride (15 mL, 0.39 mmol) under nitrogen. The reaction was stirred at room temperature for 2 h and then concentrated in vacuo. The residue was taken up in dichloromethane and washed with water. The organic layer was dried over MQSO$_4$, filtered and concentrated in vacuo to provide alcohol 112B (90 mg, 91%) which was used in the next reaction without further purification.

Example 112

Preparation of Compound 361

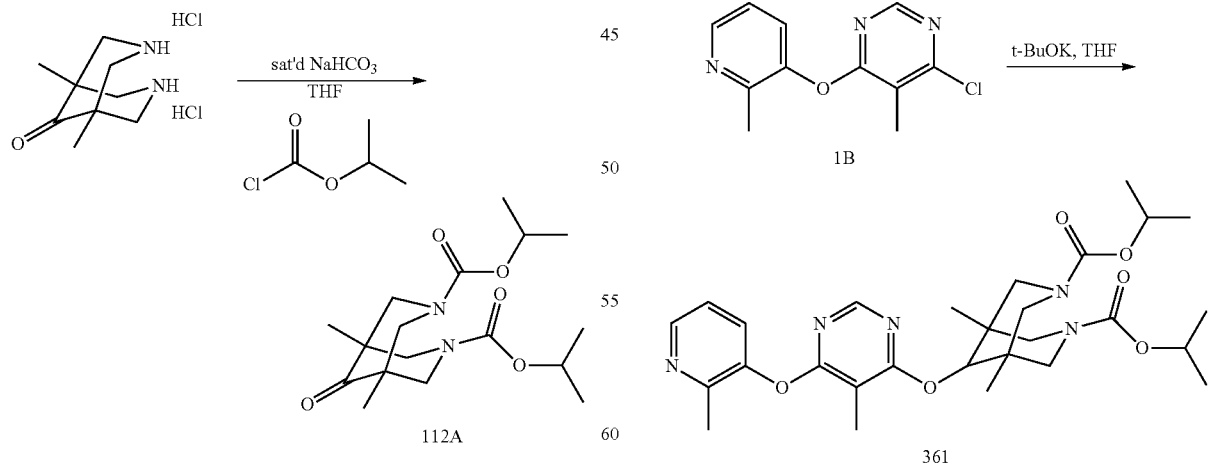

1,5-Dimethyl-3,7-diazo-bicyclo[3.3.1]nonan-9-one dihydrochloride (75 mg, 0.31 mmol) was reacted according to the method described in Example 111 to provide carbamate; 112A (105 mg, 100%) which was used in the next reaction without further purification.

Alcohol 112B (90 mg, 0.26 mmol) was reacted with compound 1B (62 mg, 0.26 m ol) using the method described in Example 111 to provide compound 361 (43 mg, 31%). M+H=542

Example 113

Preparation of Compound 363

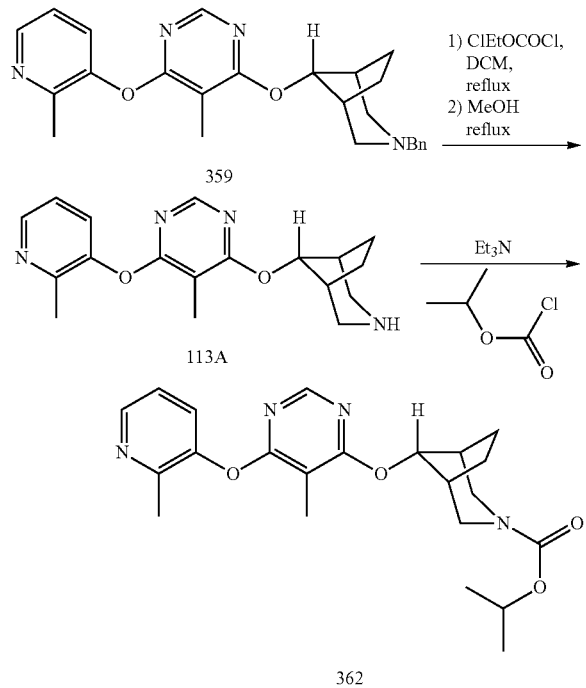

Step A—Synthesis of Compound 113A

Under N₂ atmosphere., to a 0° C. solution of 359 (810 mg, 1.94 mmol) in anhydrous dichloromethane (30 mL) was added slowly 1-chloroethyl chloroformate (0.43 mL, 3.89 mmol). The cold bath was removed after the addition and the reaction was allowed to stir until room temperature was reached, then the reaction was heated to reflux and allowed to stir at this temperature for an additional 2 hours. The reaction mixture was then cooled to room temperature and concentrated in vacuo. The residue obtained was dissolved in methanol (30 mL), placed under N₂ atmosphere, heated to reflux and allowed to stir at this temperature for 1 hour. The reaction mixture was then cooled to room temperature, concentrated in vacuo and the residue obtained was dissolved in dichloromethane (100 mL) and water (100 mL), and the resulting solution was brought to neutral pH using saturated aqueous NaHCO₃. The organic phase was separated and the aqueous was extracted with dichloromethane (2×100 mL). The combined organic layers were dried over Na₂SO₄, filtered and concentrated in vacuo and the resulting residue was purified using a silica gel column CISCO) with MeOH (NH₃) in dichloromethane (0→10%) to provide compound 113A (160 mg, 26% yield, not complete reaction). LCMS: 326.4

Step B—Synthesis of Compound 363

To a solution of compound 113A (50 mg) and isopropyl chlorocarbamate (0.3 mL, 1.0 M in toluene) in dichloromethane (3 mL) at 0° C., was added Et₃N (0.1 mL). The cold water bath was then removed and the reaction was allowed to stir at room temperature for 6 hours. The reaction was quenched with saturated aqueous NaHCO₃, extracted with dichloromethane (3×10 mL) and the combined organic layers were dried over Na₂SO₄, filtered and concentrated in vacuo. The residue obtained was purified using a silica gel column (ISCO) with MeOH (NH₃) in dichloromethane (0→5%) to provide compound 363 (55 mg, 87% yield). LCMS: 412.5

The following compounds of the present invention were made using the above method and substituting the appropriate chloroformate in Step B:

| Cpd. No. | Structure | LCMS |
|---|---|---|
| 493 | 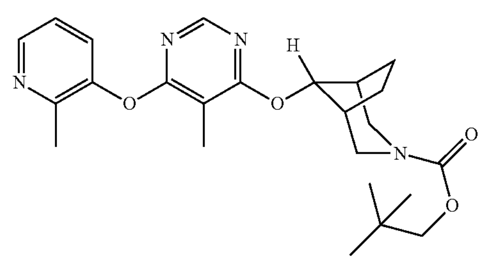 [SMILES: Cc1ncccc1Oc1ncnc(OC2C3CCC2CN(C(=O)OCC(C)(C)C)C3)c1C] | 440.5 |
| 494 | 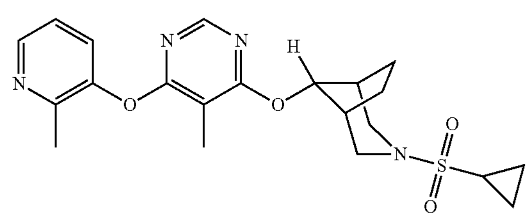 [SMILES: Cc1ncccc1Oc1ncnc(OC2C3CCC2CN(S(=O)(=O)C2CC2)C3)c1C] | 430.5 |

-continued

| Cpd. No. | Structure | LCMS |
|---|---|---|
| 495 | 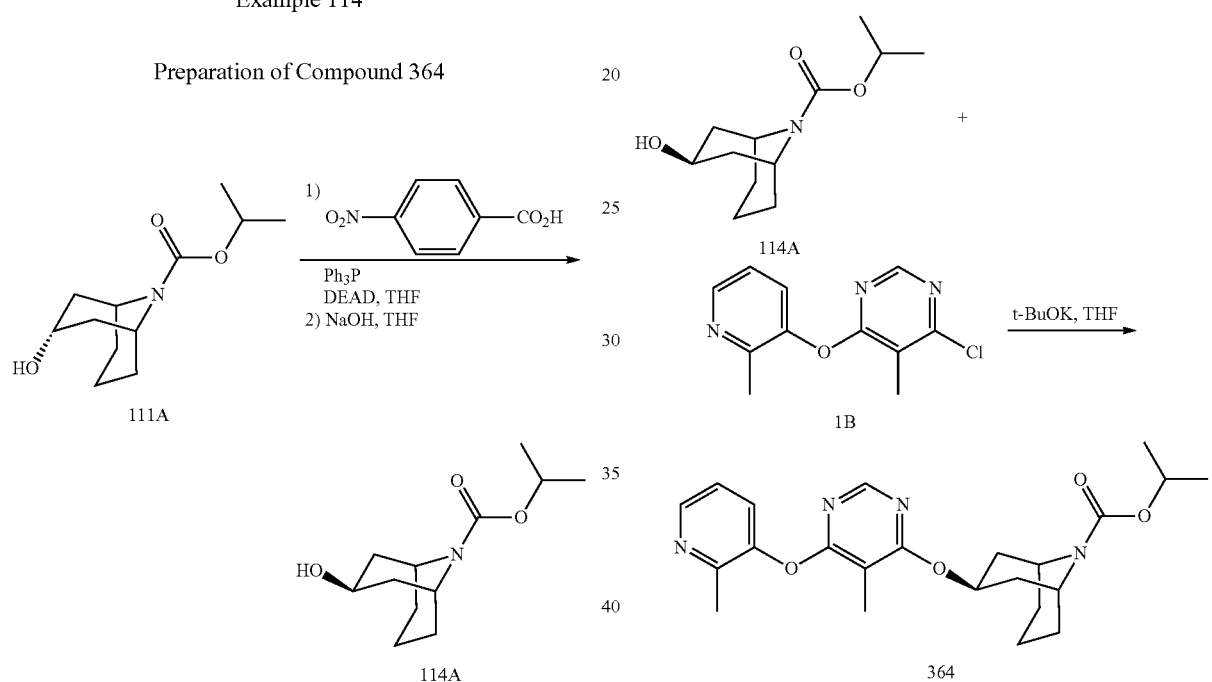 | 384.4 |

Example 114

Preparation of Compound 364

To a solution of the endo alcohol 111A (170 mg, 0.75 mmol)) in THF (5 mL) was added 4-nitrobenzoic acid (145 mg, 0.84 mmol), followed by triphenyl phosphine (245 mg, 0.93 mmol) and diethyl azodicarboxylate (0.15 mL, 0.90 mmol). The reaction was stirred at room temperature under nitrogen for 18 hours. The reaction was concentrated in vacuo, and then purified by preparative thin layer chromatography (25% acetone/hexanes) to provide the nitrobenzyloxy intermediate (78 mg, 28%).

To a solution of the intermediate (78 mg, 0.16 mmol) in THF (3 mL) was added a solution of sodium hydroxide (4 N, 0.12 mL) under nitrogen. After stirring at room temperature for 16 hours, the reaction was diluted with water and ether and then washed with sodium hydroxide (2N) and brine. The organic layer was dried over MgSO₄, filtered and concentrated in vacuo to provide the crude exo alcohol 114A (36 mg, 100%) which was used in the next reaction without further purification.

Alcohol 114A (32 mg, 0.15 mmol) was reacted with compound 1B (3(ng, 0.15 mmol) using the method described in Example 111 to provide compound 364 (24 mg, 38%). M+H=427

Example 115

Preparation of Compound 365

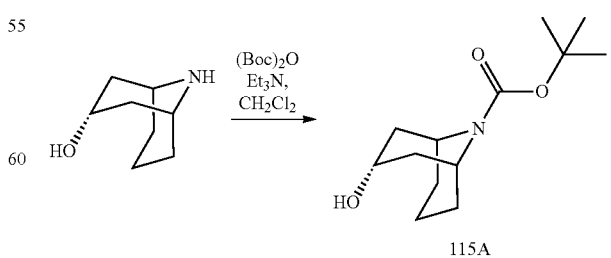

To a mixture of 4-azabicyclo[3.3.1]nonyl-3-endo-ol (120 mg, 0.85 mmol) in dichloromethane (8 mL) was added triethylamine (0.13 mL, 0.93 mmol) under nitrogen. The reaction was cooled to 0° C. and (Boc)$_2$O (203 mg, 0.93 mmol) was added. The reaction was warmed to room temperature and stirred for 18 hours. The reaction was quenched with water and extracted with dichloromethane. The organic layer was dried over MgSO$_4$, filtered and concentrated to provide compound 115A (130 mg, 76 which was used in the next reaction without further purification.

mL) at 0 under nitrogen. After 18 hours, the reaction was diluted with dichloromethane and washed with saturated aqueous NaHCO$_3$. The organic layer 1.5 was dried over MgSO$_4$, filtered and concentrated in vacuo to provide the free amine 116B (75 mg, 100%) which was used in next reaction without further purification.

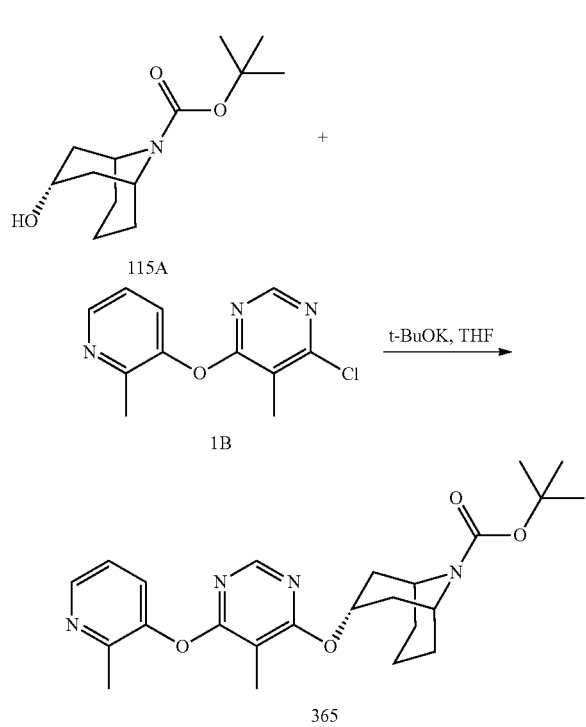

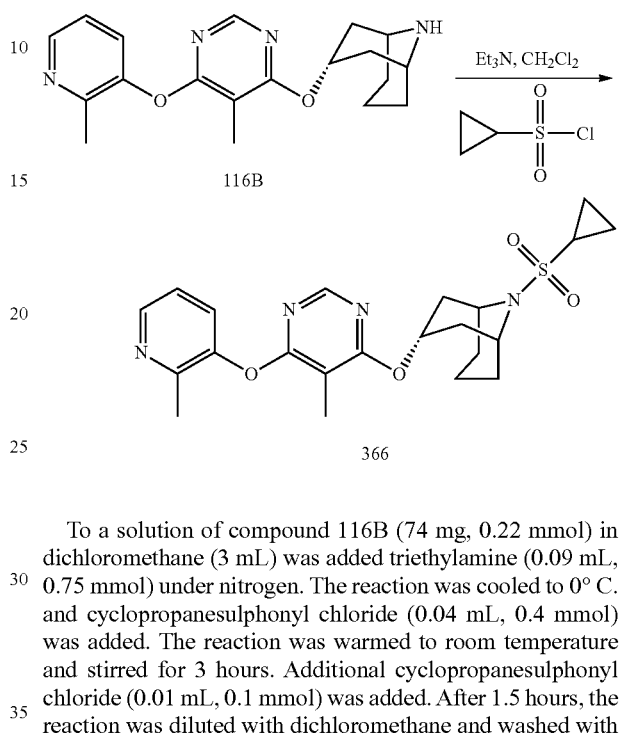

Alcohol 115A (170 mg, 0.71 mmol) was reacted with compound 1B (165 mg, 0.71 mmol) using the method described in Example 111 to provide compound 365 (100 mg, 32%). M+H=441

To a solution of compound 116B (74 mg, 0.22 mmol) in dichloromethane (3 mL) was added triethylamine (0.09 mL, 0.75 mmol) under nitrogen. The reaction was cooled to 0° C. and cyclopropanesulphonyl chloride (0.04 mL, 0.4 mmol) was added. The reaction was warmed to room temperature and stirred for 3 hours. Additional cyclopropanesulphonyl chloride (0.01 mL, 0.1 mmol) was added. After 1.5 hours, the reaction was diluted with dichloromethane and washed with saturated aqueous NaHCO$_3$. The organic layer was dried over MgSO$_4$, filtered and concentrated in vacuo to provide the crude product which was purified by preparative thin layer chromatography (5% MeOH/dichloromethane) to provide compound 366 (32 mg, 33%). M+H=445

Example 116

Preparation of Compound 366

Example 117

Preparation of Compound 367

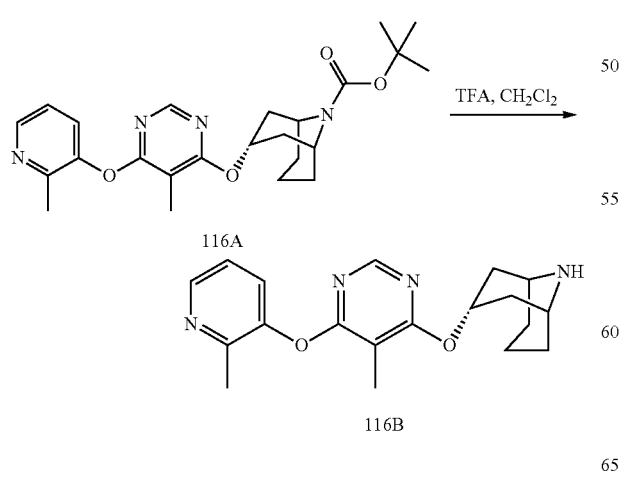

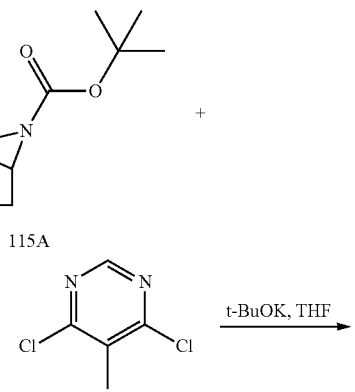

Trifluoroacetic acid (0.1 mL) was added dropwise to a solution of 11.6A (98 rug, 0.22 mmol) in dichloromethane (3

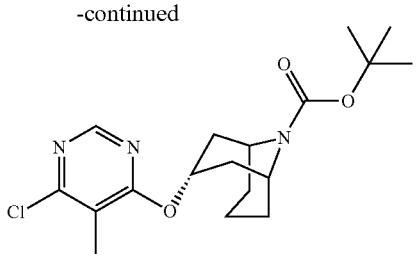

117A

A solution of potassium t-butoxide (1.0 M in THF, 13.3 mL) was added dropwise to a solution of 4,6-dichloro-5-methylpyrimidine (2.16 g, 13.3 mmol) and the endo alcohol 115A (3.20 g, 13.3 mmol) in THF (40 mL) at 0° C. under nitrogen. The reaction was warmed to room temperature and stirred. After 5 hours, the reaction was quenched with water and extracted with dichloromethane. The organic layer was dried over MgSO$_4$, filtered and concentrated in vacuo. The crude material was purified by silica gel flash chromatography (0-20% EtOAc/hexanes) to provide compound 117A (4.3 g, 88%).

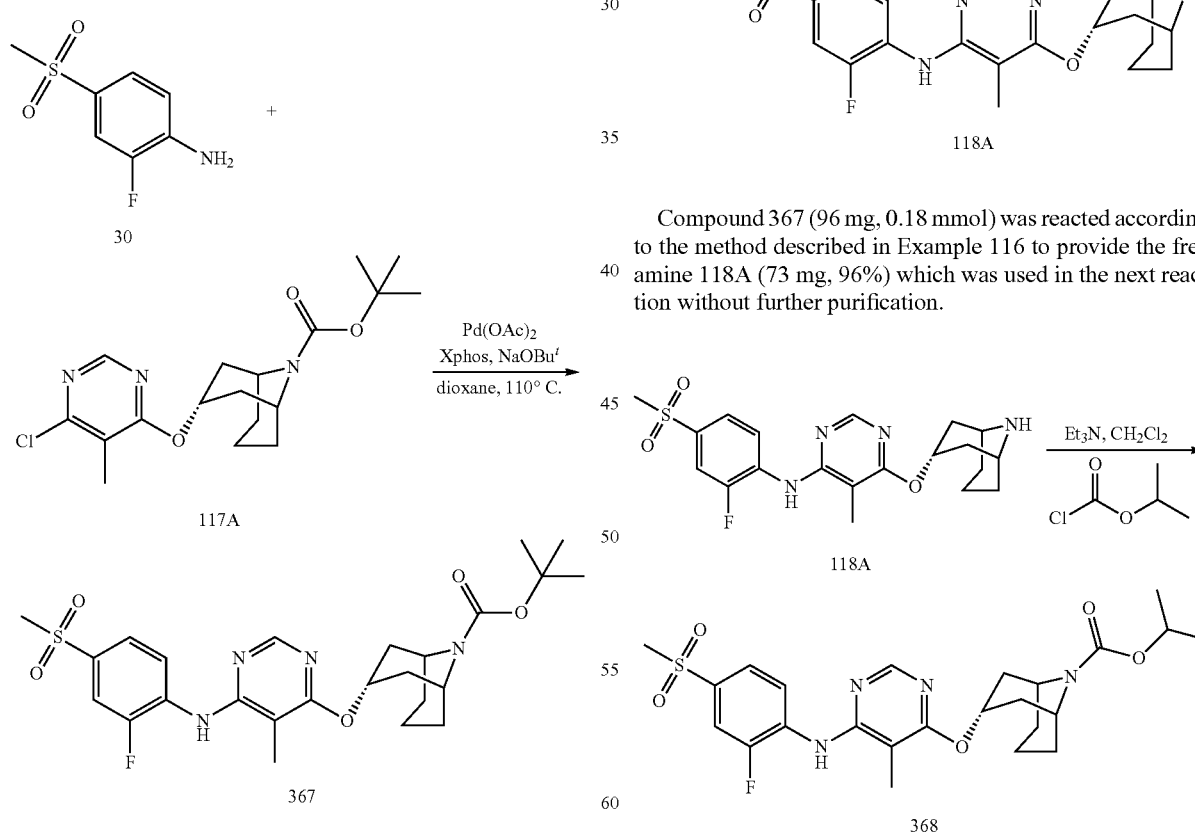

A mixture of the chloro-pyrimidine 117A (144 mg, 0.39 mmol), 2-fluoro-4-(methylsulfonyl)aniline (89 mg, 0.47 mmol), Xphos (38 ma, 0.080 mmol) and sodium t-butoxide (56 mg, 0.59 mmol) in dioxane (3.5 mL) was heated to 110° C. in a sealed tube. After 16 hours, the reaction was cooled to room temperature and the solids were filtered off. The filtrate was concentrated in vacuo and purified by preparative thin layer chromatography (50% EtOAc/hexanes) to provide compound 367 (96 mg, 47%). M+H=521

Example 118

Preparation of Compound 368

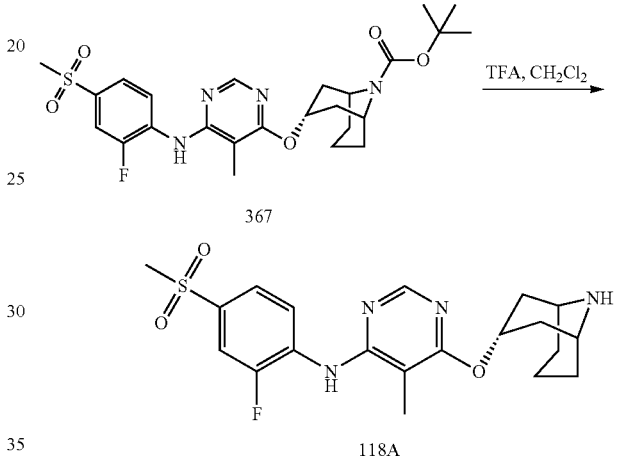

Compound 367 (96 mg, 0.18 mmol) was reacted according to the method described in Example 116 to provide the free amine 118A (73 mg, 96%) which was used in the next reaction without further purification.

The free amine 118A (35 mg, 0.083 mmol) was reacted according to the method described in Example 109 using dichloromethane as the solvent to provide compound 368 (18 mg, 43%). H+H=507

Example 119

Preparation of Compound 369

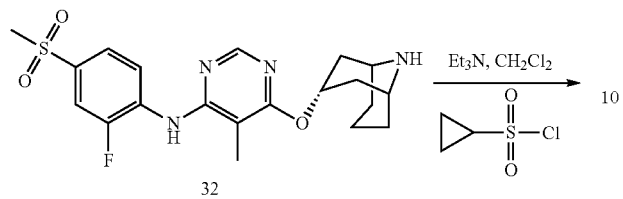

The free amine 32 (35 mg, 0.083 mmol) was reacted according to the method described in Example 116 to provide compound 369 (18 mg, 41%). M+H=525

Example 120

Preparation of Compound 370

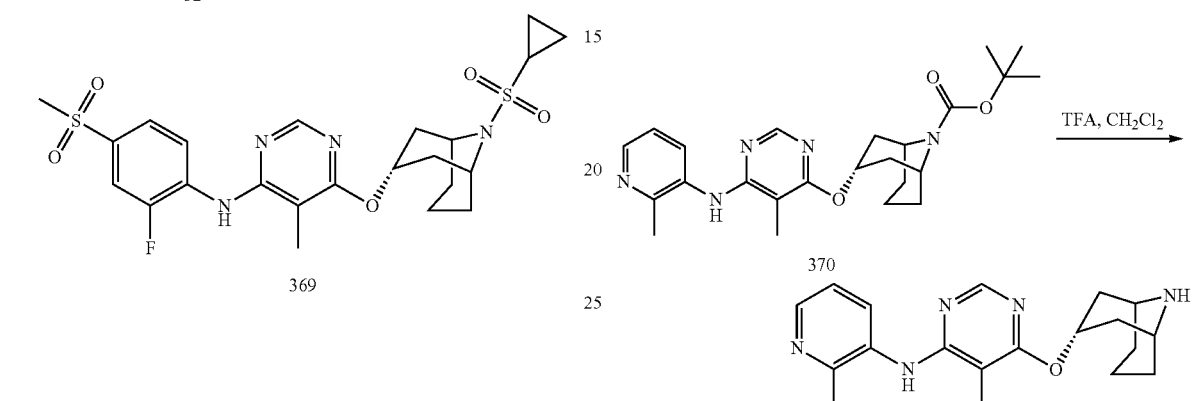

2-Methylpyridin-3-amine (51 mg, 0.47 mmol) was reacted with compound 117A (144 mg, 0.39 mmol) using the method described in Example 117 to provide compound 370 (45 mg, 26%). M+H=440

Example 121

Preparation of Compound 371

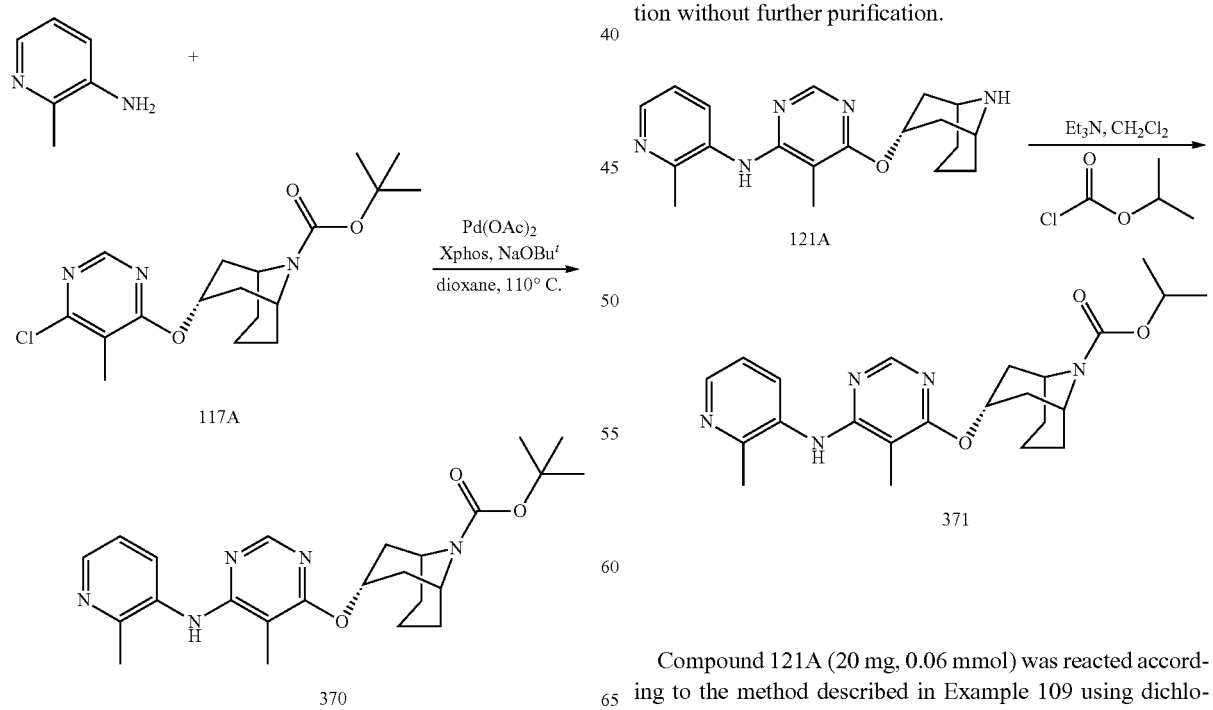

Compound 370 (40 mg, 0.09 mmol) was reacted according to the method described in Example 116 to provide the free amine 121A (20 mg, 67%) which was used in the next reaction without further purification.

Compound 121A (20 mg, 0.06 mmol) was reacted according to the method described in Example 109 using dichloromethane as the solvent to provide compound 371 (24 mg, 96%). M+H=427

Example 122

Preparation of Compound 372

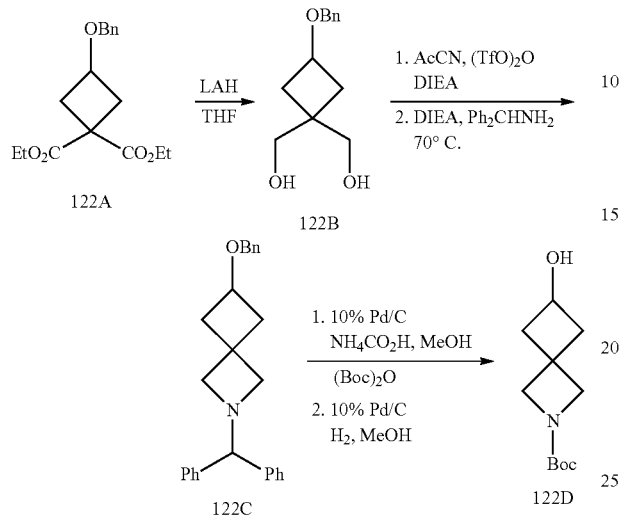

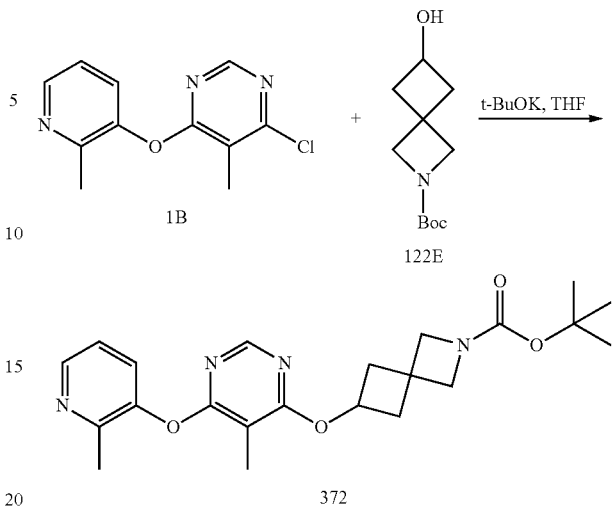

Lithium aluminum hydride (1 M in THF, 1.6 mL) was added dropwise to a solution of diethyl 3-(benzyloxy)cyclobutane-1,1-dicarboxylate 122A (280 rug, 0.91 mmol) in THF (10 mL) at 0° C. under nitrogen. The reaction was warmed to room temperature and stirred for 18 hours. The reaction was poured onto ice and extracted with ether. The organic layer was dried over $MgSO_4$, filtered and concentrated in vacuo to provide diol 122B (202 mg, 100%) which was used in the next reaction without further purification.

To a solution of dial 122B (185 mg, 0.83 mmol) in dry acetonitrile (8 mL) at −20° C. ($CCl_4$/dry ice) was added trifluoromethane sulfonic anhydride (0.29 mL, 1.75 mmol) dropwise over 10 minutes, followed by MEA (0.36 mL, 2.08 mmol). The resulting mixture was stirred for 10 min and additional DIEA (0.36 mL, 2.08 mmol) was added over 5 minutes, followed by aminodiphenyl methane (0.14 mL, 0.79 mmol). The reaction was warmed to room temperature, and then heated to 70° C. After 2 hours, the solvent was concentrated in vacuo. The crude material was purified by silica gel flash chromatography (0-20% EtOAc/hexanes to provide compound 122C (137 mg, 47%).

To compound 1220 (52 mg, 0.14 mmol) in MeOH (2 mL) was added ammonium formate (67 mg, 1.1 mmol), $(Boc)_2O$ (37 mg, 0.17 mmol) and 10% Pd/C (22 mg) under nitrogen. The resulting mixture was refluxed for 22 h and then cooled to room temperature. The reaction was filtered through celite and washed with MeOH. The filtrate was concentrated in vacuo to provide the crude material which was purified by preparative thin layer chromatography (30° A EtOAc/hexanes) to provide the Boc protected amine 1221 (15 mg, 36%).

A mixture of the Boc-protected amine 122D (15 mg, 0.05 mmol) in MeOH (5 mL) and 10% Pd/C (9 mg) was hydrogenated at 1 atm. for 16 hours. The reaction was filtered through celite, washed with MeOH and concentrated in vacuo to provide alcohol 122E (10 mg, 94%) which was used in the next reaction without further purification.

Alcohol 122E (10 mg, 0.05 mmol) was reacted with compound 1B (11 mg, 0.05 mmol) using the method described in Example 111 to provide compound 372 (5 mg, 25%). M+H=413

Example 123

Preparation of Compound 373

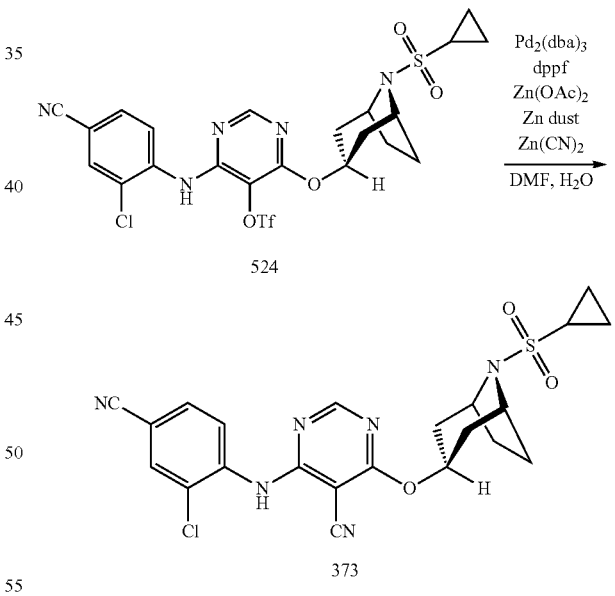

To a nitrogen purged vessel containing a solution of compound 524 (6 mg, 0.01 mmol) in dimethylformamide (0.6 mL) and water (6 microliters) was added tris(dibenzylideneacetone) dipalladium (5 mg, 0.005 mmol), 1,1'-bis(diphenylphosphino)ferrocene (3 ing, 0.005 mmol), zinc acetate (2 mg, 0.01 mmol), zinc dust (0.6 mg, 0.01 mmol), and zinc cyanide (1 mg, 0.01 mmol). The resulting reaction was heated to 100° C. and allowed to stir at this temperature for 18 hours. The reaction was cooled to room temperature, concentrated in vacuo and the resulting residue was taken up in dichloromethane. The organic phase was washed with aqueous saturated ammonium chloride solution, dried over MgSO₄, filtered, and concentrated in vacuo. The resulting residue was purified using preparative TLC on silica gel (hexanes/ethyl acetate—60/40), followed by a second preparative TLC on silica gel (dichloromethane/ethyl acetate—95/5) to provide compound 373 (2.7 mg, 56%) as an off-white solid. LCMS: 485.3 (MH⁺).

Example 124

Preparation of Compound 374

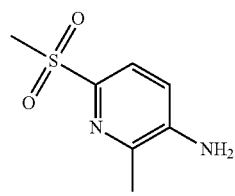

124A

+

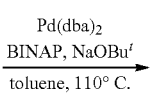

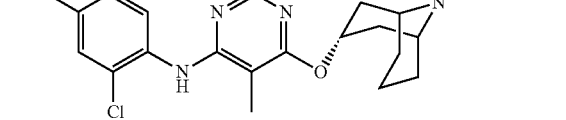

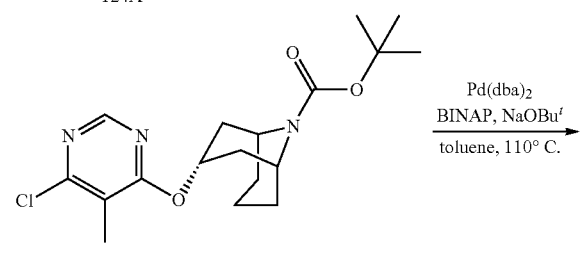

374

A mixture of compound 117A (42 mg, 0.12 mmol), 2-methyl-6-(methylsulfonyl)pyridin-3-amine 124A (20 mg, 0.11 mmol), Pd(dba)₂ (4.0 mg). BINAP (11 mg, 0.02 mmol) and sodium t-butoxide (19 mg, 0.20 mmol) in toluene (3.5 mL) was heated to 110° C. in a sealed tube. After 17 hours, the reaction was concentrated in vacuo and purified by preparative thin layer chromatography (50% acetone/hexanes) to provide compound 374 (23 mg, 41%). M+H=517

Example 125

Preparation of Compound 375

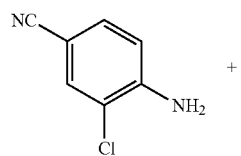

+

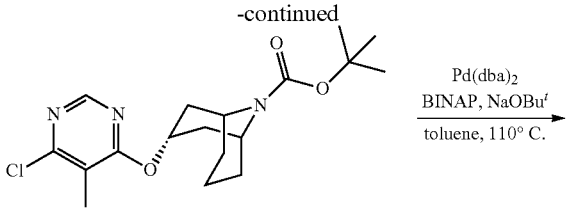

117A

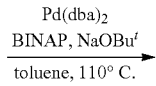

51

4-Amino-3-chlorobenzonitrile (50 mg, 0.32 mmol) was reacted with compound 117A (163 mg, 0.44 mmol) using the method described in Example 124 to provide compound 375 (49 mg, 23%). M+H=484

Example 126

Preparation of Compound 376

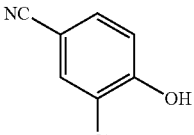

+

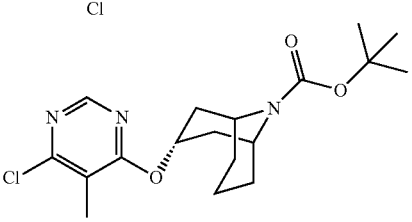

117A

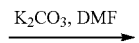

K₂CO₃, DMF

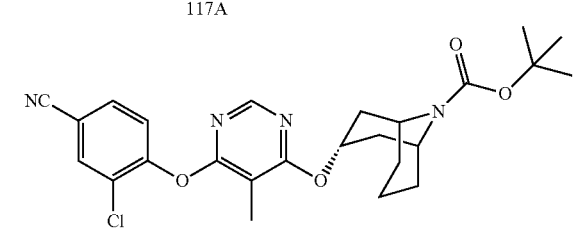

376

A mixture of compound 117A (153 mg, 0.41 mmol), 3-chloro-4-hydroxybenzonitrile 52 (125 mg, 0.82 mmol) and K₂CO₃ (113 mg, 0.82 mmol) in DMF (2.5 mL) was heated to 190° C., in the microwave for 40 min at high absorption. The reaction mixture was concentrated in vacuo. The residue was partitioned between water and ether. The organic layer was dried over MgSO₄, filtered and concentrated in vacuo. Purification by preparative thin layer chromatography (20% acetone/hexanes) provided compound 376 (48 mg, 24%). M+H=485

Example 127

Preparation of Compound 377

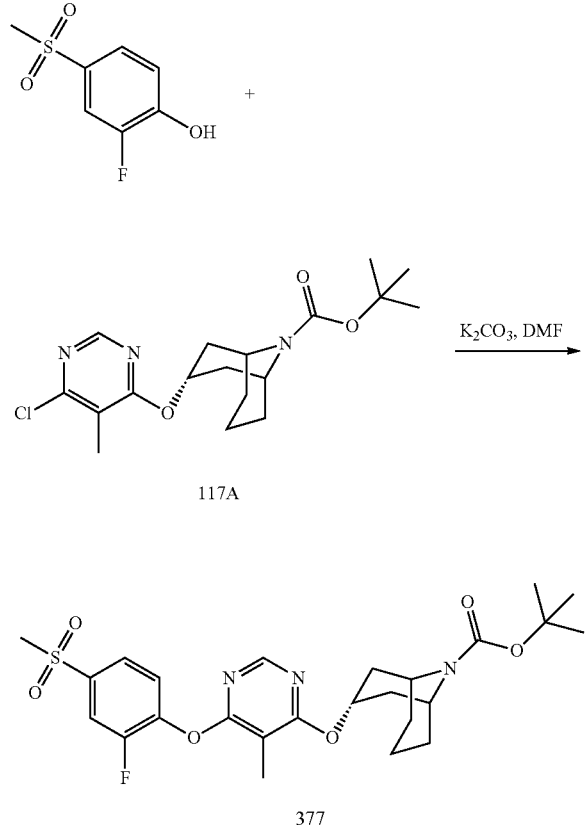

2-Fluoro-4-(methylsulfonyl)phenol (156 mg, 0.82 mmol) was reacted with compound 117A (150 mg, 0.41 mmol) using the method described in Example 126 to provide compound 377 (52 mg, 24%). M+H=522

Example 128

Preparation of Compound 378

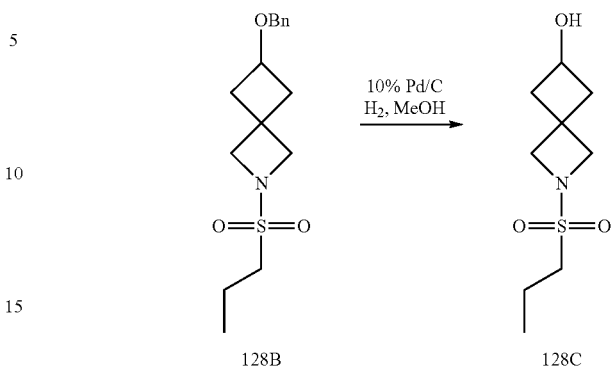

To compound 122C (137 mg, 0.37 mmol) in MeOH (6 mL) was added ammonium formate (167 mg, 2.65 mmol) and 10% Pd/C; (55 mg) under nitrogen. The resulting mixture was refluxed for 18 h and then cooled to room temperature. The reaction was filtered through celite and washed with MeOH. The filtrate was concentrated in vacuo to provide the crude amine 128A (75 mg, 100%) which was used in the next reaction without further purification.

To a solution of amine 128A (75 mg, 0.37 mmol) in dichloromethane (5.5 mL) was added triethylamine (0.15 mL, 1.11 mmol) under nitrogen. The reaction was cooled to 0° C. and n-propyl sulfonyl chloride (0.08 mL, 0.74 mmol) was added. The reaction was warmed to room temperature and stirred for 20 hours. The reaction mixture was diluted with dichloromethane and washed with water several times. The organic layer was dried over MgSO$_4$, filtered and concentrated in mow. Purification by silica gel flash chromatography (0-30% EtOAc/hexanes) provided the desired compound 128B (15 mg, 13%).

A mixture of the benzyl ether 128B (15 mg, 0.05 mmol) in MeOH (3 mL) and 3 Pd/C (9 mg) was hydrogenated at 1 atm for 16 hours. The reaction was filtered through celite, washed with MeOH and concentrated in vacuo to provide the desired alcohol 128C (8 mg, 75%) which was used in the next reaction without further purification.

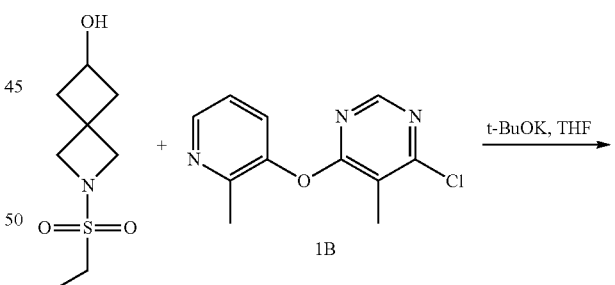

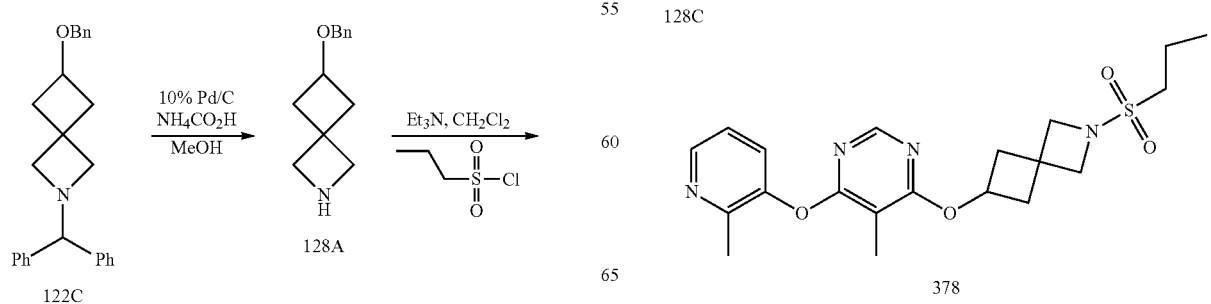

Alcohol 128C (8 mg, 0.04 mmol) was reacted with compound 1B (9 mg, 0.04 mmol) using the method described in Example 109 to provide compound 378 (1.4 mg, 8%). MH=419

Example 129

Preparation of Compound 379

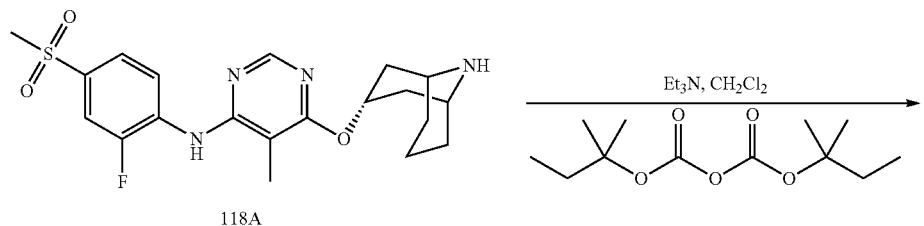

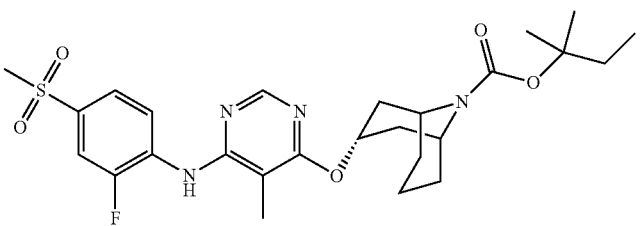

To a solution of amine 118A (31 mg, 0.074 mmol) in dichloromethane (2 mL) was added triethylamine (0.03 mL, 0.2 mmol) under nitrogen. The reaction was cooled to 0° C. and di-tort-amyl dicarbonate (0.04 mL, 0.2 mmol) was added. The reaction was warmed to room temperature and stirred for 18 hours. The reaction mixture was diluted with dichloromethane and washed with water several times. The organic layer was dried over MgSO₄, filtered and concentrated in vacuo. Purification by preparative thin flash chromatography (50% EtOAc/hexanes) provided the desired compound 379 (25 mg, 64%). M+H=533

Example 130

Preparation of Compound 380

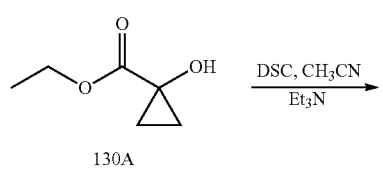

-continued

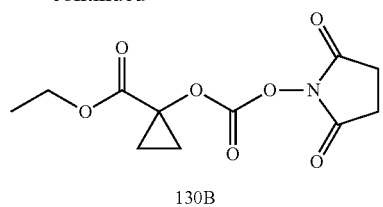

To ethyl 1-hydroxycyclopropanecarboxylate 130A (250 mg, 1.9 mmol) in acetonitrile (2 mL) was added N,N-disuccinimidyl carbonate (590 mg, 2.3 mmol) under nitrogen. The reaction was stirred for 5 min and then triethylamine (0.8 mL, 5.8 mmol) was added dropwise. After 20 hours, the reaction was diluted with EtOAc and washed with saturated aqueous NaHCO₃, followed by brine. The organic layer was dried over MgSO₄, filtered and concentrated to provide the crude product 130B (275 mg, 53%) which was used in the next reaction without further purification.

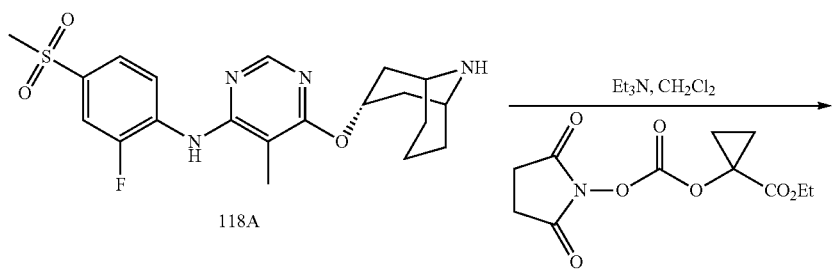

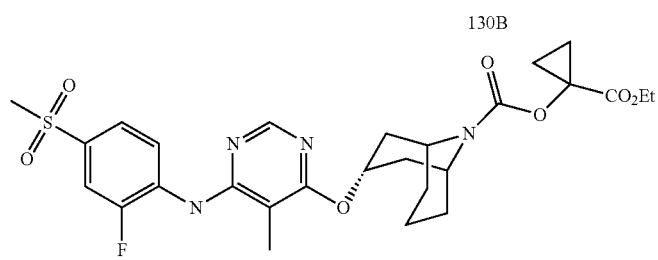

To a solution of amine 118A (25 mg, 0.06 mmol) in dichloromethane (2.5 mL) was added triethylamine (0.03 mL, 0.18 mmol), followed by a solution of ethyl 1-((2-dioxopyrrolidin-1-yloxy)carbonyloxy)cyclopropanecarboxylate 130B (33 ing, 0.12 mmol) in dichloromethane (1 mL). The reaction was stirred at room temperature under nitrogen for 20 hours. The reaction was diluted with dichloromethane and washed with water. The organic layer was dried over $MgSO_4$, filtered and concentrated in vacuo. Purification by preparative thin layer chromatography (50% EtOAc/hexanes) provided compound 380 (18 mg, 51%). M+H=577

Example 131

Preparation of Compound 381

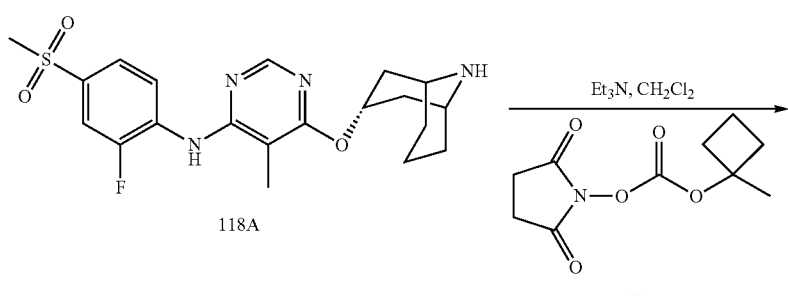

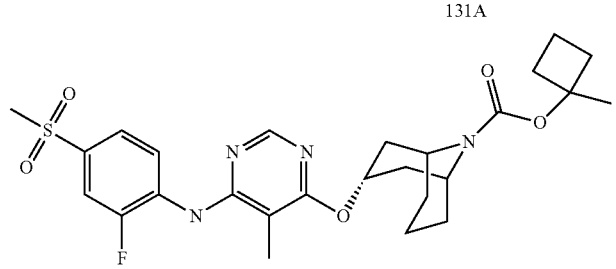

Amine 118A (31 mg, 0.074 mmol) was reacted according to the method described in Example 130 using 2,5-dioxopyrrolidin-1-yl 1-methylcyclobutyl carbonate 131A (34 mg, 0.15 mmol) to provide the desired compound 381 (16 mg, 42%). M+H=535

Example 132

Preparation of Compound 382

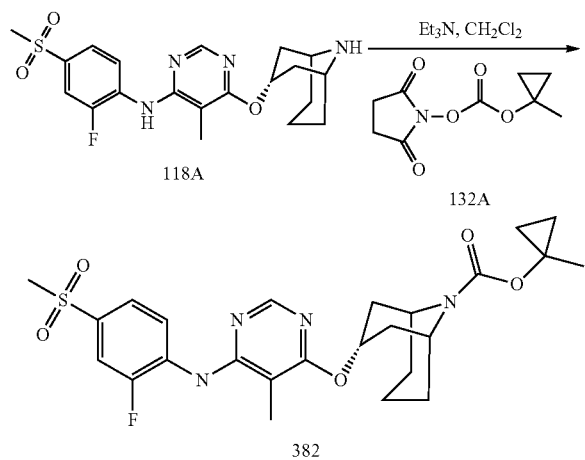

Amine 118A (25 mg, 0.06 mmol) was reacted according to the method described in Example 130 using 2,5-dioxopyrrolidin-1-yl 1-methylcyclopropyl carbonate 132A (26 mg, 0.12 mmol) to provide compound 382 (18 mg, 58%). M+H=519

Example 133

Preparation of Compound 383

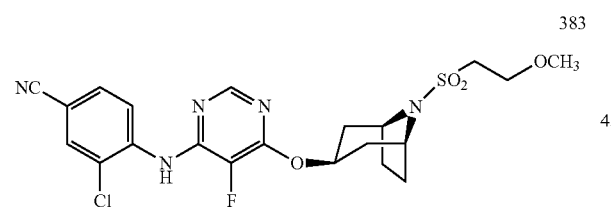

Compound 383 was prepared using the method described in Example 249, and by substituting cyclopropylsulfonyl chloride with 2-methoxyethanesulfonyl chloride (made as described in European Patent Publication No. EP 176327).

Example 134

Preparation of Compound 384

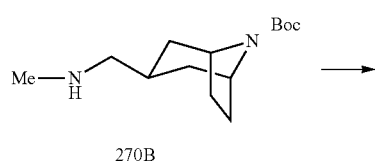

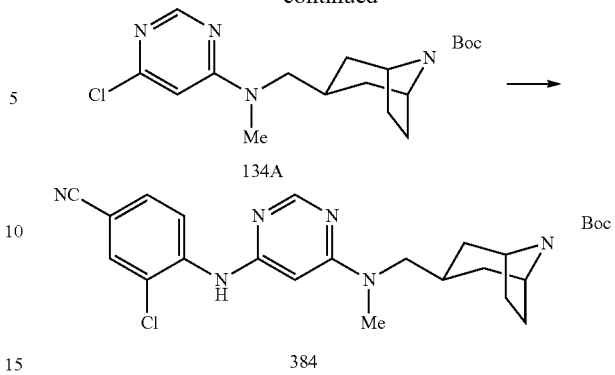

Step A—Synthesis of Compound 134A

Compound 270B (0.359 g, 1.42 mmol) was combined with 4,6-dichloropyrimidine (0.150 g, 1.00 mmol) and $K_2CO_3$ (0.195 g, 1.41 mmol) in dioxane (5 mL). The resulting reaction was heated to 100° C. and allowed to stir at this temperature for 0.22 hours, then cooled to room temperature and concentrated in vacuo. The residue obtained was purified using preparative TLC to provide compound 134A as a yellow oil.

Step B—Synthesis of Compound 384

Compound 134A (0.080 g, 0.22 mol), 4-amino -chlorobenzonitrile (0.045 g, 0.29 mmol), (±)-BINAP (0.008 g, 0.01 mmol), $Pd_2$ $dba_3$ (0.0025 g, 0.004 mmol) and NaO-tBu (0.027 g, 0.28 mmol) were combined in toluene (4 mL) and the resulting reaction was heated to 110° C. and allowed to stir at this temperature for 20 hours. The reaction mixture was allowed to cool to room temperature, then was concentrated in vacuo and the residue obtained was purified using preparative TLC to provide compound 384 as a yellow gum. MS: m/e 483, 485.

Example 135

Preparation of Compound 385

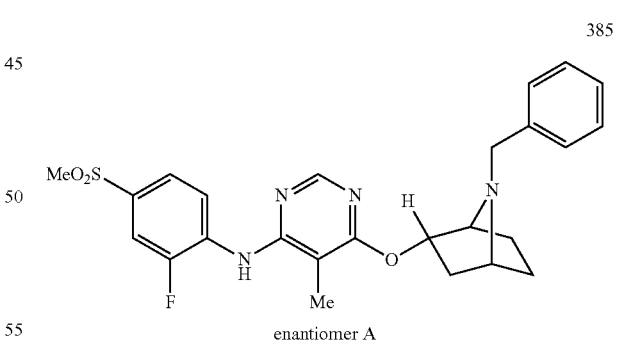

Compound 586 was deprotected according to the method described in the first step of Example 116. The resulting hydrochloride salt (0.020 g, 0.047 mmol) was combined with DIPEA (0.033 mL, 0.19 mmol) and benzyl bromide (0.024 g, 0.14 mmol) in dioxane (2 mL), The mixture was heated to 90° C. and allowed to stir at this temperature for 8 hours, then the reaction mixture was allowed to cool to room temperature and concentrated in vacuo. The residue obtained was then purified using preparative TLC to provide compound 385 as a yellow solid. MS: m/e 483.

Example 136
Preparation of Compound 386
271B ⟶
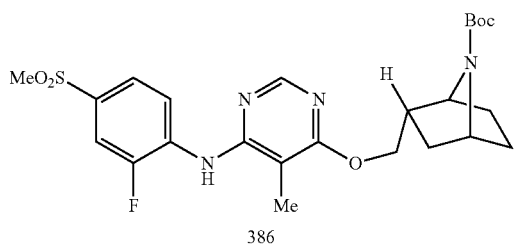
386
Compound 271B was reacted according to the method described in Example 56 to provide compound 386 as a white solid. MS: m/e 507.
Using various methods described herein, compound 386 was deprotected and converted the following compounds of the present invention:
Example 137
Preparation of Compound 387
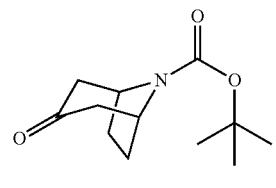
137A
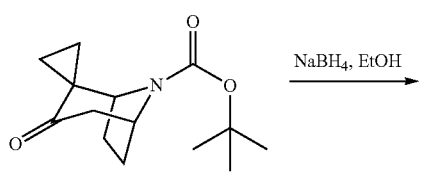
137B
| Cpd. No. | Structure | LCMS (MH+) |
|---|---|---|
| 496 | 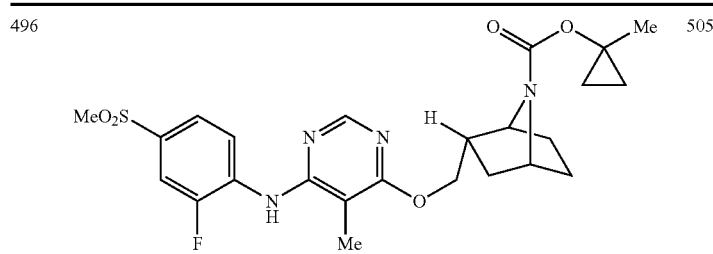 | 505 |
| 497 | 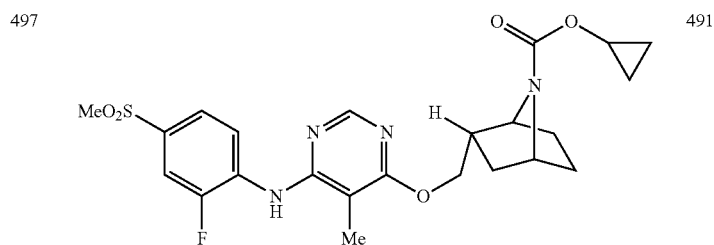 | 491 |
| 498 | 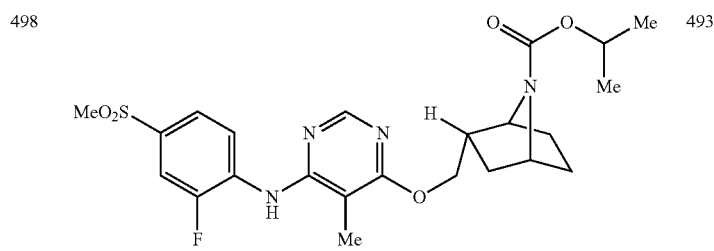 | 493 |

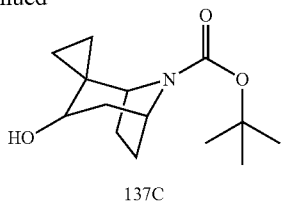

137C

To a solution of potassium t-butoxide (1 equivalent) in butanol (36 mL) was added N-Boc-nortropinone 137A (500 mg, 2.22 mmol) under nitrogen. After 5 minutes, 2-chlorethyldimethyl sulfonium iodide (1 equivalent) was added in portions over 10 minutes. 2-Chloroethyldimethyl sulfonium iodide was prepared according to Tet. Lett. 1984, 25:5501-04. After stirring for 2 hours, more potassium t-butoxide (1.1 equivalent) in t-butanol (36 mL) was added and the reaction was stirred at room temperature for 16 hours. The reaction mixture was poured onto water and extracted with EtOAc. The combined organics were dried over $MgSO_4$, filtered and concentrated in vacuo. Purification by silica gel flash chromatography (0-40% EtOAc/hexanes) provided compound 137B (100 mg, 18%).

To a solution of ketone 137B (100 mg, 0.40 mmol) in EtOH (28 mL) was added sodium borohydride (1.4 equivalent) under nitrogen at 0° C. The reaction was warmed to room temperature and stirred for 18 hours. The reaction was quenched with water and extracted with dichloromethane. The organic layer was dried over $Na_2SO_4$, filtered and concentrated in vacuo to provide the crude product 137C (100 mg, 99%) which was used in next reaction without further purification.

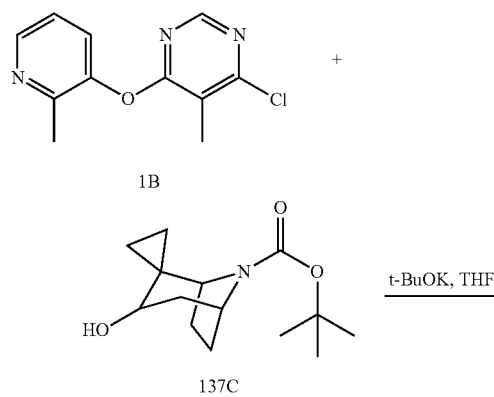

1B

137C

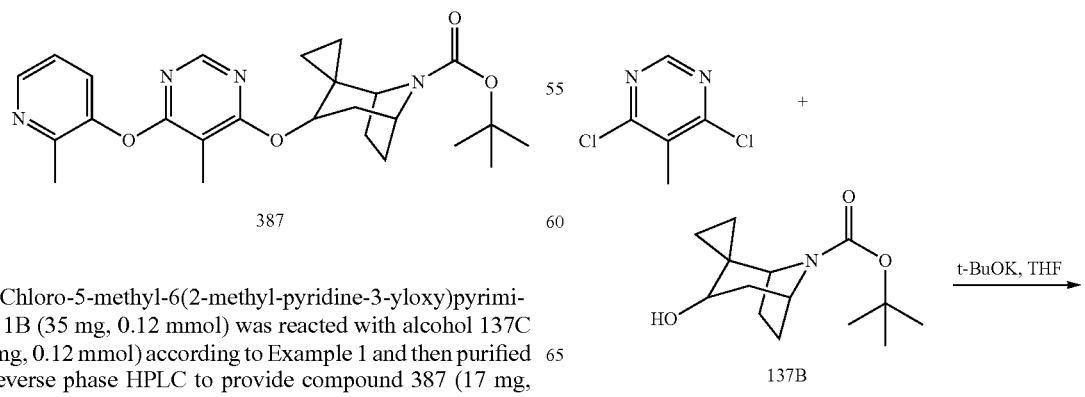

387

4-Chloro-5-methyl-6(2-methyl-pyridine-3-yloxy)pyrimidine 1B (35 mg, 0.12 mmol) was reacted with alcohol 137C (30 mg, 0.12 mmol) according to Example 1 and then purified by reverse phase HPLC to provide compound 387 (17 mg, 56%). M+H=453

Example 138

Preparation of Compound 388

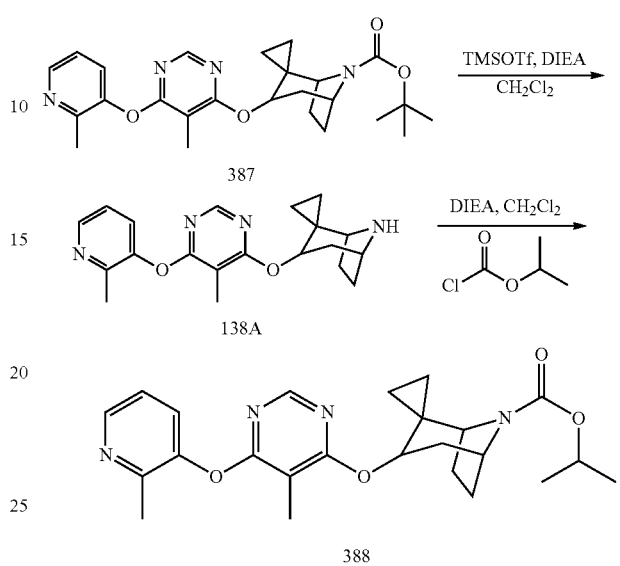

387

138A

388

To a solution of compound 387 (15 mg, 0.033 mmol) in dichloromethane (3 mL) was added DEA (3 equivalents), followed by trimethylsilyl trifluoromethanesulfonate (1.5 equivalents) at 0° C. under nitrogen. The reaction was warmed to room temperature and stirred for 1.5 hours. The reaction was quenched with water and extracted with DCM. The organic layer was dried over $MgSO_4$, filtered and concentrated to give the free amine 138A (12 mg, 100%) which was used in the next reaction without further purification.

To the free amine 138A (12 mg, 0.033 mmol) in DCM (3 mL) was added DIEA (3 equivalents) followed by isopropyl chloroformate (2 equivalents) at 0° C. under nitrogen. The reaction was warmed to room temperature and stirred for 2 hours. The reaction was diluted with DCM and washed with saturated aqueous $NH_4Cl$. Purification by preparative thin layer chromatography (4% MeOH/DCM) afforded the desired compound 388 (9 mg, 64° A). M+H=439.

Example 139

Preparation of Compound 389

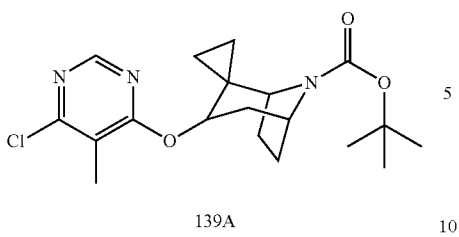

139A

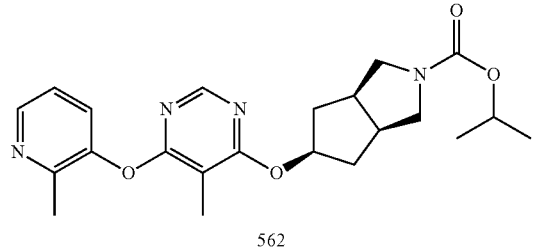

562

Alcohol 137B (30 mg, 0.12 mmol) was reacted with 4,6-dichloro-5-methylpyrimidine (25 mg, 0.15 mmol) using the method described in Example 1 to provide compound 139A (155 mg, 75%).

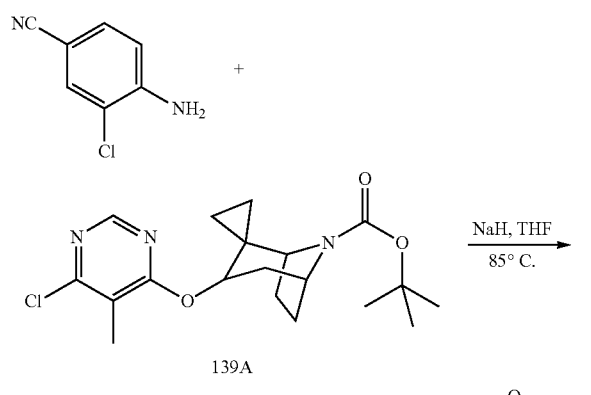

389

4-Amino-3-chlorobenzonitrile (13 mg, 0.08 mmol) was reacted with compound 139 (30 mg, 0.08 mmol) using the method described in Example 36 to provide compound 389 (32 mg, 81%). M+H=496

Example 140

Preparation of Compound 562

Trifluoroacetic acid (10 mL, 20% in DCM) was added to a solution of compound 359 (1.0 g) in DCM (5 mL) at room temperature and the resulting reaction was allowed to stir for 2 hours. The reaction mixture was then concentrated in vacuo and the residue obtained (50 mg) was taken up with isopropyl chlorocarbamate (0.3 M in toluene) in dichloromethane (3 mL) and the resulting solution was cooled to 0° C. To the cooled solution was added Et$_3$N (0.2 mL) and the ice water bath was then removed and the reaction was allowed to stir at room temperature for an additional 16 hours. The reaction was quenched with saturated aqueous NaHCO$_3$, extracted with dichloromethane (3×10 mL) and the combined organic layers were dried over Na$_2$SO$_4$, filtered and concentrated in vacuo. The resulting residue was purified using in vacuo a silica gel column (ISCO) with MeOH (NH$_3$) in dichloromethane (0→5%) to provide compound 562 (25 mg). LCMS: 412.5

Example 141

Preparation of Compound 563

563

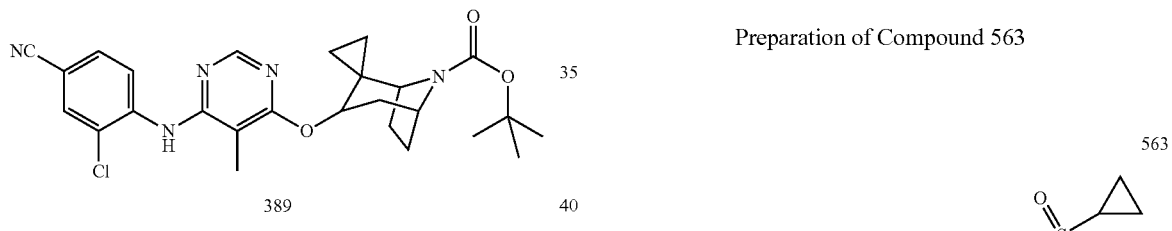

Using the method described in Example 140 and substituting cyclopropylsulfonyl chloride for isopropyl chlorocarbamate, compound 563 was made. LCMS (MH$^+$)=430.5

Example 142

Preparation of Compound 392

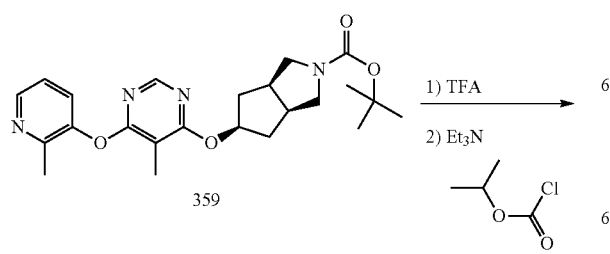

359

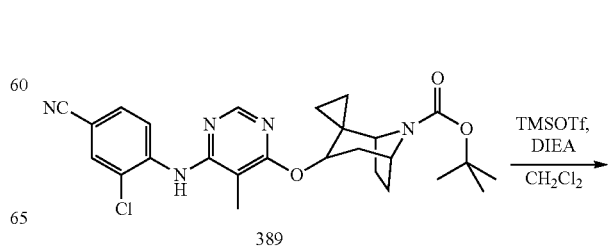

389

347

-continued

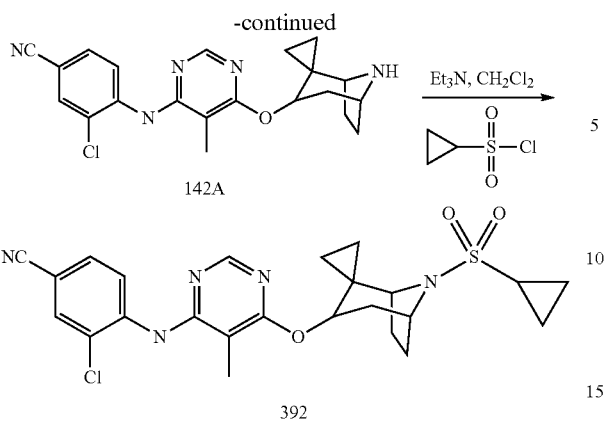

142A

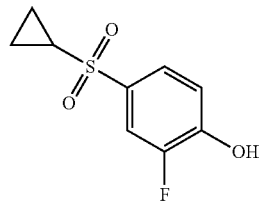

392

Compound 389 (20 mg, 0.043 mmol) was reacted using the method described in Example 138 to provide the free amine 142A (17 mg, 100%) which was used in the next reaction without further purification.

The free amine 142A (17 mg, 0.043 mmol) was reacted using the method described in Example 116 to provide compound 392 (13 mg, 62%). M+H=500

Example 143

Preparation of Compound 143A

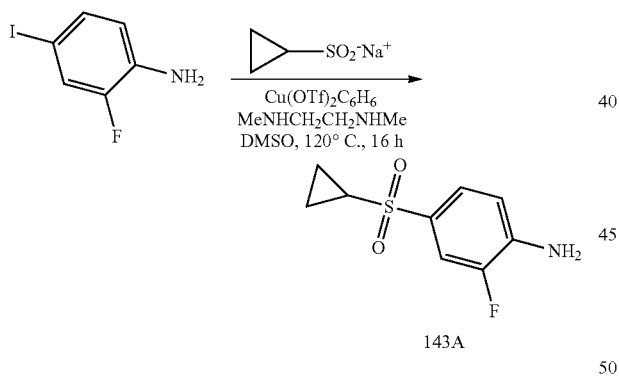

143A

To 2-fluoro-4-iodoaniline (1.0 g, 4.2 mmol) in DMSO (5 mL) were added cyclopropanesulfonic acid, sodium salt (0.65 g, 5.1 mmol), copper trifluoromethanesulfonate benzene complex (106 mg, 0.21 mmol), and N,N'-dimethylethene diamine (0.045 mL, 0.42 mmol), and the solution was stirred at 120T for 16 h. Allowed to cool, added H$_2$O (100 mL), added EtOAc (100 mL), mixed, separated layers, extracted aqueous layer with EtOAc, combined organic layers, dried (MgSO$_4$), filtered, and concentrated. Purified by column chromatography on silica gel using (30% EtOAc-hexanes) to provide compound 143A as a tan solid (0.9 g, 99%).

348

Example 144

Preparation of Compound 144A

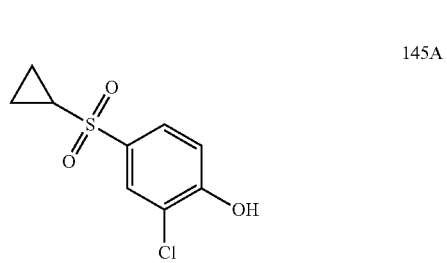 [SMILES: O=S(=O)(c1ccc(O)c(Cl)c1)C1CC1]

Using the method described in Example 143 and substituting 4-bromo-2-fluorophenol for 4-iodo-2-fluoroaniline, compound 144A was prepared.

Example 145

Preparation of Compound 145A

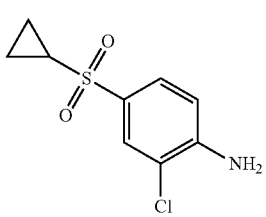

Using the method described in Example 143 and substituting 4-bromo-2-chlorophenol for 4-iodo-2-fluoroaniline, compound 145A was prepared.

Example 146

Preparation of Compound 146A

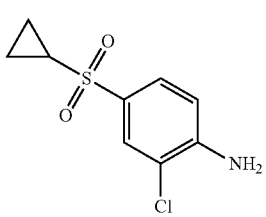

Using the method described in Example 143 and substituting 4-bromo-2-chloroaniline for 4-iodo-2-fluoroaniline, compound 146A was prepared.

Example 147

Preparation of Compound 147A

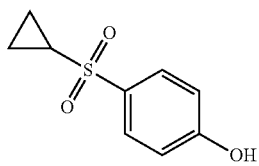

147A

Using the method described in Example 143 and substituting 4-bromophenol for 4-iodo-2-fluoroaniline, compound 147A was prepared.

Example 148

Preparation of Compound 148A

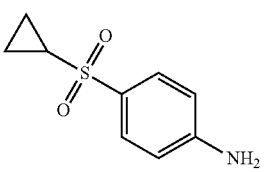

148A

Using the method described in Example 143 and substituting 4-iodo niline for 4-iodo-2-fluoroaniline, compound 148A was prepared.

Example 149

Preparation of Compound 149A

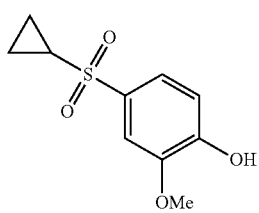

149A

Using the method described in Example 143 and substituting 4-bromo-2-methoxyphenol for 4-iodo-2-fluoroaniline, compound 149A was prepared.

Example 150

Preparation of Compound 150A

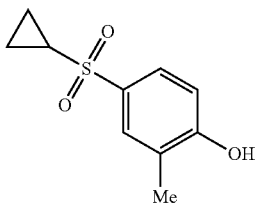

150A

Using the method described in Example 143 and substituting 4-bromo-2-methylphenol for 4-iodo-2-fluoroaniline, compound 150A was prepared.

Example 151

Preparation of Compound 151A

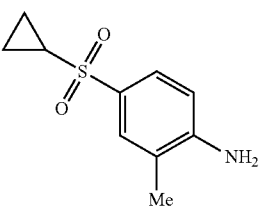

151A

Using the method described in Example 143 and substituting 4-bromo-2-methylaniline for 4-iodo-2-fluoroaniline, compound 151A was prepared.

Example 152

Preparation of Compound 152A

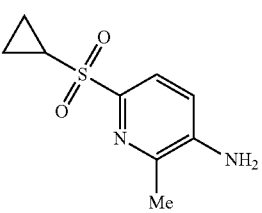

152A

Using the method described in Example 143 and substituting 3-amino-6-chloro-2-picoline for 4-iodo-2-fluoroaniline, compound 152A was prepared.

Example 153

Preparation of Compound 153B

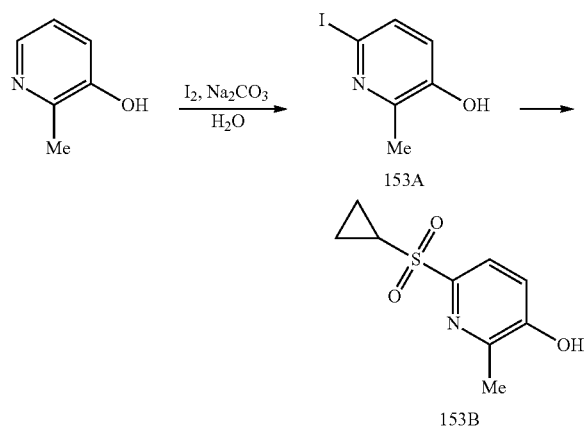

To a solution of 3-hydroxy-2-methylpyridine (2.0 g, 18.3 mmol), $Na_2CO_3$ (3.9 g, 36.6 mmol) in $H_2O$ (50 mL) was added $I_2$ (4.8 g, 19 mmol) and the solution was stirred for 3 h. The reaction was neutralized with 1N HCl to a pH ~5. Precipitate was collected by filtration, rinsed with $H_2O$, rinsed with aqueous 1N sodium bisulfite solution, and dried under vacuum to provide compound 153A (2.0 g, 46%). Using the method described in Example 143 and substituting compound 153A for 4-iodo-2-fluoroaniline, compound 153B was prepared.

Example 154

Preparation of Compound 154A

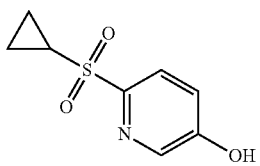

Using the method described in Example 143 and substituting 5-hydroxy-2-bromopyridine for 4-iodo-2-fluoroaniline, compound 154A was prepared.

Example 155

Preparation of Compound 155A

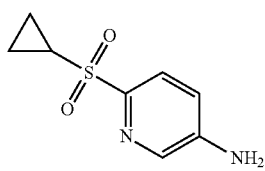

Using the method described in Example 143 and substituting 5-amino-2-iodopyridine for 4-iodo-2-fluoroaniline, compound 155A was prepared.

Example 156

Preparation of Compound 393

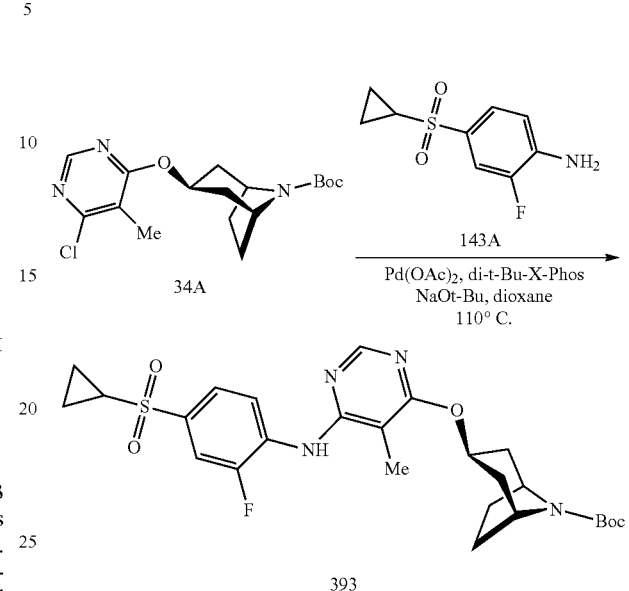

To a solution of compound 34A (300 mg, 0.80 mmol) in dioxane (2 mL) was added compound 143A (183 mg, 0.80 mmol), $Pd(OAc)_2$ (10 mg, 0.04 mmol), di-tert-butyl-X-Phos (22 mg, 0.05 mmol) and NaOt-Bu (204 mg, 2.1 mmol). The resulting reaction heated to 110° C. and allowed to stir at this temperature for 16 hours, then allowed to cool to room temperature and concentrated in vacuo. The resulting residue was purified using preparative thin layer chromatography (35% Acetone-Hexanes) to provide compound 393 (126 mg, 30%). LCMS $(M+H)^+=533.3$

Example 157

Preparation of Compound 394

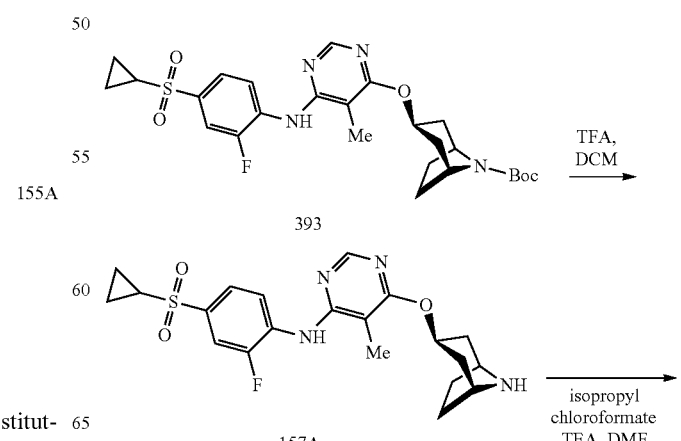

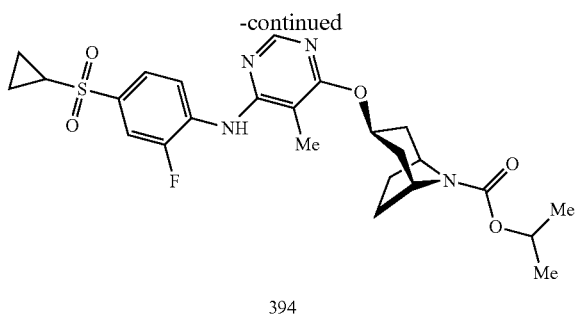

394

Trifluoroacetic acid (150 μL) was added to a solution of compound 393 (105 mg, 0.20 mmol) in DCM (500 μL) at room temperature and stirred for 3 h. The solution was concentrated in vacuo and to the resulting crude residue of compound 157A was added DMF (650 μL), TEA (110 μL, 0.8 mmol), and isopropyl chloroformate (55 μL, 1.0 M in toluene, 0.4 mmol) at room temperature and stirred overnight. The solution was concentrated in vacuo and purified by preparative thin layer chromatography using (25% Acetone-Hexanes) to provide compound 394 (36 mg, 35%). LCMS (M+H)$^+$=519.2

Example 158

Preparation of Compound 395

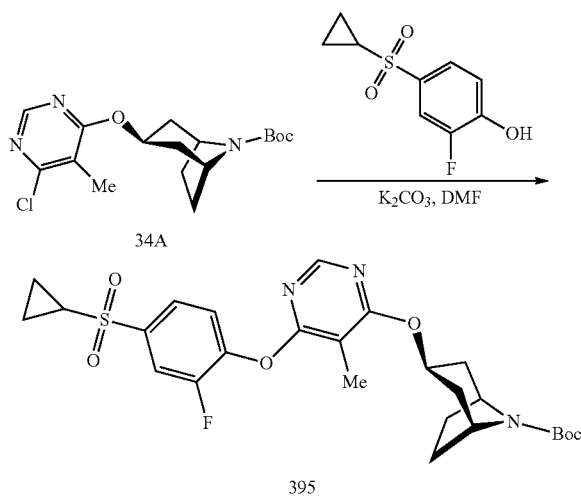

395

To a solution of compound 34A (540 mg, 1.5 mmol) and compound 144A (300 mg, 1.4 mmol) in DMF (4.6 mL) was added $K_2CO_3$ (230 mg, 1.7 mmol) and the solution was stirred and heated to 120° C. overnight. Allowed reaction to cool, concentrated in vacuo, and purified by preparative thin layer chromatography using (30% Acetone-Hexanes) to provide compound 395 (234 mg, 31%). LCMS (M+H)$^+$=534.3

Example 159

Preparation of Compound 396

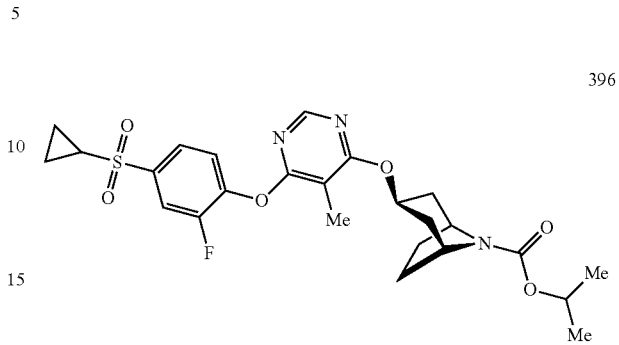

396

Using the method described in Example 157 and substituting compound 395 for compound 393, compound 396 was prepared. LCMS (M+H)$^+$=520.3

Example 160

Preparation of Compound 397

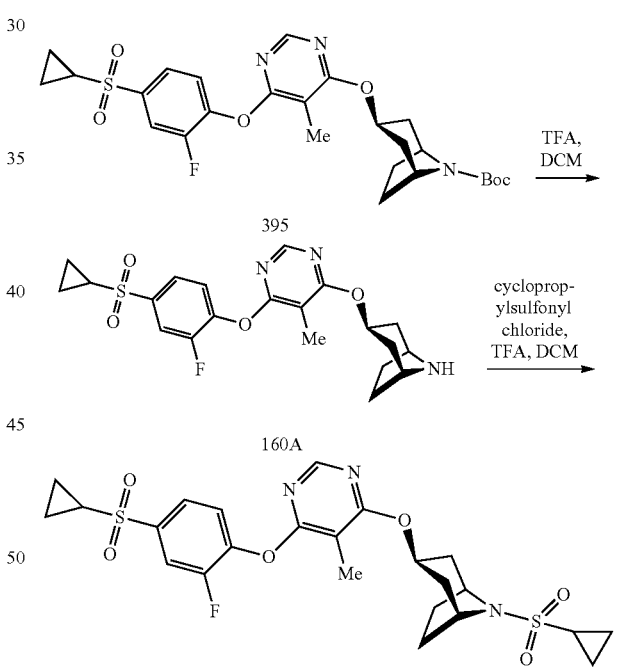

397

Trifluoroacetic acid (285 μL) was added to a solution of compound 395 (100 g, 0.20 mmol) in DCM (1.5 mL) at room temperature and stirred for 2 h. The solution was concentrated in vacuo to provide compound 160A. To the crude residue of compound 160A were added DCM (1.5 mL), TEA (105 μL, 0.8 mmol), and cyclopropylsulfonyl chloride (35 μL, 0.4 mmol) at room temperature and stirred 1.5 h. The solution was concentrated in vacuo and purified by preparative thin layer chromatography using (30% Acetone-Hexanes) to provide compound 397 (61 mg, 57%). LCMS (M+H)$^+$=538.3

Example 161

Preparation of Compound 398

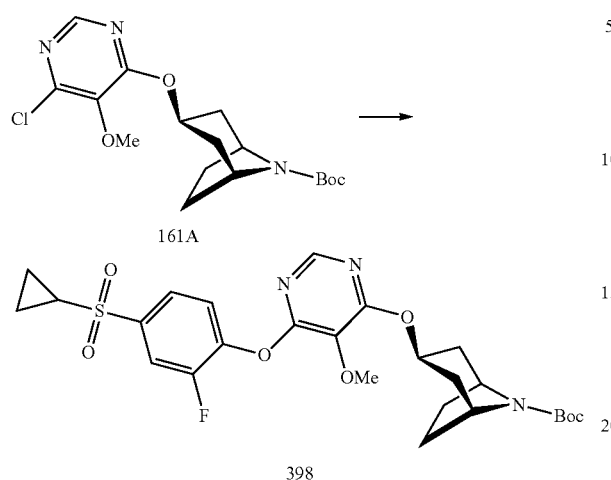

398

Using the method of Example 1 and substituting 4,6-dichloro-5-methoxypyrimidine for 4,6-dichloro-5-methylpyrimidine, compound 161A was prepared. Using the method of Example 3, substituting compound 161A for compound 1B, compound 398 was prepared. LCMS (M+H)$^+$=550.3

Example 162

Preparation of Compound 399

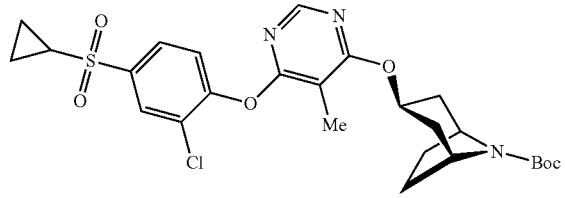

399

Using the method described in Example 153 and substituting compound 145A for compound 144A, compound 399 was prepared. LCMS (M+H)$^+$=550.3.

Example 163

Preparation of Compound 400

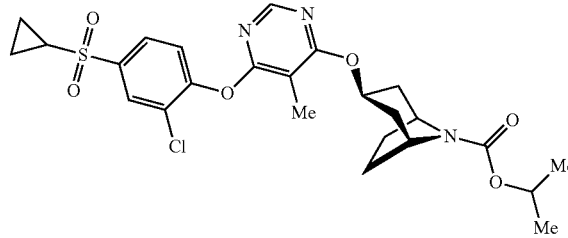

400

Using the method described in Example 157 and substituting compound 399 for compound 393, compound 400 was prepared. LCMS (M+H)$^+$=536.3

Example 164

Preparation of Compound 401

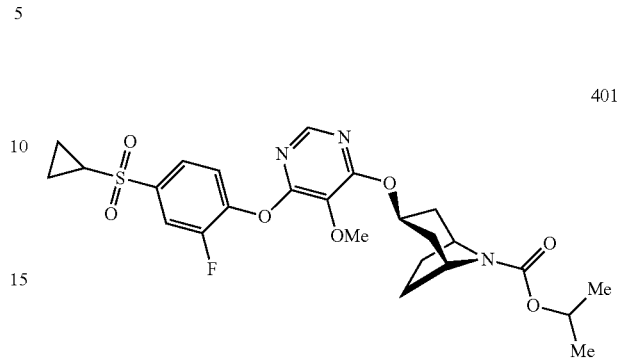

401

Using the method described in Example 157 and substituting compound 398 for compound 393, compound 401 was prepared. LCMS (M+H)$^+$=536.3

Example 165

Preparation of Compound 402

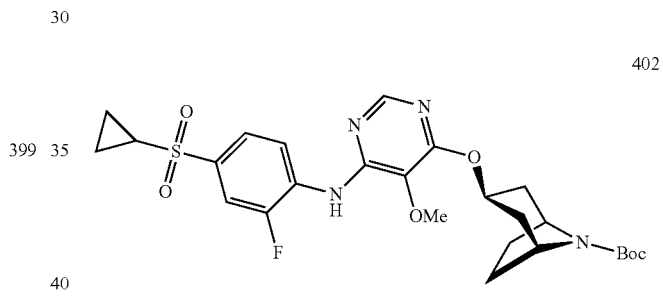

402

Using the method described in Example 161, substituting compound 161A for compound 1B, compound 402 was prepared. LCMS (M+H)$^+$=549.3

Example 166

Preparation of Compound 403

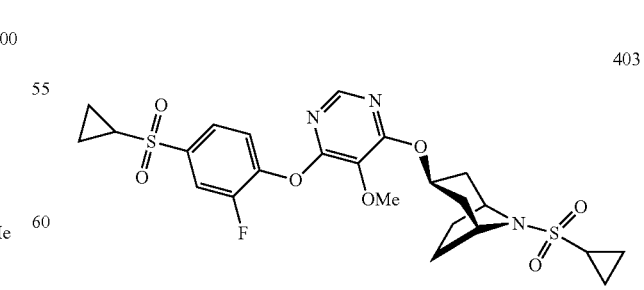

403

Using the method described in Example 160 substituting compound 398 for compound 395, compound 403 was prepared. LCMS (M+H)$^+$=554.3

Example 167

Preparation of Compound 404

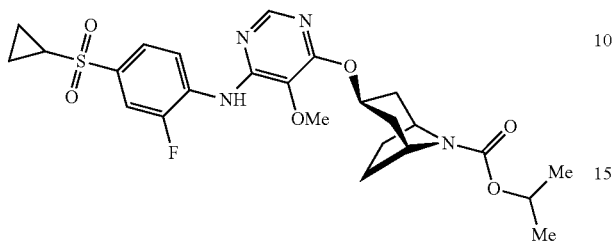

404

Using the method described in Example 157, substituting compound 402 for compound 393, compound 404 was prepared. LCMS (M+H)$^+$=535.3

Example 168

Preparation of Compound 405

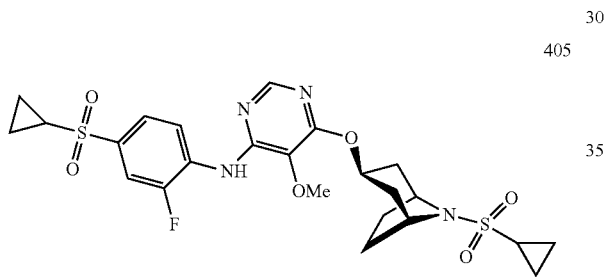

405

Using the method described in Example 160, substituting compound 402 for compound 395, compound 405 was prepared. LCMS (M+H)$^+$=553.3

Example 169

Preparation of Compound 406

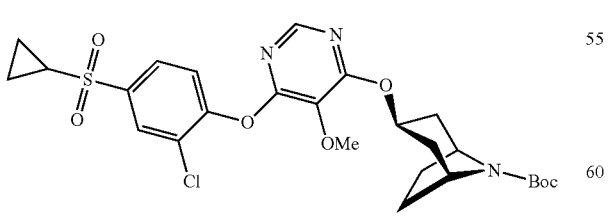

406

Using the method described in Example 158, substituting compound 145A for compound 144A and substituting compound 161A for compound 1B, compound 406 was prepared. LCMS (M+H)$^+$=566.3

Example 170

Preparation of Compound 407

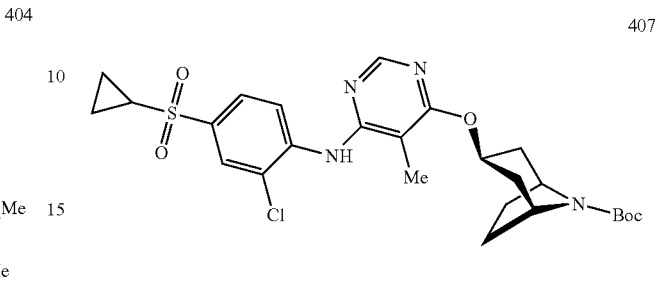

407

Using the method described in Example 156, substituting compound 146A for compound 144A, compound 407 was prepared. LCMS (M+H)$^+$=549.3

Example 171

Preparation of Compound 408

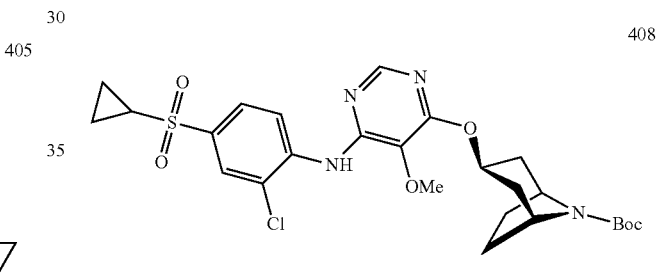

408

Using the method described in Example 156, substituting compound 146A for compound 144A and substituting compound 161A for 18, compound 408 was prepared. LCMS (M+H)$^+$=565.3

Example 172

Preparation of Compound 409

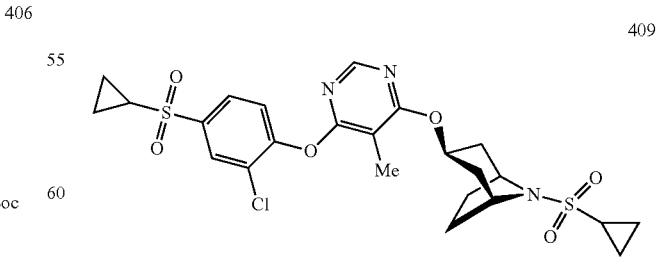

409

Using the method described in Example 160, substituting compound 399 for compound 395, compound 409 was prepared. LCMS (M+H)$^+$=554.3

Example 173

Preparation of Compound 410

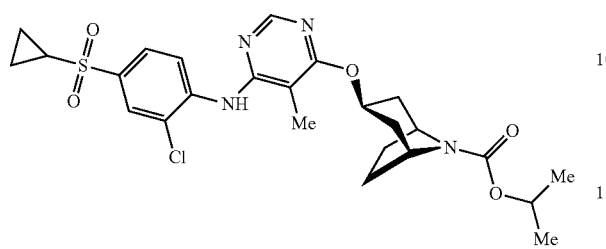

Using the method described in Example 157, substituting compound 407 for compound 393, compound 410 was prepared. LCMS (M+H)$^+$=535.3

Example 174

Preparation of Compound 411

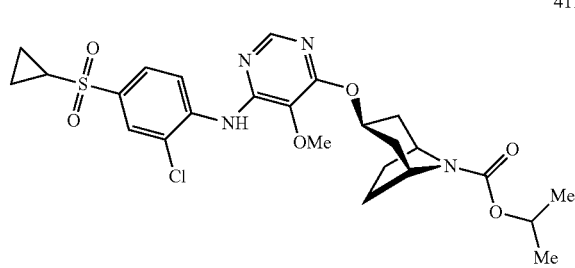

Using the method described in Example 157, substituting compound 408 for compound 393, compound 411 was prepared. LCMS (M+H)$^+$=551.3

Example 175

Preparation of Compound 412

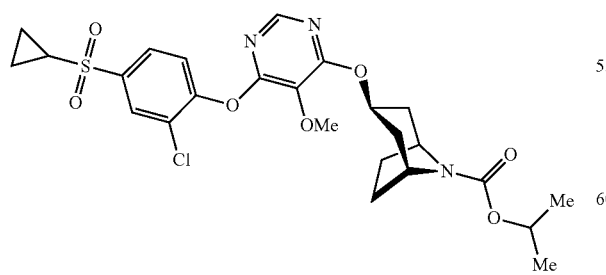

Using the method described in Example 157, substituting compound 406 for compound 393, compound 412 was prepared, LCMS (M+H)$^+$=552.3

Example 176

Preparation of Compound 413

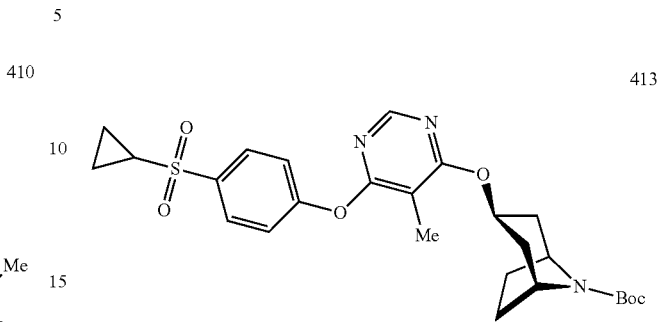

Using the method described in Example 158, substituting compound 147A for compound 144A, compound 413 was prepared. LCMS (M+H)$^+$=516.3

Example 177

Preparation of Compound 414

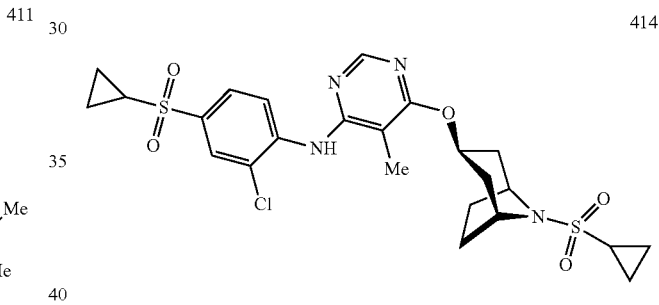

Using the method described in Example 160, substituting compound 407 for compound 395, compound 414 was prepared. LCMS (M+H)$^+$=553.3

Example 178

Preparation of Compound 415

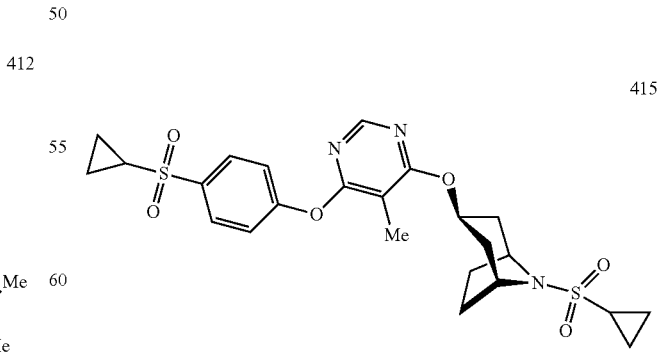

Using the method described in Example 160, substituting compound 413 for compound 395, compound 415 was prepared. LCMS (M+H)$^+$=520.3

Example 179

Preparation of Compound 416

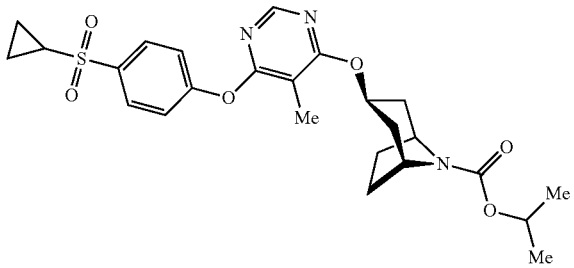

416

Using the method described in Example 157, substituting compound 413 for compound 393, compound 416 was prepared. LCMS (M+H)+=502.3

Example 180

Preparation of Compound 417

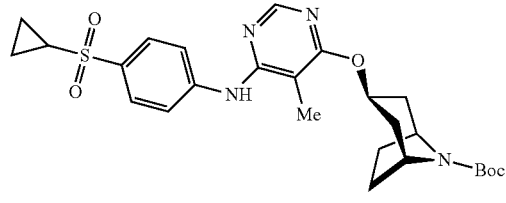

180A

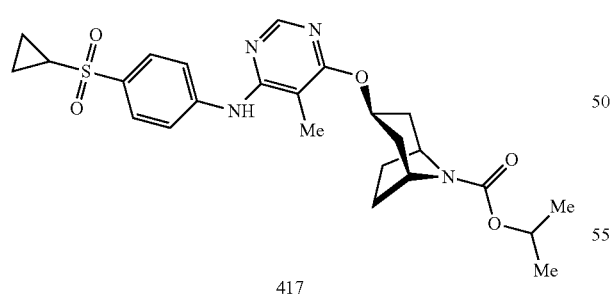

417

Using the method described in Example 156, substituting compound 148A for the starting material in step A, compound 180A was prepared. Using the method described in Example 157, substituting compound 180A for compound 393, compound 417 was prepared. LCMS (M+H)+=501.3

Example 181

Preparation of Compound 418

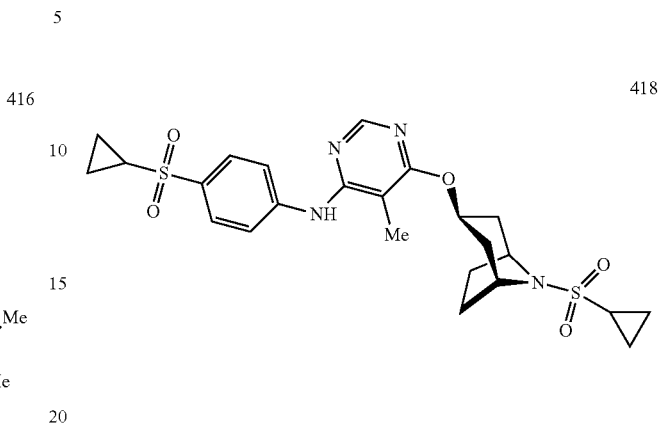

418

Using the method described in Example 160, substituting compound 180A for compound 395, compound 418 was prepared. LCMS (M+H)+=519.3

Example 182

Preparation of Compound 419

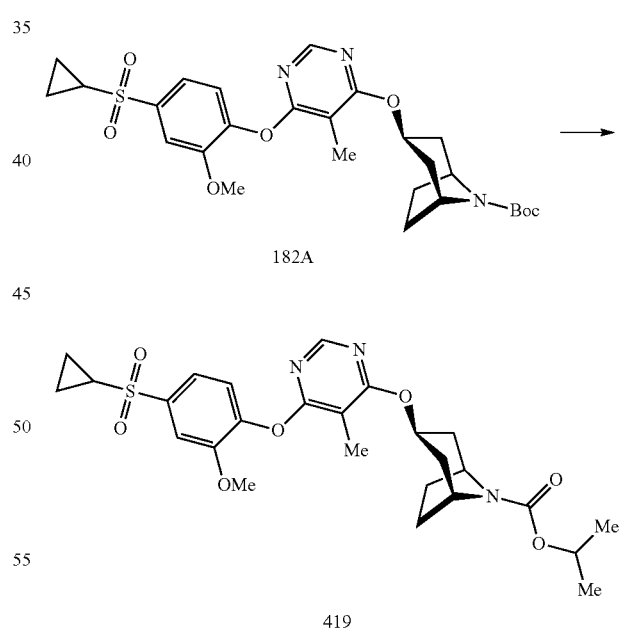

182A

419

Using the method described in Example 158, substituting compound 149A for compound 144A, compound 182A was prepared. Using the method described in Example 157, substituting compound 182A for compound 393, compound 419 was prepared. LCMS (M+H)+=532.3

Example 183

Preparation of Compound 420

Using the method described in Example 160, substituting compound 182A for compound 395, compound 420 was prepared. LCMS (M+H)+=550.3

Example 184

Preparation of Compound 421

Using the method described in Example 158, substituting compound 150A for compound 144A, compound 184A was prepared. Using the method described in Example 160, substituting compound 184A for compound 395, compound 421 was prepared. LCMS (M+H)+=534.3

Example 185

Preparation of Compound 422

Using the method described in Example 157, substituting compound 184A for compound 393, compound 422 was prepared. LCMS (M+H)+=516.3

Example 186

Preparation of Compound 423 p A—Synthesis of Compound 186B

Using the method described in Example 56, Step A, substituting compound 186A (prepared as described in Hodgson et al., *Tetrahedron* 60:5185 (2004)) as the starting material, compound 186B was prepared.

Step B—Synthesis of Compound 423

Iodotrimethylsilane (450 μL, 3.4 mmol) was added to a solution of compound 186B (350 mg, 1.13 mmol) in DCM (4 mL) at room temperature and the resulting solution was heated at 50° C. for 1.5 h. The reaction mixture was cooled to room temperature, saturated NaHCO₃, solution was added and the resulting solution was extracted with DCM. The organic layer was dried (MgSO₄) and concentrated in vacuo to provide compound 186C which was subsequently converted to compound 423 using the method described in Example 160, substituting compound 186C for compound 160A, followed by the method described in Example 158, substituting compound 145A for compound 144A. LCMS (M+H)+=552.3 (for compound 423).

Example 187

Preparation of Compound 424

Using the method described in Example 156, Step B, substituting compound 151A for compound 143A, compound 187A was prepared. Using the method described in Example 157, substituting compound 187A for compound 393, compound 424 was prepared. LCMS (M+H)+=515.3

Example 188

Preparation of Compound 425

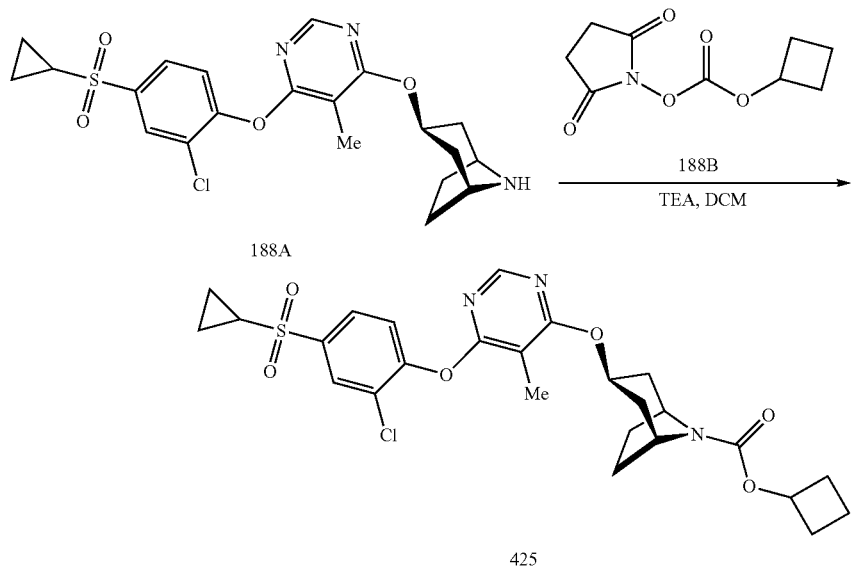

Using the method described in Example 157, Step A, substituting compound 399 for compound 393, compound 188A was prepared. To a solution of 188A (67 mg, 0.15 mmol) and TEA (50 µL, 0.36 mmol) in DCM (0.7 mL) was added compound 188B (31 mg, 0.15 mmol, prepared as described in WO 05/14577 to Zhu et al.) and the resulting reaction was allowed to stir for 4 hours. The solution was concentrated in vacuo and purified by preparative thin layer chromatography using (20% EtOAc-DCM) to provide compound 425 (81 mg, 98%). LCMS (M+H)+=548.3

Example 189

Preparation of Compound 426

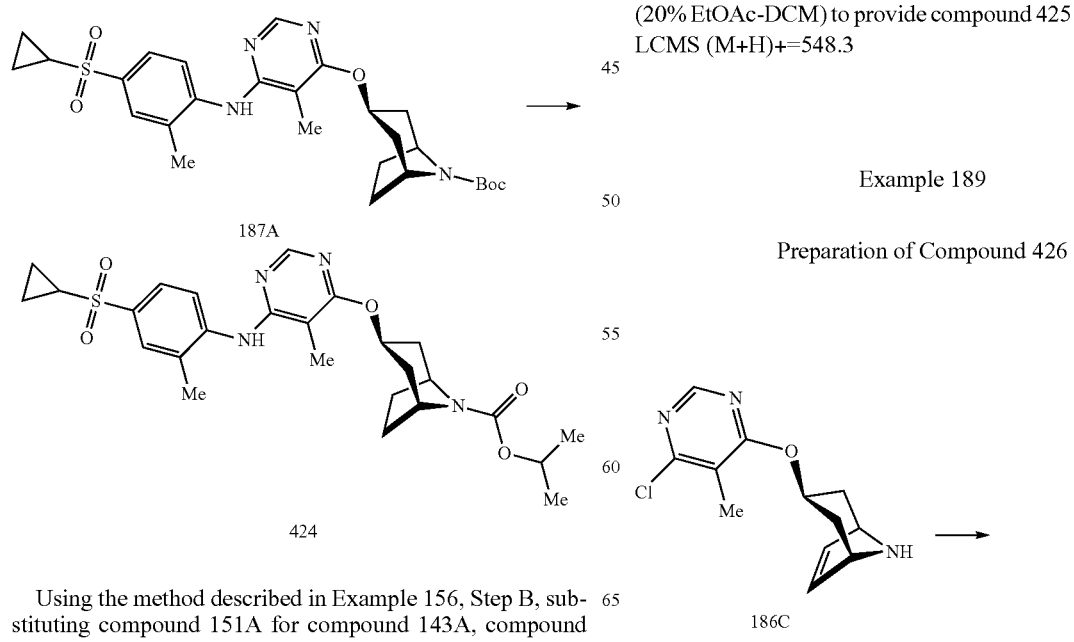

367

-continued

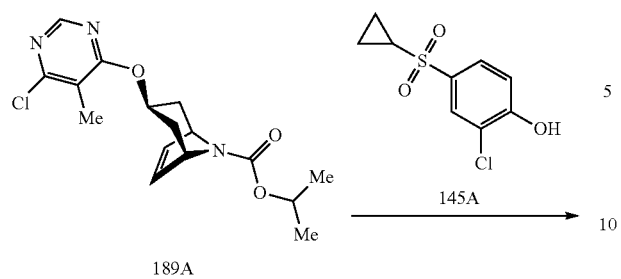

189A

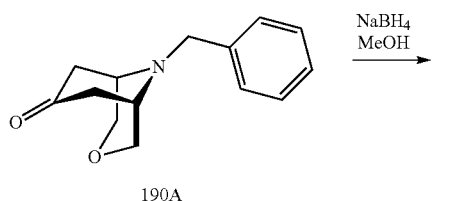

426

Using the method described in Example 157, Step B, substituting compound 186C for compound 393, compound 189A was prepared. Compound 189A was then reacted with compound 145A using the method described in Example 158 to provide compound 426. LCMS (M+H)+=534.3

Example 190

Preparation of Compound 427

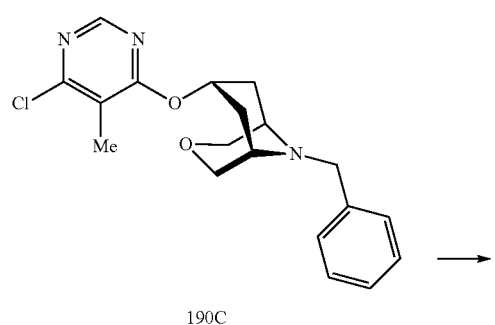

368

-continued

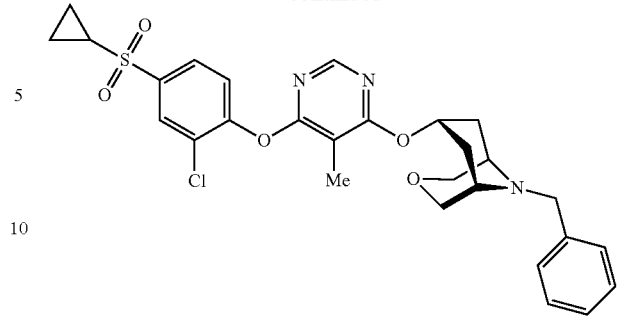

427

Step A—Synthesis of Compound 190A

To a solution of 1,4-anhydroerythritol (5.0 g, 48 mmol) in 1-170 (60 mL) was added NaIO$_4$ (5.1 g, 24 mmol). The solution was allowed to stir overnight at room temperature. To the solution was added MeCN (80 mL) and the solution was stirred for 30 minutes. The white precipitate was removed by filtration and the filtrate was concentrated in vacuo to remove the MeCN. To the aqueous layer 1,3-acetonedicarboxylic acid (7.0 g, 48 mmol) benzylamine (6.1 mL, 52 mmol), concentrated HCl (2.5 mL) were added and the solution was stirred at room temperature for 1 h and at 50° C. for 2 h. Cooled to 0° C., added 1 m NaOH to a pH ~10 and extracted with EtOAc and DCM. The organic layer was dried (MgSO$_4$) and concentrated in vacuo. The residue was purified using a silica gel cartridge (eluting with EtOAc in Hexanes 30%-100%) to provide compound 190A (3.2 g, 29%).

Step B—Synthesis of Compound 190B

To a solution of compound 190A (1.5 g, 6.5 mmol) in MeOH (20 mL) was added NaBH$_4$ (320 mg, 8.4 mmol) and the solution was stirred at room temperature for 10 h. Added H$_2$O (100 mL), extracted with EtOAc, dried the organic layer (MgSO$_4$), and concentrated in vacuo to provide compound 190B (1.4 g, 98%).

Step C—Synthesis of Compound 190C

Using the method described in Example 156, Step A and using compound 190B as the starting material, compound 190C was prepared.

Step D—Synthesis of Compound 427

Compound 427 was prepared by reacting compound 190C with compound 145A according to the method described in Example 158. LCMS (M+H)+=556.3

Example 191

Preparation of Compound 428

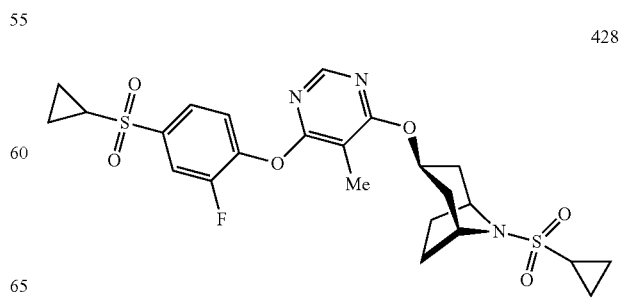

428

Using the method described in Example 158, substituting compound 186D for compound 34A, compound 428 was prepared. LCMS (M 536.3

Example 192

Preparation of Compound 429

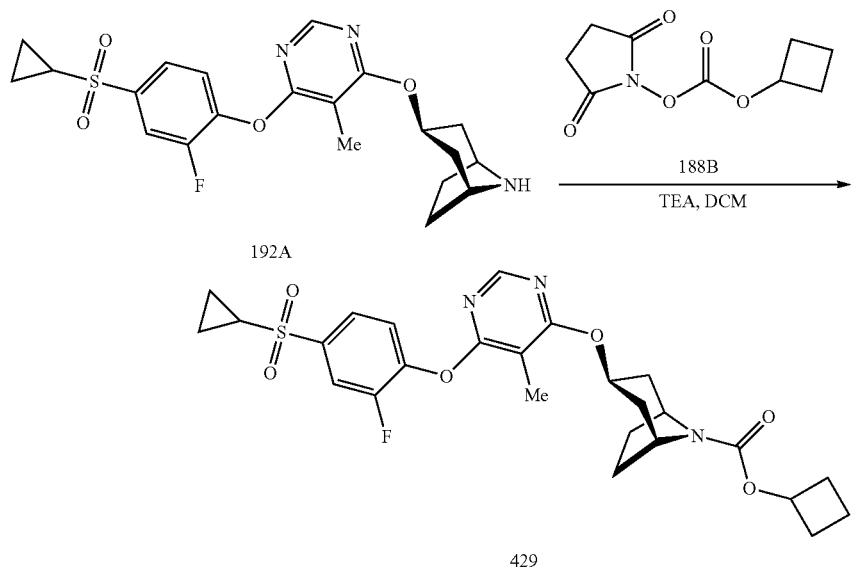

Using the method described in Example 157, Step A and substituting compound 395 for compound 393, compound 192A was prepared. Using, the method described in Example 33, substituting compound 37A for compound 33A, compound 429 was prepared. LCMS (M+H)+=532.3

Example 193

Preparation of Compound 430

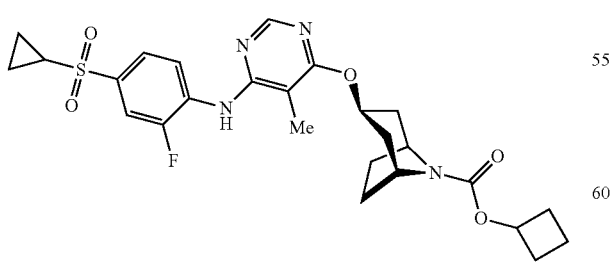

Using the method described in Example 188 and substituting compound 157A for compound 188A, compound 430 was prepared. LCMS (M+H)+=531.3

Example 194

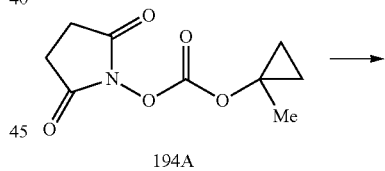

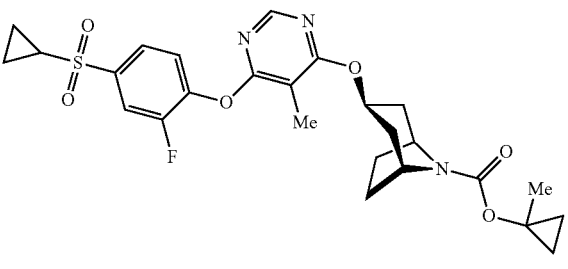

Using the method described in Example 188, and substituting compound 194A (prepared as described in WO 05/14577 to Zhu et. al.) for compound 188B and substituting compound 192A for compound 188A, compound 431 was prepared. LCMS (M+H)+=532.3

Example 195

Preparation of Compound 432

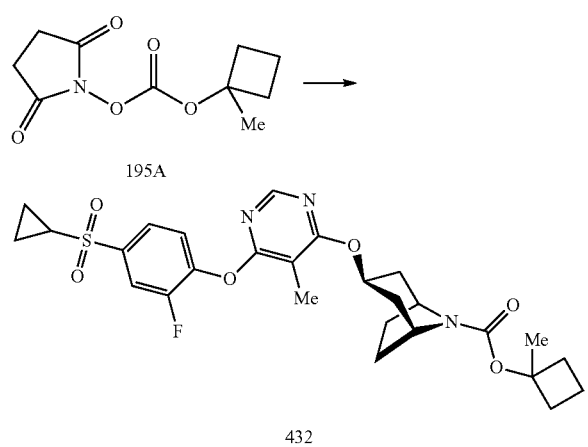

Using the method described in Example 188, substituting compound 195A (prepared as described in WO 05/14577 to Zhu et. al.) for compound 188B and substituting compound 192A for compound 188A, compound 432 was prepared. LCMS (M+H)+=546.3

Example 196

Preparation of Compound 433

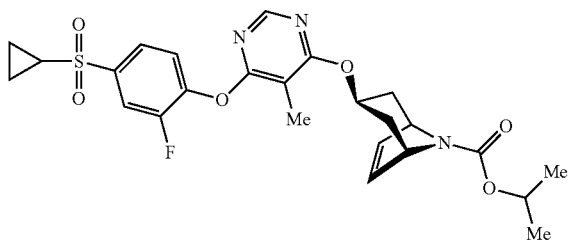

Using the method described in Example 158, substituting compound 189A for compound 34A, compound 433 was prepared. LCMS (M+H)+=518.3

Example 197

Preparation of Compound 434

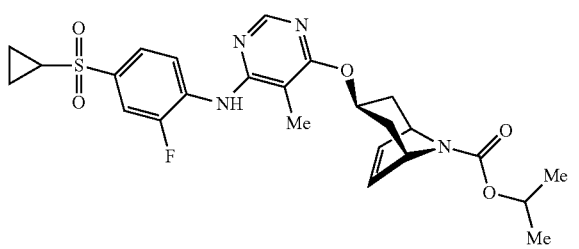

Using the method described in Example 156, Step B and substituting compound 189A compound 34A, compound 434 was prepared. LCMS (M+H)+=517.3

Example 198

Preparation of Compound 435

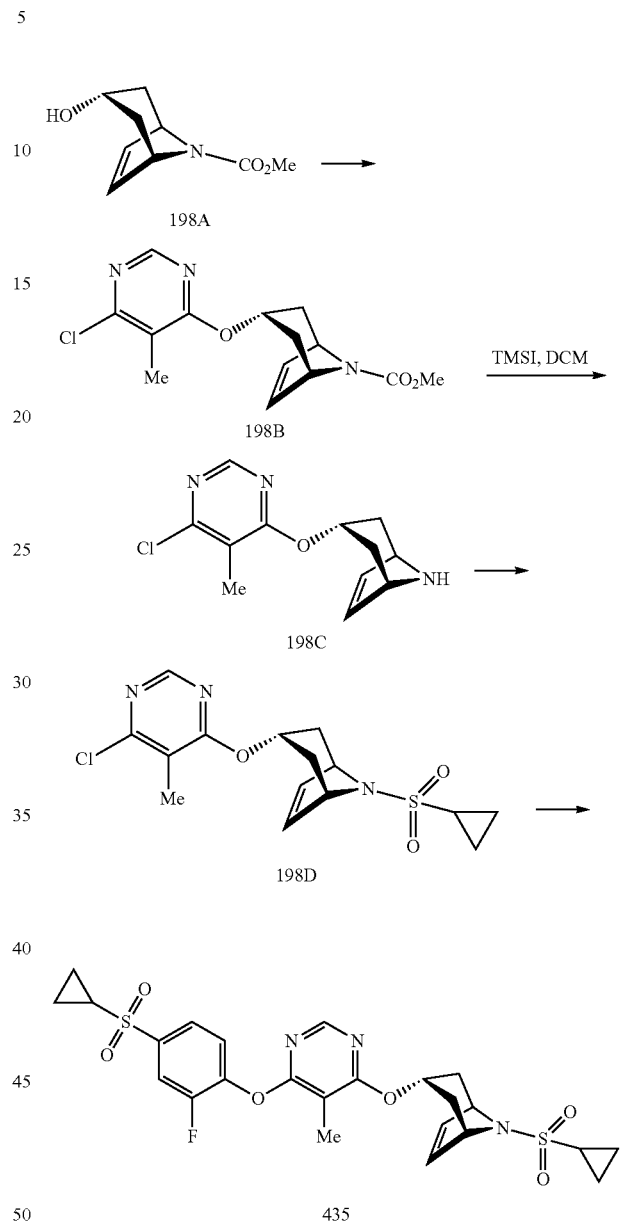

Using the method described in Example 186, substituting compound 198A (prepared as described in Hodgson et. al. *Tetrahedron* 60:5185 (2004)) for compound 186A, compound 198C was prepared. Using the method described in Example 160 and substituting compound 198C for compound 395, compound 198D was prepared. Using the method described in Example 158 and substituting compound 198D for compound 34A, compound 435 was prepared. LCMS (M+H)+=536.3

Example 199

Preparation of Compound 436

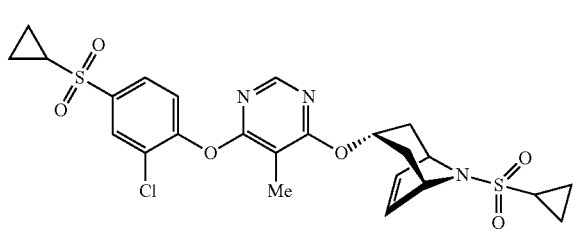

436

Using the method described in Example 158 and substituting compound 145A for compound 144A and substituting compound 198D for compound 34A, compound 436 was prepared. LCMS (M+H)+=552.3

Example 200

Preparation of Compound 437

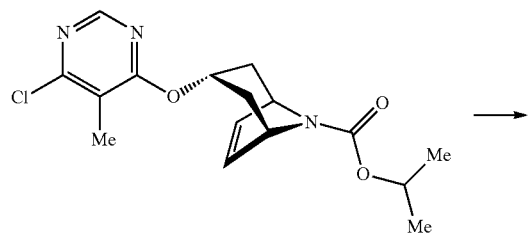

200A

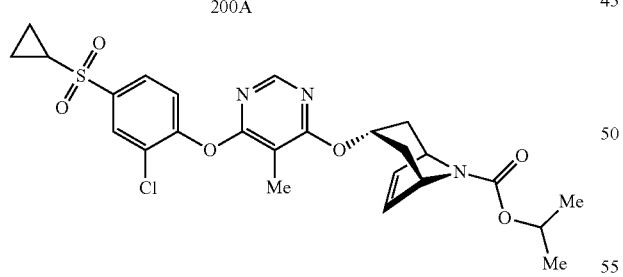

437

Using the method described in Example 157, substituting compound 198C for compound 394, compound 200A was prepared. Using the method described in Example 158, substituting compound 145A for compound 144A and substituting compound 200A for compound 34A, compound 437 was prepared. LCMS (M+H)+=534.3

Example 201

Preparation of Compound 438

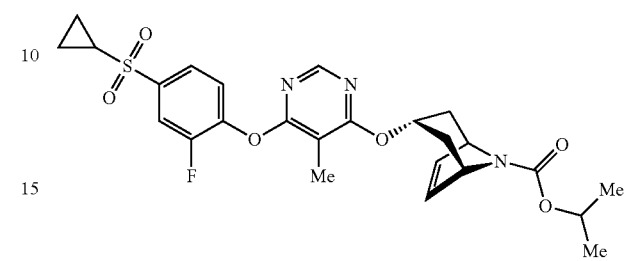

438

Using the method described in Example 158, substituting compound 200A for compound 34A, compound 438 was prepared. LCMS (M+H)+=518.3

Example 202

Preparation of Compound 439

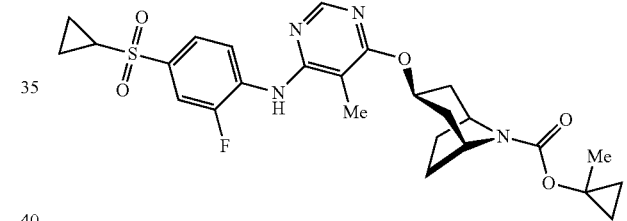

439

Using the method described in Example 188, substituting compound 157A for 188A and substituting compound 194A for compound 188B, compound 439 was prepared. LCMS (M+H)+=531.3

Example 203

Preparation of Compound 440

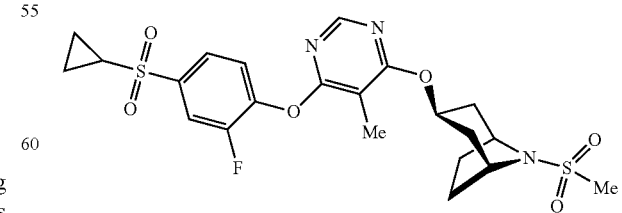

440

Using the method described in Example 160 and substituting methanesulfonyl chloride for cyclopropylsulfonyl chloride, compound 440 was prepared. LCMS (M+H)+=512.3

Example 204

Preparation of Compound 441

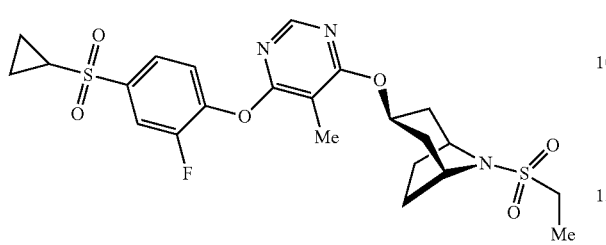

Using the method described in Example 160 and substituting ethylsulfonyl chloride for cyclopropylsulfonyl chloride, compound 441 was prepared. LCMS (M+H)+=526.3

Example 205

Preparation of Compound 442

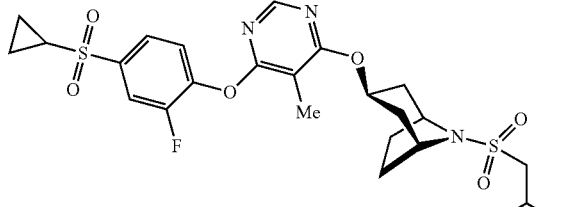

Using the method described in Example 160 and substituting 2-methylpropane-1-sulfonyl chloride for cyclopropylsulfonyl chloride, compound 442 was prepared. LCMS (M+H)+=554.3

Example 206

Preparation of Compound 443

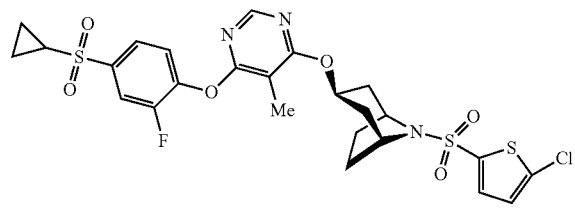

Using the method described in Example 160 and substituting 5-chlorothiophene-2-sulfonyl chloride for cyclopropylsulfonyl chloride, compound 443 was prepared. LCMS (M+H)+=614.3

Example 207

Preparation of Compound 444

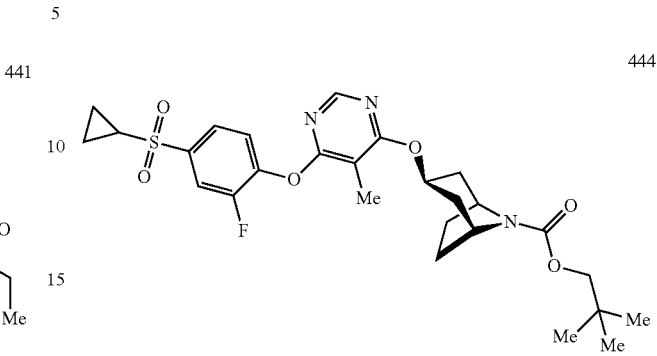

Using the method described in Example 160 and substituting neopentyl chloride for cyclopropylsulfonyl chloride, compound 444 was prepared. LCMS (M+H)+=548.3

Example 208

Preparation of Compound 445

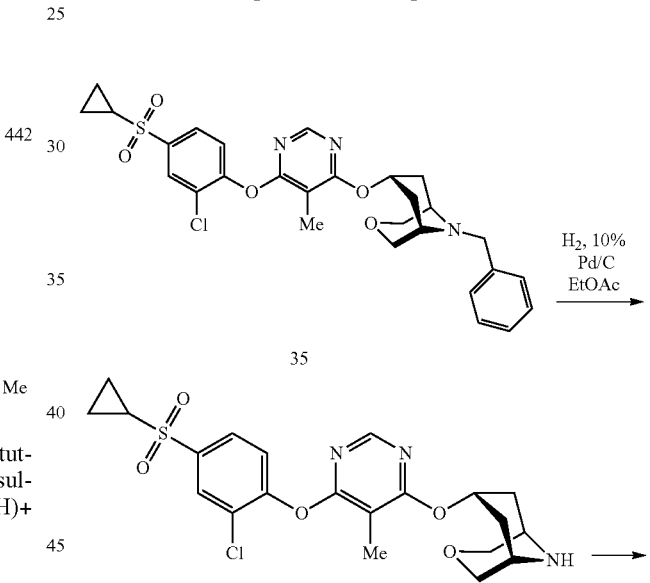

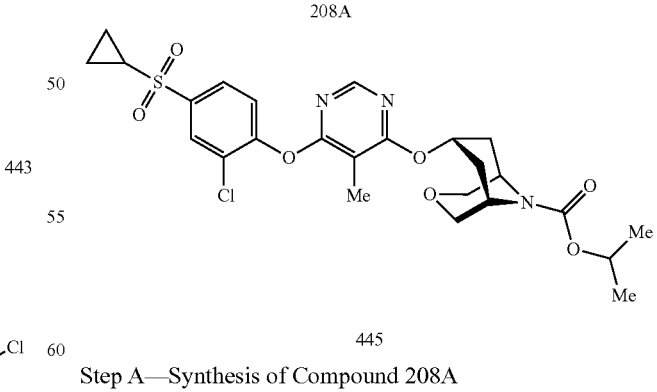

Step A—Synthesis of Compound 208A

To a solution of compound 427 (100 mg, 0.18 mmol) in EtOAc (5 mL) was added 10% Pd/C (100 mg) and the reaction vessel was evacuated and re-filled with H₂ from a balloon (3×). The reaction was stirred for 16 h. Reaction was filtered through a pad of celite and concentrated in vacuo to provide compound 208A (70 n g, 84(N).

Step B—Synthesis of Compound 445

Using the method described in Example 157, substituting compound 208A for compound 157A, compound 445 was prepared. LCMS (M+H)+=552.3

Example 209

Preparation of Compound 446

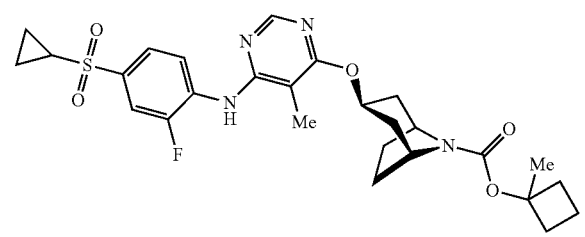

446

Using the method described in Example 195, substituting compound 157A for compound 188A, compound 445 was prepared. LCMS (M+H)+=534.3

Example 210

Preparation of Compound 447

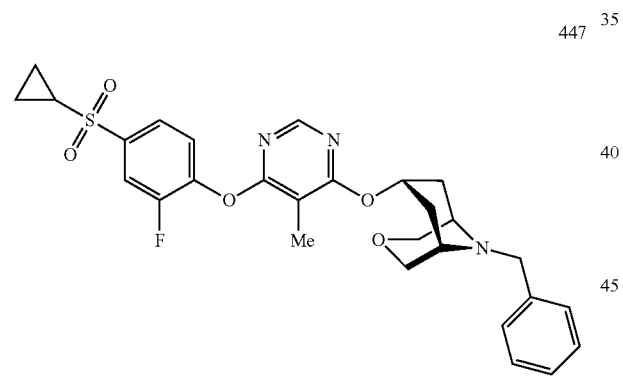

447

Using the method described in Example 158, substituting compound 190C for compound 34A, compound 447 was prepared. LCMS (M+H)+=540.3

Example 211

Preparation of Compound 448

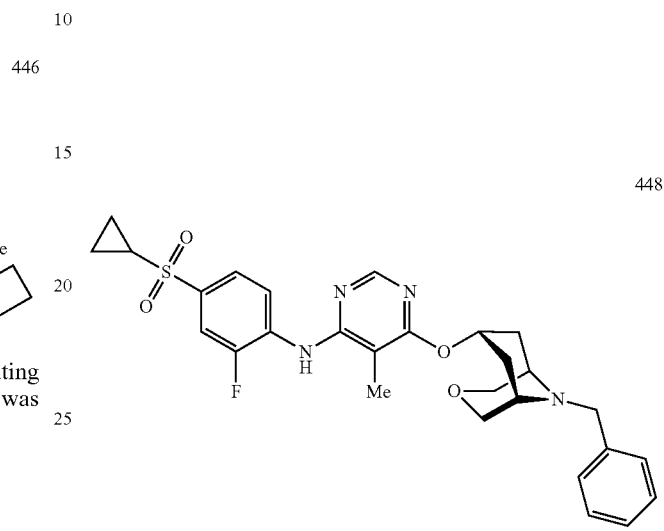

448

Using the method described in Example 155, Step B, substituting compound 190C for compound 34A, compound 448 was prepared. LCMS (M+H)+=539.3

Example 212

Preparation of Compound 449

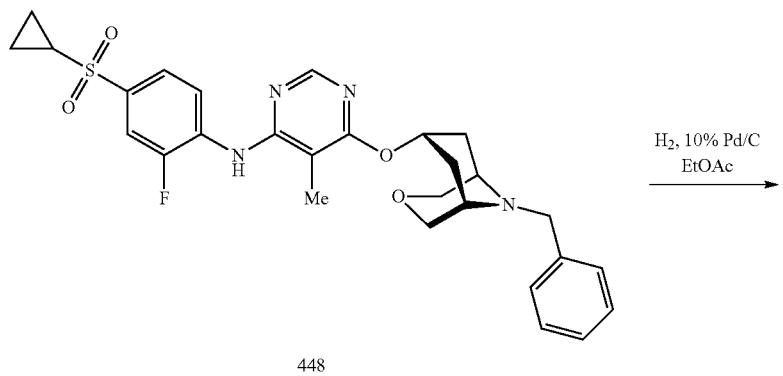

448

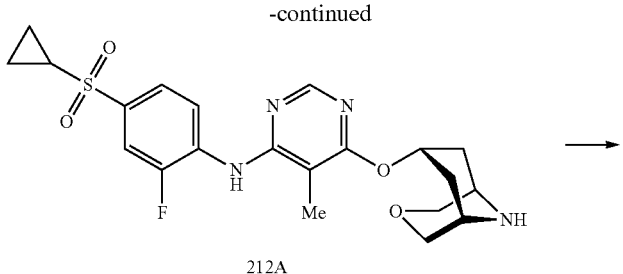

212A

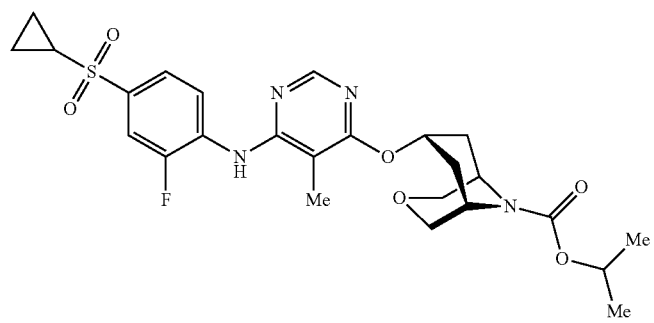

449

Step A—Synthesis of Compound 212A

Using the method described in Example 208 Step A, substituting compound 448 for compound 427, compound 212A was prepared.

Step B—Synthesis of Compound 449

Using the method described in Example 157, substituting compound 212A for compound 157A, compound 449 was prepared. LCMS (M+H)+=535.3

Example 213

Preparation of Compound 450

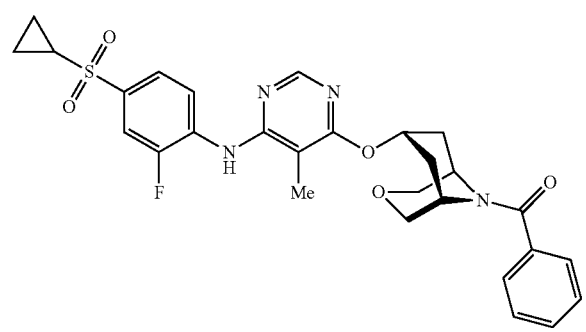

450

Using the method described in Example 160, substituting compound 212A for compound 160A and substituting benzoyl chloride for cyclopropylsulfonyl chloride, compound 450 was prepared. LCMS (M+H)+=553.3

Example 214

Preparation of Compound 451

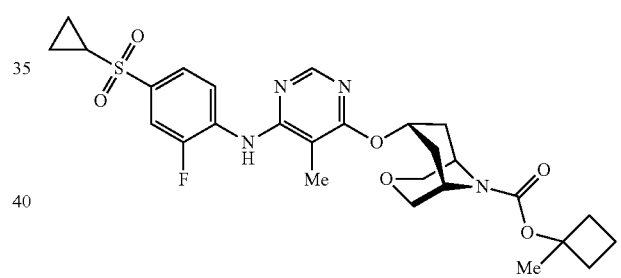

451

Using the method described in Example 195, substituting compound 212A for compound 188A, compound 451 was prepared. LCMS (M+H)+=561.3

Example 215

Preparation of Compound 452

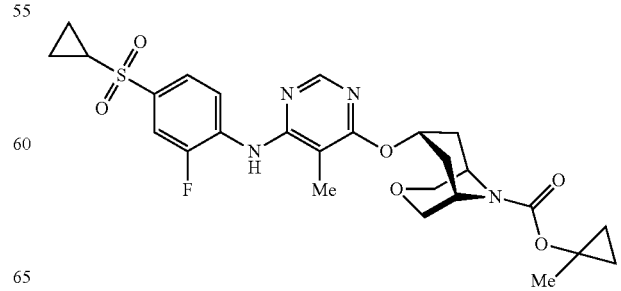

452

Using the method described in Example 194, substituting compound 212A for compound 188A, compound 452 was prepared. LCMS (M+H)+=547.3

Example 216

Preparation of Compound 453

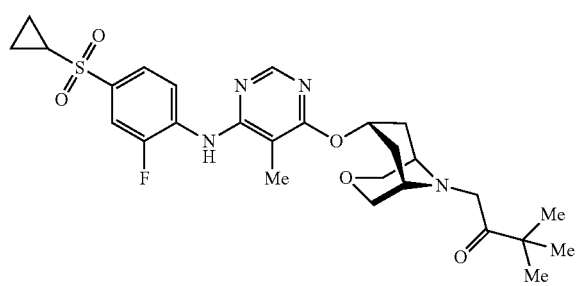

453

To a solution of compound 212A (45 mg, 0.10 mmol) and $K_2CO_3$ (21 mg, 0.15 mmol) in DMF (1 mL) was added 1-bromo-3,3-dimethylbutan-2-one (16 µL, 0.12 mmol) and the solution was stirred for 6 h at room temperature. The reaction was concentrated in vacuo and purified by preparative thin layer chromatography using (50% EtOAc-Hexanes) to provide compound 453 (23 mg, 42%). LCMS (M+H)+=547.3

Example 217

Preparation of Compound 454

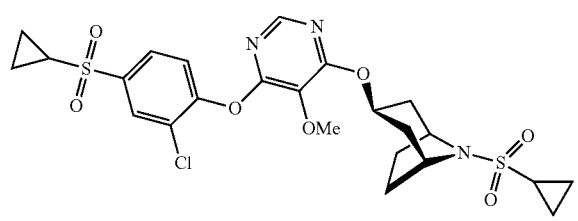

454

Using the method described in Example 160, substituting compound 406 for compound 395, compound 454 was prepared. LCMS (M+H)+=570.3

Example 218

Preparation of Compound 455

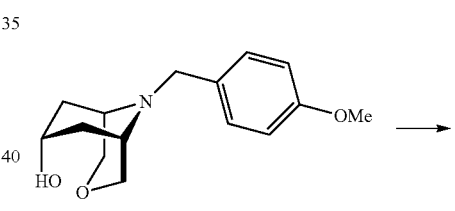

455

Using the method described in Example 160, substituting compound 399 for compound 395 and substituting 2-methylpropane-1-sulfonyl chloride for cyclopropylsulfonyl chloride, compound 455 was prepared. LCMS (M+H)+=570.3

Example 219

Preparation of Compound 456

219A

456

Using the method described in Example 156 and using compound 219A (prepared using the method described in Example 100, substituting 4-methoxybenzyl amine for benzylamine as the starting material, compound 456 was prepared. LCMS (M+H)+=569.3

Example 220

Preparation of Compound 457

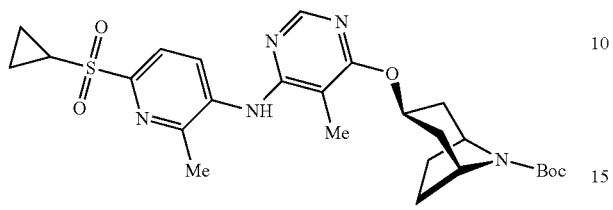

Using the method described in Example 156, Step B and substituting compound 152A for compound 143A, compound 457 was prepared. LCMS (M+H)+=530.3

Example 221

Preparation of Compound 458

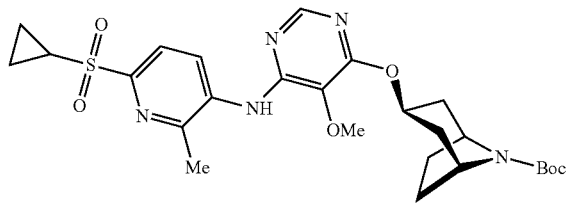

Using the method described in Example 156, Step B and substituting compound 152A for compound 143A and compound 161A for compound 34A, compound 458 was prepared. LCMS (M+H)+=546.3

Example 222

Preparation of Compound 459

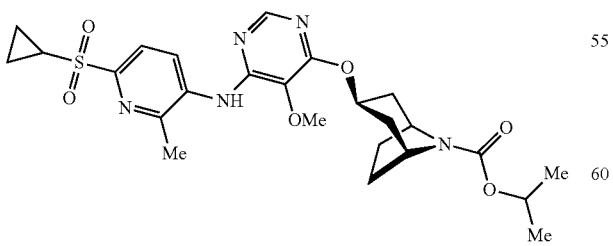

Using the method described in Example 157 and substituting compound 458 for compound 393, compound 459 was prepared. LCMS (M+H)+=532.3

Example 223

Preparation of Compound 460

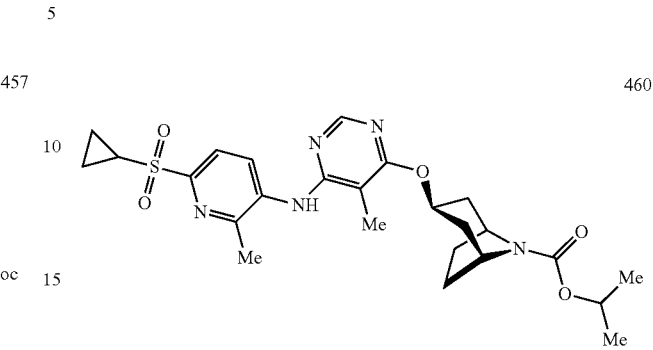

Using the method described in Example 157, substituting compound 457 for compound 393, compound 460 was prepared. LCMS (M+H)+=516.3

Example 224

Preparation of Compound 461

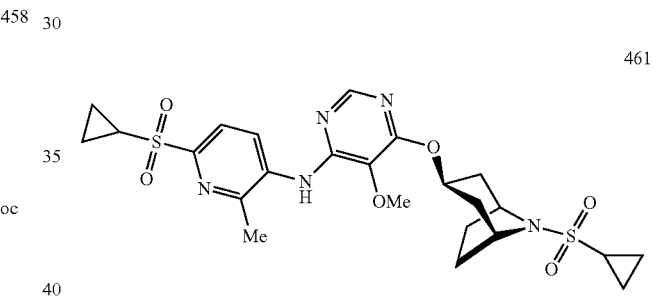

Using the method described in Example 160 and substituting compound 458 for compound 395, compound 461 was prepared. LCMS (M+H)+=550.3

Example 225

Preparation of Compound 462

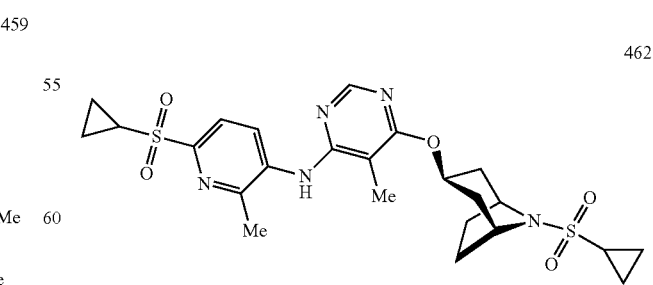

Using the method described in Example 160 and substituting compound 457 for compound 395, compound 462 was prepared. LCMS (M+H)+=534.3

Example 226

Preparation of Compound 463

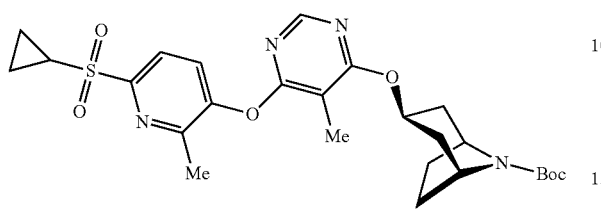

Using the method described in Example 158 and substituting compound 153B for compound 144A, compound 463 was prepared. LCMS (M+H)+=531.3

Example 227

Preparation of Compound 464

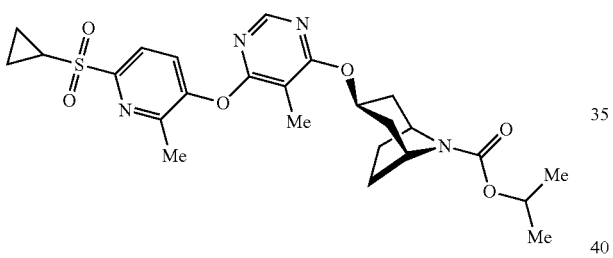

Using the method described in Example 157, substituting, compound 463 for compound 393, compound 464 was prepared. LCMS (M+H)+=517.3

Example 228

Preparation of Compound 465

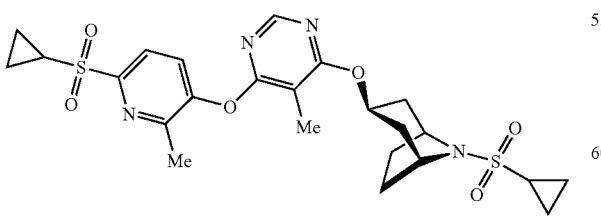

Using the method described in Example 160 and substituting compound 43 for compound 395, compound 465 was prepared. LCMS (M+H)+=535.3

Example 229

Preparation of Compound 466

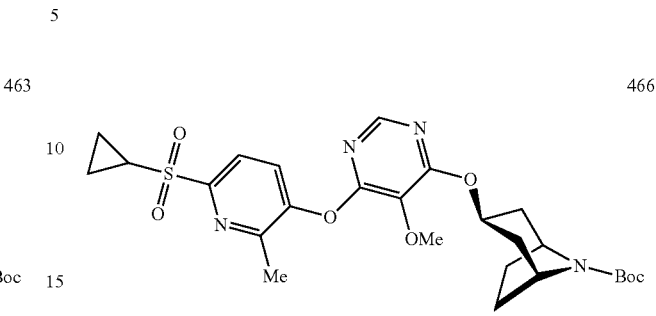

Using the method described in Example 158, substituting compound 161A for compound 34A, and substituting compound 153B for compound 144A, compound 466 was prepared. LCMS (M+H)+=547.3

Example 230

Preparation of Compound 467

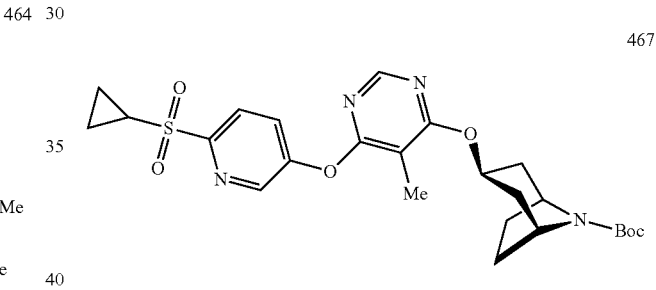

Using the method described in Example 158, substituting compound 154A for compound 144A, compound 467 was prepared. LCMS (M+H)+=517.3

Example 231

Preparation of Compound 468

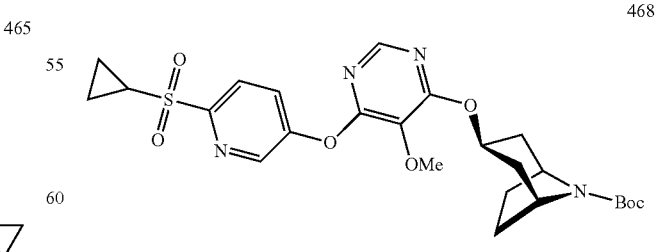

Using the method described in Example 158, substituting compound 161A for compound 34A, and substituting compound 154A for compound 144A, compound 468 was prepared. LCMS (M+H)+=533.3

Example 232

Preparation of Compound 469

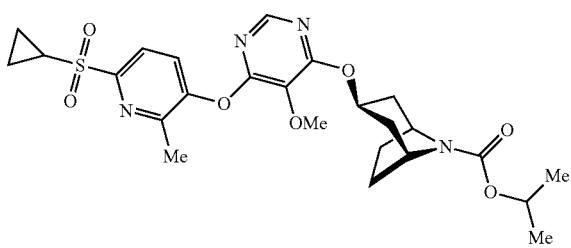

Using the method described in Example 157, substituting compound 466 for compound 393, compound 469 was prepared, LCMS (M+H)+=533.3

Example 233

Preparation of Compound 470

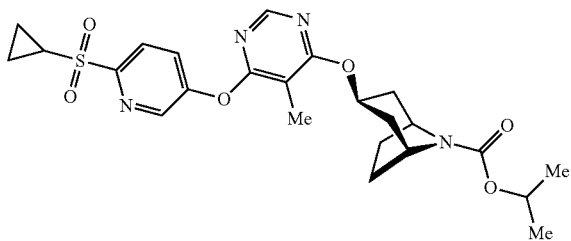

Using the method described in Example 157, substituting compound 467 for compound 393, compound 470 was prepared. LCMS (M+H)+=503.3

Example 234

Preparation of Compound 471

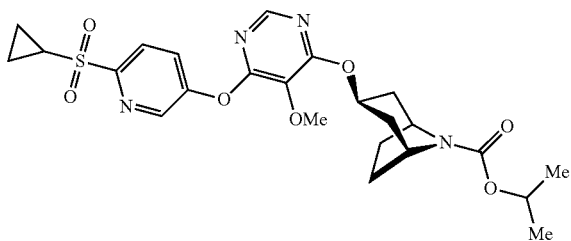

Using the method described in Example 0.157, substituting compound 468 for compound 393, compound 471 was prepared. LCMS (M+H)+=519.3

Example 235

Preparation of Compound 472

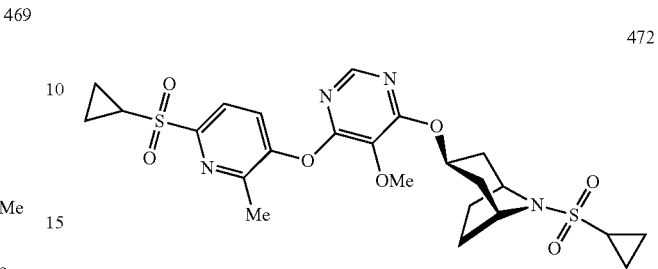

Using the method described in Example 160 and substituting compound 466 for compound 395, compound 472 was prepared, LCMS (M+H)+=551.3

Example 236

Preparation of Compound 473

Using the method described in Example 160 and substituting compound 467 for compound 395, compound 473 was prepared. LCMS (M+H)+=521.3

Example 237

Preparation of Compound 474

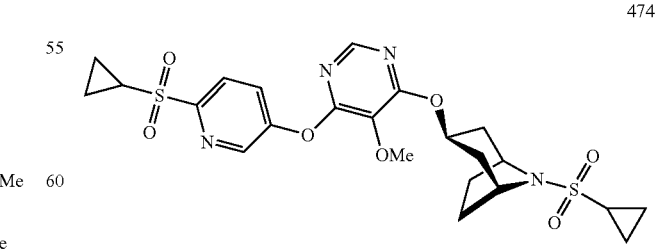

Using the method described in Example 160 and substituting compound 468 for compound 393, compound 474 was prepared. LCMS (M+H)+=537.3

Example 238

Preparation of Compound 475

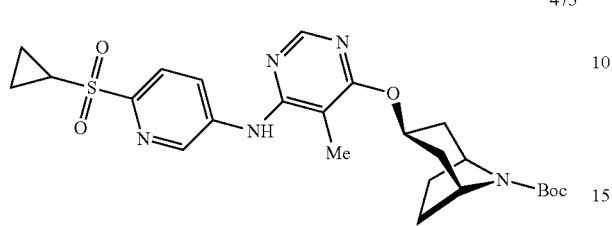

Using the method described in Example 156, Step B and substituting compound 155A for compound 143A, compound 475 was prepared. LCMS (M—H)+=5163

Example 239

Preparation of Compound 476

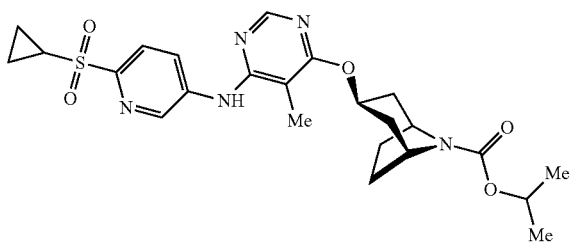

Using the method described in Example 157, substituting compound 475 for compound 393, compound 476 was prepared. LCMS (M+H)+=502.3

Example 240

Preparation of Compound 477

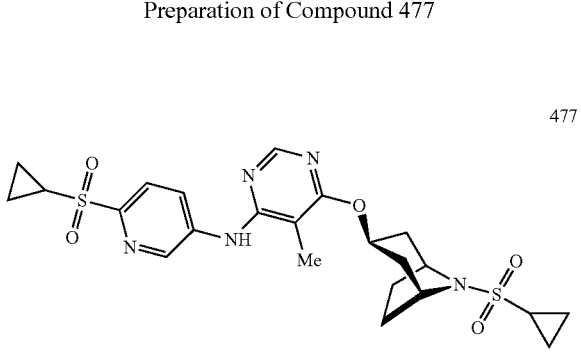

Using the method described in Example 160 and substituting compound 475 for compound 395, compound 477 was prepared. LCMS (M+H)+=5220.3

Example 241

Preparation of Compound 478

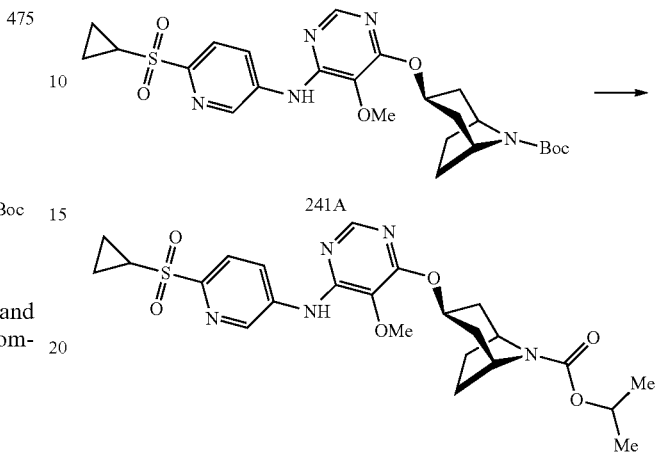

Using the method described in Example 156, Step B, substituting compound 155A for compound 143A and compound 161A for compound 1B, compound 241A was prepared.

Using the method described in Example 157 and substituting compound 241A for compound 393, compound 478 was prepared. LCMS (M+H)+=518.3

Example 242

Preparation of Compound 479

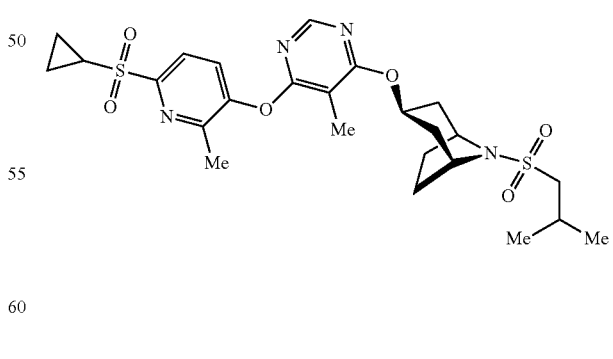

Using the method described in Example 160 and substituting, compound 463 for compound 395 and substituting 2-methylpropane-1-sulfonyl chloride for cyclopropylsulfonyl chloride, compound 479 was prepared. LCMS (M+H)+=551.3

Example 243

Preparation of Compound 480

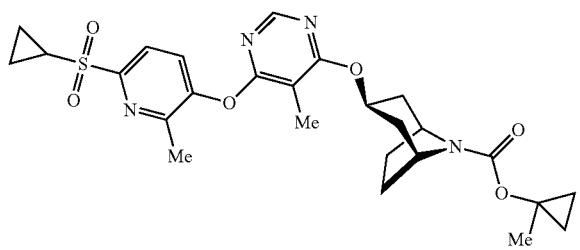

480

Using the method described in Example 157, Step A, substituting compound 463 for compound 393, followed immediately by the method described in Example 194, compound 480 was prepared. LCMS (M+H)+=529.3

Example 244

Preparation of Compound 481

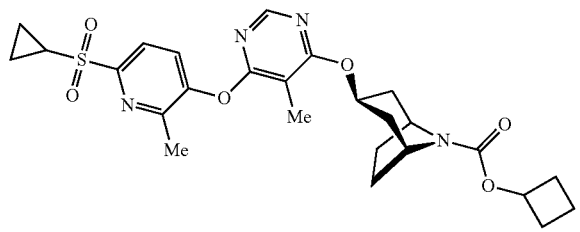

481

Using the method described in Example 157, Step A, substituting compound 463 for compound 393, followed immediately by the method described in Example 188, compound 481 was prepared. LCMS (M+H)+=529.3

Example 245

Preparation of Compound 482

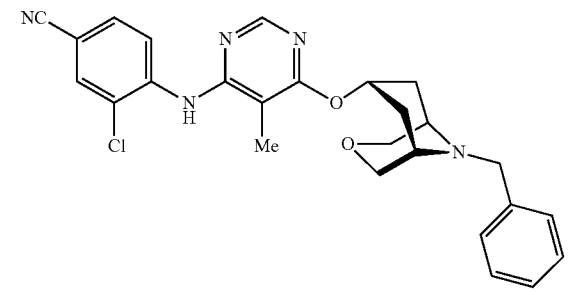

482

Using the method described in Example 156, Step B, substituting compound 190C for compound 34A, and substituting 2-chloro-4-cyanoaniline for compound 143A, compound 482 was prepared. LCMS (M+H)+=476.3

Example 246

Preparation of Compound 483

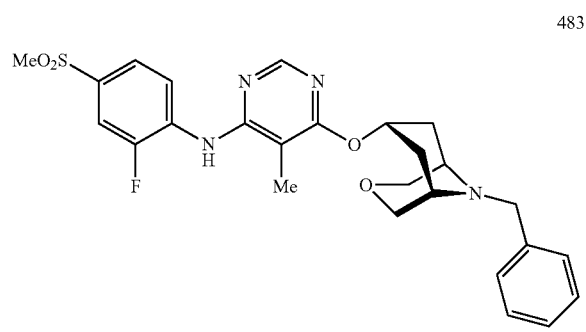

483

Using the method described in Example 156, Step B, substituting compound 190C for compound 34A, and substituting 2-fluoro-4-methylsulfonylaniline for compound 143A, compound 483 was prepared. LCMS (M+H)+=513.3

Example 247

Preparation of Compound 484

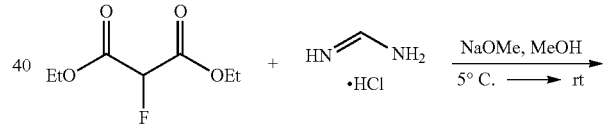

247A

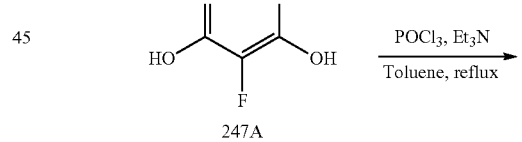

247B

247C

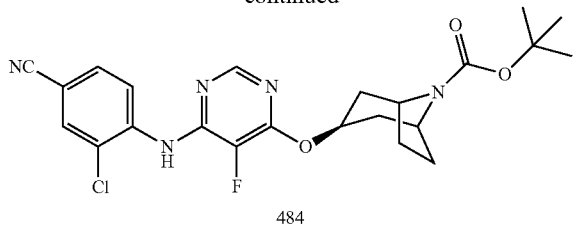

484

Step A—Synthesis of Compound 247A

To a cold suspension of sodium methoxide (30% solution in methanol) (1.46 g, 80.83 mmol) in methanol (~36 mL) at 5° C. was added formamidine hydrochloride (1.36 g, 16.84 mmol) and stirred for 10 minutes. This was followed by the addition of diethyl fluoromalonate (3.052., 16.84 mmol) and the resulting reaction mixture was stirred overnight at room temperature. The reaction mixture was concentrated in metro to remove methanol. The solid obtained was dissolved in ice cold water (~100 mL) and acidified to pH=7. The white precipitate obtained was filtered, washed with water and dried to get the product 247A (0.7 g, 81%).

Step B—Synthesis of Compound 247B

Compound 247A (1.78 g, 13.07 mmol) was dissolved in toluene (25 mL) and triethylamine was added to it and the mixture was heated to near refluxing. $POCl_3$ dissolved in toluene (4 mL) was added to the mixture slowly and the resulting mixture was refluxed overnight at 110° C. The reaction mixture was poured over crushed ice, extracted 2 times with toluene and the organic layers were separated. Combined organic layers were washed with saturated $NaHCO_3$ solution and then with brine. The organic layer was dried over anhydrous $MgSO_4$, filtered, concentrated in vacuo to get the product 247B (0.74 g, 32.5%).

Step C—Synthesis of Compound 247C

To a stirred solution of NaH (0.44 g, 11.08 mmol) in tetrahydrofuran (10 mL) was added a solution of 4-amino-3-chloro benzonitrile (0.32 g, 2.08 mmol) in tetrahydrofuran (15 mL) and stirred for 30 minutes. After 30 minutes, the reaction mixture was cooled to 0° C. and a solution of starting material 247B (0.37 g, 2.22 mmol) in tetrahydrofuran (15 mL) was added to it and stirred at 0° C. for 30 minutes and then overnight at room temperature. The reaction was quenched with water, extracted 2 times with ethyl acetate. The combined organic layer was dried over anhydrous $Na_2SO_4$, filtered, concentrated in vacuo, and purified sing silica column chromatography using 1% (7N $NH_3$ in MeOH)—99% $CH_2Cl_2$ as a solvent system and the product 247C (0.3 g, 48%) was isolated.

Step D—Synthesis of Compound 484

The exo-alcohol 1A (0.11 g, 0.5 mmol) was dissolved in tetrahydrofuran (3 mL) and KOBu$^t$ (1 mL, 1 M in THF, 1 mmol) was added to it followed by the starting material 247C (0.14 g, 0.5 mmol) dissolved in tetrahydrofuran (5 MO and the resulting mixture was refluxed at 84° C. overnight. The reaction was quenched with water and extracted 2 times with ethyl acetate. Combined organic layers were dried over anhydrous $Na_2SO_4$, filtered, concentrated in vacuo, purified using preparative TLC using 100% $CH_2Cl_2$ as mobile phase and the product, 484 (0.075 g, 32%) was isolated.

Example 248

Preparation of Compound 485

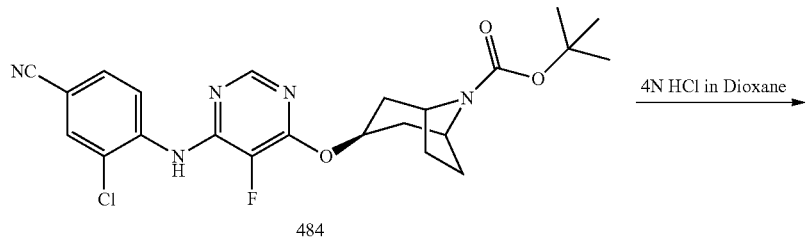

484

4N HCl in Dioxane →

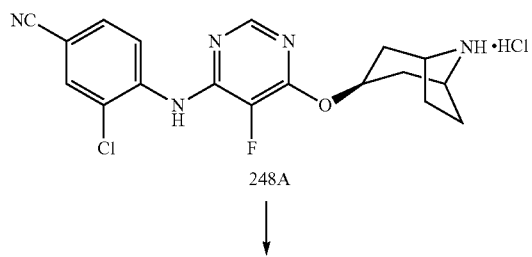

248A

-continued

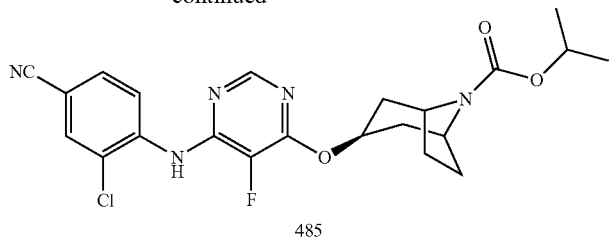

485

Step A—Synthesis of Compound 248A

Compound 484 (0.065 g, 0.14 mmol) was added to 4N HCl in dioxane (1) and stirred for an hour at room temperature. The mixture was concentrated in vacuo to remove excess acid in vacuo to get the amine hydrochloride salt, 248A (0.05 g, 96%).

Step B—Synthesis of compound 485

Compound 248A (0.012 g, 0.03 mmol) was dissolved in CH$_2$Cl$_2$ (2 mL) and triethylamine (0.01 mL, 0.09 mmol) was added to it and stirred for 10 minutes. This was followed by the addition of isopropyl chloro formate (0.03 mL, 0.03 mmol) and the resulting mixture was stirred for 1 hour at room temperature. The reaction was quenched with saturated ammonium chloride solution and extracted 2 times with CH$_2$Cl$_2$. Combined organic layers were dried over anhydrous Na$_2$SO$_4$, filtered, concentrated in vacuo, purified using preparative TLC using 20% acetone 80% hexane as mobile phase and the product, 485 (0.01 g, 74.6%) was isolated.

Example 249

Preparation of Compound 486

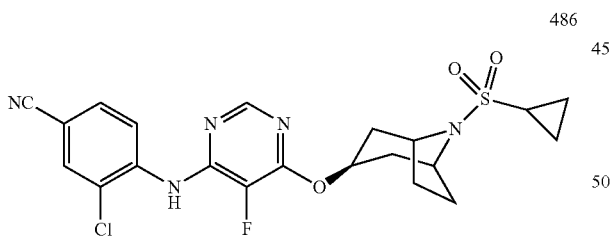

486

Compound 248A (0.012 g, 0.03 mmol) was dissolved in CH$_2$Cl$_2$ (2 mL), triethylamine (0.01 mL, 0.09 mmol) was added to it and stirred for 10 minutes. This was followed by the addition of cyclopropyl sulfonyl chloride (0.003 ml, 0.03 mmol) and the resulting mixture was stirred for 1 hour at room temperature. The reaction was quenched with saturated ammonium chloride solution and extracted 2 times with CH$_2$Cl$_2$. Combined organic layer was dried over anhydrous Na$_2$SO$_4$, filtered, concentrated in vacuo, purified using preparative TLC using 27% acetone—73% hexane followed by 45% EtOAc—55% hexane and finally with CH$_2$Cl$_2$ (containing 4 drops of 7N NH$_3$ in MeOH) as mobile phase and the product, 486 (0.007 g, 46.7%) was isolated.

Example 250

Preparation of Compounds 487 and 488

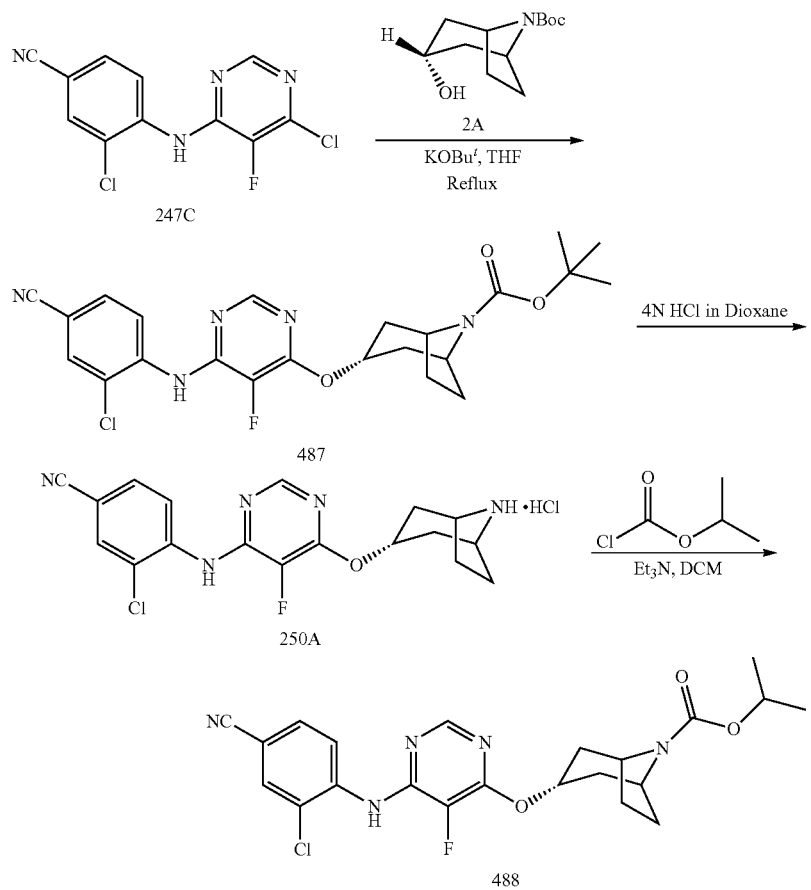

Step A—Synthesis of Compound 487

Compound 487 was synthesized from the endo-alcohol 2A and compound 247C using the method described in Example 247, Step D.

Step B—Synthesis of Compound 488

Compound 488 was synthesized from compound 487 using the method described in Example 248.

Example 251

Preparation of Compounds 489 and 490

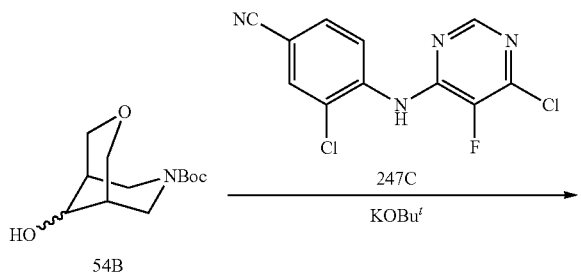

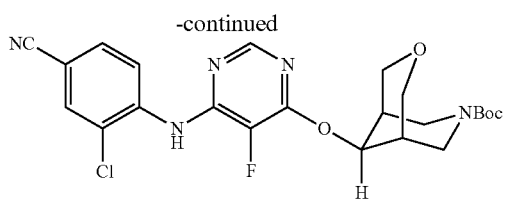

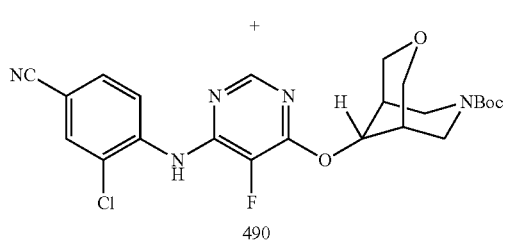

Compounds 489 and 490 were synthesized by coupling compounds 54B and 247C according to the method described in Example 247, Step D.

Compounds 489 and 490 were subsequently converted to compounds 491 and 492 by first removing their BOC protecting group according to the method described in Example 8, then reacting the resulting amines according to the method described in Example 132.

| Cpd. No. | Structure | LCMS (M + H) |
|---|---|---|
| 491 | 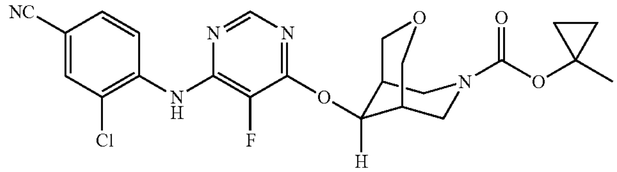 [SMILES: CC1(OC(=O)N2CC3COCC(C2)C3Oc2ncnc(Nc3ccc(C#N)cc3Cl)c2F)CC1] | 488 |
| 492 | 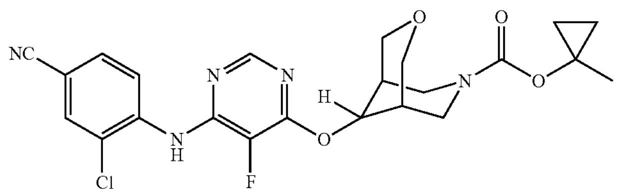 [SMILES: CC1(OC(=O)N2CC3COCC(C2)C3Oc2ncnc(Nc3ccc(C#N)cc3Cl)c2F)CC1] | 488 |

Example 252

Preparation of Compound 502

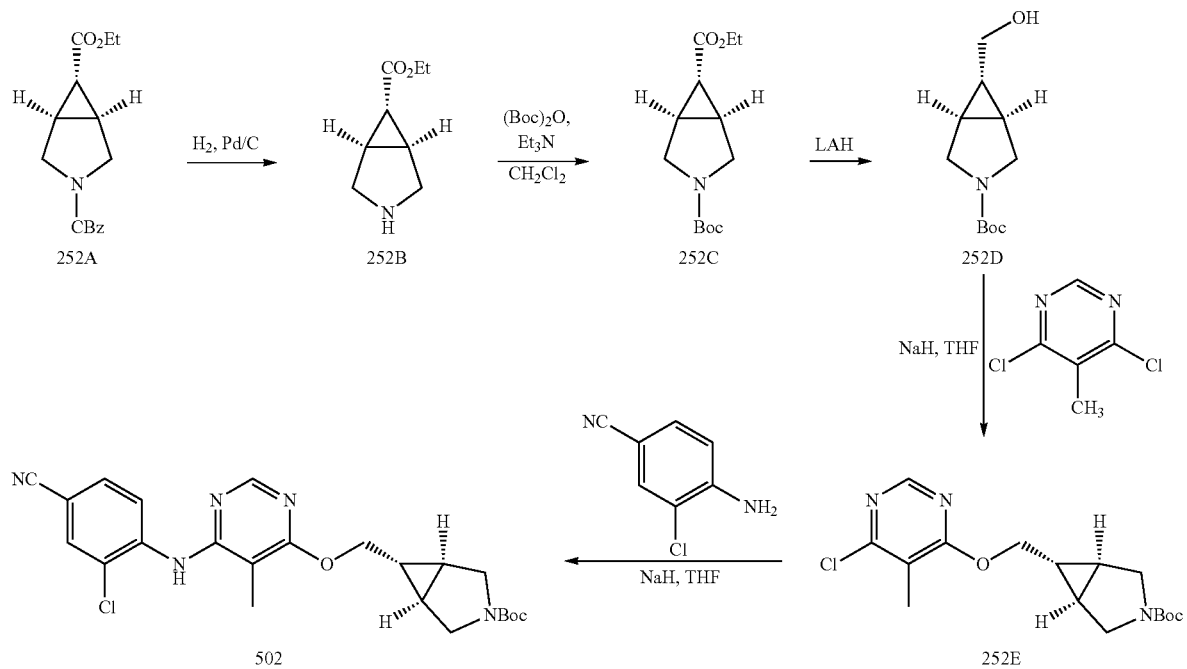

Step A—Preparation Compound 252B

Compound 252A (160 mg, 0.55 mmol, prepared according to Brighty et al., *Synlett*, (11) 1097-1098 (1996)), was dissolved in methanol (5 mL) and treated with 10% Pd/C (18 mg) and stirred at room temperature under a hydrogen atmosphere for 44 hours. The reaction mixture was filtered through celite and washed with methanol to provide compound 252B (83 mg, 97%) which was used in the next reaction without further purification.

Step B Preparation of Compound 252C

To a solution of compound 252B (83 mg, 0.53 mmol) in CH$_2$Cl$_2$ (6 mL) was added triethylamine (0.08 mL, 0.59 mmol) under nitrogen. The reaction was cooled to 0° C. and (Boc)$_2$O (129 mg, 0.59 mmol) was added. The reaction was warmed to room temperature and stirred for 16 hours. The reaction was diluted with CH$_2$Cl$_2$ and washed with water several times. The organic layer was dried over MgSO$_4$, filtered and concentrated. The resulting residue was purified using flash column chromatography on silica (0-20% EtOAc/hexanes) to provide compound 252C (80 mg, 53%).

Step C—Preparation of Compound 252D

To a solution of compound 252C (80 mg, 0.31 mmol) in THF (8 mL) was added LAH (1.0 M in THF, 0.3 mL) at room temperature. The reaction was heated to reflux for 18 hours, then poured onto ice water and extracted with ether several times. The organic layer was dried over MgSO$_4$, filtered and concentrated in vacuo to provide compound 252D (60 mg, 91%) which was used in next reaction without further purification.

Step D—Preparation of Compound 252E

To a mixture of compound 252C (60 mg, 0.28 mmol) and 4,6-dichloro-5-methyl pyrimidine (50 mg, 0.31 mmol) in THF (5 mL) was added NaH (60% in oil, 48 mg) under nitrogen. The reaction was stirred at room temperature for 5.5 hours, and then quenched with saturated ammonium chloride and extracted with CH₂Cl₂. The combined organics were dried over MgSO₄, filtered and concentrated in vacuo. The resulting residue was purified using preparative thin layer chromatography (30 EtOAc/hexanes) to provide compound 252E (69 mg, 66%).

Step E—Preparation of Compound 502

2-Chloro-4-cyano aniline (30.5 mg, 0.29 mmol) was added to a mixture of NaH (60% in oil, 19 mg) in THF (2 mL) at 0° C. After stirring at 0° C. for 30 minutes, compound 252E (34 mg, 0.10 mmol) was added. The reaction was heated to reflux and allowed to stir at this temperature for 42 hours. The reaction was cooled to room temperature and diluted with CH₂Cl₂. The organic layer was washed with saturated ammonium chloride, dried over MgSO₄, filtered and concentrated in vacuo. The resulting residue was purified using preparative thin layer chromatography (20% acetone/hexanes) to provide compound 502 (3 mg, 7),

Example 253

Preparation of Compound 503

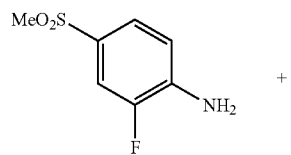

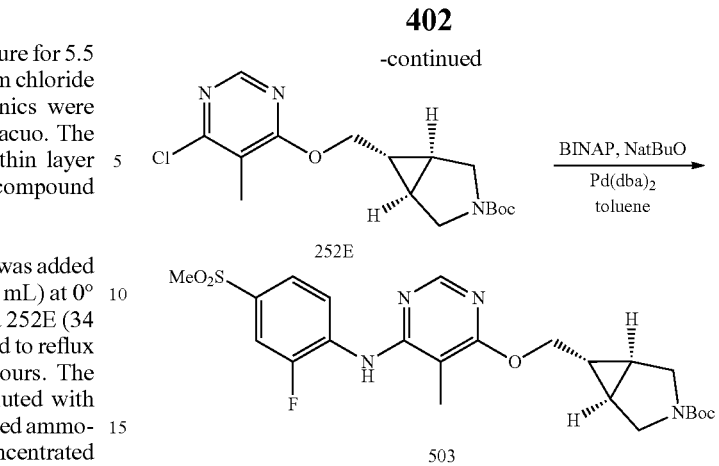

A mixture of compound 252E (29 mg, 0.09 mmol), 2 fluoro-4-(methylsulfonyl)aniline (18 mg, 0.09 mmol), Pd(dba)₂ (5 mg), BINAP (9 mg) and sodium i-butoxide (17 mg, 0.18 mmol) in toluene (3 mL) was heated to 110° C. in a sealed tube for 16 hours. The reaction was cooled to room temperature, filtered through celite, washed with EtOAc and concentrated in vacuo. The resulting residue was purified using preparative thin layer chromatography (30 acetone/hexanes) to provide compound 503 (9.5 mg, 33%).

The following compounds of the present invention were made using the above method and substituting the appropriate reactants and reagents:

| Cpd. No. | Structure | LCMS (M + H) |
|---|---|---|
| 504 | 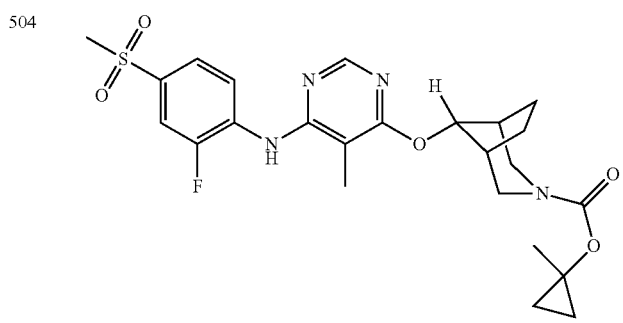 | 504.6 |
| 505 | 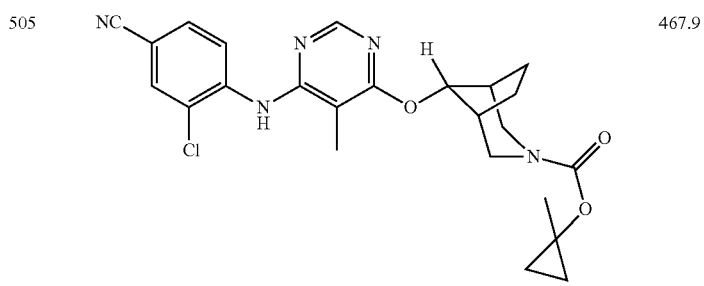 | 467.9 |

-continued

| Cpd. No. | Structure | LCMS (M + H) |
|---|---|---|
| 506 | 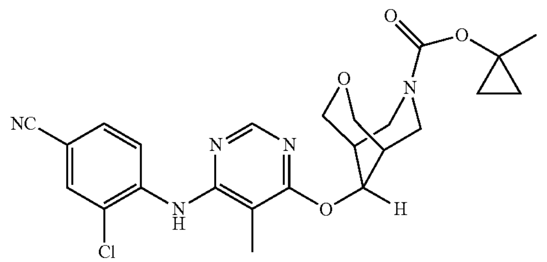 [SMILES: Cc1c(Nc2ccc(C#N)cc2Cl)ncnc1OC1C2COCC1CN(C(=O)OC1(C)CC1)C2] | 483.9 |
| 507 | 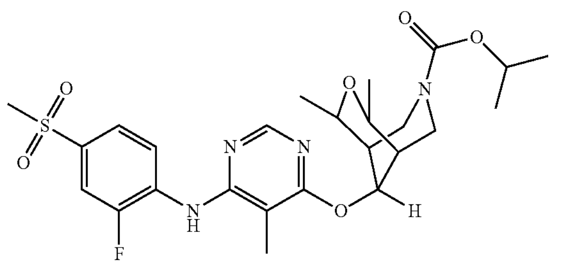 [SMILES: Cc1c(Nc2ccc(S(C)(=O)=O)cc2F)ncnc1OC1C2CN(C(=O)OC(C)C)CC1C(C)OC2C] | 536.6 |
| 508 | 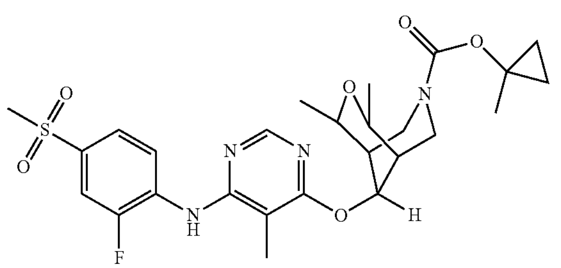 [SMILES: Cc1c(Nc2ccc(S(C)(=O)=O)cc2F)ncnc1OC1C2CN(C(=O)OC3(C)CC3)CC1C(C)OC2C] | 548.6 |
| 509 | 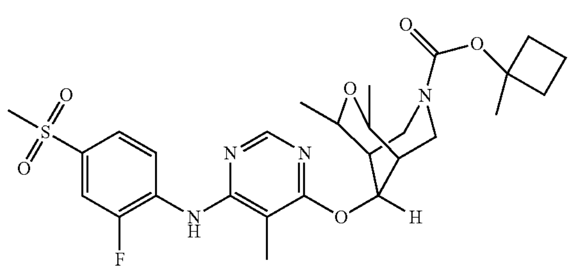 [SMILES: Cc1c(Nc2ccc(S(C)(=O)=O)cc2F)ncnc1OC1C2CN(C(=O)OC3(C)CCC3)CC1C(C)OC2C] | 562.7 |
| 510 | 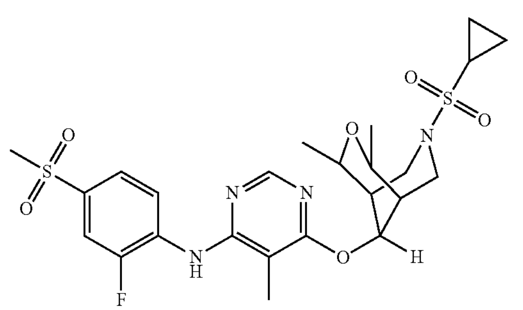 [SMILES: Cc1c(Nc2ccc(S(C)(=O)=O)cc2F)ncnc1OC1C2CN(S(=O)(=O)C3CC3)CC1C(C)OC2C] | 554.7 |

Example 268

Preparation of Compound 524

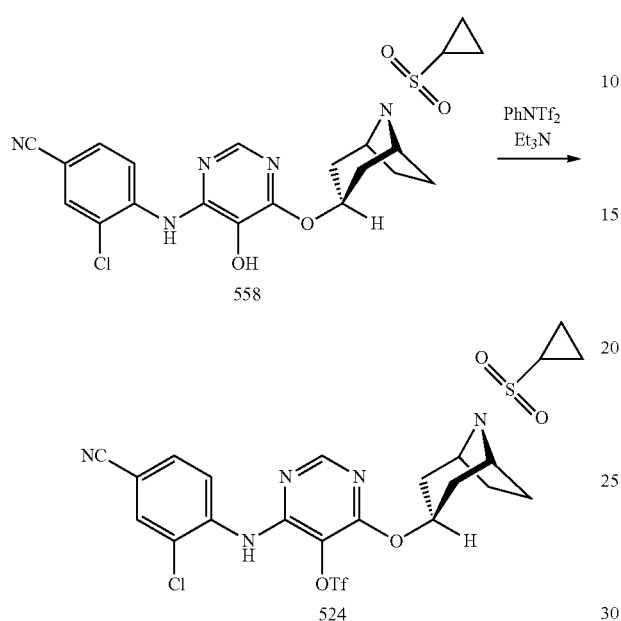

To a solution of compound 558 (24 mg, 0.05 mmol) and triethylamine (25 mg, 0.25 mmol) in acetonitrile (1 mL) was added bis(trifluoromethanesulfonyl)aniline (54 mg, 0.15 mmol) and the resulting, reaction was allowed to stir at room temperature for 20 hours. The reaction mixture was then concentrated in vacuo and the resulting residue was taken up in dichloromethane. The organic phase was washed with aqueous saturated ammonium chloride solution, dried over MgSO$_4$, filtered, and concentrated in vacuo. The resulting residue was purified using preparative TLC on silica gel (dichloromethane/ethyl acetate=95/5) and the product was subjected to a second preparative TLC on silica gel acetate=60/40) to provide compound 524 (8 mg, 26%) as an off-white solid. LCMS: 608.3 (MH$^+$).

Example 255

Preparation of Compound 524

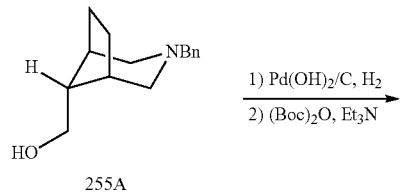

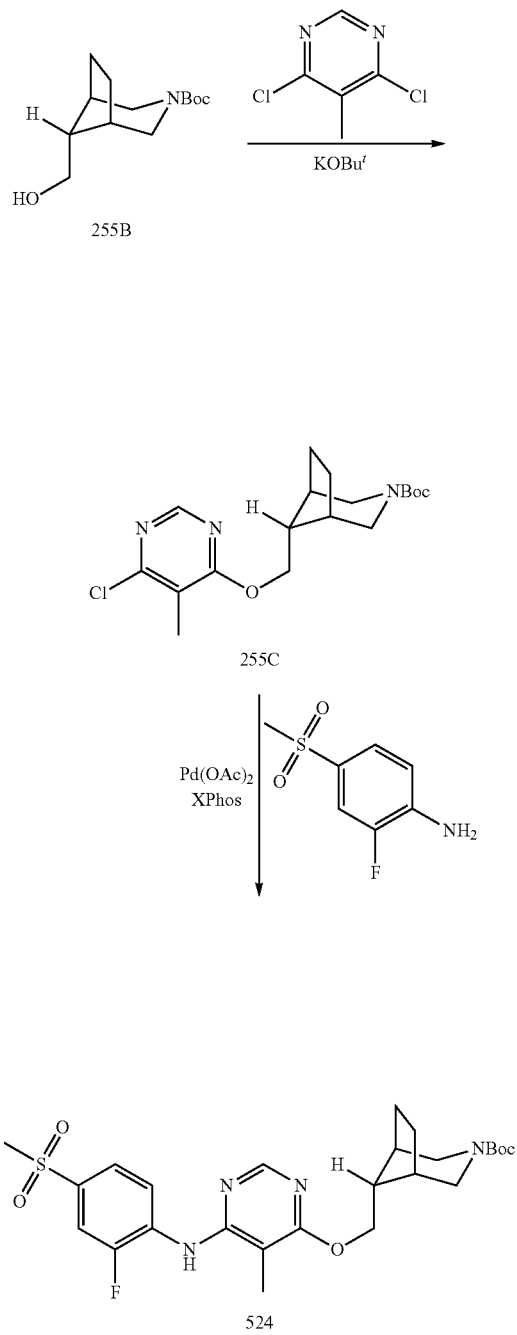

Step A—Synthesis of Compound 255C

Compound 255C was prepared from compound 255A (prepared according to the method described in International Publication No. WO 2006/035303) using the method described in Example 54.

Step B—Synthesis of Compound 524

Compound 524 was prepared from compound 255C using the method described in Example 56.

The following table sets forth compounds of the present invention which were made using the method described above and substituting the appropriate reactants and reagents.

| Cpd. No. | Structure | LCMS (M + H) |
|---|---|---|
| 525 | 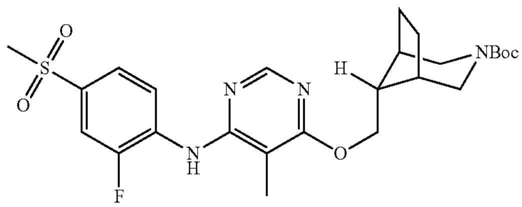 [SMILES: Cc1c(Nc2ccc(S(C)(=O)=O)cc2F)ncnc1OCC1C2CCC1CN(C(=O)OC(C)(C)C)C2] | 520.6 |
| 526 | 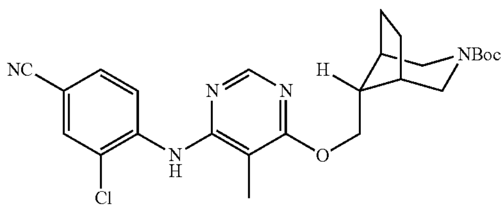 [SMILES: Cc1c(Nc2ccc(C#N)cc2Cl)ncnc1OCC1C2CCC1CN(C(=O)OC(C)(C)C)C2] | 484.0 |
| 527 | 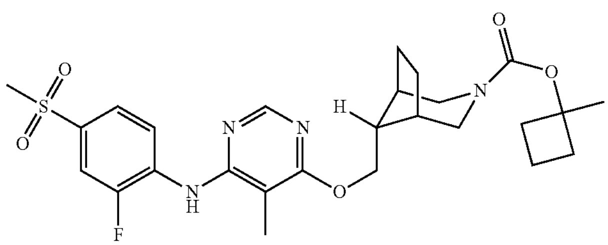 | 532.6 |
| 528 | 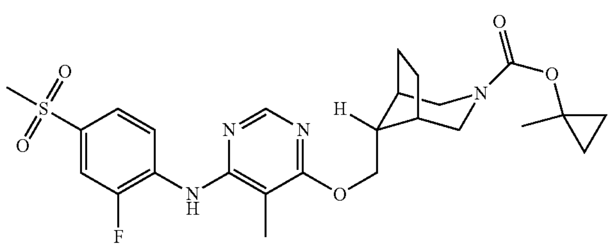 [SMILES: Cc1c(Nc2ccc(S(C)(=O)=O)cc2F)ncnc1OCC1C2CCC1CN(C(=O)OC1(C)CC1)C2] | 518.6 |
| 529 | 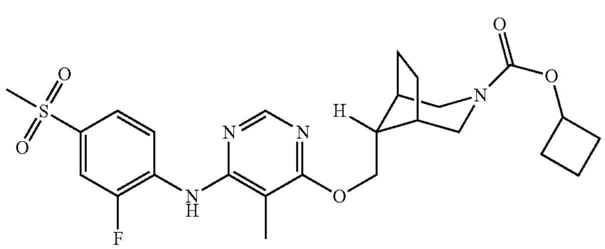 [SMILES: Cc1c(Nc2ccc(S(C)(=O)=O)cc2F)ncnc1OCC1C2CCC1CN(C(=O)OC1CCC1)C2] | 518.6 |
| 530 | 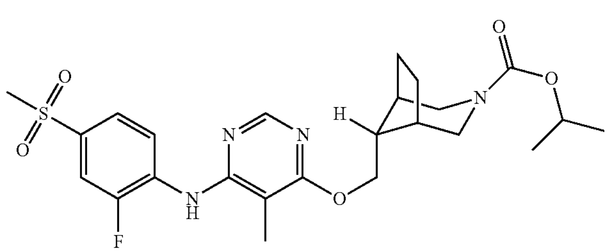 [SMILES: Cc1c(Nc2ccc(S(C)(=O)=O)cc2F)ncnc1OCC1C2CCC1CN(C(=O)OC(C)C)C2] | 506.6 |

-continued

| Cpd. No. | Structure | LCMS (M + H) |
|---|---|---|
| 531 | 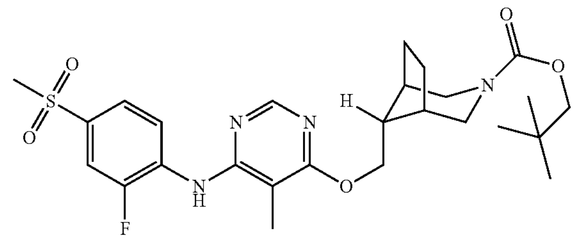 [SMILES: Cc1c(Nc2ccc(S(C)(=O)=O)cc2F)ncnc1OCC1C2CCC1CN(C(=O)OCC(C)(C)C)C2] | 534.6 |
| 532 | 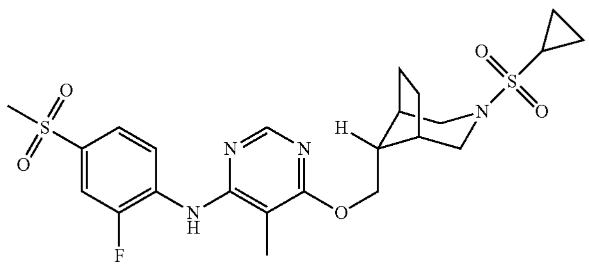 [SMILES: Cc1c(Nc2ccc(S(C)(=O)=O)cc2F)ncnc1OCC1C2CCC1CN(S(=O)(=O)C1CC1)C2] | 524.6 |
| 533 | 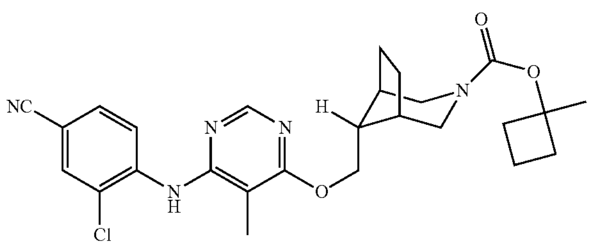 [SMILES: Cc1c(Nc2ccc(C#N)cc2Cl)ncnc1OCC1C2CCC1CN(C(=O)OC1(C)CCC1)C2] | 496.0 |
| 534 | 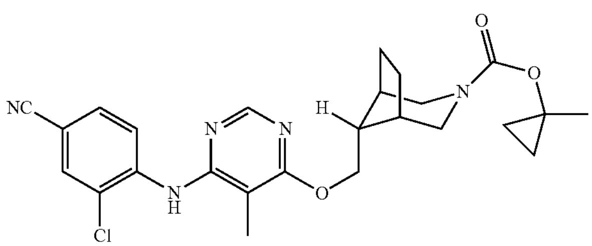 [SMILES: Cc1c(Nc2ccc(C#N)cc2Cl)ncnc1OCC1C2CCC1CN(C(=O)OC1(C)CC1)C2] | 482.0 |
| 535 | 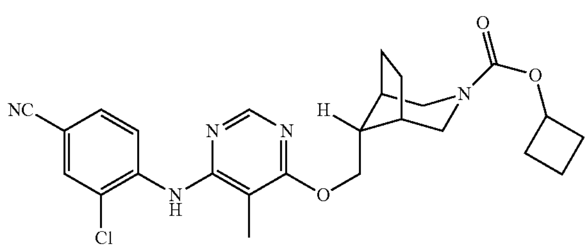 [SMILES: Cc1c(Nc2ccc(C#N)cc2Cl)ncnc1OCC1C2CCC1CN(C(=O)OC1CCC1)C2] | 482.0 |
| 536 | 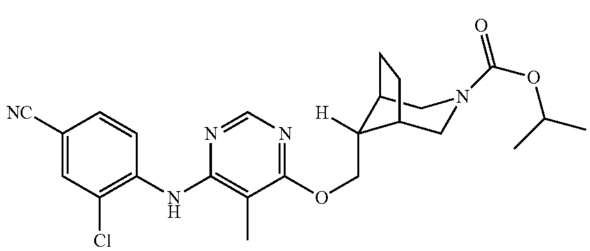 [SMILES: Cc1c(Nc2ccc(C#N)cc2Cl)ncnc1OCC1C2CCC1CN(C(=O)OC(C)C)C2] | 470.0 |

-continued

| Cpd. No. | Structure | LCMS (M + H) |
|---|---|---|
| 537 | 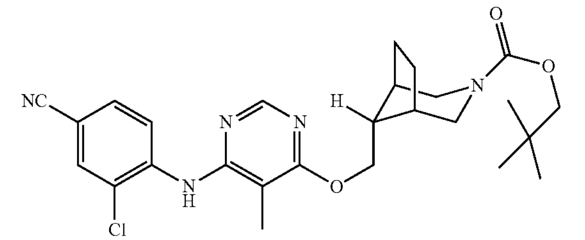 [SMILES: Cc1c(Nc2ccc(C#N)cc2Cl)ncnc1OCC1C2CCC1CN(C(=O)OCC(C)(C)C)C2] | 498.0 |
| 538 | 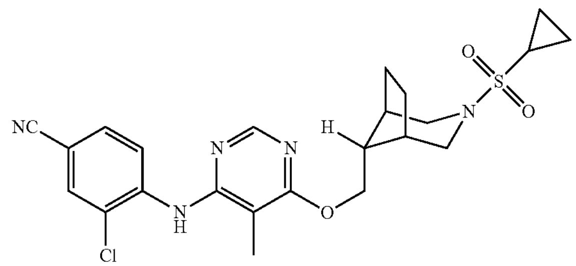 [SMILES: Cc1c(Nc2ccc(C#N)cc2Cl)ncnc1OCC1C2CCC1CN(S(=O)(=O)C1CC1)C2] | 488.0 |

Example 256

Preparation of Compound 539

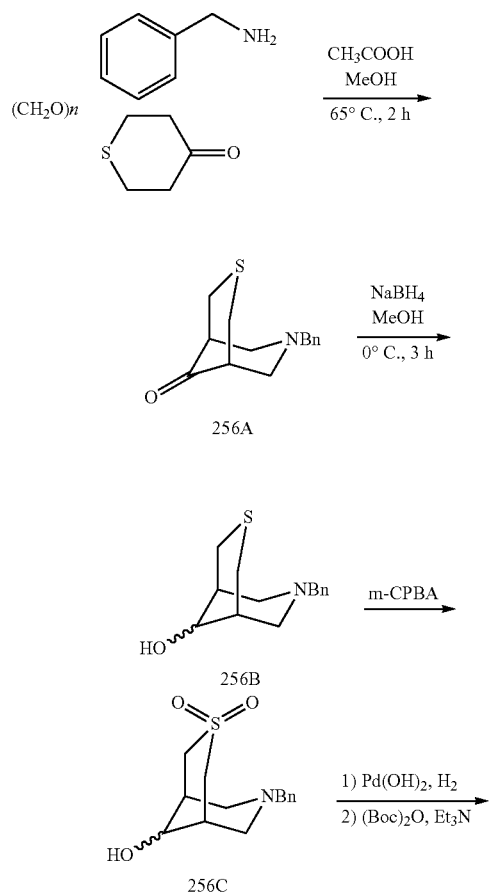

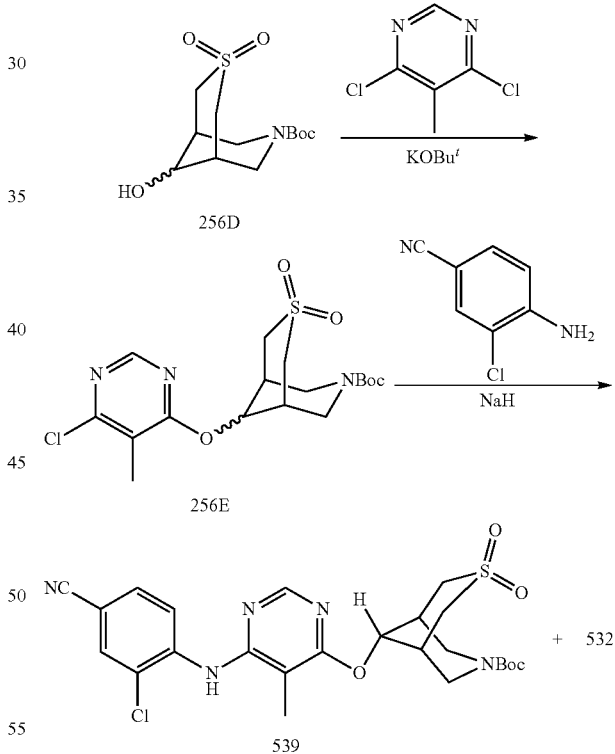

Step A—Synthesis of Compound 256A

A solution of dihydro-2H-thiopyran-4(3H)-one (4.65 g, 40.0 mmol), benzylamine (9.2 mL, 84 mmol) and acetic acid (4.56 mL, 80.0 mmol) in dry methanol (150 mL) was added over a period of 1 hour to a suspension of coarse-grained paraformaldehyde (5.32 g, 177 mmol) in dry methanol (150 mL) at 65° C. Another portion of paraformaldehyde (5.32 g, 177 mmol) was added and the mixture was stirred for 1 hour at 65° C. After cooling water (300 mL) and 1 N NaOH solution (80 mL) were added, and the aqueous phase was extracted with diethyl ether (3×600 mL). The combined organic layers were dried over MgSO₄ and the solvent was evaporated in vacuo. The residue was purified by flash chromatography on silica gel (0% to 20% ethyl acetate/n-hexane) to yield 256A as an oil (5.0 g, 51%).

Step B—Synthesis of Compound 256B

Compound 256B was prepared from compound 256A method described Example 50, Step A.

Step C—Synthesis of Compound 256C

To a solution of 256B (3.0 g) in dichloromethane (60 mL) was added m-CPBA (2.6 g) at 0° C. with stirring and the mixture was stirred at the same temperature for 2 hours. The reaction mixture was washed with 1 N NaOH solution and brine, dried over MgSO₄ and concentrated. To a mixture of the residue, MeOH (20 mL) and THF (40 mL) was added 1 N NaOH (24 mL) at room temperature for 2 hours. The reaction was diluted with EtOAc, washed with 1 N HCl and brine, dried and concentrated. The residue was purified by flash chromatography on silica gel (0% to 80% ethyl acetate/n-hexane) to yield 256C as a foam (0.42 g, 12%).

Step D—Synthesis of Compound 539

Compound 539 was prepared from compound 256C using the method described in Example 54.

The following table sets forth compounds of the present invention which were made using the method described above and substituting the appropriate reactants and reagents.

EXAMPLE 257

Preparation of Compound 544

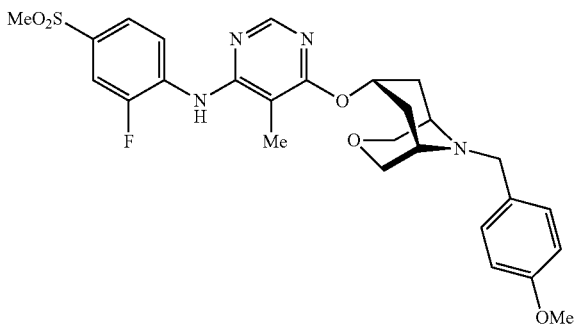

Using the method described in Example 34, Step A, substituting compound 219A for compound 1A and using the method described in Example 156 substituting 2-fluoro-4-methylsulfonylaniline for compound 143A, compound 544 was prepared. LCMS (M+H)⁺=543.3

| Cpd. No. | Structure | LCMS (M + H) |
|---|---|---|
| 540 | 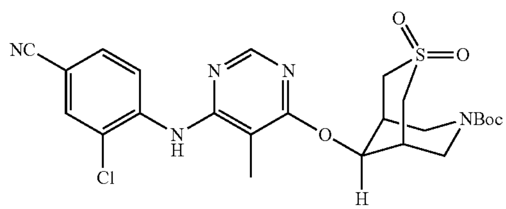 [SMILES: Cc1c(Nc2ccc(C#N)cc2Cl)ncnc1OC1C2CN(C(=O)OC(C)(C)C)CC1CS(=O)(=O)C2] | 534.0 |
| 541 | 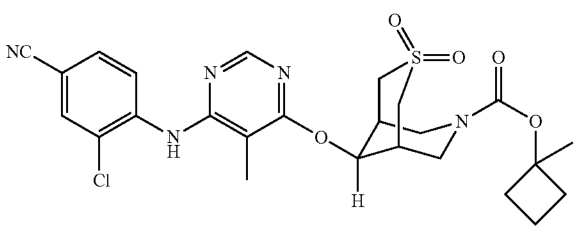 [SMILES: Cc1c(Nc2ccc(C#N)cc2Cl)ncnc1OC1C2CN(C(=O)OC3(C)CCC3)CC1CS(=O)(=O)C2] | 546.0 |
| 542 | 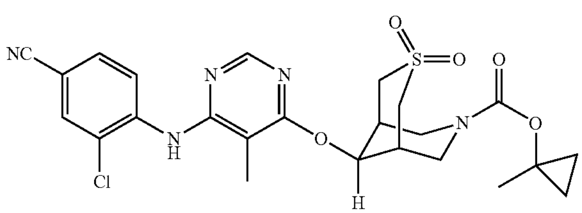 [SMILES: Cc1c(Nc2ccc(C#N)cc2Cl)ncnc1OC1C2CN(C(=O)OC3(C)CC3)CC1CS(=O)(=O)C2] | 532.0 |
| 543 | 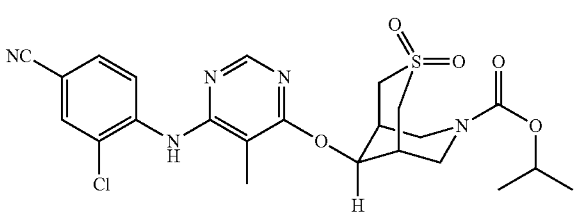 [SMILES: Cc1c(Nc2ccc(C#N)cc2Cl)ncnc1OC1C2CN(C(=O)OC(C)C)CC1CS(=O)(=O)C2] | 520.0 |

EXAMPLE 258

Preparation of Compound 545

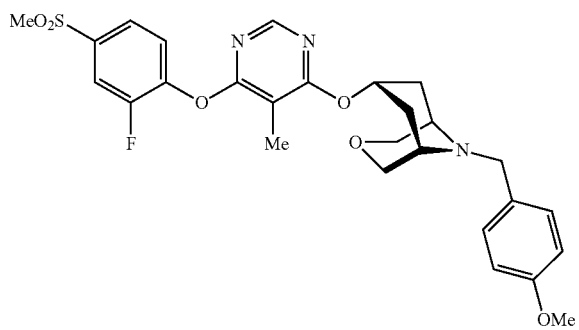

545

Using the method described in Example 34, Step A, substituting compound 219A for compound 1A and using the method described in Example 158 substituting 2-fluoro-4-methylsulfonylphenol for 4-(cyclopropylsulfonyl)-2-fluorophenol, compound 545 was prepared. LCMS (M+H)$^+$= 544.3

EXAMPLE 259

Preparation of Compound 546

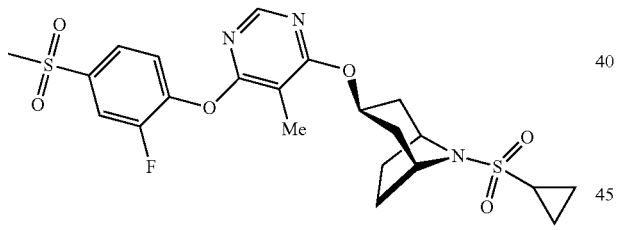

546

Using the method described in Example 158 substituting 2-fluoro-4-methylsulfonylphenol for 4-(cyclopropylsulfonyl)-2-fluorophenol and using the method described in Example 160, compound 546 was prepared. LCMS (M+H)$^+$=512.1.

EXAMPLE 260

Preparation of Compound 547

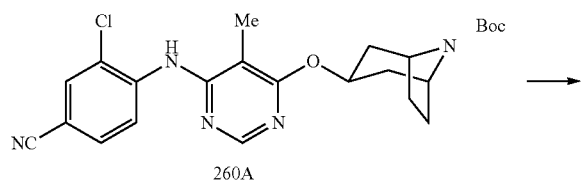

260A

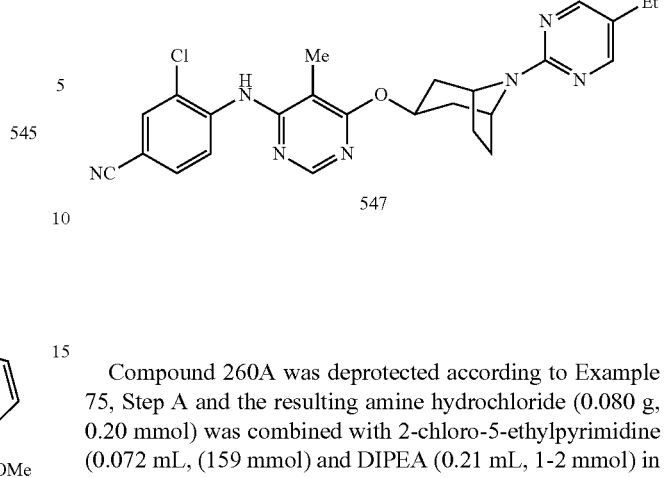

547

Compound 260A was deprotected according to Example 75, Step A and the resulting amine hydrochloride (0.080 g, 0.20 mmol) was combined with 2-chloro-5-ethylpyrimidine (0.072 mL, (159 mmol) and DIPEA (0.21 mL, 1-2 mmol) in dioxane (3 mL). The reaction was heated in a sealed tube at 110° C. for 72 hours, then concentrated in vacuo and purified using preparative TLC to provide compound 547 as a white solid. MS: m/e 476, 478.

EXAMPLE 261

Preparation of Compound 548

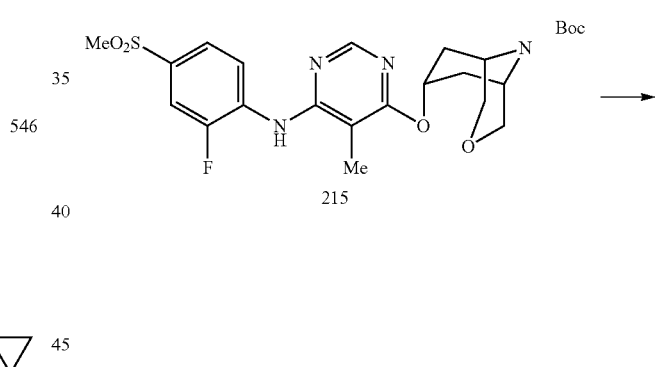

215

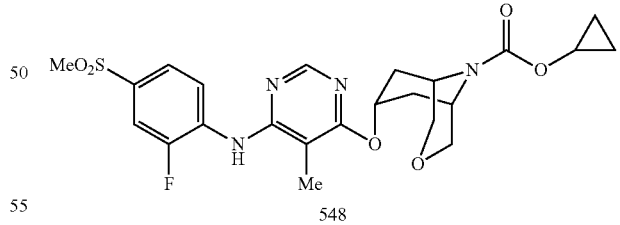

548

Compound 215 was reacted with compound 317C using the method described in Example 75 to provide compound 548 as a white gum. MS: m/e 507.

In similar fashion, the appropriate Boc derivatives were converted to the following compounds of the present invention:

| Cpd. No. | Structure | MS (MH+) |
|---|---|---|
| 549 | 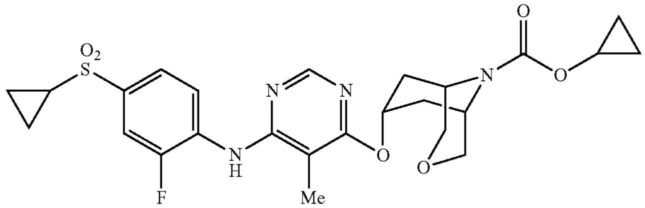 [SMILES: Cc1c(Nc2ccc(S(=O)(=O)C3CC3)cc2F)ncnc1OC1CC2COCC(C1)N2C(=O)OC1CC1] | 533 |
| 550 | 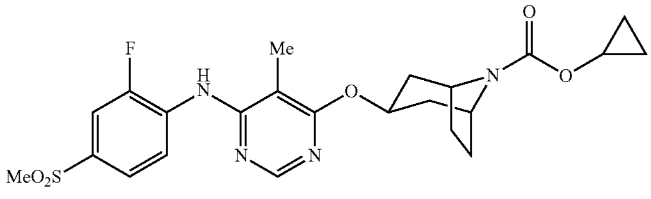 [SMILES: Cc1c(Nc2ccc(S(C)(=O)=O)cc2F)ncnc1OC1CC2CCC(C1)N2C(=O)OC1CC1] | 491 |
| 551 | 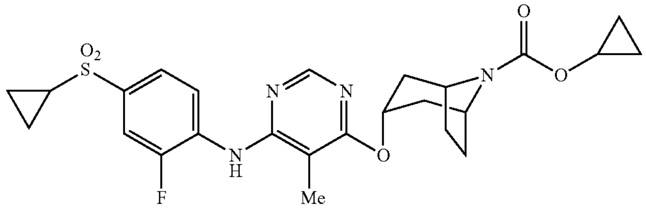 [SMILES: Cc1c(Nc2ccc(S(=O)(=O)C3CC3)cc2F)ncnc1OC1CC2CCC(C1)N2C(=O)OC1CC1] | 491 |

EXAMPLE 262

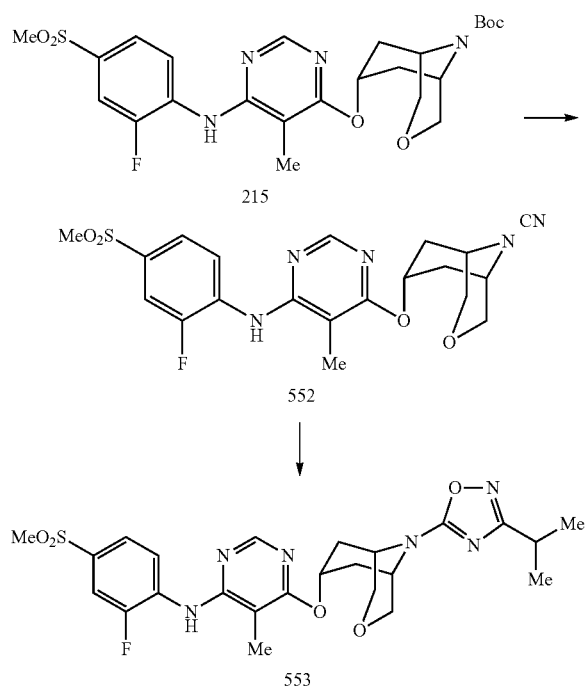

Step A—Synthesis of Compound 552

Compound 215 was deprotected according to Example 75, Step A and the resulting amine hydrochloride (0.060 g, 0.13 mmol) in CH$_2$Cl$_2$ (2 mL) treated with Et$_3$N (0.073 mL, 0.54 mmol) and then BrCN (3.0M in CH$_2$Cl$_2$, 0.087 mL, 0.26 mmol). After stirring for 4 hours, the reaction mixture was concentrated in vacuo to provide compound 552, which was used in the next step without further purification.

Step B—Synthesis of Compound 553

Compound 552 was dissolved in THF (3 mL) and treated with isobutyramide oxime (0.040 g, 0.39 mmol), then ZnCl$_2$ (0.017 g, 0.13 mmol). The reaction was stirred for 30 minutes at room temperature, then was heated tea 40° C.' and allowed to stir at this temperature for 30 minutes. Concentrated HCl (0.30 mL) was then added, and the resulting reaction was heated to reflux and allowed to stir at this temperature for 2 hours, then allowed to cool to room temperature and partitioned between ethyl acetate and 1 N aqueous NaOH. The organic phase was dried (MgSO$_4$), filtered and concentrated in vacuo and the residue obtained was purified using preparative TLC (30% acetone/hexane) to provide compound 553 as a white solid, MS: m/e 533.

EXAMPLE 263

Preparation of Compound 554

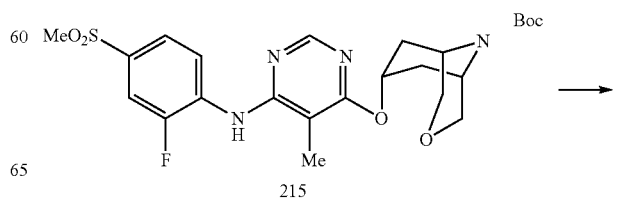

-continued
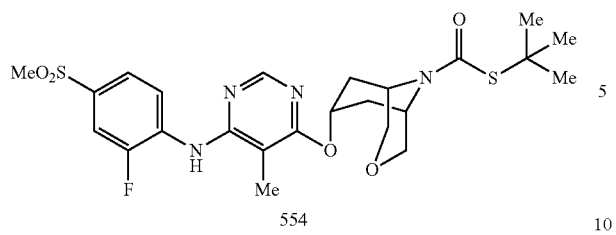
554
Compound 215 was reacted with t-butyl chlorothioformate according to the method described in Example 75 to provide compound 554 as a white solid, MS: m/e 539.
In similar fashion; the appropriate Boc derivatives were converted to the following compounds of the present invention:
| Cpd. No. | Structure | MS (MH+) |
|---|---|---|
| 555 | 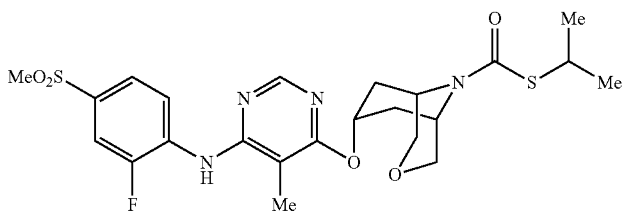 [SMILES: Cc1c(Nc2ccc(S(C)(=O)=O)cc2F)ncnc1OC1CC2COCC(C1)N2C(=O)SC(C)C] | 525 |
| 556 | 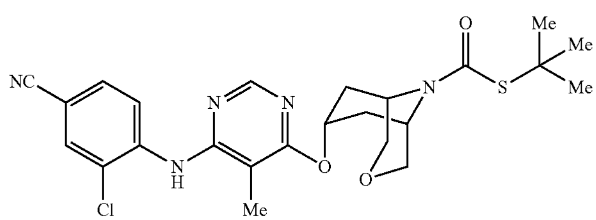 [SMILES: Cc1c(Nc2ccc(C#N)cc2Cl)ncnc1OC1CC2COCC(C1)N2C(=O)SC(C)(C)C] | 502, 504 |
| 557 | 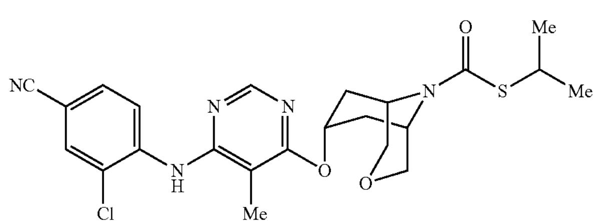 [SMILES: Cc1c(Nc2ccc(C#N)cc2Cl)ncnc1OC1CC2COCC(C1)N2C(=O)SC(C)C] | 488, 490 |

EXAMPLE 264

Preparation of Compound 558

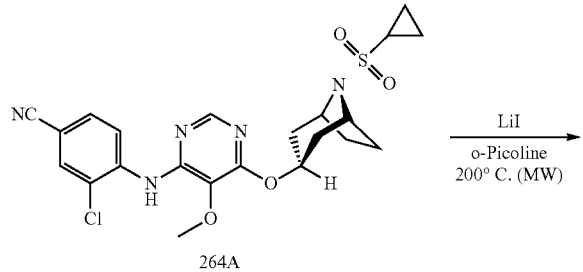

264A

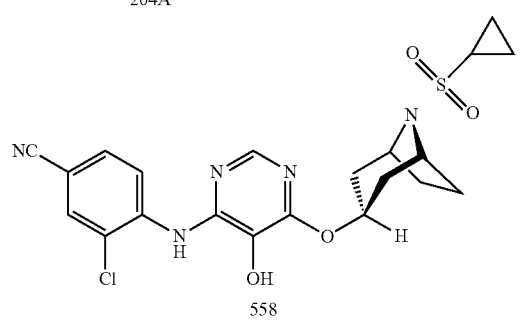

558

A solution of compound 264A (97 mg, 0.2 mmol, prepared starting from 66A using the method described in Examples 34 and 36) and lithium iodide (420 mg, 3.2 mmol) in o-picoline (2 mL) was heated in a microwave reactor for ten minutes set on fixed hold time, at high absorbance, at a temperature of 200° C. The reaction was then concentrated in vacuo, the resulting residue was taken up in dichloromethane and the organic phase was washed with 10% aqueous HCl, dried over MgSO₄, filtered and concentrated in vacuo to provide compound 558 (86 rug, 90%) as a tan solid which was used without further purification. LCMS: 476.3 (MH⁺).

EXAMPLE 265

Preparation of Compound 559

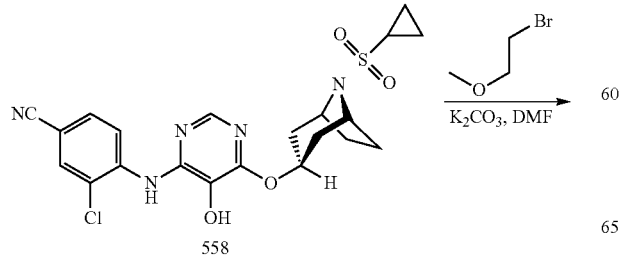

558

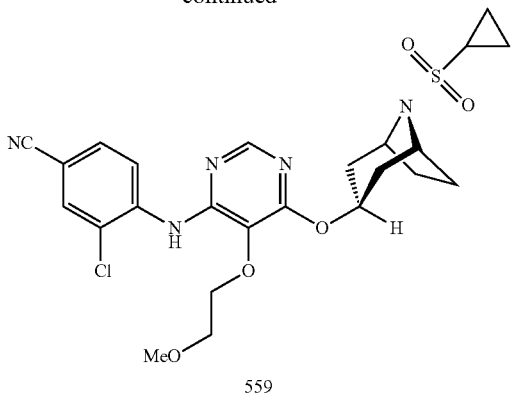

559

To a solution of compound 558 (21 mg, 0.044 mmol) and 2-bromoethyl methyl ether (12 mg, 0.088 mmol) in dimethylformamide (1 nit) was added potassium carbonate (24 mg, 0.176 mmol) and the resulting reaction was allowed to stir at room temperature for 60 hours. The reaction mixture was then concentrated in vacuo and the resulting residue was taken up in dichloromethane. The organic solution was washed with aqueous saturated ammonium chloride solution, dried over MgSO₄, filtered, and concentrated in vacuo. The resulting residue was purified using preparative TLC on silica gel (dichloromethane/ethyl acetate=95/5) to provide compound 559, (14 mg, 95%) as an off-white solid. LCMS: 534.3 (MH⁺).

EXAMPLE 266

Preparation of Compound 560

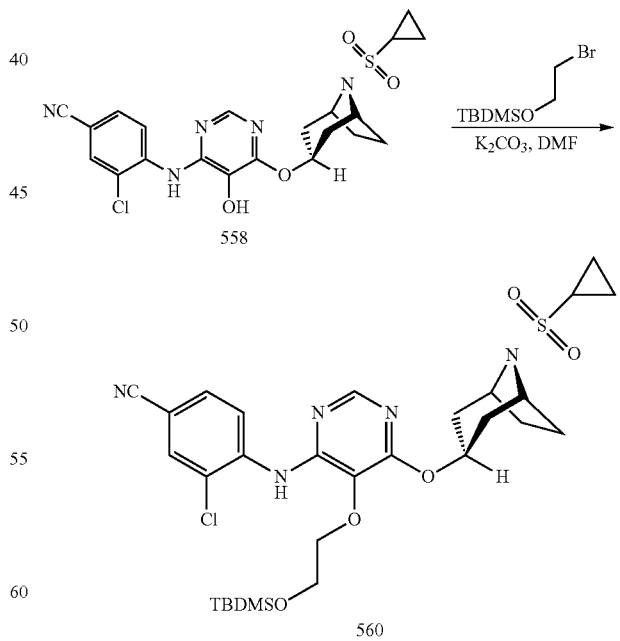

To a solution of compound 558 (24 mg, 0.05 mmol) and 2-bromoethoxy-tert-butyldimethylsilane (36 mg, 0.15 mmol) in dimethylformamide (1 mL) was added potassium carbonate (90 mg, 0.65 mmol) and the resulting reaction was allowed to stir at room temperature for 20 hours. The reaction mixture was then concentrated in vacuo and the resulting residue was taken up in dichloromethane. The organic solution was washed with aqueous saturated ammonium chloride solution, dried over MgSO$_4$, filtered, and concentrated in vacuo. The resulting residue was purified using preparative TLC on silica gel (dichloromethane/ethyl acetate=95/5) to provide compound 560 (14 mg, 44%) as an off-white solid. LCMS: 634.3 (MH$^+$).

EXAMPLE 267

Preparation of Compound 561

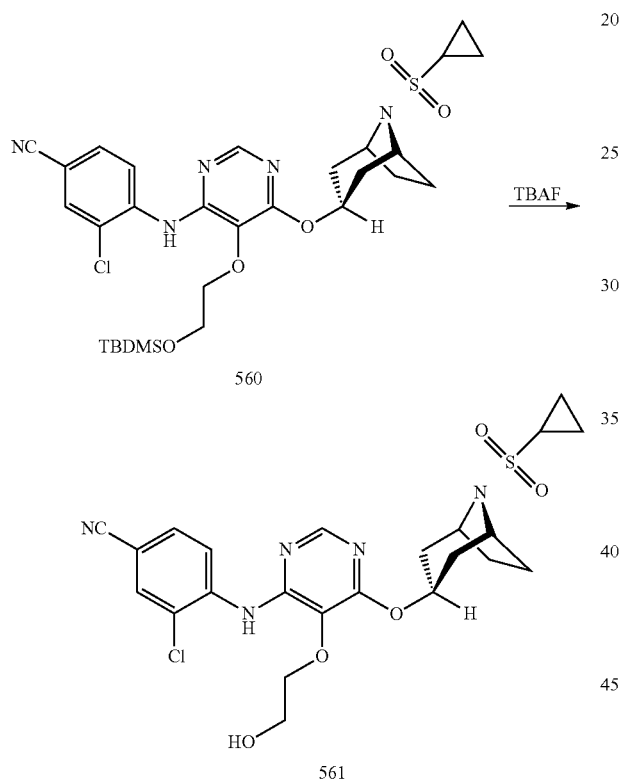

To a 1 M solution of tetrabutylammoniumfluoride in THF (1 mL) at room temperature was added compound 560 (12 mg, 0.019 mmol). The resulting reaction was allowed to stir at room temperature for 16 hours, then it was concentrated in vacuo and the resulting residue was taken up in dichloromethane. The organic solution was washed with aqueous saturated ammonium chloride solution, dried over MgSO$_4$, filtered, and concentrated in vacuo. The resulting residue was purified using, preparative TLC on silica gel (dichloromethane/ethyl acetate=80/20) to provide compound 561 (9 mg, 91%) as a white solid. LCMS: 520.3 (MH$^+$).

EXAMPLE 268

Preparation of Compound 268A

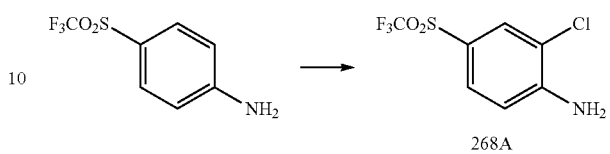

4-(Trifluoromethylsulfonyl)aniline was chlorinated according to the method described in Example 72. Extractive workup (hexane) provided compound 268A as a yellow solid.

EXAMPLE 209A

Preparation of Compound 269A

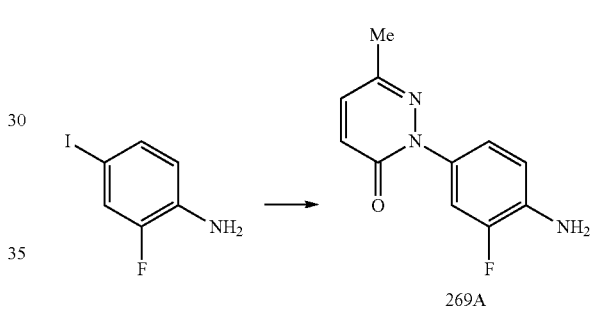

2-Fluoro-4-iodoaniline (3.00 g, 12.7 mmol), 6-methylpyridazine-2-one (1.74 g, 15.8 mmol, 8-hydroxyquinoline (0.276 g, 1.9 mmol), CuI (0.362 g, 1.9 mmol) and K$_2$CO$_3$ (1.92 g, 13.9 mmol) were combined in DMSO (1.2 mL) and the resulting react was heated to 130° C. and allowed to stir at this temperature for 20 hours. The reaction mixture was cooled to room temperature, then diluted with EtOAc and water. Charcoal was added to the resulting solution and the mixture was filtered. The filtrate was transferred to a separatory funnel and the organic phase was collected and washed with brine, dried (MgSO$_4$), filtered and concentrated in vacuo. The resulting residue was purified using flash column chromatography on silica to provide compound 269A as a yellow solid.

EXAMPLE 270

Preparation of Compound 270B

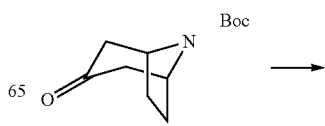

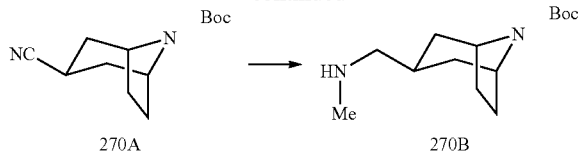

270A → 270B

Step A—Synthesis of Compound 270A

Boc-nortropinone (2.00 g, 8.9 mmol) and toluenesulfonylmethyl isocyanide (11.6 mmol) were combined in 1,2-dimethoxyethane (30 mL) and ethanol (1.0 mL) and the resulting solution was cooled to 0° C. To the cooled solution was added potassium tort-butoxide (2.39 g, 2.13 mmol) in portions, while maintaining the reaction temperature below 10° C. The mixture was stirred for 1 hour alter addition was complete, then the cold bath was removed and the reaction was allowed to stir for an additional 90 hours. The reaction mixture was then filtered and the collected solid was washed with ethyl acetate. The combined filtrates were concentrated in vacuo to provide compound 270A as a yellow oil.

Seep B—Synthesis of Compound 270B

Compound 270A (0.88 g, 3.7 mmol) was taken up in a mixture of MeOH (5 mL) and 2.0N MeNH$_2$ in MeOH (20 mL), and to the resulting solution was added 10% Pd/C. The mixture was hydrogenated at 50 psi for 120 hours, then filtered through a short pad of Celite. The filtrate was concentrated in vacuo to provide compound 270B as a white solid, which was used without further purification.

EXAMPLE 271

Preparation of Compound 271B

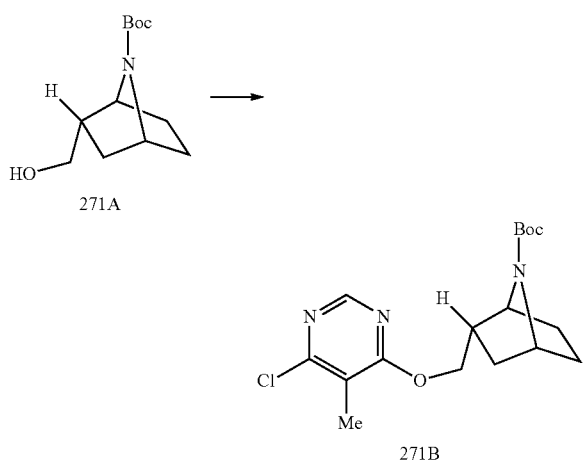

Compound 271A was reacted according to the method described in Example 61 to provide compound 271B as a yellow oil after purification via flash chromatography on silica gel.

EXAMPLE 272

Preparation of Compound 272A

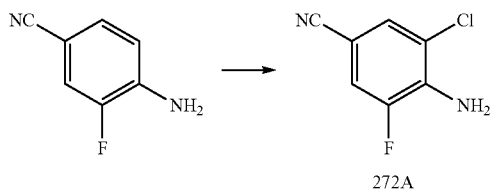 [SMILES: N#Cc1ccc(N)c(F)c1 ; N#Cc1cc(F)c(N)c(Cl)c1]

4-Amino-3-fluorobenzonitrile was chlorinated according to the method described in Example 72 and substituting acetic acid for DMF as solvent to provide compound 272A as an off-white solid.

EXAMPLE 273

Preparation of Compound 273C

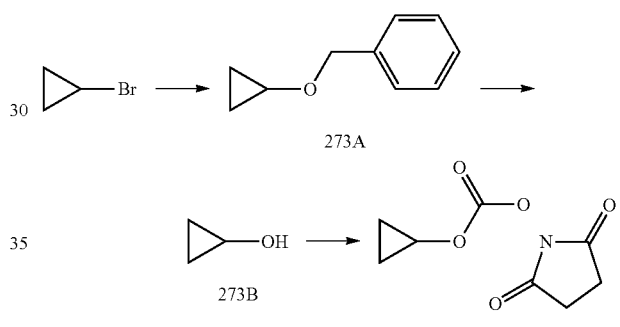

Step A—Synthesis of compound 273A

Bromocyclopropane (2.50 g, 20.8 mmol), benzyl alcohol (4.50 g, 41.7 mmol) and NaO-tBu (4.00 g, 41.7 mmol) were taken up in dioxane (20 mL) and the resulting reaction was heated to 100° C. and allowed to stir at this temperature for 3 hours. The reaction mixture was then allowed to cool to room temperature and was concentrated in vacuo and the residue obtained was purified using flash column chromatography on silica (0-20% CH$_2$Cl$_2$/hexane) to provide compound 273A as an oil.

Step B—Synthesis of Compound 273B

To a solution of compound 273A (0.60 g, 4.1 mmol) in ethyl acetate (5 mL) was added 10% Pd/C (0.30 g). The mixture was hydrogenated at 50 psi for 70 hours, then was filtered and the collected catalyst was washed with MeCN (2×10 mL). The filtrate, which contains compound 273B, was then used in the next step.

Step C—Synthesis of Compound 273C

To the solution from Step B, which contains compound 273B, was added disuccinimidyl carbonate (2.11 g, 8.2 mmol) and Et$_3$N (2.4 mL, 17 mmol) and the resulting reaction was allowed to stir for 3 hours at room temperature. The reaction mixture was then partitioned between ethyl acetate and saturated aqueous NaHCO$_3$. The organic phase as dried (MgSO$_4$), filtered and concentrated in vacuo to provide compound 273C as a yellow oil.

EXAMPLE 274 cAMP Assay

The ability of illustrative compounds of the invention to activate GPR119 and stimulate increases in cAMP levels was determined using the LANCE™ cAMP kit (Perkin Elmer). HEK293 cells expressing human GPR119 were maintained in culture flasks at 37° C./5% CO, in DMEM containing 10% fetal bovine serum, 100 U/ml Pen/Strep, and 0.5 mg/ml geneticin. The media was changed to Optimem and cells were incubated overnight at 37° C./5% $CO_2$. The Optimem was then aspirated and the cells were removed from the flasks using room temperature Hank's balanced saline solution (HBSS). The cells were pelleted using centrifugation (1300 rpm, 7 minutes, room temperature), then resuspended in stimulation buffer (HESS, 0.1% BSA, 5 mM HEPES, 15 µM RO-20) at $2.5 \times 10^6$ cells/mL. Alexa Fluor 647-anti cAMP antibody (1:100) was then added to the cell suspension and incubated for 30 minutes. A representative Bicyclic Heterocycle Derivative (6 µl at 2× concentration) in stimulation buffer containing 2% DMSO were then added to white 384 well Matrix plates. Cell suspension mix (6 µl) was added to each well and incubated with the Bicyclic Heterocycle Derivative for 30 minutes. A cAMP standard curve was also created in each assay according to the kit protocol. Standard concentrations of cAMP in stimulation buffer (6 µl) were added to white 384 well plates. Subsequently, 6 µl of 1:100 anti-cAMP antibody was added to each well. Following the 30 minute incubation period, 12 µl of detection mix (included in kit) was added to all wells and incubated for 2-3 hours at room temperature. Fluorescence was detected on the plates using an Envision instrument. The level of cAMP in each well is determined by extrapolation from the cAMP standard curve.

Using this assay, $EC_{50}$ values for various illustrative Bicyclic Heterocycle Derivatives of the present invention were calculated and range from about 1 nM to about 20 µM.

EXAMPLE 275

Effect of the Compounds of the Invention in Oral Glucose Tolerance Test

Male C57Bl/6NCrl mice (6-8 week old) were fasted overnight and randomly dosed with either vehicle (20% hydropropyl-β-cyclodextrin) or a representative compound of the invention (at 3, 10 or 30 mg/kg) via oral gavage (n—-8 mice/group). Glucose was administered to the animals 30 minutes post-dosing (3 g/kg p.o.). Blood glucose was measured prior to administration of test compound and glucose, and at 20 minutes after glucose administration using a hand-held glucometer (Ascensia Elite, Bayer).

Using this protocol, the effects of various Bicyclic Heterocycle Derivatives of the present invention were measured and indicate that the Bicyclic Heterocycle Derivatives of the present invention are effective in lowering blood glucose levels after glucose challenge.

EXAMPLE 276

Effect of the Compounds of the Invention in an Animal Model of Diabetes

Four week old male C57Bl/6NCrl mice can be used to generate a nongenetic model of type 2 diabetes mellitus as previously described (*Metabolism* 47(6): 663-668, 1998). Briefly, mice are made insulin resistant by high fat feeding (60% of kcal as fat) and hyperglycemia is then induced using a low dose of streptozotocin (100 mg/kg i.p.). Eight weeks after streptozotocin administration, the diabetic mice are placed into one of 4 groups (n=13/gp) receiving the following treatments: vehicle (20% hydroxypropyl-β-cyclodextrin p.o.), compound to be tested (30 mg/kg p.o.), glipizide (20 mg/kg p.o.) or exendin-4 (10 ug/kg i.p.).

Mice are dosed once daily for 13 consecutive days, and blood glucose levels are measured daily using, for example, a hand held glucometer, to determine the effects of the test compound(s) on glucose levels of the diabetic animals.

Uses of the Bicyclic Heterocycle Derivatives

The Bicyclic Heterocycle Derivatives are useful in human and veterinary medicine for treating or preventing a Condition in a patient. In accordance with the invention, the Bicyclic Heterocycle Derivatives can be administered to a patient in need of treatment or prevention (of a Condition.

Treatment of Obesity and Obesity-Related Disorders

The Bicyclic Heterocycle Derivatives can also be useful for treating obesity or an obesity-related disorder.

Accordingly, in one embodiment, the invention provides methods for treating obesity or an obesity-related disorder in a patient, wherein the method comprises administering to the patient an effective amount of one or more Bicyclic Heterocycle Derivatives, or a pharmaceutically acceptable salt, solvate, ester, prodrug car stereoisomer thereof.

Treatment of Diabetes

The Bicyclic Heterocycle Derivatives are useful for treating diabetes in a patient. Accordingly, in one embodiment, the present invention provides a method for treating diabetes in a patient, comprising administering to the patient an effective amount of one or more Bicyclic Heterocycle Derivatives.

Examples of diabetes treatable or preventable using the Bicyclic Heterocycle Derivatives include, but are not limited to, type I diabetes(insulin-dependent diabetes mellitus), type II diabetes (non-insulin dependent diabetes mellitus), gestational diabetes, autoimmune diabetes, insulinopathies, idiopathic type I diabetes (Type Ib), latent autoimmune diabetes in adults, early-onset type 2 diabetes (EOD), youth-onset atypical diabetes (YOAD), maturity onset diabetes of the young (MODY), malnutrition-related diabetes, diabetes due to pancreatic disease, diabetes associated with other endocrine diseases (such as Cushing's Syndrome, acromeaaly, pheochromocytoma, glucagonoma, primary aldosteronism or somatostatinoma), type A insulin resistance syndrome, type B insulin resistance syndrome, lipatrophic diabetes, diabetes induced by β-cell toxins, and diabetes induced by drug therapy (such as diabetes induced by antipsychotic agents).

In one embodiment, the diabetes is type I diabetes.

In another embodiment, the diabetes is type II diabetes.

Treatment of a Diabetic Complication

The Bicyclic Heterocycle Derivatives are also useful for treating a diabetic complication in a patient. Accordingly, in one embodiment, the present invention prow ides a method for treating a diabetic complication in a patient, comprising administering to the patient an effective amount of one or more Bicyclic Heterocycle Derivatives.

Examples of diabetic complications treatable or preventable using the Bicyclic Heterocycle Derivatives include, but are not hinted to, diabetic cataract, glaucoma, retinopathy, aneuropathy (such as diabetic neuropathy, polyneuropathy, mononeuropathy, autonomic neuropathy, microaluminuria and progressive diabetic neuropathyl), nephropathy, gangrene of the feet, immune-complex vasculitis, systemic lupsus erythematosus (SLE), atherosclerotic coronary arterial disease, peripheral arterial disease, nonketotic hyperglycemic-hyperosmolar coma, foot ulcers, joint problems, a skin or mucous membrane complication (such as an infection, a shin spot, a candidal infection or necrobiosis lipoidica diabeticorumobesity), hyperlipidemia, cataract, hypertension, syndrome of insulin resistance, coronary artery disease, a fungal infection, a bacterial infection, and cardiomyopathy.

Treatment of a Metabolic Disorder

The Bicyclic Heterocycle Derivatives can also be useful for treating a metabolic disorder. Examples of metabolic disorders treatable include, but are not limited to, syndrome; (also known as "Syndrome X"), impaired glucose tolerance, impaired fasting glucose, hypercholesterolemia, hyperlipidemia, hypertriglyceridemia, low HDL levels, hypertension, phenylketonuria, post-prandial lipidemia, a glycogen-storage disease. Gaucher's Disease, Tay-Sachs Disease, Niemann-Pick Disease, ketosis and acidosis.

Accordingly, in one embodiment, the invention provides methods for treating a metabolic disorder in a patient, wherein the method comprises administering to the patient effective amount of one or more Bicyclic Heterocycle Derivatives, or a pharmaceutically acceptable salt, solvate, ester, prodrug or stereoisomer thereof.

In one embodiment, the metabolic disorder is hypercholesterolemia.

In another embodiment, the metabolic disorder is hyperlipidemia.

In another embodiment, the metabolic disorder is hypertriglyceridemia.

In still another embodiment, the metabolic disorder is metabolic syndrome.

In a further embodiment, the metabolic disorder is low HDL levels.

Methods For Treating a Cardiovascular Disease

The Bicyclic Heterocycle Derivatives are useful for treating or preventing a cardiovascular disease in a patient.

Accordingly, in one embodiment, the present invention provides a method for treating a cardiovascular disease in a patient, comprising administering to the patient an effective amount of one or more Bicyclic Heterocycle Derivatives.

Illustrative examples of cardiovascular diseases treatable or preventable using the present methods, include, but are not limited to atherosclerosis, congestive heart failure, cardiac arrhythmia, myocardial infarction, atrial fibrillation, atrial flutter, circulatory shock, left ventricular hypertrophy, ventricular tachycardia, supraventricular tachycardia, coronary artery disease, angina, infective endocarditis, non-infective endocarditis, cardiomyopathy, peripheral artery disease, Reynaud's phenomenon, deep venous thrombosis, aortic stenosis, mitral stenosis, pulmonic stenosis and tricuspid stenosis.

In one embodiment, the cardiovascular disease is atherosclerosis.

In another embodiment, the cardiovascular disease is congestive heart failure.

In another embodiment, the cardiovascular disease is coronary artery disease.

Combination Therapy

In one embodiment, the present invention provides methods for treating a Condition a patient, the method comprising administering to the patient one or more Bicyclic Heterocyle Derivatives, or a pharmaceutically acceptable salt, solvate, ester, prodrug or stereoisomer thereof and at least one additional therapeutic agent that is not a Bicyclic Heterocycle Derivative, wherein the amounts administered are together effective to treat or prevent a Condition.

Non-limiting examples of additional therapeutic agents useful in the present methods for treating or preventing a Condition include, anti-obesity agents, antidiabetic agents, any agent useful for treating metabolic syndrome, any agent useful for treating a cardiovascular disease, cholesterol biosynthesis inhibitors, cholesterol absorption inhibitors, bile acid sequestrants, probucol derivatives, IBAT inhibitors, nicotinic acid receptor (NAR) agonists, ACAT inhibitors, cholesteryl ester transfer protea (CETP) inhibitors, low-density lipoprotein (LDL) activators, fish oil, water-soluble fibers, plant sterols, plant stanols, fatty acid esters of plant stanols, or any combination of two or more of these additional therapeutic agents.

Non-limiting examples of anti-obesity agents useful in the present methods for treating a Condition include CBI antagonists in ver agonists such as rimonabant, neuropeptide Y antagonists, MCR4 agonists, MCH receptor antagonists, histamine $H_3$ receptor antagonists or inverse agonists, metabolic rate enhancers, nutrient absorption inhibitors, leptin, appetite suppressants and lipase inhibitors.

Non-limiting examples of appetite suppressant agents useful in the present methods for treating or preventing a Condition include cannabinoid receptor 1 ($CB_1$) antagonists or inverse agonists (e.g., rimonabant); Neuropeptide Y (NPY1, NPY2, NPY4 and NPY5) antagonists; metabotropic glutamate subtype 5 receptor (mGluR5) antagonists (e.g., 2-methyl-6-(phenylethynyl)-pyridine and 3[(2-methyl-1,4-thiazol-4-yl)ethynyl]pyridine); melanin-concentrating hormone receptor (MCH1R and MCH2R) antagonists; melanocortin receptor agonists (e.g., Melanotan-II and Mc4r agonists); serotonin uptake inhibitors (e.g., dexfenfluramine and fluoxetine); serotonin (5HT) transport inhibitors paroxetine, fluoxetine, fenfluramine, fluvoxamine, sertaline and imipramine); norepinephrine (NE) transporter inhibitors (e.g., desipramine, talsupram and nomifensine); ghrelin antagonists; leptin or derivatives thereof; opioid antagonists (e.g., nalmefene, 3-methoxynaltrexone, naloxone and nalterxone), orexin antagonists: bombesin receptor subtype 3 (BRS3) agonists; Cholecystokinin-A (CCK-A) agonists neurotrophic fetor (CNTF) or derivatives Thereof (e.g., butabindide and axokine); monoamine reuptake inhibitors (e.g., sibutramine); Glucagon-like peptide 1 (GLP-1) agonists; topiramate; and phytopharm compound 57.

Non-limiting examples of metabolic rate enhancers useful in the present methods for treating or preventing a Condition include acetyl-CoA carboxylase-2 (ACC2) inhibitors; beta adrenergic receptor 3 ($\beta$3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, amrinone, milrinone, cilostamide, rolipram and cilomilast); thyroid hormone $\beta$ agonists; uncoupling protein activators (UCP-1, 2 or 3) (e.g., phytanic acid, 4-[(E)-2-(5,6, 7,8-tetramethyl-2-naphthalenyl)-1-propenyl]benzoic acid and retinoic acid); acyl-estrogens (e.g., oleoyl-estrone); glucocorticoid antagonists; 11-beta hydroxy steroid dehydrogenase type 1 (11β HSD-1) inhibitors; melanocortin-3 receptor (Mc3r) agonists; and stearoyl-CoA desaturase-1 (SCD-1) compounds.

Non-limiting examples of nutrient absorption inhibitors useful in the present methods for treating or preventing a Condition include lipase inhibitors (e.g., orlistat, lipstatin, tetrahydrolipstatin, teasaponin and diethylumbelliferyl phosphate); fatty acid transporter inhibitors; dicarboxylate transporter inhibitors; glucose transporter inhibitors; and phosphate transporter inhibitors.

Non-limiting examples of cholesterol biosynthesis inhibitors useful in the present methods for treating or preventing a Condition include HMG-CoA reductase inhibitors, squalene synthase inhibitors, squalene epoxidase inhibitors, and mixtures thereof.

Non-limiting examples of cholesterol absorption inhibitors useful in the present methods for treating or preventing a Condition include ezetimibe. In one embodiment, the cholesterol absorption inhibitor is ezetimibe.

HMG-CoA reductase inhibitors useful in the present methods for treating or preventing a Condition include, but are not limited to, statins such as lovastatin, pravastatin fluvastatin, simvastatin, atorvastatin, cerivastatin, Cl-981, resuvastatin, rivastatin, pitavastatin, rosuvastatin or L-659,699 ((E,E)-11-[3'R-(hydroxy-methyl)-4'-oxo-2'R-oxetanyl]-3,5,7R-trimethyl-2,4-undecadienoic acid).

Squalene synthesis inhibitors useful in the present methods for treating or preventing Condition include, but are not limited to, squalene synthetase inhibitors; squalestatin 1; and squalene epoxidase inhibitors, such as NB-SOS 4E)-N-ethyl-N-(6,6-dimethyl-2-hepten-4-ynyl)-3-[(3,3'-bithiophen-5-yl)methoxy]benzene-methanamine hydrochloride).

Bile acid sequestrants useful in methods for treating or preventing a Condition include, but are not limited to, cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colosevelam hydrochloride (such as WelChol® Tablets (poly (allylaanine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof. Suitable inorganic cholesterol sequestrants include bismuth salicylate plus montmorillonite clay, aluminum hydroxide and calcium carbonate antacids.

Probucol derivatives useful in the present methods for treating or preventing a Condition include, but are not limited to, AGI-1067 and others disclosed in U.S. Pat. Nos. 6,121,319 and 6,147,250.

IBAT inhibitors useful in the present methods for treating or preventing a Condition include, but are not limited to, benzothiepines such as therapeutic compounds comprising a 2,3,4,5-tetrahydro-1-benzothiepine 1,1-dioxide structure such as are disclosed in International Publication No. WO 00/38727.

Nicotinic acid receptor agonists useful in the present methods for treating or preventing a Condition include, but are not limited to, those having a pyridine-3-carboxylate structure or a pyrazine-2-carboxylate structure, including acid forms, salts, esters, zwitterions and tautomers, where available. Other examples of nicotinic acid receptor agonists useful in the present methods include nicotinic acid, niceritrol, nicofuranose and acipimox. An example of a suitable nicotinic acid product is NIASPAN® (niacin extended-release tablets) which are available from Kos Pharmaceuticals, Inc. (Cranbury, N.J.). Further nicotinic acid receptor agonists useful in the present methods for treating pr venting a Condition include, but are not limited to, the compounds disclosed in U.S. Patent Publication Nos. 2006/0264489 and 2007/0066630, and U.S. patent application Ser. No 11/771,538, each of which is incorporated herein by reference.

ACAT inhibitors useful in the present methods for treating or preventing a Condition include, but are not limited to, avasimibe, HL-004, lecimibide and CL-277082 (N-(2,4-ditluorophenyl)-N-[[4-(2,2-dimethylpropyl)phenyl]-methyl]-N-heptylurea). See P. Chang et al., "Current, New and Future Treatments in Dyslipidaemia and Atherosclerosis", *Drugs* 2000 Jul; 60(1); 55-93, which is incorporated by reference herein.

CETP inhibitors useful in the present methods for treating or preventing a Condition include, but are not limited to, those disclosed in International Publication No, WO 00/38721 and U.S. Pat. No. 6,147,090, which are incorporated herein by reference.

LDL-receptor activators useful in the present methods for treating or preventing a Condition include, but are not limited to, include HOE-402, an imidazolidinyl-pyrimidine derivative that directly stimulates LDL receptor activity. See M. Huettinger et al., "Hypolipidemic activity of HOE-402 is Mediated by Stimulation of the LDL Receptor Pathway", *Arterioscler. Thromb.* 1993; 13:1005-12.

Natural water-soluble fibers useful in the present methods for treating or preventing a Condition include, but are not limited to, psyllium, guar, oat and pectin.

Fatty acid esters of plant stanols useful in the present methods for treating or preventing a Condition include, but are not limited to, the sitostanol ester used in BENECOL® margarine, Non-limiting examples of antidiabetic agents useful in the present methods for treating a Condition include insulin sensitizers, β-glucosidase inhibitors, DPP-IV inhibitors, insulin secretagogues, hepatic glucose output lowering compounds, antihypertensive agents, sodium glucose uptake transporter 2 (SGLT-2) inhibitors, insulin and insulin-containing compositions, and anti-obesity agents as set forth above.

In one embodiment, the antidiabetic agent is an insulin secretagogue. In one embodiment, the insulin secretagogue is a sulfonylurea.

Non-limiting examples of sulfonylureas useful in the present methods include glipizide, tolbutamide, glyhuride, glimepiride, chlorpropamide, acetohexamide, gliamilide, gliclazide, gliquidone, glibenclamide and tolazamide.

In another embodiment, the insulin secretagogue is a meglitinide.

Non-limiting examples of meglitinides useful in the present methods for treating Condition include repaglinide, mitiglinide, and nateglinide.

In still another embodiment, the insulin secretagogue is GLP-1 or a GLP-1 mimetic.

Non-limiting examples of GLP-1 mimetics useful in the present methods include Byetta-Exanatide, Liraglutinide, CJC-1131 (ConjuChern, Exanatide-LAR (Amylin), BIM-51077 (Ipsen/LaRoche), ZP-10 (Zealand Pharmaceuticals), and compounds disclosed in International Publication No. WO 00/07617.

Other non-limiting examples of insulin secretagogues useful in the present methods include exendin, GIP and secretin.

In another embodiment, the antidiabetic agent is an insulin sensitizer.

Non-limiting examples of insulin sensitizers useful in the present methods include PPAR activators or agonists, such as troglitazone, rosiglitone, pioglitazone and enylitazone; biguanidines such as metformin and phenformin; PTP-1B inhibitors; and glucokinase activators.

In another embodiment, the antidiabetic agent is a β-Glucosidase inhibitor.

Non-limiting examples of β-Glucosidase inhibitors useful the present methods include miglitol, acarbose, and voglibose.

In another embodiment, the antidiabetic agent is an hepatic glucose output lowering agent.

Non-limiting examples of hepatic glucose output lowering agents useful in the present methods include Glucophage and Glueophage XR.

In yet another embodiment, the antidiabetic agent is insulin, including all formulations of insulin, such as long acting and short acting forms of insulin.

Non-limiting examples of orally administrable insulin and insulin containing compositions include AL-401 from Autoimmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In another embodiment, the antidiabetic agent is a DPP-IV inhibitor.

Non-limiting examples of DPP-IV inhibitors useful in the present methods include sitagliptin, saxagliptin (Januvia™, Merck), denagliptin, vildagliptin (Galvus™, Novartis), alogliptin aloaliptin benzoate, ABT-279 and ABT-341 (Abbott). ALS-2-0426 (Alantos), 2243 (Arisaph), BI-A and BI-B (Boehringer Ingelheim), SYR-322 (Takeda), MP-513 (Mitsubishi), DP-893 (Pfizer) RO-0730699 (Roche) or a combination of sitagliptin/metformin HCl (Janumet™, Merck).

In a further embodiment, the antidiabetic agent is a SGLT-2 inhibitor.

Non-limiting examples of SGLT-2 inhibitors useful in the present methods include dapagliflozin and sergliflozin, AVE2268 (Sanofi-Aventis) and T-1095(t (Tanabe Seiyaku).

Non-limiting examples of antihypertensive agents useful in the present methods for treating a Condition include β-blockers and calcium channel blockers (for example diltiazem, verapamil, nifedipine, amlopidine, and mybefradil), ACE inhibitors r example captopril, lisinopril, enalapril, spirapril, ceranopril, zefenopril, fosinopril, cilazapril, and quinapril), AT-1 receptor antagonists (for example losartan, irbesartan, and valsartan), renin inhibitors and endothelin receptor antagonists (for example sitaxsentan).

In one embodiment, the antidiabetic agent is an agent that slows or blocks the breakdown of starches and certain sugars.

Non-limiting examples of antidiabetic agents that slow or block the breakdown of starches and certain sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following, meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in International Publication No. WO 00/07617, Other specific additional therapeutic agents useful in the present methods for treating or preventing a Condition include, but are not limited to rimonabant, 2-methyl-6-(phenylethynyl)-pyridine, 3[(2-methyl-1,4-thiazol-4-yl)ethynyl] pyridine, Melanotan-II, dexfenfluramine, fluoxetine, paroxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, amrinone, milrinone, cilostamide, rolipram, cilomilast, phytanic acid, 4-[(E)-2-(5,6,7,8-tetramethyl-2-naphthalenyl)-1-propenyl]benzoic acid, retinoic acid, oleoyl-estrone, orlistat, lipstatin, tetrahydrolipstatin teasaponin and diethylumbelliferyl phosphate.

In one embodiment, the present combination therapies for treating or preventing diabetes comprise administering a Bicyclic Heterocycle Derivative, an antidiabetic agent and/or an antiobesity agent.

In another embodiment, the present combination therapies for treating or preventing diabetes comprise administering a Bicyclic Heterocyle Derivative and an antidiabetic agent.

In another embodiment, the present combination therapies for treating or preventing diabetes comprise administering a Bicyclic Heterocycle Derivative and an anti-obesity agent.

In one embodiment, the present combination therapies for treating or preventing obesity comprise administering a Bicyclic Heterocycle: Derivative, an antidiabetic agent and/or an antiobesity agent.

In another embodiment, the present combination therapies for treating or preventing obesity comprise administering a Bicyclic Heterocycle Derivative and an antidiabetic agent.

In another embodiment, the present combination therapies for treating or preventing obesity comprise administering a Bicyclic Heterocycle Derivative and an anti-obesity agent.

In one embodiment, the present combination therapies for treating or preventing metabolic syndrome comprise administering a Bicyclic Heterocycle Derivative and one or more additional therapeutic agents selected from: anti-obesity agents, antidiabetic agents, any agent useful for treating metabolic syndrome, any agent useful for treating a cardiovascular disease, cholesterol biosynthesis inhibitors, sterol absorption inhibitors, bile acid sequestrants, probucol derivatives, IBAT inhibitors, nicotinic acid receptor (NAR) agonists, ACAT inhibitors, cholesteryl ester transfer protea (CETP) inhibitors, low-density lipoprotein (LDL) activators, fish oil, water-soluble fibers, plant sterols, plant stanols and fatty acid esters of plant stanols.

In one embodiment, the additional therapeutic agent is a cholesterol biosynthesis inhibitor. In another embodiment, the cholesterol biosynthesis inhibitor is a squalene synthetase inhibitor. In another embodiment, the cholesterol biosynthesis inhibitor is as squalene epoxidase inhibitor. In still another embodiment, the cholesterol biosynthesis inhibitor is an HMG-CoA reductase inhibitor. In another embodiment, the HMG-CoA reductase inhibitor is a statin. In yet another embodiment, the statin is lovastatin, pravastatin, simvastatin or atorvastatin.

In one embodiment, the additional therapeutic agent is a cholesterol absorption inhibitor. In another embodiment, the cholesterol absorption inhibitor is ezetimibe.

In one embodiment, the additional therapeutic agent comprises a cholesterol absorption inhibitor and a cholesterol biosynthesis inhibitor. In another embodiment, the additional therapeutic agent comprises a cholesterol absorption inhibitor and a statin. In another embodiment, the additional therapeutic agent comprises ezetimibe and a statin. In another embodiment, the additional therapeutic agent comprises ezetimibe and simvastatin.

In one embodiment, the present combination therapies for treating or preventing metabolic syndrome comprise administering a Bicyclic Heterocycle Derivative, an antidiabetic agent and/or an antiobesity agent.

In another embodiment, the present combination therapies for treating or preventing metabolic syndrome comprise administering a Bicyclic Heterocycle Derivative and an antidiabetic agent.

In another embodiment, the present combination therapies for treating or preventing metabolic syndrome comprise administering a Bicyclic Heterocycle Derivative and an antiobesity agent.

In one embodiment, the present combination therapies for treating or preventing a cardiovascular disease comprise administering one or more Bicyclic Heterocycle Derivatives, and an additional agent useful for treating or preventing a cardiovascular disease.

When administering a combination therapy to a patient in need of such administration, the therapeutic agents in the combination, or a pharmaceutical composition or compositions comprising the therapeutic agents, may be administered in any order such as, for example, sequentially, concurrently, to nether, simultaneously and the like. The amounts of the various actives in such combination therapy may be different amounts (different dosage amounts) or same amounts (same dosage amounts).

In one embodiment, the one or more Bicyclic Heterocycle Derivatives are administered during a time when the additional therapeutic agent(s) exert their prophylactic or therapeutic effect, or vice versa.

In another embodiment, the one or more Bicyclic Heterocyle Derivatives and the additional therapeutic agent(s) are administered in doses commonly employed when such agents are used as monotherapy for treating a Condition.

In another embodiment, the one or more Bicyclic Heterocycle Derivatives and the additional therapeutic agent(s) are administered in doses lower than the doses commonly employed when such agents are used as monotherapy for treating a Condition.

In still al her embodiment, the one or more Bicyclic Heterocycle Derivatives and the additional therapeutic agent(s) act synergistically and are administered in doses lower than the doses commonly employed when such agents are used as monotherapy for treating a Condition.

In one embodiment, the one or more Bicyclic Heterocycle Derivatives and the additional therapeutic agent(s) are present in the same composition. In one embodiment, this composition is suitable for oral administration. In another embodiment, this composition is suitable for intravenous administration.

The one or more Bicyclic Heterocycle Derivatives and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Bicyclic Heterocycle Derivatives and the additional therapeutic agent(s) may inhibit the resistance of a Condition to these agents.

In one embodiment, when the patient is treated for diabetes or a diabetic oomph cation, the additional therapeutic agent is an antidiabetic agent which not a Bicyclic Heterocycle Derivative. In another embodiment, the additional therapeutic agent is an agent useful for reducing any potential side effect of a Bicyclic Heterocycle Derivative. Such potential side effects include, but are not limited to, nausea, vomiting, headache, fever, lethargy, muscle aches, diarrhea, general pain, and pain at an injection site.

In one embodiment, the additional therapeutic agent is used at its known therapeutically of dose. In another embodiment, the additional therapeutic agent is used at its normally prescribed dosage. In another embodiment, the additional therapeutic agent is used at less than its normally prescribed dosage or its known therapeutically effective dose.

The doses and dosage regimen of the other agents used in therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When admin stored in combination, the Bicyclic Heterocycle Derivative(s) and the other agent(s) for treating diseases or conditions listed above can be administered simultaneously or sequentially. This particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Bicyclic Heterocycle Derivatives and the additional therapeutic agent(s) can when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a dose or in 2-4 divided doses.

Compositions and Administration

In one embodiment, the invention provides compositions comprising an effective amount of one or more Bicyclic Heterocycle Derivatives or a pharmaceutically acceptable salt, solvate, ester, prodrug or stereoisomer thereof, and a pharmaceutically acceptable carrier.

For preparing compositions comprising one or more Bicyclic Heterocycle Derivatives, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, a Bicyclic Heterocyle Derivative is administered orally. In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation is from about 0.1 to about 2000 mg. Variations will necessarily occur depending on the target of the therapy, the patient and the route of administration. In one embodiment, the unit dose dosage is from about 0.2 to about 1000 mg. In another embodiment, the unit dose dosage is from about 1 to about 500 mg. In another embodiment, the unit dose dosage is from about 1 to about 100 mg/day. In still another embodiment, the unit dose dosage is from about 1 to about 50 mg. In yet another embodiment, the unit dose dosage is from about 1 to about 10 mg.

The actual dosage employed may be varied depending upon the requirements of the patient and the severity or the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, the condition and size of the patient, as well as severity of the symptoms being treated. A typical recommended daily dosage regimen for oral administration can range from about 1 mg/day to about 1000 mg/day, 1 mg/day to about 500 mg/day, 1 mg/day to about 300 mg/day, 1 mg/day to about 75 mg/day, 1 mg/day to about 50 mg/day, or 1 mg/day to about 20 mg/day, in one dose or in two to four divided doses.

When the invention comprises a combination of one or more Bicyclic Heterocycle Derivatives and an additional therapeutic agent, the two active components may be co-administered simultaneously or sequentially, or a single composition comprising one or more Bicyclic Heterocycle Derivatives and the additional therapeutic agent(s) in a pharmaceutically acceptable carrier can be administered. The components of the combination can be administered individually or together in any conventional dosage form such as capsule, tablet, powder, cachet, suspension, solution, suppository, nasal spray, etc. The dosage of the additional therapeutic agent can be determined from published material, and may range from about 1 to about 1000 mg per dose. In one embodiment, when used in combination, the dosage levels of the individual components are lower than the recommended individual dosages of an advantageous effect of the combination.

In one embodiment, the components of a combination therapy regimen are to be administered simultaneously, they can be administered in a single composition with a pharmaceutically acceptable carrier.

In another embodiment, when the components of a combination therapy regimen are to be administered separately or sequentially, they can be administered in separate compositions, each containing a pharmaceutically acceptable carrier.

Kits

In one aspect, the present invention provides a kit comprising an effective amount of one or more Bicyclic Heterocycle Derivatives, or a pharmaceutically acceptable salt, solvate, ester, prodrug or stereoisomer thereof, and a pharmaceutically acceptable carrier.

In another aspect the present invention provides a kit comprising an amount of one fit more Bicyclic Heterocycle Derivatives, or a pharmaceutically acceptable salt, solvate, ester, prodrug stereoisomer thereof, and an amount or one or more additional therapeutic agents listed above, wherein the combined amounts are effective for treating or preventing a Condition in a patient.

When the components of a combination therapy regimen are to be administered in more than one composition, they can be provided in a kit comprising a signal package containing one or more containers, wherein one container contains one or more Bicyclic Heterocycle Derivatives in a pharmaceutically acceptable carrier, and a second, separate container comprises an additional therapeutic agent in a pharmaceutically acceptable carrier, with the active components of each composition being present in amounts such that the combination is therapeutically effective.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula:

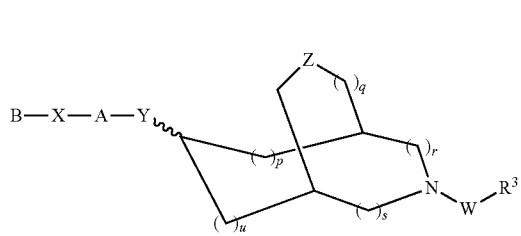

or a pharmaceutically acceptable salt thereof, wherein:

W is a bond, —C(O)—O— or —S(O)$_2$—;

X is —O— or —NH—;

Y is —O—, such that the group —Y-A-X—B— can be in an exo- or endo- configuration with respect to the bicyclic ring to which variable Y is attached;

Z is a bond, —CH$_2$— or —O—;

A is

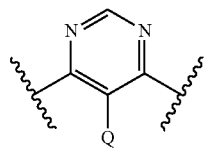

wherein Q is H, alkyl, halo or —O-alkyl

B is aryl or a -5- or 6-membered heteroaryl group, each of which can be unsubstituted or optionally substituted with up to 3 groups, which can be the same or different, and are selected from: alkyl, heteroaryl, halo, —CN, —S(O)$_2$-alkyl and —S(O)$_2$-cycloalkyl;

R$^3$ is alkyl, -alkylene-aryl, -cycloalkyl, -alkylene-O-alkyl or haloalkyl, wherein a cycloalkyl group can be unsubstituted or substituted with an alkyl group;

p is 0, 1 or 2;

q is 0, 1 or 2;

r is 0, 1 or 2;

s is 0, 1 or 2; and u is 0, 1 or 2.

2. The compound of claim 1, or a pharmaceutically acceptable salt thereof, wherein the group B—X-A-Y is:

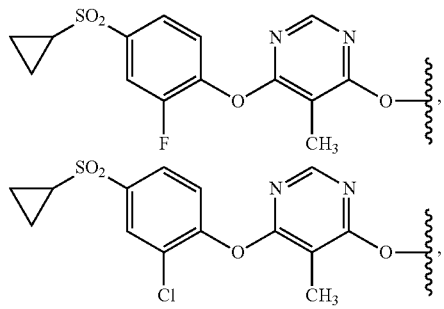

3. The compound of claim 2, or a pharmaceutically acceptable salt thereof, wherein the group B—X-A-Y is:

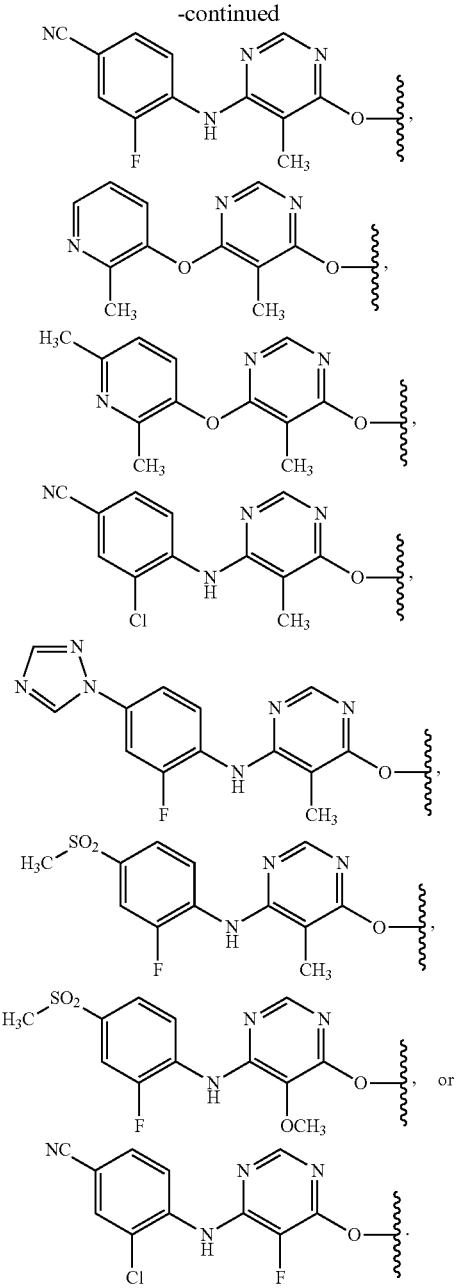

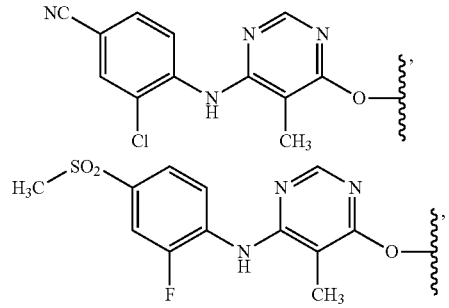

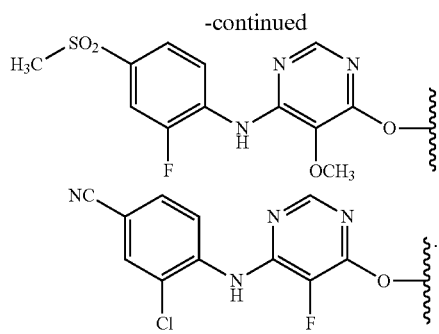
4. The compound of claim 2, or a pharmaceutically acceptable salt thereof, wherein the group
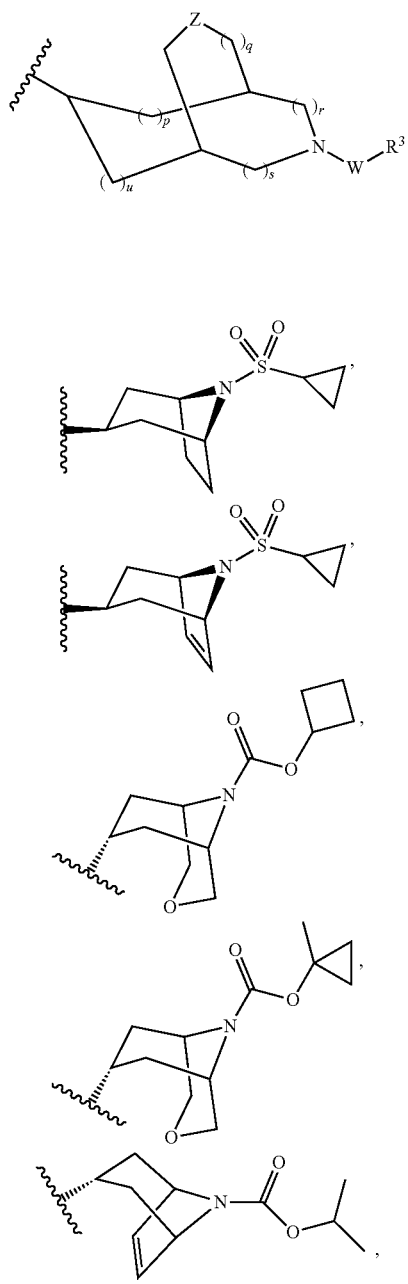
is:
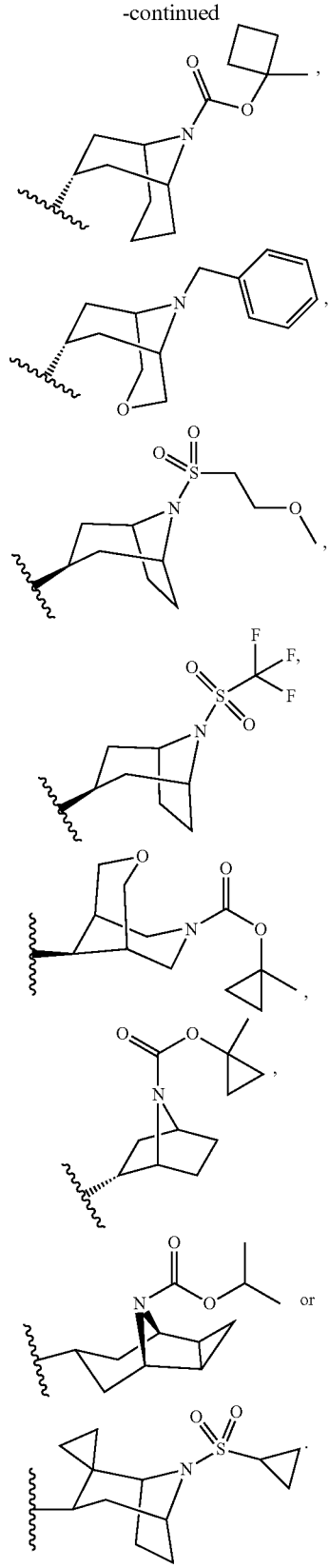
5. A composition comprising one or more compounds of claim 1 or a pharmaceutically acceptable salt thereof, and at least one pharmaceutically acceptable carrier.

6. The compound of claim 1, or a pharmaceutically acceptable salt thereof, wherein the group B—X-A-Y— is:
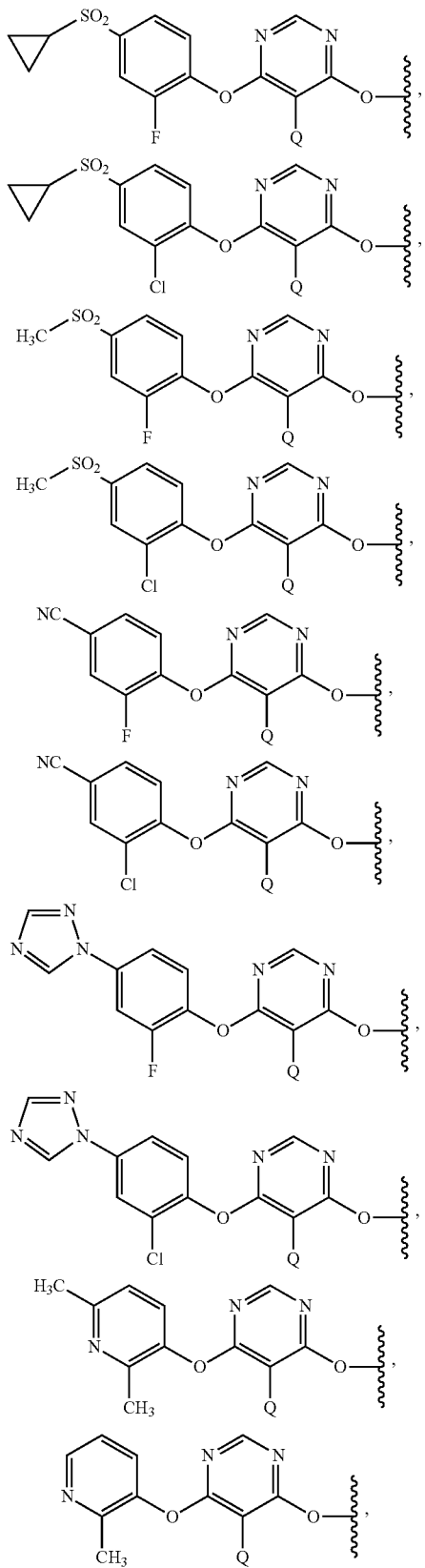
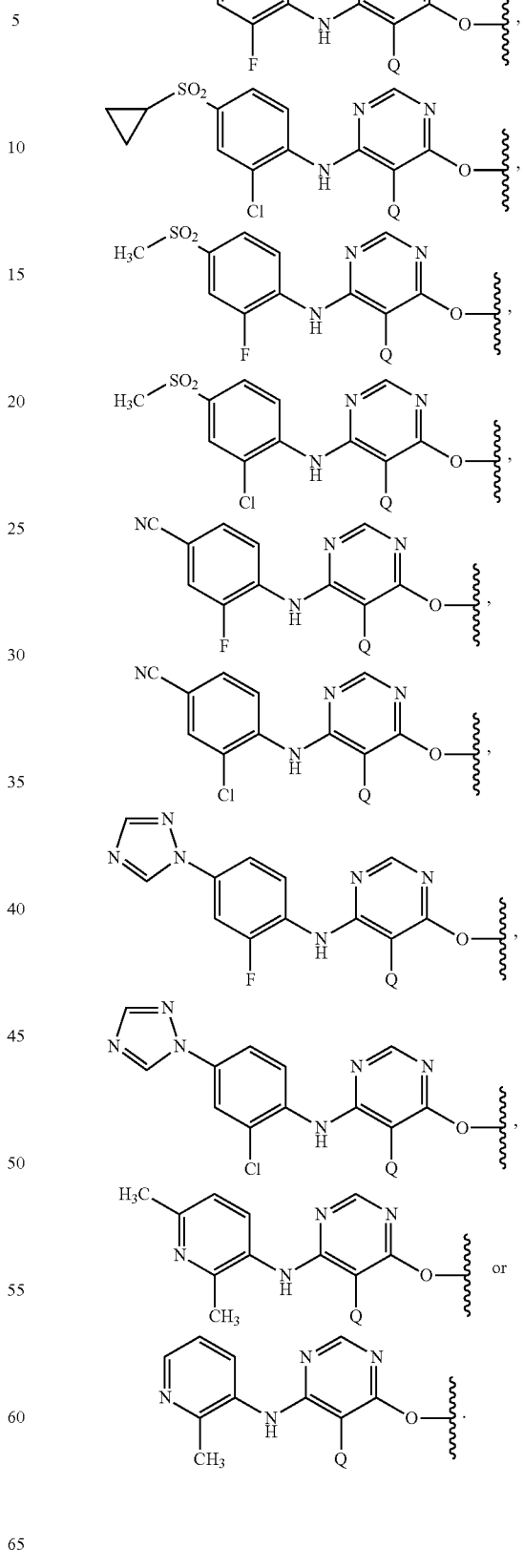
and wherein Q is H, alkyl, halo or —O-alkyl.

7. A compound selected from:
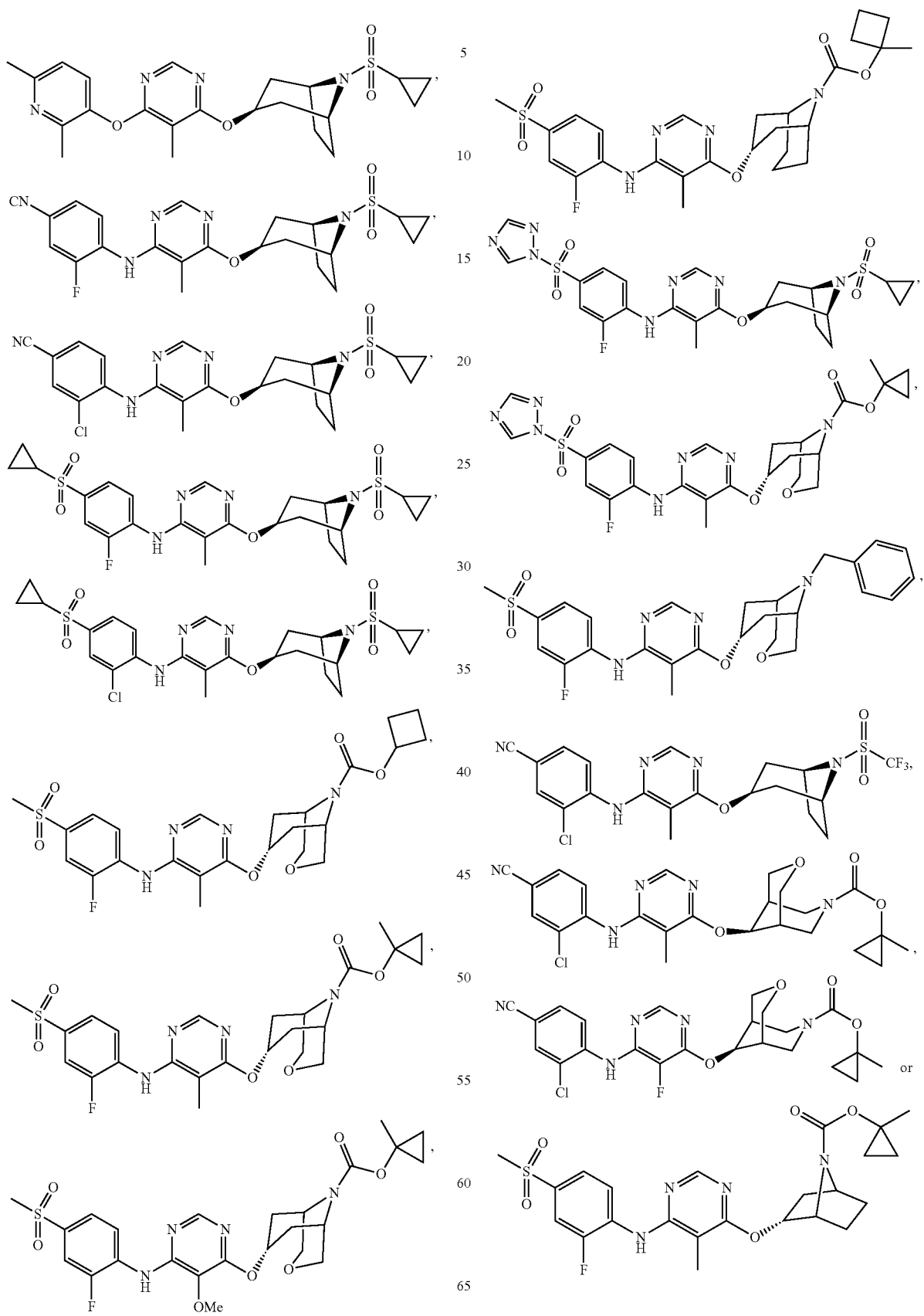
or a pharmaceutically acceptable salt thereof.

8. A compound having the structure:

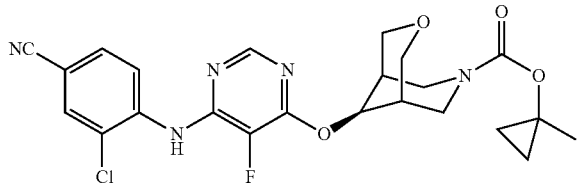

or a pharmaceutically acceptable salt thereof.

9. A compound having the structure:

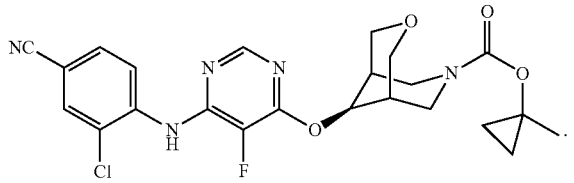

10. A composition comprising a compound of claim 8 or a pharmaceutically acceptable salt thereof, and at least one pharmaceutically acceptable carrier.

11. A method for treating diabetes in a patient, the method comprising administering to the patient an effective amount of one or more compounds of claim 1 or a pharmaceutically acceptable salt thereof.

12. The method of claim 11 further comprising administering to the patient one or more additional therapeutic agents selected from antidiabetic agents.

13. A method for treating diabetes, in a patient, the method comprising administering to the patient an effective amount of one or more compounds of claim 8 or a pharmaceutically acceptable salt thereof.

14. The method of claim 13 further comprising administering to the patient one or more additional therapeutic agents selected from antidiabetic agents, therapeutic agents are selected from antidiabetic agents and antiobesity agents.

* * * * *